(12) United States Patent
Nagarathnam et al.

(10) Patent No.: US 10,322,130 B2
(45) Date of Patent: Jun. 18, 2019

(54) SUBSTITUTED CHROMENONES AS MODULATORS OF PROTEIN KINASES

(71) Applicant: Rhizen Pharmaceuticals SA, La Chaux-de-Fonds (CH)

(72) Inventors: Dhanapalan Nagarathnam, Bethany, CT (US); Swaroop K. Vakkalanka, La Chaux-de-Fonds (CH); Meyyappan Muthuppalaniappan, Hyderabad (IN); Srikant Viswanadha, Hyderabad (IN); Govindarajulu Babu, Hyderabad (IN); Prashant K. Bhavar, Hyderabad (IN)

(73) Assignee: RHIZEN PHARMACEUTICALS SA, La Chaux-de-Fonds (CH)

( * ) Notice: Subject to any disclaimer, the term of this patent is extended or adjusted under 35 U.S.C. 154(b) by 0 days.

(21) Appl. No.: 15/677,614

(22) Filed: Aug. 15, 2017

(65) Prior Publication Data

US 2018/0110783 A1 Apr. 26, 2018
US 2019/0105324 A9 Apr. 11, 2019

Related U.S. Application Data

(63) Continuation of application No. 13/464,587, filed on May 4, 2012, now Pat. No. 9,775,841.

(30) Foreign Application Priority Data

May 4, 2011 (IN) .......................... 1542/CHE/2011
Jan. 9, 2012 (IN) .............................. 81/CHE/2012

(51) Int. Cl.
| | |
|---|---|
| *A61K 31/352* | (2006.01) |
| *C07D 311/22* | (2006.01) |
| *A61K 31/519* | (2006.01) |
| *A61K 31/52* | (2006.01) |
| *A61K 31/5377* | (2006.01) |
| *A61K 31/185* | (2006.01) |
| *A61K 31/5355* | (2006.01) |
| *A61K 45/06* | (2006.01) |
| *C07D 311/36* | (2006.01) |
| *C07D 405/06* | (2006.01) |
| *C07D 473/18* | (2006.01) |
| *C07D 473/34* | (2006.01) |
| *C07D 473/40* | (2006.01) |
| *C07D 487/04* | (2006.01) |

(52) U.S. Cl.
CPC .......... *A61K 31/519* (2013.01); *A61K 31/185* (2013.01); *A61K 31/52* (2013.01); *A61K 31/5355* (2013.01); *A61K 31/5377* (2013.01); *A61K 45/06* (2013.01); *C07D 311/22* (2013.01); *C07D 311/36* (2013.01); *C07D 405/06* (2013.01); *C07D 473/18* (2013.01); *C07D 473/34* (2013.01); *C07D 473/40* (2013.01); *C07D 487/04* (2013.01); *Y02A 50/422* (2018.01)

(58) Field of Classification Search
CPC ........................... A61K 31/352; C07D 311/22
USPC ........................................... 514/456; 549/401
See application file for complete search history.

(56) References Cited

U.S. PATENT DOCUMENTS

| | | | |
|---|---|---|---|
| 4,841,077 A | 6/1989 | Ito et al. | |
| 4,960,908 A | 10/1990 | Ito et al. | |
| 6,403,588 B1 | 6/2002 | Hayakawa et al. | |
| 6,608,053 B2 | 8/2003 | Hayakawa et al. | |
| 6,608,056 B1 | 8/2003 | Hayakawa et al. | |
| 6,653,320 B2 | 11/2003 | Hayakawa et al. | |
| 6,703,414 B2 | 3/2004 | Powis et al. | |
| 6,770,641 B2 | 8/2004 | Hayakawa et al. | |
| 6,838,457 B2 | 1/2005 | Hayakawa et al. | |
| 7,037,915 B2 | 5/2006 | Hayakawa et al. | |
| 7,173,029 B2 | 2/2007 | Hayakawa et al. | |
| 7,589,101 B2 | 9/2009 | Okram et al. | |
| 7,592,342 B2 | 9/2009 | Feng et al. | |
| 7,595,320 B2 | 9/2009 | Barberis et al. | |

(Continued)

FOREIGN PATENT DOCUMENTS

| | | |
|---|---|---|
| EP | 0245518 A1 | 11/1987 |
| EP | 1417976 A1 | 5/2004 |

(Continued)

OTHER PUBLICATIONS

Jordan, V. C. Nature Reviews: Drug Discovery, 2, 2003, 205-213.*
Dörwald, F. Zaragoza. Side Reactions in Organic Synthesis: A Guide to Successful Synthesis Design, Weinheim: Wiley-VCH Verlag GmbH & Co. KGaA, 2005, Preface.*
Wolff, Manfred E., Ed. Burger's Medicinal Chemistry and Drug Discovery—Fifth Edition, vol. 1: Principles and Practice, New York: John Wiley & Sons, 1994, 975-977.*
Hackam, et al. JAMA, 296(14), 2006, 1731-1732.*

(Continued)

*Primary Examiner* — Douglas M Willis
(74) *Attorney, Agent, or Firm* — Blank Rome LLP

(57) ABSTRACT

The present invention provides PI3K protein kinase modulators of formula

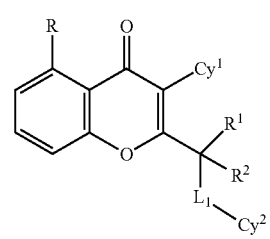

(I)

wherein R, $Cy^1$, $R^1$, $R^2$, $L_1$ and $Cy^2$ are as defined herein. The present invention also relates to methods of preparing compounds of formula (I) to pharmaceutical compositions containing them and to methods of treatment, prevention and/or amelioration of kinase mediated diseases or disorders with them.

35 Claims, No Drawings

(56) References Cited

U.S. PATENT DOCUMENTS

| | | |
|---|---|---|
| 7,595,330 B2 | 9/2009 | Cheung et al. |
| 7,598,245 B2 | 10/2009 | Arnost et al. |
| 7,601,718 B2 | 10/2009 | Green et al. |
| 7,601,724 B2 | 10/2009 | Guzi et al. |
| 7,605,155 B2 | 10/2009 | Guzi et al. |
| 7,605,160 B2 | 10/2009 | Fink et al. |
| 7,608,622 B2 | 10/2009 | Liu et al. |
| 8,642,607 B2 | 2/2014 | Muthuppalaniappan |
| 9,018,375 B2 | 4/2015 | Muthuppalaniappan et al. |
| 9,150,579 B2 | 10/2015 | Vakkalanka et al. |
| 2003/0149074 A1 | 8/2003 | Melese et al. |
| 2003/0158212 A1 | 8/2003 | Melese et al. |
| 2004/0053946 A1 | 3/2004 | Lackey et al. |
| 2004/0092561 A1 | 5/2004 | Ruckle et al. |
| 2004/0176440 A1 | 9/2004 | Mujica-Fernaud et al. |
| 2006/0270673 A1 | 11/2006 | Duggan et al. |
| 2008/0039459 A1 | 2/2008 | Folkes et al. |
| 2008/0076768 A1 | 3/2008 | Chuckowree et al. |
| 2008/0207611 A1 | 8/2008 | Shuttleworth et al. |
| 2009/0233926 A1 | 9/2009 | Butterworth et al. |
| 2009/0233950 A1 | 9/2009 | Jung et al. |
| 2009/0234132 A1 | 9/2009 | Budd et al. |
| 2009/0238828 A1 | 9/2009 | Munzert et al. |
| 2009/0239847 A1 | 9/2009 | Bruce et al. |
| 2009/0239859 A1 | 9/2009 | Chua et al. |
| 2009/0239936 A1 | 9/2009 | Sugimoto et al. |
| 2009/0247538 A1 | 10/2009 | Berdini et al. |
| 2009/0247554 A1 | 10/2009 | Dong et al. |
| 2009/0247565 A1 | 10/2009 | Lim et al. |
| 2009/0247567 A1 | 10/2009 | Do et al. |
| 2009/0258852 A1 | 10/2009 | Arrington et al. |
| 2009/0263397 A1 | 10/2009 | Buck et al. |
| 2009/0263398 A1 | 10/2009 | Lyons et al. |
| 2009/0270430 A1 | 10/2009 | Baik et al. |
| 2009/0270445 A1 | 10/2009 | Zeng et al. |
| 2009/0270621 A1 | 10/2009 | Wallace et al. |
| 2011/0118257 A1 | 5/2011 | Muthuppalaniappan et al. |

FOREIGN PATENT DOCUMENTS

| | | |
|---|---|---|
| GB | 1428094 A | 3/1976 |
| JP | S50018469 | 2/1975 |
| JP | 08175990 A | 7/1996 |
| JP | 08176070 A | 7/1996 |
| JP | 2001247477 A | 9/2001 |
| WO | WO-9715658 A1 | 5/1997 |
| WO | WO-2003034997 A2 | 5/2003 |
| WO | WO-2003035618 A2 | 5/2003 |
| WO | WO-2003037886 A2 | 5/2003 |
| WO | WO-2004006916 A1 | 1/2004 |
| WO | WO-2004007491 A1 | 1/2004 |
| WO | WO-2004017950 A2 | 3/2004 |
| WO | WO-2005056014 A1 | 6/2005 |
| WO | WO-2005113556 A1 | 12/2005 |
| WO | WO-2006046031 A1 | 5/2006 |
| WO | WO-2006046035 A1 | 5/2006 |
| WO | WO-2006046040 A1 | 5/2006 |
| WO | WO-2007042806 A1 | 4/2007 |
| WO | WO-2007042810 A1 | 4/2007 |
| WO | WO-2007114926 A2 | 10/2007 |
| WO | WO-2007126841 A2 | 11/2007 |
| WO | WO-2008064018 A1 | 5/2008 |
| WO | WO-2008070740 A1 | 6/2008 |
| WO | WO-2008073785 A2 | 6/2008 |
| WO | WO-2008118454 A2 | 10/2008 |
| WO | WO-2008127226 A2 | 10/2008 |
| WO | WO-2009088986 A1 | 7/2009 |
| WO | WO-2009088990 A1 | 7/2009 |
| WO | WO-2009105712 A1 | 8/2009 |
| WO | WO-2009109867 A2 | 9/2009 |
| WO | WO-2009111531 A1 | 9/2009 |
| WO | WO-2009111547 A1 | 9/2009 |
| WO | WO-2009112565 A1 | 9/2009 |
| WO | WO-2009114870 A2 | 9/2009 |
| WO | WO-2009114874 A2 | 9/2009 |
| WO | WO-2009117097 A1 | 9/2009 |
| WO | WO-2009117482 A1 | 9/2009 |
| WO | WO-2009120094 A2 | 10/2009 |
| WO | WO-2009126635 A1 | 10/2009 |
| WO | WO-2009129211 A1 | 10/2009 |
| WO | WO-2009129259 A2 | 10/2009 |
| WO | WO-2010036380 A1 | 4/2010 |
| WO | WO-2010045542 A2 | 4/2010 |
| WO | WO-2010048149 A2 | 4/2010 |
| WO | WO-2010059593 A1 | 5/2010 |
| WO | WO-2010151740 A2 | 12/2010 |
| WO | WO-2011055215 A2 | 5/2011 |
| WO | WO-2011153553 A2 | 12/2011 |
| WO | WO-2012151525 A1 | 11/2012 |
| WO | WO-2014004470 A1 | 1/2014 |
| WO | WO-2014060431 A1 | 4/2014 |
| WO | WO-2014071105 A1 | 5/2014 |
| WO | WO-2014071109 A1 | 5/2014 |

OTHER PUBLICATIONS

Okombi, et al., A one-step synthesis of 2-alkyl-5-hydroxychromones and 3-alkoyl-2-alkyl-5-hydroxychromones, Chem. Pharm. Bull., vol. 53, No. 11, 2005, pp. 1460-1462. Shaw, et al., Synthesis of 2-styrylchromones as a novel class of antiproliferative agents targeting carcinoma cells, European Journal of Medicinal Chemistry, Editions Scientifique Elsevier, Paris, FR, vol. 44, No. 6, Jun. 1, 2009, pp. 2552-2562.

International Search Report issued in PCT/US2012/036594 dated Aug. 23, 2012.

Daia, et al., Tetrahedron Lettters, 1998, 39:10:1215-1218.

Apsel, et al., Targeted Polypharmacology: Discovery of Dual Inhibitors of Tyrosine and Phosphoinositide Kinases, Nat Chem Biol, 2008, 4(11):691-699.

Berndt, et al., The p110δ Crystal Structure Uncovers Mechanisms for Selectivity and Potency of Novel PI3K Inhibitors, Nat Chem Biol., 2010, 6:2:117-124.

Knight, et al., A Pharmacological Map of the PI3-K Family Defines a Role for p 110α in Insulin Signaling, Cell, 2006, 125:4:733-747.

Williams, et al., Discovery of Dual Inhibitors of the Immune Cell PI3k p110δ and p110γ: a Prototype for New Anti-inflammatory Drugs, Chem Biol., 2010, 17:2:123-134.

Carnero, Novel Inhibitors of the PI3K Family, Expert Opin. Investig. Drugs, 2009, 18:9: 265-1277.

Chiosis, et al., LY294002-geldanamycin Heterodimers as Selective Inhibitors of the PI3K and PI3K-related Family, Bioorganic & Medicinal Chemistry Letters, 2001, 11:909-913.

Cushing, et al., PI3Kδ and PI3Kγ as Targets for Autoimmune and Inflammatory Diseases, Journal of Medicinal Chemistry, 2012, 55:20:8559-8581.

Marone, et al., Targeting Phosphoinositide 3-Kinase-Moving Towards Therapy, Biochimica et Biophysica Acta, 2008, 1784:159-185.

Sawyer, Cancer Metastasis Therapeutic Targets and Drug Discovery: Emerging Small-Molecule Protein Kinase Inhibitors, Expert Opinion Investig. Drugs, 2004, 13:1:1-19.

Vivanco, et al., The Phosphatidylinositol 3-Kinase-AKT Pathway in Human Cancer, Nature Reviews Cancer, 2002, 2:489-501.

Registry (STN) [online] Nov. 10, 2006, RN:912906-15-1.

Ares, et al., Synthesis and Biological Evaluation of Flavonoids and Related Compounds as Gastroprotective Agents, Bioorganic & Medicinal Chemistry Letters, 1996, 6:8:995-998.

Murata, et al., Flourescence Reaction of Beryllium with 5-hydroxyflavone, 5-hydroxyisoflavone and Their Derivatives, Analytic Chemistry, 1974, 23:11:1349-1355.

Ogawara, et al., Inhibition of Tyrosine Protein Kinase activity by Synthetic Isoflavones and Flavones, Journal of Antibiotics, 1989, 42:2:340-343.

Walker, et al., Structural Determinants of Phosphoinositide 3-Kinase Inhibition by Wortmannin, LY294002, Quercetin, Myricetin, and Staurosporine, Molecular Cell, 2000, 6:909-919.

* cited by examiner

SUBSTITUTED CHROMENONES AS MODULATORS OF PROTEIN KINASES

This application is a continuation of U.S. patent application Ser. No. 13/464,587, filed May 4, 2012, which claims the benefit of Indian Provisional Patent Application Nos. 1542/CHE/2011 dated 4 May 2011 and 81/CHE/2012 dated 9 Jan. 2012, each of which is hereby incorporated by reference.

FIELD OF THE INVENTION

The present invention provides PI3K protein kinase modulators, methods of preparing them, pharmaceutical compositions containing them and methods of treatment, prevention and/or amelioration of kinase mediated diseases or disorders with them.

BACKGROUND OF THE INVENTION

In the recent past immense research has been dedicated to the discovery and understanding of the structure and functions of enzymes and bio-molecules associated with various diseases. One such important class of enzymes that has been the subject of extensive research is Protein Kinase.

In general, protein kinases represent a set of structurally related phosphoryl transferases having conserved structures and catalytic functions. These enzymes modify proteins by chemically adding phosphate groups (phosphorylation). Phosphorylation involves the removal of a phosphate group from ATP and covalently attaching it to amino acids that have a free hydroxyl group such as serine, threonine or tyrosine. Phosphorylation usually results in a functional change of the target protein (substrate) by altering enzyme activity, cellular localization or association with other proteins. Up to 30% of all proteins may be modified by kinase activity.

This class of proteins are classified into subsets depending upon the substrate they act upon such as tyrosine kinase, serine/theronine kinase, histidine kinase and the like. These proteins can also be classified based on their localization into receptor tyrosine kinases (RTKs) or non-receptor tyrosine kinases.

Receptor tyrosine kinases (RTKs) have an extracellular portion, a transmembrane domain, and an intracellular portion, while non-receptor tyrosine kinases are entirely intracellular. Receptor tyrosine kinase mediated signal transduction is typically initiated by an extracellular interaction with a specific growth factor (ligand), followed by receptor dimerization, stimulation of the intrinsic protein tyrosine kinase activity, and phosphorylation of amino acid residues. The ensuing conformational change leads to the formation of complexes with a spectrum of cytoplasmic signalling molecules and facilitates a myriad of responses such as cell division, differentiation, metabolic effects, and changes in the extracellular microenvironment.

Protein kinases are known to control a wide variety of biological processes such as cell growth, survival and differentiation, organ formation and morphogenesis, neovascularisation, tissue repair and regeneration. In addition to their functions in normal tissues/organs, many protein kinases also play specialized roles in a host of human diseases including cancer. A subset of protein kinases (also referred to as oncogenic protein kinases), when dysregulated, can cause tumor formation and growth and contribute to tumor maintenance and progression (Blume-Jensen P et al, Nature 2001, 411(6835):355-365). Thus far, oncogenic protein kinases represent one of the largest and most attractive groups of protein targets for therapeutic intervention and drug development.

Both receptor and non-receptor protein kinases have been found to be attractive targets for small molecule drug discovery due to their impact on cell physiology and signalling. Dysregulation of protein kinase activity thus leads to altered cellular responses including uncontrolled cell growth associated with cancer. In addition to oncological indications, altered kinase signalling is implicated in numerous other pathological diseases. These include, but are not limited to immunological disorders, cardiovascular diseases, inflammatory diseases, and degenerative diseases.

Modulation (particularly inhibition) of cell proliferation and angiogenesis, the two key cellular processes needed for tumor growth and survival is an attractive goal for development of small-molecule drugs (Matter A. Drug Disc Technol 2001, 6, 1005-1024). Anti-angiogenic therapy represents a potentially important approach for the treatment of solid tumors and other diseases associated with dysregulated vascularisation including ischemic coronary artery disease, diabetic retinopathy, psoriasis and rheumatoid arthritis. Similarly, cell antiproliferative agents are desirable to slow or inhibit the growth of tumors.

Phosphatidylinositol (hereinafter abbreviated as "PI") is one of a number of phospholipids found in cell membranes. In recent years it has become clear that PI plays an important role in intracellular signal transduction. Cell signaling via 3'-phosphorylated phosphoinositide has been implicated in a variety of cellular processes, e.g., malignant transformation, growth factor signaling, inflammation, and immunity (Rameh et al (1999) J. Biol Chem, 274:8347-8350). The enzyme responsible for generating these phosphorylated signaling products, phosphatidylinositol 3-kinase (also referred to as PI 3-kinase or PI3K), was originally identified as an activity associated with viral oncoproteins and growth factor receptor tyrosine kinases that phosphorylate phosphatidylinositol (PI) and its phosphorylated derivatives at the 3'-hydroxyl of the inositol ring (Panayotou et al (1992) Trends Cell Biol 2:358-60).

The phosphoinositide 3-kinases (PI3Ks) are a family of enzymes that regulate diverse biological functions in every cell type by generating phosphoinositide second-messenger molecules. As the activity of these phosphoinositide second messengers is determined by their phosphorylation state, the kinases and phosphatises that act to modify these lipids are central to the correct execution of intracellular signaling events. Phosphoinositide 3-kinases (PI3K) phosphorylate lipids at the 3-hydroxyl residue of an inositol ring (Whitman et al (1988) Nature, 332:664) to generate phosphorylated phospholipids (PIP3s) which act as second messengers recruiting kinases with lipid binding domains (including plekstrin homology (PH) regions), such as Akt and phosphoinositide-dependent kinase-1 (PDK1). Binding of Akt to membrane PIP3s causes the translocation of Akt to the plasma membrane, bringing Akt into contact with PDK1, which is responsible for activating Akt. The tumor-suppressor phosphatase, PTEN, dephosphorylates PIP3 and therefore acts as a negative regulator of Akt activation. The PI3-kinases Akt and PDK1 are important in the regulation of many cellular processes including cell cycle regulation, proliferation, survival, apoptosis and motility and are significant components of the molecular mechanisms of diseases such as cancer, diabetes and immune inflammation (Vivanco et al (2002) Nature Rev. Cancer 2:489; Phillips et al (1998) Cancer 83:41).

The PI3K family is constituted by four different classes: classes I, II and III are lipid kinases while members of class IV are Ser/Thr protein kinases.

The members of the class I family of PI3Ks are dimers of a regulatory and a catalytic subunit. The class I family consists of four isoforms, determined by the catalytic subunits α, β, γ and δ (see Engelman J A, Nat Rev Genet 2006; 7:606-19; Carnero A, Curr Cancer Drug Targets 2008; 8:187-98; Vanhaesebroeck B, Trends Biochem Sci 2005; 30:194-204). Class I can be subdivided into two subclasses: Ia, formed by the combination of p110 α β and δ and a regulatory subunit (p85, p55 or p50) and Ib, formed by p110 γ and p101 regulatory subunits. The regulatory subunit p85 contains Src homology 2 domains, which bind to phosphotyrosines and bring the attached catalytic subunit p110 into the complexes located in the membrane around the receptor. The activation of PI3K is induced by growth factors and insulin targeting the catalytic subunit to the membrane where it is in close proximity with its substrates, mainly PIP2. Alternatively, GTP-bound Ras can bind and activate p110 subunits in a p85-independent manner. Class I phosphoinositide 3-kinases (PI3Ks) are lipid kinases that phosphorylate phosphatidyl-inositol lipids (PI) at the D3 position of the inositol ring producing lipid second messengers (PIPs). The products of PI3K activity, mainly PI(3,4,5)-P3 (PIP3), are present in very low level in quiescent cells but are rapidly produced during cell stimulation and are involved in the regulation of several biological responses including mitogenesis, apoptosis, vesicular trafficking and cytoskeleton rearrangement. The result of rising PIP3 levels is the activation of 3-phosphoinositide-dependent protein kinase-1 and its substrate AKT, which triggers most of the biological activities of the pathway. Phosphatase and tensin homolog in chromosome 10 (PTEN) is a lipidic phosphatase which constitutes the main negative regulator of the route by dephosphorylating PIP3 to PI(4,5)-P2 (PIP2). Class II displays the ability to phosphorylate PI and PI-4 phosphate in vitro. Class III, composed by Vps34 only member, phosphorylates PI at position 3 generating PI 3-phosphate. Vps34 has been implicated in Golgi trafficking of proteins, autophagy and activation of mammalian target of rapamycin (mTOR) by amino acids (see Backer J M. Biochem J 2008; 410:1-17). These classes are generally resistant to class I PI3K inhibitors. Class IV, however, is important because it constitutes the major cross-activity proteins for class I inhibitors. This class includes enzymes involved in signal transduction and DNA damage response such as mTOR, DNA-dependent protein kinase (DNA-PK) or ATM. This fourth class of PI3K-related enzymes contains a catalytic core similar to the PI3K, which can account for the cross-inhibition by class I 'selective' compounds. However, small differences, especially in the hinge region, and the solving of the PI3K-related structures might lead to the fine tuning of different paralog selective PI3K-members. (see *Expert Opin. Investig. Drugs* (2009) 18(9): 1265-1277)

There is now considerable evidence indicating that Class Ia PI3K enzymes contribute to tumourigenesis in a wide variety of human cancers, either directly or indirectly (Vivanco and Sawyers, Nature Reviews Cancer, 2002, 2, 489-501). For example, the pi 10a subunit is amplified in some tumours such as those of the ovary (Shayesteh et al, Nature Genetics. 1999, 21: 99-102) and cervix (Ma et al, Oncogene, 2000, 19: 2739-2744). More recently, activating mutations within the catalytic site of pi 10a have been associated with various other tumours such as those of the colorectal region and of the breast and lung (Samuels et al, Science, 2004, 304, 554). Tumour-related mutations in p85a have also been identified in cancers such as those of the ovary and colon (Philp et al., Cancer Research, 2001, 61, 7426-7429). In addition to direct effects, it is believed that activation of Class Ia PI3K contributes to tumourigenic events that occur upstream in signalling pathways, for example by way of ligand-dependent or ligand-independent activation of receptor tyrosine kinases, GPCR systems or integrins (Vara et al, Cancer Treatment Reviews, 2004, 30, 193-204). Examples of such upstream signalling pathways include over-expression of the receptor tyrosine kinase Erb2 in a variety of tumours leading to activation of PI3K-mediated pathways (Harari et al., Oncogene, 2000, 19, 6102-6114) and over-expression of the oncogene Ras (Kauffmann-Zeh et al., Nature, 1997, 385, 544-548). In addition, Class Ia PBKs may contribute indirectly to tumourigenesis caused by various downstream signalling events. For example, loss of the effect of the PTEN tumour-suppressor phosphatase that catalyses conversion of PI(3,4,5)P3 back to PI(4,5)P2 is associated with a very broad range of tumours via deregulation of PI3K-mediated production of PI(3,4,5)P3 (Simpson and Parsons, Exp. Cell Res. 2001, 264, 29-41). Furthermore, augmentation of the effects of other PI3K-mediated signalling events is believed to contribute to a variety of cancers, for example by activation of Akt (Nicholson and Anderson, Cellular Signalling, 2002, H, 381-395).

In addition to a role in mediating proliferative and survival signalling in tumour cells, there is also good evidence that Class Ia PI3K enzymes will also contribute to tumourigenesis via its function in tumour-associated stromal cells. For example, PI3K signalling is known to play an important role in mediating angiogenic events in endothelial cells in response to pro-angiogenic factors such as VEGF (Abid et al., Arterioscler. Thromb. Vase. Biol., 2004, 24, 294-300). As Class I PI3K enzymes are also involved in motility and migration (Sawyer, Expert Opinion Investig. Drugs, 2004, JJ., 1-19), PI3K inhibitors should provide therapeutic benefit via inhibition of tumour cell invasion and metastasis.

In addition, Class I PI3K enzymes play an important role in the regulation of immune cells with PI3K activity contributing to pro-tumourigenic effects of inflammatory cells (Coussens and Werb, Nature, 2002, 420, 860-867). These findings suggest that pharmacological inhibitors of Class I PI3K enzymes should be of therapeutic value for treatment of the various forms of the disease of cancer comprising solid tumours such as carcinomas and sarcomas and the leukaemias and lymphoid malignancies. In particular, inhibitors of Class I PI3K enzymes should be of therapeutic value for treatment of, for example, cancer of the breast, colorectum, lung (including small cell lung cancer, non-small cell lung cancer and bronchioalveolar cancer) and prostate, and of cancer of the bile duct, bone, bladder, head and neck, kidney, liver, gastrointestinal tissue, oesophagus, ovary, pancreas, skin, testes, thyroid, uterus, cervix and vulva, and of leukaemias (including ALL and CML), multiple myeloma and lymphomas.

A recent review by Romina Marone et. al., Biochimica et Biophysica Acta 1784 (2008) 159-185, describes the activation of the PI3K signalling cascade having a positive effect on cell growth, survival and proliferation. Constitutive up-regulation of PI3K signaling can have a deleterious effect on cells leading to uncontrolled proliferation, enhanced migration and adhesion-independent growth. These events favor not only the formation of malignant tumors, but also the development of inflammatory and autoimmune disease indicating the role of PI3K in various diseases including chronic inflammation & allergy, Cardiovascular diseases, cancer and metabolic disorders.

Several components of the PI3-kinase/Akt/PTEN pathway are implicated in oncogenesis. In addition to growth factor receptor tyrosine kinases, integrin-dependent cell adhesion and G-protein coupled receptors activate PI3-kinase both directly and indirectly through adaptor molecules. Functional loss of PTEN (the most commonly mutated tumor-suppressor gene in cancer after p53), oncogene mutations in PI3 kinase (Samuels et al (2004) Science 304:554), amplification of PI3-kinase and overexpression of Akt have been established in many malignancies. In addition, persistent signaling through the PI3-kinase/Akt pathway by stimulation of the insulin-like growth factor receptor is a mechanism of resistance to epidermal growth factor receptor inhibitors such as AG1478 and trastuzumab. Oncogenic mutations of p110alpha have been found at a significant frequency in colon, breast, brain, liver, ovarian, gastric, lung, and head and neck solid tumors. PTEN abnormalities are found in glioblastoma, melanoma, prostate, endometrial, ovarian, breast, lung, head and neck, hepatocellular, and thyroid cancers.

The levels of phosphatidylinositol-3,4,5-triphosphate (PIP3), the primary product of PI3-kinase activation, increase upon treatment of cells with a variety of agonists. PI3-kinase activation, therefore, is believed to be involved in a range of cellular responses including cell growth, differentiation, and apoptosis (Parker et al (1995) Current Biology, 5:577-99; Yao et al (1995) Science, 267:2003-05). Though the downstream targets of phosphorylated lipids generated following PI3 kinase activation have not been well characterized, emerging evidence suggests that pleckstrin-homology domain- and FYVE-finger domain-containing proteins are activated when binding to various phosphatidylinositol lipids (Sternmark et al (1999) J Cell Sci, 112:4175-83; Lemmon et al (1997) Trends Cell Biol, 7:237-42). In vitro, some isoforms of protein kinase C (PKC) are directly activated by PIP3, and the PKC-related protein kinase, PKB, has been shown to be activated by PI3 kinase (Burgering et al (1995) Nature, 376:599-602).

PI3 kinase also appears involved in leukocyte activation. A p85-associated PI3 kinase activity has been shown to physically associate with the cytoplasmic domain of CD28, which is an important costimulatory molecule for the activation of T-cells in response to antigen (Pages et al (1994) Nature, 369:327-29; Rudd, (1996) Immunity 4:527-34). Activation of T cells through CD28 lowers the threshold for activation by antigen and increases the magnitude and duration of the proliferative response. These effects are linked to increases in the transcription of a number of genes including interleukin-2 (IL2), an important T cell growth factor (Fraser et al (1991) Science, 251:313-16). Mutation of CD28 such that it can no longer interact with PI3 kinase leads to a failure to initiate IL2 production, suggesting a critical role for PI3 kinase in T cell activation.

Inhibition of class I PI3 kinase induces apoptosis, blocks tumor induced angiogenesis in vivo, and increases the radiosensitivity of certain tumors. At least two compounds, LY294002 and wortmannin, have been widely used as PI3 kinase inhibitors. These compounds, however, are nonspecific PI3K inhibitors, as they do not distinguish among the four members of Class I PI3 kinases. For example, the IC50 values of wortmannin (U.S. Pat. No. 6,703,414) against each of the various Class 1 PI3 kinases are in the range of 1-10 nanomolar (nM). LY294002 (2-(4-morpholinyl)-8-phenyl-4H-1-benzopyran-4-one) is a well known specific inhibitor of class I PI3 kinases and has anti-cancer properties (Chiosis et al (2001) Bioorganic & Med. Chem. Lett. 11:909-913; Vlahos et al (1994) J. Biol. Chem. 269(7):5241-5248; Walker et al (2000) Mol. Cell 6:909-919; Fruman et al (1998) Ann Rev Biochem, 67:481-507).

Patent literature belonging to various research groups around the world includes several such patents and/or patent applications viz., U.S. Pat. Nos. 6,608,056; 6,608,053; 6,838,457; 6,770,641; 6,653,320; 6,403,588; WO 2004017950; US 2004092561; WO 2004007491; WO 2004006916; WO 2003037886; US 2003149074; WO 2003035618; WO 2003034997; US 2003158212; EP 1417976; US 2004053946; JP 2001247477; JP 08175990; JP 08176070). WO 97/15658, U.S. Pat. Nos. 7,173,029; 7,037,915; 6,703,414; WO 2006/046031; WO 2006/046035; WO 2006/046040; WO 2007/042806; WO 2007/042810; WO 2004/017950; US 2004/092561; WO 2004/007491; WO2004/006916; WO 2003/037886; US 2003/149074; WO 2003/035618; WO 2003/034997; including p110 alpha binding activity US 2008/0207611; US 2008/0039459; US 2008/0076768; WO 2008/073785; WO 2008/070740; US20090270430A1; US2006270673 A1; WO2009129211A1; US2009 0263398A1; US20090263397A1; WO2009129259A2; U.S. Pat. Nos. 7,605,160; 7,605,155; 7,608,622; US20090270621; US20090270445; US20090247567A1; U.S. Pat. No. 7,592,342; US20090239847A1; U.S. Pat. No. 7,595,320; US20090247538A1; US20090239936A1; U.S. Pat. No. 7,595,330; US20090239859A1; WO2009117482A1; WO2009117097A1; US20090247565A1; WO2009120094A2; US20090258852A1; U.S. Pat. No. 7,601,724; WO2009126635A1; U.S. Pat. Nos. 7,601,718; 7,598,245; US20090239859A1; US20090247554; US20090238828; WO2009114874A2; WO2009114870A2; US20090234132A1; WO2009112565A1; US20090233950A1; US20090233926A1; U.S. Pat. No. 7,589,101; WO2009111547A1; WO2009111531A1; WO2009109867A2 and WO2009105712A1.

Reviews and studies regarding PI3K and related protein kinase pathways have been given by Pixu Liu et. al. (*Nature Reviews Drug Discovery,* 2009, 8, 627-644); Nathan T. et. al. (Mol Cancer Ther., 2009; 8 (1) January, 2009); Romina Marone et, al. (Biochimica et Biophysica Acta 1784 (2008) 159-185) and B. Markman et. al. (Annals of oncology Advance access published August 2009). All of these patents and/or patent applications and literature disclosures are incorporated herein as reference in their entirety for all purposes.

There still remains an unmet and dire need for small molecule kinase modulators in order to regulate and/or modulate transduction of kinases, particularly PI3K and related protein kinase for the treatment of diseases and disorders associated with kinases-mediated events.

Further a reference is made herein to International patent Application No. PCT/IB2010/002804, filed Nov. 3, 2010, and U.S. patent application Ser. No. 12/938,609 filed Nov. 3, 2010 which generally disclose 2,3 disubstituted-4H-chromen-4-one and are incorporated herein by reference in their entirety for all purposes.

SUMMARY OF INVENTION

The present invention is directed to compounds, which are useful as PI3K protein kinase modulators and in particular as PI3K inhibitors. In one embodiment, the compound of the present invention has the formula:

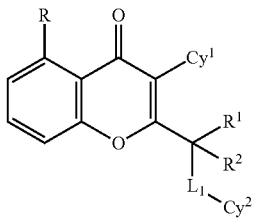

(I)

wherein
each occurrence of R is independently selected from hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, —COOR$^x$, —C(O)R$^x$, —C(S)R$^x$, —C(O)NR$^x$R$^y$, —C(O)ONR$^x$R$^y$, —NR$^x$R$^y$, —NR$^x$CONR$^y$R$^y$, —N(R$^x$)SOR$^x$, —N(R$^x$)SO$_2$R$^y$, —(=N—N(R$^x$)R$^y$), —NR$^x$C(O)OR$^y$, —NR$^x$R$^y$, —NR$^x$C(O)R$^y$—, —NR$^x$C(S)R$^y$—NR$^x$C(S)NR$^x$R$^y$, —SONR$^x$R$^y$—, —SO$_2$NR$^x$R$^y$—, —OR$^x$—, —OR$^x$C(O)NR$^x$R$^y$, —OR$^x$C(O)OR$^x$—, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^x$R$^y$, —R$^x$C(O)R$^y$, —R$^x$OC(O)R$^y$, —SR$^x$, —SOR$^x$, —SO$_2$R$^x$, —ONO$_2$, wherein R$^x$, R$^y$ and R$^z$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted heteroaryl, substituted or unsubstituted heteroarylalkyl, substituted or unsubstituted cycloalkyl, substituted or unsubstituted cycloalkylalkyl, substituted or unsubstituted cycloalkenyl, substituted or unsubstituted heterocyclic ring, substituted heterocyclylalkyl ring, or substituted or unsubstituted amino, or (i) any two of R$^x$ and R$^y$ may be joined to form a substituted or unsubstituted, saturated or unsaturated 3-14 membered ring, which may optionally include heteroatoms which may be the same or different and are selected from O, NR$^z$ or S, or (ii) any two of R$^x$ and R$^y$ join to form a oxo (=O), thio (=S) or imino (=NR$^f$) (wherein R$^f$ is hydrogen or substituted or unsubstituted alkyl).

R$^1$ and R$^2$ may be the same or different and are independently selected from hydrogen, halogen, substituted or unsubstituted C$_{1-6}$ alkyl, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl and substituted or unsubstituted heterocyclyl or both R$^1$ and R$^2$ directly bound to a common atom, may be joined to form an oxo group (=O) or a substituted or unsubstituted, saturated or unsaturated 3-10 member ring (including the carbon atom to which R$^1$ and R$^2$ are bound), which may optionally include one or more heteroatoms which may be the same or different and are selected from O, NR$^a$ and S;

Cy$^1$ is selected from substituted or unsubstituted cycloalkyl, substituted or unsubstituted heterocyclic group, substituted or unsubstituted aryl and substituted or unsubstituted heteroaryl;

Cy$^2$ is selected from a substituted or unsubstituted heterocyclic group, substituted or unsubstituted aryl and substituted or unsubstituted heteroaryl;

L$_1$ is absent or selected from —(CR$^a$R$^b$)$_q$—, —O—, —S(=O)$_q$—, —NR$^a$— or —C(=Y)—.

each occurrence of R$^a$ and R$^b$ may be the same or different and are independently selected from hydrogen, halogen, hydroxy, cyano, substituted or unsubstituted (C$_{1-6}$)alkyl, —NR$^c$R$^d$ (wherein R$^c$ and R$^d$ are independently hydrogen, halogen, hydroxy, cyano, substituted or unsubstituted (C$_{1-6}$)alkyl, or (C$_{1-6}$)alkoxy) and —OR$^c$ (wherein R$^c$ is substituted or unsubstituted (C$_{1-6}$)alkyl) or when R$^a$ and R$^b$ are directly bound to a common atom, they may be joined to form an oxo group (=O) or form a substituted or unsubstituted, saturated or unsaturated 3-10 member ring (including the common atom to which R$^a$ and R$^b$ are directly bound), which may optionally include one or more heteroatoms which may be the same or different and are selected from O, NR$^d$ (wherein R$^d$ is hydrogen or substituted or unsubstituted (C$_{1-6}$)alkyl) or S;

Y is selected from O, S, and NR$^a$; and
q is 0, 1 or 2
or a tautomer thereof, N-oxide thereof, pharmaceutically acceptable ester thereof, prodrug thereof, or pharmaceutically acceptable salt thereof.

Yet another embodiment is a compound having the formula (I-A)

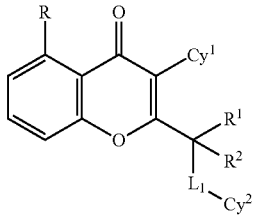

(IA)

wherein
each occurrence of R is independently selected from halogen, CN, substituted or unsubstituted C$_{1-6}$ alkyl, substituted or unsubstituted alkoxy, substituted or unsubstituted C$_{2-6}$ alkenyl, substituted or unsubstituted C$_{2-6}$ alkynyl, substituted or unsubstituted C$_{3-8}$ cycloalkyl, and substituted or unsubstituted heterocyclic group;

R$^1$ and R$^2$ may be the same or different and are independently selected from hydrogen, halogen, and substituted or unsubstituted C$_{1-6}$ alkyl, or both R$^1$ and R$^2$ directly bound to a common atom, may be joined to form an oxo group (=O) or a substituted or unsubstituted, saturated or unsaturated 3-10 member ring (including the carbon atom to which R$^1$ and R$^2$ are bound), which may optionally include one or more heteroatoms which may be the same or different and are selected from O, NR$^a$ and S;

Cy$^1$ is a monocyclic group selected from substituted or unsubstituted cycloalkyl, substituted or unsubstituted heterocyclic group, substituted or unsubstituted aryl and substituted or unsubstituted heteroaryl;

Cy$^2$ is selected from a substituted or unsubstituted heterocyclic group, substituted or unsubstituted aryl and substituted or unsubstituted heteroaryl;

L$_1$ is absent or selected from —(CR$^a$R$^b$)$_q$—, —O—, —S(=O)$_q$—, —NR$^a$— or —C(=Y)—.

each occurrence of R$^a$ and R$^b$ may be the same or different and are independently selected from hydrogen, halogen, hydroxy, cyano, substituted or unsubstituted (C$_{1-6}$)alkyl, —NR$^c$R$^d$ (wherein R$^c$ and R$^d$ are independently hydrogen, halogen, hydroxy, cyano, substituted or unsubstituted (C$_{1-6}$)alkyl or (C$_{1-6}$)alkoxy) and —OR$^c$ (wherein R$^c$ is substituted or unsubstituted (C$_{1-6}$)alkyl) or when R$^a$ and R$^b$ are directly bound to a common atom, they may be joined to form an oxo group (=O) or form a substituted or unsubstituted, saturated or unsaturated 3-10 member ring (including the common atom to which R$^a$ and R$^b$ are directly bound), which may optionally include one or more heteroatoms which may be the same or different and are selected from O, NR$^d$ (wherein R$^d$ is hydrogen or substituted or unsubstituted (C$_{1-6}$)alkyl) or S;

Y is selected from O, S, and NR$^a$; and q is 0, 1 or 2 or a tautomer thereof, N-oxide thereof, pharmaceutically acceptable ester thereof, prodrug thereof, or pharmaceutically acceptable salt thereof.

Yet another embodiment is a compound having the formula (I) or (IA) wherein R is selected from halogen, substituted or unsubstituted C$_{1-6}$ alkyl, substituted or unsubstituted C$_{3-8}$ cycloalkyl, and substituted or unsubstituted heterocyclic group or OR$^a$.

Yet another embodiment is a compound having the formula (I) or (IA) wherein R is selected from fluoro, methyl, morpholine or —OCH$_3$.

Further preferred is a compound having the formula (I) or (IA) wherein Cy$^1$ is selected from substituted or unsubstituted aryl and substituted or unsubstituted heteroaryl.

Illustrative examples of optionally substituted Cy$^1$ groups include those shown below:

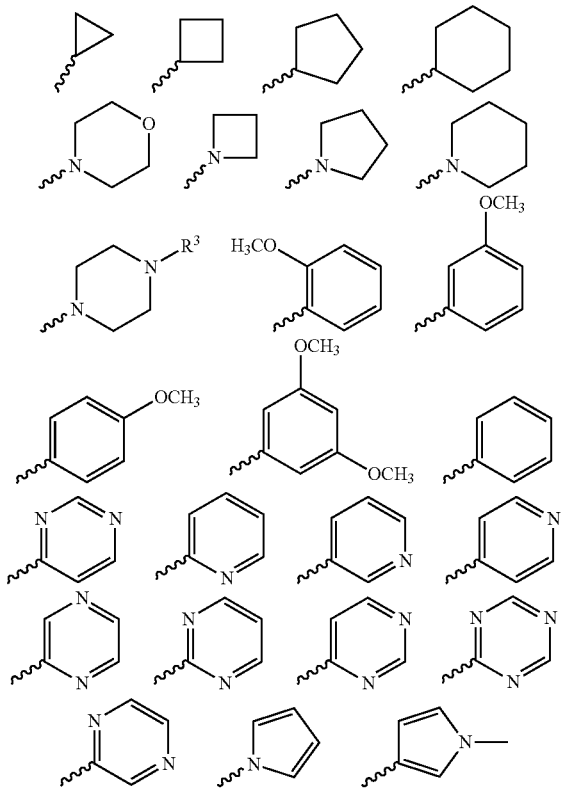
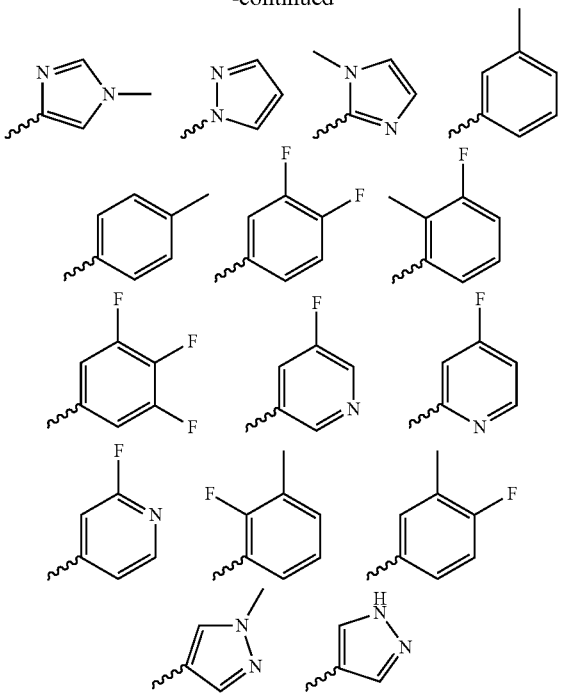

Further preferred is a compound having the formula (I) or (IA), wherein Cy$^1$ is selected from

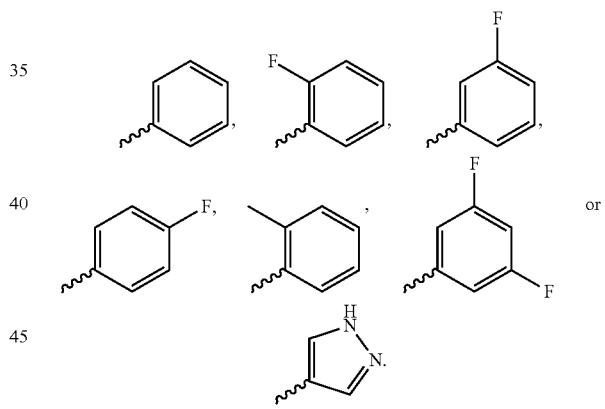

Further preferred is a compound having the formula (I) or (IA), wherein Cy$^1$ is substituted or unsubstituted phenyl or pyrazole.

Further preferred is a compound having the formula (I) or (IA) wherein Cy$^1$ is substituted phenyl.

Further preferred is a compound having the formula (I) or (IA), wherein Cy$^1$ is 2-methyl phenyl, 2-fluoro phenyl, 3-fluoro phenyl, 4-fluoro phenyl or pyrazol-4-yl.

Yet another embodiment is a compound having the formula (I) or (IA), wherein R$^1$ and R$^2$ independently represent hydrogen or substituted or unsubstituted C$_{1-6}$ alkyl (for example, methyl).

Yet another embodiment is a compound having the formula (I) or (IA), wherein L$_1$ is selected from —S(=O)$_q$— or —NR$^a$.

Yet another embodiment is a compound having the formula (I) or (IA), wherein q is 0.

Yet another embodiment is a compound having the formula (I) or (IA), wherein R$^a$ hydrogen.

Yet another embodiment is a compound having the formula (I) or (IA), wherein $L_1$ is absent.

Yet another embodiment is a compound having the formula (I) or (IA), wherein $L_1$-$Cy^2$ is selected from

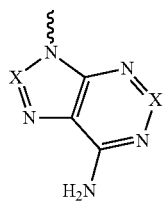 a

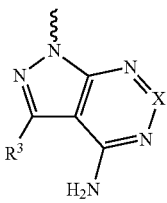 b

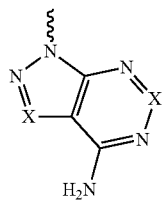 c

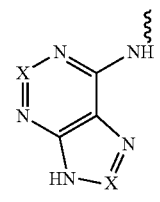 d

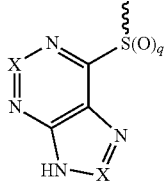 e

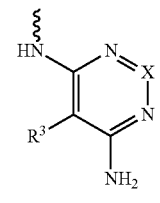 f wherein

X is $CR^3$; and each occurrence of $R^3$ is independently selected from hydrogen, hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted heterocyclic ring, or unsubstituted heterocyclyalkyl ring, substituted or unsubstituted aryl, substituted or unsubstituted arylalkyl, substituted or unsubstituted heteroaryl, substituted or unsubstituted heteroarylalkyl, substituted or unsubstituted guanidine, —$COOR^x$, —$C(O)R^x$, —$C(S)R^x$, —$C(O)NR^xR^y$, —$C(O)ONR^xR^y$, —$NR^yR^z$, —$NR^xCONR^yR^z$, —$N(R^x)SOR^y$, —$N(R^x)SO_2R^y$, —(=N—N($R^x$)$R^y$), —$NR^xC(O)OR^y$, —$NR^xR^y$, —$NR^xC(O)R^y$—, —$NR^xC(S)R^y$—$NR^xC(S)NR^yR^z$, —$SONR^xR^y$—, —$SO_2NR^zR^y$—, —$OR^x$, —$OR^xC(O)NR^yR^z$, —$OR^xC(O)OR^y$—, —$OC(O)R^x$, —$OC(O)NR^xR^y$, —$R^xNR^yC(O)R^z$, —$R^xOR^y$, —$R^xC(O)OR^y$, —$R^xC(O)NR^yR^z$, —$R^xC(O)R^x$, —$R^xOC(O)R^y$, —$SR^x$, —$SOR^x$, —$SO_2R^x$, or —$ONO_2$, wherein $R^x$, $R^y$ and $R^z$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted heteroaryl, substituted or unsubstituted heteroarylalkyl, substituted or unsubstituted cycloalkyl, substituted or unsubstituted cycloalkylalkyl, substituted or unsubstituted cycloalkenyl, substituted or unsubstituted heterocyclic ring, substituted heterocyclylalkyl ring, or substituted or unsubstituted amino, or any two of $R^x$, $R^y$ and $R^z$ may be joined to form a substituted or unsubstituted, saturated or unsaturated 3-10 membered ring, which may optionally include heteroatoms which may be the same or different and are selected from O, $NR^f$ or S (wherein $R^f$ is hydrogen or substituted or unsubstituted alkyl).

Yet another embodiment is a compound having the formula (I) and (IA), wherein $L_1$-$Cy^2$ is selected from

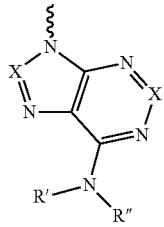 a¹

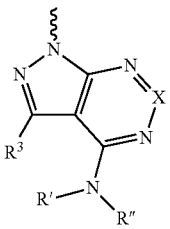 b¹

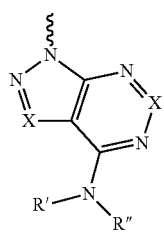 c¹

-continued

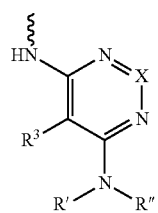
f¹

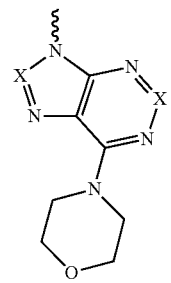
a²

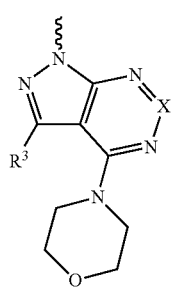
b²

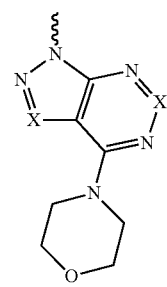
c²

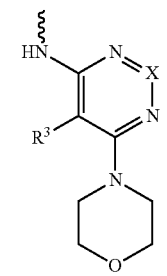
f² wherein

X and R³ are the same as defined above; and each occurrence of R' and R" is independently selected from hydrogen, hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted heteroaryl, substituted or unsubstituted heteroarylalkyl, substituted or unsubstituted heterocyclic ring, substituted or unsubstituted heterocyclylalkyl ring, substituted or unsubstituted guanidine, —COOR$^x$, —C(O)R$^x$, —C(S)R$^x$, —C(O)NR$^x$R$^y$, —C(O)ONR$^x$R$^y$, —NR$^y$R$^z$, —NR$^x$CONR$^y$R$^z$, —N(R$^x$)SOR$^y$, —N(R$^x$)SO$_2$R$^y$, —(=N—N(R$^x$)R$^y$), —NR$^x$C(O)OR$^y$, —NR$^x$R$^y$, —NR$^x$C(O)R$^y$—, —NR$^x$C(S)R$^y$—NR$^x$C(S)NR$^y$R$^z$, —SONR$^x$R$^y$—, —SO$_2$NR$^x$R$^y$—, —OR$^x$, —OR$^x$C(O)NR$^y$R$^z$, —OR$^x$C(O)OR$^y$—, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, and —ONO$_2$, or both the R' and R" together with the nitrogen atom may be joined to form a substituted or unsubstituted, saturated or unsaturated 3-10 membered ring, which may optionally include heteroatoms which may be the same or different and are selected from O, NR$^f$ (wherein R$^f$ is hydrogen or substituted or unsubstituted alkyl) or S;

R$^x$, R$^y$ and R$^z$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted heteroaryl, substituted or unsubstituted heteroarylalkyl, substituted or unsubstituted cycloalkyl, substituted or unsubstituted cycloalkylalkyl, substituted or unsubstituted cycloalkenyl, substituted or unsubstituted heterocyclic ring, substituted heterocyclylalkyl ring, or substituted or unsubstituted amino, or any two of R$^x$, R$^y$ and R$^z$ may be joined to form a substituted or unsubstituted, saturated or unsaturated 3-10 membered ring, which may optionally include heteroatoms which may be the same or different and are selected from O, NR$^f$ or S (wherein R$^f$ is hydrogen or substituted or unsubstituted alkyl); and q is 0, 1 or 2.

Yet another embodiment is a compound having the formula (I) and (IA), wherein L$_1$-Cy² is selected from wherein X and R³ are the same as defined above.

For example, L$_1$-Cy² is represented as formula a, b c, d e, or f above can be

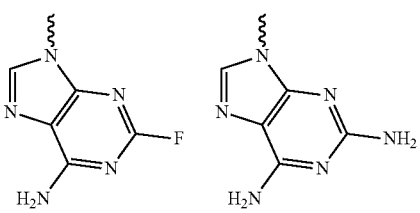

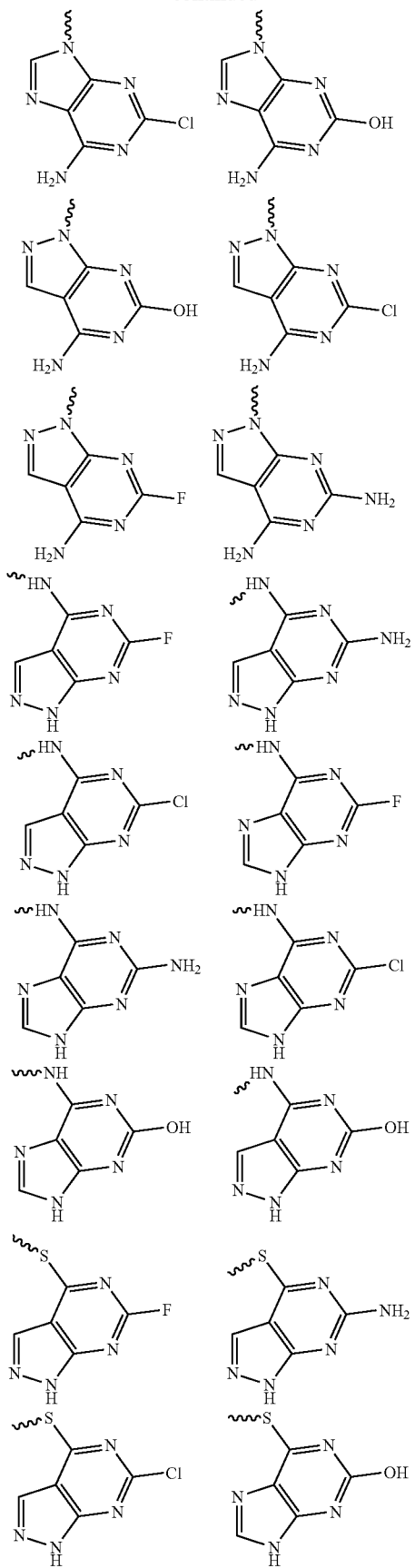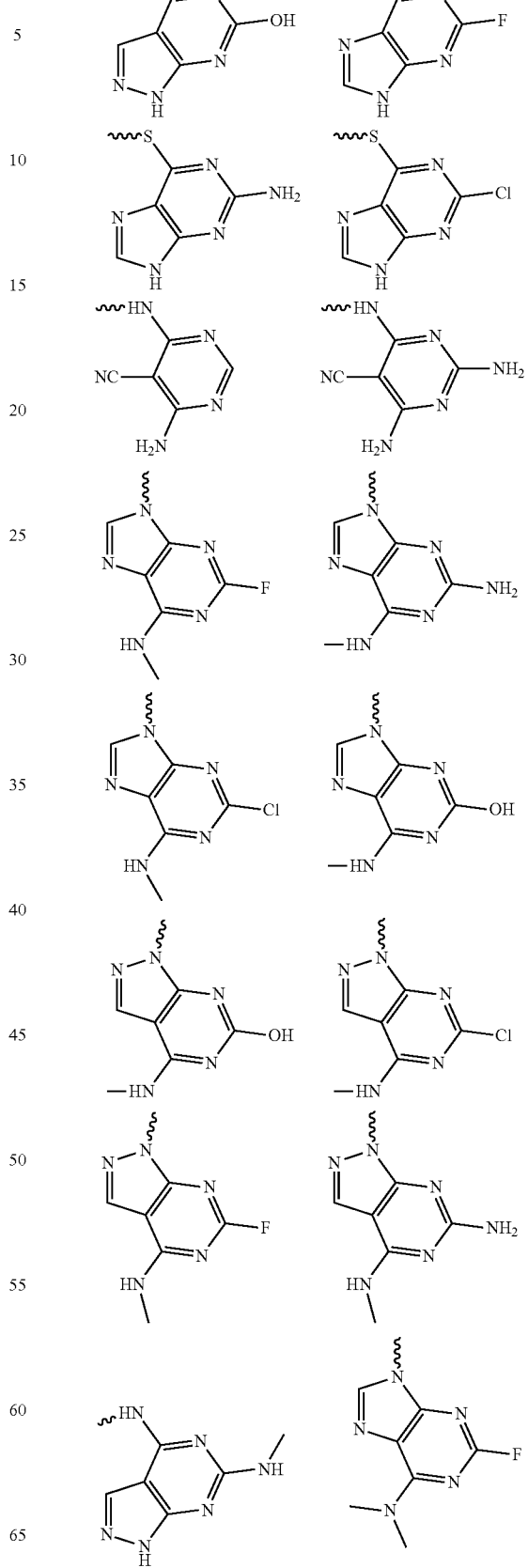

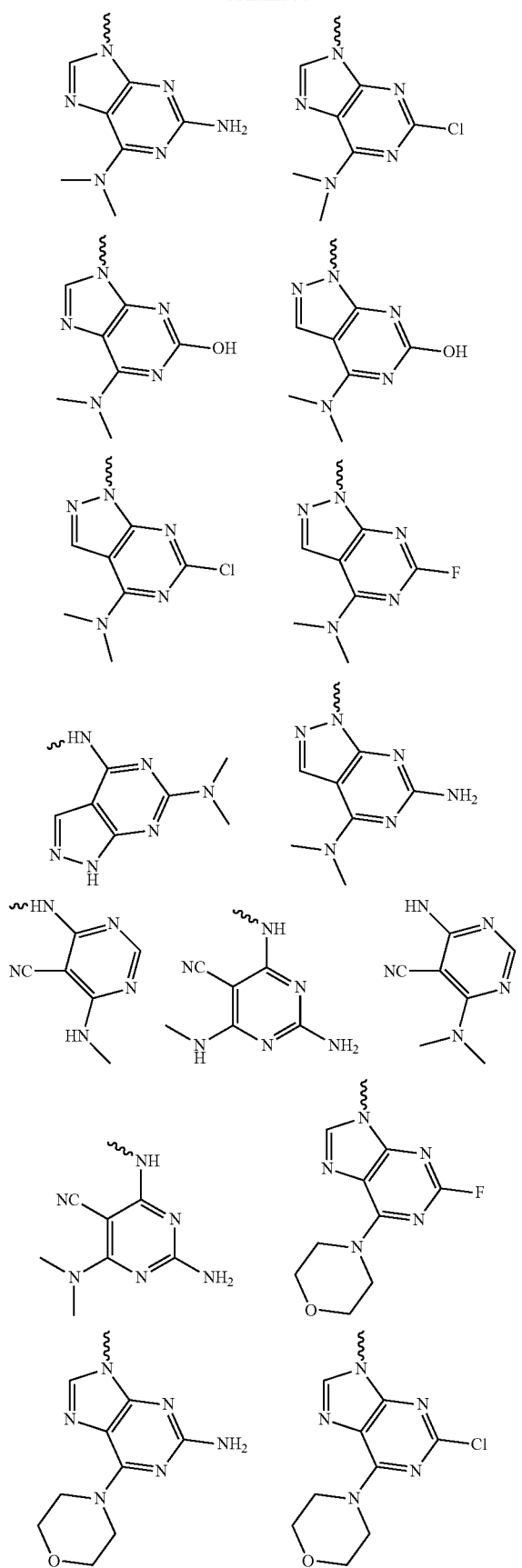
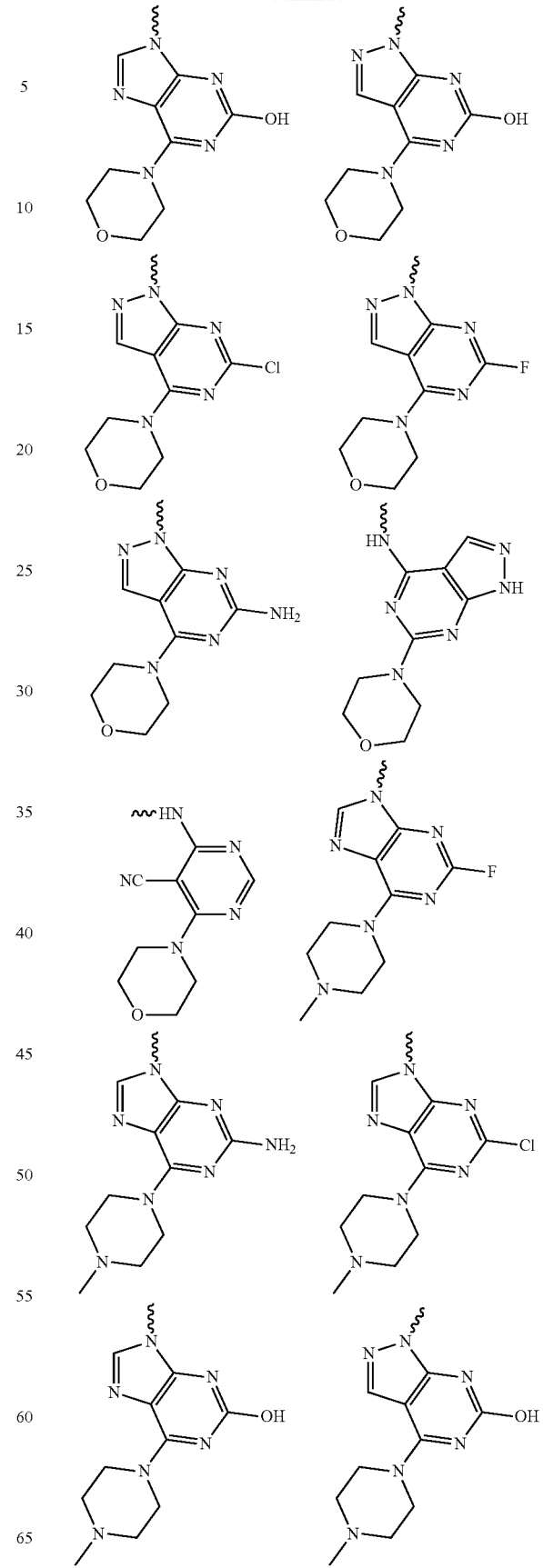

-continued
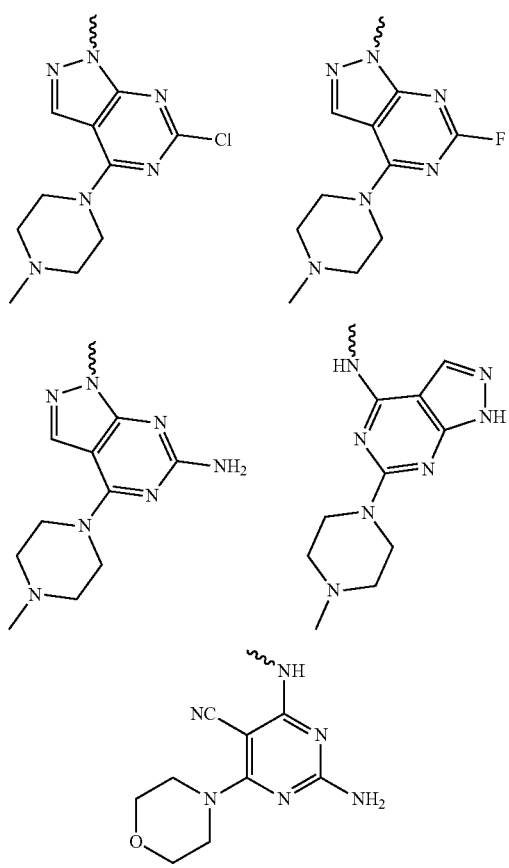
Yet another embodiment is a compound having the formula (I) and (IA) wherein $L_1$-$Cy^2$ is selected from
-continued
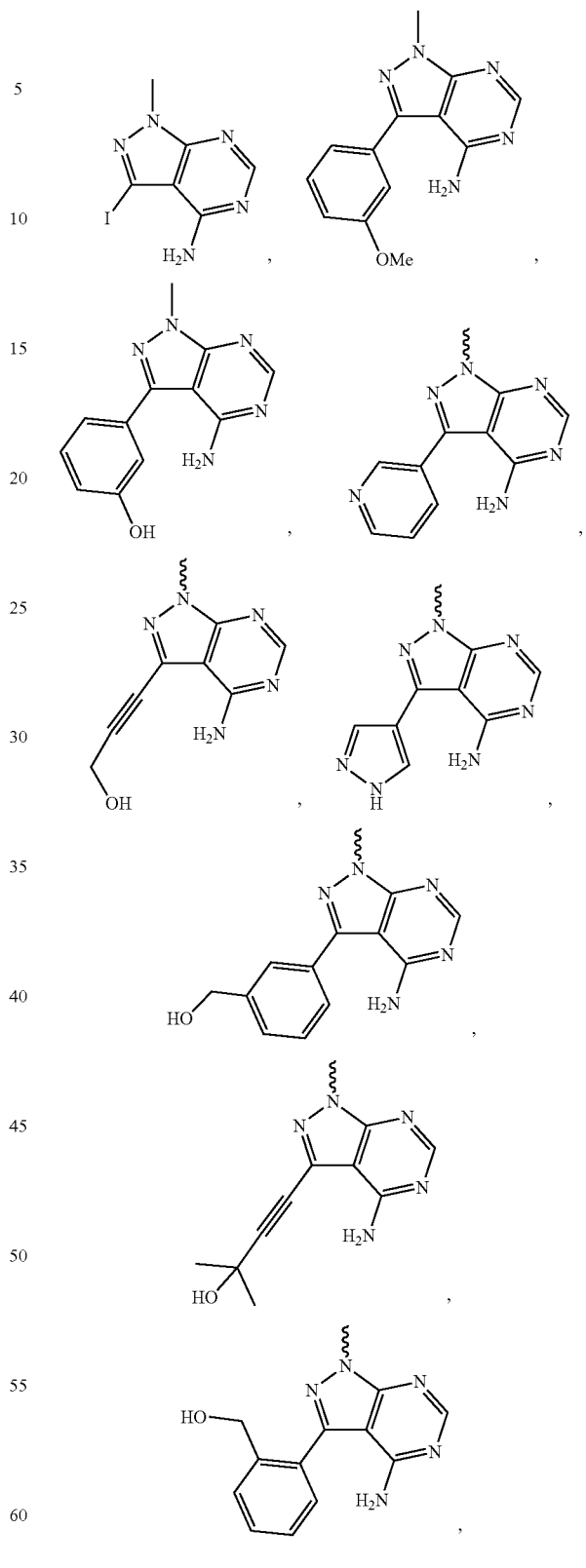

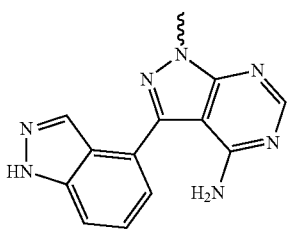
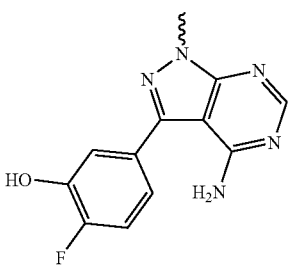
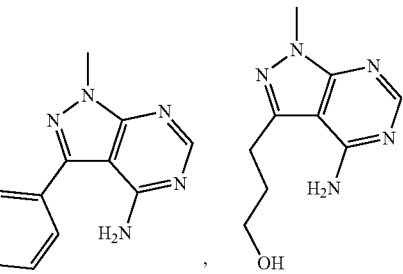
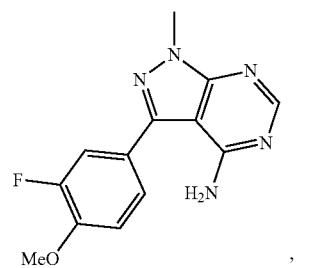
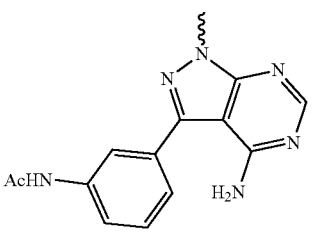
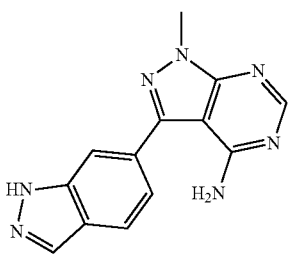
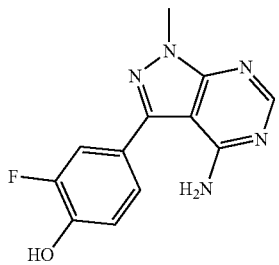
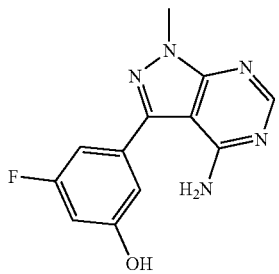
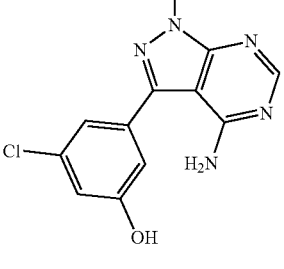
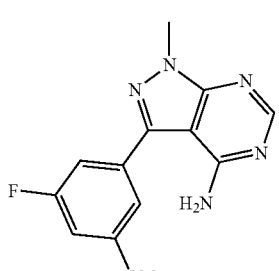
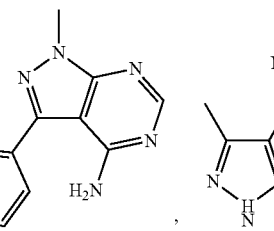
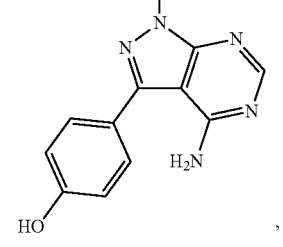

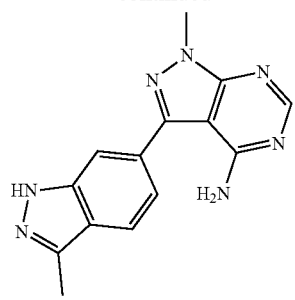,
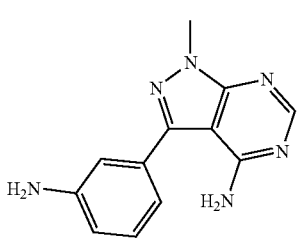,
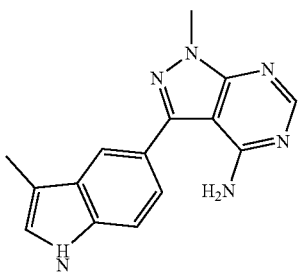,
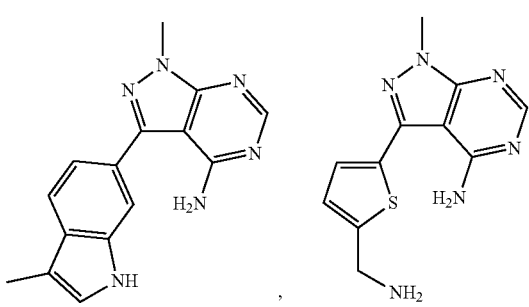,
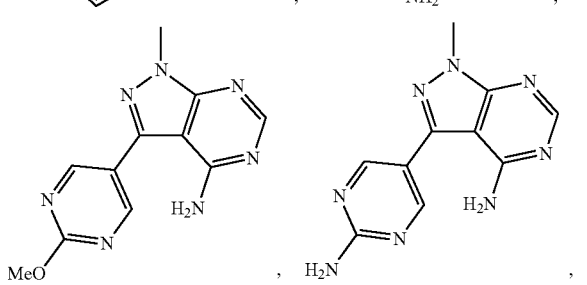,
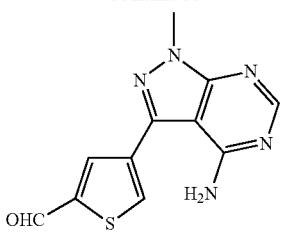,
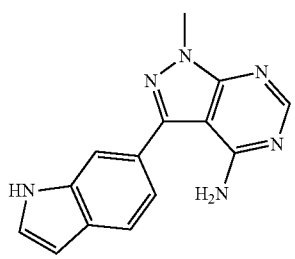,
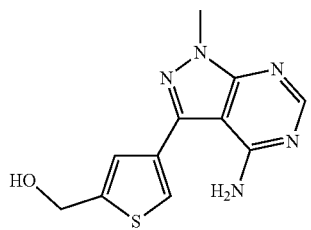,
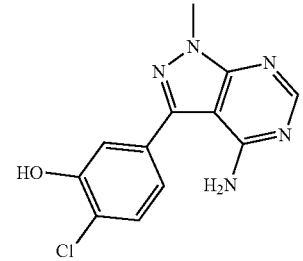,
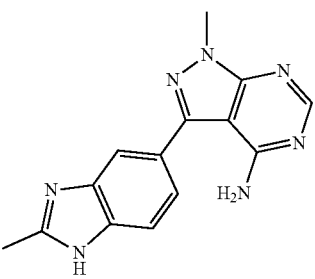,
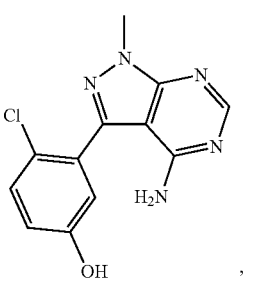, -continued
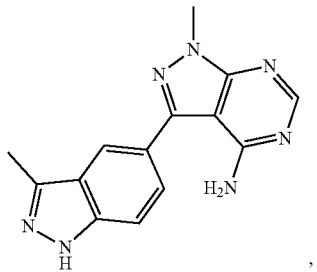
,
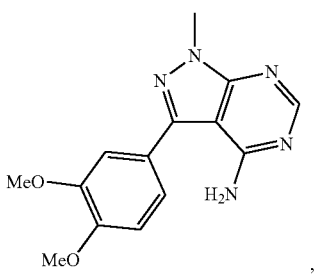
,
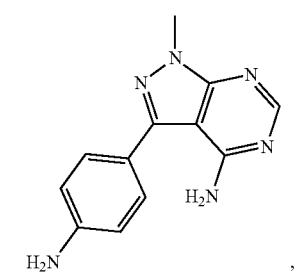
,
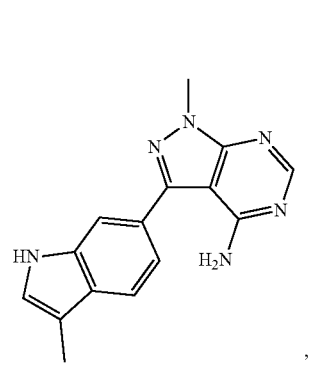
,
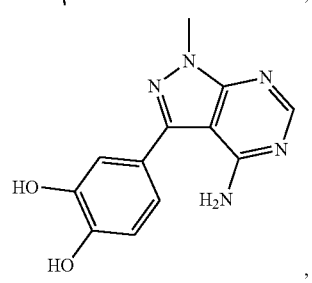
,
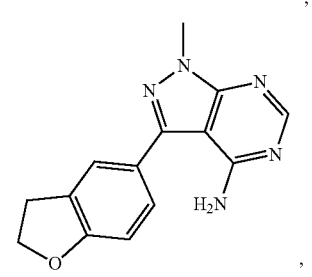
,
-continued
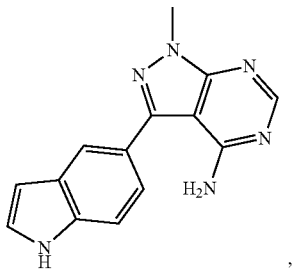
,
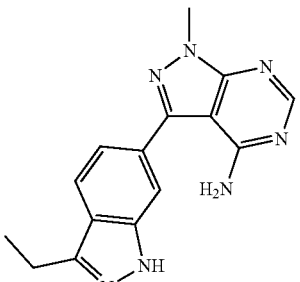
,
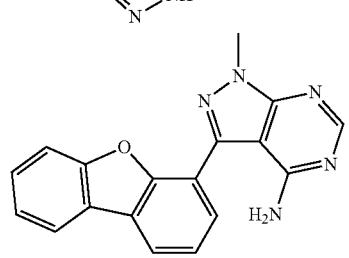
,
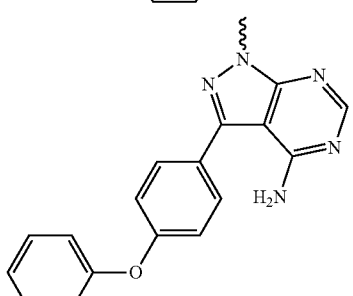
,
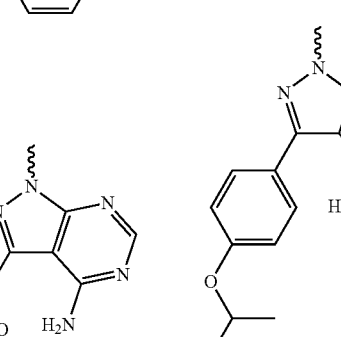
,
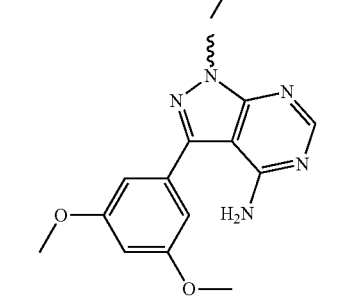

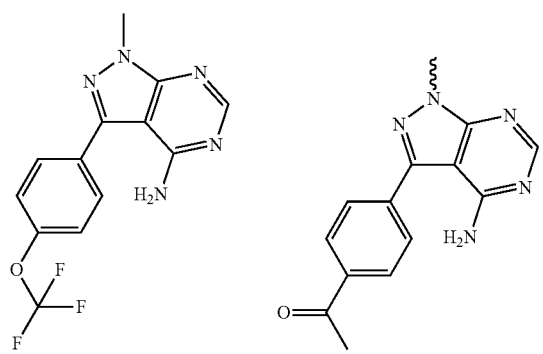
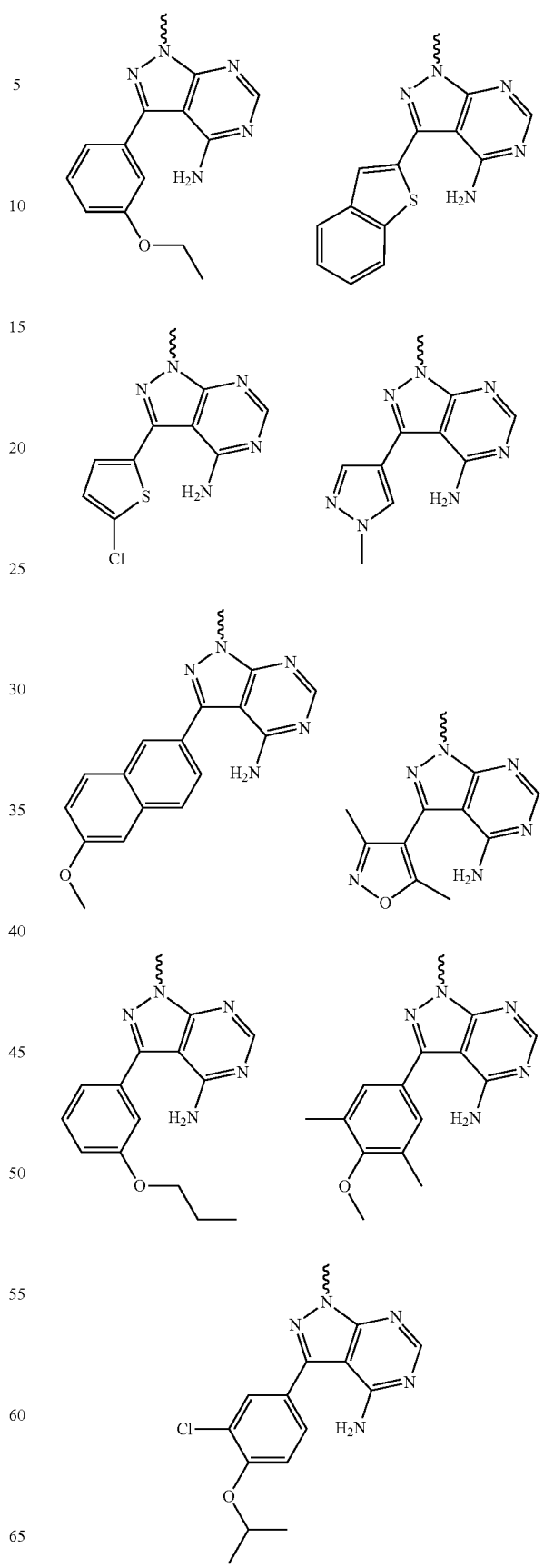

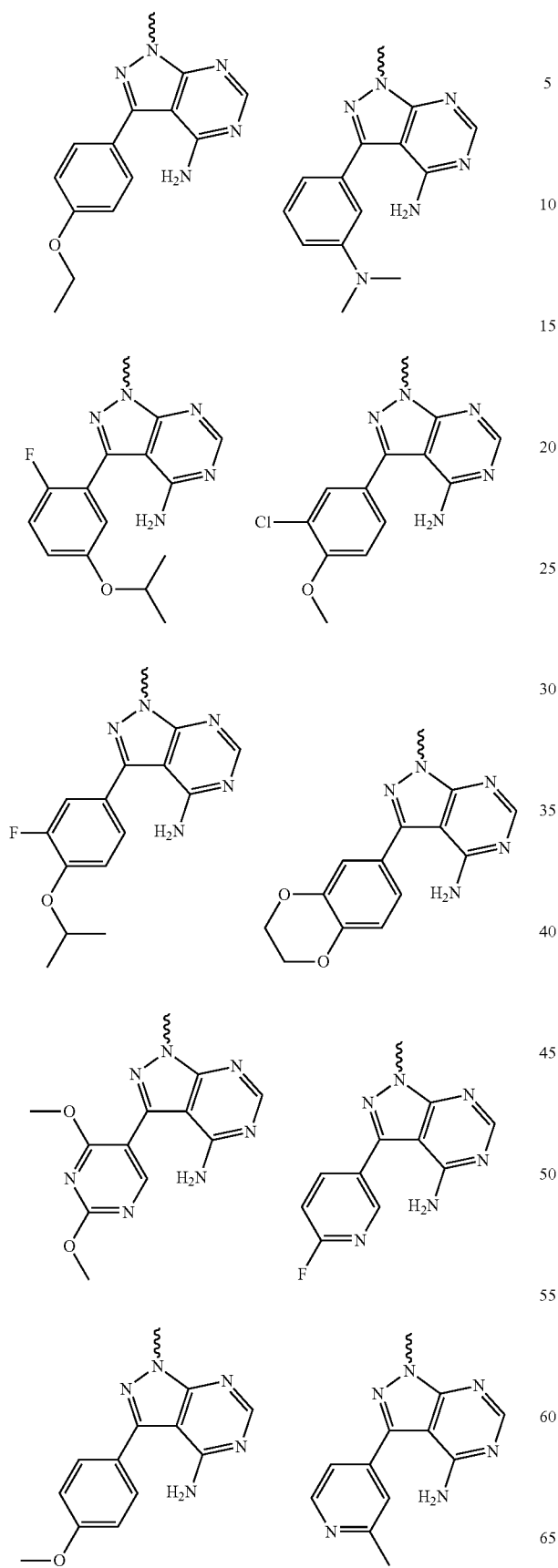

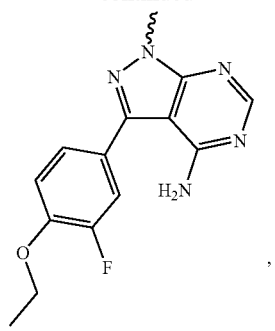
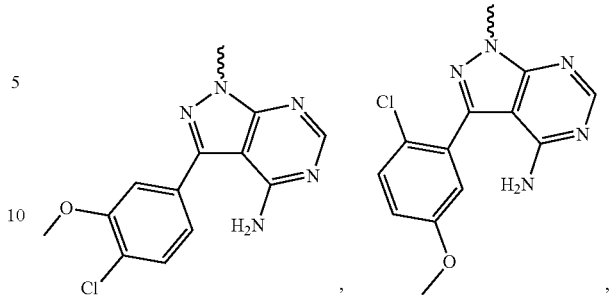
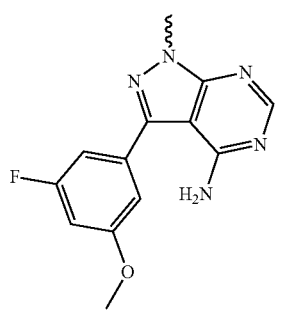
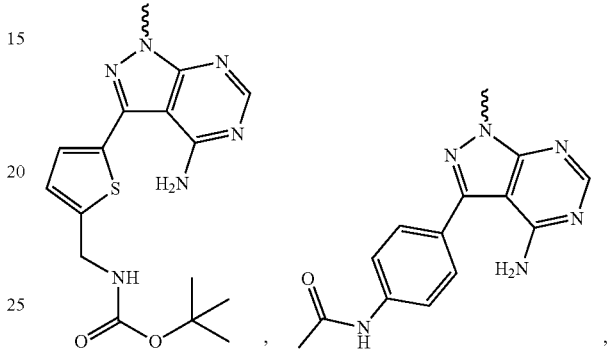
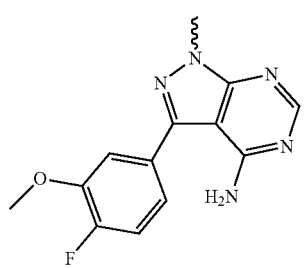
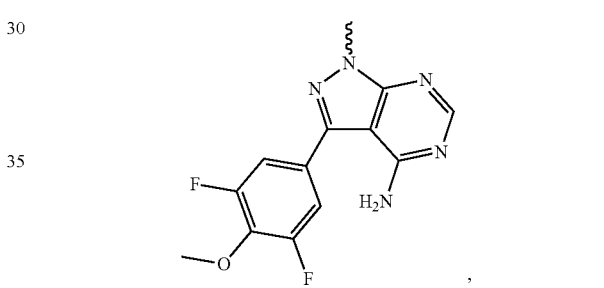
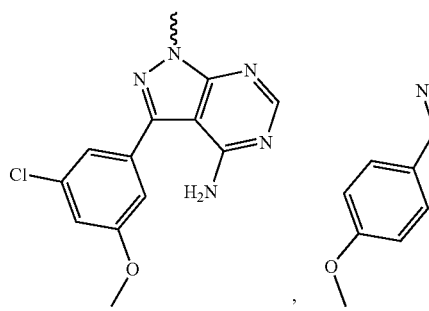
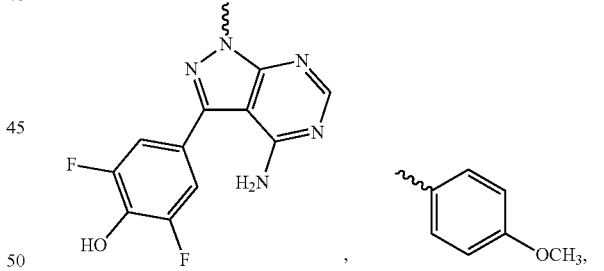
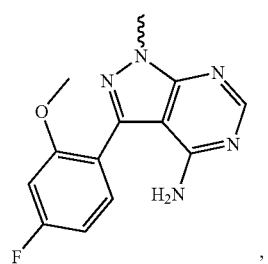
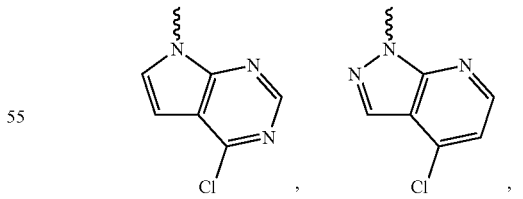
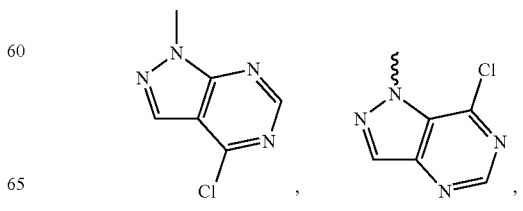

33
-continued
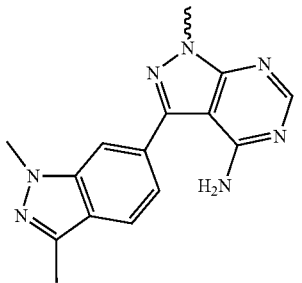
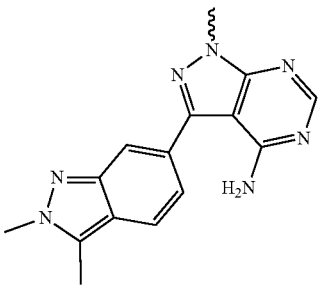
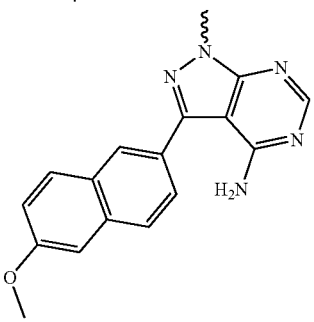
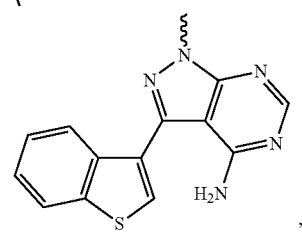
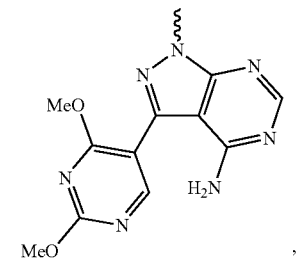
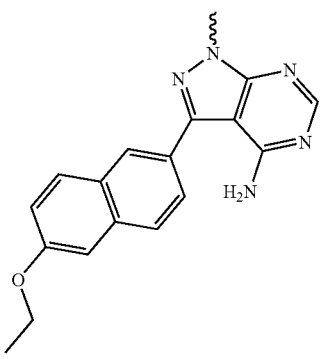
34
-continued
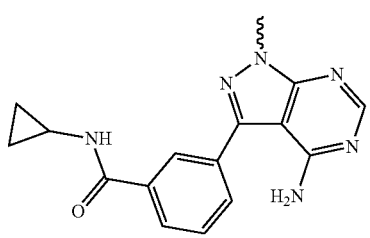
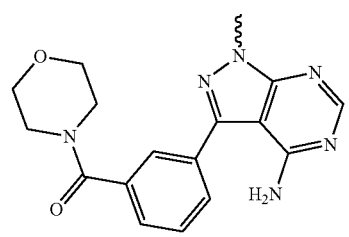
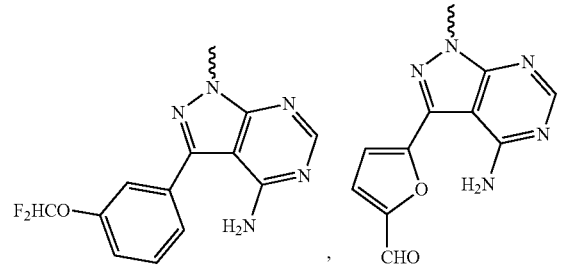
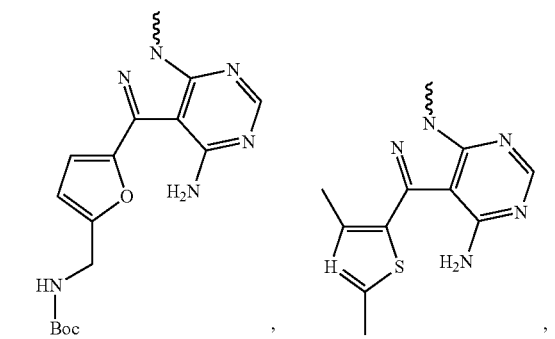
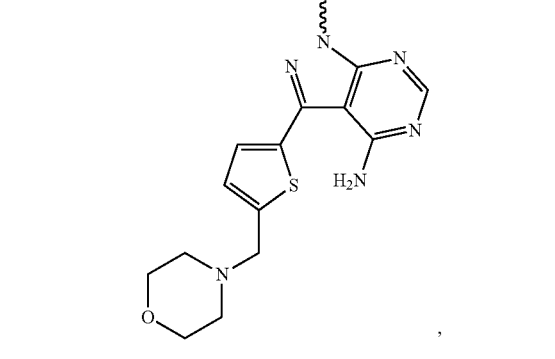

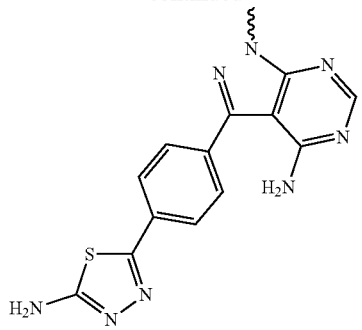,
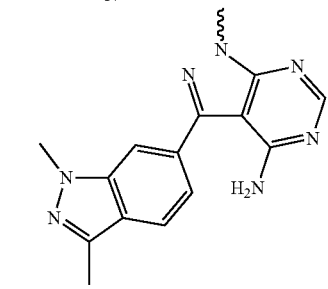,
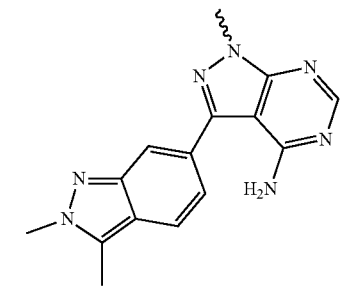,
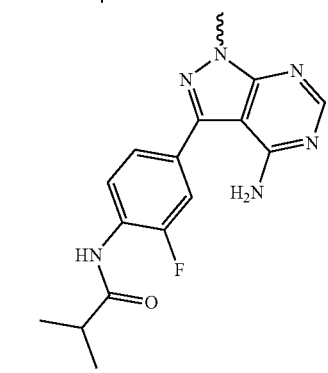,
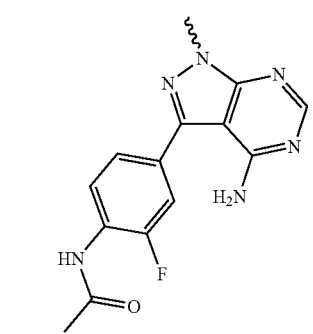,
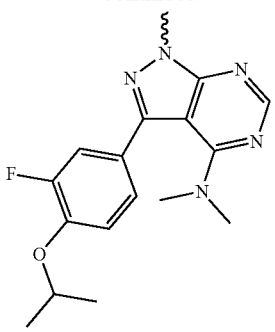,
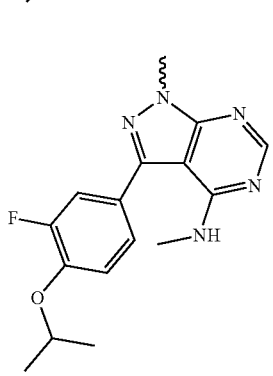,
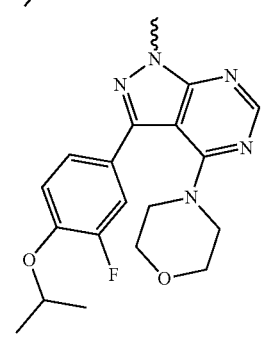,
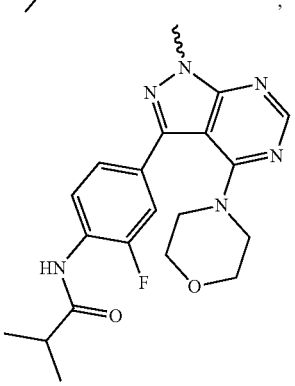,
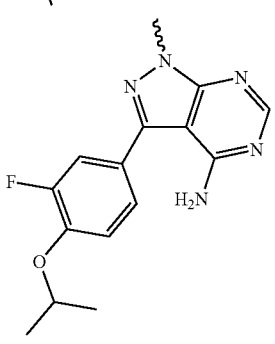,

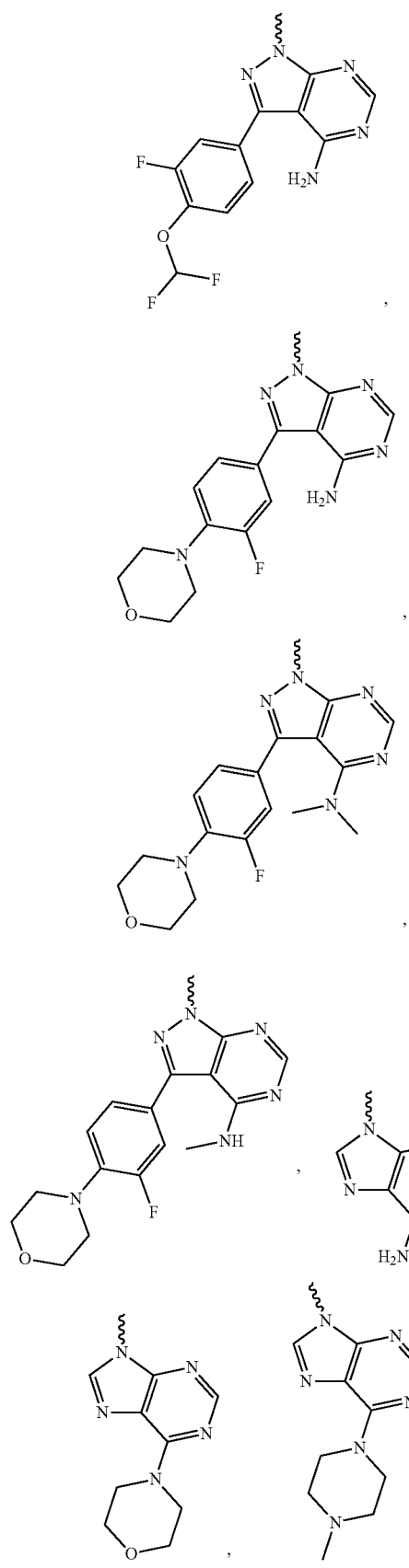
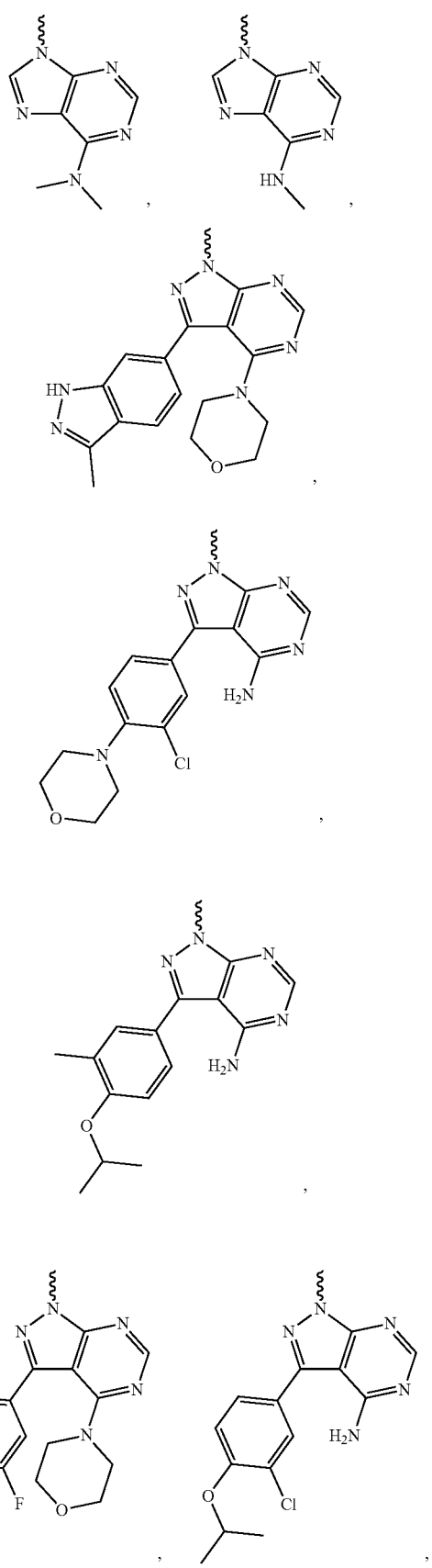

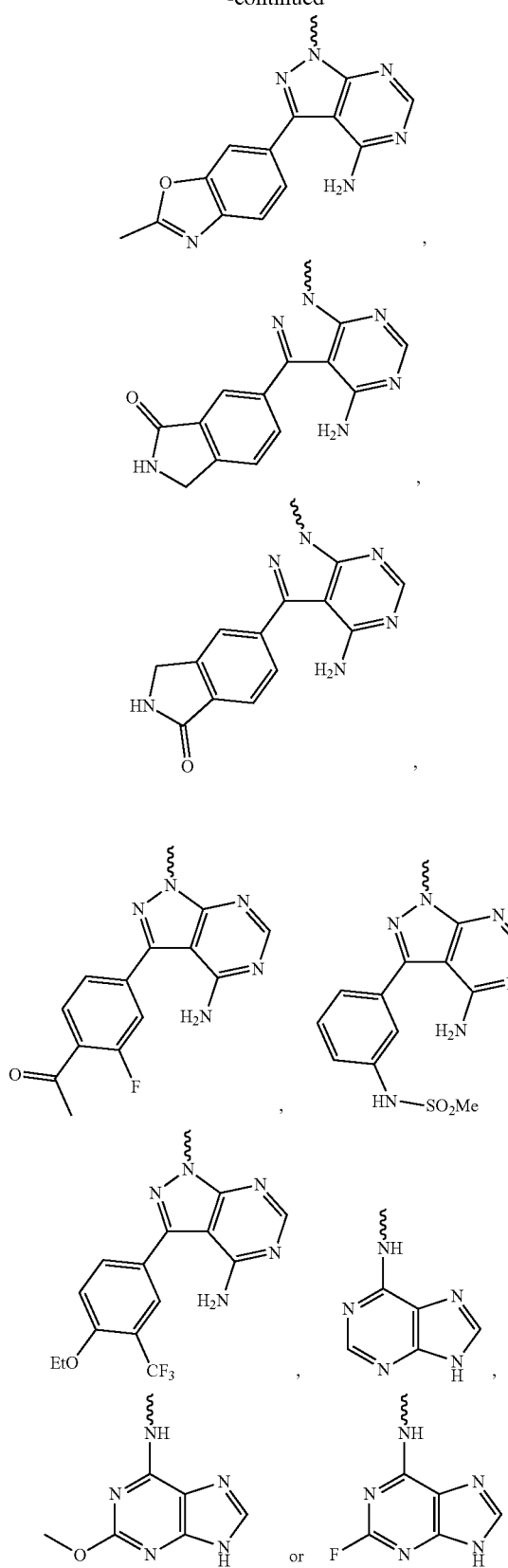
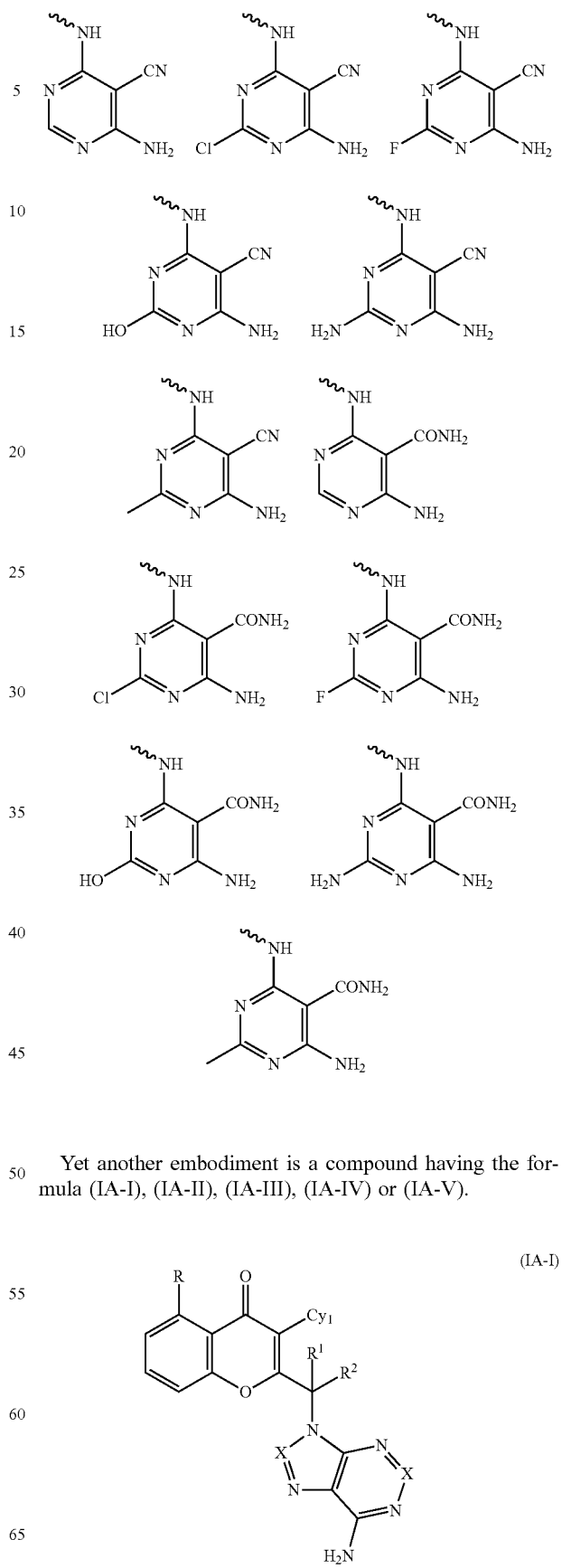
Yet another embodiment is a compound having the formula (I) and (IA) wherein $L_1$-$Cy^2$ is selected from
Yet another embodiment is a compound having the formula (IA-I), (IA-II), (IA-III), (IA-IV) or (IA-V).
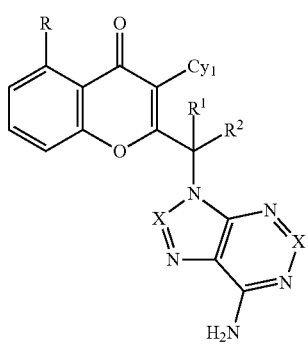

-continued

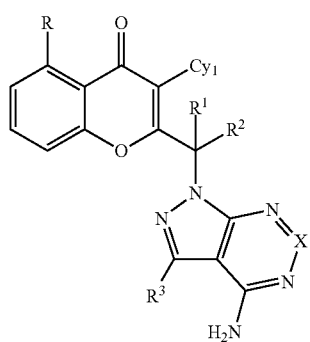

(IA-II)

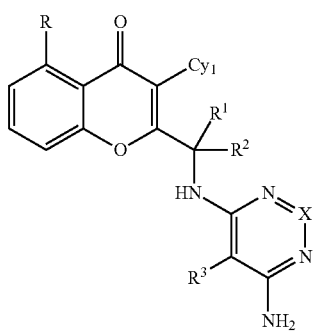

(IA-III)

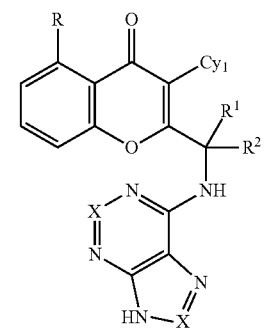

(IA-IV)

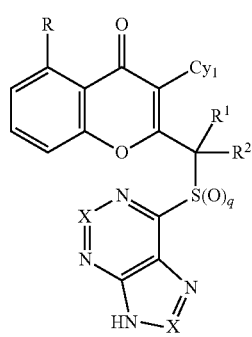

(IA-V)

or a tautomer thereof, N-oxide thereof, pharmaceutically acceptable ester thereof, prodrug thereof, or pharmaceutically acceptable salt thereof,
wherein:

R is selected from hydrogen, halogen, —OR$^a$, CN, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, and substituted or unsubstituted heterocyclic group;

$R^1$ and $R^2$ may be the same or different and are independently selected from hydrogen, halogen, and substituted or unsubstituted $C_{1-6}$ alkyl or both $R^1$ and $R^2$ directly bound to a common atom, may be joined to form an oxo group (═O) or may be joined to form a substituted or unsubstituted saturated or unsaturated 3-10 member ring (including the common atom to which $R^1$ and $R^2$ are directly bound), which may optionally include one or more heteroatoms which may be the same or different and are selected from O, NR$^a$ and S;

Cy$^1$ is a monocyclic group selected from substituted or unsubstituted cycloalkyl, substituted or unsubstituted heterocyclic group, substituted or unsubstituted aryl and substituted or unsubstituted heteroaryl;

each occurrence of X is independently selected from CR$^3$ or N;

each occurrence of R$^3$ is independently selected from hydrogen, hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted heterocyclic ring, or unsubstituted heterocyclyalkyl ring, substituted or unsubstituted aryl, substituted or unsubstituted arylalkyl, substituted or unsubstituted heteroaryl, substituted or unsubstituted heteroarylalkyl, substituted or unsubstituted guanidine, —COOR$^x$, —C(O)R$^x$, —C(S)R$^x$, —C(O)NR$^x$R$^y$, —C(O)ONR$^x$R$^y$, —NR$^y$R$^z$, —NR$^x$CONR$^y$R$^z$, —N(R$^x$)SOR$^y$, —N(R$^x$)SO$_2$R$^y$, —(═N—N(R$^x$)R$^y$), —NR$^x$C(O)OR$^y$, —NR$^x$R$^y$, —NR$^x$C(O)R$^y$—, —NR$^x$C(S)R$^y$—NR$^x$C(S)NR$^y$R$^z$, —SONR$^x$R$^y$—, —SO$_2$NR$^x$R$^y$—, —OR$^x$, —OR$^x$C(O)NR$^y$R$^z$, —OR$^x$C(O)OR$^y$—, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, or —ONO$_2$, wherein R$^x$, R$^y$ and R$^z$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted heteroaryl, substituted or unsubstituted heteroarylalkyl, substituted or unsubstituted cycloalkyl, substituted or unsubstituted cycloalkylalkyl, substituted or unsubstituted cycloalkenyl, substituted or unsubstituted heterocyclic ring, substituted heterocyclylalkyl ring, or substituted or unsubstituted amino, or any two of R$^x$, R$^y$ and R$^z$ may be joined to form a substituted or unsubstituted, saturated or unsaturated 3-10 membered ring, which may optionally include heteroatoms which may be the same or different and are selected from O, NR$^f$ (wherein R$^f$ is hydrogen or substituted or unsubstituted alkyl) or S; and q is 0, 1 or 2.

Yet another embodiment is a compound having the formula (IA-Ia), (IA-IIa), (IA-IIIa), (IA-Ib) or (IA-IIb).

(IA-Ia)

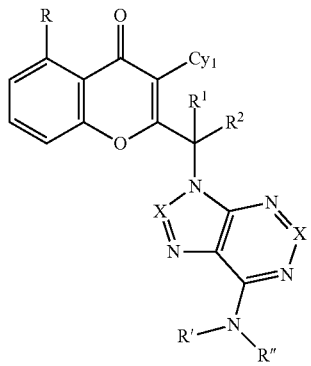

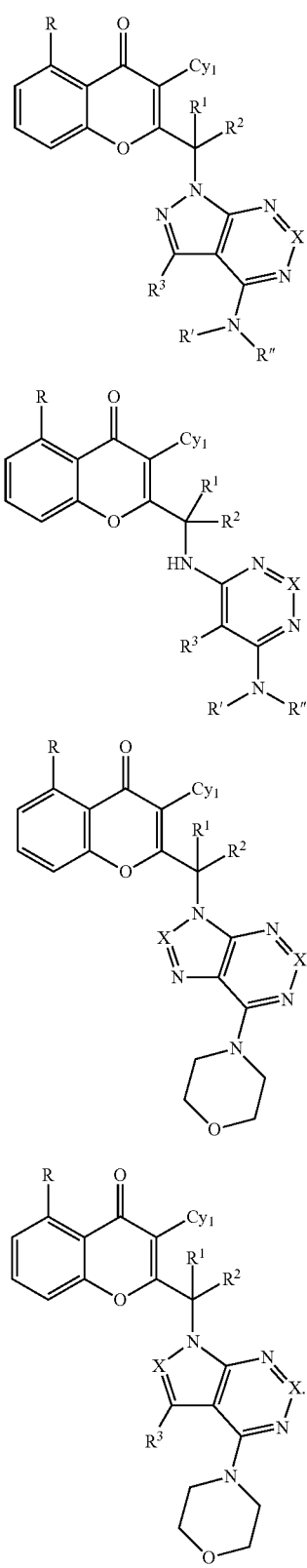

(IA-IIa)

(IA-IIIa)

(IA-Ib)

(IA-IIb)

wherein X, R³, R' and R" are the same as defined above.

Yet another embodiment is a compound having the formula (IA-I), (IA-II), (IA-III), (IA-IV), (IA-V), (IA-Ia), (IA-IIa), (IA-IIIa), (IA-Ib) or (IA-IIb) wherein R is selected from hydrogen, halogen, substituted or unsubstituted C$_{1-6}$ alkyl, OR$^a$ or morpholine.

Yet another embodiment is a compound having the formula (IA-I), (IA-II), (IA-III), (IA-IV), (IA-V), (IA-Ia), (IA-IIa), (IA-IIIa), (IA-Ib) or (IA-IIb) wherein R is selected from hydrogen, halogen, OR$^a$ or morpholine.

Yet another embodiment is a compound having the formula (IA-I), (IA-II), (IA-III), (IA-IV), (IA-V), (IA-Ia), (IA-IIa), (IA-IIIa), (IA-Ib) or (IA-IIb) wherein Cy¹ is selected from

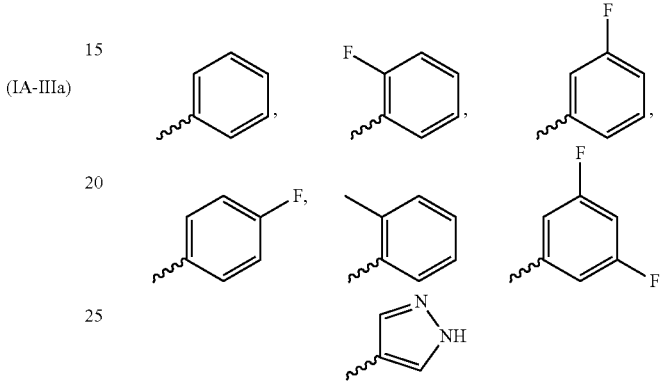

Yet another embodiment is a compound having the formula (IA-I), (IA-II), (IA-III), (IA-IV), (IA-V), (IA-Ia), (IA-IIa), (IA-IIIa), (IA-Ib) or (IA-IIb) wherein R¹ and R² independently represent hydrogen or substituted or unsubstituted C$_{1-6}$ alkyl Yet another embodiment is a compound having the formula (IA-II), (IA-III), (IA-IIa), (IA-IIIa) or (IA-IIb) wherein R³ is selected from iodo, cyano, substituted or unsubstituted alkynyl, substituted or unsubstituted aryl, and substituted or unsubstituted heteroaryl.

Yet another embodiment is a compound having the formula (IA-II), (IA-III), (IA-IIa), (IA-IIIa) or (IA-IIb) wherein R³ is selected from substituted or unsubstituted alkynyl, substituted or unsubstituted aryl, and substituted or unsubstituted heteroaryl Yet another embodiment is a compound having the formula (IA-II), (IA-III), (IA-IIa), (IA-IIIa) or (IA-IIb) wherein R³ is selected from

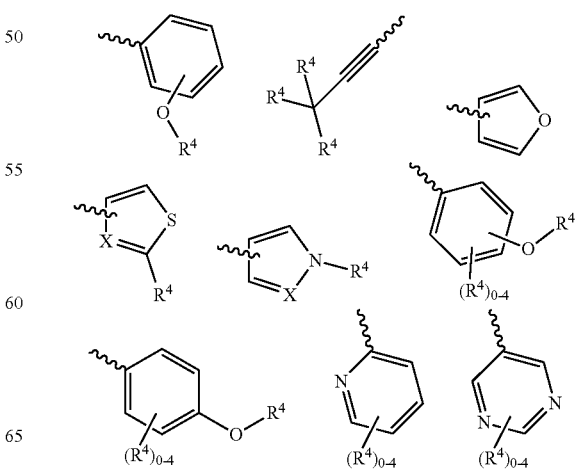

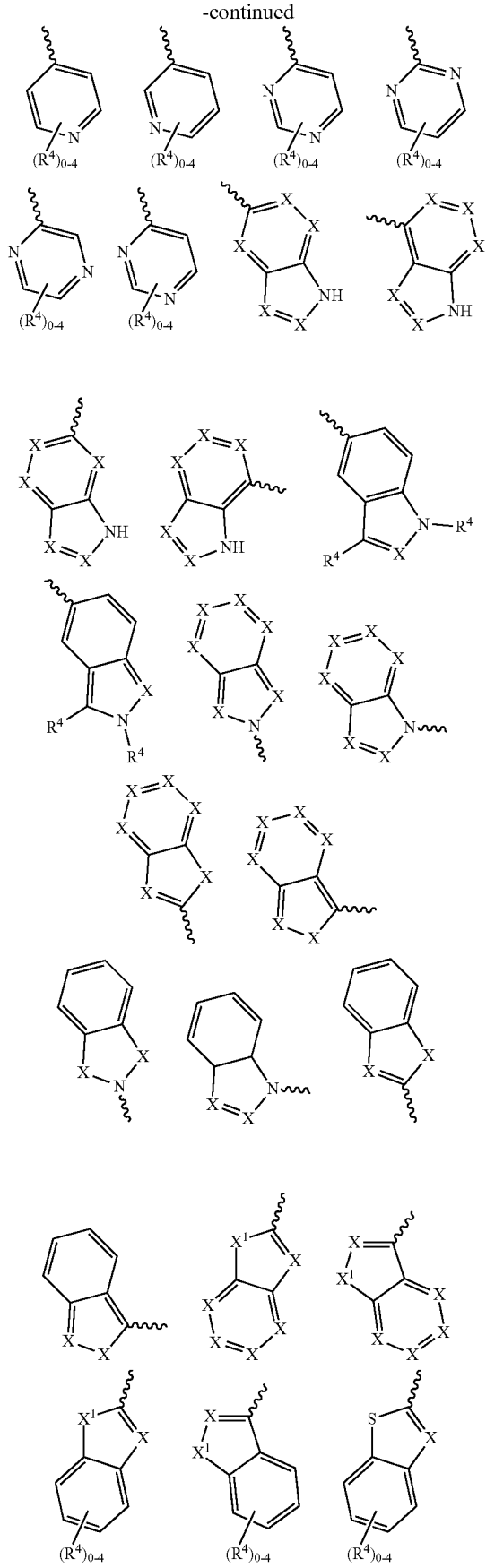
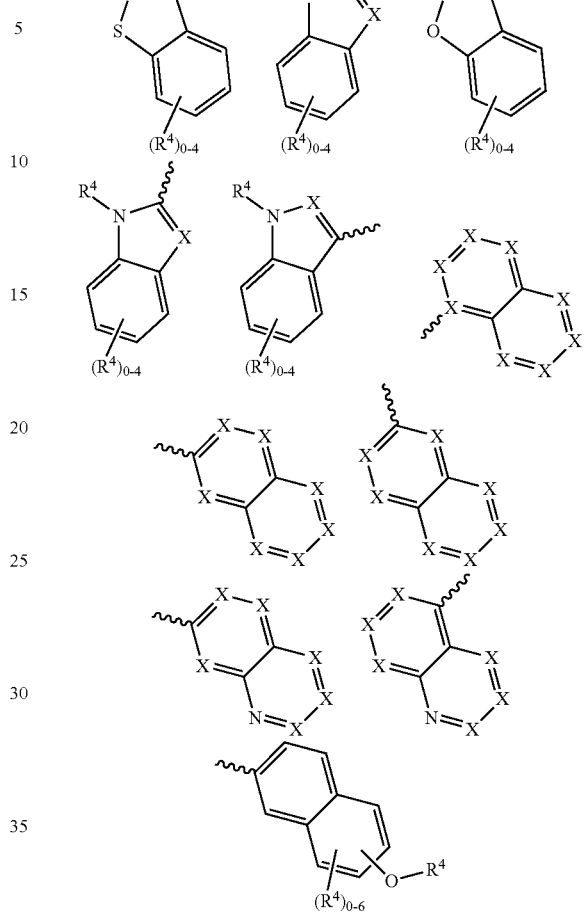

wherein
each occurrence of X is independently $CR^4$ or N;
$X^1$ is O, S, or $NR^4$; and
each occurrence of $R^4$ is independently selected from hydrogen, hydroxy, halogen, carboxyl, cyano, nitro, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted heterocyclic ring, or unsubstituted heterocyclyalkyl ring, substituted or unsubstituted aryl, substituted or unsubstituted arylalkyl, substituted or unsubstituted heteroaryl, substituted or unsubstituted heteroarylalkyl, substituted or unsubstituted guanidine, —COOR$^x$, —C(O)R$^x$, —C(S)R$^x$, —C(O)NR$^x$R$^y$, —C(O)ONR$^x$R$^y$, —NR$^y$R$^z$, —NR$^x$CONR$^y$R$^z$, —N(R$^x$)SOR$^y$, —N(R$^x$)SO$_2$R$^y$, —(=N—N(R$^x$)R$^y$), —NR$^x$C(O)OR$^y$, —NR$^x$R$^y$, —NR$^x$C(O)R$^y$—, —NR$^x$C(S)R$^y$—NR$^x$C(S)NR$^y$R$^z$, —SONR$^x$R$^y$—, —SO$_2$NR$^x$R$^y$—, —OR$^x$, —OR$^x$C(O)NR$^y$R$^z$, —OR$^x$C(O)OR$^y$—, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^x$, —R$^x$OC(O)R$^y$, —SR$^x$—, —SOR$^x$, —SO$_2$R$^x$, or —ONO$_2$, wherein R$^x$, R$^y$ and R$^z$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted heteroaryl, substituted or unsubstituted heteroarylalkyl, substituted or unsubstituted cycloalkyl, substituted or unsubstituted cycloalkylalkyl, substituted or unsubstituted cycloalkenyl, substituted or unsubstituted heterocyclic ring, substituted heterocyclylalkyl ring, or substituted or unsubstituted amino, or any two of $R^x$, $R^y$ and $R^z$ may be joined to form a substituted or unsubstituted, saturated or unsaturated 3-10 membered ring, which may optionally include heteroatoms which may be the same or different and are selected from O, $NR^f$ (wherein $R^f$ is hydrogen or substituted or unsubstituted alkyl) or S;

For example, $R^3$ can be any one of the following:

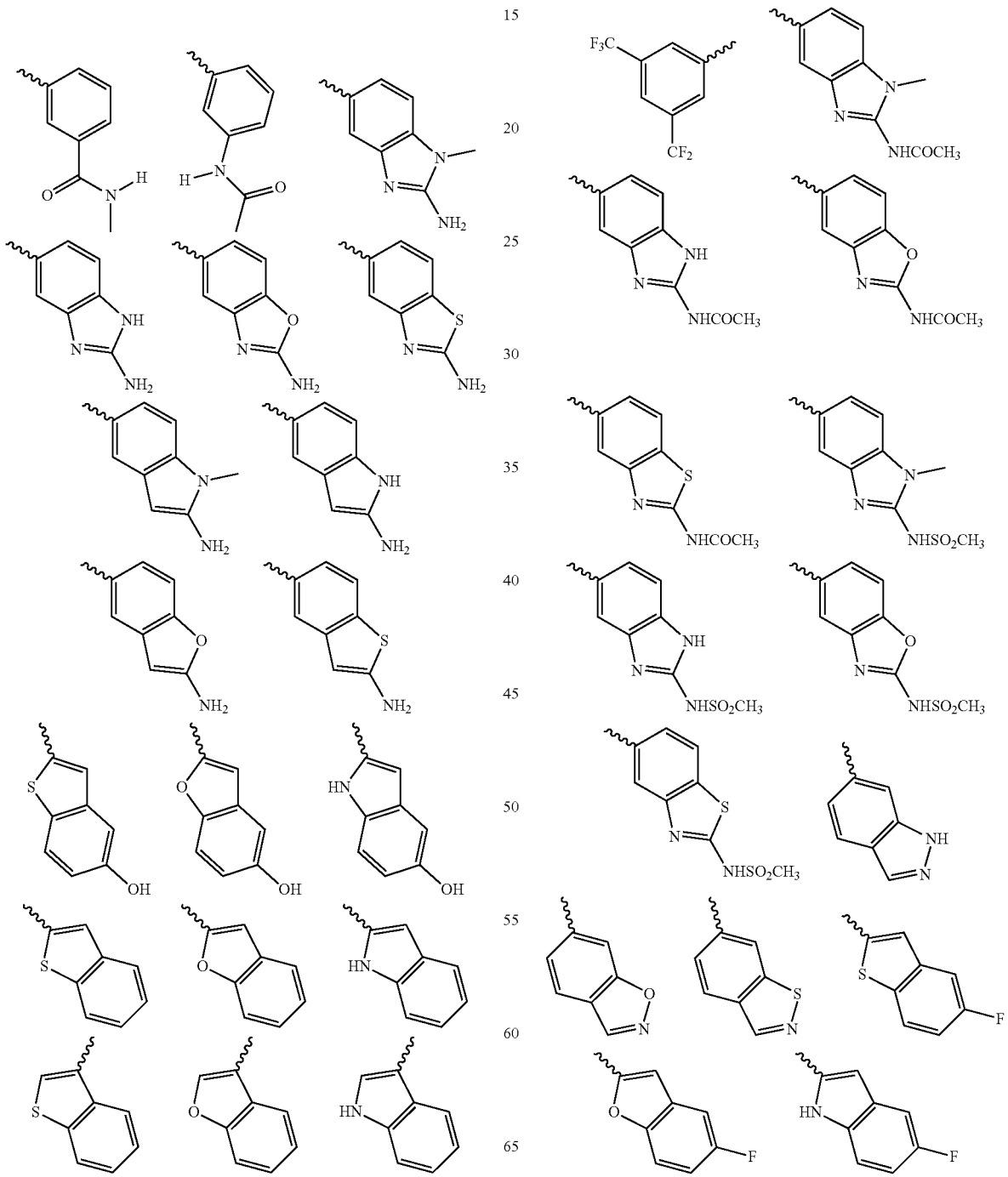

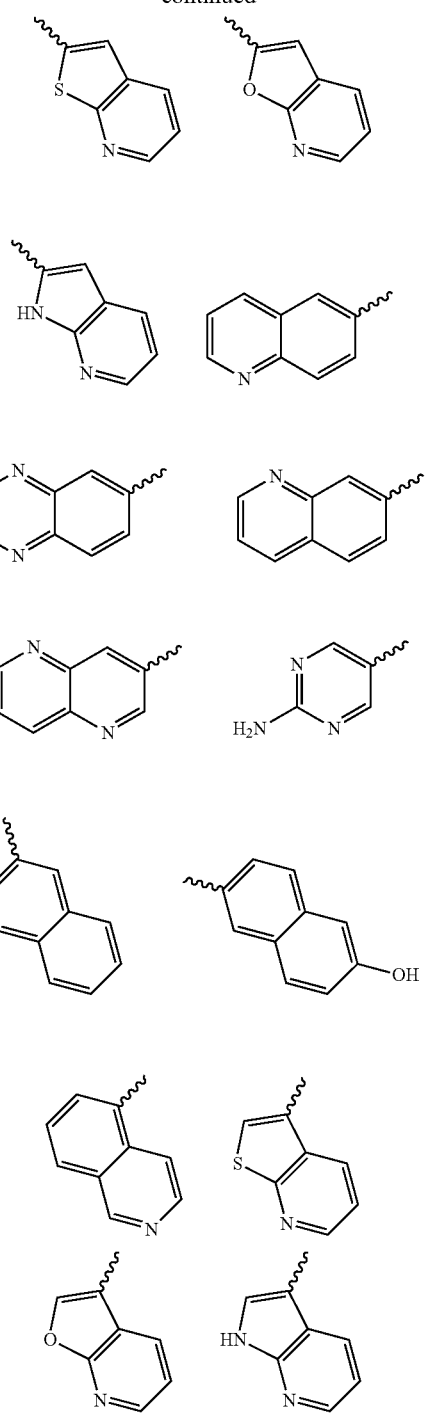

Yet another embodiment is a compound having the formula (IA-III) or (IA-IIIa) wherein $R^3$ is selected from iodo, cyano and substituted or unsubstituted alkynyl.

Yet another embodiment is a compound having the formula (IA-I), (IA-II), (IA-III), (IA-IV), (IA-V), (IA-Ia), (IA-IIa), (IA-IIIa), (IA-Ib) or (IA-IIb) wherein X is $CR^3$ and each occurrence of $R^3$ is independently hydrogen, halogen, hydroxyl or $NH_2$.

Yet another embodiment is a compound of formula (IA-VI)

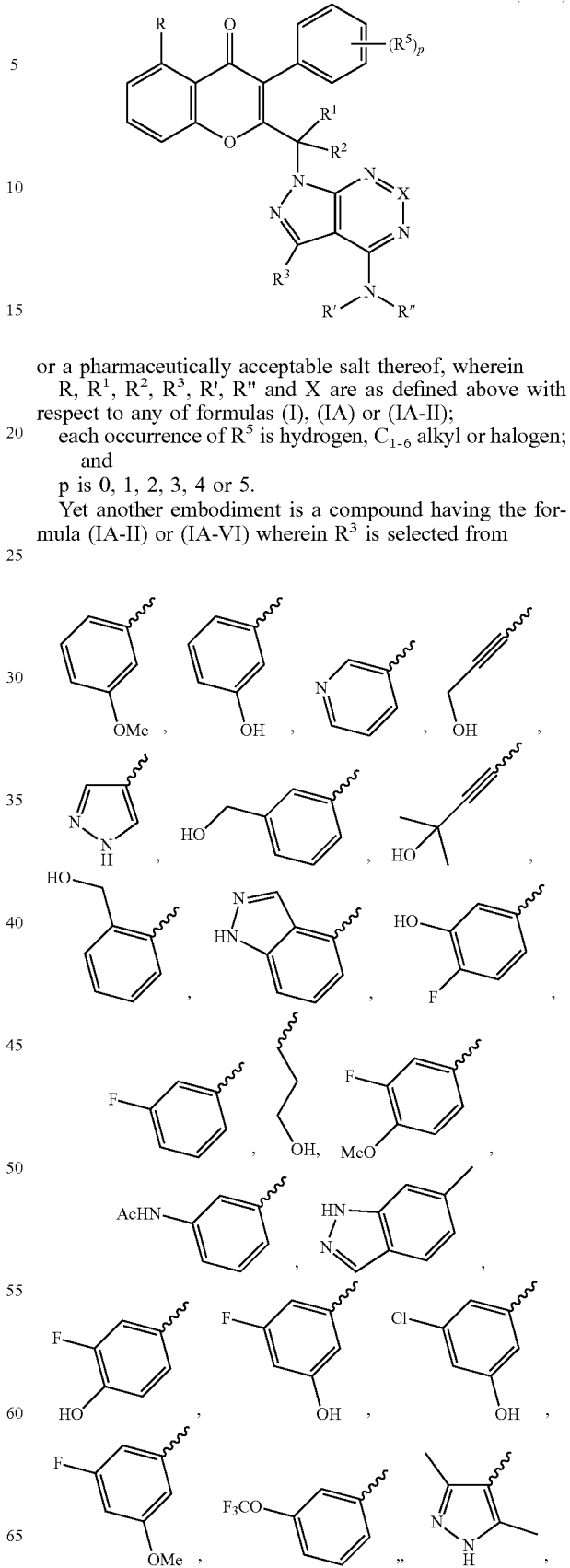

or a pharmaceutically acceptable salt thereof, wherein
$R$, $R^1$, $R^2$, $R^3$, $R'$, $R''$ and X are as defined above with respect to any of formulas (I), (IA) or (IA-II);
each occurrence of $R^5$ is hydrogen, $C_{1-6}$ alkyl or halogen; and
p is 0, 1, 2, 3, 4 or 5.

Yet another embodiment is a compound having the formula (IA-II) or (IA-VI) wherein $R^3$ is selected from

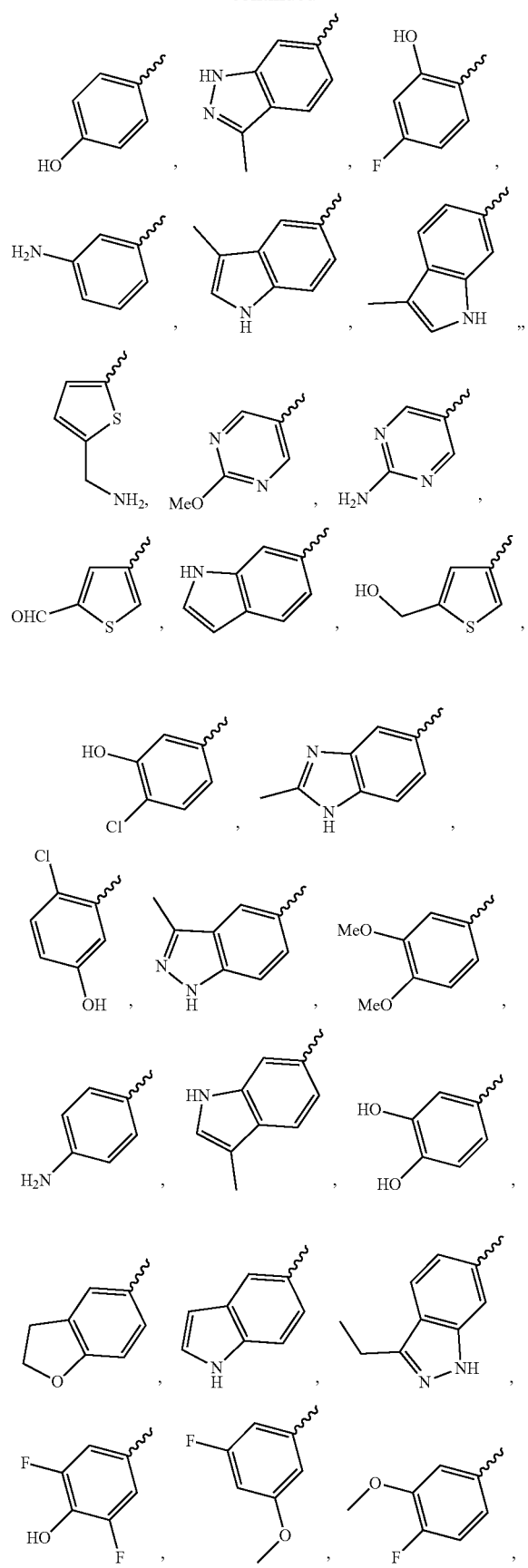
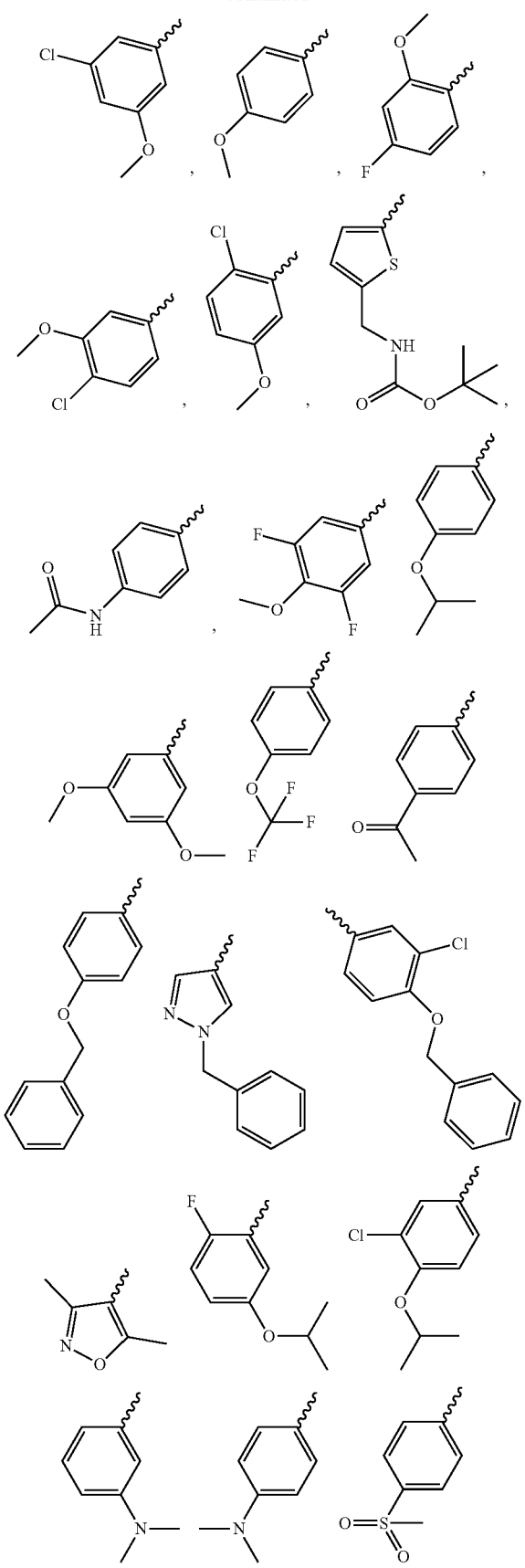

-continued
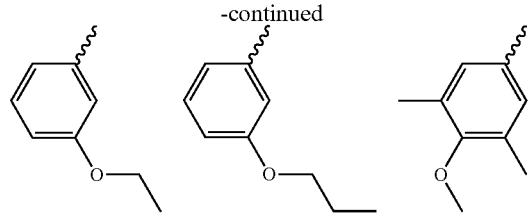
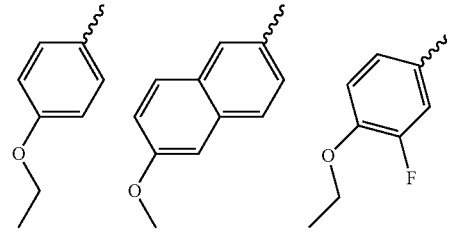
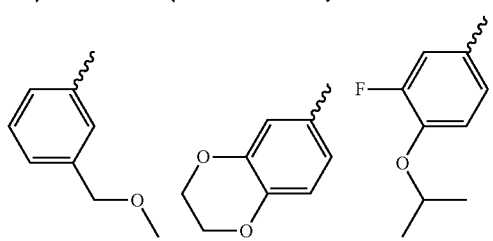
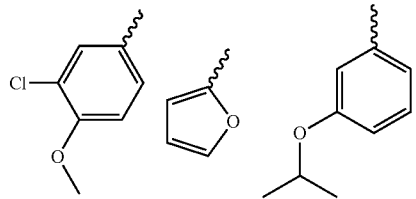
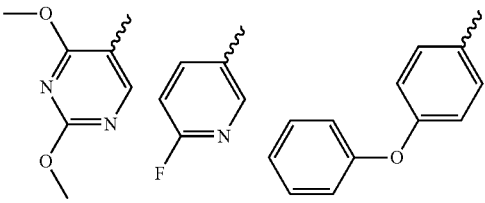
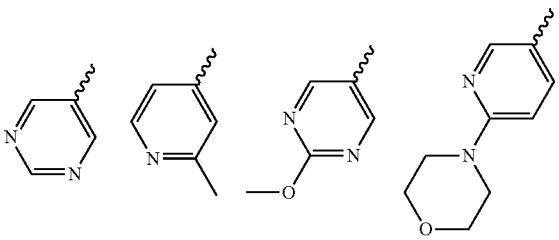
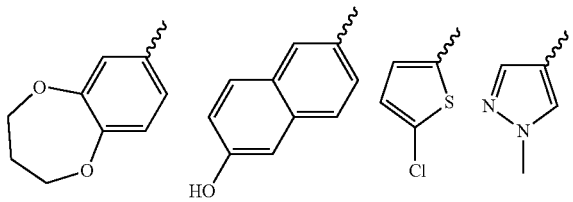
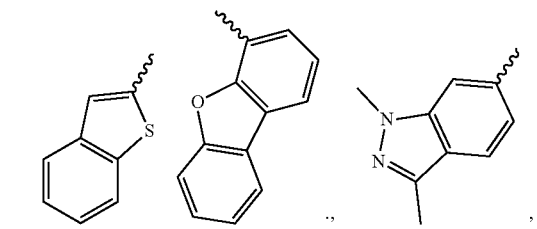
-continued
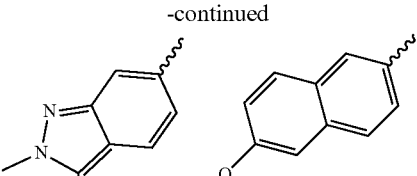
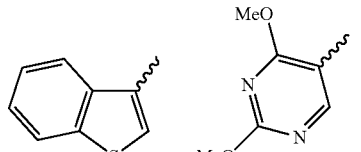
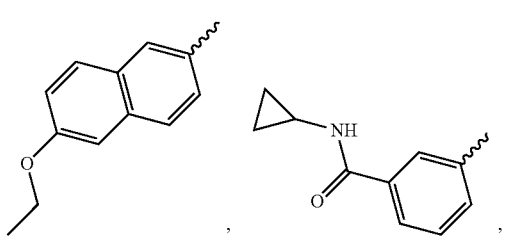
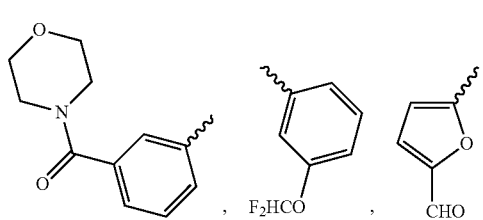
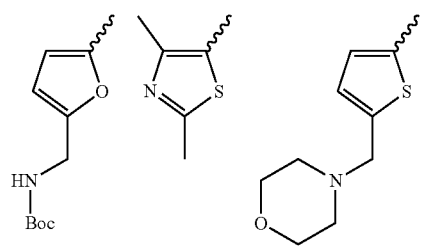
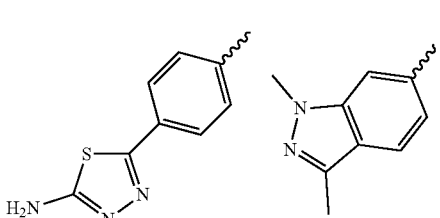
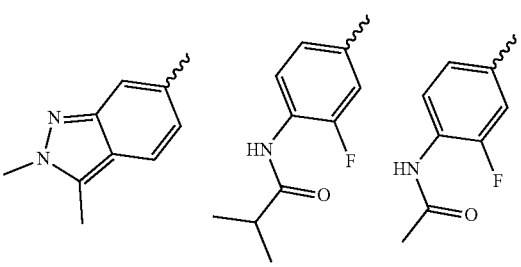

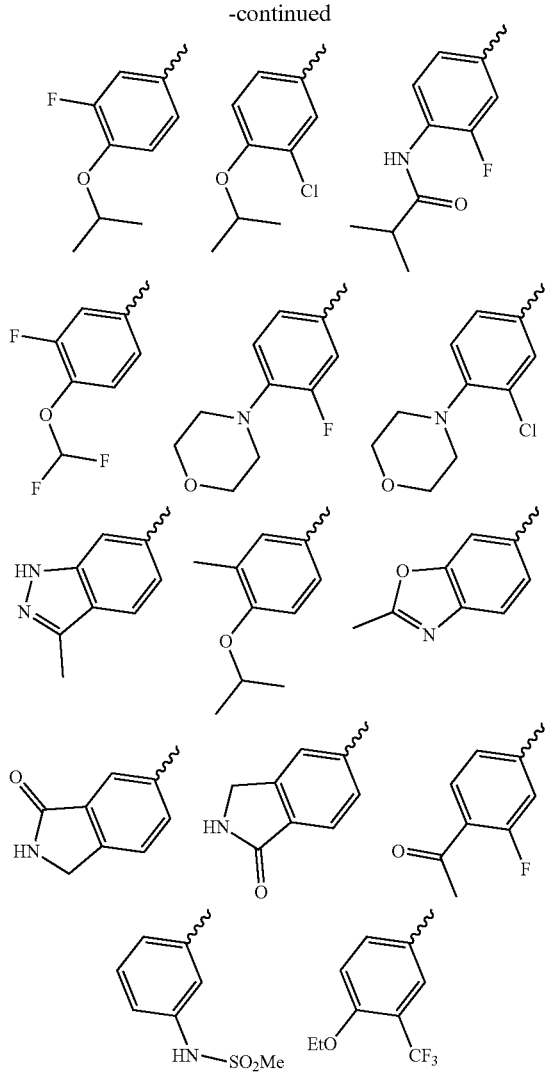

Yet another embodiment is a compound having the formula (IA-VII)

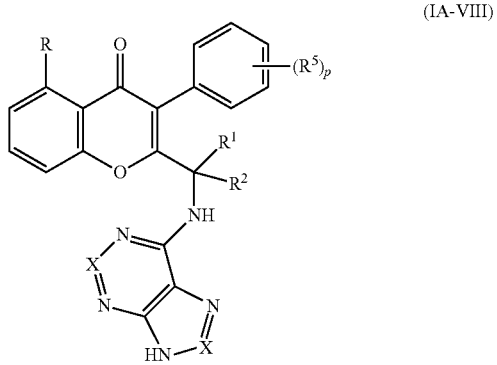

or a pharmaceutically acceptable salt thereof, wherein
R, R¹, R², R³ and X are as defined above with respect to any of formulas (I), (IA) or (IA-III);
each occurrence of R⁵ is hydrogen, $C_{1-6}$ alkyl or halogen; and
p is 0, 1, 2, 3, 4 or 5.

Yet another embodiment is a compound having the formula (IA-VII) wherein R³ is halogen or cyano.

Yet another embodiment is a compound of formula (IA-VIII)

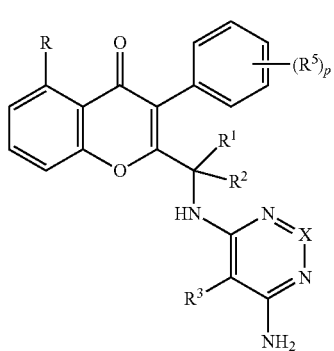

(IA-VIII)

or a pharmaceutically acceptable salt thereof, wherein
R, R¹, R² and X are as defined above with respect to any of formulas are as defined above with respect to any of formulas (I), (IA) or (IA-IV);
each occurrence of R⁵ is hydrogen, $C_{1-6}$ alkyl or halogen; and
p is 0, 1, 2, 3, 4 or 5.

Yet another embodiment is a compound having the formula (IA-VI), (IA-VII) or (IA-VIII) wherein R is halogen (such as fluoro) or $C_{1-6}$ alkyl (such as methyl).

Yet another embodiment is a compound having the formula (IA-VI), (IA-VII) or (IA-VIII) wherein p is 0.

Yet another embodiment is a compound having the formula (IA-VI), (IA-VII) or (IA-VIII) wherein p is 1 and R⁵ is 3-fluoro, 2-fluoro, 4-fluoro or 2-methyl.

Yet another embodiment is a compound having the formula (IA-VI), (IA-VII) or (IA-VIII) wherein R¹ is methyl and R² is hydrogen.

Yet another embodiment is a compound having the formula (IA-VI), (IA-VII) or (IA-VIII) wherein R¹ is ethyl and R² is hydrogen.

Yet another embodiment is a compound having the formula (IA-VI), (IA-VII) or (IA-VIII) wherein R¹ and R² are hydrogen.

Yet another embodiment is a compound having the formula (IA-VI), (IA-VII) or (IA-VIII) wherein X is C—H, C—F, C—Cl, C—NH₂ or C—OH.

Further preferred is a compound having the formula (IA-VI), (IA-VII) or (IA-VIII) wherein X is C—H.

Yet another embodiment is a compound having the formula (IA-VI) wherein each of R' and R" is selected from is hydrogen or $C_{1-6}$ alkyl (such as methyl).

Yet another embodiment is a compound having the formula (IA-VI) wherein —NR'R" together represents

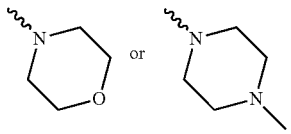

Representative compounds of the present invention include those specified below and pharmaceutically acceptable salts thereof. The present invention should not be construed to be limited to them.

1. 2-(6-Amino-9H-purin-9-yl) methyl)-3-(3-fluorophenyl)-5-methoxy-4H-chromen-4-one
2. 2-((4-Amino-3-(3-fluoro-4-isopropoxyphenyl)-1H-pyrazolo[3,4-d]pyrimidin-1-yl)methyl)-3-(3-fluorophenyl)-5-methoxy-4H-chromen-4-one
3. 2-((4-amino-3-(3-fluoro-4-isopropoxyphenyl)-1H-pyrazolo[3,4-d]pyrimidin-1-yl)methyl)-5-fluoro-3-(3-fluorophenyl)-4H-chromen-4-one
4. 2-((4-amino-3-(3-fluoro-5-methoxyphenyl)-1H-pyrazolo[3,4-d]pyrimidin-1-yl)methyl)-5-fluoro-3-(3-fluorophenyl)-4H-chromen-4-one
5. 2-((4-amino-3-(3-fluoro-5-hydroxyphenyl)-1H-pyrazolo[3,4-d]pyrimidin-1-yl)methyl)-5-fluoro-3-(3-fluorophenyl)-4H-chromen-4-one
6. 2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one
7. (+)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one
8. (−)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one
9. 2-(1-(4-amino-3-(3-methyl-1H-indazol-6-yl)-1H-pyrazolo[3,4-d]pyrimidin-1-yl)ethyl)-5-fluoro-3-(3-fluorophenyl)-4H-chromen-4-one
9a. (+)-2-(1-(4-amino-3-(3-methyl-1H-indazol-6-yl)-1H-pyrazolo[3,4-d]pyrimidin-1-yl)ethyl)-5-fluoro-3-(3-fluorophenyl)-4H-chromen-4-one
9b. (−)-2-(1-(4-amino-3-(3-methyl-1H-indazol-6-yl)-1H-pyrazolo[3,4-d]pyrimidin-1-yl)ethyl)-5-fluoro-3-(3-fluorophenyl)-4H-chromen-4-one
10. 2-(1-(4-amino-3-(1H-pyrazol-4-yl)-1H-pyrazolo[3,4-d]pyrimidin-1-yl)ethyl)-5-fluoro-3-(3-fluorophenyl)-4H-chromen-4-one
11. 2-(1-(6-amino-9H-purin-9-yl)ethyl)-5-fluoro-3-(3-fluorophenyl)-4H-chromen-4-one
12. 2-(1-(4-amino-3-(3-fluoro-4-isopropoxyphenyl)-1H-pyrazolo[3,4-d]pyrimidin-1-yl)ethyl)-5-fluoro-3-(4-fluorophenyl)-4H-chromen-4-one
13. 2-(1-(4-amino-3-(3-fluoro-4-isopropoxyphenyl)-1H-pyrazolo[3,4-d]pyrimidin-1-yl)ethyl)-5-fluoro-3-phenyl-4H-chromen-4-one
14. 2-(1-(4-amino-3-(benzofuran-2-yl)-1H-pyrazolo[3,4-d]pyrimidin-1-yl)ethyl)-5-fluoro-3-(3-fluorophenyl)-4H-chromen-4-one
15. 2-(1-(9H-purin-6-ylamino)ethyl)-5-fluoro-3-(3-fluorophenyl)-1H-chromen-one
16. 2-(1-(4-amino-1H-pyrazolo[3,4-d]pyrimidin-1-yl)ethyl)-5-fluoro-3-(3-fluorophenyl)-4H-chromen-4-one
16a. (+)-2-(1-(4-amino-1H-pyrazolo[3,4-d]pyrimidin-1-yl)ethyl)-5-fluoro-3-(3-fluorophenyl)-4H-chromen-4-one
16b. (−)-2-(1-(4-amino-1H-pyrazolo[3,4-d]pyrimidin-1-yl)ethyl)-5-fluoro-3-(3-fluorophenyl)-4H-chromen-4-one
17. 2-(1-(4-amino-3-(4-(difluoromethoxy)-3-fluorophenyl)-1H-pyrazolo[3,4-d]pyrimidin-1-yl)ethyl)-5-fluoro-3-(3-fluorophenyl)-4H-chromen-4-one
18. 2-(1-(4-amino-3-(3-fluoro-4-isopropoxyphenyl)-1H-pyrazolo[3,4-d]pyrimidin-1-yl)ethyl)-5-fluoro-3-(1H-pyrazol-4-yl)-4H-chromen-4-one
19. 2-(1-(4-amino-3-(3-fluoro-(tetrahydro-2H-pyran-4-yloxy)phenyl)-1H-pyrazolo[3,4-d]pyrimidin-1-yl)ethyl)-5-fluoro-3-(3-fluorophenyl)-4H-chromen-4-one
20. 2-(1-(4-amino-3-(3-isopropyl-1H-indazol-6-yl)-1H-pyrazolo[3,4-d]pyrimidin-1-yl)ethyl)-5-fluoro-3-(3-fluorophenyl)-4H-chromen-4-one
21. 2-(1-(4-amino-3-(3-fluoro-4-(piperidin-4-yloxy)phenyl)-1H-pyrazolo[3,4-d]pyrimidin-1-yl)ethyl)-5-fluoro-3-(3-fluorophenyl)-4H-chromen-4-one
22. 2-(1-(4-amino-3-(3-fluoro-4-(2-hydroxyethylamino)phenyl)-1H-pyrazolo[3,4-d]pyrimidin-1-yl)ethyl)-5-fluoro-3-(3-fluorophenyl)-4H-chromen-4-one
23. 2-(1-(4-amino-3-(3-fluoro-4-(isopropylamino)phenyl)-1H-pyrazolo[3,4-d]pyrimidin-1-yl)ethyl)-5-fluoro-3-(3-fluorophenyl)-4H-chromen-4-one
24. 2-(1-(4-amino-3-(4-(dimethylamino)-3-fluorophenyl)-1H-pyrazolo[3,4-d]pyrimidin-1-yl)ethyl)-5-fluoro-3-(3-fluorophenyl)-4H-chromen-4-one
25. 2-(1-(4-amino-3-(3-fluoro-4-morpholinophenyl)-1H-pyrazolo[3,4-d]pyrimidin-1-yl)ethyl)-5-fluoro-3-(3-fluorophenyl)-4H-chromen-4-one
26. 2-(1-(4-amino-3-(2-methyl-1H-benzo[d]imidazol-5-yl)-1H-pyrazolo[3,4-d]pyrimidin-1-yl)ethyl)-1-fluoro-3-(3-fluorophenyl)-4H-chromen-4-one
27. 2-(1-(4-amino-3-(3-fluoro-4-(4-methylpiperazin-1-yl)phenyl)-1H-pyrazolo[3,4-d]pyrimidin-1-yl)ethyl)-5-fluoro-3-(3-fluorophenyl)-4H-chromen-4-one
28. 2-(1-(4-(dimethylamino)-1H-pyrazolo[3,4-d]pyrimidin-1-yl)ethyl)-5-fluoro-3-(3-fluorophenyl)-4H-chromen-4-one
29. 2-(1-(4-amino-1H-pyrazolo[3,4-d]pyrimidin-1-yl)ethyl)-5-fluoro-3-phenyl-4H-chromen-4-one
30. 2-(1-(4-amino-1H-pyrazolo[3,4-d]pyrimidin-1-yl)ethyl)-5-fluoro-3-(4-fluorophenyl)-4H-chromen-4-one
31. 2-(1-(4-amino-3-(4-(difluoromethoxy)-3-fluorophenyl)-1H-pyrazolo[3,4-d]pyrimidin-1-yl)ethyl)-5-fluoro-3-(4-fluorophenyl)-4H-chromen-4-one
32. 2-(1-(4-amino-3-(4-(difluoromethoxy)-3-fluorophenyl)-1H-pyrazolo[3,4-d]pyrimidin-1-yl)ethyl)-5-fluoro-3-phenyl-4H-chromen-4-one
33. 2-(1-(4-amino-3-methyl-1H-pyrazolo[3,4-d]pyrimidin-1-yl)ethyl)-5-fluoro-3-(3-fluorophenyl)-4H-chromen-4-one
34. 2-(1-(4-amino-3-ethyl-1H-pyrazolo[3,4-d]pyrimidin-1-yl)ethyl)-5-fluoro-3-(3-fluorophenyl)-4H-chromen-4-one
35. 2-(1-(4-amino-3-isopropyl-1H-pyrazolo[3,4-d]pyrimidin-1-yl)ethyl)-5-fluoro-3-(3-fluorophenyl)-4H-chromen-4-one
36. 2-(1-(4-amino-3-(benzo[b]thiophen-2-yl)-1H-pyrazolo[3,4-d]pyrimidin-1-yl)ethyl)-5-fluoro-3-(3-fluorophenyl)-4H-chromen-4-one
37. 2-(1-(4-amino-3-morpholino-1H-pyrazolo[3,4-d]pyrimidin-1-yl)ethyl)-5-fluoro-3-(3-fluorophenyl)-4H-chromen-4-one
38. 2-(1-(4-amino-3-(dimethylamino)-1H-pyrazolo[3,4-d]pyrimidin-1-yl)ethyl)-5-fluoro-3-(3-fluorophenyl)-4H-chromen-4-one
39. 2-(1-(4-amino-3-(piperidin-1-yl)-1H-pyrazolo[3,4-d]pyrimidin-1-yl)ethyl)-5-fluoro-3-(3-fluorophenyl)-4H-chromen-4-one
40. 2-(1-(4-amino-3-(6-isopropoxypyridin-3-yl)-1H-pyrazolo[3,4-d]pyrimidin-1-yl)ethyl)-5-fluoro-3-(3-fluorophenyl)-4H-chromen-4-one
41. 2-(1-(4-amino-3-(methylthio)-1H-pyrazolo[3,4-d]pyrimidin-1-yl)ethyl)-5-fluoro-3-(3-fluorophenyl)-4H-chromen-4-one
42. 2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one 4-methylbenzenesulfonate 43. 2-(1-(4-amino-3-(3-methyl-1H-indazol-6-yl)-1H-pyrazolo[3,4-d]pyrimidin-1-yl)ethyl)-5-fluoro-3-(3-fluorophenyl)-4H-chromen-4-one 4-methylbenzenesulfonate
44. 2-(1-(4-amino-3-(4-(1-benzhydrylazetidin-3-yloxy)-3-fluorophenyl)-1H-pyrazolo[3,4-d]pyrimidin-1-yl)ethyl)-5-fluoro-3-(3-fluorophenyl)-4H-chromen-4-one
45. 2-(1-(4-amino-3-(4-fluoro-4-(trifluoromethoxy)phenyl)-1H-pyrazolo[3,4-d]pyrimidin-1-yl)ethyl)-5-fluoro-3-(3-fluorophenyl)-4H-chromen-4-one
46. 2-(1-(4-amino-3-(3-fluoro-4-(oxetan-3-yloxy)phenyl)-1H-pyrazolo[3,4-d]pyrimidin-1-yl)ethyl)-5-fluoro-3-(3-fluorophenyl)-4H-chromen-4-one
47. 2-(1-(4-amino-3-(pyrrolidin-1-yl)-1H-pyrazolo[3,4-d]pyrimidin-1-yl)ethyl)-5-fluoro-3-(3-fluorophenyl)-4H-chromen-4-one
48. N-(4-(4-amino-1-(1-(5-fluoro-3-(3-fluorophenyl)-4-oxo-4H-chromen-2-yl)ethyl)-1H-pyrazolo[3,4-d]pyrimidin-3-yl)phenyl)isobutyramide
49. 2-(1-(4-amino-3-(4-isobutylphenyl)-1H-pyrazolo[3,4-d]pyrimidin-1-yl)ethyl)-5-fluoro-3-(3-fluorophenyl)-4H-chromen-4-one
50. 2-(1-(4-amino-3-(4-isopropoxy-3-methylphenyl)-1H-pyrazolo[3,4-d]pyrimidin-1-yl)ethyl)-5-fluoro-3-(3-fluorophenyl)-4H-chromen-4-one
51. 2-(1-(4-amino-3-(4-(5,6-dihydro-4H-1,3-oxazin-2-yl)phenyl)-1H-pyrazolo[3,4-d]pyrimidin-1-yl)ethyl)-5-fluoro-3-(3-fluorophenyl)-4H-chromen-4-one
52. 4-(4-amino-1-(1-(5-fluoro-3-(3-fluorophenyl)-4-oxo-4H-chromen-2-yl)ethyl)-1H-pyrazolo[3,4-d]pyrimidin-3-yl)-N-methylbenzenesulfonamide
53. 4-(4-amino-1-(1-(5-fluoro-3-(3-fluorophenyl)-4-oxo-4H-chromen-2-yl)ethyl)-1H-pyrazolo[3,4-d]pyrimidin-3-yl)-2-fluoro-N-isopropylbenzamide
54. 2-(1-(4-amino-3-(4-(5-(methylamino)-1,3,4-thiadiazol-2-yl)phenyl)-1H-pyrazolo[3,4-d]pyrimidin-1-yl)ethyl)-5-fluoro-3-(3-fluorophenyl)-4H-chromen-4-one
55. N-(4-(4-amino-1-(1-(5-fluoro-3-(3-fluorophenyl)-4-oxo-4H-chromen-2-yl)ethyl)-1H-pyrazolo[3,4-d]pyrimidin-3-yl)benzyl)methanesulfonamide
56. 4-(4-amino-1-(1-(5-fluoro-3-(3-fluorophenyl)-4-oxo-4H-chromen-2-yl)ethyl)-1H-pyrazolo[3,4-d]pyrimidin-3-yl)-N-isopropylbenzenesulfonamide
57. 4-(4-amino-1-(1-(5-fluoro-3-(3-fluorophenyl)-4-oxo-4H-chromen-2-yl)ethyl)-1H-pyrazolo[3,4-d]pyrimidin-3-yl)-N-cyclopropylbenzenesulfonamide
58. 2-(1-(4-amino-3-(2-isopropoxypyrimidin-5-yl)-1H-pyrazolo[3,4-d]pyrimidin-1-yl)ethyl)-5-fluoro-3-(3-fluorophenyl)-4H-chromen-4-one
59. (R)/(S)-2-(1-(4-amino-3-(3-fluoro-4-morpholinophenyl)-1H-pyrazolo[3,4-d]pyrimidin-1-yl)ethyl)-5-fluoro-3-(3-fluorophenyl)-4H-chromen-4-one
60. 4-(4-amino-1-(1-(5-fluoro-3-(3-fluorophenyl)-4-oxo-4H-chromen-2-yl)ethyl)-1H-pyrazolo[3,4-d]pyrimidin-3-yl)benzenesulfonamide
61. methyl 4-(4-amino-1-(1-(5-fluoro-3-(3-fluorophenyl)-4-oxo-4H-chromen-2-yl)ethyl)-1H-pyrazolo[3,4-d]pyrimidin-3-yl)thiophene-2-carboxylate
62. 2-(1-(4-amino-3-(5-methylthiophen-2-yl)-1H-pyrazolo[3,4-d]pyrimidin-1-yl)ethyl)-5-fluoro-3-(3-fluorophenyl)-4H-chromen-4-one
63. 2-(1-(4-amino-3-(1H-pyrrolo[2,3-b]pyridin-5-yl)-1H-pyrazolo[3,4-d]pyrimidin-1-yl)ethyl)-5-fluoro-3-(3-fluorophenyl)-4H-chromen-4-one
64. methyl 4-(4-amino-1-(1-(5-fluoro-3-(3-fluorophenyl)-4-oxo-4H-chromen-2-yl)ethyl)-1H-pyrazolo[3,4-d]pyrimidin-3-yl)-3-fluorobenzoate
65. 2-(1-(9H-purin-6-ylamino)propyl)-5-fluoro-3-phenyl-4H-chromen-4-one
66. 2-(1-(4-amino-3-(3-hydroxyprop-1l-ynyl)-1H-pyrazolo[3,4-d]pyrimidin-1-yl)ethyl)-5-fluoro-3-(3-fluorophenyl)-4H-chromen-4-one
67. (S)/(R)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one 4-methylbenzenesulfonate
68. (+)-2-(1-(9H-purin-6-ylamino)ethyl)-5-fluoro-3-(3-fluorophenyl)-4H-chromen-4-one
69. 2-(1-(9H-purin-6-ylamino)ethyl)-5-fluoro-3-(3-fluorophenyl)-4H-chromen-4-one
70. (R)/(S)-2-(1-(4-amino-3-(3-fluoro-4-morpholinophenyl)-1H-pyrazolo[3,4-d]pyrimidin-1-yl)ethyl)-5-fluoro-3-(3-fluorophenyl)-4H-chromen-4-one
71. 2-(1-(4-amino-3-(4-methoxy-3,5-dimethylphenyl)-1H-pyrazolo[3,4-d]pyrimidin-1-yl)ethyl)-5-fluoro-3-(3-fluorophenyl)-4H-chromen-4-one
72. 2-(1-(4-amino-3-(4-(methoxymethyl)phenyl)-1H-pyrazolo[3,4-d]pyrimidin-1-yl)ethyl)-5-fluoro-3-(3-fluorophenyl)-4H-chromen-4-one or
73. 2-(1-(4-amino-3-(imidazo[1,2-a]pyridin-6-yl)-1H-pyrazolo[3,4-d]pyrimidin-1-yl)ethyl)-5-fluoro-3-(3-fluorophenyl)-4H-chromen-4-one
74. tert-butyl (5-(4-amino-1-(1-(5-fluoro-3-(3-fluorophenyl)-4-oxo-4H-chromen-2-yl)ethyl)-1H-pyrazolo[3,4-d]pyrimidin-3-yl)furan-2-yl)methylcarbamate
75. 2-(1-(4-amino-3-(2,4-dimethylthiazol-5-yl)-1H-pyrazolo[3,4-d]pyrimidin-1-yl)ethyl)-5-fluoro-3-(3-fluorophenyl)-4H-chromen-4-one
76. 2-(1-(4-amino-3-(5-(morpholinomethyl)thiophen-2-yl)-1H-pyrazolo[3,4-d]pyrimidin-1-yl)ethyl)-5-fluoro-3-(3-fluorophenyl)-4H-chromen-4-one
77. 2-(1-(4-amino-3-(4-(5-amino-1,3,4-thiadiazol-2-yl)phenyl)-1H-pyrazolo[3,4-d]pyrimidin-1-yl)ethyl)-5-fluoro-3-(3-fluorophenyl)-4H-chromen-4-one
78. (−)-2-(1-(9H-purin-6-ylamino)ethyl)-5-fluoro-3-(3-fluorophenyl)-4H-chromen-4-one
79. 2-(1-(4-amino-3-(1,3-dimethyl-1H-indazol-6-yl)-1H-pyrazolo[3,4-d]pyrimidin-1-yl)ethyl)-5-fluoro-3-(3-fluorophenyl)-4H-chromen-4-one
80. 2-(1-(4-amino-3-(2,3-dimethyl-2H-indazol-6-yl)-1H-pyrazolo[3,4-d]pyrimidin-1-yl)ethyl)-5-fluoro-3-(3-fluorophenyl)-4H-chromen-4-one
81. N-(4-(4-amino-1-(1-(5-fluoro-3-(3-fluorophenyl)-4-oxo-4H-chromen-2-yl)ethyl)-1H-pyrazolo[3,4-d]pyrimidin-3-yl)-2-fluorophenyl)isobutyramide
82. N-(4-(4-amino-1-(1-(5-fluoro-3-(3-fluorophenyl)-4-oxo-4H-chromen-2-yl)ethyl)-1H-pyrazolo[3,4-d]pyrimidin-3-yl)-2-fluorophenyl)acetamide
83. 2-(1-(4-(dimethylamino)-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one
84. 5-fluoro-2-(1-(3-(3-fluoro-4-isopropoxyphenyl)-4-(methylamino)-1H-pyrazolo[3,4-d]pyrimidin-1-yl)ethyl)-3-(3-fluorophenyl)-4H-chromen-4-one
85. 5-fluoro-2-(1-(3-(3-fluoro-4-isopropoxyphenyl)-4-morpholino-1H-pyrazolo[3,4-d]pyrimidin-1-yl)ethyl)-3-(3-fluorophenyl)-4H-chromen-1-one
86. N-(2-fluoro-4-(1-(1-(5-fluoro-3-(4-fluorophenyl)-4-oxo-4H-chromen-2-yl)ethyl)-4-morpholino-1H-pyrazolo[3,4-d]pyrimidin-3-yl)phenyl)isobutyramide
87. N-(2-fluoro-4-(1-(1-(5-fluoro-3-(3-fluorophenyl)-4-oxo-4H-chromen-2-yl)ethyl)-4-morpholino-1H-pyrazolo[3,4-d]pyrimidin-3-yl)phenyl)isobutyramide 88. (S)/(R)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one sulphate
89. (S)/(R)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one
90. (S)/(R)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one camphorsulphonate
91. 2-(1-(4-amino-3-(4-(difluoromethoxy)-3-fluorophenyl)-1H-pyrazolo[3,4-d]pyrimidin-1-yl)ethyl)-5-fluoro-3-(1H-pyrazol-4-yl)-4H-chromen-4-one
92. 2-(1-(4-amino-3-(3-fluoro-4-morpholinophenyl)-1H-pyrazolo[3,4-d]pyrimidin-1-yl)ethyl)-5-fluoro-3-phenyl-4H-chromen-4-one
93. 2-(1-(4-amino-3-(3-fluoro-4-morpholinophenyl)-1H-pyrazolo[3,4-d]pyrimidin-1-yl)ethyl)-5-fluoro-3-(4-fluorophenyl)-4H-chromen-4-one
94. and 95. (S)-2-(1-(4-amino-3-(3-fluoro-4-isopropoxyphenyl)-1H-pyrazolo[3,4-d]pyrimidin-1-yl)ethyl)-5-fluoro-3-(4-fluorophenyl)-4H-chromen-4-one and (R)-2-(1-(4-amino-3-(3-fluoro-4-isopropoxyphenyl)-1H-pyrazolo[3,4-d]pyrimidin-1-yl)ethyl)-5-fluoro-3-(4-fluorophenyl)-4H-chromen-4-one.
96. and 97. (S)-2-(1-(4-amino-3-(4-(difluoromethoxy)-3-fluorophenyl)-1H-pyrazolo[3,4-d]pyrimidin-1-yl)ethyl)-5-fluoro-3-(4-fluorophenyl)-4H-chromen-4-one and (R)-2-(1-(4-amino-3-(4-(difluoromethoxy)-3-fluorophenyl)-1H-pyrazolo[3,4-d]pyrimidin-1-yl)ethyl)-5-fluoro-3-(4-fluorophenyl)-4H-chromen-4-one
98. 2-(1-(4-(dimethylamino)-3-(3-fluoro-4-morpholinophenyl)-1H-pyrazolo[3,4-d]pyrimidin-1-yl)ethyl)-5-fluoro-3-(3-fluorophenyl)-4H-chromen-4-one
99. 5-fluoro-2-(1-(3-(3-fluoro-4-morpholinophenyl)-4-(methylamino)-1H-pyrazolo[3,4-d]pyrimidin-1-yl)ethyl)-3-(3-fluorophenyl)-4H-chromen-4-one
100. and 101. (S)-2-(1-(4-amino-3-(3-fluoro-4-isopropoxyphenyl)-1H-pyrazolo[3,4-d]pyrimidin-1-yl)ethyl)-5-fluoro-3-phenyl-4H-chromen-4-one and (R)-2-(1-(4-amino-3-(3-fluoro-4-isopropoxyphenyl)-1H-pyrazolo[3,4-d]pyrimidin-1-yl)ethyl)-5-fluoro-3-phenyl-H-chromen-4-one.
102. and 103. (5)-2-(1-(4-amino-3-(4-(difluoromethoxy)-3-fluorophenyl)-1H-pyrazolo[3,4-d]pyrimidin-1-yl)ethyl)-5-fluoro-3-phenyl-4H-chromen-4-one and (R)-2-(1-(4-amino-3-(4-(difluoromethoxy)-3-fluorophenyl)-1H-pyrazolo[3,4-d]pyrimidin-1-yl)ethyl)-5-fluoro-3-phenyl-4H-chromen-4-one
104. (+)-5-fluoro-2-(1-(3-(3-fluoro-4-isopropoxyphenyl)-4-(methylamino)-1H-pyrazolo[3,4-d]pyrimidin-1-yl)ethyl)-3-(3-fluorophenyl)-4H-chromen-4-one and
105. (−)-5-fluoro-2-(1-(3-(3-fluoro-4-isopropoxyphenyl)-4-(methylamino)-1H-pyrazolo[3,4-d]pyrimidin-1-yl)ethyl)-3-(3-fluorophenyl)-4H-chromen-4-one.
106. 2-(1-(6-amino-2-fluoro-9H-purin-9-yl)ethyl)-5-fluoro-3-(3-fluorophenyl)-4H-chromen-4-one
107. 2-(1-(6-amino-2-fluoro-9H-purin-9-yl)ethyl)-5-fluoro-3-(4-fluorophenyl)-4H-chromen-4-one
108. 5-fluoro-3-(4-fluorophenyl)-2-(1-(6-morpholino-9H-purin-9-yl)ethyl)-4H-chromen-4-one
109. 5-fluoro-3-(4-fluorophenyl)-2-(1-(6-(4-methylpiperazin-1-yl)-9H-purin-9-yl)ethyl)-4H-chromen-4-one
110. 2-(1-(6-(dimethylamino)-9H-purin-9-yl)ethyl)-5-fluoro-3-(3-fluorophenyl)-4H-chromen-4-one
111. 2-(1-(6-(dimethylamino)-9H-purin-9-yl)ethyl)-5-fluoro-3-(3-fluorophenyl)-4H-chromen-4-one
112. 5-fluoro-3-(3-fluorophenyl)-2-(1-(3-(3-methyl-1H-indazol-6-yl)-4-morpholino-1H-pyrazolo[3,4-d]pyrimidin-1-yl)ethyl)-4H-chromen-4-one
113. 2-(1-(4-amino-3-(3-chloro-4-morpholinophenyl)-1H-pyrazolo[3,4-d]pyrimidin-1-yl)ethyl)-5-fluoro-3-(3-fluorophenyl)-4H-chromen-4-one
114. (+)-2-(1-(4-amino-3-(4-isopropoxy-3-methylphenyl)-1H-pyrazolo[3,4-d]pyrimidin-1-yl)ethyl)-5-fluoro-3-(3-fluorophenyl)-4H-chromen-4-one
115. (−)-2-(1-(4-amino-3-(4-isopropoxy-3-methylphenyl)-1H-pyrazolo[3,4-d]pyrimidin-1-yl)ethyl)-5-fluoro-3-(3-fluorophenyl)-4H-chromen-4-one
116. (S)/(R)-5-fluoro-2-(1-(3-(3-fluoro-4-isopropoxyphenyl)-4-morpholino-1H-pyrazolo[3,4-d]pyrimidin-1-yl)ethyl)-3-(3-fluorophenyl)-4H-chromen-4-one
117. 2-(1-(4-amino-3-(3-chloro-4-isopropoxyphenyl)-1H-pyrazolo[3,4-d]pyrimidin-1-yl)ethyl)-5-fluoro-3-(3-fluorophenyl)-4H-chromen-4-one
118. 2-(1-(4-amino-3-(2-methylbenzo[d]oxazol-6-yl)-1H-pyrazolo[3,4-d]pyrimidin-1-yl)ethyl)-5-fluoro-3-(3-fluorophenyl)-4H-chromen-4-one
119. 5-fluoro-3-(3-fluorophenyl)-2-(1-(6-morpholino-9H-purin-9-yl)ethyl)-4H-chromen-4-one
120. 2-(1-(4-amino-3-(3-fluoro-4-isopropoxyphenyl)-1H-pyrazolo[3,4-d]pyrimidin-1-yl)ethyl)-3-(3-fluorophenyl)-5-morpholino-4H-chromen-4-one
121. 2-(1-(4-amino-3-(3-fluoro-4-isopropoxyphenyl)-1H-pyrazolo[3,4-d]pyrimidin-1-yl)ethyl)-5-morpholino-3-phenyl-4H-chromen-4-one
122. 6-(4-amino-1-(1-(S-fluoro-3-(3-fluorophenyl)-4-oxo-4H-chromen-2-yl)ethyl)-1H-pyrazolo[3,4-d]pyrimidin-3-yl)isoindolin-1-one
123. 5-(4-amino-1-(1-(5-fluoro-3-(3-fluorophenyl)-4-oxo-4H-chromen-2-yl)ethyl)-1H-pyrazolo[3,4-d]pyrimidin-3-yl)isoindolin-1-one
124. 2-(1-(3-(4-acetyl-3-fluorophenyl)-4-amino-1H-pyrazolo[3,4-d]pyrimidin-1-yl)ethyl)-5-fluoro-3-(3-fluorophenyl)-4H-chromen-4-one
125. 5-fluoro-3-(3-fluorophenyl)-2-(1-(6-(4-methylpiperazin-1-yl)-9H-purin-9-yl)ethyl)-4H-chromen-4-one
126. and 127. (S)-2-(1-(4-amino-3-(3-chloro-4-morpholinophenyl)-1H-pyrazolo[3,4-d]pyrimidin-1-yl)ethyl)-5-fluoro-3-(3-fluorophenyl)-4H-chromen-4-one and (R)-2-(1-(4-amino-3-(3-chloro-4-morpholinophenyl)-1H-pyrazolo[3,4-d]pyrimidin-1-yl)ethyl)-5-fluoro-3-(3-fluorophenyl)-4H-chromen-4-one
128. N-(3-(4-amino-1-(1-(5-fluoro-3-(3-fluorophenyl)-4-oxo-4H-chromen-2-yl)ethyl)-1H-pyrazolo[3,4-d]pyrimidin-3-yl)phenyl)methanesulfonamide
129. and 130. (5)-2-(1-(6-(dimethylamino)-9H-purin-9-yl)ethyl)-5-fluoro-3-(3-fluorophenyl)-4H-chromen-4-one and (R)-2-(1-(6-(dimethylamino)-9H-purin-9-yl)ethyl)-5-fluoro-3-(3-fluorophenyl)-4H-chromen-4-one
131. 2-(1-(9H-purin-6-ylamino)ethyl)-5-fluoro-3-(2-fluorophenyl)-4H-chromen-4-one
132. 2-(1-(4-amino-3-(4-ethoxy-3-(trifluoromethyl)phenyl)-1H-pyrazolo[3,4-d]pyrimidin-1-yl)ethyl)-5-fluoro-3-(3-fluorophenyl)-4H-chromen-4-one
133. 2-(1-(4-amino-3-(3-fluoro-4-isopropoxyphenyl)-1H-pyrazolo[3,4-d]pyrimidin-1-yl)propyl)-5-fluoro-3-(3-fluorophenyl)-4H-chromen-4-one
134. and 135. (S)-5-fluoro-3-(3-fluorophenyl)-2-(1-(2-methoxy-9H-purin-6-ylamino)ethyl)-4H-chromen-4-one and (R)-5-fluoro-3-(3-fluorophenyl)-2-(1-(2-methoxy-9H-purin-6-ylamino)ethyl)-4H-chromen-4-one.
136. (S)(R)-5-fluoro-2-(1-(2-fluoro-9H-purin-6-ylamino)ethyl)-3-(3-fluoro phenyl)-4H-chromen-4-one 137. (S)/(R)-2-(1-(4-amino-3-(3-fluoro-4-isopropoxyphenyl)-1H-pyrazolo[3,4-d]pyrimidin-1-yl)ethyl)-5-methyl-3-phenyl-4H-chromen-4-one
138. 2-(1-(9H-purin-6-ylamino)ethyl)-5-fluoro-3-o-tolyl-4H-chromen-4-one and pharmaceutically acceptable salts thereof

TABLE-1

| Ex. | Structure |
|---|---|
| 1. | 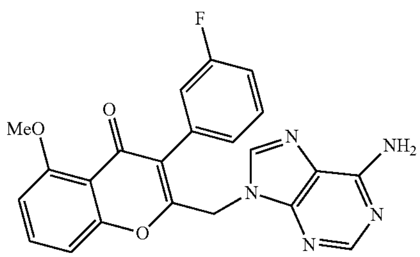 [SMILES: COc1cccc2oc(Cn3cnc4c(N)ncnc43)c(-c3cccc(F)c3)c(=O)c12] |
| 2. | 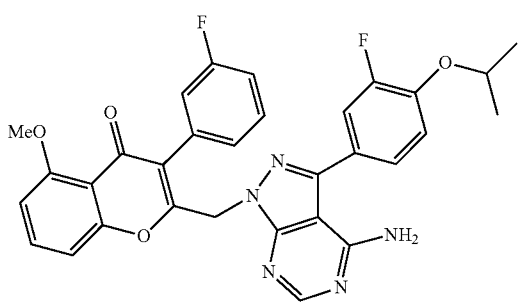 [SMILES: COc1cccc2oc(Cn3nc(-c4ccc(OC(C)C)c(F)c4)c4c(N)ncnc43)c(-c3cccc(F)c3)c(=O)c12] |
| 3. | 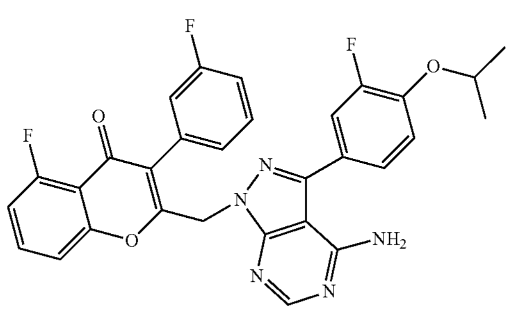 [SMILES: CC(C)Oc1ccc(-c2nn(Cc3oc4cccc(F)c4c(=O)c3-c3cccc(F)c3)c3ncnc(N)c23)cc1F] |
| 4. | 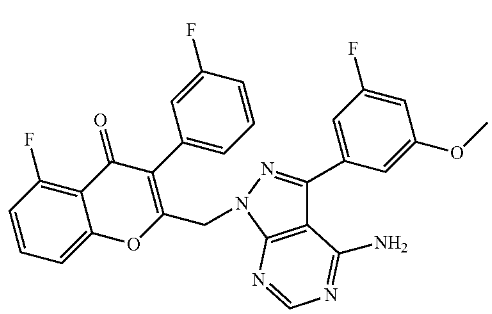 [SMILES: COc1cc(F)cc(-c2nn(Cc3oc4cccc(F)c4c(=O)c3-c3cccc(F)c3)c3ncnc(N)c23)c1] |
| 5. | |
| 6. | |
| 6a. | |

TABLE-1-continued
| Ex. | Structure |
|---|---|
| 6b. | 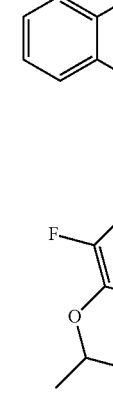 |
| 7. | 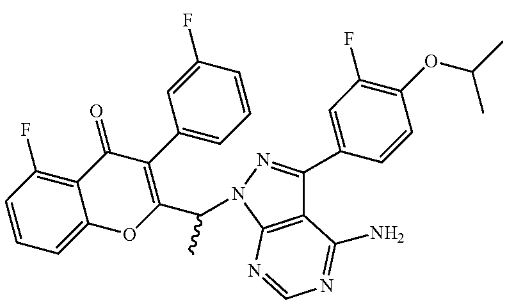 [SMILES: CC(C)Oc1ccc(-c2nn(C(C)c3oc4cccc(F)c4c(=O)c3-c3cccc(F)c3)c3ncnc(N)c23)cc1F] |
| 8. | 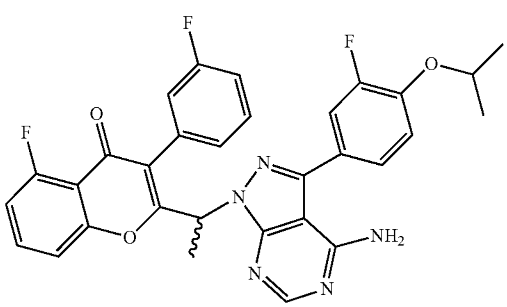 [SMILES: CC(C)Oc1ccc(-c2nn(C(C)c3oc4cccc(F)c4c(=O)c3-c3cccc(F)c3)c3ncnc(N)c23)cc1F] |
| 9. | 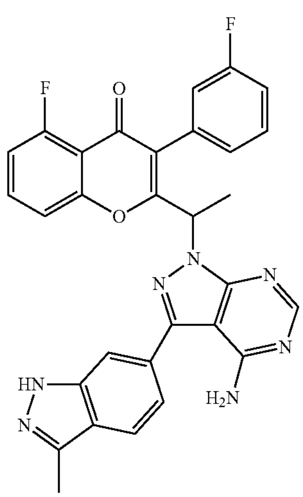 [SMILES: Cc1n[nH]c2cc(-c3nn(C(C)c4oc5cccc(F)c5c(=O)c4-c4cccc(F)c4)c4ncnc(N)c34)ccc12] |
TABLE-1-continued
| Ex. | Structure |
|---|---|
| 9a. | 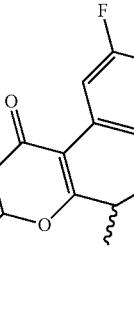 |
| 9b. | 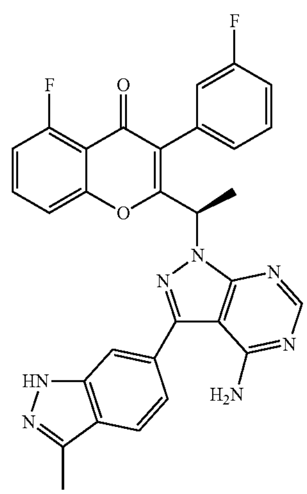 [SMILES: Cc1n[nH]c2cc(-c3nn([C@H](C)c4oc5cccc(F)c5c(=O)c4-c4cccc(F)c4)c4ncnc(N)c34)ccc12] |
| 10. | 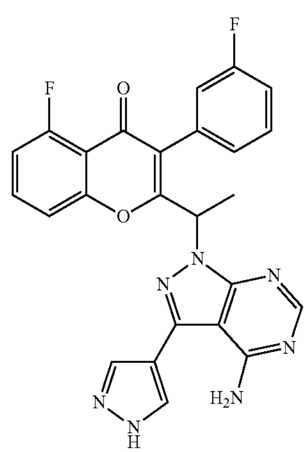 [SMILES: CC(c1oc2cccc(F)c2c(=O)c1-c1cccc(F)c1)n1nc(-c2cn[nH]c2)c2c(N)ncnc21] |

TABLE-1-continued
| Ex. | Structure |
|---|---|
| 11. | 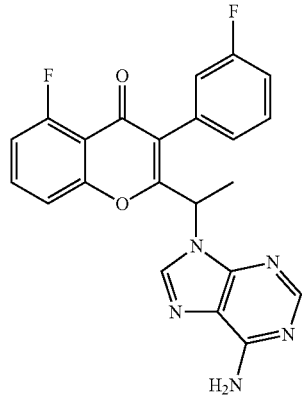 [SMILES: CC(c1oc2cccc(F)c2c(=O)c1-c1cccc(F)c1)n1cnc2c(N)ncnc21] |
| 12. | 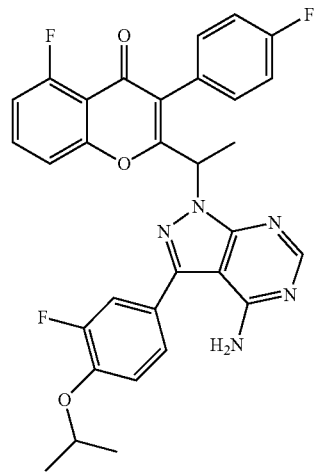 [SMILES: CC(C)Oc1ccc(-c2nn(C(C)c3oc4cccc(F)c4c(=O)c3-c3ccc(F)cc3)c3ncnc(N)c23)cc1F] |
| 13. | 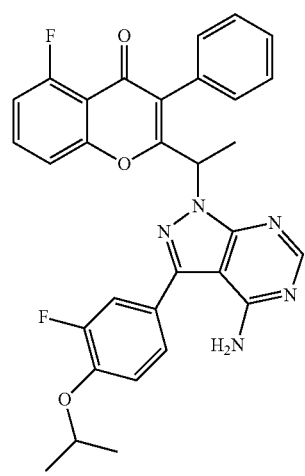 [SMILES: CC(C)Oc1ccc(-c2nn(C(C)c3oc4cccc(F)c4c(=O)c3-c3ccccc3)c3ncnc(N)c23)cc1F] |
TABLE-1-continued
| Ex. | Structure |
|---|---|
| 14. | 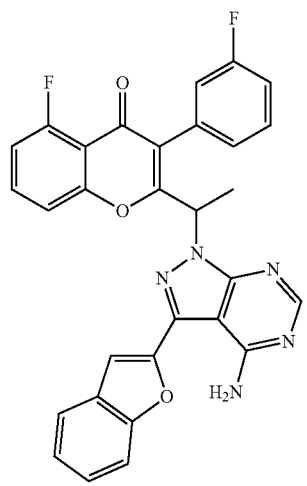 [SMILES: CC(c1oc2cccc(F)c2c(=O)c1-c1cccc(F)c1)n1nc(-c2cc3ccccc3o2)c2c(N)ncnc21] |
| 15. | 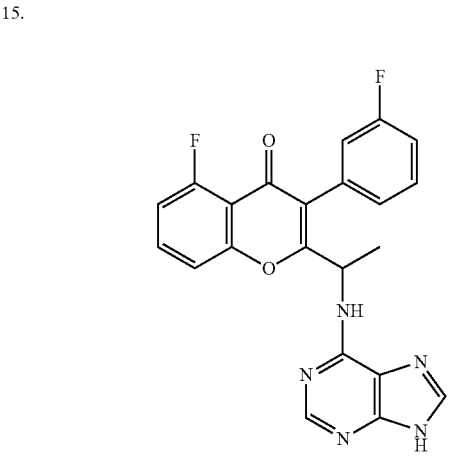 |
| 16. | 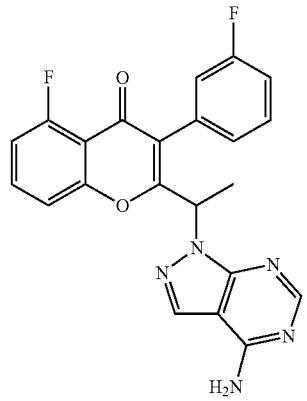 [SMILES: CC(c1oc2cccc(F)c2c(=O)c1-c1cccc(F)c1)n1ncc2c(N)ncnc21] |

TABLE-1-continued
| Ex. | Structure |
|---|---|
| 16a. | 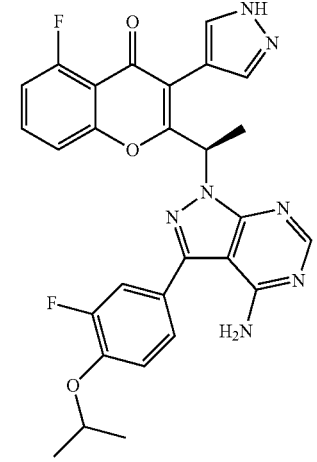 |
| 16b | 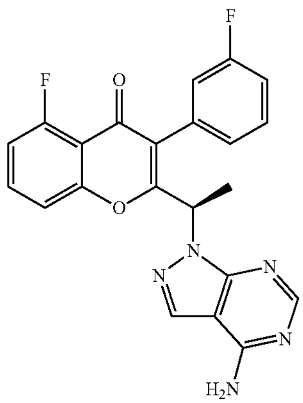 [SMILES: C[C@H](c1oc2cccc(F)c2c(=O)c1-c1cccc(F)c1)n1ncc2c(N)ncnc21] |
| 17. | 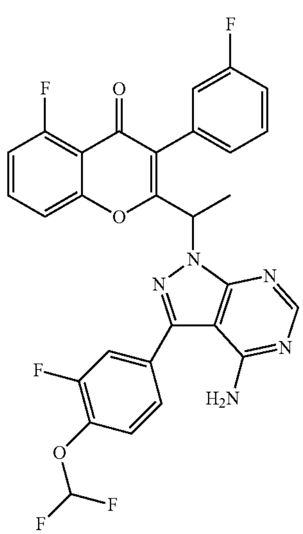 [SMILES: CC(c1oc2cccc(F)c2c(=O)c1-c1cccc(F)c1)n1nc(-c2ccc(OC(F)F)c(F)c2)c2c(N)ncnc21] |
TABLE-1-continued
| Ex. | Structure |
|---|---|
| 18. | 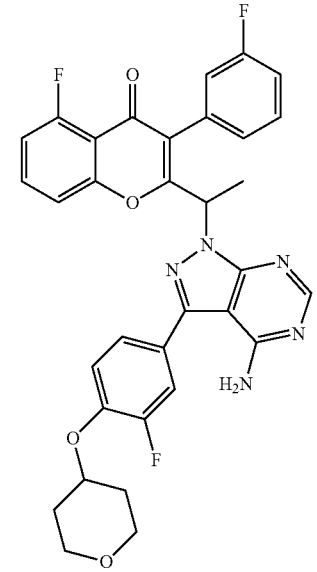 [SMILES: CC(c1oc2cccc(F)c2c(=O)c1-c1cccc(F)c1)n1nc(-c2ccc(OC3CCOCC3)c(F)c2)c2c(N)ncnc21] |
| 19. | |
| 20. | 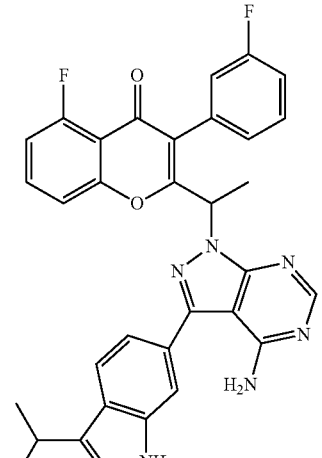 |

TABLE-1-continued
| Ex. | Structure |
|---|---|
| 21. | 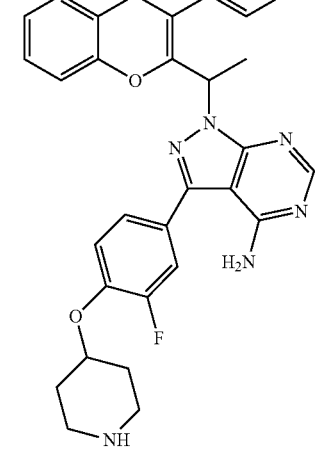 |
| 22. | 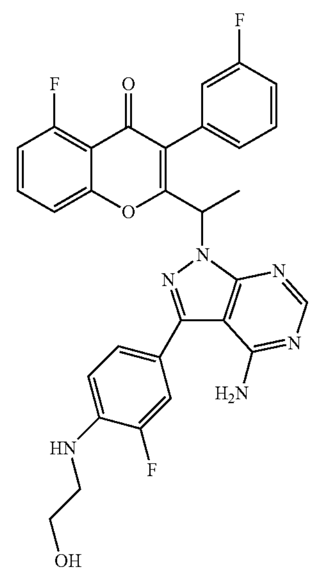 [SMILES: CC(c1oc2cccc(F)c2c(=O)c1-c1cccc(F)c1)n1nc(-c2ccc(NCCO)c(F)c2)c2c(N)ncnc21] |
| 23. | 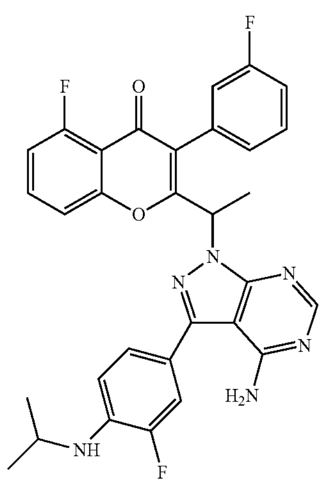 [SMILES: CC(C)Nc1ccc(-c2nn(C(C)c3oc4cccc(F)c4c(=O)c3-c3cccc(F)c3)c3ncnc(N)c23)cc1F] |
TABLE-1-continued
| Ex. | Structure |
|---|---|
| 24. | 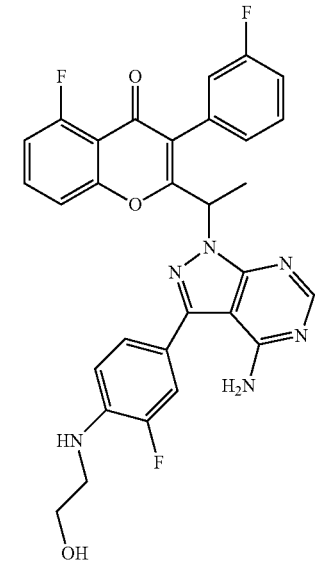 |
| 25. | 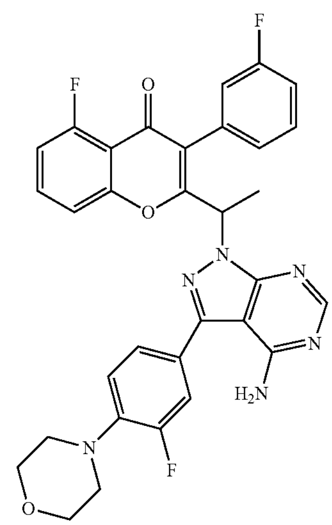 [SMILES: CC(c1oc2cccc(F)c2c(=O)c1-c1cccc(F)c1)n1nc(-c2ccc(N3CCOCC3)c(F)c2)c2c(N)ncnc21] |
| 26. | 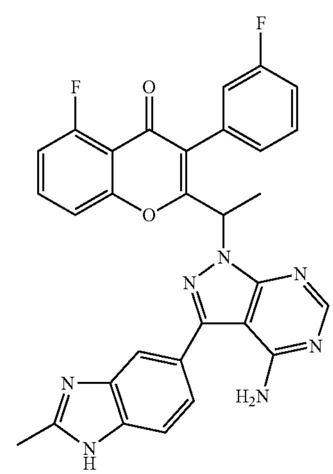 [SMILES: Cc1nc2cc(-c3nn(C(C)c4oc5cccc(F)c5c(=O)c4-c4cccc(F)c4)c4ncnc(N)c34)ccc2[nH]1] |

TABLE-1-continued
| Ex. | Structure |
|---|---|
| 27. | 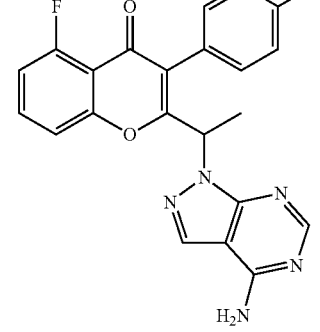 |
| 28. | 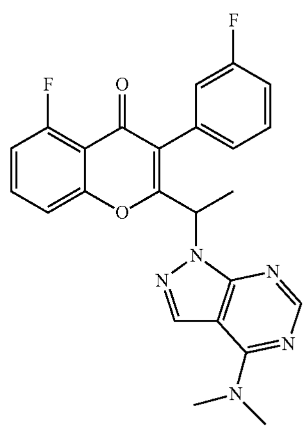 [SMILES: CC(c1oc2cccc(F)c2c(=O)c1-c1cccc(F)c1)n1ncc2c(N(C)C)ncnc21] |
| 29. | 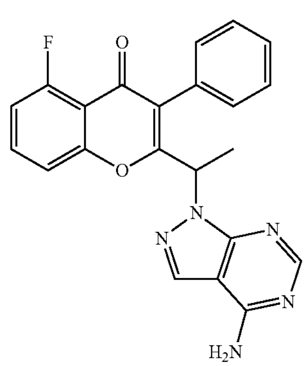 [SMILES: CC(c1oc2cccc(F)c2c(=O)c1-c1ccccc1)n1ncc2c(N)ncnc21] |
TABLE-1-continued
| Ex. | Structure |
|---|---|
| 30. | 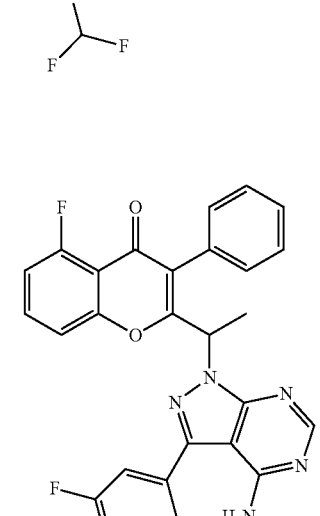 |
| 31. | 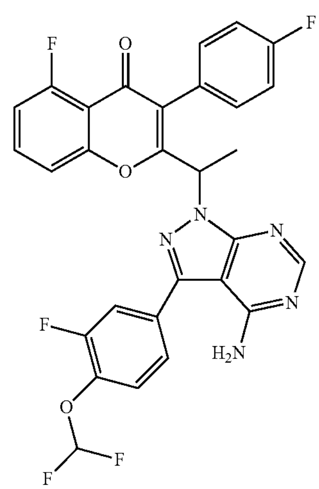 [SMILES: CC(c1oc2cccc(F)c2c(=O)c1-c1ccc(F)cc1)n1nc(-c2ccc(OC(F)F)c(F)c2)c2c(N)ncnc21] |
| 32. | 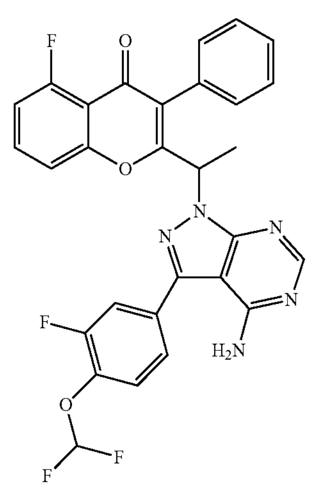 [SMILES: CC(c1oc2cccc(F)c2c(=O)c1-c1ccccc1)n1nc(-c2ccc(OC(F)F)c(F)c2)c2c(N)ncnc21] |

TABLE-1-continued
| Ex. | Structure |
|---|---|
| 33. | 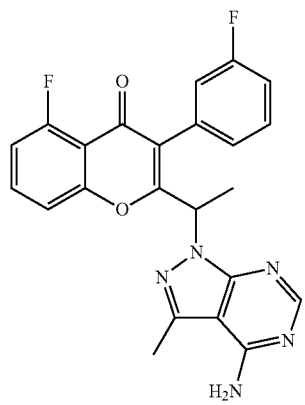 [SMILES: Cc1nn(C(C)c2oc3cccc(F)c3c(=O)c2-c2cccc(F)c2)c2ncnc(N)c12] |
| 34. | 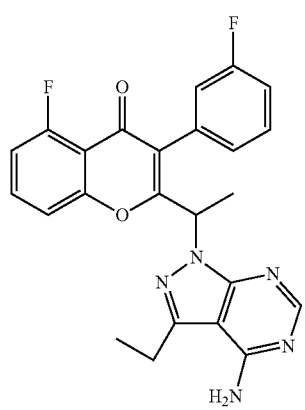 [SMILES: CCc1nn(C(C)c2oc3cccc(F)c3c(=O)c2-c2cccc(F)c2)c2ncnc(N)c12] |
| 35. | 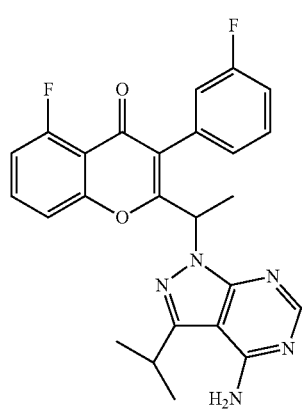 [SMILES: CC(C)c1nn(C(C)c2oc3cccc(F)c3c(=O)c2-c2cccc(F)c2)c2ncnc(N)c12] |
TABLE-1-continued
| Ex. | Structure |
|---|---|
| 36. | 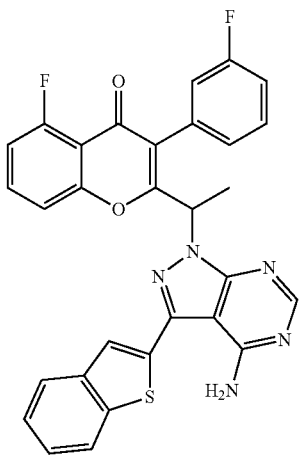 [SMILES: CC(c1oc2cccc(F)c2c(=O)c1-c1cccc(F)c1)n1nc(-c2cc3ccccc3s2)c2c(N)ncnc21] |
| 37. | 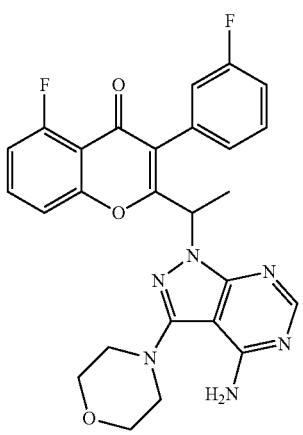 [SMILES: CC(c1oc2cccc(F)c2c(=O)c1-c1cccc(F)c1)n1nc(N2CCOCC2)c2c(N)ncnc21] |
| 38. | 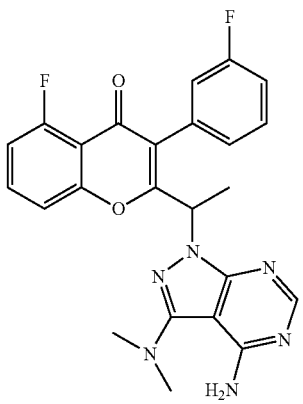 [SMILES: CC(c1oc2cccc(F)c2c(=O)c1-c1cccc(F)c1)n1nc(N(C)C)c2c(N)ncnc21] |

TABLE-1-continued

| Ex. | Structure |
|---|---|
| 39. | 5-fluoro-3-(3-fluorophenyl)-2-(1-(3-(piperidin-1-yl)-4-amino-1H-pyrazolo[3,4-d]pyrimidin-1-yl)ethyl)-4H-chromen-4-one |
| 40. | 5-fluoro-3-(3-fluorophenyl)-2-(1-(3-(6-isopropoxypyridin-3-yl)-4-amino-1H-pyrazolo[3,4-d]pyrimidin-1-yl)ethyl)-4H-chromen-4-one |
| 41. | 5-fluoro-3-(3-fluorophenyl)-2-(1-(3-(methylthio)-4-amino-1H-pyrazolo[3,4-d]pyrimidin-1-yl)ethyl)-4H-chromen-4-one |
| 42. | 5-fluoro-3-(3-fluorophenyl)-2-(1-(3-(3-fluoro-4-isopropoxyphenyl)-4-amino-1H-pyrazolo[3,4-d]pyrimidin-1-yl)ethyl)-4H-chromen-4-one, p-toluenesulfonic acid salt |
| 43. | 5-fluoro-3-(3-fluorophenyl)-2-(1-(3-(3-methyl-1H-indazol-6-yl)-4-amino-1H-pyrazolo[3,4-d]pyrimidin-1-yl)ethyl)-4H-chromen-4-one, p-toluenesulfonic acid salt |
| 44. | 2-(1-(3-(4-((1-benzhydrylazetidin-3-yl)oxy)-3-fluorophenyl)-4-amino-1H-pyrazolo[3,4-d]pyrimidin-1-yl)ethyl)-5-fluoro-3-(3-fluorophenyl)-4H-chromen-4-one |

TABLE-1-continued
| Ex. | Structure |
|---|---|
| 45. | 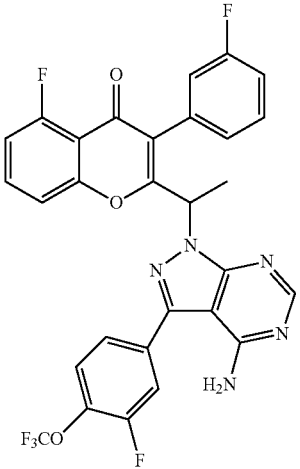 [SMILES: CC(c1oc2cccc(F)c2c(=O)c1-c1cccc(F)c1)n1nc(-c2ccc(OC(F)(F)F)c(F)c2)c2c(N)ncnc21] |
| 46. | 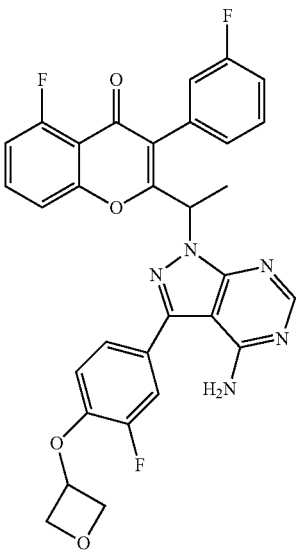 [SMILES: CC(c1oc2cccc(F)c2c(=O)c1-c1cccc(F)c1)n1nc(-c2ccc(OC3COC3)c(F)c2)c2c(N)ncnc21] |
| 47. | 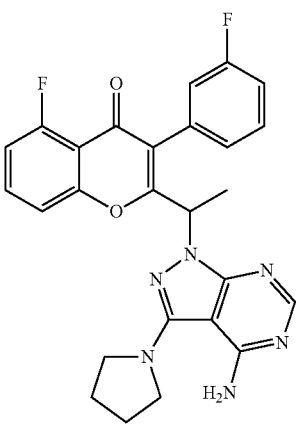 [SMILES: CC(c1oc2cccc(F)c2c(=O)c1-c1cccc(F)c1)n1nc(N2CCCC2)c2c(N)ncnc21] |
| 48. | 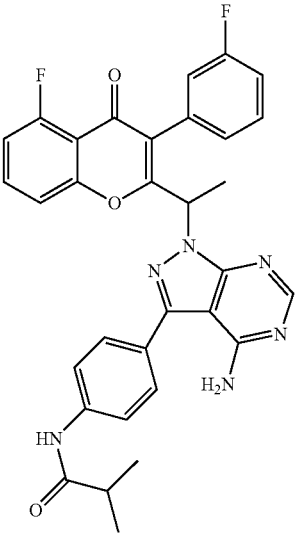 [SMILES: CC(C)C(=O)Nc1ccc(-c2nn(C(C)c3oc4cccc(F)c4c(=O)c3-c3cccc(F)c3)c3ncnc(N)c23)cc1] |
| 49. | 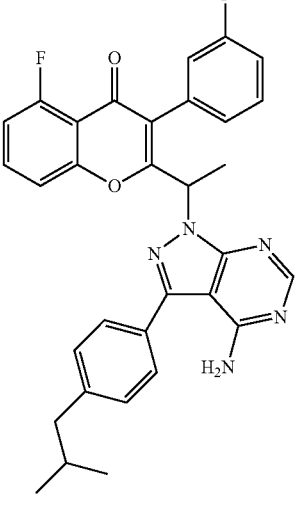 |
| 50. | 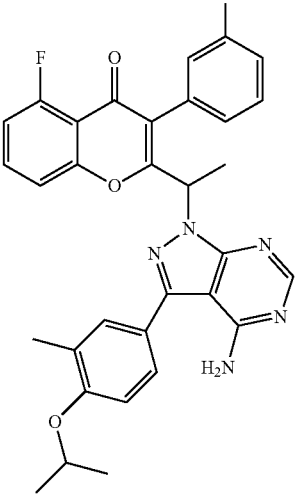 |

TABLE-1-continued
| Ex. | Structure |
|---|---|
| 51. | 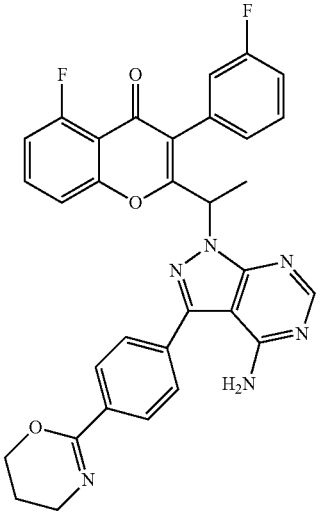 [SMILES: CC(c1oc2cccc(F)c2c(=O)c1-c1cccc(F)c1)n1nc(-c2ccc(C3=NCCCO3)cc2)c2c(N)ncnc21] |
| 52. | 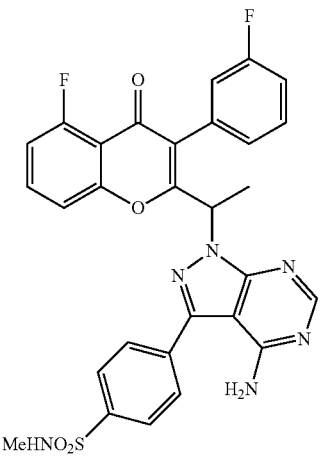 |
| 53. | 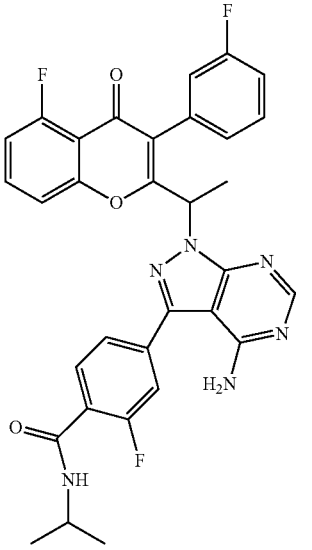 [SMILES: CC(C)NC(=O)c1ccc(-c2nn(C(C)c3oc4cccc(F)c4c(=O)c3-c3cccc(F)c3)c3ncnc(N)c23)cc1F] |
| 54. | 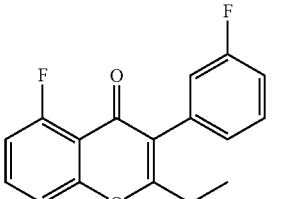 |
| 55. | 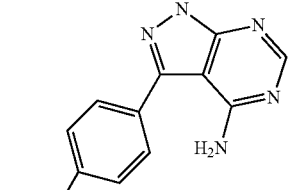 |
| 56. | 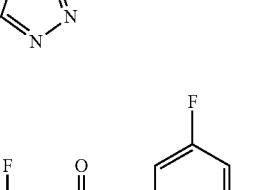 |

TABLE-1-continued

| Ex. | Structure |
|---|---|
| 57. | 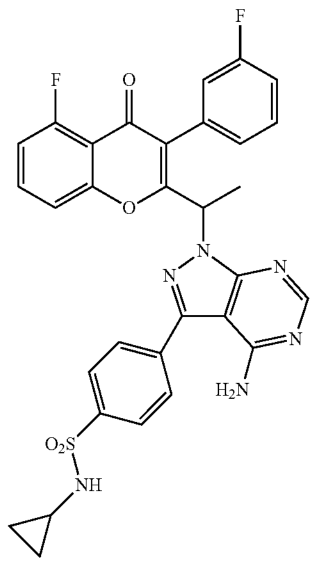 [SMILES: CC(c1oc2cccc(F)c2c(=O)c1-c1cccc(F)c1)n1nc(-c2ccc(S(=O)(=O)NC3CC3)cc2)c2c(N)ncnc21] |
| 58. | 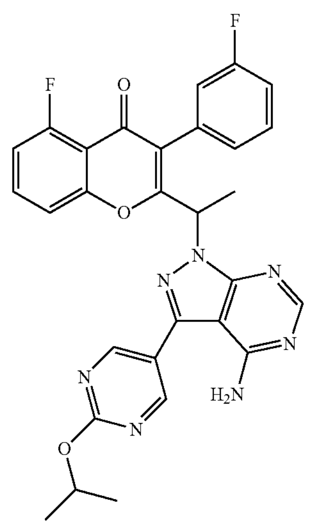 [SMILES: CC(C)Oc1ncc(-c2nn(C(C)c3oc4cccc(F)c4c(=O)c3-c3cccc(F)c3)c3ncnc(N)c23)cn1] |
| 59. | 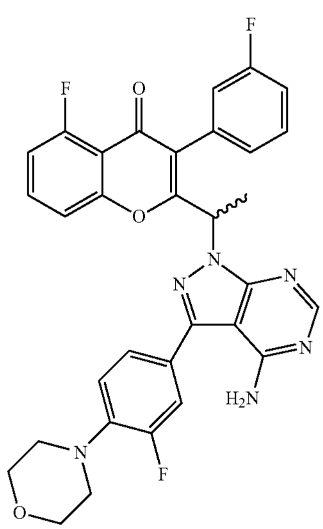 [SMILES: CC(c1oc2cccc(F)c2c(=O)c1-c1cccc(F)c1)n1nc(-c2ccc(N3CCOCC3)c(F)c2)c2c(N)ncnc21] |
| 60. | |
| 61. | |
| 62. | |

TABLE-1-continued
| Ex. | Structure |
|---|---|
| 63. | 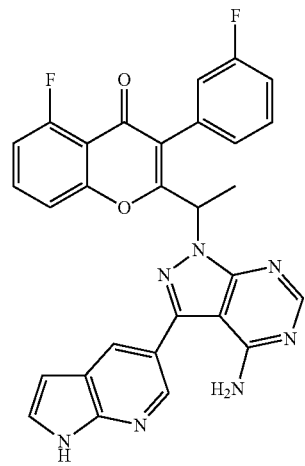 [SMILES: CC(c1oc2cccc(F)c2c(=O)c1-c1cccc(F)c1)n1nc(-c2cnc3[nH]ccc3c2)c2c(N)ncnc21] |
| 64. | 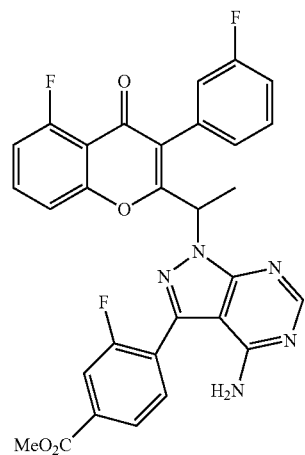 [SMILES: COC(=O)c1ccc(-c2nn(C(C)c3oc4cccc(F)c4c(=O)c3-c3cccc(F)c3)c3ncnc(N)c23)c(F)c1] |
| 65. | 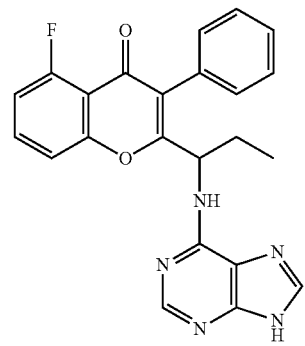 [SMILES: CCC(Nc1ncnc2[nH]cnc12)c1oc2cccc(F)c2c(=O)c1-c1ccccc1] |
TABLE-1-continued
| Ex. | Structure |
|---|---|
| 66. | 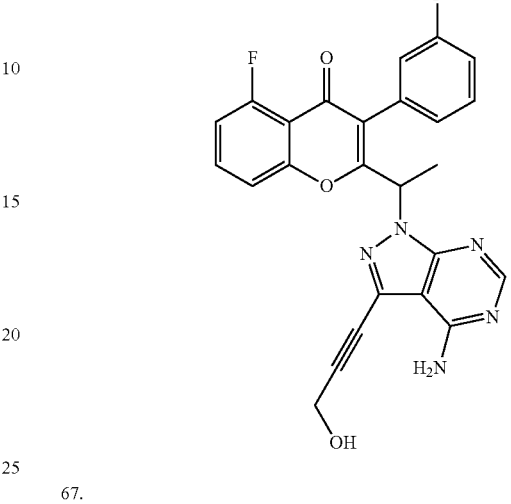 |
| 67. | 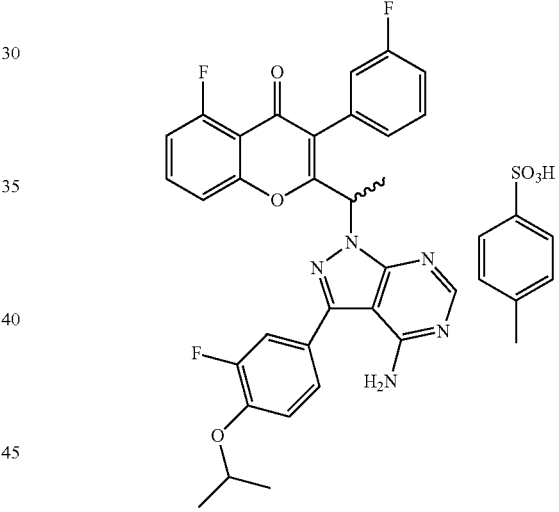 |
| 68. | 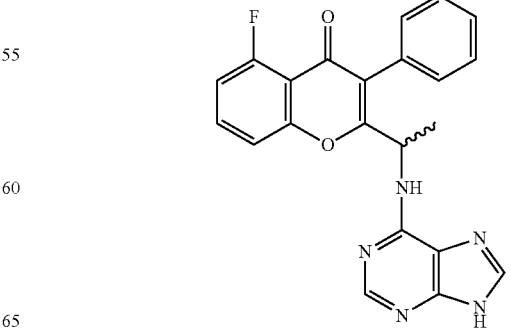 |

TABLE-1-continued
| Ex. | Structure |
|---|---|
| 69. | 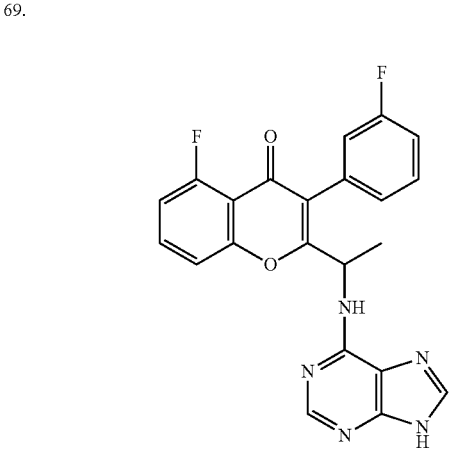 |
| 70. | 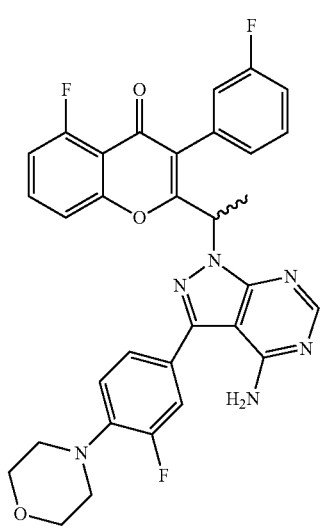 [SMILES: CC(c1oc2cccc(F)c2c(=O)c1-c1cccc(F)c1)n1nc(-c2ccc(N3CCOCC3)c(F)c2)c2c(N)ncnc21] |
| 71. | 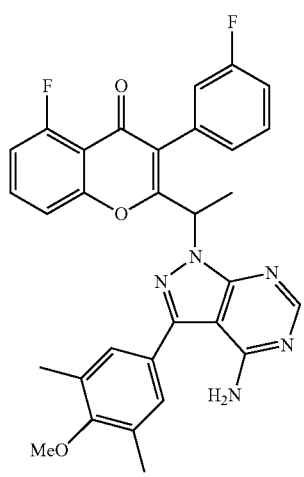 [SMILES: COc1c(C)cc(-c2nn(C(C)c3oc4cccc(F)c4c(=O)c3-c3cccc(F)c3)c3ncnc(N)c23)cc1C] |
TABLE-1-continued
| Ex. | Structure |
|---|---|
| 72. | 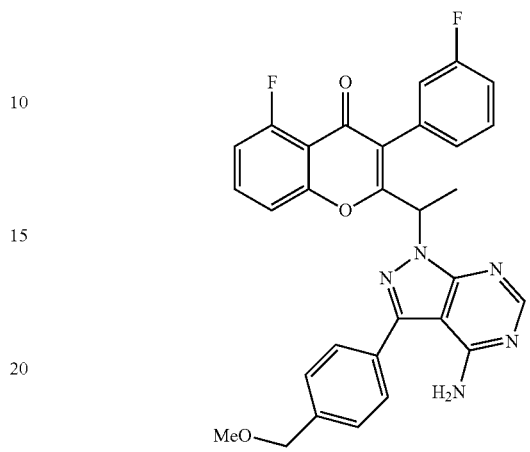 |
| 73. | 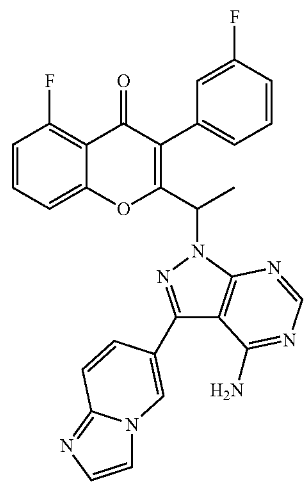 [SMILES: CC(c1oc2cccc(F)c2c(=O)c1-c1cccc(F)c1)n1nc(-c2ccc3nccn3c2)c2c(N)ncnc21] |
| 74. | 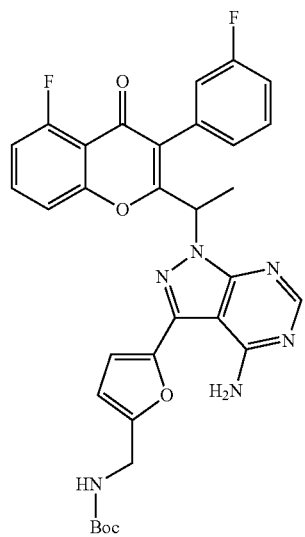 [SMILES: CC(c1oc2cccc(F)c2c(=O)c1-c1cccc(F)c1)n1nc(-c2ccc(CNC(=O)OC(C)(C)C)o2)c2c(N)ncnc21] |

TABLE-1-continued
| Ex. | Structure |
|---|---|
| 75. | 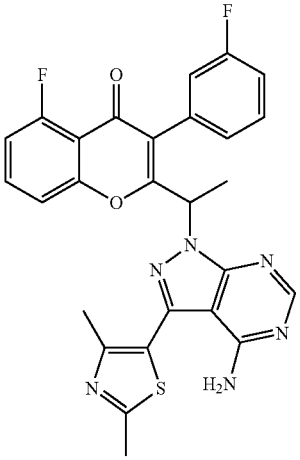 [SMILES: Cc1nc(C)c(-c2nn(C(C)c3oc4cccc(F)c4c(=O)c3-c3cccc(F)c3)c3ncnc(N)c23)s1] |
| 76. | 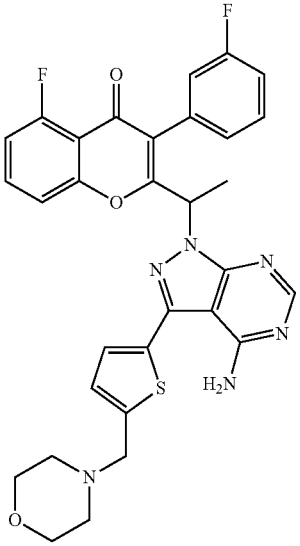 [SMILES: CC(c1oc2cccc(F)c2c(=O)c1-c1cccc(F)c1)n1nc(-c2ccc(CN3CCOCC3)s2)c2c(N)ncnc21] |
| 77. | 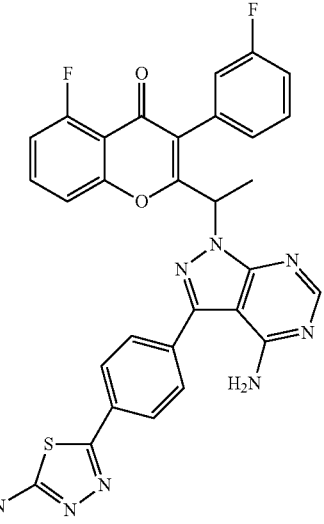 |
TABLE-1-continued
| Ex. | Structure |
|---|---|
| 78. | 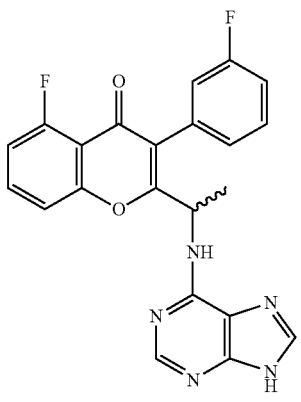 [SMILES: CC(Nc1ncnc2[nH]cnc12)c1oc2cccc(F)c2c(=O)c1-c1cccc(F)c1] |
| 79. | 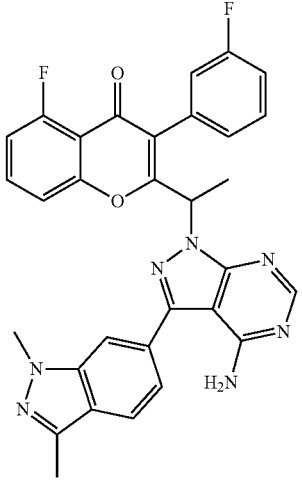 [SMILES: Cc1nn(C)c2cc(-c3nn(C(C)c4oc5cccc(F)c5c(=O)c4-c4cccc(F)c4)c4ncnc(N)c34)ccc12] |
| 80. | 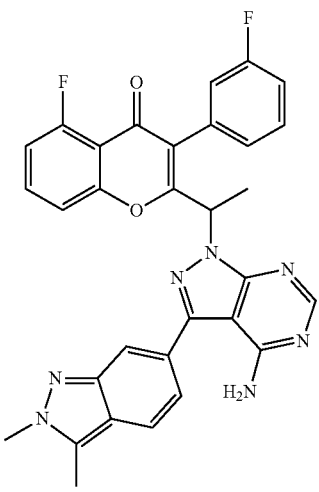 [SMILES: Cc1c2ccc(-c3nn(C(C)c4oc5cccc(F)c5c(=O)c4-c4cccc(F)c4)c4ncnc(N)c34)cc2nn1C] |

TABLE-1-continued
| Ex. | Structure |
|---|---|
| 81. | 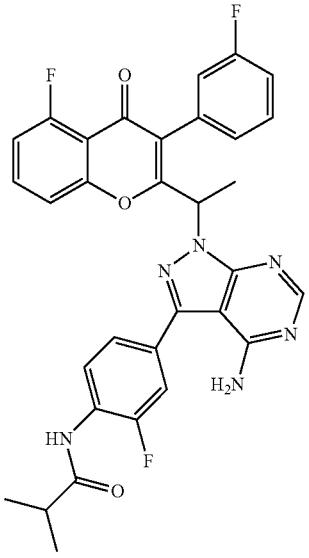 [SMILES: CC(C)C(=O)Nc1ccc(-c2nn(C(C)c3oc4cccc(F)c4c(=O)c3-c3cccc(F)c3)c3ncnc(N)c23)cc1F] |
| 82. | 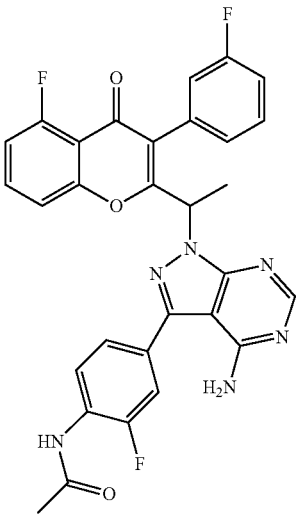 [SMILES: CC(=O)Nc1ccc(-c2nn(C(C)c3oc4cccc(F)c4c(=O)c3-c3cccc(F)c3)c3ncnc(N)c23)cc1F] |
| 83. | 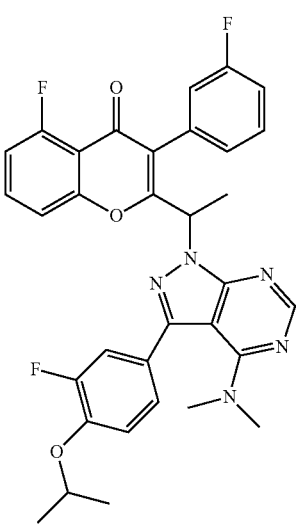 [SMILES: CC(C)Oc1ccc(-c2nn(C(C)c3oc4cccc(F)c4c(=O)c3-c3cccc(F)c3)c3ncnc(N(C)C)c23)cc1F] |
| 84. | 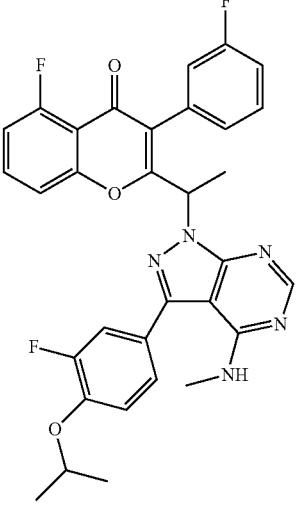 |
| 85. | 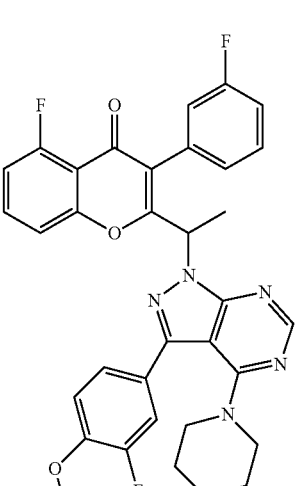 |
| 86. | 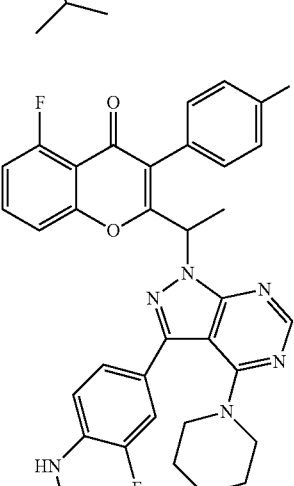 |

TABLE-1-continued

| Ex. | Structure |
|---|---|
| 87. | (structure) |
| 88. | (structure) ·H₂SO₄ |
| 89. | (structure) ·C₆H₅SO₃H |
| 90. | (structure) ·camphorsulfonic acid |
| 91. | (structure) |
| 92. | (structure) |

TABLE-1-continued
| Ex. | Structure |
|---|---|
| 93. | 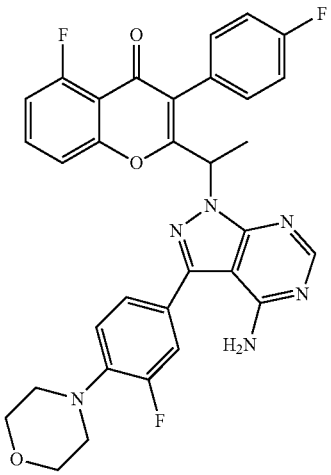 [SMILES: CC(c1oc2cccc(F)c2c(=O)c1-c1ccc(F)cc1)n1nc(-c2ccc(N3CCOCC3)c(F)c2)c2c(N)ncnc21] |
| 94. | 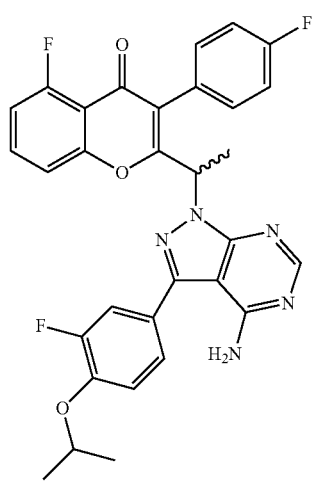 [SMILES: CC(C)Oc1ccc(-c2nn(C(C)c3oc4cccc(F)c4c(=O)c3-c3ccc(F)cc3)c3ncnc(N)c23)cc1F] |
| 95. | 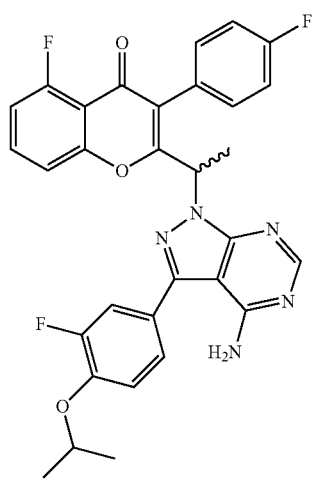 [SMILES: CC(C)Oc1ccc(-c2nn(C(C)c3oc4cccc(F)c4c(=O)c3-c3ccc(F)cc3)c3ncnc(N)c23)cc1F] |
| 96. | 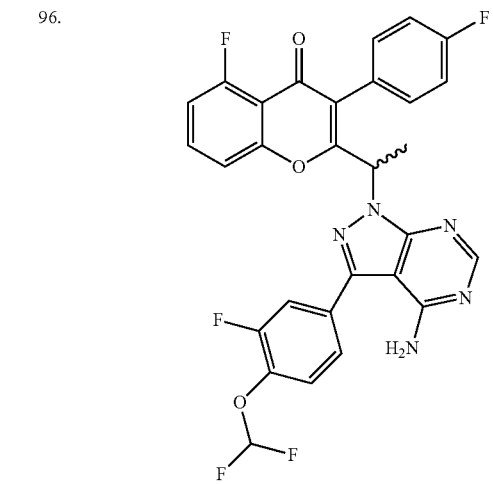 |
| 97. | 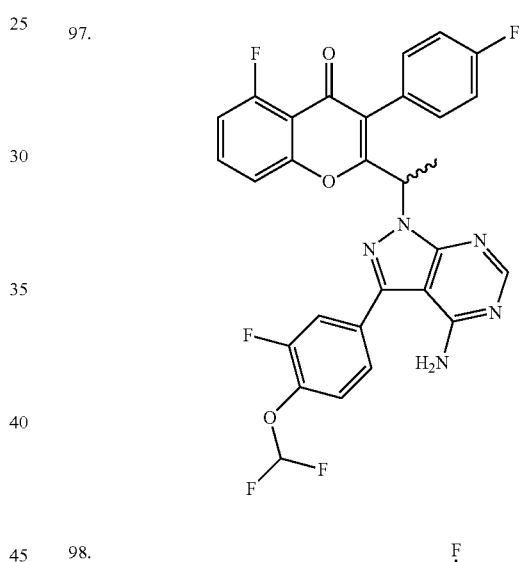 |
| 98. | 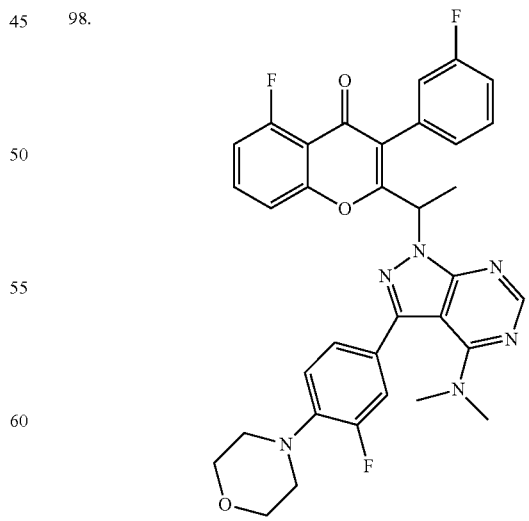 |

TABLE-1-continued
| Ex. | Structure |
|---|---|
| 99. | 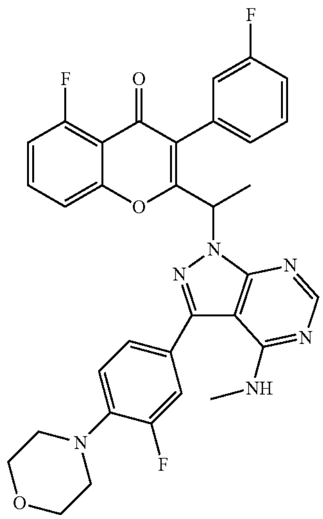 [SMILES: CNc1ncnc2c1c(-c1ccc(N3CCOCC3)c(F)c1)nn2C(C)c1oc2cccc(F)c2c(=O)c1-c1cccc(F)c1] |
| 100. | 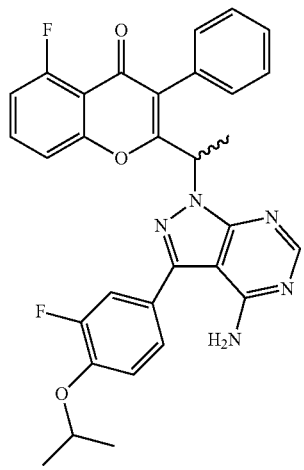 [SMILES: CC(C)Oc1ccc(-c2nn(C(C)c3oc4cccc(F)c4c(=O)c3-c3ccccc3)c3ncnc(N)c23)cc1F] |
| 101. | 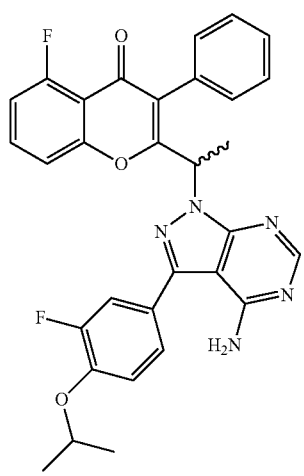 [SMILES: CC(C)Oc1ccc(-c2nn(C(C)c3oc4cccc(F)c4c(=O)c3-c3ccccc3)c3ncnc(N)c23)cc1F] |
TABLE-1-continued
| Ex. | Structure |
|---|---|
| 102. | 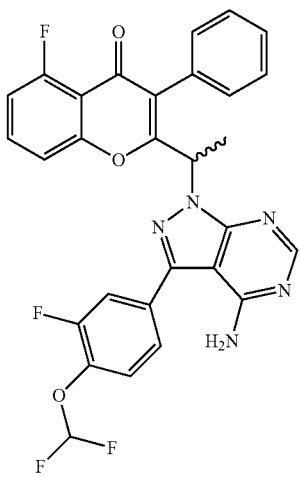 [SMILES: CC(c1oc2cccc(F)c2c(=O)c1-c1ccccc1)n1nc(-c2ccc(OC(F)F)c(F)c2)c2c(N)ncnc21] |
| 103. | 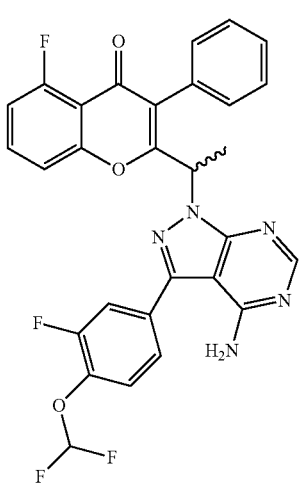 [SMILES: CC(c1oc2cccc(F)c2c(=O)c1-c1ccccc1)n1nc(-c2ccc(OC(F)F)c(F)c2)c2c(N)ncnc21] |
| 104. | 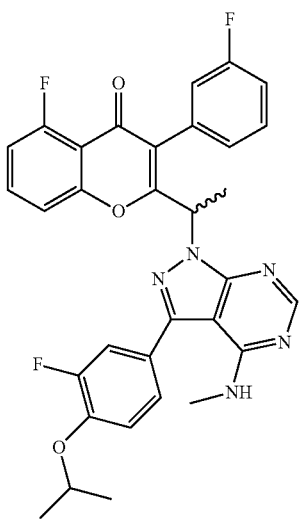 [SMILES: CNc1ncnc2c1c(-c1ccc(OC(C)C)c(F)c1)nn2C(C)c1oc2cccc(F)c2c(=O)c1-c1cccc(F)c1] |

TABLE-1-continued
| Ex. | Structure |
|---|---|
| 105. | 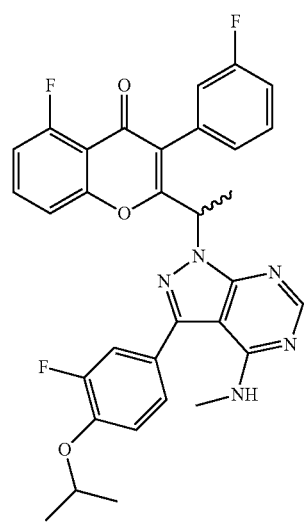 [SMILES: CNc1ncnc2c1c(-c1ccc(OC(C)C)c(F)c1)nn2C(C)c1oc2cccc(F)c2c(=O)c1-c1cccc(F)c1] |
| 106. | 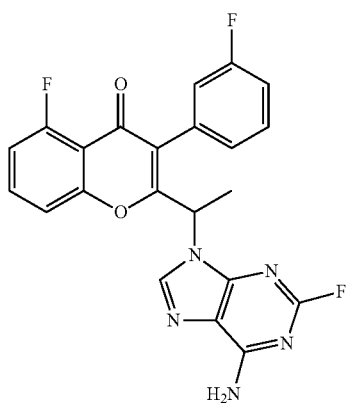 [SMILES: CC(c1oc2cccc(F)c2c(=O)c1-c1cccc(F)c1)n1cnc2c(N)nc(F)nc21] |
| 107. | 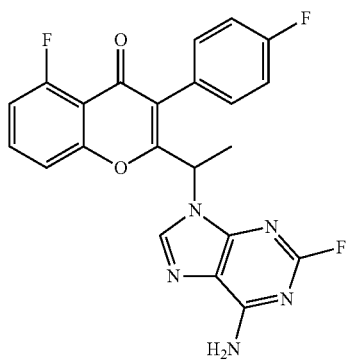 [SMILES: CC(c1oc2cccc(F)c2c(=O)c1-c1ccc(F)cc1)n1cnc2c(N)nc(F)nc21] |
TABLE-1-continued
| Ex. | Structure |
|---|---|
| 108. | 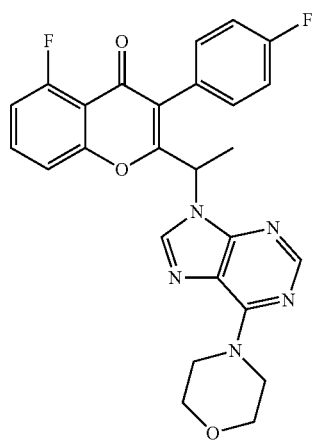 [SMILES: CC(c1oc2cccc(F)c2c(=O)c1-c1ccc(F)cc1)n1cnc2c(N3CCOCC3)ncnc21] |
| 109. | 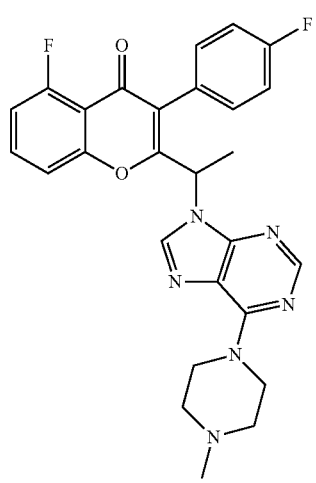 [SMILES: CC(c1oc2cccc(F)c2c(=O)c1-c1ccc(F)cc1)n1cnc2c(N3CCN(C)CC3)ncnc21] |
| 110. | 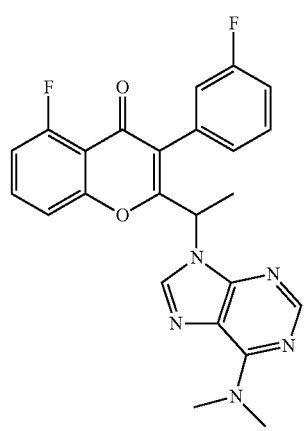 [SMILES: CC(c1oc2cccc(F)c2c(=O)c1-c1cccc(F)c1)n1cnc2c(N(C)C)ncnc21] |

TABLE-1-continued

| Ex. | Structure |
|---|---|
| 111. | 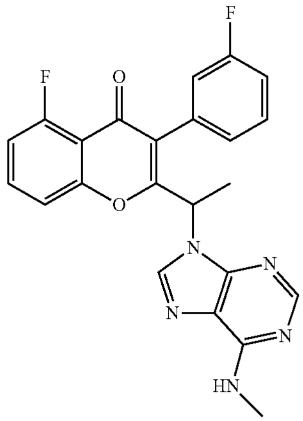 [SMILES: CNc1ncnc2c1ncn2C(C)c1oc2cccc(F)c2c(=O)c1-c1cccc(F)c1] |
| 112. | 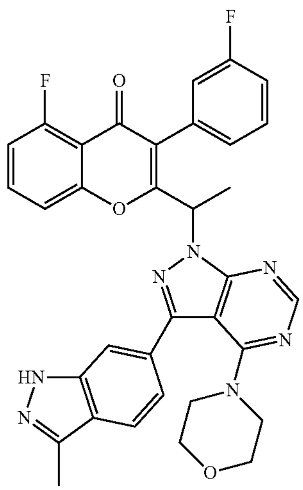 [SMILES: Cc1n[nH]c2cc(-c3nn(C(C)c4oc5cccc(F)c5c(=O)c4-c4cccc(F)c4)c4ncnc(N5CCOCC5)c34)ccc12] |
| 113. | 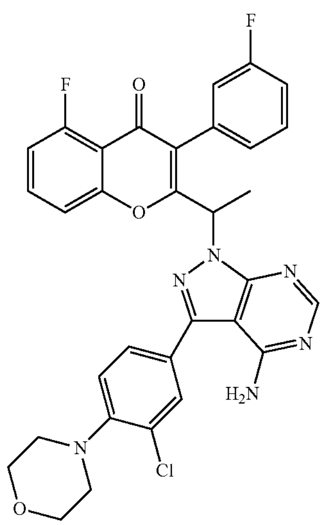 [SMILES: CC(c1oc2cccc(F)c2c(=O)c1-c1cccc(F)c1)n1nc(-c2ccc(N3CCOCC3)c(Cl)c2)c2c(N)ncnc21] |
| 114. | |
| 115. | |
| 116. | |

TABLE-1-continued
| Ex. | Structure |
|---|---|
| 117. | 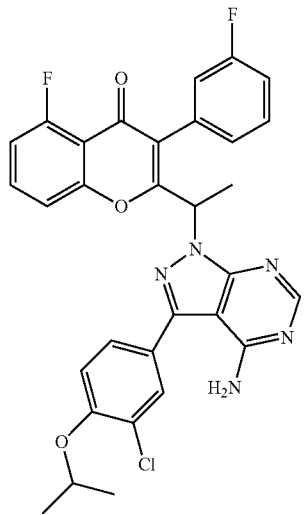 [SMILES: CC(C)Oc1ccc(-c2nn(C(C)c3oc4cccc(F)c4c(=O)c3-c3cccc(F)c3)c3ncnc(N)c23)cc1Cl] |
| 118. | 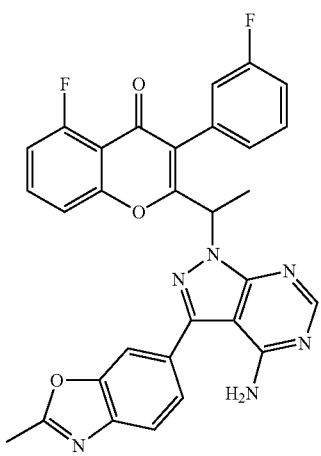 [SMILES: Cc1nc2ccc(-c3nn(C(C)c4oc5cccc(F)c5c(=O)c4-c4cccc(F)c4)c4ncnc(N)c34)cc2o1] |
| 119. | 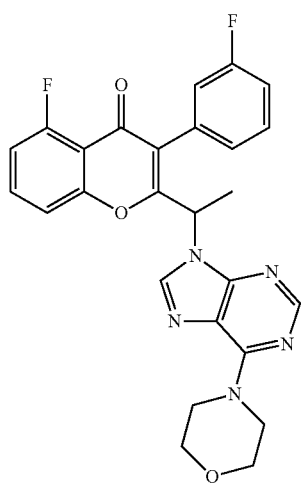 [SMILES: CC(c1oc2cccc(F)c2c(=O)c1-c1cccc(F)c1)n1cnc2c(N3CCOCC3)ncnc21] |
| 120. | 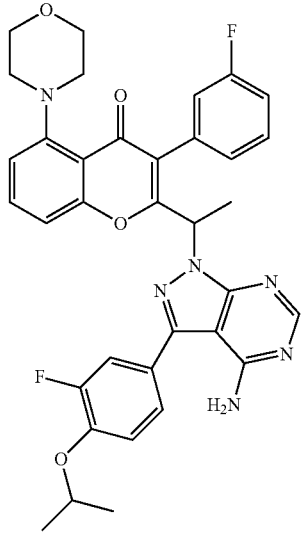 [SMILES: CC(C)Oc1ccc(-c2nn(C(C)c3oc4cccc(N5CCOCC5)c4c(=O)c3-c3cccc(F)c3)c3ncnc(N)c23)cc1F] |
| 121. | 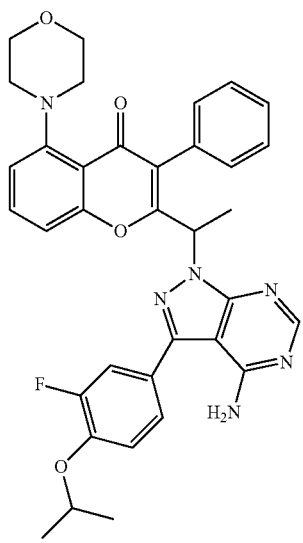 [SMILES: CC(C)Oc1ccc(-c2nn(C(C)c3oc4cccc(N5CCOCC5)c4c(=O)c3-c3ccccc3)c3ncnc(N)c23)cc1F] |
| 122. | 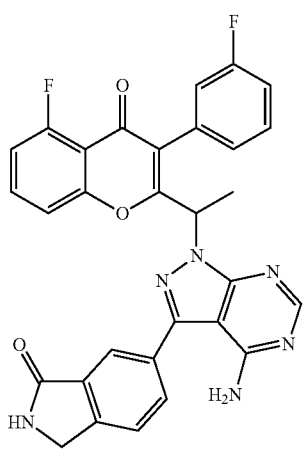 [SMILES: CC(c1oc2cccc(F)c2c(=O)c1-c1cccc(F)c1)n1nc(-c2ccc3c(c2)C(=O)NC3)c2c(N)ncnc21] |

TABLE-1-continued

| Ex. | Structure |
|---|---|
| 123. | (structure) |
| 124. | (structure) |
| 125. | (structure) |
| 126. | (structure) |
| 127. | (structure) |
| 128. | (structure) |

TABLE-1-continued

| Ex. | Structure |
|---|---|
| 129. | 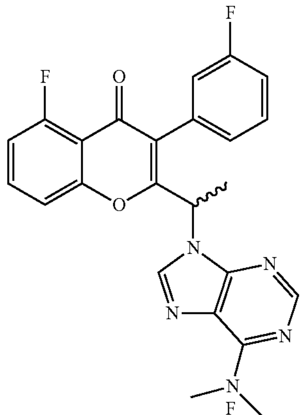 [SMILES: CC(c1oc2cccc(F)c2c(=O)c1-c1cccc(F)c1)n1cnc2c(N(C)C)ncnc21] |
| 130. | 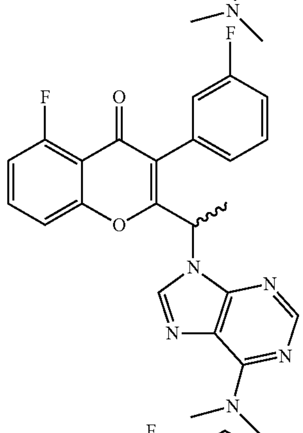 |
| 131. | 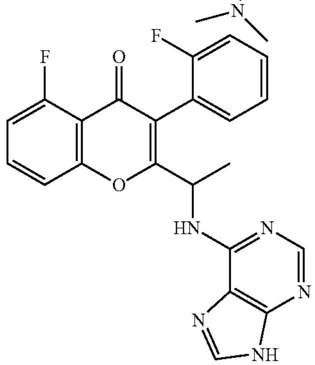 |
| 132. | 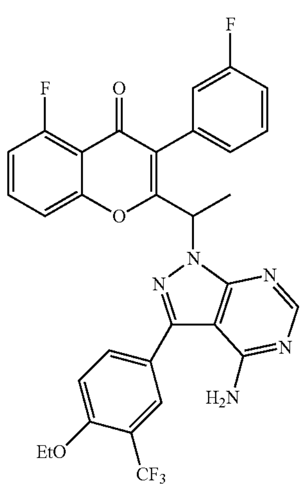 [SMILES: CCOc1ccc(-c2nn(C(C)c3oc4cccc(F)c4c(=O)c3-c3cccc(F)c3)c3ncnc(N)c23)cc1C(F)(F)F] |
| 133 | |
| 134 | |
| 135 | |

TABLE-1-continued

| Ex. | Structure |
|---|---|
| 136 | 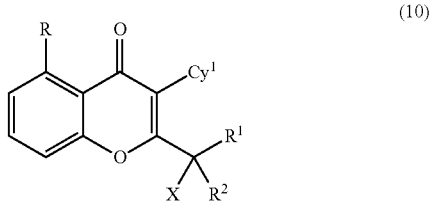 |
| 137 | 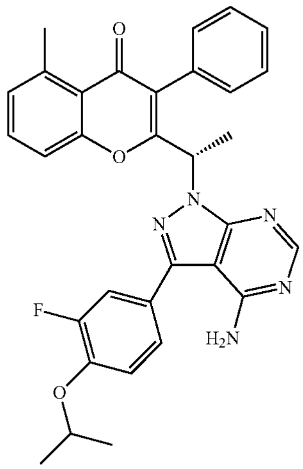 [SMILES: Cc1cccc2oc([C@H](C)n3nc(-c4ccc(OC(C)C)c(F)c4)c4c(N)ncnc43)c(-c3ccccc3)c(=O)c12] |
| 138 | 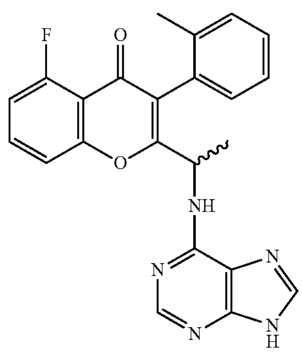 [SMILES: Cc1ccccc1-c1c(C(C)Nc2ncnc3[nH]cnc23)oc2cccc(F)c2c1=O] |

Yet another embodiment of the present invention is a compound of formula

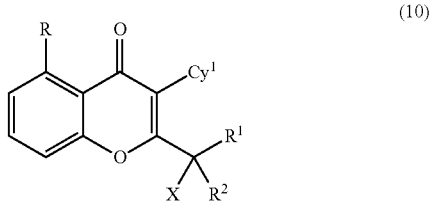

(10)

wherein the variables are the same as defined above.

Yet another embodiment of the present invention is a process for preparing the compound of formula

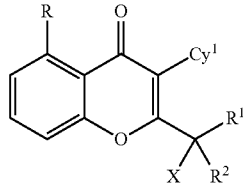

(10)

comprising the steps as depicted in scheme 1 below.

Yet another embodiment of the present invention is a compound of formula

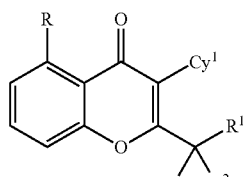

(12)

wherein the variables are the same as defined above.

Yet another embodiment of the present invention is a process for preparing the compound of formula

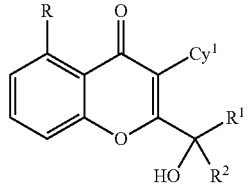

(12)

comprising the steps as depicted and described in scheme 1A below.

Yet another embodiment of the present invention is a process for preparing the compound of formula (I) comprising the steps of converting a compound of formula (10) as depicted and described in Scheme 2, 3 or 4 below.

Yet another embodiment of the present invention is a process for preparing the compound of formula (I) comprising the steps of converting compound of formula (12) as depicted and described in Scheme 2, 3 or 4 below.

Yet another embodiment of the present invention is a process for preparing the compound of formula (10), (14) or (15) comprising the steps of converting compound of formula (12) as depicted and described in Scheme 1A below.

Yet another embodiment of the present invention is a method for inhibiting PI3K in a patient by administering to the patient an effective amount of at least one compound of the present invention (for instance, a compound of formula (I), (IA), (IA-I), (IA-II), (IA-III) (IA-IV), (IA-V), (IA-VI), (IA-VII), (IA-VIII), (IA-Ia), (IA-IIa), (IA-IIIa), (IA-Ib) or (IA-IIb) as defined above).

Yet another embodiment of the present invention is a method for treating a proliferative disease via modulation of a protein kinase (such as PI3K) by administering to a patient in need of such treatment an effective amount of at least one compound of the present invention. In one embodiment, the compound of the present invention inhibits a protein kinase (such as PI3K).

Yet another embodiment of the present invention is a method for treating a proliferative disease via modulation of a protein kinase (such as PI3K) by administering to a patient in need of such treatment an effective amount of at least one compound of the present invention, in combination (simultaneously or sequentially) with at least one other anti-cancer agent. In one embodiment, the compound of formula I), (IA), (IA-I), (IA-II), (IA-III) (IA-IV), (IA-V), (IA-VI), (IA-VII), (IA-VIII), (IA-Ia), (IA-IIa), (IA-IIIa), (IA-Ib) or (IA-IIb) inhibits a protein kinase (such as PI3K).

More particularly, the compounds of formula I), (IA), (IA-I), (IA-II), (IA-III) (IA-IV), (IA-V), (IA-VI), (IA-VII), (IA-VIII), (IA-Ia), (IA-IIa), (IA-IIIa), (IA-Ib) or (IA-IIb) and pharmaceutically acceptable esters or salts thereof can be administered for the treatment, prevention and/or amelioration of PI3K and related protein kinase mediated diseases or disorders, including but not limited to, cancer and other proliferative diseases or disorders.

The compounds of the present invention are useful in the treatment of a variety of cancers, including, but not limited to, the following:

carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma;

hematopoietic tumors of myeloid lineage, including acute and chronic myelogenous leukemias, myelodysplastic syndrome and promyelocytic leukemia;

tumors of mesenchymal origin, including fibrosarcoma and rhabdomyosarcoma;

tumors of the central and peripheral nervous system, including astrocytoma, neuroblastoma, glioma and schwannomas; and other tumors, including melanoma, seminoma, teratocarcinoma, osteosarcoma, xenoderoma pigmentosum, keratoctanthoma, thyroid follicular cancer and Kaposi's sarcoma.

Due to the key role of protein kinases in the regulation of cellular proliferation in general, the protein kinase inhibitors of the present invention could act as reversible cytostatic agents which may be useful in the treatment of any disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulonephritis, restenosis following angioplasty or vascular surgery, hypertrophic scar formation, inflammatory bowel disease, transplantation rejection, endotoxic shock, and fungal infections.

The compounds of the present invention as modulators of apoptosis are useful in the treatment of cancer (including but not limited to those types mentioned herein above), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

The compounds of present invention can modulate the level of cellular RNA and DNA synthesis. These agents are therefore useful in the treatment of viral infections (including but not limited to HIV, human papilloma virus, herpesvirus, poxvirus, Epstein-Barr virus, Sindbis virus and adenovirus).

The compounds of the present invention are useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse. The compounds are also useful in inhibiting tumor angiogenesis and metastasis. One embodiment of the invention is a method of inhibiting tumor angiogenesis or metastasis in a patient in need thereof by administering an effective amount of one or more compounds of the present invention.

Another embodiment of the present invention is a method of treating an immune system-related disease (e.g., an autoimmune disease), a disease or disorder involving inflammation (e.g., asthma, chronic obstructive pulmonary disease, rheumatoid arthritis, inflammatory bowel disease, glomerulonephritis, neuroinflammatory diseases, multiple sclerosis, uveitis and disorders of the immune system), cancer or other proliferative disease, a hepatic disease or disorder, a renal disease or disorder. The method includes administering an effective amount of one or more compounds of the present invention.

Examples of immune disorders include psoriasis, rheumatoid arthritis, vasculitis, inflammatory bowel disease, dermatitis, osteoarthritis, asthma, inflammatory muscle disease, allergic rhinitis, vaginitis, interstitial cystitis, scleroderma, osteoporosis, eczema, allogeneic or xenogeneic transplantation (organ, bone marrow, stem cells and other cells and tissues) graft rejection, graft-versus-host disease, lupus erythematosus, inflammatory disease, type I diabetes, pulmonary fibrosis, dermatomyositis, Sjogren's syndrome, thyroiditis (e.g., Hashimoto's and autoimmune thyroiditis), myasthenia gravis, autoimmune hemolytic anemia, multiple sclerosis, cystic fibrosis, chronic relapsing hepatitis, primary biliary cirrhosis, allergic conjunctivitis and atopic dermatitis.

In one embodiment, the compounds described herein are used as immunosuppresants to prevent transplant graft rejections, allogeneic or xenogeneic transplantation rejection (organ, bone marrow, stem cells, other cells and tissues), and graft-versus-host disease. In other embodiments, transplant graft rejections result from tissue or organ transplants. In further embodiments, graft-versus-host disease results from bone marrow or stem cell transplantation. One embodiment is a method of preventing or decreasing the risk of transplant graft rejection, allogeneic or xenogeneic transplantation rejection (organ, bone marrow, stem cells, other cells and tissues), or graft-versus-host disease by administering an effective amount of one or more compounds of the present invention.

The compounds of the present invention are also useful in combination (administered together or sequentially) with known anti-cancer treatments such as radiation therapy or with cytostatic or cytotoxic or anticancer agents, such as for example, but not limited to, DNA interactive agents, such as cisplatin or doxorubicin; topoisomerase II inhibitors, such as etoposide; topoisomerase I inhibitors such as CPT-11 or topotecan; tubulin interacting agents, such as paclitaxel, docetaxel or the epothilones (for example ixabepilone), either naturally occurring or synthetic; hormonal agents, such as tamoxifen; thymidilate synthase inhibitors, such as 5-fluorouracil; and anti-metabolites, such as methotrexate, other tyrosine kinase inhibitors such as Iressa and OSI-774; angiogenesis inhibitors; EGF inhibitors; VEGF inhibitors; CDK inhibitors; SRC inhibitors; c-Kit inhibitors; Her1/2 inhibitors and monoclonal antibodies directed against growth factor receptors such as erbitux (EGF) and herceptin (Her2) and other protein kinase modulators as well.

The compounds of the present invention are also useful in combination (administered together or sequentially) with one or more steroidal anti-inflammatory drugs, non-steroidal anti-inflammatory drugs (NSAIDs) or Immune Selective Anti-Inflammatory Derivatives (ImSAIDs).

The invention further provides a pharmaceutical composition comprising one or more compounds of the present invention (such as a compound having formula (I), (IA), (IA-I), (IA-II), (IA-III) (IA-IV), (IA-V), (IA-VI), (IA-VII), (IA-VII), (IA-Ia), (IA-IIa), (IA-ma), (IA-Ib) or (IA-IIb)) together with a pharmaceutically acceptable carrier. The pharmaceutical composition may further comprise one or more of the active ingredients identified above, such as other anti-cancer agents.

In one embodiment, the pharmaceutical composition includes a therapeutically effective amount of one or more compounds of formula (I), (IA), (IA-I), (IA-II), (IA-III) (IA-IV), (IA-V), (IA-VI), (IA-VII), (IA-VIII), (IA-Ia), (IA-IIa), (IA-IIIa), (IA-Ib) or (IA-IIb).

Yet another embodiment is a method of treating leukemia in a patient in need thereof by administering a therapeutically effective amount of a compound of the present invention. For example, the compounds of the present invention are effective for treating chronic lymphocytic leukemia (CLL), non-Hodgkin lymphoma (NHL), acute myeloid leukemia (AML), multiple myeloma (MM), small lymphocytic lymphoma (SLL), and indolent non-Hodgkin's lymphoma (I-NHL).

Yet another embodiment is a method of treating allergic rhinitis in a patient in need thereof by administering a therapeutically effective amount of a compound of the present invention.

DETAILED DESCRIPTION OF THE INVENTION

As used herein the following definitions shall apply unless otherwise indicated. Further many of the groups defined herein can be optionally substituted. The listing of substituents in the definition is exemplary and is not to be construed to limit the substituents defined elsewhere in the specification.

The term "alkyl", unless otherwise specified, refers to a straight or branched hydrocarbon chain radical consisting solely of carbon and hydrogen atoms, containing no unsaturation, having from one to eight carbon atoms, and which is attached to the rest of the molecule by a single bond, e.g., methyl, ethyl, n-propyl, 1-methylethyl (isopropyl), n-butyl, n-pentyl, and 1,1-dimethylethyl (t-butyl). The term "($C_{1-6}$) alkyl" refers to an alkyl group as defined above having up to 6 carbon atoms.

The term "alkenyl", unless otherwise specified, refers to an aliphatic hydrocarbon group containing a carbon-carbon double bond and which may be a straight or branched or branched chain having about 2 to about 10 carbon atoms, e.g., ethenyl, 1-propenyl, 2-propenyl (allyl), iso-propenyl, 2-methyl-1-propenyl, 1-butenyl, and 2-butenyl. The term "($C_{2-6}$)alkenyl" refers to an alkenyl group as defined above having up to 6 carbon atoms.

The term "alkynyl", unless otherwise specified, refers to a straight or branched chain hydrocarbyl radical having at least one carbon-carbon triple bond, and having in the range of 2 to up to 12 carbon atoms (with radicals having in the range of 2 to up to 10 carbon atoms presently being preferred) e.g., ethynyl, propynyl, and butynyl. The term "($C_{2-6}$) alkynyl" refers to an alkynyl group as defined above having up to 6 carbon atoms.

The term "alkoxy" unless otherwise specified, denotes an alkyl, cycloalkyl, or cycloalkylalkyl group as defined above attached via an oxygen linkage to the rest of the molecule. The term "substituted alkoxy" refers to an alkoxy group where the alkyl constituent is substituted (i.e., —O-(substituted alkyl) wherein the term "substituted alkyl" is the same as defined above for "alkyl". For example "alkoxy" refers to the group —O-alkyl, including from 1 to 8 carbon atoms of a straight, branched, cyclic configuration and combinations thereof attached to the parent structure through oxygen. Examples include methoxy, ethoxy, propoxy, isopropoxy, cyclopropyloxy, and cyclohexyloxy.

The term "cycloalkyl", unless otherwise specified, denotes a non-aromatic mono or multicyclic ring system of about 3 to 12 carbon atoms such as cyclopropyl, cyclobutyl, cyclopentyl, and cyclohexyl. Examples of multicyclic cycloalkyl groups include perhydronaphthyl, adamantyl and norbornyl groups, bridged cyclic groups, and sprirobicyclic groups, e.g., sprio (4,4) non-2-yl. The term "($C_{3-8}$) cycloalkyl" refers to a cycloalkyl group as defined above having up to 8 carbon atoms.

The term "cycloalkylalkyl", unless otherwise specified, refers to a cyclic ring-containing radical containing in the range of about 3 up to 8 carbon atoms directly attached to an alkyl group which are then attached to the main structure at any carbon from the alkyl group that results in the creation of a stable structure such as cyclopropylmethyl, cyclobutylethyl, and cyclopentylethyl.

The term "cycloalkenyl", unless otherwise specified, refers to cyclic ring-containing radicals containing in the range of about 3 up to 8 carbon atoms with at least one carbon-carbon double bond such as cyclopropenyl, cyclobutenyl, and cyclopentenyl. The term "cycloalkenylalkyl" refers to a cycloalkenyl group directly attached to an alkyl group which are then attached to the main structure at any carbon from the alkyl group that results in the creation of a stable structure.

The term "aryl", unless otherwise specified, refers to aromatic radicals having in the range of 6 up to 20 carbon atoms such as phenyl, naphthyl, tetrahydronaphthyl, indanyl, and biphenyl.

The term "arylalkyl", unless otherwise specified, refers to an aryl group as defined above directly bonded to an alkyl group as defined above, e.g., —$CH_2C_6H_5$ and —$C_2H_5C_6H_5$.

The term "heterocyclic ring", unless otherwise specified, refers to a non-aromatic 3 to 15 member ring radical which consists of carbon atoms and at least one heteroatom selected from nitrogen, phosphorus, oxygen and sulfur. For purposes of this invention, the heterocyclic ring radical may be a mono-, bi-, tri- or tetracyclic ring system, which may include fused, bridged or spiro ring systems, and the nitrogen, phosphorus, carbon, oxygen or sulfur atoms in the heterocyclic ring radical may be optionally oxidized to various oxidation states. In addition, the nitrogen atom may be optionally quaternized. The heterocyclic ring radical may be attached to the main structure at any heteroatom or carbon atom that results in the creation of a stable structure.

The term "heterocyclyl", unless otherwise specified, refers to a heterocylic ring radical as defined above. The heterocyclyl ring radical may be attached to the main structure at any heteroatom or carbon atom that results in the creation of a stable structure.

The term "heterocyclylalkyl", unless otherwise specified, refers to a heterocylic ring radical as defined above directly bonded to an alkyl group. The heterocyclylalkyl radical may be attached to the main structure at carbon atom in the alkyl group that results in the creation of a stable structure. Examples of such heterocycloalkyl radicals include, but are not limited to, dioxolanyl, thienyl[1,3]dithianyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl, piperazinyl, 4-piperidonyl, pyrrolidinyl, pyrazolidinyl, quinuclidinyl, thiazolidinyl, tetrahydrofuryl, trithianyl, tetrahydropyranyl, thiomorpholinyl, thiamorpholinyl, 1-oxo-thiomorpholinyl, and 1,1-dioxo-thiomorpholinyl.

The term "heteroaryl", unless otherwise specified, refers to an optionally substituted 5 to 14 member aromatic ring having one or more heteroatoms selected from N, O, and S as ring atoms. The heteroaryl may be a mono-, bi- or tricyclic ring system. Examples of such "heterocyclic ring" or "heteroaryl" radicals include, but are not limited to, oxazolyl, thiazolyl, imidazolyl, pyrrolyl, furanyl, pyridinyl, pyrimidinyl, pyrazinyl, benzofuranyl, indolyl, benzothiazolyl, benzoxazolyl, carbazolyl, quinolyl, isoquinolyl, azetidinyl, acridinyl, benzodioxolyl, benzodioxanyl, benzofuranyl, carbazolyl, cinnolinyl, dioxolanyl, indolizinyl, naphthyridinyl, perhydroazepinyl, phenazinyl, phenothiazinyl, phenoxazinyl, phthalazinyl, pteridinyl, purinyl, quinazolinyl, quinoxalinyl, tetrazoyl, tetrahydroisoquinolyl, piperidinyl, piperazinyl, 2-oxopiperazinyl, 2-oxopiperidinyl, 2-oxopyrrolidinyl, 2-oxoazepinyl, azepinyl, 4-piperidonyl, pyrrolidinyl, pyridazinyl, oxazolinyl, oxazolidinyl, triazolyl, indanyl, isoxazolyl, isoxazolidinyl, morpholinyl, thiazolinyl, thiazolidinyl, isothiazolyl, quinuclidinyl, isothiazolidinyl, isoindolyl, indolinyl, isoindolinyl, octahydroindolyl, octahydroisoindolyl, decahydroisoquinolyl, benzimidazolyl, thiadiazolyl, benzopyranyl, tetrahydrofuryl, tetrahydropyranyl, thienyl, benzothienyl, thiamorpholinyl, thiamorpholinyl sulfoxide, thiamorpholinyl sulfone, dioxaphospholanyl, oxadiazolyl, chromanyl, and isochromanyl. The heteroaryl ring radical may be attached to the main structure at any heteroatom or carbon atom that results in the creation of a stable structure. The term "substituted heteroaryl" also includes ring systems substituted with one or more oxide (—O—) substituents, such as pyridinyl N-oxides.

The term "heteroarylalkyl", unless otherwise specified, refers to a heteroaryl ring radical as defined above directly bonded to an alkyl group. The heteroarylalkyl radical may be attached to the main structure at any carbon atom from alkyl group that results in the creation of a stable structure.

The term "cyclic ring" refers to a cyclic ring containing 3 to 10 carbon atoms.

The term "substituted" unless otherwise specified, refers to substitution with any one or any combination of the following substituents which may be the same or different and are independently selected from hydrogen, hydroxy, halogen, carboxyl, cyano, nitro, oxo (=O), thio (=S), substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted cycloalkenylalkyl, substituted or unsubstituted heteroaryl, substituted or unsubstituted heteroarylalkyl, substituted or unsubstituted heterocyclic ring, substituted heterocyclylalkyl ring, substituted or unsubstituted guanidine, —COOR$^x$, —C(O)R$^x$, —C(S)R$^x$, —C(O)NR$^x$R$^y$, —C(O)ONR$^x$R$^y$, —NR$^y$R$^z$, —NR$^x$CONR$^y$R$^z$, —N(R$^x$)SOR$^y$, —N(R$^x$)SO$_2$R$^y$, —(=N—N(R$^x$)R$^y$), —NR$^x$C(O)OR$^y$, —NR$^x$R$^y$, —NR$^x$C(O)R$^y$—, —NR$^x$C(S)R$^y$—NR$^x$C(S)NR$^y$R$^z$, —SONR$^x$R$^y$—, —SO$_2$NR$^x$R$^y$—, —OR, —OR$^x$C(O)NR$^y$R$^z$, —OR$^x$C(O)OR$^y$—, —OC(O)R$^x$, —OC(O)NR$^x$R$^y$, —R$^x$NR$^y$C(O)R$^z$, —R$^x$OR$^y$, —R$^x$C(O) OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, and —ONO$_2$, wherein R$^x$, R$^y$ and R$^z$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted amino, substituted or unsubstituted heteroaryl, substituted or unsubstituted heteroarylalkyl, substituted or unsubstituted heterocyclic ring, or substituted heterocyclylalkyl ring, or any two of R$^x$, R$^y$ and R$^z$ may be joined to form a substituted or unsubstituted saturated or unsaturated 3-10 membered ring, which may optionally include heteroatoms which may be the same or different and are selected from O, NR$^x$ (e.g., R$^x$ can be hydrogen or C$_{1-6}$ alkyl) or S. Substitution or the combinations of substituents envisioned by this invention are preferably those that result in the formation of a stable or chemically feasible compound. The term stable as used herein refers to the compounds or the structure that are not substantially altered when subjected to conditions to allow for their production, detection and preferably their recovery, purification and incorporation into a pharmaceutical composition. The substituents in the aforementioned "substituted" groups cannot be further substituted. For example, when the substituent on "substituted alkyl" is "substituted aryl", the substituent on "substituted aryl" cannot be "substituted alkenyl".

The term "halo", "halide", or, alternatively, "halogen" means fluoro, chloro, bromo or iodo. The terms "haloalkyl," "haloalkenyl," "haloalkynyl" and "haloalkoxy" include alkyl, alkenyl, alkynyl and alkoxy structures that are substituted with one or more halo groups or with combinations thereof. For example, the terms "fluoroalkyl" and "fluoroalkoxy" include haloalkyl and haloalkoxy groups, respectively, in which the halo is fluorine.

The term "protecting group" or "PG" refers to a substituent that is employed to block or protect a particular functionality. Other functional groups on the compound may remain reactive. For example, an "amino-protecting group" is a substituent attached to an amino group that blocks or protects the amino functionality in the compound. Suitable amino-protecting groups include, but are not limited to, acetyl, trifluoroacetyl, tert-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable hydroxy-protecting groups include, but are not limited to, acetyl and silyl. A "carboxyprotecting group" refers to a substituent of the carboxy group that blocks or protects the carboxy functionality. Suitable carboxy-protecting groups include, but are not limited to, —$CH_2CH_2SO_2Ph$, cyanoethyl, 2-(trimethylsilyl)ethyl, 2-(trimethylsilyl)ethoxymethyl, -2-(p-toluenesulfonyl)ethyl, 2-(p-nitrophenylsulfenyl)ethyl, 2-(diphenylphosphino)-ethyl, and nitroethyl. For a general description of protecting groups and their use, see T. W. Greene, Protective Groups in Organic Synthesis, John Wiley & Sons, New York, 1991.

Certain of the compounds described herein contain one or more asymmetric centers and can thus give rise to enantiomers, diastereomers, and other stereoisomeric forms that can be defined, in terms of absolute stereochemistry, as (R)- or (S)—. The present chemical entities, pharmaceutical compositions and methods are meant to include all such possible isomers, including racemic mixtures, optically pure forms and intermediate mixtures. For the instance the non-limiting example of intermediate mixtures include a mixture of isomers in a ratio of 10:90, 13:87, 17:83, 20:80, or 22:78. Optically active (R)- and (S)-isomers can be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers.

The term "tautomers" refers to compounds, which are characterized by relatively easy interconversion of isomeric forms in equilibrium. These isomers are intended to be covered by this invention. "Tautomers" are structurally distinct isomers that interconvert by tautomerization. "Tautomerization" is a form of isomerization and includes prototropic or proton-shift tautomerization, which is considered a subset of acid-base chemistry. "Prototropic tautomerization" or "proton-shift tautomerization" involves the migration of a proton accompanied by changes in bond order, often the interchange of a single bond with an adjacent double bond. Where tautomerization is possible (e.g. in solution), a chemical equilibrium of tautomers can be reached. An example of tautomerization is keto-enol tautomerization. A specific example of keto-enol tautomerization is the interconversion of pentane-2,4-dione and 4-hydroxypent-3-en-2-one tautomers. Another example of tautomerization is phenol-keto tautomerization. A specific example of phenol-keto tautomerization is the interconversion of pyridin-4-ol and pyridin-4(1H)-one tautomers.

A "leaving group or atom" is any group or atom that will, under the reaction conditions, cleave from the starting material, thus promoting reaction at a specified site. Suitable examples of such groups unless otherwise specified are halogen atoms and mesyloxy, p-nitrobenzensulphonyloxy and tosyloxy groups.

The term "prodrug" refers to a compound, which is an inactive precursor of a compound, converted into its active form in the body by normal metabolic processes. Prodrug design is discussed generally in Hardma, et al. (Eds.), Goodman and Gilman's The Pharmacological Basis of Therapeutics, 9th ed., pp. 11-16 (1996). A thorough discussion is provided in Higuchi, et al., Prodrugs as Novel Delivery Systems, Vol. 14, ASCD Symposium Series, and in Roche (ed.), Bioreversible Carriers in Drug Design, American Pharmaceutical Association and Pergamon Press (1987). To illustrate, prodrugs can be converted into a pharmacologically active form through hydrolysis of, for example, an ester or amide linkage, thereby introducing or exposing a functional group on the resultant product. The prodrugs can be designed to react with an endogenous compound to form a water-soluble conjugate that further enhances the pharmacological properties of the compound, for example, increased circulatory half-life. Alternatively, prodrugs can be designed to undergo covalent modification on a functional group with, for example, glucuronic acid, sulfate, glutathione, amino acids, or acetate. The resulting conjugate can be inactivated and excreted in the urine, or rendered more potent than the parent compound. High molecular weight conjugates also can be excreted into the bile, subjected to enzymatic cleavage, and released back into the circulation, thereby effectively increasing the biological half-life of the originally administered compound.

The term "ester" refers to a compound, which is formed by reaction between an acid and an alcohol with elimination of water. An ester can be represented by the general formula RCOOR'.

These prodrugs and esters are intended to be covered within the scope of this invention.

Additionally the instant invention also includes the compounds which differ only in the presence of one or more isotopically enriched atoms for example replacement of hydrogen with deuterium or tritium, or the replacement of a carbon by $^{13}C$- or $^{14}C$-enriched carbon.

The compounds of the present invention may also contain unnatural proportions of atomic isotopes at one or more of atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present invention, whether radioactive or not, are encompassed within the scope of the present invention.

Pharmaceutically acceptable salts forming part of this invention include salts derived from inorganic bases such as Li, Na, K, Ca, Mg, Fe, Cu, Zn, and Mn; salts of organic bases such as N,N'-diacetylethylenediamine, glucamine, triethylamine, choline, hydroxide, dicyclohexylamine, metformin, benzylamine, trialkylamine, and thiamine; chiral bases such as alkylphenylamine, glycinol, and phenyl glycinol; salts of natural amino acids such as glycine, alanine, valine, leucine, isoleucine, norleucine, tyrosine, cystine, cysteine, methionine, proline, hydroxy proline, histidine, ornithine, lysine, arginine, and serine; quaternary ammonium salts of the compounds of invention with alkyl halides, alkyl sulphates such as MeI and $(Me)_2SO_4$; non-natural amino acids such as D-isomers or substituted amino acids; guanidine; and substituted guanidine wherein the substituents are selected from nitro, amino, alkyl, alkenyl, alkynyl, ammonium or substituted ammonium salts and aluminum salts. Salts may include acid addition salts where appropriate which are sulphates, nitrates, phosphates, perchlorates, borates, hydrohalides, acetates, tartrates, maleates, citrates, fumarates, succinates, palmoates, methanesulphonates, benzoates, salicylates, benzenesulfonates, ascorbates, glycerophosphates, and ketoglutarates.

When ranges are used herein for physical properties, such as molecular weight, or chemical properties, such as chemical formulae, all combinations and subcombinations of ranges and specific embodiments therein are intended to be included. The term "about" when referring to a number or a numerical range means that the number or numerical range referred to is an approximation within experimental variability (or within statistical experimental error), and thus the number or numerical range may vary from, for example, between 1% and 15% of the stated number or numerical range. The term "comprising" (and related terms such as "comprise" or "comprises" or "having" or "including") includes those embodiments, for example, an embodiment of any composition of matter, composition, method, or process, or the like, that "consist of" or "consist essentially of" the described features.

The following abbreviations and terms have the indicated meanings throughout: PI3-K=Phosphoinositide 3-kinase; PI=phosphatidylinositol; PDK=Phosphoinositide Dependent Kinase; DNA-PK=Deoxyribose Nucleic Acid Dependent Protein Kinase; PTEN=Phosphatase and Tensin homolog deleted on chromosome Ten; PIKK=Phosphoinositide Kinase Like Kinase; AIDS=Acquired Immuno Deficiency Syndrome; HIV=Human Immunodeficiency Virus; MeI=Methyl Iodide; POCI$_3$=Phosphorous Oxychloride; KCNS=Potassium Iso-Thiocyanate; TLC=Thin Layer Chromatography; MeOH=Methanol; and CHCI$_3$=Chloroform.

Abbreviations used herein have their conventional meaning within the chemical and biological arts.

The term "cell proliferation" refers to a phenomenon by which the cell number has changed as a result of division. This term also encompasses cell growth by which the cell morphology has changed (e.g., increased in size) consistent with a proliferative signal.

The term "co-administration," "administered in combination with," and their grammatical equivalents, as used herein, encompasses administration of two or more agents to an animal so that both agents and/or their metabolites are present in the animal at the same time. Co-administration includes simultaneous administration in separate compositions, administration at different times in separate compositions, or administration in a composition in which both agents are present.

The term "effective amount" or "therapeutically effective amount" refers to that amount of a compound described herein that is sufficient to effect the intended application including but not limited to disease treatment, as defined below. The therapeutically effective amount may vary depending upon the intended application (in vitro or in vivo), or the subject and disease condition being treated, e.g., the weight and age of the subject, the severity of the disease condition, the manner of administration and the like, which can readily be determined by one of ordinary skill in the art. The term also applies to a dose that will induce a particular response in target cells, e.g. reduction of platelet adhesion and/or cell migration. The specific dose will vary depending on the particular compounds chosen, the dosing regimen to be followed, whether it is administered in combination with other compounds, timing of administration, the tissue to which it is administered, and the physical delivery system in which it is carried.

As used herein, "treatment," "treating," or "ameliorating" are used interchangeably. These terms refers to an approach for obtaining beneficial or desired results including but not limited to therapeutic benefit and/or a prophylactic benefit. By therapeutic benefit is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

A "therapeutic effect," as that term is used herein, encompasses a therapeutic benefit and/or a prophylactic benefit as described above. A prophylactic effect includes delaying or eliminating the appearance of a disease or condition, delaying or eliminating the onset of symptoms of a disease or condition, slowing, halting, or reversing the progression of a disease or condition, or any combination thereof.

The term "subject" or "patient" refers to an animal, such as a mammal, for example a human. The methods described herein can be useful in both human therapeutics and veterinary applications. In some embodiments, the patient is a mammal, and in some embodiments, the patient is human.

"Radiation therapy" means exposing a patient, using routine methods and compositions known to the practitioner, to radiation emitters such as alpha-particle emitting radionuclides (e.g., actinium and thorium radionuclides), low linear energy transfer (LET) radiation emitters (i.e. beta emitters), conversion electron emitters (e.g. strontium-89 and samarium-153-EDTMP, or high-energy radiation, including without limitation x-rays, gamma rays, and neutrons.

"Signal transduction" is a process during which stimulatory or inhibitory signals are transmitted into and within a cell to elicit an intracellular response. A modulator of a signal transduction pathway refers to a compound which modulates the activity of one or more cellular proteins mapped to the same specific signal transduction pathway. A modulator may augment (agonist) or suppress (antagonist) the activity of a signaling molecule.

The term "selective inhibition" or "selectively inhibit" as applied to a biologically active agent refers to the agent's ability to selectively reduce the target signaling activity as compared to off-target signaling activity, via direct or indirect interaction with the target.

The term "pharmaceutically acceptable carrier" or "pharmaceutically acceptable excipient" includes, but is not limited to, any and all solvents, dispersion media, coatings, antibacterial and antifungal agents, isotonic and absorption delaying agents, one or more suitable diluents, fillers, salts, disintegrants, binders, lubricants, glidants, wetting agents, controlled release matrices, colorants/flavoring, carriers, excipients, buffers, stabilizers, solubilizers, and combinations thereof. Except insofar as any conventional media or agent is incompatible with the active ingredient, its use in the therapeutic compositions of the invention is contemplated. Supplementary active ingredients can also be incorporated into the compositions.

In some embodiments, one or more subject compounds bind specifically to a PI3 kinase or a protein kinase selected from the group consisting of mTor, DNA-dependent protein kinase (Pubmed protein accession number (PPAN) AAA79184), AbI tyrosine kinase (CAA52387), Bcr-Abl, hemopoietic cell kinase (PPAN CAI19695), Src (PPAN CAA24495), vascular endothelial growth factor receptor 2 (PPAN ABB82619), epidermal growth factor receptor (PPAN AG43241), EPH receptor B4 (PPAN EAL23820), stem cell factor receptor (PPAN AAF22141), Tyrosine-protein kinase receptor TIE-2 (PPAN Q02858), fms-related tyrosine kinase 3 (PPAN NP_004110), platelet-derived growth factor receptor alpha (PPAN NP_990080), RET (PPAN CAA73131), and any other related protein kinases, as well as any functional mutants thereof.

In some embodiments, the IC50 of a subject compound for pi 10α, pi 10β, pi 10γ, or pi 10δ is less than about 1 uM, less than about 100 nM, less than about 50 nM, less than about 10 nM, less than 1 nM or even less than about 0.5 nM. In some embodiments, the IC50 of a subject compound for mTor is less than about 1 uM, less than about 100 nM, less than about 50 nM, less than about 10 nM, less than 1 nM or even less than about 0.5 nM. In some other embodiments, one or more subject compounds exhibit dual binding specificity and are capable of inhibiting a PI3 kinase (e.g., a class I PI3 kinase) as well as a protein kinase (e.g., mTor) with an IC50 value less than about 1 uM, less than about 100 nM, less than about 50 nM, less than about 10 nM, less than 1 nM or even less than about 0.5 nM.

In some embodiments, the compounds of the present invention exhibit one or more functional characteristics disclosed herein. For example, one or more subject compounds bind specifically to a PI3 kinase. In some embodiments, the IC50 of a subject compound for pi 10α, pi 10β, pi 10γ, or pi 10δ is less than about 1 uM, less than about 100 nM, less than about 50 nM, less than about 10 nM, less than about 1 nM, less than about 0.5 nM, less than about 100 pM, or less than about 50 pM.

In some embodiments, one or more of the subject compounds may selectively inhibit one or more members of type I or class I phosphatidylinositol 3-kinases (PI3-kinase) with an IC50 value of about 100 nM, 50 nM, 10 nM, 5 nM, 100 pM, 10 pM or 1 pM, or less as measured in an in vitro kinase assay.

In some embodiments, one or more of the subject compound may selectively inhibit one or two members of type I or class I phosphatidylinositol 3-kinases (PI3-kinase) consisting of PI3-kinase α, PI3-kinase β, PI3-kinase γ, and PI3-kinase δ. In some aspects, some of the subject compounds selectively inhibit PI3-kinase δ as compared to all other type I PI3-kinases. In other aspects, some of the subject compounds selectively inhibit PI3-kinase δ and PI3-kinase γ as compared to the rest of the type I PI3-kinases. In yet other aspects, some of the subject compounds selectively inhibit PI3-kinase α and PI3-kinase β as compared to the rest of the type I PI3-kinases. In still yet some other aspects, some of the subject compounds selectively inhibit PI3-kinase δ and PI3-kinase α as compared to the rest of the type I PI3-kinases. In still yet some other aspects, some of the subject compounds selectively inhibit PI3-kinase δ and PI3-kinase β as compared to the rest of the type I PI3-kinases, or selectively inhibit PI3-kinase δ and PI3-kinase α as compared to the rest of the type I PI3-kinases, or selectively inhibit PI3-kinase α and PI3-kinase γ as compared to the rest of the type I PI3-kinases, or selectively inhibit PI3-kinase γ and PI3-kinase β as compared to the rest of the type I PI3-kinases.

In yet another aspect, an inhibitor that selectively inhibits one or more members of type I PI3-kinases, or an inhibitor that selectively inhibits one or more type I PI3-kinase mediated signaling pathways, alternatively can be understood to refer to a compound that exhibits a 50% inhibitory concentration (IC50) with respect to a given type I PI3-kinase, that is at least at least 10-fold, at least 20-fold, at least 50-fold, at least 100-fold, at least 1000-fold, or lower, than the inhibitor's IC50 with respect to the rest of the other type I PI3-kinases.

As used herein, the term "PI3-kinase δ selective inhibitor" generally refers to a compound that inhibits the activity of the PI3-kinase δ isozyme more effectively than other isozymes of the PI3K family. A PI3-kinase δ selective inhibitor compound is therefore more selective for PI3-kinase δ than conventional PI3K inhibitors such as wortmannin and LY294002, which are "nonselective PI3K inhibitors."

Inhibition of PI3-kinase δ may be of therapeutic benefit in treatment of various conditions, e.g., conditions characterized by an inflammatory response including but not limited to autoimmune diseases, allergic diseases, and arthritic diseases. Importantly, inhibition of PI3-kinase δ function does not appear to affect biological functions such as viability and fertility.

"Inflammatory response" as used herein is characterized by redness, heat, swelling and pain (i.e., inflammation) and typically involves tissue injury or destruction. An inflammatory response is usually a localized, protective response elicited by injury or destruction of tissues, which serves to destroy, dilute or wall off (sequester) both the injurious agent and the injured tissue. Inflammatory responses are notably associated with the influx of leukocytes and/or leukocyte (e.g., neutrophil) chemotaxis. Inflammatory responses may result from infection with pathogenic organisms and viruses, noninfectious means such as trauma or reperfusion following myocardial infarction or stroke, immune responses to foreign antigens, and autoimmune diseases. Inflammatory responses amenable to treatment with the methods and compounds according to the invention encompass conditions associated with reactions of the specific defense system as well as conditions associated with reactions of the non-specific defense system.

The therapeutic methods of the invention include methods for the amelioration of conditions associated with inflammatory cell activation. "Inflammatory cell activation" refers to the induction by a stimulus (including but not limited to, cytokines, antigens or auto-antibodies) of a proliferative cellular response, the production of soluble mediators (including but not limited to cytokines, oxygen radicals, enzymes, prostanoids, or vasoactive amines), or cell surface expression of new or increased numbers of mediators (including but not limited to, major histocompatibility antigens or cell adhesion molecules) in inflammatory cells (including but not limited to monocytes, macrophages, T lymphocytes, B lymphocytes, granulocytes (polymorphonuclear leukocytes including neutrophils, basophils, and eosinophils) mast cells, dendritic cells, Langerhans cells, and endothelial cells). It will be appreciated by persons skilled in the art that the activation of one or a combination of these phenotypes in these cells can contribute to the initiation, perpetuation, or exacerbation of an inflammatory condition.

"Autoimmune disease" as used herein refers to any group of disorders in which tissue injury is associated with humoral or cell-mediated responses to the body's own constituents. "Transplant rejection" as used herein refers-to any immune response directed against grafted tissue (including organs or cells (e.g., bone marrow), characterized by a loss of function of the grafted and surrounding tissues, pain, swelling, leukocytosis, and thrombocytopenia). "Allergic disease" as used herein refers to any symptoms, tissue damage, or loss of tissue function resulting from allergy. "Arthritic disease" as used herein refers to any disease that is characterized by inflammatory lesions of the joints attributable to a variety of etiologies. "Dermatitis" as used herein refers to any of a large family of diseases of the skin that are characterized by inflammation of the skin attributable to a variety of etiologies.

As previously described, the term "PI3-kinase δ selective inhibitor" generally refers to a compound that inhibits the activity of the PI3-kinase δ isozyme more effectively than other isozymes of the PI3K family. The relative efficacies of compounds as inhibitors of an enzyme activity (or other biological activity) can be established by determining the concentrations at which each compound inhibits the activity to a predefined extent and then comparing the results. Typically, the preferred determination is the concentration that inhibits 50% of the activity in a biochemical assay, i.e., the 50% inhibitory concentration or "IC50". IC50 determinations can be accomplished using conventional techniques known in the art. In general, an IC50 can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the IC50 value. Analogously, other inhibitory concentrations can be defined through appropriate determinations of activity. For example, in some settings it can be desirable to establish a 90% inhibitory concentration, i.e., IC90, etc.

Accordingly, a PI3-kinase δ selective inhibitor alternatively can be understood to refer to a compound that exhibits a 50% inhibitory concentration (IC50) with respect to PI3-kinase δ, that is at least 10-fold, in another aspect at least 20-fold, and in another aspect at least 30-fold, lower than the IC50 value with respect to any or all of the other class I PI3K family members. In an alternative embodiment of the invention, the term PI3-kinase δ selective inhibitor can be understood to refer to a compound that exhibits an IC50 with respect to PI3-kinase δ that is at least 50-fold, in another aspect at least 100-fold, in an additional aspect at least 200-fold, and in yet another aspect at least 500-fold, lower than the IC50 with respect to any or all of the other PI3K class I family members. A PI3-kinase δ selective inhibitor is typically administered in an amount such that it selectively inhibits PI3-kinase δ activity, as described above.

The methods of the invention may be applied to cell populations in vivo or ex vivo. "In vivo" means within a living individual, as within an animal or human or in a subject's body. In this context, the methods of the invention may be used therapeutically or prophylactically in an individual. "Ex vivo" or "In vitro" means outside of a living individual. Examples of ex vivo cell populations include in vitro cell cultures and biological samples including but not limited to fluid or tissue samples obtained from individuals. Such samples may be obtained by methods known in the art. Exemplary biological fluid samples include blood, cerebrospinal fluid, urine, and saliva. Exemplary tissue samples include tumors and biopsies thereof. In this context, the invention may be used for a variety of purposes, including therapeutic and experimental purposes. For example, the invention may be used ex vivo or in vitro to determine the optimal schedule and/or dosing of administration of a PI3-kinase δ selective inhibitor for a given indication, cell type, individual, and other parameters. Information gleaned from such use may be used for experimental or diagnostic purposes or in the clinic to set protocols for in vivo treatment. Other ex vivo uses for which the invention may be suited are described below or will become apparent to those skilled in the art.

Pharmaceutical Compositions

The invention provides a pharmaceutical composition comprising one or more compounds of the present invention. The pharmaceutical composition may include one or more additional active ingredients as described herein. The pharmaceutical composition may be administered for any of the disorders described herein In some embodiments, the invention provides pharmaceutical compositions for treating diseases or conditions related to an undesirable, over-active, harmful or deleterious immune response in a mammal. Such undesirable immune response can be associated with or result in, e.g., asthma, emphysema, bronchitis, psoriasis, allergy, anaphylaxis, auto-immune diseases, rheumatoid arthritis, graft versus host disease, and lupus erythematosus. The pharmaceutical compositions of the present invention can be used to treat other respiratory diseases including but not limited to diseases affecting the lobes of lung, pleural cavity, bronchial tubes, trachea, upper respiratory tract, or the nerves and muscle for breathing.

In some embodiments, the invention provides pharmaceutical compositions for the treatment of disorders such as hyperproliferative disorder including but not limited to cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS related (e.g. Lymphoma and Kaposi's Sarcoma) or Viral-Induced cancer. In some embodiments, the pharmaceutical composition is for the treatment of a non-cancerous hyperproliferative disorder such as benign hyperplasia of the skin (e. g., psoriasis), restenosis, or prostate (e. g., benign prostatic hypertrophy (BPH)).

The invention also relates to a composition for treating a disease related to vasculogenesis or angiogenesis in a mammal which can manifest as tumor angiogenesis, chronic inflammatory disease such as rheumatoid arthritis, inflammatory bowel disease, atherosclerosis, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

The invention also provides compositions for the treatment of liver diseases (including diabetes), pancreatitis or kidney disease (including proliferative glomerulonephritis and diabetes-induced renal disease) or pain in a mammal.

The invention further provides a composition for the prevention of blastocyte implantation in a mammal.

The subject pharmaceutical compositions are typically formulated to provide a therapeutically effective amount of a compound of the present invention as the active ingredient, or a pharmaceutically acceptable salt, ester, or prodrug thereof. Where desired, the pharmaceutical compositions contain a compound of the present invention as the active ingredient or a pharmaceutically acceptable salt and/or coordination complex thereof, and one or more pharmaceutically acceptable excipients, carriers, such as inert solid diluents and fillers, diluents, including sterile aqueous solution and various organic solvents, permeation enhancers, solubilizers and adjuvants.

The subject pharmaceutical compositions can be administered alone or in combination with one or more other agents, which are also typically administered in the form of pharmaceutical compositions. Where desired, the subject compounds and other agent(s) may be mixed into a preparation or both components may be formulated into separate preparations to use them in combination separately or at the same time.

Methods include administration of an inhibitor by itself, or in combination as described herein, and in each case optionally including one or more suitable diluents, fillers, salts, disintegrants, binders, lubricants, glidants, wetting agents, controlled release matrices, colorants/flavoring, carriers, excipients, buffers, stabilizers, solubilizers, and combinations thereof.

Preparations of various pharmaceutical compositions are known in the art. See, e.g., Anderson, Philip O.; Knoben, James E.; Troutman, William G, eds., Handbook of Clinical Drug Data, Tenth Edition, McGraw-Hill, 2002; Pratt and Taylor, eds., Principles of Drug Action, Third Edition, Churchill Livingston, N.Y., 1990; Katzung, ed., Basic and Clinical Pharmacology, Ninth Edition, McGraw Hill, 2003; Goodman and Gilman, eds., The Pharmacological Basis of Therapeutics, Tenth Edition, McGraw Hill, 2001; Remingtons Pharmaceutical Sciences, 20th Ed., Lippincott Williams & Wilkins., 2000; Martindale, The Extra Pharmacopoeia, Thirty-Second Edition (The Pharmaceutical Press, London, 1999), all of which are incorporated by reference herein in their entirety.

The compounds or pharmaceutical composition of the present invention can be administered by any route that enables delivery of the compounds to the site of action, such asoral routes, intraduodenal routes, parenteral injection (including intravenous, intraarterial, subcutaneous, intramuscular, intravascular, intraperitoneal or infusion), topical administration (e.g. transdermal application), rectal administration, via local delivery by catheter or stent or through inhalation. The compounds can also be administered intraadiposally or intrathecally.

The compositions can be administered in solid, semi-solid, liquid or gaseous form, or may be in dried powder, such as lyophilized form. The pharmaceutical compositions can be packaged in forms convenient for delivery, including, for example, solid dosage forms such as capsules, sachets, cachets, gelatins, papers, tablets, capsules, suppositories, pellets, pills, troches, and lozenges. The type of packaging will generally depend on the desired route of administration. Implantable sustained release formulations are also contemplated, as are transdermal formulations.

Routes of Administration

In the methods according to the invention, the inhibitor compounds may be administered by various routes. For example, pharmaceutical compositions may be for injection, or for oral, nasal, transdermal or other forms of administration, including, e.g., by intravenous, intradermal, intramuscular, intramammary, intraperitoneal, intrathecal, intraocular, retrobulbar, intrapulmonary (e.g., aerosolized drugs) or subcutaneous injection (including depot administration for long term release e.g., embedded-under the-splenic capsule, brain, or in the cornea); by sublingual, anal, or vaginal administration, or by surgical implantation, e.g., embedded under the splenic capsule, brain, or in the cornea. The treatment may consist of a single dose or a plurality of doses over a period of time. In general, the methods of the invention involve administering effective amounts of a modulator of the invention together with one or more pharmaceutically acceptable diluents, preservatives, solubilizers, emulsifiers, adjuvants and/or carriers, as described above.

The subject pharmaceutical composition may, for example, be in a form suitable for oral administration as a tablet, capsule, pill, powder, sustained release formulations, solution, suspension, for parenteral injection as a sterile solution, suspension or emulsion, for topical administration as an ointment or cream or for rectal administration as a suppository. The pharmaceutical composition may be in unit dosage forms suitable for single administration of precise dosages. The pharmaceutical composition will include a conventional pharmaceutical carrier or excipient and a compound according to the invention as an active ingredient. In addition, it may include other medicinal or pharmaceutical agents, carriers, and adjuvants.

In one aspect, the invention provides methods for oral administration of a pharmaceutical composition of the invention. Oral solid dosage forms are described generally in Remington's Pharmaceutical Sciences, supra at Chapter 89. Solid dosage forms include tablets, capsules, pills, troches or lozenges, and cachets or pellets. Also, liposomal or proteinoid encapsulation may be used to formulate the compositions (as, for example, proteinoid microspheres reported in U.S. Pat. No. 4,925,673). Liposomal encapsulation may include liposomes that are derivatized with various polymers (e.g., U.S. Pat. No. 5,013,556). The formulation may include a compound of the invention and inert ingredients which protect against degradation in the stomach and which permit release of the biologically active material in the intestine.

Toxicity and therapeutic efficacy of the PI3-kinase δ selective compounds can be determined by standard pharmaceutical procedures in cell cultures or experimental animals, e.g., for determining the LD50 (the dose lethal to 50% of the population) and the ED50 (the dose therapeutically effective in 50% of the population). Additionally, this information can be determined in cell cultures or experimental animals additionally treated with other therapies including but not limited to radiation, chemotherapeutic agents, photodynamic therapies, radiofrequency ablation, anti-angiogenic agents, and combinations thereof.

The amount of the compound administered will be dependent on the mammal being treated, the severity of the disorder or condition, the rate of administration, the disposition of the compound and the discretion of the prescribing physician. However, an effective dosage is in the range of about 0.001 to about 100 mg per kg body weight per day, preferably about 1 to about 35 mg/kg/day, in single or divided doses. For a 70 kg human, this would amount to about 0.05 to 7 g/day, preferably about 0.05 to about 2.5 g/day. In some instances, dosage levels below the lower limit of the aforesaid range may be more than adequate, while in other cases still larger doses may be employed without causing any harmful side effect, e.g. by dividing such larger doses into several small doses for administration throughout the day.

In some embodiments, a compound of the invention is administered in a single dose. Typically, such administration will be by injection, e.g., intravenous injection, in order to introduce the agent quickly. However, other routes may be used as appropriate. A single dose of a compound of the invention may also be used for treatment of an acute condition.

In practice of the methods of the invention, the pharmaceutical compositions are generally provided in doses ranging from 1 pg compound/kg body weight to 1000 mg/kg, 0.1 mg/kg to 100 mg/kg, 0.1 mg/kg to 50 mg/kg, and 1 to 20 mg/kg, given in daily doses or in equivalent doses at longer or shorter intervals, e.g., every other day, twice weekly, weekly, or twice or three times daily. The inhibitor compositions may be administered by an initial bolus followed by a continuous infusion to maintain therapeutic circulating levels of drug product. Those of ordinary skill in the art will readily optimize effective dosages and administration regimens as determined by good medical practice and the clinical condition of the individual to be treated. The frequency of dosing will depend on the pharmacokinetic parameters of the agents and the route of administration. The optimal pharmaceutical formulation will be determined by one skilled in the art depending upon the route of administration and desired dosage [see, for example, Remington's Pharmaceutical Sciences, pp. 1435-1712, the disclosure of which is hereby incorporated by reference]. Such formulations may influence the physical state, stability, rate of in vivo release, and rate of in vivo clearance of the administered agents. Depending on the route of administration, a suitable dose may be calculated according to body weight, body surface area or organ size. Further refinement of the calculations necessary to determine the appropriate dosage for treatment involving each of the above mentioned formulations is routinely made by those of ordinary skill in the art without undue experimentation, especially in light of the dosage information and assays disclosed herein, as well as the pharmacokinetic data observed in human clinical trials. Appropriate dosages may be ascertained by using established assays for determining blood level dosages in conjunction with an appropriate physician considering various factors which modify the action of drugs, e.g., the drug's specific activity, the severity of the indication, and the responsiveness of the individual, the age, condition, body weight, sex and diet of the individual, the time of administration and other clinical factors. As studies are conducted, further information will emerge regarding the appropriate dosage levels and duration of treatment for various diseases and conditions capable of being treated with the methods of the invention.

In some embodiments, a compound of the invention is administered in multiple doses. Dosing may be about once, twice, three times, four times, five times, six times, or more than six times per day. Dosing may be about once a month, once every two weeks, once a week, or once every other day. In another embodiment a compound of the invention and another agent are administered together about once per day to about 6 times per day. In another embodiment the administration of a compound of the invention and an agent continues for less than about 7 days. In yet another embodiment the administration continues for more than about 6, 10, 14, 28 days, two months, six months, or one year. In some cases, continuous dosing is achieved and maintained as long as necessary.

Administration of the agents of the invention may continue as long as necessary. In some embodiments, an agent of the invention is administered for more than 1, 2, 3, 4, 5, 6, 7, 14, or 28 days. In some embodiments, an agent of the invention is administered for less than 28, 14, 7, 6, 5, 4, 3, 2, or 1 day. In some embodiments, an agent of the invention is administered chronically on an ongoing basis, e.g., for the treatment of chronic effects.

An effective amount of a compound of the invention may be administered in either single or multiple doses by any of the accepted modes of administration of agents having similar utilities, including rectal, buccal, intranasal and transdermal routes, by intraarterial injection, intravenously, intraperitoneally, parenterally, intramuscularly, subcutaneously, orally, topically, or as an inhalant.

The compounds of the invention may be administered in dosages. It is known in the art that due to intersubject variability in compound pharmacokinetics, individualization of dosing regimen is necessary for optimal therapy. Dosing for a compound of the invention may be found by routine experimentation in light of the instant disclosure.

When a compound of the invention, is administered in a composition that comprises one or more agents, and the agent has a shorter half-life than the compound of the invention unit dose forms of the agent and the compound of the invention may be adjusted accordingly.

The inhibitors of the invention may be covalently or noncovalently associated with a carrier molecule including but not limited to a linear polymer (e.g., polyethylene glycol, polylysine, dextran, etc.), a branched-chain polymer (see U.S. Pat. Nos. 4,289,872 and 5,229,490; PCT Publication No. WO 93/21259), a lipid, a cholesterol group (such as a steroid), or a carbohydrate or oligosaccharide. Specific examples of carriers for use in the pharmaceutical compositions of the invention include carbohydrate-based polymers such as trehalose, mannitol, xylitol, sucrose, lactose, sorbitol, dextrans such as cyclodextran, cellulose, and cellulose derivatives. Also, the use of liposomes, microcapsules or microspheres, inclusion complexes, or other types of carriers is contemplated.

Other carriers include one or more water soluble polymer attachments such as polyoxyethylene glycol, or polypropylene glycol as described U.S. Pat. Nos. 4,640,835, 4,496,689, 4,301,144, 4,670,417, 4,791,192 and 4,179,337. Still other useful carrier polymers known in the art include monomethoxy-polyethylene glycol, poly-(N-vinyl pyrrolidone)-polyethylene glycol, propylene glycol homopolymers, a polypropylene oxidelethylene oxide co-polymer, polyoxyethylated polyols (e.g., glycerol) and polyvinyl alcohol, as well as mixtures of these polymers.

Derivitization with bifunctional agents is useful for cross-linking a compound of the invention to a support matrix or to a carrier. One such carrier is polyethylene glycol (PEG). The PEG group may be of any convenient molecular weight and may be straight chain or branched. The average molecular weight of the PEG can range from about 2 kDa to about 100 kDa, in another aspect from about 5 kDa to about 50 kDa, and in a further aspect from about 5 kDa to about 10 kDa. The PEG groups will generally be attached to the compounds of the invention via acylation, reductive alkylation, Michael addition, thiol alkylation or other chemoselective conjugation/ligation methods through a reactive group on the PEG moiety (e.g., an aldehyde, amino, ester, thiol, ci-haloacetyl, maleimido or hydrazino group) to a reactive group on the target inhibitor compound (e.g., an aldehyde, amino, ester, thiol, a-haloacetyl, maleimido or hydrazino group). Cross-linking agents can include, e.g., esters with 4-azidosalicylic acid, homobifunctional imidoesters, including disuccinimidyl esters such as 3,3'-dithiobis (succinimidylpropionate), and bifunctional maleimides such as bis-N-maleimido-1,8-octane. Derivatizing agents such as methyl-3-[(p-azidophenyl)dithiolpropioimidate yield photoactivatable intermediates that are capable of forming crosslinks in the presence of light. Alternatively, reactive water-insoluble matrices such as cyanogen bromide-activated carbohydrates and the reactive substrates described in U.S. Pat. Nos. 3,969,287; 3,691,016; 4,195,128; 4,247,642; 4,229,537; and 4,330,440 may be employed for inhibitor immobilization.

Method of Treatment

The invention also provides methods of using the compounds or pharmaceutical compositions of the present invention to treat disease conditions, including but not limited to diseases associated with malfunctioning of one or more types of PI3 kinase. A detailed description of conditions and disorders mediated by pi 10δ kinase activity is set forth in WO 2001/81346 and US 2005/043239, both of which are incorporated herein by reference in their entireties for all purposes.

The treatment methods provided herein comprise administering to the subject a therapeutically effective amount of a compound of the invention. In one embodiment, the present invention provides a method of treating an inflammation disorder, including autoimmune diseases in a mammal. The method comprises administering to said mammal a therapeutically effective amount of a compound of the present invention, or a pharmaceutically acceptable salt, ester, prodrug, solvate, hydrate or derivative thereof.

The disorders, diseases, or conditions treatable with a compound provided herein, include, but are not limited to, inflammatory or allergic diseases, including systemic anaphylaxis and hypersensitivity disorders, atopic dermatitis, urticaria, drug allergies, insect sting allergies, food allergies (including celiac disease and the like), anaphylaxis, serum sickness, drug reactions, insect venom allergies, hypersensitivity pneumonitis, angioedema, erythema multiforme, Stevens-Johnson syndrome, atopic keratoconjunctivitis, venereal keratoconjunctivitis, giant papillary conjunctivitis, and mastocytosis;

inflammatory bowel diseases, including Crohn's disease, ulcerative colitis, ileitis, enteritis, and necrotizing enterocolitis;

vasculitis, and Behcet's syndrome;

psoriasis and inflammatory dermatoses, including dermatitis, eczema, allergic contact dermatitis, viral cutaneous pathologies including those derived from human papillomavirus, HIV or RLV infection, bacterial, flugal, and other parasital cutaneous pathologies, and cutaneous lupus erythematosus;

asthma and respiratory allergic diseases, including allergic asthma, exercise induced asthma, allergic rhinitis, otitis media, hypersensitivity lung diseases, chronic obstructive pulmonary disease and other respiratory problems;

autoimmune diseases and inflammatory conditions, including but are not limited to acute disseminated encephalomyelitis (ADEM), Addison's disease, antiphospholipid antibody syndrome (APS), aplastic anemia, autoimmune hepatitis, coeliac disease, Crohn's disease, Diabetes mellitus (type 1), Goodpasture's syndrome, Graves' disease, Guillain-Barre syndrome (GBS), Reynaud's syndrome, Hashimoto's disease, lupus erythematosus, systemic lupus erythematosus (SLE), multiple sclerosis, myasthenia gravis, opsoclonus myoclonus syndrome (OMS), optic neuritis, Ord's thyroiditis, oemphigus, polyarthritis, primary biliary cirrhosis, psoriasis, rheumatoid arthritis, psoriatic arthritis, gouty arthritis, spondylitis, reactive arthritis, chronic or acute glomerulonephritis, lupus nephritis, Reiter's syndrome, Takayasu's arteritis, temporal arteritis (also known as "giant cell arteritis"), warm autoimmune hemolytic anemia, Wegener's granulomatosis, alopecia universalis, Chagas' disease, chronic fatigue syndrome, dysautonomia, endometriosis, hidradenitis suppurativa, interstitial cystitis, neuromyotonia, sarcoidosis, scleroderma, ulcerative colitis, connective tissue disease, autoimmune pulmonary inflammation, autoimmune thyroiditis, autoimmune inflammatory eye disease, vitiligo, and vulvodynia. Other disorders include bone-resorption disorders and thrombosis;

tissue or organ transplant rejection disorders including but not limited to graft rejection (including allograft rejection and graft-v-host disease (GVHD)), e.g., skin graft rejection, solid organ transplant rejection, bone marrow transplant rejection;

fever, cardiovascular disorders, including acute heart failure, hypotension, hypertension, angina pectoris, myocardial infarction, cardiomyopathy, congestive heart failure, atherosclerosis, coronary artery disease, restenosis, and vascular stenosis;

cerebrovascular disorders, including traumatic brain injury, stroke, ischemic reperfusion injury and aneurysm;

cancers of the breast, skin, prostate, cervix, uterus, ovary, testes, bladder, lung, liver, larynx, oral cavity, colon and gastrointestinal tract (e.g., esophagus, stomach, pancreas), brain, thyroid, blood, and lymphatic system;

fibrosis, connective tissue disease, and sarcoidosis;

genital and reproductive conditions, including erectile dysfunction;

gastrointestinal disorders, including gastritis, ulcers, nausea, pancreatitis, and vomiting;

neurologic disorders, including Alzheimer's disease;

sleep disorders, including insomnia, narcolepsy, sleep apnea syndrome, and Pickwick Syndrome;

pain, myalgias due to infection;

renal disorders;

ocular disorders, including glaucoma;

infectious diseases, including HIV;

sepsis; septic shock; endotoxic shock; gram negative sepsis; gram positive sepsis; toxic shock syndrome; multiple organ injury syndrome secondary to septicemia, trauma, or hemorrhage;

pulmonary or respiratory conditions including but not limited to asthma, chronic bronchitis, allergic rhinitis, adult respiratory distress syndrome (ARDS), severe acute respiratory syndrome (SARS), chronic pulmonary inflammatory diseases (e.g., chronic obstructive pulmonary disease), silicosis, pulmonary sarcoidosis, pleurisy, alveolitis, vasculitis, pneumonia, bronchiectasis, hereditary emphysema, and pulmonary oxygen toxicity;

ischemic-reperfusion injury, e.g., of the myocardium, brain, or extremities;

fibrosis including but not limited to cystic fibrosis; keloid formation or scar tissue formation;

central or peripheral nervous system inflammatory conditions including but not limited to meningitis (e.g., acute purulent meningitis), encephalitis, and brain or spinal cord injury due to minor trauma;

Sjorgren's syndrome; diseases involving leukocyte diapedesis; alcoholic hepatitis; bacterial pneumonia; community acquired pneumonia (CAP); *Pneumocystis carinii* pneumonia (PCP); antigen-antibody complex mediated diseases; hypovolemic shock; acute and delayed hypersensitivity; disease states due to leukocyte dyscrasia and metastasis; thermal injury; granulocyte transfusion associated syndromes; cytokine-induced toxicity; stroke; pancreatitis; myocardial infarction, respiratory syncytial virus (RSV) infection; and spinal cord injury.

In certain embodiments, the cancer or cancers treatable with the methods provided herein includes, but is or are not limited to, leukemias, including, but not limited to, acute leukemia, acute lymphocytic leukemia, acute myelocytic leukemias such as myeloblasts, promyelocyte, myelomonocytic, monocytic, erythroleukemia leukemias and myelodysplastic syndrome or a symptom thereof (such as anemia, thrombocytopenia, neutropenia, bicytopenia or pancytopenia), refractory anemia (RA), RA with ringed sideroblasts (RARS), RA with excess blasts (RAEB), RAEB in transformation (RAEB-T), preleukemia, and chronic myelomonocytic leukemia (CMML);

chronic leukemias, including, but not limited to, chronic myelocytic (granulocytic) leukemia, chronic lymphocytic leukemia, and hairy cell leukemia;

polycythemia vera;

lymphomas, including, but not limited to, Hodgkin's disease and non-Hodgkin's disease;

multiple myelomas, including, but not limited to, smoldering multiple myeloma, nonsecretory myeloma, osteosclerotic myeloma, plasma cell leukemia, solitary plasmacytoma, and extramedullary plasmacytoma;

Waldenstrom's macroglobulinemia;

monoclonal gammopathy of undetermined significance;

benign monoclonal gammopathy;

heavy chain disease;

bone and connective tissue sarcomas, including, but not limited to, bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, metastatic cancers, neurilemmoma, rhabdomyosarcoma, and synovial sarcoma;

brain tumors, including, but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, and primary brain lymphoma;

breast cancer, including, but not limited to, adenocarcinoma, lobular (small cell) carcinoma, intraductal carcinoma, medullary breast cancer, mucinous breast cancer, tubular breast cancer, papillary breast cancer, primary cancers, Paget's disease, and inflammatory breast cancer;

adrenal cancer, including, but not limited to, pheochromocytom and adrenocortical carcinoma;

thyroid cancer, including, but not limited to, papillary or follicular thyroid cancer, medullary thyroid cancer, and anaplastic thyroid cancer, pancreatic cancer, including, but not limited to, insulinoma, gastrinoma, glucagonoma, vipoma, somatostatin-secreting tumor, and carcinoid or islet cell tumor, pituitary cancer, including, but limited to, Cushing's disease, prolactin-secreting tumor, acromegaly, and diabetes insipidus;

eye cancer, including, but not limited, to ocular melanoma such as iris melanoma, choroidal melanoma, and cilliary body melanoma, and retinoblastoma;

vaginal cancer, including, but not limited to, squamous cell carcinoma, adenocarcinoma, and melanoma;

vulvar cancer, including, but not limited to, squamous cell carcinoma, melanoma, adenocarcinoma, basal cell carcinoma, sarcoma, and Paget's disease;

cervical cancers, including, but not limited to, squamous cell carcinoma, and adenocarcinoma;

uterine cancer, including, but not limited to, endometrial carcinoma and uterine sarcoma;

ovarian cancer, including, but not limited to, ovarian epithelial carcinoma, borderline tumor, germ cell tumor, and stromal tumor;

esophageal cancer, including, but not limited to, squamous cancer, adenocarcinoma, adenoid cystic carcinoma, mucoepidermoid carcinoma, adenosquamous carcinoma, sarcoma, melanoma, plasmacytoma, verrucous carcinoma, and oat cell (small cell) carcinoma;

stomach cancer, including, but not limited to, adenocarcinoma, fungating (polypoid), ulcerating, superficial spreading, diffusely spreading, malignant lymphoma, liposarcoma, fibrosarcoma, and carcinosarcoma;

colon cancer;

rectal cancer;

liver cancer, including, but not limited to, hepatocellular carcinoma and hepatoblastoma;

gallbladder cancer, including, but not limited to, adenocarcinoma;

cholangiocarcinomas, including, but not limited to, pappillary, nodular, and diffuse;

lung cancer, including, but not limited to, non-small cell lung cancer, squamous cell carcinoma (epidermoid carcinoma), adenocarcinoma, large-cell carcinoma, and small-cell lung cancer, testicular cancer, including, but not limited to, germinal tumor, seminoma, anaplastic, classic (typical), spermatocytic, nonseminoma, embryonal carcinoma, teratoma carcinoma, and choriocarcinoma (yolk-sac tumor);

prostate cancer, including, but not limited to, adenocarcinoma, leiomyosarcoma, and rhabdomyosarcoma;

penal cancer, oral cancer, including, but not limited to, squamous cell carcinoma;

basal cancer, salivary gland cancer, including, but not limited to, adenocarcinoma, mucoepidermoid carcinoma, and adenoid-cystic carcinoma;

pharynx cancer, including, but not limited to, squamous cell cancer and verrucous;

skin cancer, including, but not limited to, basal cell carcinoma, squamous cell carcinoma and melanoma, superficial spreading melanoma, nodular melanoma, lentigo malignant melanoma, and acral lentiginous melanoma;

kidney cancer, including, but not limited to, renal cell cancer, adenocarcinoma, hypernephroma, fibrosarcoma, and transitional cell cancer (renal pelvis and/or uterer);

Wilms' tumor;

bladder cancer, including, but not limited to, transitional cell carcinoma, squamous cell cancer, adenocarcinoma, and carcinosarcoma; and other cancer, including, not limited to, myxosarcoma, osteogenic sarcoma, endotheliosarcoma, lymphangio-endotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma, and papillary adenocarcinomas See Fishman et al., 1985, Medicine, 2d Ed., J.B. Lippincott Co., Philadelphia and Murphy et al., 1997, Informed Decisions: The Complete Book of Cancer Diagnosis, Treatment, and Recovery, Viking Penguin, Penguin Books U.S.A., Inc., United States of America.

It will be appreciated that the treatment methods of the invention are useful in the fields of human medicine and veterinary medicine. Thus, the individual to be treated may be a mammal, preferably human, or other animals. For veterinary purposes, individuals include but are not limited to farm animals including cows, sheep, pigs, horses, and goats; companion animals such as dogs and cats; exotic and/or zoo animals; laboratory animals including mice, rats, rabbits, guinea pigs, and hamsters; and poultry such as chickens, turkeys, ducks, and geese.

In some embodiments, the method of treating inflammatory or autoimmune diseases comprises administering to a subject (e.g. a mammal) a therapeutically effective amount of one or more compounds of the present invention that selectively inhibit PI3K-δ and/or PI3K-γ as compared to all other type I PI3 kinases. Such selective inhibition of PI3K-δ and/or PI3K-γ may be advantageous for treating any of the diseases or conditions described herein. For example, selective inhibition of PI3K-δ may inhibit inflammatory responses associated with inflammatory diseases, autoimmune disease, or diseases related to an undesirable immune response including but not limited to asthma, emphysema, allergy, dermatitis, rheumatoid arthritis, psoriasis, lupus erythematosus, or graft versus host disease. Selective inhibition of POK-δ may further provide for a reduction in the inflammatory or undesirable immune response without a concomittant reduction in the ability to reduce a bacterial, viral, and/or fungal infection. Selective inhibition of both PI3K-δ and PI3K-γ may be advantageous for inhibiting the inflammatory response in the subject to a greater degree than that would be provided for by inhibitors that selectively inhibit PI3K-δ or PI3K-γ alone. In one aspect, one or more of the subject methods are effective in reducing antigen specific antibody production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more. In another aspect, one or more of the subject methods are effective in reducing antigen specific IgG3 and/or IgGM production in vivo by about 2-fold, 3-fold, 4-fold, 5-fold, 7.5-fold, 10-fold, 25-fold, 50-fold, 100-fold, 250-fold, 500-fold, 750-fold, or about 1000-fold or more.

In one aspect, one of more of the subject methods are effective in ameliorating symptoms associated with rhuematoid arthritis including but not limited to a reduction in the swelling of joints, a reduction in serum anti-collagen levels, and/or a reduction in joint pathology such as bone resorption, cartilage damage, pannus, and/or inflammation. In another aspect, the subject methods are effective in reducing ankle inflammation by at least about 2%, 5%, 10%, 15%, 20%, 25%, 30%, 50%, 60%, or about 75% to 90%. In another aspect, the subject methods are effective in reducing knee inflammation by at least about 2%, 5%, 10%, 15%, 20%, 25%, 30%, 50%, 60%, or about 75% to 90% or more. In still another aspect, the subject methods are effective in reducing serum anti-type II collagen levels by at least about 10%, 12%, 15%, 20%, 24%, 25%, 30%, 35%, 50%, 60%, 75%, 80%, 86%, 87%, or about 90% or more. In another aspect, the subject methods are effective in reducing ankle histopathology scores by about 5%, 10%, 15%, 20%, 25%, 30%, 40%, 50%, 60%, 75%, 80%, 90% or more. In still another aspect, the subject methods are effective in reducing knee histopathology scores by about 5%, 10%, 15%, 20%, 25%, 30%, 40%, 50%, 60%, 75%, 80%, 90% or more.

In other embodiments, the present invention provides methods of using the compounds or pharmaceutical compositions to treat respiratory diseases including but not limited to diseases affecting the lobes of lung, pleural cavity, bronchial tubes, trachea, upper respiratory tract, or the nerves and muscle for breathing. For example, methods are provided to treat obstructive pulmonary disease. Chronic obstructive pulmonary disease (COPD) is an umbrella term for a group of respiratory tract diseases that are characterized by airflow obstruction or limitation. Conditions included in this umbrella term are: chronic bronchitis, emphysema, and bronchiectasis.

In another embodiment, the compounds described herein are used for the treatment of asthma. Also, the compounds or pharmaceutical compositions described herein may be used for the treatment of endotoxemia and sepsis. In one embodiment, the compounds or pharmaceutical compositions described herein are used to for the treatment of rheumatoid arthritis (RA). In yet another embodiment, the compounds or pharmaceutical compositions described herein is used for the treatment of contact or atopic dermatitis. Contact dermatitis includes irritant dermatitis, phototoxic dermatitis, allergic dermatitis, photoallergic dermatitis, contact urticaria, systemic contact-type dermatitis and the like. Irritant dermatitis can occur when too much of a substance is used on the skin of when the skin is sensitive to certain substance. Atopic dermatitis, sometimes called eczema, is a kind of dermatitis, an atopic skin disease.

The invention also relates to a method of treating a hyperproliferative disorder in a mammal that comprises administering to said mammal a therapeutically effective amount of a compound of the present invention, or a pharmaceutically acceptable salt, ester, prodrug, solvate, hydrate or derivative thereof. In some embodiments, said method relates to the treatment of cancer such as acute myeloid leukemia, thymus, brain, lung, squamous cell, skin, eye, retinoblastoma, intraocular melanoma, oral cavity and oropharyngeal, bladder, gastric, stomach, pancreatic, bladder, breast, cervical, head, neck, renal, kidney, liver, ovarian, prostate, colorectal, esophageal, testicular, gynecological, thyroid, CNS, PNS, AIDS-related (e.g. Lymphoma and Kaposi's Sarcoma) or viral-induced cancer. In some embodiments, said method relates to the treatment of a non-cancerous hyperproliferative disorder such as benign hyperplasia of the skin (e. g., psoriasis), restenosis, or prostate (e.g., benign prostatic hypertrophy (BPH)).

The invention also relates to a method of treating diseases related to vasculogenesis or angiogenesis in a mammal that comprises administering to said mammal a therapeutically effective amount of a compound of the present invention, or a pharmaceutically acceptable salt, ester, prodrug, solvate, hydrate or derivative thereof. In some embodiments, said method is for treating a disease selected from the group consisting of tumor angiogenesis, chronic inflammatory disease such as rheumatoid arthritis, atherosclerosis, inflammatory bowel disease, skin diseases such as psoriasis, eczema, and scleroderma, diabetes, diabetic retinopathy, retinopathy of prematurity, age-related macular degeneration, hemangioma, glioma, melanoma, Kaposi's sarcoma and ovarian, breast, lung, pancreatic, prostate, colon and epidermoid cancer.

Patients that can be treated with compounds of the present invention, or pharmaceutically acceptable salt, ester, prodrug, solvate, hydrate or derivative of said compounds, according to the methods of this invention include, for example, patients that have been diagnosed as having psoriasis; restenosis; atherosclerosis; BPH; breast cancer such as a ductal carcinoma in duct tissue in a mammary gland, medullary carcinomas, colloid carcinomas, tubular carcinomas, and inflammatory breast cancer; ovarian cancer, including epithelial ovarian tumors such as adenocarcinoma in the ovary and an adenocarcinoma that has migrated from the ovary into the abdominal cavity; uterine cancer; cervical cancer such as adenocarcinoma in the cervix epithelial including squamous cell carcinoma and adenocarcinomas; prostate cancer, such as a prostate cancer selected from the following: an adenocarcinoma or an adenocarinoma that has migrated to the bone; pancreatic cancer such as epitheliod carcinoma in the pancreatic duct tissue and an adenocarcinoma in a pancreatic duct; bladder cancer such as a transitional cell carcinoma in urinary bladder, urothelial carcinomas (transitional cell carcinomas), tumors in the urothelial cells that line the bladder, squamous cell carcinomas, adenocarcinomas, and small cell cancers; leukemia such as acute myeloid leukemia (AML), acute lymphocytic leukemia, chronic lymphocytic leukemia, chronic myeloid leukemia, hairy cell leukemia, myelodysplasia, myeloproliferative disorders, acute myelogenous leukemia (AML), chronic myelogenous leukemia (CML), mastocytosis, chronic lymphocytic leukemia (CLL), multiple myeloma (MM), and myelodysplastic syndrome (MDS); bone cancer, lung cancer such as non-small cell lung cancer (NSCLC), which is divided into squamous cell carcinomas, adenocarcinomas, and large cell undifferentiated carcinomas, and small cell lung cancer; skin cancer such as basal cell carcinoma, melanoma, squamous cell carcinoma and actinic keratosis, which is a skin condition that sometimes develops into squamous cell carcinoma; eye retinoblastoma; cutaneous or intraocular (eye) melanoma; primary liver cancer (cancer that begins in the liver); kidney cancer, thyroid cancer such as papillary, follicular, medullary and anaplastic; AIDS-related lymphoma such as diffuse large B-cell lymphoma, B-cell immunoblastic lymphoma and small non-cleaved cell lymphoma; Kaposi's Sarcoma; viral-induced cancers including hepatitis B virus (HBV), hepatitis C virus (HCV), and hepatocellular carcinoma; human lymphotropic virus-type 1 (HTLV-I) and adult T-cell leukemia/lymphoma; and human papilloma virus (HPV) and cervical cancer; central nervous system cancers (CNS) such as primary brain tumor, which includes gliomas (astrocytoma, anaplastic astrocytoma, or glioblastoma multiforme), Oligodendroglioma, Ependymoma, Meningioma, Lymphoma, Schwannoma, and Medulloblastoma; peripheral nervous system (PNS) cancers such as acoustic neuromas and malignant peripheral nerve sheath tumor (MPNST) including neurofibromas and schwannomas, malignant fibrous cytoma, malignant fibrous histiocytoma, malignant meningioma, malignant mesothelioma, and malignant mixed Müllerian tumor, oral cavity and oropharyngeal cancer such as, hypopharyngeal cancer, laryngeal cancer, nasopharyngeal cancer, and oropharyngeal cancer, stomach cancer such as lymphomas, gastric stromal tumors, and carcinoid tumors; testicular cancer such as germ cell tumors (GCTs), which include seminomas and nonseminomas, and gonadal stromal tumors, which include Leydig cell tumors and Sertoli cell tumors; thymus cancer such as to thymomas, thymic carcinomas, Hodgkin disease, non-Hodgkin lymphomas carcinoids or carcinoid tumors; rectal cancer; and colon cancer.

The invention also relates to a method of treating diabetes in a mammal that comprises administering to said mammal a therapeutically effective amount of a compound of the present invention, or a pharmaceutically acceptable salt, ester, prodrug, solvate, hydrate or derivative thereof.

In addition, the compounds described herein may be used to treat acne.

In addition, the compounds described herein may be used for the treatment of arteriosclerosis, including atherosclerosis. Arteriosclerosis is a general term describing any hardening of medium or large arteries. Atherosclerosis is a hardening of an artery specifically due to an atheromatous plaque.

Further the compounds described herein may be used for the treatment of glomerulonephritis. Glomerulonephritis is a primary or secondary autoimmune renal disease characterized by inflammation of the glomeruli. It may be asymptomatic, or present with hematuria and/or proteinuria. There are many recognized types, divided in acute, subacute or chronic glomerulonephritis. Causes are infectious (bacterial, viral or parasitic pathogens), autoimmune or paraneoplastic.

Additionally, the compounds described herein may be used for the treatment of bursitis, lupus, acute disseminated encephalomyelitis (ADEM), addison's disease, antiphospholipid antibody syndrome (APS), aplastic anemia, autoimmune hepatitis, coeliac disease, Crohn's disease, diabetes mellitus (type I), goodpasture's syndrome, graves' disease, guillain-barre syndrome (GBS), hashimoto's disease, inflammatory bowel disease, lupus erythematosus, myasthenia gravis, opsoclonus myoclonus syndrome (OMS), optic neuritis, ord's thyroiditiSjOstheoarthritis, uveoretinitis, pemphigus, polyarthritis, primary biliary cirrhosis, reiter's syndrome, takayasu's arteritis, temporal arteritis, warm autoimmune hemolytic anemia, Wegener's granulomatosis, alopecia universalis, chagas' disease, chronic fatigue syndrome, dysautonomia, endometriosis, hidradenitis suppurativa, interstitial cystitis, neuromyotonia, sarcoidosis, scleroderma, ulcerative colitis, vitiligo, vulvodynia, appendicitis, arteritis, arthritis, blepharitis, bronchiolitis, bronchitis, cervicitis, cholangitis, cholecystitis, chorioamnionitis, colitis, conjunctivitis, cystitis, dacryoadenitis, dermatomyositis, endocarditis, endometritis, enteritis, enterocolitis, epicondylitis, epididymitis, fasciitis, fibrositis, gastritis, gastroenteritis, gingivitis, hepatitis, hidradenitis, ileitis, iritis, laryngitis, mastitis, meningitis, myelitis, myocarditis, myositis, nephritis, omphalitis, oophoritis, orchitis, osteitis, otitis, pancreatitis, parotitis, pericarditis, peritonitis, pharyngitis, pleuritis, phlebitis, pneumonitis, proctitis, prostatitis, pyelonephritis, rhinitis, salpingitis, sinusitis, stomatitis, synovitis, tendonitis, tonsillitis, uveitis, vaginitis, vasculitis, or vulvitis.

The invention also relates to a method of treating a cardiovascular disease in a mammal that comprises administering to said mammal a therapeutically effective amount of a compound of the present invention, or a pharmaceutically acceptable salt, ester, prodrug, solvate, hydrate or derivative thereof. Examples of cardiovascular conditions include, but are not limited to, atherosclerosis, restenosis, vascular occlusion and carotid obstructive disease.

In another aspect, the present invention provides methods of disrupting the function of a leukocyte or disrupting a function of an osteoclast. The method includes contacting the leukocyte or the osteoclast with a function disrupting amount of a compound of the invention.

In another aspect of the present invention, methods are provided for treating ophthalmic disease by administering one or more of the subject compounds or pharmaceutical compositions to the eye of a subject.

The invention further provides methods of modulating kinase activity by contacting a kinase with an amount of a compound of the invention sufficient to modulate the activity of the kinase. Modulate can be inhibiting or activating kinase activity. In some embodiments, the invention provides methods of inhibiting kinase activity by contacting a kinase with an amount of a compound of the invention sufficient to inhibit the activity of the kinase. In some embodiments, the invention provides methods of inhibiting kinase activity in a solution by contacting said solution with an amount of a compound of the invention sufficient to inhibit the activity of the kinase in said solution. In some embodiments, the invention provides methods of inhibiting kinase activity in a cell by contacting said cell with an amount of a compound of the invention sufficient to inhibit the activity of the kinase in said cell. In some embodiments, the invention provides methods of inhibiting kinase activity in a tissue by contacting said tissue with an amount of a compound of the invention sufficient to inhibit the activity of the kinase in said tissue. In some embodiments, the invention provides methods of inhibiting kinase activity in an organism by contacting said organism with an amount of a compound of the invention sufficient to inhibit the activity of the kinase in said organism. In some embodiments, the invention provides methods of inhibiting kinase activity in an animal by contacting said animal with an amount of a compound of the invention sufficient to inhibit the activity of the kinase in said animal. In some embodiments, the invention provides methods of inhibiting kinase activity in a mammal by contacting said mammal with an amount of a compound of the invention sufficient to inhibit the activity of the kinase in said mammal. In some embodiments, the invention provides methods of inhibiting kinase activity in a human by contacting said human with an amount of a compound of the invention sufficient to inhibit the activity of the kinase in said human. In some embodiments, the % of kinase activity after contacting a kinase with a compound of the invention is less than 1, 5, 10, 20, 30, 40, 50, 60, 70, 80, 90, 95, or 99% of the kinase activity in the absence of said contacting step.

In some embodiments, the kinase is a lipid kinase or a protein kinase. In some embodiments, the kinase is selected from the group consisting of PI3 kinase including different isoforms such as PI3 kinase α, PI3 kinase β, PI3 kinase γ, PI3 kinase δ; DNA-PK; mTor; Abl, VEGFR, Ephrin receptor B4 (EphB4); TEK receptor tyrosine kinase (HE2); FMS-related tyrosine kinase 3 (FLT-3); Platelet derived growth factor receptor (PDGFR); RET; ATM; ATR; hSmg-1; Hck; Src; Epidermal growth factor receptor (EGFR); KIT; Inulsin Receptor (IR) and IGFR.

The invention further provides methods of modulating PI3 kinase activity by contacting a PI3 kinase with an amount of a compound of the invention sufficient to modulate the activity of the PI3 kinase. Modulate can be inhibiting or activating PI3 kinase activity. In some embodiments, the invention provides methods of inhibiting PI3 kinase activity by contacting a PI3 kinase with an amount of a compound of the invention sufficient to inhibit the activity of the PI3 kinase. In some embodiments, the invention provides methods of inhibiting PI3 kinase activity. Such inhibition can take place in solution, in a cell expressing one or more PI3 kinases, in a tissue comprising a cell expressing one or more PI3 kinases, or in an organism expressing one or more PI3 kinases. In some embodiments, the invention provides methods of inhibiting PI3 kinase activity in an animal (including mammal such as humans) by contacting said animal with an amount of a compound of the invention sufficient to inhibit the activity of the PI3 kinase in said animal.

The ability of the compounds of the invention to treat arthritis can be demonstrated in a murine collagen-induced arthritis model [Kakimoto, et al., Cell. Immunol., 142:326-337 (1992)], in a rat collagen-induced arthritis model [Knoerzer, et al., Toxicol. Pathol., 25:13-19-(1997)], in a rat adjuvant arthritis model [Halloran, et al., Arthritis Rheum., 39:810-819 (1996)], in a rat streptococcal cell wall-induced arthritis model [Schimmer, et al., J. Immunol., 160:1466-1477 (1998)], or in a SCID-mouse human rheumatoid arthritis model [Oppenheimer-Marks, et al., J. Clin. Invest., 101: 1261-1272 (1998)].

The ability of the compounds of the invention to treat Lyme arthritis can be demonstrated according to the method of Gross, et al., Science, 218:703-706, (1998).

The ability of the compounds of the invention to treat asthma can be demonstrated in a murine allergic asthma model according to the method of Wegner, et al., Science, 247:456-459 (1990), or in a murine non-allergic asthma model according to the method of Bloemen, et al, Am. J. Respir. Crit. Care Med., 153:521-529 (1996).

The ability of the compounds of the invention to treat inflammatory lung injury can be demonstrated in a murine oxygen-induced lung injury model according to the method of Wegner, et al., Lung, 170:267-279 (1992), in a murine immune complex-induced lung injury model according to the method of Mulligan, et al., J. Immunol., 154:1350-1363 (1995), or in a murine acid-induced lung injury model according to the method of Nagase, et al., Am. J. Respir. Crit. Care Med., 154:504-510 (1996).

The ability of the compounds of the invention to treat inflammatory bowel disease can be demonstrated in a murine chemical-induced colitis model according to the method of Bennett, et al., J. Pharmacol. Exp. Ther., 280: 988-1000 (1997).

The ability of the compounds of the invention to treat autoimmune diabetes can be demonstrated in an NOD mouse model according to the method of Hasagawa, et al., Int. Immunol., 6:831-838 (1994), or in a murine streptozotocin-induced diabetes model according to the method of Herrold, et al., Cell Immunol., 157:489-500 (1994).

The ability of the compounds of the invention to treat inflammatory liver injury can be demonstrated in a murine liver injury model according to the method of Tanaka, et al., J. Immunol., 151:5088-5095 (1993).

The ability of the compounds of the invention to treat inflammatory glomerular injury can be demonstrated in a rat nephrotoxic serum nephritis model according to the method of Kawasaki, et al., J. Immunol., 150: 1074-1083 (1993).

The ability of the compounds of the invention to treat radiation-induced enteritis can be demonstrated in a rat abdominal irradiation model according to the method of Panes, et al., Gastroenterology, 108:1761-1769 (1995).

The ability of the PI3K delta selective inhibitors to treat radiation pneumonitis can be demonstrated in a murine pulmonary irradiation model according to the method of Hallahan, et al., Proc. Natl. Acad. Sci (USA), 94:6432-6437 (1997).

The ability of the compounds of the invention to treat reperfusion injury can be demonstrated in the isolated heart according to the method of Tamiya, et al., Immunopharmacology, 29:53-63 (1995), or in the anesthetized dog according to the model of Hartman, et al., Cardiovasc. Res., 30:47-54 (1995).

The ability of the compounds of the invention to treat pulmonary reperfusion injury can be demonstrated in a rat lung allograft reperfusion injury model according to the method of DeMeester, et al., Transplantation, 62:1477-1485 (1996), or in a rabbit pulmonary edema model according to the method of Horgan, et al., Am. J. Physiol., 261:H1578-H1584 (1991).

The ability of the compounds of the invention to treat stroke can be demonstrated in a rabbit cerebral embolism stroke model according to the method of Bowes, et al., Exp. Neurol., 119:215-219 (1993), in a rat middle cerebral artery ischemia-reperfusion model according to the method of Chopp, et al., Stroke, 25:869-875 (1994), or in a rabbit reversible spinal cord ischemia model according to the method of Clark, et al., Neurosurg., 75:623-627 (1991).

The ability of the compounds of the invention to treat cerebral vasospasm can be demonstrated in a rat experimental vasospasm model according to the method of Oshiro, et al., Stroke, 28:2031-2038 (1997).

The ability of the compounds of the invention to treat peripheral artery occlusion can be demonstrated in a rat skeletal muscle ischemia/reperfusion model according to the method of Gute, et al., Mol. Cell Biochem., 179:169-187 (1998).

The ability of the compounds of the invention to treat graft rejection can be demonstrated in a murine cardiac allograft rejection model according to the method of Isobe, et al., Science, 255:1125-1127 (1992), in a murine thyroid gland kidney capsule model according to the method of Talento, et al., Transplantation, 55:418-422 (1993), in a cynomolgus monkey renal allograft model according to the method of Cosimi, et al., J. Immunol., 144:4604-4612 (1990), in a rat nerve allograft model according to the method of Nakao, et al., Muscle Nerve, 18:93-102 (1995), in a murine skin allograft model according to the method of Gorczynski and Wojcik, J. Immunol., 152:2011-2019 (1994), in a murine corneal allograft model according to the method of He, et al., Opthalmol. Vis. Sci., 35:3218-3225 (1994), or in a xenogeneic pancreatic islet cell transplantation model according to the method of Zeng, et al., Transplantation, 58:681-689 (1994).

The ability of the compounds of the invention to treat graft-versus-host disease (GVHD) can be demonstrated in a murine lethal GVHD model according to the method of Harning, et al., Transplantation, 52:842-845 (1991).

The ability of the compounds of the invention to treat cancers can be demonstrated in a human lymphoma metastasis model (in mice) according to the method of Aoudjit, et al., J. Immunol., 161:2333-2338 (1998).

Combination Treatment

The present invention also provides methods for combination therapies in which an agent known to modulate other pathways, or other components of the same pathway, or even overlapping sets of target enzymes are used in combination with a compound of the present invention, or a pharmaceutically acceptable salt, ester, prodrug, solvate, hydrate or derivative thereof. In one aspect, such therapy includes but is not limited to the combination of the subject compound with chemotherapeutic agents, therapeutic antibodies, and radiation treatment, to provide a synergistic or additive therapeutic effect.

In one aspect, the compounds or pharmaceutical compositions of the present invention may present synergistic or additive efficacy when administered in combination with agents that inhibit IgE production or activity. Such combination can reduce the undesired effect of high level of IgE associated with the use of one or more PI3KS inhibitors, if such effect occurs. This may be particularly useful in treatment of autoimmune and inflammatory disorders (AIID) such as rheumatoid arthritis. Additionally, the administration of PI3Kδ or PI3Kδ/γ inhibitors of the present invention in combination with inhibitors of mTOR may also exhibit synergy through enhanced inhibition of the PI3K pathway.

In a separate but related aspect, the present invention provides a combination treatment of a disease associated with PI3Kδ comprising administering a PI3K δ inhibitor and an agent that inhibits IgE production or activity. Other exemplary PI3Kδ inhibitors are applicable for this combination and they are described, e.g., U.S. Pat. No. 6,800,620. Such combination treatment is particularly useful for treating autoimmune and inflammatory diseases (AIID) including but not limited to rheumatoid arthritis.

Agents that inhibit IgE production are known in the art and they include but are not limited to one or more of TEI-9874, 2-(4-(6-cyclohexyloxy-2-naphthyloxy)phenylacetamide)benzoic acid, rapamycin, rapamycin analogs (i.e. rapalogs), TORC1/mTORC1 inhibitors, mTORC2/TORC2 inhibitors, and any other compounds that inhibit TORC1/mTORC1 and mTORC2/TORC2. Agents that inhibit IgE activity include, for example, anti-IgE antibodies such as for example Omalizumab and TNX-901.

For treatment of autoimmune diseases, the subject compounds or pharmaceutical compositions can be used in combination with commonly prescribed drugs including but not limited to Enbrel®, Remicade®, Humira®, Avonex®, and Rebit®. For treatment of respiratory diseases, the subject compounds or pharmaceutical compositions can be administered in combination with commonly prescribed drugs including but not limited to Xolair®, Advair®, Singulair®, and Spiriva®.

The compounds of the invention may be formulated or administered in conjunction with other agents that act to relieve the symptoms of inflammatory conditions such as encephalomyelitis, asthma, and the other diseases described herein. These agents include non-steroidal anti-inflammatory drugs (NSAIDs), e.g. acetylsalicylic acid; ibuprofen; naproxen; indomethacin; nabumetone; tolmetin; etc. Corticosteroids are used to reduce inflammation and suppress activity of the immune system. The most commonly prescribed drug of this type is Prednisone. Chloroquine (Aralen) or hydroxychloroquine (Plaquenil) may also be very useful in some individuals with lupus. They are most often prescribed for skin and joint symptoms of lupus. Azathioprine (Imuran) and cyclophosphamide (Cytoxan) suppress inflammation and tend to suppress the immune system. Other agents, e.g. methotrexate and cyclosporin are used to control the symptoms of lupus. Anticoagulants are employed to prevent blood from clotting rapidly. They range from aspirin at very low dose which prevents platelets from sticking, to heparin/coumadin.

In another one aspect, this invention also relates to a pharmaceutical composition for inhibiting abnormal cell growth in a mammal which comprises an amount of a compound of the present invention, or a pharmaceutically acceptable salt, ester, prodrug, solvate, hydrate or derivative thereof, in combination with an amount of an anti-cancer agent (e.g. a chemotherapeutic agent). Many chemotherapeutics are presently known in the art and can be used in combination with the compounds of the invention.

In some embodiments, the chemotherapeutic is selected from the group consisting of mitotic inhibitors, alkylating agents, anti-metabolites, intercalating antibiotics, growth factor inhibitors, cell cycle inhibitors, enzymes, topoisomerase inhibitors, biological response modifiers, anti-hormones, angiogenesis inhibitors, and anti-androgens. Non-limiting examples are chemotherapeutic agents, cytotoxic agents, and non-peptide small molecules such as Gleevec (Imatinib Mesylate), Velcade (bortezomib), Iressa (gefitinib), Sprycel (Dasatinib), and Adriamycin as well as a host of chemotherapeutic agents. Non-limiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylencmelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, Casodex™, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, pĸ)tfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfomithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK.R™-; razoxane; sizofiran; spirogermanium; tenuazonic acid; triaziquone; 2,2',2"-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (TAXOL™, Bristol-Myers Squibb Oncology, Princeton, N.J.) and docetaxel (TAXOTERE™, Rhone-Poulenc Rorer, Antony, France); retinoic acid; esperamicins; capecitabine; and pharmaceutically acceptable salts, acids or derivatives of any of the above. Also included as suitable chemotherapeutic cell conditioners are anti-hormonal agents that act to regulate or inhibit hormone action on tumors such as anti-estrogens including for example tamoxifen (Nolvadex™), raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide (Casodex), leuprolide, and goserelin (Zoladex); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; camptothecin-11 (CPT-11); topoisomerase inhibitor RFS 2000; difluoromethylornithine (DMFO), 17α-Ethinylestradiol, Diethylstilbestrol, Testosterone, Prednisone, Fluoxymesterone, Megestrolacetate, Methylprednisolone, Methyl-testosterone, Prednisolone, Triamcinolone, chlorotrianisene, Hydroxyprogesterone, Aminoglutethimide, Medroxyprogesteroneacetate, matrix metalloproteinase inhibitors, EGFR inhibitors, Pan Her inhibitors, VEGF inhibitors, including as anti-VEGF antibodies such as Avastin, and small molecules such as ZD6474 and SU6668, vatalanib, BAY-43-9006, SU11248, CP-547632, and CEP-7055. Anti-Her2 antibodies (such as Herceptin from Genentech) may also be utilized. Suitable EGFR inhibitors include gefitinib, erlotinib, and cetuximab. Pan Her inhibitors include canertinib, EKB-569, and GW-572016. Further suitable anticancer agents include, but are not limited to, Src inhibitors, MEK-1 kinase inhibitors, MAPK kinase inhibitors, PI3 kinase inhibitors, and PDGF inhibitors, such as imatinib. Also included are anti-angiogenic and antivascular agents which, by interrupting blood flow to solid tumors, render cancer cells quiescent by depriving them of nutrition. Castration which also renders androgen dependent carcinomas non-proliferative, may also be utilized. Also included are IGF1R inhibitors, inhibitors of non-receptor and receptor tyrosine kinases, and inhibitors of integrin signalling. Additional anticancer agents include microtubule-stabilizing agents 7-O-methylthiomethylpaclitaxel (disclosed in U.S. Pat. No. 5,646,176), 4-desacetyl-4-methylcarbonatepaclitaxel, 3'-tert-butyl-3'-N-tert-butyloxycarbonyl-4-desacetyl-3'-dephenyl-3'-N-debenzoyl-4-O-methoxycarbonyl-paclitaxel (disclosed in U.S. Ser. No. 09/712,352 filed on Nov. 14, 2000), C-4 methyl carbonate paclitaxel, epothilone A, epothilone B, epothilone C, epothilone D, desoxyepothilone A, desoxyepothilone B, [1S-[1R*,3R*(E),7R*,10S*, 11R*,12R*,16S*]]-7-11-dihydroxy-8,8,10,12,16-pentamethyl-3-[1-methyl-2-(2-methyl-4-thiazolyl)ethenyl]-4-aza-17 oxabicyclo[14.1.0] heptadecane-5,9-dione (disclosed in WO 99/02514), [1S-[1R*,3R*(E),7R*,10S*,11R*,12R*,16S*]]-3-[2-[2-(aminomethyl)-4-thiazolyl]-1-methyl ethenyl]-7,11-dihydroxy-8,8,10,12,16-pentamethyl-4-17-dioxabicyclo [14.1.0]-heptadecane-5,-9-dione (as disclosed in U.S. Pat. No. 6,262,094) and derivatives thereof; and microtubule-disrupter agents. Also suitable are CDK inhibitors, an antiproliferative cell cycle inhibitor, epidophyllotoxin; an antineoplastic enzyme; biological response modifiers; growth inhibitors; antihormonal therapeutic agents; leucovorin; tegafur, and haematopoietic growth factors.

Additional cytotoxic agents include, hexamethyl melamine, idatrexate, L-asparaginase, camptothecin, topotecan, pyridobenzoindole derivatives, interferons, and interleukins. Where desired, the compounds or pharmaceutical composition of the present invention can be used in combination with commonly prescribed anti-cancer drugs such as Herceptin®, Avastin®, Erbitux®, Rituxan®, Taxol®, Arimidex®, Taxotere®, and Velcade®

This invention further relates to a method for using the compounds or pharmaceutical composition in combination with radiation therapy in inhibiting abnormal cell growth or treating the hyperproliferative disorder in the mammal. Techniques for administering radiation therapy are known in the art, and these techniques can be used in the combination therapy described herein. The administration of the compound of the invention in this combination therapy can be determined as described herein.

Radiation therapy can be administered through one of several methods, or a combination of methods, including without limitation external-beam therapy, internal radiation therapy, implant radiation, stereotactic radiosurgery, systemic radiation therapy, radiotherapy and permanent or temporary interstitial brachytherapy. The term "brachytherapy," as used herein, refers to radiation therapy delivered by a spatially confined radioactive material inserted into the body at or near a tumor or other proliferative tissue disease site. The term is intended without limitation to include exposure to radioactive isotopes (e.g. At-211, I-131, I-125, Y-90, Re-186, Re-188, Sm-153, Bi-212, P-32, and radioactive isotopes of Lu). Suitable radiation sources for use as a cell conditioner of the present invention include both solids and liquids. By way of non-limiting example, the radiation source can be a radionuclide, such as 1-125, 1-131, Yb-169, Ir-192 as a solid source, 1-125 as a solid source, or other radionuclides that emit photons, beta particles, gamma radiation, or other therapeutic rays. The radioactive material can also be a fluid made from any 5 solution of radionuclides), e.g., a solution of 1-125 or 1-131, or a radioactive fluid can be produced using a slurry of a suitable fluid containing small particles of solid radionuclides, such as Au-198, Y-90. Moreover, the radionuclide(s) can be embodied in a gel or radioactive micro spheres.

Without being limited by any theory, the compounds of the present invention can render abnormal cells more sensitive to treatment with radiation for purposes of killing and/or inhibiting the growth of such cells. Accordingly, this invention further relates to a method for sensitizing abnormal cells in a mammal to treatment with radiation which comprises administering to the mammal an amount of a compound of the present invention or pharmaceutically acceptable salt, ester, prodrug, solvate, hydrate or derivative thereof, which amount is effective is sensitizing abnormal cells to treatment with radiation. The amount of the compound, salt, or solvate in this method can be determined according to the means for ascertaining effective amounts of such compounds described herein.

The compounds or pharmaceutical compositions of the present invention can be used in combination with an amount of one or more substances selected from anti-angiogenesis agents, signal transduction inhibitors, and anti-proliferative agents.

Anti-angiogenesis agents, such as MMP-2 (matrix-metalloprotienase 2) inhibitors, MMP-9 (matrix-metalloprotienase 9) inhibitors, and COX—H (cyclooxygenase 11) inhibitors, can be used in conjunction with a compound of the present invention and pharmaceutical compositions described herein. Examples of useful COX-II inhibitors include CELEBREX™ (alecoxib), valdecoxib, and rofecoxib. Examples of useful matrix metalloproteinase inhibitors are described in WO 96/33172 (published Oct. 24,1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13,1994), European Patent Publication 931, 788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain Patent Application No. 9912961.1 (filed Jun. 3, 1999), U.S. Provisional Application No. 60/148,464 (filed Aug. 12,1999), U.S. Pat. No. 5,863, 949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference. Preferred MMP-2 and MMP-9 inhibitors are those that have little or no activity inhibiting MMP-I. More preferred, are those that selectively inhibit MMP-2 and/or AMP-9 relative to the other matrix-metalloproteinases (i. e., MAP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, and RS 13-0830.

The invention also relates to a method of and to a pharmaceutical composition of treating a cardiovascular disease in a mammal which comprises an amount of a compound of the present invention, or a pharmaceutically acceptable salt, ester, prodrug, solvate, hydrate or derivative thereof, or an isotopically-labeled derivative thereof, and an amount of one or more therapeutic agents use for the treatment of cardiovascular diseases.

Examples for use in cardiovascular disease applications are anti-thrombotic agents, e.g., prostacyclin and salicylates, thrombolytic agents, e.g., streptokinase, urokinase, tissue plasminogen activator (TPA) and anisoylated plasminogen-streptokinase activator complex (APSAC), anti-platelets agents, e.g., acetyl-salicylic acid (ASA) and clopidrogel, vasodilating agents, e.g., nitrates, calcium channel blocking drugs, antiproliferative agents, e.g., colchicine and alkylating agents, intercalating agents, growth modulating factors such as interleukins, transformation growth factor-beta and congeners of platelet derived growth factor, monoclonal antibodies directed against growth factors, anti-inflammatory agents, both steroidal and non-steroidal, and other agents that can modulate vessel tone, function, arteriosclerosis, and the healing response to vessel or organ injury post intervention. Antibiotics can also be included in combinations or coatings comprised by the invention. Moreover, a coating can be used to effect therapeutic delivery focally within the vessel wall. By incorporation of the active agent in a swellable polymer, the active agent will be released upon swelling of the polymer.

Other exemplary therapeutic agents useful for a combination therapy include but are not limited to agents as described above, radiation therapy, hormone antagonists, hormones and their releasing factors, thyroid and antithyroid drugs, estrogens and progestins, androgens, adrenocorticotropic hormone; adrenocortical steroids and their synthetic analogs; inhibitors of the synthesis and actions of adrenocortical hormones, insulin, oral hypoglycemic agents, and the pharmacology of the endocrine pancreas, agents affecting calcification and bone turnover: calcium, phosphate, parathyroid hormone, vitamin D, calcitonin, vitamins such as water-soluble vitamins, vitamin B complex, ascorbic acid, fat-soluble vitamins, vitamins A, K, and E, growth factors, cytokines, chemokines, muscarinic receptor agonists and antagonists; anticholinesterase agents; agents acting at the neuromuscular junction and/or autonomic ganglia; catecholamines, sympathomimetic drugs, and adrenergic receptor agonists or antagonists; and 5-hydroxytryptamine (5-HT, serotonin) receptor agonists and antagonists.

Therapeutic agents can also include agents for pain and inflammation such as histamine and histamine antagonists, bradykinin and bradykinin antagonists, 5-hydroxytryptamine (serotonin), lipid substances that are generated by biotransformation of the products of the selective hydrolysis of membrane phospholipids, eicosanoids, prostaglandins, thromboxanes, leukotrienes, aspirin, nonsteroidal anti-inflammatory agents, analgesic-antipyretic agents, agents that inhibit the synthesis of prostaglandins and thromboxanes, selective inhibitors of the inducible cyclooxygenase, selective inhibitors of the inducible cyclooxygenase-2, autacoids, paracrine hormones, somatostatin, gastrin, cytokines that mediate interactions involved in humoral and cellular immune responses, lipid-derived autacoids, eicosanoids, β-adrenergic agonists, ipratropium, glucocorticoids, methylxanthines, sodium channel blockers, opioid receptor agonists, calcium channel blockers, membrane stabilizers and leukotriene inhibitors.

Additional therapeutic agents contemplated herein include diuretics, vasopressin, agents affecting the renal conservation of water, rennin, angiotensin, agents useful in the treatment of myocardial ischemia, anti-hypertensive agents, angiotensin converting enzyme inhibitors, β-adrenergic receptor antagonists, agents for the treatment of hypercholesterolemia, and agents for the treatment of dyslipidemia.

Other therapeutic agents contemplated include drugs used for control of gastric acidity, agents for the treatment of peptic ulcers, agents for the treatment of gastroesophageal reflux disease, prokinetic agents, antiemetics, agents used in irritable bowel syndrome, agents used for diarrhea, agents used for constipation, agents used for inflammatory bowel disease, agents used for biliary disease, agents used for pancreatic disease. Therapeutic agents used to treat protozoan infections, drugs used to treat Malaria, Amebiasis, Giardiasis, Trichomoniasis, Trypanosomiasis, and/or Leishmaniasis, and/or drugs used in the chemotherapy of helminthiasis. Other therapeutic agents include antimicrobial agents, sulfonamides, trimethoprim-sulfamethoxazole quinolones, and agents for urinary tract infections, penicillins, cephalosporins, and other, β-Lactam antibiotics, an agent comprising an aminoglycoside, protein synthesis inhibitors, drugs used in the chemotherapy of tuberculosis, *mycobacterium avium* complex disease, and leprosy, antifungal agents, antiviral agents including nonretroviral agents and antiretroviral agents.

Examples of therapeutic antibodies that can be combined with a subject compound include but are not limited to anti-receptor tyrosine kinase antibodies (cetuximab, panitumumab, trastuzumab), anti CD20 antibodies (rituximab, tositumomab), and other antibodies such as alemtuzumab, bevacizumab, and gemtuzumab.

Moreover, therapeutic agents used for immunomodulation, such as immunomodulators, immunosuppressive agents, tolerogens, and immunostimulants are contemplated by the methods herein. In addition, therapeutic agents acting on the blood and the blood-forming organs, hematopoietic agents, growth factors, minerals, and vitamins, anticoagulant, thrombolytic, and antiplatelet drugs.

Further therapeutic agents that can be combined with a subject compound may be found in Goodman and Gilman's "The Pharmacological Basis of Therapeutics" Tenth Edition edited by Hardman, Limbird and Gilman or the Physician's Desk Reference, both of which are incorporated herein by reference in their entirety.

The compounds described herein can be used in combination with the agents disclosed herein or other suitable agents, depending on the condition being treated. Hence, in some embodiments the compounds of the invention will be co-administered with other agents as described above. When used in combination therapy, the compounds described herein may be administered with the second agent simultaneously or separately. This administration in combination can include simultaneous administration of the two agents in the same dosage form, simultaneous administration in separate dosage forms, and separate administration. That is, a compound described herein and any of the agents described above can be formulated together in the same dosage form and administered simultaneously. Alternatively, a compound of the present invention and any of the agents described above can be simultaneously administered, wherein both the agents are present in separate formulations. In another alternative, a compound of the present invention can be administered just followed by and any of the agents described above, or vice versa. In the separate administration protocol, a compound of the present invention and any of the agents described above may be administered a few minutes apart, or a few hours apart, or a few days apart.

The methods in accordance with the invention may include administering a PI3-kinase δ selective inhibitor with one or more other agents that either enhance the activity of the inhibitor or compliment its activity or use in treatment. Such additional factors and/or agents may produce an augmented or even synergistic effect when administered with a PI3-kinase δ selective inhibitor, or minimize side effects.

In one embodiment, the methods of the invention may include administering formulations comprising a PI3-kinase δ selective inhibitor of the invention with a particular cytokine, lymphokine, other hematopoietic factor, thrombolytic or anti-thrombotic factor, or anti-inflammatory agent before, during, or after administration of the PI3-kinase δ selective inhibitor. One of ordinary skill can easily determine if a particular cytokine, lymphokine, hematopoietic factor, thrombolytic of anti-thrombotic factor, and/or anti-inflammatory agent enhances or compliments the activity or use of the PI3-kinase δ selective inhibitors in treatment.

More specifically, and without limitation, the methods of the invention may comprise administering a PI3-kinase δ selective inhibitor with one or more of TNF, IL-1, IL-2, IL-3, IL4, IL-5, IL-6, IL-7, IL-10, IL-10, IL-11, IL-12, IL-13, IL-14, IL-15, IL-16, IL-17, IL-18, IFN, G-CSF, Meg-CSF, GM-CSF, thrombopoietin, stem cell factor, and erythropoietin. Compositions in accordance with the invention may also include other known angiopoietins such as Ang-2, Ang4, and Ang-Y, growth factors such as bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor a, cytokine-induced neutrophil chemotactic factor 1, cytokine-induced neutrophil chemotactic factor 2 alpha, cytokine-induced neutrophil chemotactic factor 2 beta, beta endothelial cell growth factor, endothelin 1, epidermal growth factor, epithelial-derived neutrophil attractant, fibroblast growth factor 4, fibroblast growth factor 5, fibroblast growth factor 6, fibroblast growth factor 7, fibroblast growth factor 8, fibroblast growth factor 8b, fibroblast growth factor 8c, fibroblast growth factor 9, fibroblast growth factor 10, fibroblast growth factor acidic, fibroblast growth factor basic, glial cell line-derived neutrophic factor receptor a1, glial cell line-derived neutrophic factor receptor a2, growth related protein, growth related protein a, growth related protein .beta., growth related protein .gamma., heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor alpha, nerve growth factor, nerve growth factor receptor, neurotrophin-3, neurptrophin-4, placenta growth factor, placenta growth factor 2, platelet derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor a, platelet derived growth factor receptor beta, pre-B cell growth stimulating factor, stem cell factor, stem cell factor receptor, transforming growth factor alpha, transforming growth factor beta, transforming growth factor beta 1, transforming growth factor beta 1.2, transforming growth factor beta 2, transforming growth factor beta 3, transforming growth factor beta 5, latent transforming growth factor beta 1, transforming growth factor beta binding protein I, transforming growth factor beta binding protein II, transforming growth factor beta binding protein III, tumor necrosis factor receptor type I, tumor necrosis factor receptor type UI, urokinase-type plasminogen activator receptor, and chimeric proteins and biologically or immunologically active fragments thereof.

The following general methodology described herein provides the manner and process of making and using the compound of the present invention and are illustrative rather than limiting. Further modification of provided methodology and additionally new methods may also be devised in order to achieve and serve the purpose of the invention. Accordingly, it should be understood that there may be other embodiments which fall within the spirit and scope of the invention as defined by the specification hereto.

Representative compounds of the present invention include those specified above in Table 1 and pharmaceutically acceptable salts thereof. The present invention should not be construed to be limited to them.

General Method of Preparation of Compounds of the Invention

The compounds of the present invention may be prepared by the following processes. Unless otherwise indicated, the variables (e.g., R, $R^1$, $R^2$, $L_1$, $Cy^1$ and $Cy^2$) when used in the below formulae are to be understood to present those groups described above in relation to formula (I). These methods can similarly be applied to other compounds of formula as provided herein above with or without modification.

Scheme 1:

This scheme provides a synthetic route for the preparation of a compound of formula (10) wherein all the variables are as described herein above. The compound of formula (10) can then be converted to the desired compounds of the invention as provided in schemes 2 and 3 below.

Compound of formula (1) wherein PG is a protecting group such as an alkyl group can be reacted with compound of formula (A) wherein $R^3$ and $R^4$ can be alkyl or alkoxy groups in the presence of a suitable base such as n-butyl lithium or lithium diisopropylamide to give compound of formula (2). Compound of formula (2) can be reacted with a methyl Grignard reagent such as methylmagnesium iodide to give compound of formula (3), which can be oxidised by using an oxidising agent such as pyridinium dichromate to give compound of formula (4).

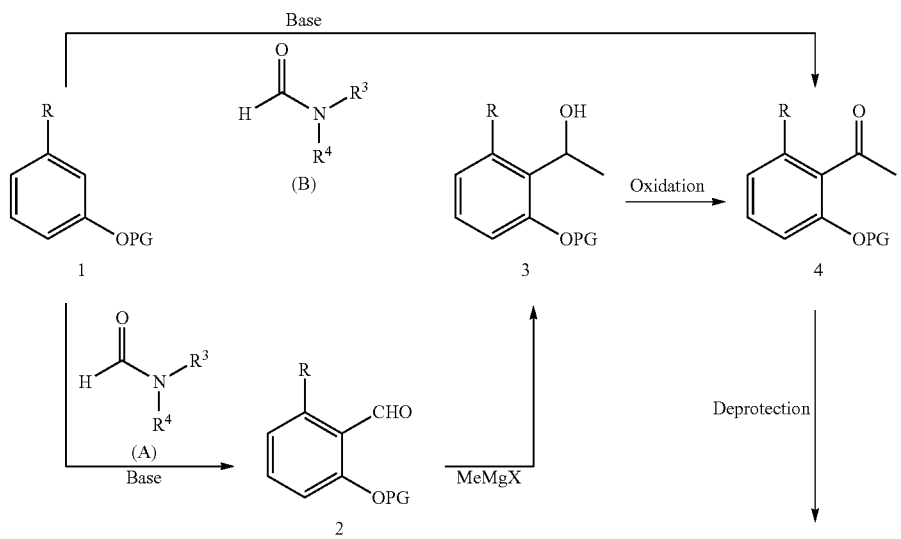

-continued

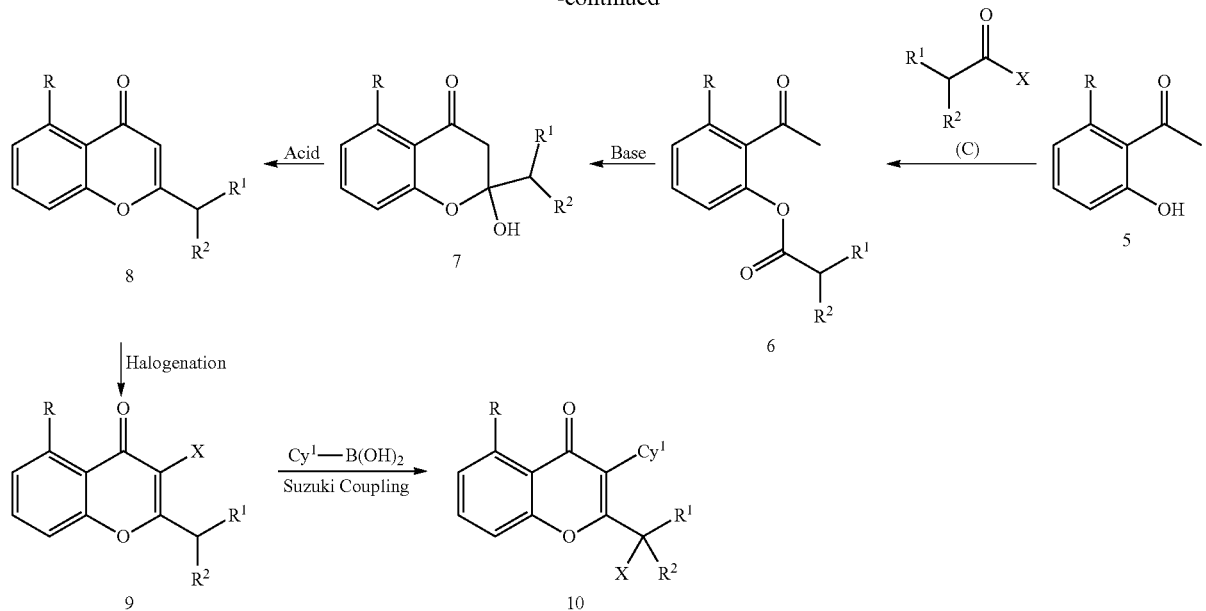

Compound of formula (1) can also be reacted with a compound of formula (B) wherein $R^3$ and $R^4$ can be alkyl or alkoxy groups in the presence of a suitable base such as n-butyl lithium or lithium diisopropylamide to give compound of formula (4). Compound of formula (4) can be deprotected to give compound of formula (5) by using a suitable reagent such as boron tribromide or aluminium chloride. Compound of formula (5) can be acylated with a compound of formula (C) in the presence of a suitable base such as pyridine to give compound of formula (6). Compound of formula (6) can undergo Baker-venkataraman rearrangement upon treatment with a suitable base such as a trialkylamine, a lithium dialkylamide or a lithium disilylamide, e.g. lithium hexamethyl disilazide, to give compound of formula (7). Compound of formula (7) can be reacted with an acid such as hydrochloric acid to give compound of formula (8). Compound of formula (8) can be halogenated to give compound of formula (9) wherein X is a halogen by reacting with a halogenating agent such as bromine or N-bromosuccinimide. Compound of formula (9) can be converted to give compound of formula (10) by reacting with a boronic acid of formula $Cy^1$-$B(OH)_2$ wherein $Cy^1$ is aryl or heteroaryl in the presence of a palladium catalyst such as tetrakis(triphenylphosphine)palladium(0) and a base such as sodium carbonate.

Scheme 1A:

This scheme provides a synthetic route for the preparation of compound of formula (10), (12), (14) and (15) wherein all the variables are as described herein in above, the compound of formula (10), (12), (14) and (15) can then be converted to the desired compounds of the invention as provided in scheme 2, 3 or 4 below.

This scheme provides a synthetic route for the preparation of compound of formula (I) wherein all the variables are as described herein in above

SCHEME 1A

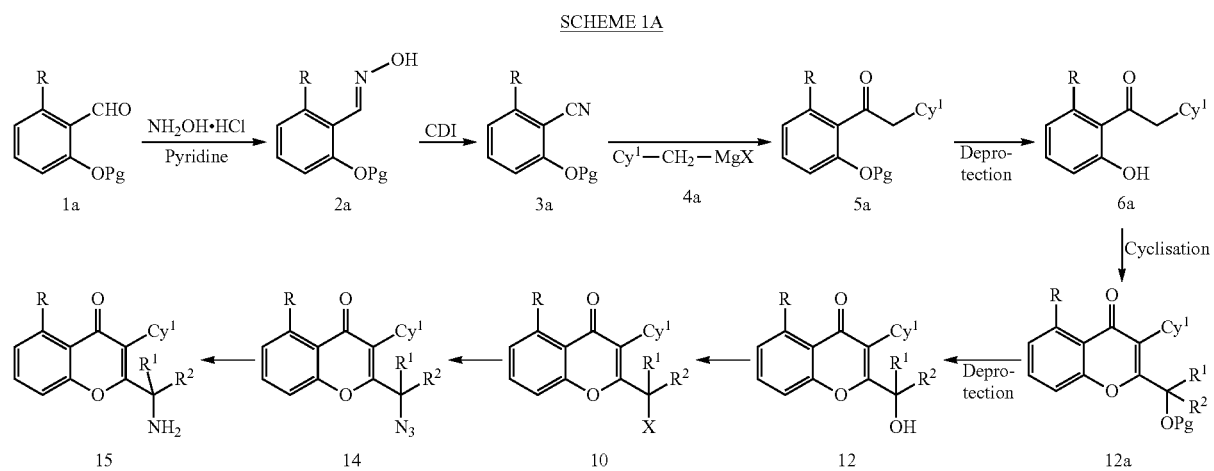

Compound of formula (1a) wherein PG is a protecting group such as alkyl group can be reacted with hydroxylamine hydrochloride to give compound of formula (2a). Compound of formula (2a) be reacted with N,N'-carbonyldiimidazole to give compound of formula (3a). Compound of formula (3a) can be reacted with compound of formula (4a) to give compound of formula (5a). Compound of formula (5a) can be deprotected to compound of formula (6a) by using a suitable reagent such as boron tribromide or aluminium chloride. Compound of formula (6a) can be cyclised with benzyllactic acid to compound of formula (12a). Compound of formula (12a) can be deprotected to compound of formula (12) by using a suitable reagent such as boron tribromide or aluminium chloride. Compound of formula (12) can be reacted with phosphorus halides to give compound of formula (10). Compound of formula (10) can be reacted with sodium azide to give compound of formula (14). Compound of formula (14) can be converted to give compound of formula (15) by reacting with triphenylphosphine.

Illustration of Scheme 1A:
Step-1

Step-2

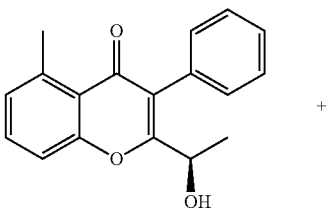

+

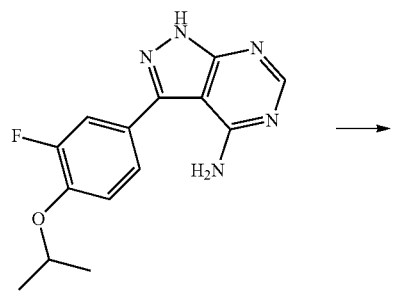

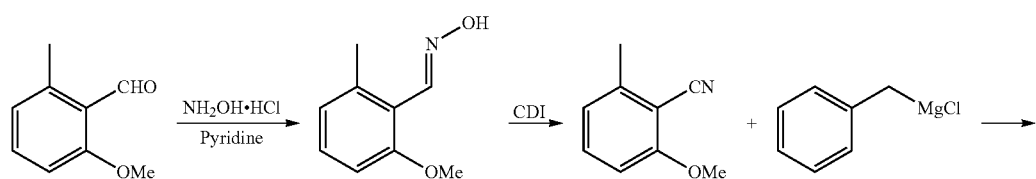

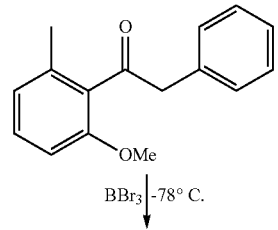

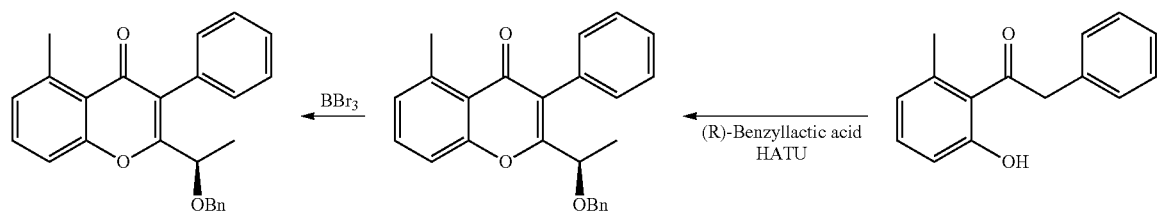

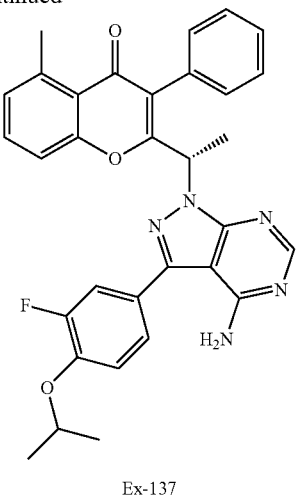

Ex-137

Scheme 2:

This scheme provides a synthetic route for the preparation of compound of formula (IA-II) from compound of formula (10) wherein all the variables are as described herein in above Compound of formula (10) can be reacted with compound of formula (11) in the presence of a base such as a metal carbonate, e.g., potassium carbonate to give compound of formula (IA-I). Alternatively compound of formula (10) can be converted into compound of formula (12) by reacting with a suitable reagent such as dimethyl sulfoxide. Compound of formula (12) can be subjected to Mitsunobu reaction with compound of formula (11) in the presence of a dialkyl azodicarboxylate and a triaryl phosphine such as triphenyl phosphine to afford compound of formula (IA-I).

Scheme 3:

This scheme provides a synthetic route for the preparation of compound of formula (IA-II) from compound of formula (10) wherein all the variables are as described herein in above Compound of formula (10) can be reacted with compound of formula (11a) in the presence of a base such as a metal carbonate, e.g., potassium carbonate to give compound of formula (IA-II). Alternatively compound of formula (10) can be converted into compound of formula (12) by reacting with a suitable reagent such as dimethyl sulfoxide. Compound of formula (12) can be subjected to Mitsunobu reaction with compound of formula (11a) in the presence of a dialkyl azodicarboxylate and a triaryl phosphine such as triphenyl phosphine to afford compound of formula (IA-II).

Scheme 2

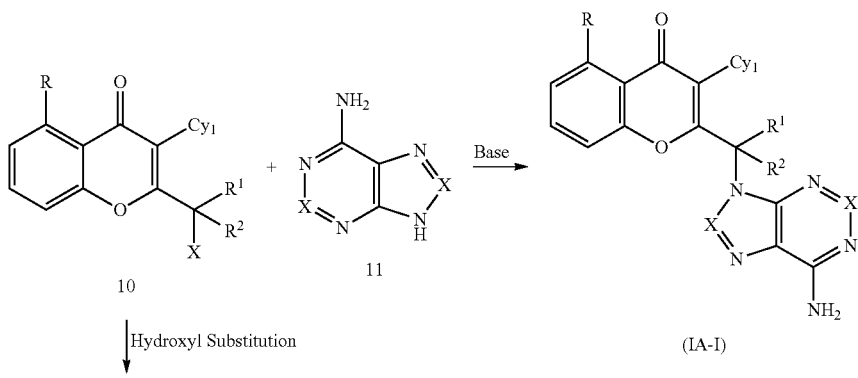

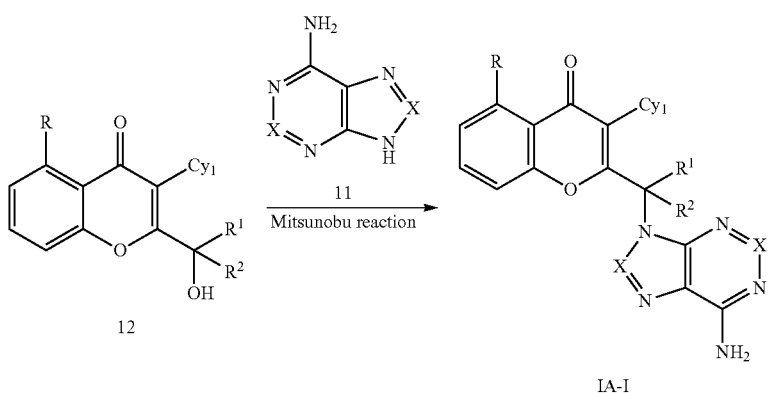

IA-I

SCHEME 3
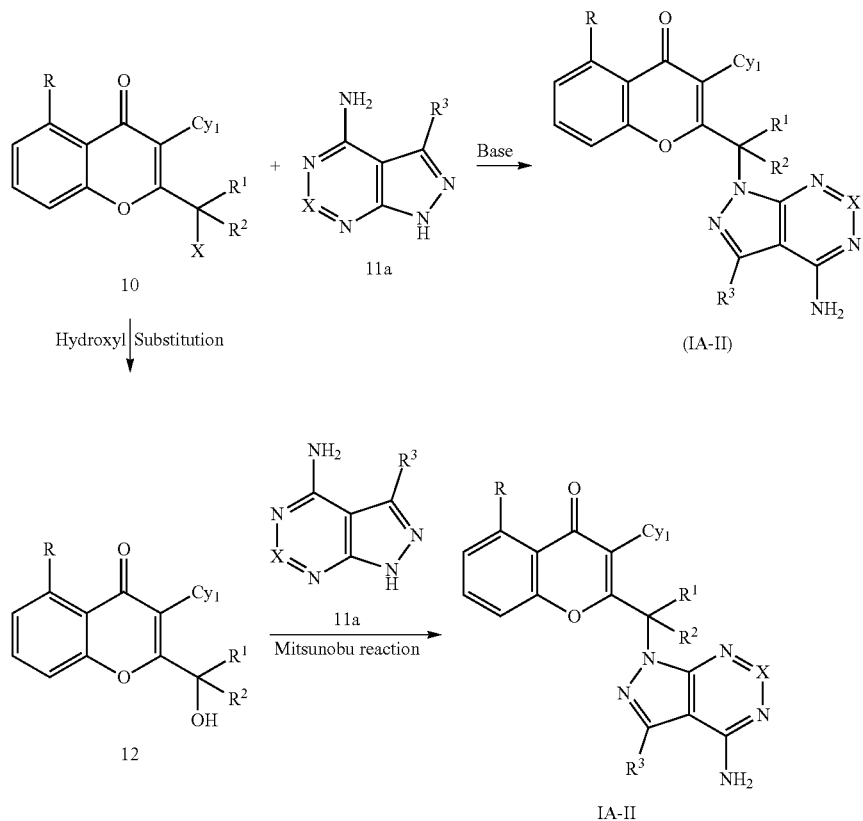
Scheme 4:
This scheme provides a synthetic route for the preparation of compound of formula (IA-IV) from compound of formula (10) wherein all the variables are as described herein in above
SCHEME 4
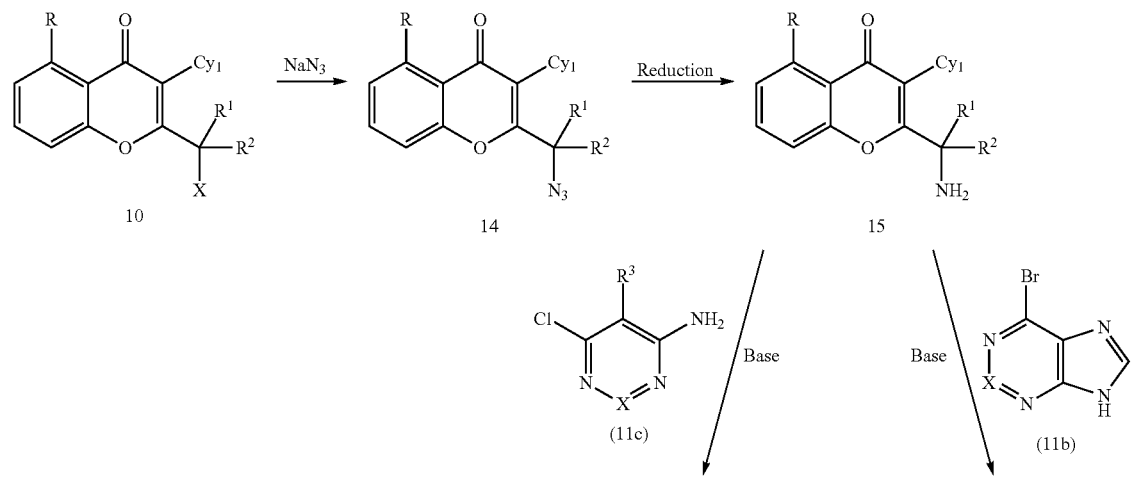

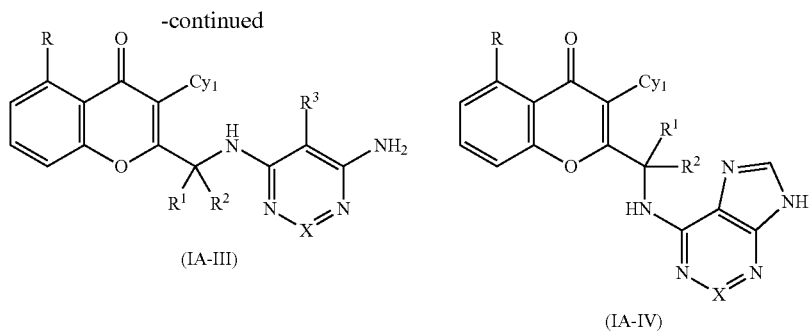

Compound of formula (10) can be reacted with a metal azide such as sodium azide to give compound of formula (14) which can be reduced to compound of formula (15) by using methods known to those skilled in the art. Compound of formula (15) can be reacted with compound of formula (11b) or (11c) in the presence of a suitable base such as N-ethyl-diisopropylamine to give respectively the compound of formula (IA-IV) and (IA-III).

Similar methodologies with certain modifications as known to those skilled in the art can be used to synthesize compound of formula of (I) and (IA) wherein all the variable are to be understood to present those groups described above in relation to formula (I) and (IA) using suitable intermediates and reagents.

EXPERIMENTAL

The examples and preparations provided below further illustrate and exemplify the compounds of the present invention and methods of preparing such compounds. It is to be understood that the scope of the present invention is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers may be obtained by methods known to those skilled in the art.

LIST OF INTERMEDIATES

Intermediate 1

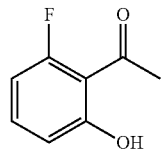

Intermediate 2

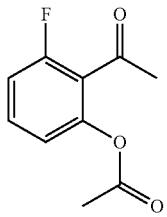

Intermediate 3

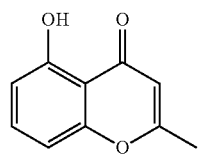

Intermediate 4

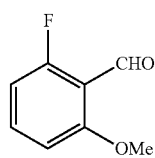

Intermediate 5

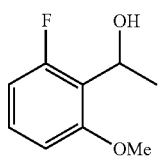

Intermediate 6

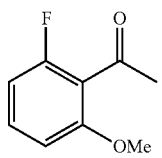

Intermediate 7

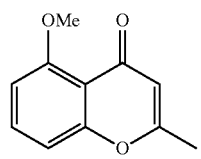

Intermediate 8

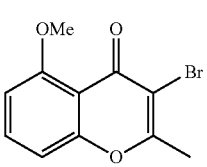

Intermediate 9

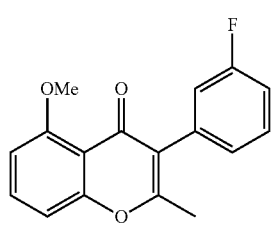

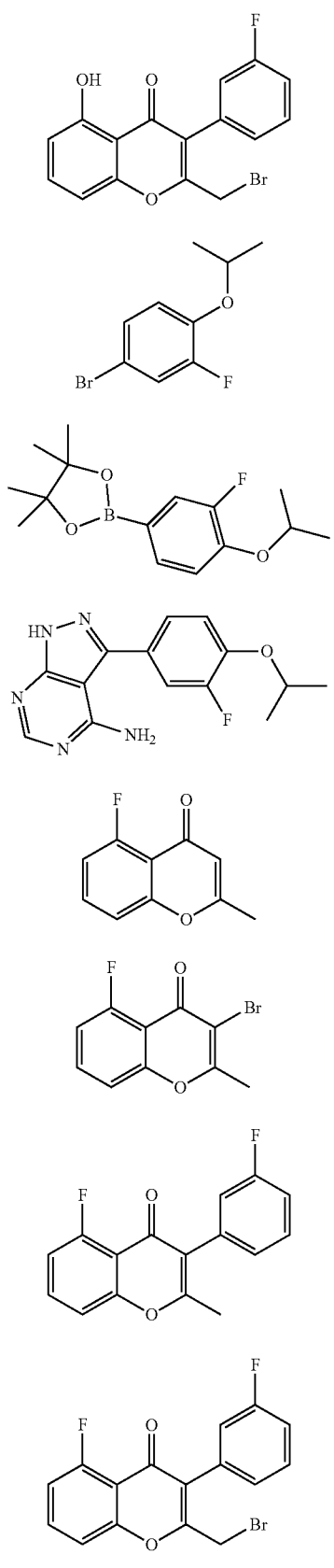
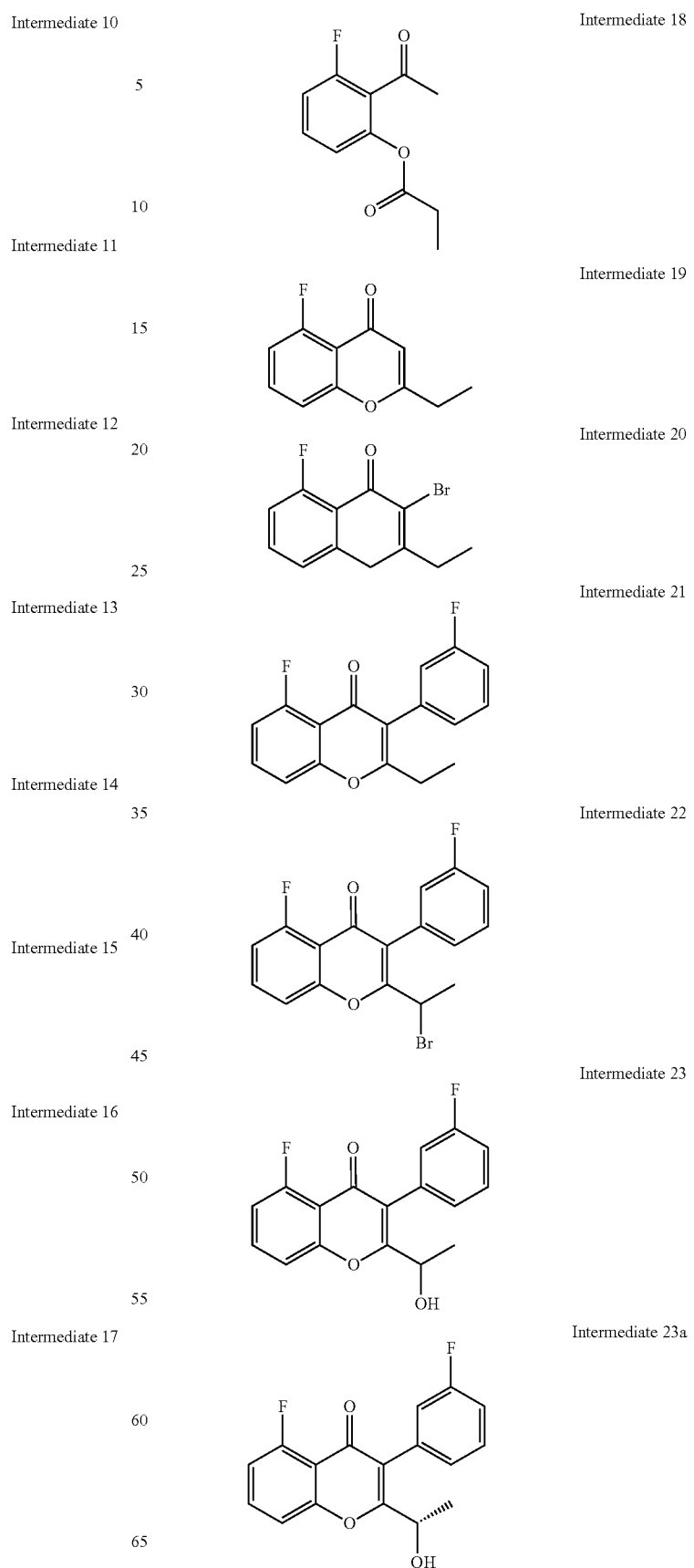

Intermediate 23b
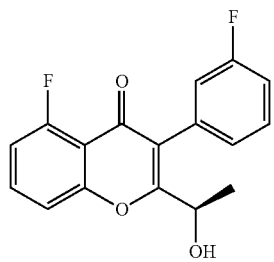
Intermediate 24
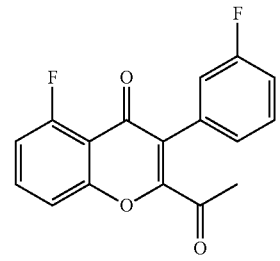
Intermediate 25
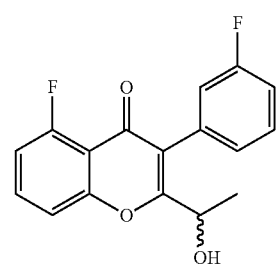
Intermediate 26
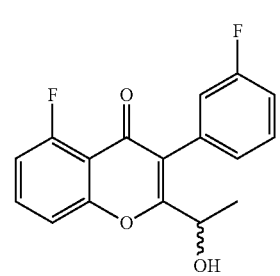
Intermediate 27
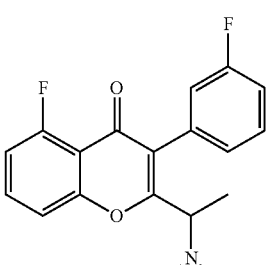
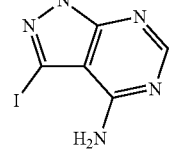
Intermediate 28
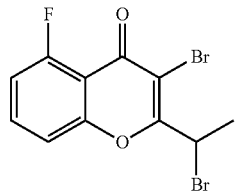
Intermediate 29
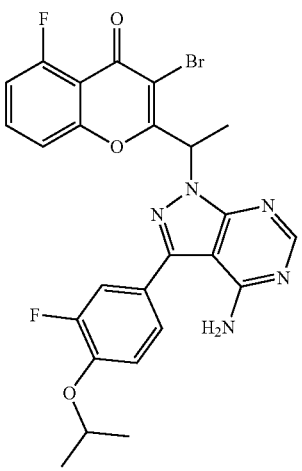
Intermediate 30
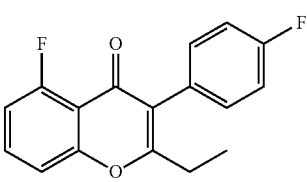
Intermediate 31
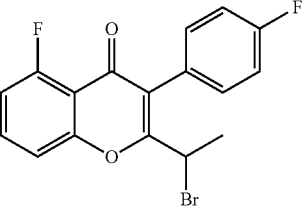
Intermediate 32
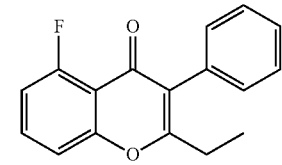
Intermediate 33
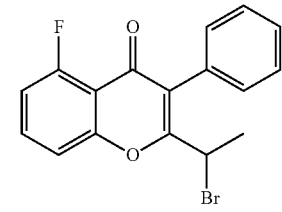

Intermediate 34
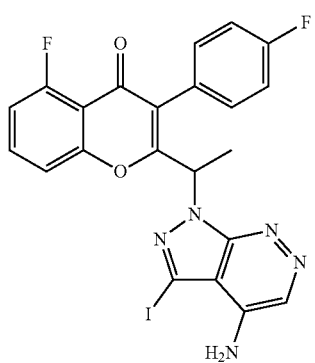
Intermediate 35
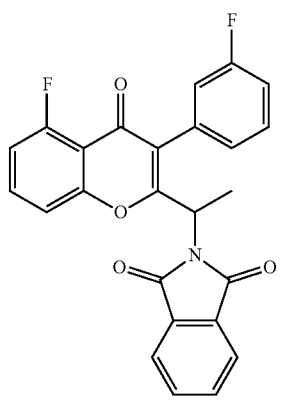
Intermediate 36
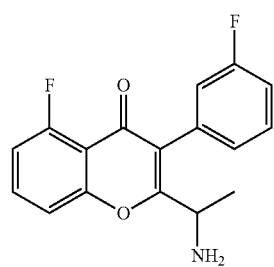
Intermediate 37
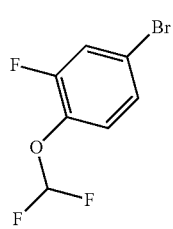
Intermediate 38
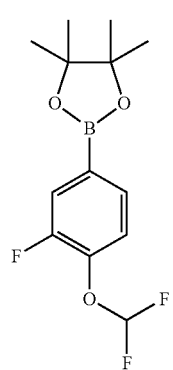
Intermediate 39
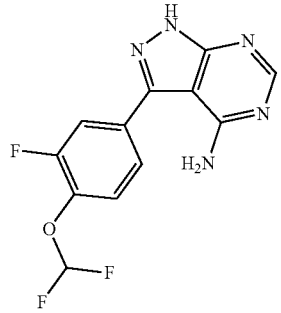
Intermediate 40
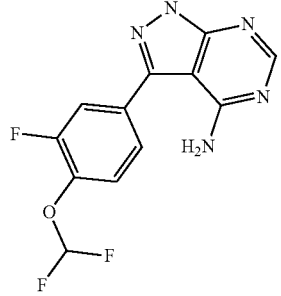
Intermediate 41
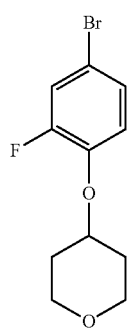
Intermediate 42
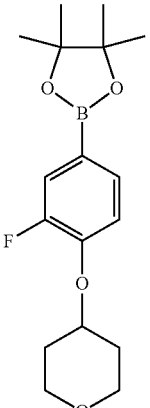
Intermediate 43
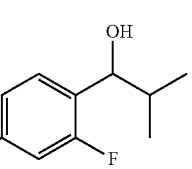
Intermediate 44
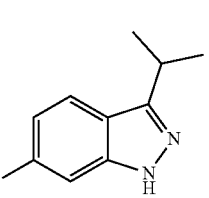

Intermediate 45
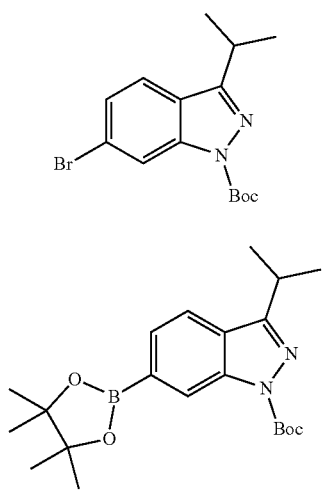
Intermediate 46
Intermediate 47
Intermediate 48
Intermediate 49
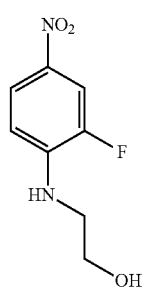
Intermediate 50
Intermediate 51
Intermediate 52
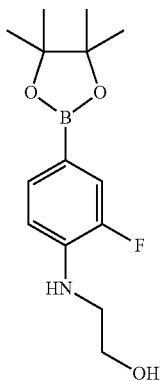
Intermediate 53
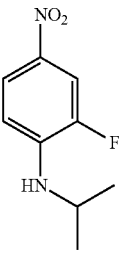
Intermediate 54

Intermediate 55
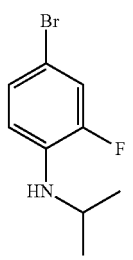
Intermediate 56
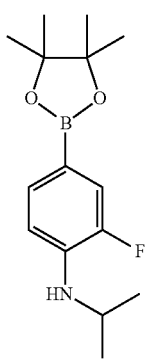
Intermediate 57
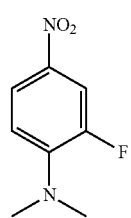
Intermediate 58
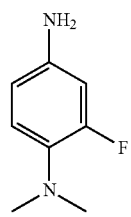
Intermediate 59
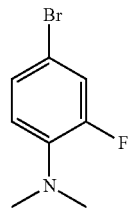
Intermediate 60
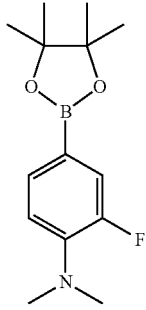
Intermediate 61
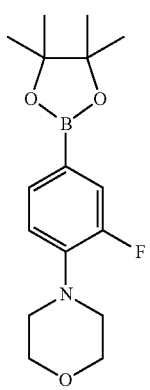
Intermediate 62
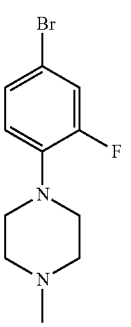
Intermediate 63
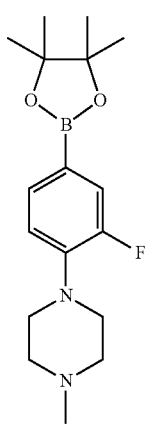
Intermediate 64
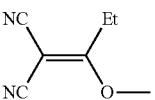
Intermediate 65
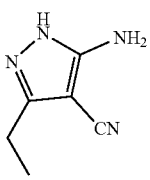
Intermediate 66
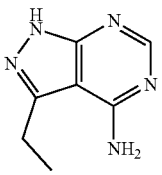

Intermediate 67
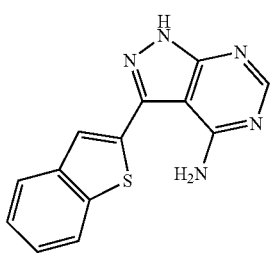
Intermediate 68
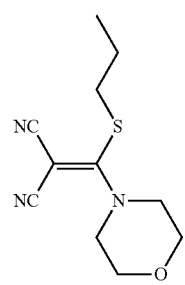
Intermediate 69
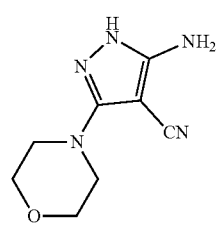
Intermediate 70
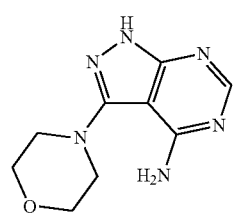
Intermediate 71
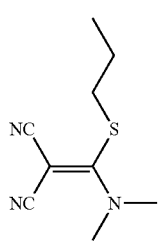
Intermediate 72
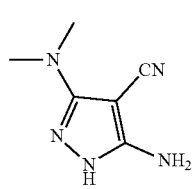
Intermediate 73
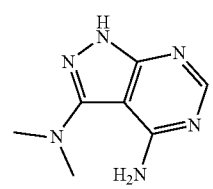
Intermediate 74
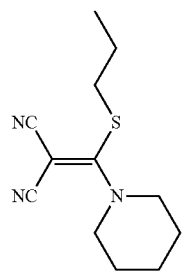
Intermediate 75
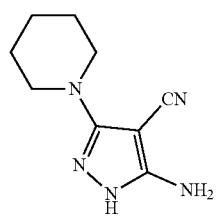
Intermediate 76
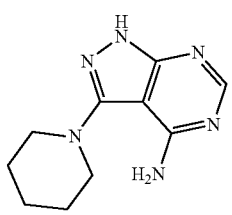
Intermediate 77
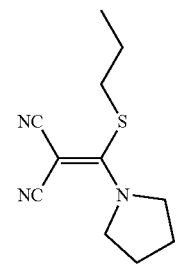
Intermediate 78
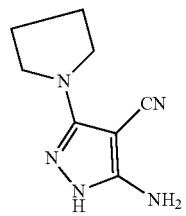
Intermediate 79
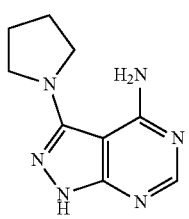

Intermediate 80
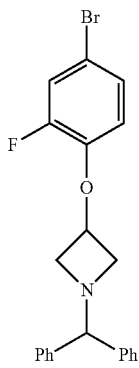
Intermediate 81
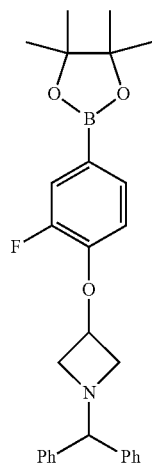
Intermediate 82
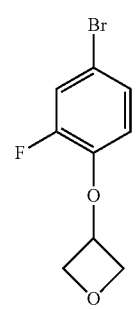
Intermediate 83
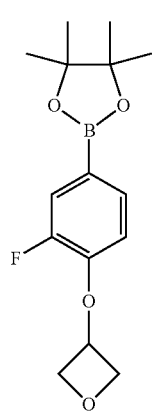
Intermediate 84
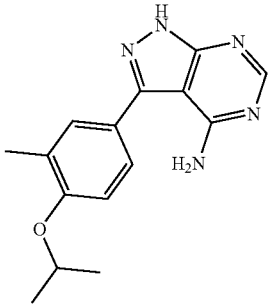
Intermediate 85
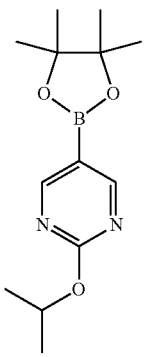
Intermediate 86
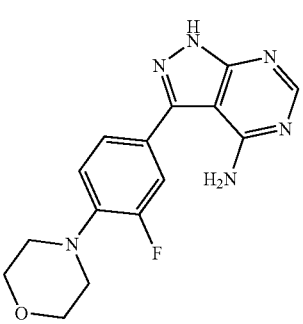
Intermediate 87
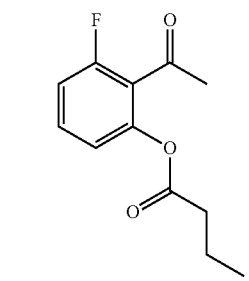
Intermediate 88
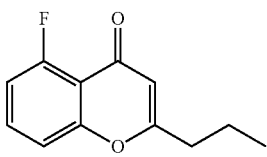
Intermediate 89
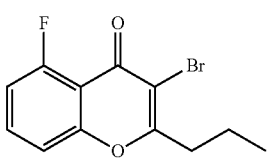

Intermediate 90
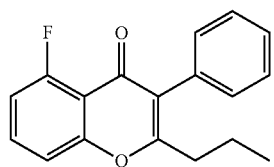
Intermediate 91
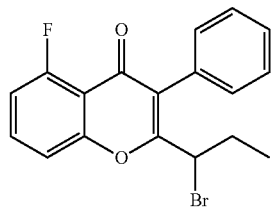
Intermediate 92
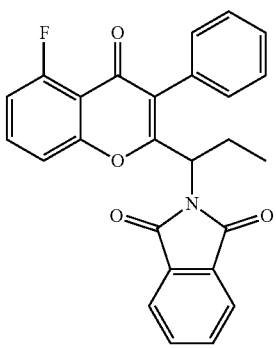
Intermediate 93
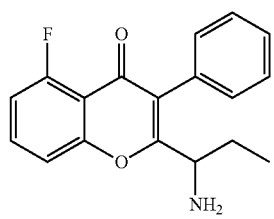
Intermediate 94
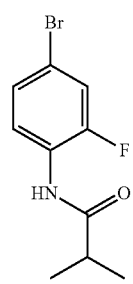
Intermediate 95
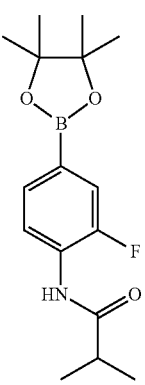
Intermediate 96
Intermediate 97
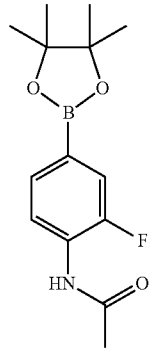
Intermediate 98
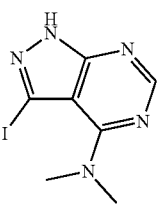
Intermediate 99
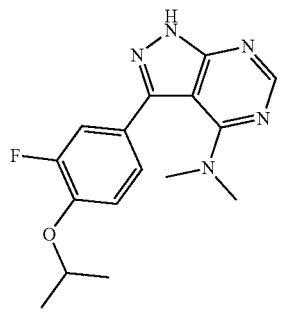
Intermediate 100
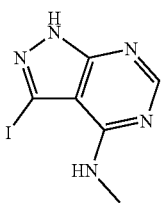

Intermediate 101
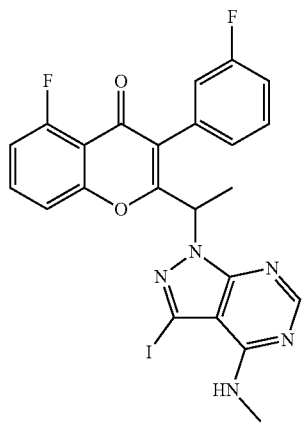
Intermediate 102
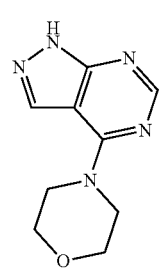
Intermediate 103
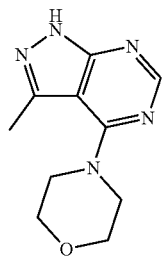
Intermediate 104
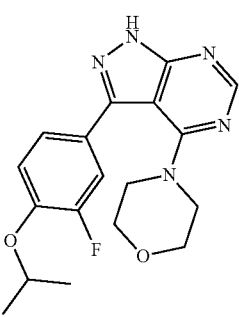
Intermediate 105
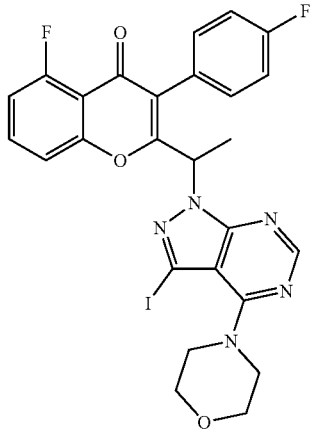
Intermediate 106
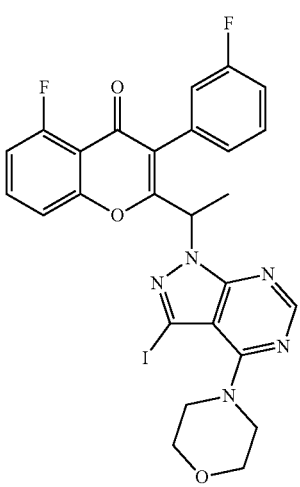
Intermediate 107
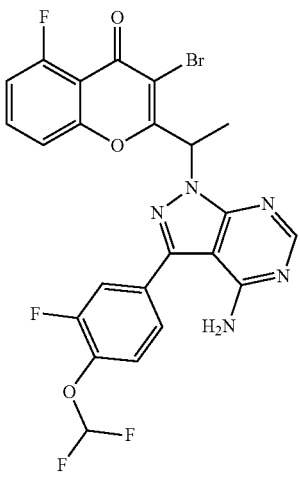

Intermediate 108
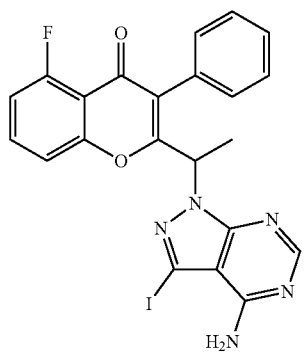
Intermediate 109
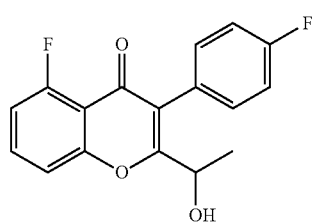
Intermediate 110
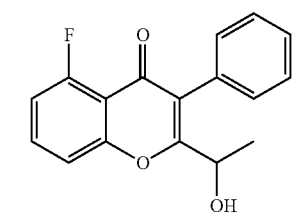
Intermediate 111
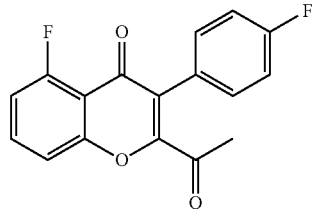
Intermediate 112
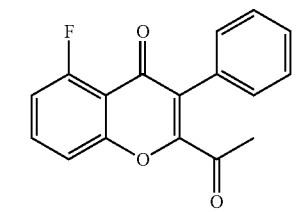
Intermediate 113
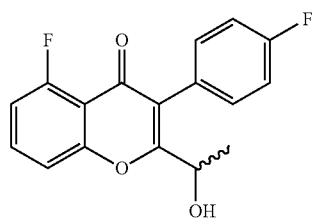
Intermediate 114
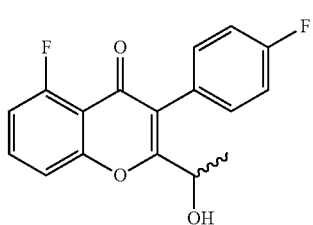
Intermediate 115
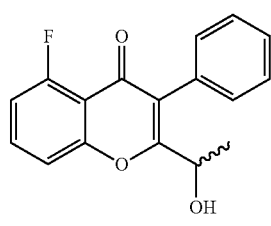
Intermediate 116
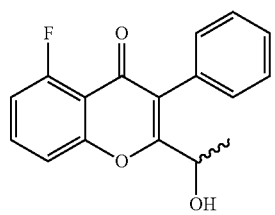
Intermediate 117
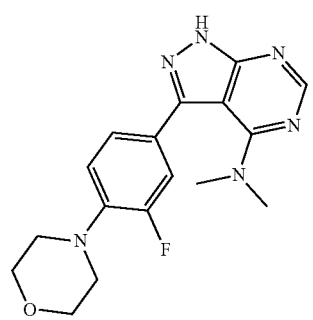
Intermediate 118
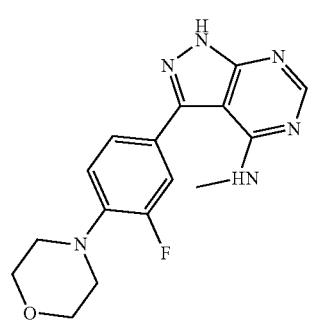
Intermediate 119
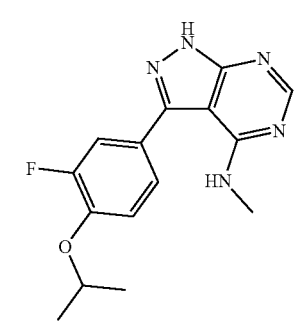

Intermediate 120
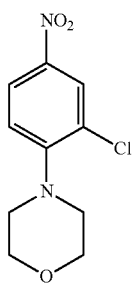
Intermediate 121
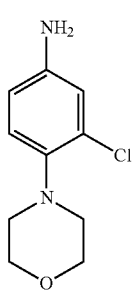
Intermediate 122
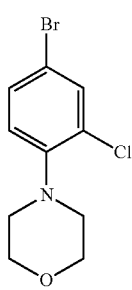
Intermediate 123
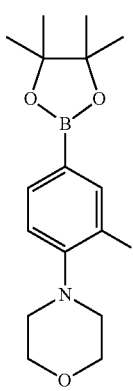
Intermediate 124
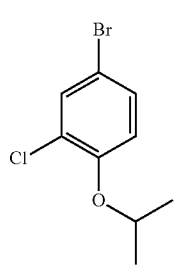
Intermediate 125
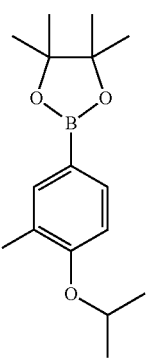
Intermediate 126
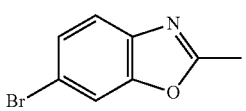
Intermediate 127
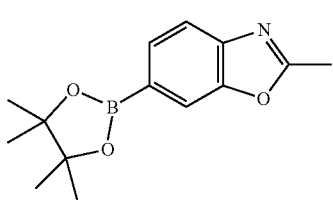
Intermediate 128
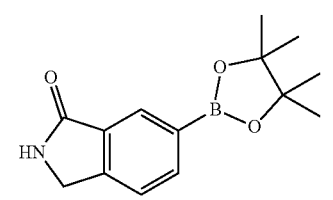
Intermediate 129
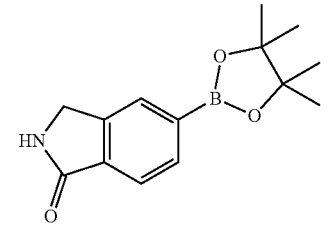
Intermediate 130
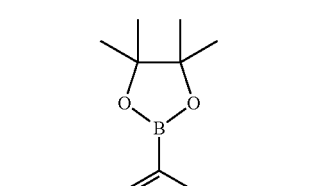

Intermediate 131
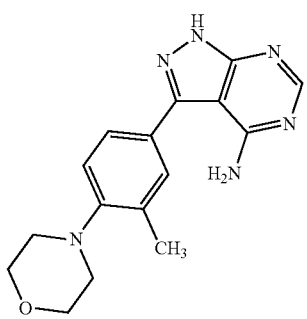
Intermediate 132
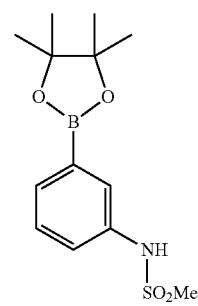
Intermediate 133
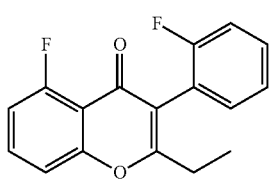
Intermediate 134
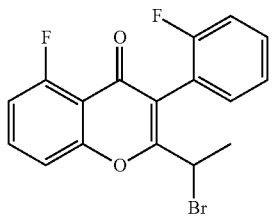
Intermediate 135
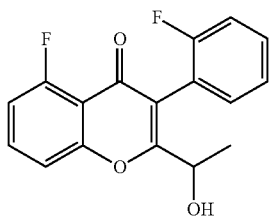
Intermediate 136
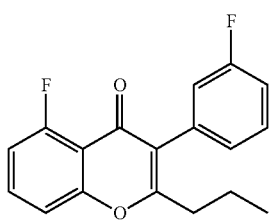
Intermediate 137
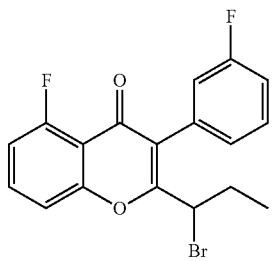
Intermediate 138
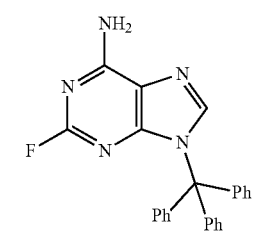
Intermediate 139
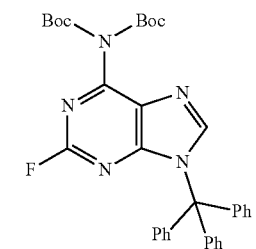
Intermediate 140
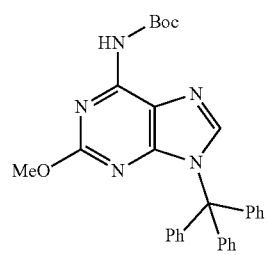
Intermediate 141
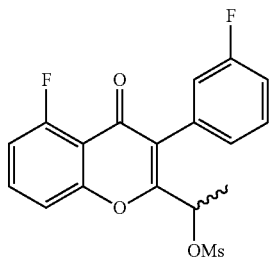
Intermediate 142
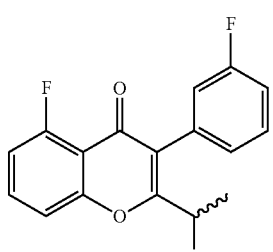

-continued

Intermediate 143

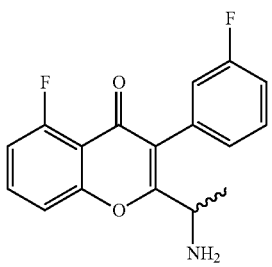

Intermediate 144

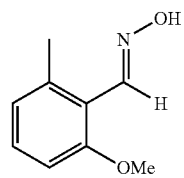

Intermediate 145

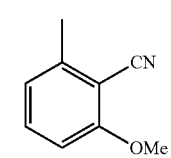

Intermediate 146

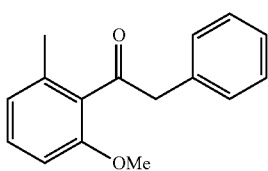

Intermediate 147

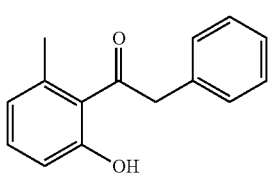

Intermediate 148

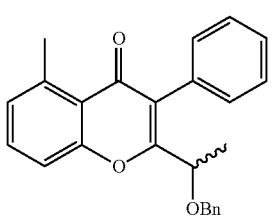

Intermediate 149

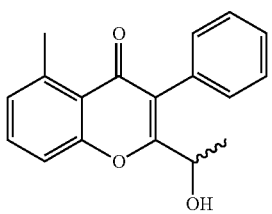

Intermediate 150

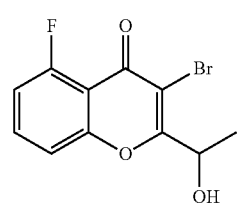

-continued

Intermediate 151

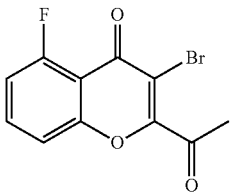

Intermediate 152

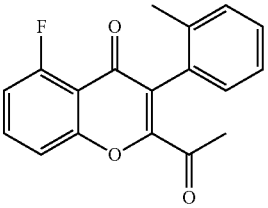

Intermediate 153

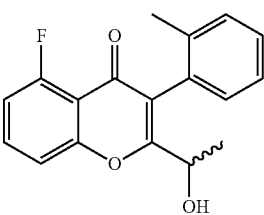

Intermediate 1

2-fluoro-6-methoxybenzaldehyde: n-BuLi (1.6M in hexane, 74.3 ml, 0.118 mol) was added dropwise to a solution of diisopropylamine (13.23 g, 0.130 mol) in THF (50 ml) at 0° C., maintained for 15 min. and cooled to −78° C. 3-Fluoroanisole (15 g, 0.118 mol) in THF (50 ml) was added, stirred at −78° C. for 1 h, and N,N-dimethylformamide (6.75 ml) was added and stirred for further 1 h. The reaction mixture was quenched with 2N HCl solution and extracted with ethyl acetate. The organic layer was dried over sodium sulphate and concentrated to afford the title compound as a red waxy solid (17.45 g, 95%) which was used without purification in the next step.

Intermediate 2

1-(2-fluoro-6-methoxyphenyl)ethanol: To an ice-cold solution of methylmagnesium iodide prepared from magnesium (8.8 g, 0.366 mol) and methyliodide (52.06 g, 0.366 mol) in diethyl ether (150 ml), intermediate 1 (18.85 g, 0.122 mol) in diethyl ether (50 ml) was added and warmed to room temperature. After 12 h, the reaction mixture was cooled to 0° C., quenched with dilute aqueous HCl and extracted with ethyl acetate. The organic layer was dried over sodium sulphate and concentrated under reduced pressure to afford the title compound as a red liquid (18.9 g, 99%) which was used without purification in the next step.

Intermediate 3

1-(2-fluoro-6-methoxyphenyl)ethanone: Pyridinium dichromate (44 g, 0.116 mol) was added to a solution of intermediate 2 (13.1 g, 0.077 mol) in DMF (130 ml) and stirred at room temperature for 12 h. Water (300 ml) was added to the reaction mixture and diluted with ethyl acetate and filtered through celite. The organic layer was washed with brine solution and dried over sodium sulphate and concentrated under reduced pressure to afford the title compound as a brown colour liquid (9.2 g, 70%). $^1$H-NMR (δ ppm, CDCl$_3$, 400 MHz): 7.73 (dd, J=15.1, 8.4 Hz, 1H), 6.73 (m, 2H), 3.85 (s, 3H), 2.53 (s, 3H).

Intermediate 4

1-(2-fluoro-6-hydroxyphenyl)ethanone: To an ice-cold solution of intermediate 3 (9.0 g, 53.5 mmol) in dichloromethane (70 ml), aluminium chloride (14.3 g, 0.107 mol) was added and warmed to room temperature. After 12 h, the reaction mixture was quenched with aqueous 2N HCl and extracted with ethyl acetate. The organic layer was washed with water, dried over sodium sulphate and concentrated under reduced pressure to afford the title compound as a brown liquid (5.48 g, 66%). $^1$H-NMR (δ ppm, CDCl$_3$, 400 MHz): 12.72 (s, 1H), 7.40 (m, 1H), 6.78 (d, J=8.5 Hz, 1H), 6.62 (dd, J=11.3, 8.3 Hz, 1H), 2.69 (d, J=7.2 Hz, 3H).

Intermediate 5

2-acetyl-3-fluorophenyl acetate: Pyridine (7.8 ml) and acetyl chloride (3.60 g, 45.93 mmol) were added to an ice-cold solution of intermediate 4 (5.9 g, 38.27 mmol) in dichloromethane (50 ml) and heated to 45° C. After 3 h, water was added to the mixture and extracted into ethyl acetate. The organic layer was washed with water, dried over sodium sulphate and the solvents evaporated. The crude product was purified by column chromatography with ethyl acetate:petroleum ether to afford the title compound as a yellow liquid (6.2 g, 82%). $^1$H-NMR (δ ppm, CDCl$_3$, 400 MHz): 7.45 (m, 1H), 705 (t, J=8.9 Hz, 1H), 6.93 (d, J=8.1 Hz, 1H), 2.56 (d, J=3.3 Hz, 3H), 2.27 (s, 3H).

Intermediate 6

5-hydroxy-2-methyl-4H-chromen-4-one: To an ice-cold solution of intermediate 5 (3.0 g, 15.29 mmol) in dimethylsulphoxide (15 ml), sodium hydride (0.367 mg, 15.29 mmol) was added and heated to 100° C. After 12 h, the reaction mixture was quenched with aqueous 10% HCl and extracted with ethyl acetate. The organic layer was washed with water, dried over sodium sulphate and concentrated under reduced pressure. The crude product was purified by column chromatography with ethyl acetate:petroleum ether to afford the title compound as a yellow liquid (1.3 g, 48%). $^1$H-NMR (δ ppm, CDCl$_3$, 400 MHz): 12.54 (s, 1H), 7.50 (t, J=8.3 Hz, 1H, 6.86 (d, J=8.4 Hz, 1H), 6.72 (d, J=8.2 Hz, 1H), 6.10 (s, 1H), 2.38 (s, 3H).

Intermediate 7

5-methoxy-2-methyl-4H-chromen-4-one: To a solution of intermediate 6 (1.12 g, 15.29 mmol) in DMF (10 ml), potassium carbonate (1.31 g, 9.53 mmol) and methyl iodide were added and heated to 50-60° C. After 12 h, water was added to the mixture and extracted with ethyl acetate. The organic layer was washed with water, dried over sodium sulphate and concentrated to afford the title compound as a yellow solid (0.85 g, 70%). $^1$H-NMR (δ ppm, CDCl$_3$, 400 MHz): 7.52 (t, J=8.4 Hz, 1H), 6.97 (d, J=8.4 Hz, 1H), 6.78 (d, J=8.3 Hz, 1H), 6.07 (s, 1H), 3.96 (s, 3H), 2.29 (s, 3H).

Intermediate 8

3-bromo-5-methoxy-2-methyl-4H-chromen-4-one: N-Bromosuccinimide (0.795 g, 4.46 mmol) was added to a solution of intermediate 7 (0.85 g, 4.46 mmol) in DMF (10 ml), at RT. After 12 h, water was added to the mixture and extracted with ethyl acetate. The organic layer was washed with water, dried over sodium sulphate and concentrated under reduced pressure to afford the title compound as a yellow solid (0.985 g, 82%). $^1$H-NMR (δ ppm, CDCl$_3$, 400 MHz): 7.56 (t, J=8.0 Hz, 1H), 6.99 (d, J=8.2 Hz, 1H), 6.82 (d, J=8.1 Hz, 1H), 3.96 (s, 3H), 2.58 (s, 3H).

Intermediate 9

3-(3-fluorophenyl)-5-methoxy-2-methyl-4H-chromen-4-one: To a solution of Intermediate 8 (0.985 g, 3.66 mmol) and 3-Fluorophenylboronic acid (0.819 g, 5.85 mmol) in dioxan (10 ml), potassium carbonate (1.51 g, 10.98 mmol) and water (2 ml) were added and degassed for 30 min. Tetrakis(triphenylphosphine)palladium(0) (0.253 g, 0.219 mmol) was added under nitrogen at RT and the reaction mixture refluxed for 12 h. The solvent was evaporated completely and water was added to the residue and extracted with ethyl acetate, organic layer dried over sodium sulphate and concentrated. The residue obtained was purified by column chromatography w to afford the title compound as a yellow solid (0.875 g, 81%). $^1$H-NMR (δ ppm, CDCl$_3$, 400 MHz): 7.55 (t, J=8.4 Hz, 1H), 7.38 (dd, J=13.9, 7.8 Hz, 1H), 7.06-6.99 (m, 4H), 6.79 (d, J=8.3 Hz, 1H), 3.94 (s, 3H), 2.25 (s, 3H).

Intermediate 10

2-(bromomethyl)-3-(3-fluorophenyl)-5-methoxy-4H-chromen-4-one: To a solution of Intermediate 9 (0.875 g, 3.07 mmol in carbon tetrachloride (10 ml) N-bromosuccinimide (0.547 g, 3.07 mmol) was added and heated to 80° C., azobisisobutyronitrile (20 mg) added and stirred at the same temperature for 12 h. The reaction mixture was cooled to RT, diluted with dichloromethane and washed with water. The organic layer was dried over sodium sulphate and concentrated under reduced pressure. The crude product was purified by column chromatography with ethyl acetate:petroleum ether to afford the title compound as an off-white solid (0.440 g, 39% yield) which was used without purification in the next step.

Intermediate 11

4-bromo-2-fluoro-1-isopropoxybenzene: To a solution of 4-bromo-2-fluorophenol (10 g, 52.35 mmol) in THF (100 ml), isopropyl alcohol (4.8 ml, 62.62 mmol) and triphenylphosphine (20.6 g, 78.52 mmol) were added and heated to 45'C followed by diisopropylazodicarboxylate (15.4 ml, 78.52 mmol). The mixture was refluxed for 1 h, concentrated and the residue was purified by column chromatography with ethyl acetate:petroleum ether to afford the title compound as a colourless liquid (13.1 g, 99%) which was used without purification in the next step.

Intermediate 12

2-(3-fluoro-4-isopropoxyphenyl)-4,4,5,5-tetramethyl-1,3,2-dioxaborolane: Potassium acetate (10.52 g, 107.2 mmol) and bis(pinacolato)diboron (15 g, 58.96 mmol) were added to a solution of intermediate 11 (10.52 g, 107.2 mmol) in dioxane (125 ml), and the solution was degassed for 30 min. [1,1'-Bis(diphenylphosphino)ferrocene]dichloro palladium (II).CH$_2$Cl$_2$ (4.4 g, 5.36 mmol) was added under nitrogen atmosphere and heated to 80° C. After 12 h. the reaction mixture was filtered through celite and concentrated. The crude product was purified by column chromatography with ethyl acetate:petroleum ether to afford the title compound as a yellow oil (13.9 g, 99%) which was used without purification in the next step.

Intermediate 13

3-(3-fluoro-4-isopropoxyphenyl)-1H-pyrazolo[3,4-d]pyrimidin-4-amine; To a solution of 3-iodo-1H-pyrazolo[3,4-d]pyrimidin-4-amine (11.0 g, 42.14 mmol) in DMF 110 ml), ethanol (55 ml) and water (55 ml), intermediate 12 (23.4 g, 84.28 mmol) and sodium carbonate (13.3 g, 126.42 mmol) were added and degassed for 30 min. Tetrakis(triphenylphosphine)palladium(0) (2.4 g, 2.10 mmol) was added under nitrogen atmosphere and heated to 80° C. After 12 h, the reaction mixture was filtered though celite, concentrated and extracted with ethyl acetate. The organic layer was dried over sodium sulphate and concentrated under reduced pressure. The crude product was triturated with diethyl ether, filtered and dried under vacuum to afford the title compound as light brown solid (3.2 g, 26% yield) which is used as such for the next step.

Intermediate 14

5-fluoro-2-methyl-4H-chromen-4-one: To a solution of Intermediate 5 (5.0 g, 25.48 mmol) in THF (70 ml) cooled to −78° C., lithium bis(trimethylsilylamide) (1M in THF, 25.45 ml, 25.48 mmol) was added maintained at the same temperature for 2 h. The mixture was warmed to RT and stirred for 4 h. The reaction was quenched by the addition aqueous ammonium chloride solution and extracted with ethyl acetate. The organic layer was washed with water, dried over sodium sulphate and the solvents removed. The crude product was dissolved in dioxane (8 ml) and sulphuric acid (8 ml) was added and heated to reflux for 4 h. Aqueous sodium bicarbonate solution was added to the mixture and extracted with ethyl acetate. The organic layer was washed with water, dried over sodium sulphate and concentrated under reduced pressure. The crude product was purified by column chromatography with ethyl acetate:petroleum ether to afford the title compound as an off-white solid (0.91 g, 20%). $^1$H-NMR (δ ppm, CDCl$_3$, 400 MHz): 7.58 (m, 1H), 7.22 (d, J=8.5 Hz, 1H), 7.03 (t, J=9.7 Hz, 1H), 6.11 (s, 1H), 2.34 (s, 3H).

Intermediate 15

3-bromo-5-fluoro-2-methyl-4H-chromen-4-one: To a solution of intermediate 14 (0.910 g, 5.10 mmol) in DMF (8 ml), N-bromosuccinimide (0.908 g, 5.10 mmol) was added at RT. After 12 h, the reaction mixture was quenched with water and extracted with ethyl acetate. The organic layer was washed with water, dried over sodium sulphate and the solvent removed to afford the title compound as an off-white solid (0.410 g, 31%). $^1$H-NMR (δ ppm, CDCl$_3$, 400 MHz): 7.62 (m, 1H), 7.25 (d, J=8.28 Hz, 1H), 7.09 (t, J=9.6 Hz, 1H), 2.63 (s, 3H).

Intermediate 16

5-fluoro-3-(3-fluorophenyl)-2-methyl-4H-chromen-4-one: To a solution of intermediate 15 (0.150 g, 0.583 mmol) and 3-fluorophenylboronic acid (0.129 g, 0.933 mmol) in dioxan (2 ml), potassium carbonate (0.241 g, 1.75 mmol) and water (0.5 ml) were added and degassed for 30 min. Tetrakis(triphenylphosphine)palladium(0) (0.040 g, 0.035 mmol) was added under nitrogen at RT and the reaction mixture was refluxed for 12 h. The solvent was evaporated completely and water was added to the residue and extracted with ethyl acetate, dried over sodium sulphate and concentrated under reduced pressure. The crude product was purified by column chromatography with ethyl acetate:petroleum ether to afford the title compound as a yellow solid (0.100 g, 63%). $^1$H-NMR (δ ppm, CDCl$_3$, 400 MHz): 7.61 (m, 1H), 7.42 (dd, J=14.2, 8.0 Hz, 1H), 7.09-6.99 (m, 4H), 2.29 (s, 3H).

Intermediate 17

2-(bromomethyl)-5-fluoro-3-(3-fluorophenyl)-4H-chromen-4-one: To a solution of Intermediate 16 (0.245 g, 0.900 mmol in carbon tetrachloride (5 ml) N-bromosuccinimide (0.160 g, 0.900 mmol) was added and heated to 80° C., azobisisobutyronitrile (10 mg) added and stirred at the same temperature for 12 h. The reaction mixture was cooled to RT, diluted with dichloromethane and washed with water. The organic layer was dried over sodium sulphate and concentrated under reduced pressure to afford the title compound as red semi solid (0.326 g) which was used without purification in the next step.

Intermediate 18

2-acetyl-3-fluorophenyl propionate: Pyridine (7.2 ml) and propionyl chloride (3.85 g, 41.65 mmol) were added to an ice-cold solution of intermediate 4 (5.35 g, 37.70 mmol) in dichloromethane (40 ml) and heated to 45° C. After 3 h, water was added to the mixture and extracted into ethyl acetate. The organic layer was washed with water, dried over sodium sulphate and the solvents evaporated. The crude product was purified by column chromatography with ethyl acetate:petroleum ether to afford the title compound as a yellow liquid (6.4 g, 81%). $^1$H-NMR (δ ppm, CDCl$_3$, 400 MHz): 7.44 (dt, J=8.2, 6.4, 1H), 705 (t, J=8.9 Hz, 1H), 6.92 (d, J=8.2 Hz, 1H), 2.59 (q, J=7.5 Hz, 2H), 2.55 (s, 3H), 1.25 (t, J=7.5 Hz, 3H).

Intermediate 19

2-ethyl-5-fluoro-4H-chromen-4-one: To a solution of Intermediate 18 (5.1 g, 24.28 mmol) in DMSO (20 ml) cooled to 0° C., sodium hydride (0.582 g, 24.28 mmol) was added maintained at the same temperature for 1 h. The mixture was warmed to RT and stirred for 12 h. The reaction was quenched by the addition of 2N HCl and extracted with ethyl acetate. The organic layer was washed with water, dried over sodium sulphate and the solvents removed. The crude product was dissolved in dioxane (20 ml) and sulphuric acid (6 ml) was added and heated to reflux for 12 h. Aqueous sodium bicarbonate solution was added to the mixture and extracted with ethyl acetate. The organic layer was washed with water, dried over sodium sulphate and concentrated under reduced pressure. The crude product was purified by column chromatography with ethyl acetate: petroleum ether to afford the title compound as yellow liquid (2.49 g, 51%). $^1$H-NMR (δ ppm, CDCl$_3$, 400 MHz): 7.58 (dt, J=13.9, 5.6 Hz, H), 7.54 (d, J=5.6 Hz, H), 7.04 (t, J=8.4 Hz, 1H), 6.14 (s, 1H), 2.66 (q, J=7.6 Hz, 2H), 1.32 (t, J=7.5 Hz, 3H).

Intermediate 20

3-bromo-2-ethyl-5-fluoro-4H-chromen-4-one: To a solution of intermediate 19 (2.49 g, 12.95 mmol) in DMF (15 ml), N-bromosuccinimide (2.30 g, 12.95 mmol) was added at RT. After 12 h, the reaction mixture was quenched with water and extracted with ethyl acetate. The organic layer was washed with water, dried over sodium sulphate and the solvent removed to afford the title compound as an reddish brown solid (2.60 g, 74%). $^1$H-NMR ($\delta$ ppm, CDCl$_3$, 400 MHz): 7. 62 (dt, J=13.8, 5.5 Hz, 1H), 7.25 (d, J=5.6 Hz, 1H), 7.09 (dt, J=9.5, 1.1 Hz, 1H), 2.99 (q, J=7.6 Hz, 2H), 1.37 (t, J=7.6 Hz, 3H).

Intermediate 21

2-ethyl-5-fluoro-3-(3-fluorophenyl)-4H-chromen-4-one: To a solution of intermediate 20 (2.60 g, 9.59 mmol) and 3-fluorophenylboronic acid (2.13 g, 15.34 mmol) in dioxan (15 ml), potassium carbonate (3.97 g, 28.77 mmol) and water (2 ml) were added and degassed for 30 min. Tetrakis (triphenylphosphine)palladium(0) (0.664 g, 0.575 mmol) was added under nitrogen at RT and the reaction mixture was refluxed for 12 h. The solvent was evaporated completely and water was added to the residue and extracted with ethyl acetate, dried over sodium sulphate and concentrated under reduced pressure. The crude product was purified by column chromatography with ethyl acetate:petroleum ether to afford the title compound as a off-white solid (1.20 g, 44%). $^1$H-NMR ($\delta$ ppm, CDCl$_3$, 400 MHz): 7. 61 (dt, J=13.8, 5.5 Hz, 1H), 7.41 (dd, J=14.0, 7.8 Hz, 1H), 7.27 (d, J=7.6 Hz, 1H), 7.10-6.98 (m, 4H), 2.59 (q, J=7.6 Hz, 2H), 1.27 (t, J=7.5 Hz, 3H).

Intermediate 22

2-(1-bromoethyl)-5-fluoro-3-(3-fluorophenyl)-4H-chromen-4-one: To a solution of Intermediate 21 (0.500 g, 1.86 mmol in carbon tetrachloride (5 ml) N-bromosuccinimide (0.331 g, 0.900 mmol) was added and heated to 80° C., azobisisobutyronitrile (5 mg) added and stirred at the same temperature for 12 h. The reaction mixture was cooled to RT, diluted with dichloromethane and washed with water. The organic layer was dried over sodium sulphate and concentrated under reduced pressure to afford the title compound as a off-white solid (0.460 g, 68%). $^1$H-NMR ($\delta$ ppm, CDCl$_3$, 400 MHz): 7.68 (dt, J=8.4, 5.4 Hz, 1H), 7.46 (dd, J=14.1, 8.0 Hz, 1H), 7.37 (d, J=8.5 Hz, 1H), 7.15-7.05 (m, 4H), 4.91 (q, J=6.9 Hz, 1H), 1.98 (d, J=6.9 Hz, 3H).

Intermediate 23

5-fluoro-3-(3-fluorophenyl)-2-(1-hydroxyethyl)-4H-chromen-4-one: To a solution of Intermediate 22 (0.950 g, 2.60 mmol) in DMSO (9.5 ml), n-butanol (0.47 ml) was added and heated to 120° C. for 3 h. The reaction mixture was cooled to RT, quenched with water and extracted with ethyl acetate. The organic layer was dried over sodium sulphate and concentrated under reduced pressure. The crude product was purified by column chromatography with ethyl acetate:petroleum ether to afford the title compound as a yellow solid (0.700 g, 89%). $^1$H-NMR ($\delta$ ppm, DMSO-D$_6$, 400 MHz): 7.84 (dt, J=14.2, 5.7 Hz, 1H), 7.53 (d, J=8.7 Hz, 1H), 7.49 (m, 1H), 7.27 (m, 2H), 7.15 (m, 2H), 5.62 (d, J=4.8 Hz, 1H), 4.44 (m, 1H), 1.37 (d, J=6.5 Hz, 3H).

Intermediate 23a and 23b (+)-5-fluoro-3-(3-fluorophenyl)-2-(1-hydroxyethyl)-4H-chromen-4-one and (−)-5-fluoro-3-(3-fluorophenyl)-2-(1-hydroxyethyl)-4H-chromen-4-one: The two enantiomerically pure isomers were separated by preparative SFC conditions from intermediate 23 (0.300 g) on a CHIRALPAK AD-H column (250×4.6 mm; 51p) using methanol:CO$_2$ (20:80) as the mobile phase at a flow rate of 3.0 ml/min.

Intermediate 23a: Off-white solid (0.140 g). e.e. 100%. Rt: 2.41 min. $[\alpha]^{25}_D$ 4.17 (c=1, MeOH). Mass: 302.9 (M$^+$).

Intermediate 23b: Off-white solid (0.143 g). e.e. 100%. Rt: 3.06 min. $[\alpha]^{25}_D$ −4.17 (C=1, MeOH). Mass: 302.9 (M$^+$).

Intermediate 24

2-acetyl-5-fluoro-3-(3-fluorophenyl)-4H-chromen-4-one DMSO (0.657 ml, 9.26 mmol) was added to dichloromethane (8 ml) cooled to −78° C., followed by oxalyl chloride (0.40 ml, 4.63 mmol). After 10 min. intermediate 23 (0.700 g, 2.31 mmol) in dichloromethane (4 ml) was added dropwise and stirred for 20 min. Triethylamine (1.3 ml) was added and stirred for 1 h. The reaction mixture was quenched with water and extracted with dichloromethane. The organic layer was dried over sodium sulphate and concentrated under reduced pressure. The crude product was purified by column chromatography with ethyl acetate: petroleum ether to afford the title compound as a yellow solid (0.450 g, 65%). $^1$H-NMR ($\delta$ ppm, CDCl$_3$, 400 MHz): 7.71 (dt, J=11.2, 2.9 Hz, 1H), 7.40 (m, 2H), 7.14-7.00 (m, 4H), 2.32 (s, 3H).

Intermediate 25

(R)/(S)-5-fluoro-3-(3-fluorophenyl)-2-(1-hydroxyethyl)-4H-chromen-4-one: To intermediate 24 (0.280 g, 0.93 mmol), S-Alpine borane (0.5M in THF, 10 ml) was added and heated to 70° C. for 24 h. The reaction mixture was quenched with aq. 2N HCl, and extracted with ethyl acetate. The organic layer was dried over sodium sulphate and concentrated under reduced pressure. The crude product was purified by column chromatography with ethyl acetate: petroleum ether to afford the title compound as an off-white solid (0.200 g, 71%). Enantiomeric excess: 73%, enriched in the late eluting isomer (retention time: 8.72 min. as determined by HPLC on a chiralpak AD-H column.

Intermediate 26

(R)/(S)-5-fluoro-3-(3-fluorophenyl)-2-(I-hydroxyethyl)-4H-chromen-4-one: To intermediate 24 (0.280 g, 0.93 mmol), R-Alpine borane (0.5M in THF, 2.8 ml) was added and heated to 60° C. for 24 h. The reaction mixture quenched with aq. 2N HCl, and extracted with ethyl acetate. The organic layer was dried over sodium sulphate and concentrated under reduced pressure. The crude product was purified by column chromatography with ethyl acetate:petroleum ether to afford the title compound as a pale yellow solid (0.110 g, 37%). Enantiomeric excess: 94.6%, enriched in the fast eluting isomer (retention time: 7.16) as determined by HPLC on a chiralpak AD-H column.

Intermediate 27

2-(1-(4-amino-3-iodo-1H-pyrazolo[3,4-d]pyrimidin-1-yl) ethyl)-5-fluoro-3-(3-fluorophenyl)-4H-chromen-4-one: To a solution of 3-iodo-1H-pyrazolo[3,4-d]pyrimidin-4-amine (0.800 g, 2.88 mmol) in DMF (5 ml), potassium carbonate (0.398 g, 2.88 mmol) was added and stirred at RT for 30 min. To this mixture intermediate 22 (0.500 g, 1.44 mmol) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as a off-white solid (0.300 g, 38%). $^1$H-NMR (δ ppm, DMSO-$d_{63}$, 400 MHz): 8.02 (s, 1H), 7.94 (s, 1H), 7.84 (dt, J=8.4, 5.7 Hz, 1H), 7.47 (d, J=8.6 Hz, 1H), 7.29 (m, 3H), 7.09 (dt, J=8.8, 2.3 Hz, 1H), 6.87 (s, 2H), 5.88 (q, J=7.0 Hz, 1H), 1.82 (d, J=7.0 Hz, 3H).

Intermediate 28

3-bromo-2-(1-bromoethyl)-5-fluoro-4H-chromen-4-one: The title compound was obtained as a brown solid (3.60 g, 94%) by using a procedure that is similar to the one described for intermediate 22 from intermediate 20 (3.0 g, 11.06 mmol), carbon tetrachloride (30 ml) N-bromosuccinimide (1.96 g, 11.06 mmol) and azobisisobutyronitrile (30 mg) which is used as such in a next step.

Intermediate 29

2-(1-(4-amino-3-(3-fluoro-4-isopropoxyphenyl)-1H-pyrazolo[3,4-d]pyrimidin-1-yl)ethyl)-3-bromo-5-fluoro-4H-chromen-4-one: The title compound was obtained as a brown solid (0.800 g, 36%) by using a procedure that is similar to the one described for intermediate 27 from intermediate 13 (1.11 g, 4.28 mmol), cesium carbonate (1.39 g, 4.28 mmol), DMF (5 ml) and intermediate 28. $^1$H-NMR (δ ppm, CDCl$_3$, 400 MHz): 8.37 (s, 1H), 7. 62 (dt, J=8.4, 5.4 Hz, 1H), 7.45 (dd, J=11.5, 2.1 Hz, 1H), 7.39 (m, 1H), 7.22 (d, J=8.6 Hz, 1H), 7.14-7.04 (m, 2H), 6.60 (q, J=7.1 Hz, 1H), 5.67 (s, 2H), 4.65 (q, J=6.0 Hz, 1H), 2.08 (d, J=7.1 Hz, 3H), 1.41 (d, J=6.1 Hz, 6H).

Intermediate 30

2-ethyl-5-fluoro-3-(4-fluorophenyl)-4H-chromen-1-one: The title compound was obtained as a off-white solid (0.680 g, 54%) by using a procedure that is similar to the one described for intermediate 21 from intermediate 20 (1.20 g, 4.42 mmol), 4-fluorophenylboronic acid (0.991 g, 7.08 mmol), dioxan (9 ml), potassium carbonate (1.83 g, 13.27 mmol), water (1.2 ml) and tetrakis(triphenylphosphine)palladium(0) (0.306 g, 0.265 mmol). $^1$H-NMR (δ ppm, CDCl$_3$, 400 MHz): 7. 60 (dt, J=8.3, 5.5 Hz, 1H), 7.27 (m, 3H), 7. 13 (t, J=8.7 Hz, 2H), 7.04 (t, J=9.1 Hz, 1H), 2.55 (q, J=7.6 Hz, 2H), 1.27 (t, J=7.6 Hz, 3H).

Intermediate 31

2-(1-bromoethyl)-5-fluoro-3-(4-fluorophenyl)-4H-chromen-4-one: The title compound was obtained as a brown solid (0.740 g, 85%) by using a procedure that is similar to the one described for intermediate 22 from intermediate 30 (0.680 g, 2.37 mmol), carbon tetrachloride (10 ml) N-bromosuccinimide (0.423 g, 2.37 mmol) and azobisisobutyronitrile (30 mg). $^1$H-NMR (δ ppm, CDCl$_3$, 400 MHz): 7.67 (dt, J=8.4, 5.5 Hz, 1H), 7.37 (m, 3H), 7. 18 (t, J=8.7 Hz, 2H), 7.09 (t, J=8.5 Hz, 1H), 4.92 (q, J=6.9 Hz, 1H), 1.97 (d, J=6.9 Hz, 3H).

Intermediate 32

2-ethyl-5-fluoro-3-phenyl-4H-chromen-4-one: The title compound was obtained as a off-white solid (0.600 g, 50%) by using a procedure that is similar to the one described for intermediate 21 from intermediate 20 (1.20 g, 4.42 mmol), phenylboronic acid (0.864 g, 7.08 mmol), dioxan (9 ml), potassium carbonate (1.83 g, 13.27 mmol), water (1.2 ml) and tetrakis(triphenylphosphine)palladium(0) (0.306 g, 0.265 mmol). $^1$H-NMR (δ ppm, CDCl$_3$, 400 MHz): 7. 61 (dt, J=8.4, 5.5 Hz, 1H), 7.45 (m, 3H), 7.28 (m, 3H), 7.05 (dt, J=8.5, 1.3 Hz, 1H), 2.60 (q, J=7.6 Hz, 2H), 1.28 (t, J=7.5 Hz, 3H).

Intermediate 33

2-(1-bromoethyl)-5-fluoro-3-phenyl-4H-chromen-4-one: The title compound was obtained as a brown solid (0.590 g, 76%) by using a procedure that is similar to the one described for intermediate 22 from intermediate 32 (0.600 g, 2.23 mmol), carbon tetrachloride (9 ml) N-bromosuccinimide (0.398 g, 2.37 mmol) and azobisisobutyronitrile (30 mg). $^1$H-NMR (δ ppm, CDCl$_3$, 400 MHz): 7. 66 (dt, J=8.4, 5.5 Hz, 1H), 7.48 (m, 3H), 7. 37 (m, 3H), 7.08 (t, J=9.8 Hz, 1H), 4.95 (q, J=6.8 Hz, 1H), 1.97 (d, J=6.9 Hz, 3H).

Intermediate 34

2-(1-(4-amino-3-iodo-1H-pyrazolo[3,4-d]pyrimidin-1-yl)ethyl)-5-fluoro-3-(4-fluorophenyl)-4H-chromen-4-one: To a solution of 3-iodo-1H-pyrazolo[3,4-d]pyrimidin-4-amine (0.800 g, 2.88 mmol) in DMF (5 ml), potassium carbonate (0.398 g, 2.88 mmol) was added and stirred at RT for 30 min. To this mixture intermediate 22 (0.500 g, 1.44 mmol) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as a off-white solid (0.300 g, 38%). $^1$H-NMR (δ ppm, DMSO-$d_{63}$, 400 MHz): 8.02 (s, 1H), 7.94 (s, 1H), 7.84 (dt, J=8.4, 5.7 Hz, 1H), 7.47 (d, J=8.6 Hz, 1H), 7.29 (m, 3H), 7.09 (dt, J=8.8, 2.3 Hz, 1H), 6.87 (s, 2H), 5.88 (q, J=7.0 Hz, 1H), 1.82 (d, J=7.0 Hz, 3H).

Intermediate 35

2-(1-(5-fluoro-3-(3-fluorophenyl)-4-oxo-4H-chromen-2-yl)ethyl)isoindoline-1,3-dione: To a solution of phthalimide (0.420 g, 2.88 mmol) in DMF (4 ml), potassium carbonate (0.43 g, 2.88 mmol) was added and stirred at RT for 30 min. To this mixture intermediate 22 (0.400 g, 2.88 mmol) was added and stirred for 12 h. The reaction Ill mixture was diluted with water and extracted with ethyl acetate. The organic layer was dried over sodium sulphate and concentrated under reduced pressure. The crude product was purified by column chromatography with ethyl acetatel:pet.ether to afford the title compound as a off-white solid (0.350 g, 32%). $^1$H-NMR (δ ppm, CDCl$_3$, 400 MHz): 7.77 (m, 4H), 7.63 (dt, J=8.4, 5.4 Hz, 1H), 7.34 (d, J=8.5 Hz, 1H), 7.28 (m, 1H), 7.08 (m, 1H), 6.97 (m, 2H), 6.86 (d, J=7.4 Hz, 1H), 5.79 (q, J=7.2 Hz, 1H), 1.81 (d, J=7.2 Hz, 3H).

Intermediate 36

2-(1-aminoethyl)-5-fluoro-3-(3-fluorophenyl)-4H-chromen-4-one: To a solution of intermediate 35 (0.350 g, 0.847 mmol) in methanol (3.5 ml), hydrazine hydrate (0.070 g, 1.27 mmol) was added and refluxed for 3 h. The reaction mass cooled, filtered and washed with chloroform. The filtrate was concentrated to afford the title compound as a brown solid (0.200 g, 78%). $^1$H-NMR ($\delta$ ppm, DMSO-d$_{63}$, 400 MHz): 7.29 (dt, J=8.0, 6.4 Hz, 1H), 7.19 (q, J=8.2 Hz, 1H), 7.02 (m, 3H), 6.69 (d, J=8.2 Hz, 1H), 6.59 (t, J=8.8 Hz, 1H), 4.12 (q, J=6.6 Hz, 1H), 1.32 (d, J=6.7 Hz, 3H).

Intermediate 37

4-bromo-1-(difluoromethoxy)-2-fluorobenzene: To a solution of 4-bromo-2-fluorophenol (1.00 g, 5.23 mmol) in DMF (17 ml) and water (2.3 ml), sodiumchlorodifluoroacetate (1.60 g, 1047 mmol) and potassium carbonate (0.866 g, 6.282 mmol) were added. The flask was purged with nitrogen for 15 min. and heated to 100° C. After 2.5 h, cooled to room temperature, con.HCl (2.5 ml) and water (2.5 ml) were added and stirred for 1 h. The reaction mixture was cooled to 0° C., quenched with aq. 1N sodium hydroxide solution, extracted with ethyl acetate and dried over sodium sulphate and concentrated. The crude product was purified by column chromatography with ethyl acetatel: pet.ether to afford the title compound as a colourless liquid (0.545 g, 43%). $^1$H-NMR ($\delta$ ppm, CDCl$_3$, 400 MHz): 7.36 (dd, J=9.7, 2.3 Hz, 1H), 7.28 (td, J=8.7, 1.5 Hz, 1H), 7.15 (t, J=8.3 Hz, 1H), 6.71 (t, J=73.0 Hz, 1H).

Intermediate 38

2-(4-(difluoromethoxy)-3-fluorophenyl)-4,4,5,5-tetramethyl-1,3,2-dioxaborolane: The title compound was obtained as a yellow liquid (0.475 g, 76%) by using a procedure that is similar to the one described for intermediate 12 from intermediate 35 (0.520 g, 2.15 mmol), potassium acetate (0.423 g, 4.31 mmol), bis(pinacolato)diboron (0.602 g, 2.37 mmol) dioxane (10 ml) and [1,1'-Bis(diphenylphosphino)ferrocene]dichloro palladium(II).CH$_2$Cl$_2$ (0.088 g, 0.107 mmol). $^1$H-NMR ($\delta$ ppm, CDCl$_3$, 400 MHz): 7. 59 (m, 2H), 7.23 (t, J=7.9 Hz, 1H), 6.75 (t, J=73.5 Hz, 1H), 1.35 (s, 12H).

Intermediate 39

3-(4-(difluoromethoxy)-3-fluorophenyl)-1H-pyrazolo[3,4-d]pyrimidin-4-amine: The title compound was obtained as a light brown solid (0.321 g, 28%) by using a procedure that is similar to the one described for intermediate 13 from intermediate 38 (1.70 g, 5.74 mmol), 3-iodo-1H-pyrazolo[3,4-d]pyrimidin-4-amine (1.0 g, 3.83 mmol), DMF (5 ml), ethanol (2.5 ml), water (2.5 ml) sodium carbonate (1.21 g, 11.49 mmol) and tetrakis(triphenylphosphine)palladium(0) (0.221 g, 0.191 mmol) $^1$H-NMR ($\delta$ ppm, DMSO-d$_6$, 400 MHz): 13.66 (s, 1H), 8.21 (s, 1H), 7.62 dd, J=10.6, 5.4 Hz, 1H), 7.51 (m, 2H), 7.48 (t, J=73.2 Hz, 1H), 6.92 (s, 2H).

Intermediate 40

4-(4-bromo-2-fluorophenoxy)tetrahydro-2H-pyran: To a solution of 4-bromo-2-fluorophenol (3.89 g, 20.39 mmol) in THF (50 ml), 4-hydroxytetrahydropyran (2.50 g, 24.47 mmol) and triphenylphosphine (8.02 g, 30.58 mmol) were added and heated to reflux for 2 h. The reaction mixture was cooled to 0° C., diisopropylazodicarboxylate (6.02 ml, 30.58 mmol) was added and heated to reflux for 12 h. The reaction mixture was concentrated and the crude product was purified by column chromatography with ethyl acetatel: pet.ether to afford the title compound as a colourless liquid (0.3.6 g, 83%). $^1$H-NMR ($\delta$ ppm, CDCl$_3$, 400 MHz): 7.26 (dd, J=10.4, 2.1 Hz, 1H), 7.18 (m, 1H), 6.90 (t, J=8.7 Hz, 1H), 4.45 (m, 1H), 4.01 (m, 2H), 3.57 (m, 2H), 2.02-1.76 (m, 4H).

Intermediate 41

2-(3-fluoro-4-(tetrahydro-2H-pyran-4-yloxy)phenyl)-4,4,5,5-tetramethyl-1,3,2-dioxaborolane: The title compound was obtained as a off-white solid (2.50 g, 59%) by using a procedure that is similar to the one described for intermediate 12 from intermediate 40 (3.50 g, 16.49 mmol), potassium acetate (3.25 g, 32.99 mmol), bis(pinacolato)diboron (4.60 g, 18.14 mmol) dioxane (40 ml) and[1,1'-Bis(diphenylphosphino)ferrocene]dichloro palladium(II).CH$_2$Cl$_2$ (1.34 g, 1.64 mmol). $^1$H-NMR ($\delta$ ppm, CDCl$_3$, 400 MHz): 7. 50 (m, 2H), 6.97 (t, J=7.9 Hz, 1H), 4.54 (m, 1H), 4.00 (m, 2H), 3.57 (m, 2H), 2.02-1.76 (m, 4H), 1.31 (s, 12H).

Intermediate 42

1-(4-bromo-2-fluorophenyl)-2-methylpropan-1-ol: To an ice-cold solution of isopropylmagnesium bromide prepared from magnesium (8.8 g, 0.147 mol) and 2-bromopropane (18.1 g, 0.147 mol) in diethyl ether (80 ml), 4-bromo-2-fluorobenzaldehyde (10.0 g, 0.049 mol) in diethyl ether (20 ml) was added and warmed to room temperature. After 12 h, the reaction mixture was cooled to 0° C., quenched with dilute aqueous HCl and extracted with ethyl acetate. The organic layer was dried over sodium sulphate and concentrated under reduced pressure to afford the title compound as a brown liquid (12.0 g, 99%) which was used without purification in the next step.

Intermediate 43

1-(4-bromo-2-fluorophenyl)-2-methylpropan-1-one: The title compound was obtained as a light brown liquid (0.5.8 g, 59%) by using a procedure that is similar to the one described for intermediate 3 from intermediate 42 (10.0 g, 40.46 mmol), pyridinium dichromate (22.8 g, 60.70 mmol) and DMF (50 ml) which was used without purification in the next step.

Intermediate 44

6-bromo-3-isopropyl-1H-indazole: To a solution of intermediate 42 (5.80 g, 23.66 mmol) in ethylene glycol (39 ml), hydrazine hydrate (2.3 g, 47.32 mmol) was added and heated to 160° C. for 12 h. The reaction mixture was cooled and quenched with ethyl acetate and extracted with ethyl acetate, dried over sodium sulphate and concentrated to afford the title compound as pale yellow solid (3.0 g, 54%). $^1$H-NMR ($\delta$ ppm, CDCl$_3$, 400 MHz): 9.80 (s, 1H), 7.63 (d, J=8.7 Hz, 1H), 7.61 (s, 1H), 7.24 (dd, J=8.5, 1.5 Hz, 1H), 3.43 (quintet, J=7.0 Hz, 1H), 1.45 (d, J=6.9 Hz, 6H).

Intermediate 45 tert-butyl 6-bromo-3-isopropyl-1H-indazole-1-carboxylate: To a solution of intermediate 44 (2.0 g, 8.36 mmol) in acetonitrile (20 ml), 4-dimethylaminopyridine (0.102 g, 0.836 mmol), Boc-anhydride (1.82 g, 8.36 mmol) were added at 20-25° C. followed by triethylamine (0.846 g, 8.36 mmol). After 12 h, the reaction mixture was concentrated and quenched with water, extracted with ethyl acetate, dried with ethyl acetate and concentrated. The crude product was purified by column chromatography with ethyl acetatel: pet.ether to afford the title compound as a colourless liquid (1.70 g, 61%). $^1$H-NMR ($\delta$ ppm, CDCl$_3$, 400 MHz): 8.29 (s, 1H), 7.60 (d, J=8.4 Hz, 1H), 7.40 (dd, J=8.5, 1.5 Hz, 1H), 3.41 (quintet, J=7.0 Hz, 1H), 1.71 (s, 9H), 1.46 (d, J=7.0 Hz, 6H).

Intermediate 46 tert-butyl 3-isopropyl-6-(4,4,5,5-tetramethyl-1,3,2-dioxaborolan-2-yl)-1H-indazole-1-carboxylate The title compound was obtained as a off-white solid (1.50 g, 79%) by using a procedure that is similar to the one described for intermediate 12 from intermediate 45 (1.70 g, 5.01 mmol), potassium acetate (0.980 g, 10.02 mmol), bis(pinacolato)diboron (1.40 g, 5.51 mmol) dioxane (17 ml) and [1,1'-Bis(diphenylphosphino)ferrocene]dichloro palladium(II).CH$_2$Cl$_2$ (0.200 g, 0.250 mmol). $^1$H-NMR (δ ppm, CDCl$_3$, 400 MHz): 8.59 (s, 1H), 7.74 (d, J=7.4 Hz, 1H), 7.68 (d, J=8.1 Hz, 1H), 3.45 (quintet, J=7.0 Hz, 1H), 1.73 (s, 9H), 1.48 (d, J=7.0 Hz, 6H), 1.36 (s, 12H).

Intermediate 47 tert-butyl 4-(4-bromo-2-fluorophenoxy)piperidine-1-carboxylate: To a solution of 4-bromo-2-fluorophenol (1.66 g, 8.69 mmol) in THF (20 ml), 4-hydroxy-1-Bocpiperidine (2.10 g, 10.43 mmol) and triphenylphosphine (3.42 g, 13.04 mmol) were added and heated to 45° C. After 30 min. diisopropylazodicarboxylate (2.56 ml, 13.04 mmol) was added and stirred for 12 h. The reaction mixture was concentrated and the crude product was purified by column chromatography with ethyl acetatel: pet.ether to afford the title compound as a colourless liquid (1.20 g, 38%). $^1$H-NMR (δ ppm, CDCl$_3$, 400 MHz): 7.25 (dd, J=8.7, 2.7 Hz, 1H), 7.18 (m, 1H), 6.89 (t, J=8.7 Hz, 1H), 4.42 (septet, J=3.6 Hz, 1H), 3.73 (m, 2H), 3.34 (m, 2H), 1.92-1.72 (m, 4H), 1.46 (s, 9H).

Intermediate 48 tert-butyl 4-(2-fluoro-4-(4,4,5,5-tetramethyl-1,3,2-dioxaborolan-2-yl)phenoxy)piperidine-1-carboxylate: The title compound was obtained as a pale yellow solid (1.90 g, 99%) by using a procedure that is similar to the one described for intermediate 12 from intermediate 47 (1.10 g, 2.92 mmol), potassium acetate (0.573 g, 5.84 mmol), bis(pinacolato)diboron (0.816 g, 3.21 mmol) dioxane (12 ml) and [1,1'-Bis(diphenylphosphino)ferrocene]dichloro palladium(II).CH$_2$Cl$_2$ (0.230 g, 0.292 mmol). $^1$H-NMR (δ ppm, CDCl$_3$, 400 MHz): 7.51 (m, 2H), 6.98 (t, J=7.9 Hz, 1H), 4.53 (septet, J=3.5 Hz, 1H), 3.72 (m, 2H), 3.36 (m, 2H), 1.92-1.74 (m, 4H), 1.45 (s, 9H), 1.31 (s, 12H).

Intermediate 49

2-(2-fluoro-4-nitrophenylamino) ethanol: To a solution of 3,4-difluoro-1-nitrobenzene (3.50 g, 22.0 mmol) in acetonitrile (35 ml), ethanolamine (1.98 ml, 33.0 mmol) was added and heated at reflux for 4 h. The reaction mass was concentrated and residue was triturated with pet.ether and filtered and dried under vacuum to afford the title compound as a yellow solid (3.2 g, 73%) which was used without purification in the next step.

Intermediate 50

2-(4-amino-2-fluorophenylamino)ethanol: To a solution of intermediate 49 (3.2 g, 15.98 mmol) in methanol, palladium on charcoal (0.800 g, 5% Pd/C) was added and hydrogenated in an autoclave at 4 kg/cm$^2$ for 4 h at room temperature. The reaction mass was filtered through celite, washed with methanol and concentrated under vacuum to afford the title compound as brown liquid (3.00 g, 99%) which was used without purification in the next step.

Intermediate 51

2-(4-bromo-2-fluorophenylamino)ethanol: To intermediate 50 (3.00 g, 17.62 mmol), 48% hydrobromic acid (36 ml) was added and cooled to 0° C., sodium nitrite (3.64 g, 52.88 mmol) in water (42 ml) was added dropwise and stirred at room temperature for 15 min. The reaction mixture was cooled again to 0° C. and copper(I)bromide (3.79 g, 26.44 mmol) was added and heated to 140° C. for 4 h. The reaction mass was cooled to room temperature and basified with saturated sodium bicarbonate solution, filtered through celite, washed with ethyl acetate. The aqueous layer was extracted with ethyl acetate, dried with sodium sulphate and concentrated. The crude product was purified by column chromatography with ethyl acetate:pet.ether to afford the title compound as a brown liquid (1.40 g, 34%). $^1$H-NMR (δ ppm, CDCl$_3$, 400 MHz): 7.14 (m, 2H), 6.61 (t, J=8.7 Hz, 1H), 4.21 (br s, 1H), 3.86 (t, J=5.1 Hz, 2H), 3.32 (t, J=5.0 Hz, 2H), 1.72 (s, 1H).

Intermediate 52

2-(2-fluoro-4-(4,4,5,5-tetramethyl-1,3,2-dioxaborolan-2-yl)phenylamino)ethanol: The title compound was obtained as a brown liquid (1.40 g, 58%) by using a procedure that is similar to the one described for intermediate 12 from intermediate 50 (1.40 g, 2.92 mmol), potassium acetate (1.17 g, 11.95 mmol), bis(pinacolato)diboron (1.67 g, 6.57 mmol) dioxane (35 ml) and [1,1'-Bis(diphenylphosphino)ferrocene]dichloro palladium(II).CH$_2$Cl$_2$ (0.240 g, 0.292 mmol). $^1$H-NMR (δ ppm, CDCl$_3$, 400 MHz): 7.46 (m, 1H), 7.39 (m, 1H), 6.71 (t, J=8.2 Hz, 1H), 4.07 (t, J=5.2 Hz, 1H), 3.86 (t, J=5.2 Hz, 2H), 3.38 (t, J=5.3 Hz, 2H), 1.97 (s, 1H), 1.31 (s, 12H).

Intermediate 53

2-fluoro-N-isopropyl-4-nitroaniline: To a solution of 3,4-difluoro-nitrobenzene (4.00 g, 25.14 mmol) in ethyl acetate (40 ml) and triethylamine (3.86 ml) cooled to 0° C., isopropylamine (2.30 ml, 27.65 mmol) was added slowly and stirred at room temperature for 24 h. The reaction mass quenched with water, extracted with ethylacetate, dried over sodium sulphate and concentrated. The crude product was purified by column chromatography with ethyl acetate: pet.ether to afford the title compound as a yellow liquid (1.80 g, 36%). $^1$H-NMR (δ ppm, DMSO-d$_6$, 400 MHz): 7.94 dd, J=9.1, 1.5 Hz, 1H), 7.89 (dd, J=12.2, 2.5 Hz, 1H), 6.84 (t, J=8.9 Hz, 1H), 6.78 (d, J=10.7 Hz, 1H), 3.83 (m, 1H), 1.20 (d, J=6.4 Hz, 6H).

Intermediate 54

2-fluoro-N1-isopropylbenzene-1,4-diamine: The title compound was obtained as a brown liquid (1.30 g, 90%) by using a procedure that is similar to the one described for intermediate 50 from intermediate 53 (1.70 g, 8.62 mmol), ethyl acetate (20 ml) and palladium on charcoal (0.170 g, 5% Pd/C) which was used without purification in the next step.

Intermediate 55

4-bromo-2-fluoro-N-isopropylaniline: The title compound was obtained as a brown liquid (2.00 g, crude) by using a procedure that is similar to the one described for intermediate 51 from intermediate 54 (1.30 g, 7.73 mmol), 48% hydrobromic acid (16 ml), sodium nitrite (1.60 g, 23.21 mmol), water (19 ml) and copper(I)bromide (1.66 g, 22.21 mmol) which was used without purification in the next step.

Intermediate 56

2-fluoro-N-isopropyl-4-(4,4,5,5-tetramethyl-1,3,2-dioxaborolan-2-yl)aniline: The title compound was obtained as a brown liquid (1.40 g, 58%) by using a procedure that is similar to the one described for intermediate 12 from intermediate 55 (2.00 g, 8.65 mmol), potassium acetate (2.50 g, 25.97 mmol), bis(pinacolato)diboron (2.60 g, 10.38 mmol) dioxane (20 ml) and [1,1'-Bis(diphenylphosphino)ferrocene] dichloro palladium(II).$CH_2Cl_2$ (0.212 g, 0.259 mmol). $^1$H-NMR (δ ppm, $CDCl_3$, 400 MHz): 7.45 (dd, J=8.1, 1.2 Hz, 1H), 7.37 (dd, J=12.3, 1.2 Hz, 1H), 6.67 (t, J=8.1 Hz, 1H), 3.95 (m, 1H), 3.68 (m, 1H), 1.26 (s, 12H), 1.24 (d, J=6.3 Hz, 6H).

Intermediate 57

2-fluoro-N,N-dimethyl-4-nitroaniline: The title compound was obtained as a yellow liquid (2.70 g, 58%) by using a procedure that is similar to the one described for intermediate 53 from of 3,4-difluoro-nitrobenzene (4.00 g, 25.14 mmol) in ethyl acetate (40 ml) and triethylamine (7.36 ml) and dimethylamine hydrochloride (2.25 g, 27.65 mmol). $^1$H-NMR (δ ppm, $CDCl_3$, 400 MHz): 7.93 (dd, J=9.1, 2.6 Hz, 1H), 7.89 (dd, J=14.1, 2.6 Hz, 1H), 6.73 (t, J=9.1 Hz, 1H), 3.09 (s, 6H).

Intermediate 58

2-fluoro-N1,N1-dimethylbenzene-1,4-diamine: The title compound was obtained as a brown liquid (2.10 g, 93%) by using a procedure that is similar to the one described for intermediate 50 from intermediate 57 (2.70 g, 14.67 mmol), ethyl acetate (20 ml) and palladium on charcoal (0.270 g, 5% Pd/C) which was used without purification in the next step.

Intermediate 59

4-bromo-2-fluoro-N,N-dimethylaniline: The title compound was obtained as a yellow liquid (2.20 g, 74%) by using a procedure that is similar to the one described for intermediate 51 from intermediate 58 (2.10 g, 13.63 mmol), 48% hydrobromic acid (26 ml), sodium nitrite (2.30 g, 40.90 mmol), water (30 ml) and copper(I)bromide (2.93 g, 20.45 mmol). $^1$H-NMR (δ ppm, $CDCl_3$, 400 MHz): 7.17 (m, 2H), 6.76 (t, J=8.6 Hz, 1H), 2.86 (s, 6H).

Intermediate 60

2-fluoro-N,N-dimethyl-4-(4,4,5,5-tetramethyl-1,3,2-dioxaborolan-2-yl)aniline: The title compound was obtained as a yellow liquid (0.950 g, 37%) by using a procedure that is similar to the one described for intermediate 12 from intermediate 59 (2.10 g, 9.67 mmol), potassium acetate (2.84 g, 29.03 mmol), bis(pinacolato)diboron (2.94 g, 11.61 mmol), dioxane (22 ml) and [1,1'-Bis (diphenylphosphino) ferrocene]dichloro palladium(II).$CH_2Cl_2$ (0.237 g, 0.290 mmol). $^1$H-NMR (δ ppm, $CDCl_3$, 400 MHz): 7.48 (dd, J=8.0, 1.4 Hz, 1H), 7.43 (dd, J=13.7, 1.4 Hz, 1H), 6.84 (t, J=8.5 Hz, 1H), 2.90 (s, 6H), 1.32 (s, 12H).

Intermediate 61

2 4-(2-fluoro-4-(4,4,5,5-tetramethyl-1,3,2-dioxaborolan-2-yl)phenyl)morpholine: The title compound was obtained as a off-white solid (2.00 g, 91%) by using a procedure that is similar to the one described for intermediate 12 from 4-(4-bromo-2-fluorophenyl)morpholine (1.90 g, 7.30 mmol; for preparation see Bioorganic Med. Chem. Lett. 2006, 16, 176-180), potassium acetate (1.43 g, 14.60 mmol), bis (pinacolato)diboron (2.00 g, 8.03 mmol), dioxane (48 ml) and [1,1'-Bis (diphenylphosphino)ferrocene]dichloro palladium(II).$CH_2Cl_2$ (0.290 g, 0.365 mmol). $^1$H-NMR (δ ppm, $CDCl_3$, 400 MHz): 7.51 (dd, J=7.9, 1.3 Hz, 1H), 7.45 (dd, J=13.5, 1.3 Hz, 1H), 6.92 (t, J=8.3 Hz, 1H), 3.87 (t, J=4.7 Hz, 4H), 3.14 (t, J=4.7 Hz, 1H), 1.32 (s, 12H).

Intermediate 62

1-(4-bromo-2-fluorophenyl)-4-methylpiperazine: The title compound was obtained as a brown liquid (1.20 g, 31%) by using a procedure that is similar to the one described for intermediate 51 from 3-fluoro-4-(4-methylpiperazin-1-yl) aniline (3.00 g, 14.31 mmol; for preparation see Synth. Commun. 2010, 40, 789-798), 48% hydrobromic acid (35 ml), sodium nitrite (2.96 g, 42.95 mmol), water (40 ml) and copper(I)bromide (3.00 g, 21.47 mmol) which was used as such in next step.

Intermediate 63

1-(2-fluoro-4-(4,4,5,5-tetramethyl-1,3,2-dioxaborolan-2-yl)phenyl)-4-methylpiperazine: The title compound was obtained as a brown liquid (0.450 g, 24%) by using a procedure that is similar to the one described for intermediate 12 from intermediate 62 (1.20 g, 4.38 mmol), potassium acetate (0.86 g, 8.77 mmol), bis(pinacolato)diboron (1.22 g, 4.82 mmol), dioxane (30 ml) and [1,1'-Bis (diphenylphosphino)ferrocene]dichloro palladium(II).$CH_2Cl_2$ (0.179 g, 0.219 mmol). $^1$H-NMR (δ ppm, $CDCl_3$, 400 MHz): 7.50 (dd, J=8.0, 1.8 Hz, 1H), 7.44 (dd, J=13.4, 1.3 Hz, 1H), 6.91 (t, J=8.3 Hz, 1H), 3.23 (t, J=4.7 Hz, 4H), 2.77 (t, J=4.5 Hz, 4H), 2.42 (s, 3H), 1.32 (s, 12H).

Intermediate 64

2-(1-methoxypropylidene)malononitrile: To malononitrile (2.24 g, 33.90 mmol), trimethylorthopropionate (5.0 g, 37.26 mmol) was added and heated to reflu for 3 h. The reaction mixture was concentrated, quenched with water, extracted with ethyl acetate, dried over sodium sulphate and concentrated to afford the title compound as brown solid (4.3 g, 93%) which was used as in a next step.

Intermediate 65

5-amino-3-ethyl-1H-pyrazole-4-carbonitrile: To a solution of intermediate 64 (4.30 g, 31.58 mmol) in ethanol (15 ml), hydrazine hydrate (2.37 g, 47.37 mmol) was added and refluxed for 12 h. The reaction mass was concentrated under reduced pressure and to the residue ice was added and the precipitate formed was filtered and dried under vacuum to afford the title compound as off-white solid (2.0 g, 47%). $^1$H-NMR (δ ppm, DMSO-$d_6$, 400 MHz): 11.61 (s, 1H), 5.85 (s, 2H), 2.52 (q, J=7.9 Hz, 2H), 1.16 (t, J=7.6 Hz, 3H).

Intermediate 66

3-ethyl-1H-pyrazolo[3,4-d]pyrimidin-4-amine: To intermediate 65 (1.00 g, 7.34 mmol), formamide (8.2 ml) was added and heated to 130°C for 12 h. The reaction mass was quenched with water and the solid formed was filtered, dried under vacuum to afford the title compound as off-white solid (0.600 g, 50%). $^1$H-NMR (δ ppm, DMSO-$d_6$, 400 MHz): 12.90 (s, 1H), 8.07 (s, 1H), 7.09 (s, 2H), 2.95 (q, J=7.4 Hz, 2H), 1.22 (t, J=7.5 Hz, 3H).

Intermediate 67

3-(benzo[b]thiophen-2-yl)-1H-pyrazolo[3,4-d]pyrimidin-4-amine: The title compound was obtained as a light brown solid (0.600 g, 30%) by using a procedure that is similar to the one described for intermediate 13 from benzothiphene-2borinic acid (2.00 g, 11.23 mmol), 3-iodo-1H-pyrazolo[3,4-d]pyrimidin-4-amine (1.95 g, 7.49 mmol), 1,2-dimethoxyethane (20 ml), water (10 ml) sodium carbonate (2.30 g, 22.47 mmol) and [1,1'-Bis (diphenylphosphino)ferrocene] dichloro palladium(II).CH$_2$Cl$_2$ (1.20 g, 1.49 mmol) in microwave oven (microwave power=100 W, temperature=100° C.) for 1 h which is used as such in next step.

Intermediate 68

2-(morpholino(propylthio)methylene)malononitrile: To a solution 2-(bis(propylthio)methylene)malononitrile (1.00 g, 4.41 mmol; for preparation see J. Med. Chem. 2003, 46, 1229-1241) in ethanol (10 ml), morpholine (0.384 g, 4.41 mmol) was added and refluxed for 4 h. The reaction mass was quenched with water, extracted with ethyl acetate, dried over sodium sulphate and concentrated to afford the title compound as brown liquid (0.810 g, 77%) which is used as such in next step.

Intermediate 69

5-amino-3-morpholino-1H-pyrazole-4-carbonitrile: To a solution of intermediate 68 (0.800 g, 3.37 mmol) in ethanol (8 ml), hydrazine hydrate (0.32 ml, 6.75 mmol) was added stirred at room temperature for 4 h. The reaction mass was concentrated and quenched with water, extracted with ethyl acetate, dried over sodium sulphate and concentrated to afford the title compound as brown solid (0.450 g, 69%) $^1$H-NMR (δ ppm, DMSO-$d_6$, 400 MHz): 11.05 (s, 1H), 6.18 (s, 2H), 3.66 (t, J=4.7 Hz, 4H), 3.11 (t, J=4.7 Hz, 4H).

Intermediate 70

3-morpholino-1H-pyrazolo[3,4-d]pyrimidin-4-amine: To intermediate 69 (0.450 g, 2.32 mmol), formamide (4 ml) was added and heated to 130° C. for 12 h. The reaction mass was quenched with water, extracted with ethyl acetate, dried over sodium sulphate and concentrated The crude product was purified by column chromatography with methanol:ethyl acetate to afford the title compound as off-white solid (0.200 g, 39%). $^1$H-NMR (δ ppm, DMSO-$d_6$, 400 MHz): 12.56 (s, 1H), 8.08 (s, 1H), 6.86 (s, 2H), 3.79 (t, J=4.5 Hz, 4H), 3.07 (t, J=4.6 Hz, 4H).

Intermediate 71

2-((dimethylaminopropylthio)methylene)malononitrile: The title compound was obtained as a brown liquid (0.830 g, 96%) by using a procedure that is similar to the one described for intermediate 68 from 2-(bis(propylthio)methylene)malononitrile (1.00 g, 4.41 mmol) in ethanol (10 ml), dimethylamine hydrochloride (0.360 g, 4.41 mmol) and triethylamine (0.446 g, 4.41 mmol) which was used as such in next step.

Intermediate 72

5-amino-3-(dimethylamino)-1H-pyrazole-4-carbonitrile: The title compound was obtained as a brown solid (0.510 g, 71%) by using a procedure that is similar to the one described for intermediate 69 from intermediate 71 (0.930 g, 4.76 mmol), ethanol (10 ml) and hydrazine hydrate (0.46 ml, 9.52 mmol) which was used as such in next step.

Intermediate 73

N3,N3-dimethyl-1H-pyrazolo[3,4-d]pyrimidine-3,4-diamine: The title compound was obtained as a brown solid (0.280 g, 47%) by using a procedure that is similar to the one described for intermediate 70 from intermediate 72 (0.510 g, 3.37 mmol) and formamide (5 ml). $^1$H-NMR (δ ppm, DMSO-$d_6$, 400 MHz): 12.37 (s, 1H), 8.04 (s, 1H), 6.88 (s, 2H), 2.76 (s, 6H).

Intermediate 74

2-(piperidin-1-yl(propylthio)methylene)malononitrile: The title compound was obtained as a brown liquid (0.840 g, 60%) by using a procedure that is similar to the one described for intermediate 68 from 2-(bis(propylthio)methylene)malononitrile (1.00 g, 4.41 mmol) in ethanol (10 ml), piperidine (0.376 g, 4.41 mmol). $^1$H-NMR (δ ppm, CDCl$_3$, 400 MHz): 3.79 (t, J=5.0 Hz, 4H), 3.01 (t, J=7.2 Hz, 2H), 1.74 (m, 6H), 1.72 (m, 2H), 1.06 (t, J=7.3 Hz, 3H).

Intermediate 75

5-amino-3-(piperidin-1-yl)-1H-pyrazole-4-carbonitrile: The title compound was obtained as a brown liquid (0.500 g, 73%) by using a procedure that is similar to the one described for intermediate 69 from intermediate 74 (0.840 g, 3.56 mmol), ethanol (10 ml) and hydrazine hydrate (0.40 ml, 8.27 mmol). $^1$H-NMR (δ ppm, DMSO-$d_6$, 400 MHz): 10.92 (s, 1H), 6.09 (s, 1H), 3.12 (m, 4H), 1.53 (m, 6H).

Intermediate 76

3-(piperidin-1-yl)-1H-pyrazolo[3,4-d]pyrimidin-4-amine: The title compound was obtained as a brown solid (0.600 g, 95%) by using a procedure that is similar to the one described for intermediate 70 from intermediate 75 (0.550 g, 2.87 mmol) and formamide (5 ml). $^1$H-NMR (δ ppm, DMSO-$d_6$, 400 MHz): 12.44 (s, 1H), 8.07 (s, 1H), 6.69 (s, 2H), 3.05 (t, J=5.1 Hz, 4H), 1.69 (m, 4H), 1.54 (m, 2H).

Intermediate 77

2-(propylthio(pyrrolidin-1-yl)methylene)malononitrile: The title compound was obtained as a brown liquid (0.950 g, 97%) by using a procedure that is similar to the one described for intermediate 68 from 2-(bis(propylthio)methylene)malononitrile (1.00 g, 4.41 mmol) in ethanol (10 ml), pyrrolidine (0.314 g, 4.41 mmol) which was used as such in next step.

Intermediate 78

5-amino-3-(pyrrolidin-1-yl)-1H-pyrazole-4-carbonitrile: The title compound was obtained as a brown liquid (0.640 g, 84%) by using a procedure that is similar to the one described for intermediate 69 from intermediate 77 (0.950 g, 4.29 mmol), ethanol (10 ml) and hydrazine hydrate (0.42 ml, 8.58 mmol) which was used as such in next step.

Intermediate 79

3-(pyrrolidin-1-yl)-1H-pyrazolo[3,4-d]pyrimidin-4-amine: The title compound was obtained as a brown solid (0.350 g, 29%) by using a procedure that is similar to the one described for intermediate 70 from intermediate 78 (0.640 g, 3.61 mmol) and formamide (6 ml). $^1$H-NMR (δ ppm, DMSO-$d_6$, 400 MHz): 12.28 (s, 1H), 8.02 (s, 1H), 6.79 (s, 2H), 3.32 (t, J=6.6 Hz, 4H), 1.89 (m, 4H).

Intermediate 80

1-benzhydryl-3-(4-bromo-2-fluorophenoxy)azetidine: The title compound was obtained as a colourless liquid (0.631 g, 30%) by using a procedure that is similar to the one described for intermediate 47 from 4-bromo-2-fluorophenol (1.00 g, 5.23 mmol) in THF (12 ml), 1-benzhydrylazetidin-3-ol (1.25 g, 5.23 mmol) and tris(4-methoxyphenyl)phosphine (2.70 g, 7.85 mmol) and diisopropylazodicarboxylate (1.60 ml, 7.85 mmol). $^1$H-NMR (δ ppm, CDCl$_3$, 400 MHz): 7.42 (m, 4H), 7.29-7.17 (m, 7H), 7.11 (m, 1H), 6.59 (t, J=8.8 Hz, 1H), 4.80 (quintet, J=5.8 Hz, 1H), 4.43 (s, 1H), 3.72 (dd, J=6.1, 2.0 Hz, 2H), 3.17 (dd, J=5.7, 1.9 Hz, 2H).

Intermediate 81

1-benzhydryl-3-(2-fluoro-4-(4,4,5,5-tetramethyl-1,3,2-dioxaborolan-2-yl)phenoxy)azetidine: The title compound was obtained as a off-white solid (0.850 g, 76%) by using a procedure that is similar to the one described for intermediate 12 from intermediate 80 (1.00 g, 2.42 mmol), potassium acetate (0.713 g, 7.27 mmol), bis(pinacolato)diboron (0.738 g, 2.90 mmol) dioxane (10 ml) and [1,1'-Bis(diphenylphosphino)ferrocene]dichloro palladium(II).CH$_2$Cl$_2$ (0.059 g, 0.072 mmol). $^1$H-NMR (δ ppm, CDCl$_3$, 400 MHz): 7.49 (dd, J=11.0, 1.3 Hz, 1H), 7.42 (m, 4H), 7.29 (m, 5H), 7.21 (m, 2H), 6.68 (t, J=8.1 Hz, 1H), 4.86 (quintet, J=5.9 Hz, 1H), 4.44 (s, 1H), 3.74 (dd, J=6.1, 1.9 Hz, 2H), 3.19 (dd, J=5.8, 1.9 Hz, 2H), 1.31 (s, 12H).

Intermediate 82

3-(4-bromo-2-fluorophenoxy)oxetane: The title compound was obtained as a brown solid (0.900 g, 54%) by using a procedure that is similar to the one described for intermediate 47 from 4-bromo-2-fluorophenol (1.28 g, 6.74 mmol) in THF (6 ml), 3-hydroxyoxetane (0.500 g, 6.74 mmol) and triphenylphosphine (2.65 g, 10.12 mmol) and diisopropylazodicarboxylate (1.99 ml, 10.12 mmol). $^1$H-NMR (δ ppm, CDCl$_3$, 400 MHz): 7.28 (dd, J=12.9, 2.4 Hz, 1H), 7.17 (m, 1H), 6.52 (t, J=8.7 Hz, 1H), 5.20 (m, 1H), 4.96 (dd, J=8.0, 7.0 Hz, 2H), 4.82 (dd, J=6.3, 5.3 Hz, 2H).

Intermediate 83

2-(3-fluoro-4-(oxetan-3-yloxy)phenyl)-4,4,5,5-tetramethyl-1,3,2-dioxaborolane: The title compound was obtained as a brown liquid (0.800 g, 80%) by using a procedure that is similar to the one described for intermediate 12 from intermediate 82 (0.900 g, 3.64 mmol), potassium acetate (1.00 g, 10.92 mmol), bis(pinacolato)diboron (1.10 g, 4.37 mmol) dioxane (10 ml) and [1,1'-Bis(diphenylphosphino)ferrocene]dichloro palladium(II).CH$_2$Cl$_2$ (0.090 g, 0.109 mmol). $^1$H-NMR (δ ppm, CDCl$_3$, 400 MHz): 7.53 (dd, J=11.8, 1.4 Hz, 1H): 7.47 (d, J=8.1 Hz, 1H), 6.58 (t, J=8.0 Hz, 1H), 5.27 (m, 1H), 4.98 (dd, J=7.7, 6.9 Hz, 2H), 4.83 (dd, J=7.9, 5.3 Hz, 2H), 1.32 (s, 12H).

Intermediate 84

3-(4-isopropoxy-3-methylphenyl)-1H-pyrazolo[3,4-d]pyrimidin-4-amine: The title compound was obtained as a pale yellow solid (0.143 g, 52%) by using a procedure that is similar to the one described for intermediate 13 from 4-isopropoxy-3-methylphenylboronic acid (0.241 g, 1.24 mmol), 3-iodo-1H-pyrazolo[3,4-d]pyrimidin-4-amine (0.250 g, 0.957 mmol), DMF (1.5 ml), ethanol (0.6 ml), water (0.6 ml), sodium carbonate (0.304 g, 2.87 mmol) and tetrakis(triphenylphosphine)palladium(0) (0.055 g, 0.047 mmol) in microwave oven (microwave power=100 W, temperature=100° C.) for 3 h. Mass: 284.1 (M$^+$+1).

Intermediate 85

2-isopropoxy-5-(4,4,5,5-tetramethyl-1,3,2-dioxaborolan-2-yl)pyrimidine: The title compound was obtained as a brown liquid (0.400 g, 65%) by using a procedure that is similar to the one described for intermediate 12 from 5-bromo-2-isopropoxypyrimidine (0.500 g, 2.30 mmol for preparation see Organic. Lett. 2010, 12, 4478-4481.), potassium acetate (0.678 g, 6.91 mmol), bis(pinacolato)diboron (0.702 g, 2.76 mmol) dioxane (5 ml) and [1,1'-Bis(diphenylphosphino)ferrocene]dichloro palladium(II).CH$_2$Cl$_2$ (0.056 g, 0.069 mmol). $^1$H-NMR (δ ppm, CDCl$_3$, 400 MHz): 8.77 (s, 2H), 5.35 (m, 1H), 1.39 (d, J=6.1 Hz, 6H), 1.33 (s, 12H).

Intermediate 86

3-(3-fluoro-4-morpholinophenyl)-1H-pyrazolo[3,4-d]pyrimidin-4-amine: The title compound was obtained as a pale yellow solid (0.095 g, 20%) by using a procedure that is similar to the one described for intermediate 13 from intermediate 61 (0.393 g, 1.505 mmol), 3-iodo-1H-pyrazolo[3,4-d]pyrimidin-4-amine (0.700 g, 2.25 mmol), DMF (2.5 ml), ethanol (1.5 ml), water (1.0 ml), sodium carbonate (0.478 g, 4.51 mmol) and tetrakis(triphenylphosphine)palladium(0) (0.087 g, 0.075 mmol) in microwave oven (microwave power=100 W, temperature=100° C.) for 2 h. Mass: 315.0 (M$^+$+1).

Intermediate 87

2-acetyl-3-fluorophenyl butyrate: Pyridine (7.2 ml) and propionyl chloride (3.85 g, 41.65 mmol) were added to an ice-cold To a solution of intermediate 4 (5.00 g, 32.43 mmol) in dichloromethane (750 ml), butyric acid (2.85 g, 32.43 mmol), dicyclohexylcarbodiimide (6.67 g, 32.43 mmol) and 4-dimethylaminopyridine (0.79 g, 6.48 mmol) were added and stirred at room temperature for 12 h. The reaction mixture was filtered, washed with dichloromethane and concentrated. The crude product was purified by column chromatography with ethyl acetate:petroleum ether to afford the title compound as a yellow liquid (2.80 g, 39%0 which was used as such in next step.

Intermediate 88

5-fluoro-2-propyl-4H-chromen-4-one: To a solution of 87 (2.8 g, 12.55 mmol) in DMSO (15 ml) cooled to 0° C., sodium hydride (0.301 g, 12.55 mmol) was added maintained at the same temperature for 1 h. The mixture was warmed to RT and stirred for 12 h. The reaction was quenched by the addition of 2N HCl and extracted with ethyl acetate. The organic layer was washed with water, dried over sodium sulphate and the solvents removed. The crude product was dissolved in dioxane (6 ml) and sulphuric acid (8 ml) was added and heated to 100° C. for 12 h. Aqueous sodium bicarbonate solution was added to the mixture and extracted with ethyl acetate. The organic layer was washed with water, dried over sodium sulphate and concentrated under reduced pressure. The crude product was purified by column chromatography with ethyl acetate:petroleum ether to afford the title compound as yellow liquid (1.6 g, 62%) which was used as such in next step.

Intermediate 89

3-bromo-5-fluoro-2-propyl-4H-chromen-4-one: To a solution of intermediate 88 (1.50 g, 7.27 mmol) in DMF (9 ml), N-bromosuccinimide (1.29 g, 7.27 mmol) was added at RT. After 12 h, the reaction mixture was quenched with water and extracted with ethyl acetate. The organic layer was washed with water, dried over sodium sulphate and the solvent removed to afford the title compound as off-white solid (1.60 g, 77%) which was used as such in next step.

Intermediate 90

5-fluoro-3-phenyl-2-propyl-4H-chromen-4-one: The title compound was obtained as a off-white solid (1.10 g, 69%) by using a procedure that is similar to the one described for intermediate 21 from intermediate 89 (1.60 g, 5.61 mmol), phenylboronic acid (1.09 g, 8.97 mmol), dioxan (18 ml), potassium carbonate (2.32 g, 16.83 mmol), water (5 ml) and tetrakis(triphenylphosphine)palladium(0) (0.388 g, 0.336 mmol). Mass: 283.4 (M$^+$+1).

Intermediate 91

2-(1-bromopropyl)-5-fluoro-3-phenyl-4H-chromen-4-one: The title compound was obtained as a off-white solid (1.3 g, 925%) by using a procedure that is similar to the one described for intermediate 22 from intermediate 90 (1.10 g, 3.89 mmol), carbon tetrachloride (22 ml) N-bromosuccinimide (0.69 g, 3.89 mmol) and azobisisobutyronitrile (42 mg). Mass: 362.8 (M$^+$+1).

Intermediate 92

2-(1-(5-fluoro-4-oxo-3-phenyl-4H-chromen-2-yl)propyl) isoindoline-1,3-dione: To a solution of potassium phthalimide (0.97 g, 5.23 mmol) in DMF (10 ml), intermediate 91 (2.0 g, 3.49 mmol) was added and stirred for 12 h. The reaction mixture was diluted with water and extracted with ethyl acetate. The organic layer was dried over sodium sulphate and concentrated under reduced pressure. The crude product was purified by column chromatography with ethyl acetatel: pet.ether to afford the title compound as a off-white solid (1.0 g, 67%). Mass: 428.1 (M$^+$+1).

Intermediate 93

2-(1-aminopropyl)-5-fluoro-3-phenyl-4H-chromen-4-one: To a solution of intermediate 92 (0.50 g, 1.16 mmol) in methanol (5 ml), hydrazine hydrate (0.087 g, 1.75 mmol) was added and refluxed for 3 h. The reaction mass cooled, filtered and washed with chloroform and concentrated. The crude product was purified by column chromatography with dichloromethane: methanol to afford the title compound as a off-white solid (0.34 g, 98%). Mass: 297.1 (M$^+$).

Intermediate 94

N-(4-bromo-2-fluorophenyl)isobutyramide: To a solution of 4-bromo-2-fluoroaniline (2.0 g, 10.51 mmol) in dichloromethane (20 ml) cooled to 0° C., triethylamine (2.90 ml, 21.02) was added followed by isobutyryl chloride (1.20 ml, 12.61 mol). After stirring at room temperature for 8 h, the reaction mixture was quenched with water, extracted with dichloromethane, dried over sodium sulphate and concentrated to afford the title compound as a off-white solid (2.60 g, 96%). $^1$H-NMR (δ ppm, CDCl$_3$, 400 MHz): 8.29 (t, J=8.4 Hz, 1H), 7.31 (br s, 1H), 7.27 (m, 2H), 2.59 (quintet, J=6.9 Hz, 1H), 1.27 (d, J=6.9 Hz, 6H).

Intermediate 95

N-(2-fluoro-4-(4,4,5,5-tetramethyl-1,3,2-dioxaborolan-2-yl)phenyl)isobutyramide: The title compound was obtained as a off-white solid (0.900 g, 77%) by using a procedure that is similar to the one described for intermediate 12 from intermediate 94 (1.00 g, 3.84 mmol), potassium acetate (0.750 g, 7.68 mmol), bis(pinacolato)diboron (1.07 g, 4.22 mmol) dioxane (15 ml) and [1,1'-Bis(diphenylphosphino) ferrocene]dichloro palladium(II).CH$_2$Cl$_2$ (0.62 g, 0.768 mmol) which was used as such in next step.

Intermediate 96

N-(4-bromo-2-fluorophenyl)acetamide: To a solution of 4-bromo-2-fluoroaniline (2.0 g, 10.51 mmol) in dichloromethane (20 ml) cooled to 0° C., triethylamine (2.90 ml, 21.02) was added followed by acetyl chloride (0.90 ml, 12.61 mol). After stirring at room temperature for 8 h, the reaction mixture was quenched with water, extracted with dichloromethane, dried over sodium sulphate and concentrated to afford the title compound as a off-white solid (2.60 g, 99%) which was used as such in next step.

Intermediate 97

(2-fluoro-4-(4,4,5,5-tetramethyl-1,3,2-dioxaborolan-2-yl) phenyl)acetamide: The title compound was obtained as a off-white solid (0.800 g, 67%) by using a procedure that is similar to the one described for intermediate 12 from intermediate 96 (1.00 g, 4.30 mmol), potassium acetate (0.840 g, 8.61 mmol), bis(pinacolato)diboron (1.20 g, 4.74 mmol) dioxane (15 ml) and [1,1'-Bis(diphenylphosphino)ferrocene] dichloro palladium(II).CH$_2$Cl$_2$ (0.70 g, 0.861 mmol) which was used as such in next step.

Intermediate 98

3-iodo-N,N-dimethyl-1H-pyrazolo[3,4-d]pyrimidin-4-amine: To a solution of N,N-dimethyl-1H-pyrazolo[3,4-d] pyrimidin-4-amine (0.500 g, 3.06 mmol for preparation see J. Amer. Chem. Soc. 1956, 784-790.) in DMF (4 ml), N-iodosuccinimide (1.00 g, 4.59 mmol) was added and stirred at 80° C. for 22 h. The reaction mixture was quenched with water, extracted with ethyl acetate, dried over sodium sulphate and concentrated to afford the title compound as a brown solid (0.460 g, 46%) which was used as such in next step.

Intermediate 99

3-(3-fluoro-4-isopropoxyphenyl)-N,N-dimethyl-1H-pyrazolo[3,4-d]pyrimidin-4-amine: The title compound was obtained as a light brown solid (0.220 g, 50%) by using a procedure that is similar to the one described for intermediate 13 from intermediate 12 (0.581 g, 2.07 mmol), intermediate 98 (0.400 g, 1.38 mmol), DMF (3 ml), ethanol (1.5 ml), water (1.5 ml) sodium carbonate (0.440 g, 4.15 mmol) and tetrakis(triphenylphosphine)palladium(0) (0.080 g, 0.069 mmol). Mass: 316.3 ($M^++1$).

Intermediate 100

3-iodo-N-methyl-1H-pyrazolo[3,4-d]pyrimidin-4-amine: To a solution of N-methyl-1H-pyrazolo[3,4-d]pyrimidin-4-amine (1.10 g, 7.37 mmol, for preparation see J. Amer. Chem. Soc. 1956, 784-790) in DMF (8 ml), N-Iodosuccinimide (2.48 g, 11.06 mmol) was added and stirred at 80° C. for 12 h. The reaction mixture was quenched with water, extracted with ethyl acetate, dried over sodium sulphate and concentrated to afford the title compound as a brown solid (0.970 g, 48%). Mass: 275.9 ($M^++1$).

Intermediate 101

5-fluoro-3-(3-fluorophenyl)-2-(1-(3-iodo-4-(methylamino)-1H-pyrazolo[3,4-d]pyrimidin-1-yl)ethyl)-4H-chromen-4-one: The title compound was obtained as a light brown solid (0.230 g, 32%) by using a procedure that is similar to the one described for intermediate 34 from intermediate 22 (0.650 g, 1.78 mmol), intermediate 100 (0.350 g, 1.27 mmol), DMF (3 ml) and potassium carbonate (0.175 g, 1.27 mmol). Mass: 560.1 ($M^++1$).

Intermediate 102

4-(1H-pyrazolo[3,4-d]pyrimidin-4-yl)morpholine: To a solution of 4-chloro-1H-pyrazolo[3,4-d]pyrimidine (2.00 g, 12.97 mmol) in Dioxan (20 ml), morpholine 5.65 g, 64.86 mmol) was added and refluxed for 2 h. The reaction mixture was quenched with water, filtered and dried under vacuum to afford the title compound as a brown solid (2.40 g, 90%). $^1$H-NMR (δ ppm, CDCl$_3$, 400 MHz): 12.49 (s, 1H), 8.33 (s, 1H), 7.94 (s, 1H), 3.95 (t, J=4.6 Hz, 4H), 3.83 (t, J=5.2 Hz, 4H).

Intermediate 103

4-(3-iodo-1H-pyrazolo[3,4-d]pyrimidin-4-yl)morpholine: To a solution of intermediate 102 (1.50 g, 7.31 mmol) in DMF (12 ml), N-Iodosuccinimide (2.46 g, 10.97 mmol) was added and stirred at 80° C. for 22 h. The reaction mixture was quenched with water, filtered, washed with pet. ether and dried under vacuum to afford the title compound as a brown solid (1.90 g, 79%). $^1$H-NMR (δ ppm, DMSO-D$_6$, 400 MHz): 14.06 (s, 1H), 8.34 (s, 1H), 3.78 (t, J=5.0 Hz, 4H), 3.73 (t, J=5.0 Hz, 4H).

Intermediate 104

4-(3-(3-fluoro-4-isopropoxyphenyl)-1H-pyrazolo[3,4-d]pyrimidin-4-yl)morpholine: The title compound was obtained as a light brown solid (0.180 g, 33%) by using a procedure that is similar to the one described for intermediate 13 from intermediate 12 (0.634 g, 2.26 mmol), intermediate 103 (0.500 g, 1.51 mmol), DMF (4 ml), ethanol (2.0 ml), water (2.0 ml) sodium carbonate (0.480 g, 4.53 mmol) and tetrakis(triphenylphosphine)palladium(0) (0.087 g, 0.075 mmol). Mass: 357.38 ($M^++1$).

Intermediate 105

5-fluoro-3-(4-fluorophenyl)-2-(1-(3-iodo-4-morpholino-1H-pyrazolo[3,4-d]pyrimidin-1-yl)ethyl)-4H-chromen-4-one: The title compound was obtained as a light brown solid (0.350 g, 53%) by using a procedure that is similar to the one described for intermediate 34 from intermediate 31 (0.734 g, 2.11 mmol), intermediate 103 (0.350 g, 1.05 mmol), DMF (4 ml) and cesium carbonate (0.343 g, 1.05 mmol). Mass: 616.2 ($M^++1$).

Intermediate 106

5-fluoro-3-(3-fluorophenyl)-2-(1-(3-iodo-4-morpholino-1H-pyrazolo[3,4-d]pyrimidin-1-yl)ethyl)-4H-chromen-4-one: The title compound was obtained as a off-white solid (0.400 g, 54%) by using a procedure that is similar to the one described for intermediate 34 from intermediate 22 (0.629 g, 1.81 mmol), intermediate 103 (0.400 g, 1.20 mmol), DMF (4 ml) and potassium carbonate (0.167 g, 1.20 mmol). Mass: 616.2 ($M^++1$).

Intermediate 107

2-(1-(4-amino-3-(4-(difluoromethoxy)-3-fluorophenyl)-1H-pyrazolo[3,4-d]pyrimidin-1-yl)ethyl)-3-bromo-5-fluoro-4H-chromen-4-one: The title compound was obtained as a brown solid (0.650 g, 68%) by using a procedure that is similar to the one described for intermediate 27 from intermediate 39 (0.500 g, 1.69 mmol), potassium carbonate (0.46 g, 3.38 mmol), DMF (10 ml) and intermediate 28 (0.82 g, 2.37 mmol) which was used as such for next step.

Intermediate 108

2-(1-(4-amino-3-iodo-1H-pyrazolo[3,4-d]pyrimidin-1-yl)ethyl)-5-fluoro-3-phenyl-4H-chromen-4-one: The title compound was obtained as a pale brown solid (2.00 g, 64%) by using a procedure that is similar to the one described for intermediate 34 from intermediate 33 (2.10 g, 6.01 mmol), 3-iodo-1H-pyrazolo[3,4-d]pyrimidin-4-amine (3.13 g, 12.02 mmol), DMF (8.4 ml) and cesium carbonate (3.91 g, 12.02 mmol) which was used as in next step.

Intermediate 109

5-fluoro-3-(4-fluorophenyl)-2-(1-hydroxyethyl)-4H-chromen-4-one: The title compound was obtained as a pale brown solid (3.50 g, 78%) by using a procedure that is similar to the one described for intermediate 23 from intermediate 31 (5.50 g, 15.01 mmol), DMSO (55 ml) and n-butanol (2.75 ml). Mass: 303.1 ($M^++1$).

Intermediate 110

5-fluoro-2-(1-hydroxyethyl)-3-phenyl-4H-chromen-4-one: The title compound was obtained as a pale brown solid (2.60 g, 60%) by using a procedure that is similar to the one described for intermediate 23 from intermediate 33 (5.30 g, 15.26 mmol), DMSO (40 ml) and n-butanol (2.20 ml). Mass: 284.8 ($M^+$).

Intermediate 111

2-acetyl-5-fluoro-3-(4-fluorophenyl)-4H-chromen-4-one: The title compound was obtained as a pale yellow solid (2.20 g, 64%) by using a procedure that is similar to the one described for intermediate 24 from intermediate 109 (3.50 g, 11.54 mmol), DMSO (3.27 ml, 46.16 mmol), dichloromethane (50 ml), oxalyl chloride (1.99 ml, 23.08 mmol) and triethylamine (7 ml) which was used as such in next step.

Intermediate 112

2-acetyl-5-fluoro-3-phenyl-4H-chromen-4-one: The title compound was obtained as a pale yellow solid (1.80 g, 63%) by using a procedure that is similar to the one described for intermediate 24 from intermediate 110 (2.50 g, 8.76 mmol), DMSO (2.48 ml, 35.05 mmol), dichloromethane (42 ml), oxalyl chloride (1.51 ml, 17.52 mmol) and triethylamine (5.5 ml) which was used as such in next step.

Intermediate 113

(R)/(S)-5-fluoro-3-(4-fluorophenyl)-2-(1-hydroxyethyl)-4H-chromen-4-one: To a solution of intermediate 111 (0.568 g, 1.89 mmol) in DMF (4 ml) under nitrogen purging, formic acid:trietylamine 5:2 azeotrope (1 ml) was added followed by [(S,S)tethTsDpenRuCl] (3 mg). The reaction mixture was heated at 80° C. for 1.5 h under continuous nitrogen purging. The reaction mixture was quenched with water, extracted with ethyl acetate, dried over sodium sulphate and concentrated. The crude product was purified by column chromatography with ethyl acetate:petroleum ether to afford the title compound as a off-white solid (0420 g, 74%). Enantiomeric excess: 74%, enriched in the late eluting isomer (retention time: 9.24 min. as determined by HPLC on a chiralpak AD-H column.

Intermediate 114

(R)/(S)-5-fluoro-3-(4-fluorophenyl)-2-(1-hydroxyethyl)-4H-chromen-4-one: To a solution of intermediate 111 (0.568 g, 1.89 mmol) in DMF (4 ml) under nitrogen purging, formic acid:trietylamine 5:2 azeotrope (1 ml) was added followed by [(R,R)tethTsDpenRuCl] (3 mg). The reaction mixture was heated at 80° C. for 1.5 h under continuous nitrogen purging. The reaction mixture was quenched with water, extracted with ethyl acetate, dried over sodium sulphate and concentrated. The crude product was purified by column chromatography with ethyl acetate:petroleum ether to afford the title compound as a off-white solid (0430 g, 75%). Enantiomeric excess: 74%, enriched in the fast eluting isomer (retention time: 7.75 min. as determined by HPLC on a chiralpak AD-H column.

Intermediate 115

(R)(S)-5-fluoro-2-(1-hydroxyethyl)-3-phenyl-4H-chromen-4-one: To a solution of intermediate 112 (0.568 g, 1.89 mmol) in DMF (4 ml) under nitrogen purging, formic acid:trietylamine 5:2 azeotrope (1 ml) was added followed by [(S,S)tethTsDpenRuCl] (3 mg). The reaction mixture was heated at 80° C. for 1.5 h under continuous nitrogen purging. The reaction mixture was quenched with water, extracted with ethyl acetate, dried over sodium sulphate and concentrated. The crude product was purified by column chromatography with ethyl acetate:petroleum ether to afford the title compound as a off-white solid (0.380 g, 66%). Enantiomeric excess: 64%, enriched in the late eluting isomer (retention time: 8.85 min. as determined by HPLC on a chiralpak AD-H column.

Intermediate 116

(R)(S)-5-fluoro-2-(1-hydroxyethyl)-3-phenyl-4H-chromen-4-one: To a solution of intermediate 112 (0.568 g, 1.89 mmol) in DMF (4 ml) under nitrogen purging, formic acid:trietylamine 5:2 azeotrope (1 ml) was added followed by [(R,R)tethTsDpenRuCl] (3 mg). The reaction mixture was heated at 80° C. for 1.5 h under continuous nitrogen purging. The reaction mixture was quenched with water, extracted with ethyl acetate, dried over sodium sulphate and concentrated. The crude product was purified by column chromatography with ethyl acetate:petroleum ether to afford the title compound as a off-white solid (0.410 g, 72%). Enantiomeric excess: 64%, enriched in the fast eluting isomer (retention time: 7.43 min. as determined by HPLC on a chiralpak AD-H column.

Intermediate 117

3-(3-fluoro-4-morpholinophenyl)-N,N-dimethyl-1H-pyrazolo[3,4-d]pyrimidin-4-amine: The title compound was obtained as a pale brown solid (0.340 g, 36%) by using a procedure that is similar to the one described for intermediate 13 from intermediate 61 (1.27 g, 4.15 mmol), intermediate 98 (0.800 g, 2.76 mmol), DMF (6 ml), ethanol (3 ml), water (3 ml), sodium carbonate (0.880 g, 8.30 mmol) and tetrakis(triphenylphosphine)palladium(0) (0.160 g, 0.138 mmol) in microwave oven (microwave power=100 W, temperature=100° C.) for 2 h. Mass: 343.1 ($M^++1$).

Intermediate 118

3-(3-fluoro-4-morpholinophenyl)-N-methyl-1H-pyrazolo[3,4-d]pyrimidin-4-amine: The title compound was obtained as a off-white solid (0.350 g, 29%) by using a procedure that is similar to the one described for intermediate 13 from intermediate 61 (1.67 g, 5.45 mmol), intermediate 100 (1.00 g, 3.63 mmol), DMF (7 ml), ethanol (3.5 ml), water (3.5 ml), sodium carbonate (1.15 g, 10.89 mmol) and tetrakis(triphenylphosphine)palladium(0) (0.209 g, 0.181 mmol) in microwave oven (microwave power=100 W, temperature=100° C.) for 2 h. Mass: 329.2 ($M^++1$).

Intermediate 119

3-(3-fluoro-4-isopropoxyphenyl)-N-methyl-1H-pyrazolo[3,4-d]pyrimidin-4-amine: The title compound was obtained as a brown solid (0.205 g, 19%) by using a procedure that is similar to the one described for intermediate 13 from intermediate 12 (1.52 g, 5.45 mmol), intermediate 100 (1.00 g, 3.63 mmol), DMF (7 ml), ethanol (3.5 ml), water (3.5 ml), sodium carbonate (1.15 g, 10.89 mmol) and tetrakis(triphenylphosphine)palladium(0) (0.209 g, 0.181 mmol) in microwave oven (microwave power=100 W, temperature=100° C.) for 2 h. Mass: 301.9 ($M^+$).

Intermediate 120

4-(2-chloro-4-nitrophenyl)morpholine: The title compound was obtained as a yellow liquid (6.70 g, 53%) by using a procedure that is similar to the one described for intermediate 53 from of 3,4-dichloro-nitrobenzene (10.00 g, 52.08 mmol) in ethyl acetate (83 ml) and triethylamine (7.99 ml) and morpholine (4.99 g, 57.29 mmol). $^1$H-NMR (δ ppm, CDCl$_3$, 400 MHz): δ 8.25 (d, J=2.6 Hz, 1H), 8.12 (dd, J=8.5, 2.6 Hz, 1H), 7.05 (d, J=8.9 Hz, 1H), 3.90 (t, J=4.5 Hz, 1H), 3.22 (t, J=4.6 Hz, 1H).

Intermediate 121

3-chloro-4-morpholinoaniline: To a solution of intermediate 120 (6.00 g, 24.72 mmol) in ethanol (60 ml) and water (30 ml), iron (6.89 g, 123.60 mmol) and ammonium chloride (2.64 g, 49.44 mmol) were added and refluxed for 3 h. The reaction mixture was filtered through celite, washed with ethyl acetate. The organic layer was dried over sodium sulphate and concentrated under reduced pressure to afford the title compound was obtained as a brown solid (5.50 g) which was used without purification in the next step.

Intermediate 122

4-(4-bromo-2-chlorophenyl)morpholine: The title compound was obtained as a brown liquid (5.20 g, 72%) by using a procedure that is similar to the one described for intermediate 51 from intermediate 121 (5.50 g, 25.85 mmol), 48% hydrobromic acid (64 ml), sodium nitrite (5.35 g, 77.57 mmol), water (73 ml) and copper(I)bromide (5.56 g, 38.78 mmol) which was used without purification in the next step.

Intermediate 123

4-(2-chloro-4-(4,4,5,5-tetramethyl-1,3,2-dioxaborolan-2-yl)phenyl)morpholine: The title compound was obtained as a colourless liquid (2.00 g, 89%) by using a procedure that is similar to the one described for intermediate 12 from intermediate 122 (2.00 g, 7.23 mmol), potassium acetate (1.41 g, 14.46 mmol), bis(pinacolato)diboron (2.01 g, 7.95 mmol), dioxane (15 ml) and [1,1'-Bis (diphenylphosphino)ferrocene]dichloro palladium(II).$CH_2C_{O2}$ (0.290 g, 0.360 mmol). $^1$H-NMR ($\delta$ ppm, $CDCl_3$, 400 MHz): 7.80 (d, J=1.4 Hz, 1H), 7.66 (dd, J=8.0, 1.4 Hz, 1H), 7.04 (d, J=8.0 Hz, 1H), 3.89 (t, J=4.4 Hz, 4H), 3.12 (t, J=4.5 Hz, 4H), 1.33 (s, 12H).

Intermediate 124

4-bromo-2-chloro-1-isopropoxybenzene: The title compound was obtained as a colourless liquid (5.60 g, 93%) by using a procedure that is similar to the one described for intermediate 47 from 4-bromo-2-chlorophenol (5.00 g, 24.10 mmol) in THF (50 ml), isopropanol (1.85 ml, 24.10 mmol), triphenylphosphine (9.48 g, 36.51 mmol) and diisopropylazodicarboxylate (7.10 ml, 36.51 mmol) which was used as such in next step.

Intermediate 125

2-(3-chloro-4-isopropoxyphenyl)-4,4,5,5-tetramethyl-1,3,2-dioxaborolane: The title compound was obtained as a yellow liquid (6.50 g, 99%) by using a procedure that is similar to the one described for intermediate 12 from intermediate 124 (6.00 g, 24.04 mmol), potassium acetate (4.71 g, 48.08 mmol), bis(pinacolato)diboron (6.71 g, 26.44 mmol) dioxane (95 ml) and [1,1'-Bis(diphenylphosphino)ferrocene]dichloro palladium(II).$CH_2Cl_2$ (0.980 g, 12.02 mmol). $^1$H-NMR ($\delta$ ppm, $CDCl_3$, 400 MHz): $\delta$ 7.79 (d, J=1.4 Hz, 1H), 7.63 (dd, J=8.2, 1.4 Hz, 1H), 6.92 (d, J=8.2 Hz, 1H), 4.64 (quintet, J=6.1 Hz, 1H), 1.38 (d, J=6.1 Hz, 6H), 1.25 (s, 12H).

Intermediate 126

6-bromo-2-methylbenzo[d]oxazole: To 2-amino-5-bromophenol (1.00 g, 5.32 mmol), acetic acid ((0.006 ml) and triethylorthoacetate (1.75 ml, 9.58 mmol) were added and refluxed for 30 min. The reaction mixture was quenched with water, extracted with ethyl acetate, dried over sodium sulphate and concentrated. The crude product was column chromatographed with ethyl acetate:petroleum ether to afford the title compound as a orange solid ((0.756 g, 65%). $^1$H-NMR ($\delta$ ppm, $CDCl_3$, 400 MHz): $\delta$ 7.64 (d, J=1.7 Hz, 1H), 7.51 (d, J=8.4 Hz, 1H), 7.43 (dd, J=8.4, 1.7 Hz, 1H), 2.67 (s, 3H).

Intermediate 127

2-methyl-6-(4,4,5,5-tetramethyl-1,3,2-dioxaborolan-2-yl)benzo[d]oxazole: The title compound was obtained as a orange solid (0.965 g, 88%) by using a procedure that is similar to the one described for intermediate 12 from intermediate 126 (0.900 g, 4.24 mmol), potassium acetate (0.833 g, 8.48 mmol), bis(pinacolato)diboron (1.18 g, 4.66 mmol) dioxane (10 ml) and [1,1'-Bis(diphenylphosphino)ferrocene] dichloro palladium(II).$CH_2Cl_2$ (0.173 g, 0.212 mmol). $^1$H-NMR ($\delta$ ppm, $CDCl_3$, 400 MHz): $\delta$ 7.90 (s, 1H), 7.76 (dd, J=7.8, 0.5 Hz, 1H), 7.64 (d, J=7.9 Hz, 1H), 2.64 (s, 3H), 1.36 (s, 12H).

Intermediate 128

6-(4,4,5,5-tetramethyl-1,3,2-dioxaborolan-2-yl)isoindolin-1-one: The title compound was obtained as a off-white solid (0.850 g, 39%) by using a procedure that is similar to the one described for intermediate 12 from 6-bromoisoindolin-1-one (1.00 g, 4.71 mmol for preparation see J. Pharm. Science & Technol. 2010, 2, 380-390.), potassium acetate (1.60 g, 16.50 mmol), bis(pinacolato)diboron (1.30 g, 5.18 mmol) dioxane (18 ml) and [1,1'-Bis(diphenylphosphino)ferrocene]dichloro palladium(II).$CH_2Cl_2$ (0.190 g, 0.235 mmol). $^1$H-NMR ($\delta$ ppm, $CDCl_3$, 400 MHz): $\delta$ 8.36 (s, 1H), 8.00 (d, J=7.5 Hz, 1H), 7.47 (d, J=7.6 Hz, 1H), 6.55 (s, 1H), 4.46 (s, 2H), 1.35 (s, 12H).

Intermediate 129

5-(4,4,5,5-tetramethyl-1,3,2-dioxaborolan-2-yl)isoindolin-1-one: The title compound was obtained as a off-white solid (0.410 g, 84%) by using a procedure that is similar to the one described for intermediate 12 from 5-bromoisoindolin-1-one (0.400 g, 1.88 mmol), potassium acetate (0.645 g, 6.58 mmol), bis(pinacolato)diboron (0.520 g, 2.07 mmol) dioxane (7 ml) and [1,1'-Bis(diphenylphosphino)ferrocene] dichloro palladium(II).$CH_2Cl_2$ (0.076 g, 0.094 mmol). $^1$H-NMR ($\delta$ ppm, $CDCl_3$, 400 MHz): $\delta$ 7.93 (m, 2H), 7.87 (d, J=7.8 Hz, 1H), 7.16 (s, 1H), 1H), 4.45 (s, 2H), 1.36 (s, 12H).

Intermediate 130

1-(2-fluoro-4-(4,4,5,5-tetramethyl-1,3,2-dioxaborolan-2-yl)phenyl)ethanone: The title compound was obtained as a colourless liquid (1.50 g, 82%) by using a procedure that is similar to the one described for intermediate 12 from 1-(4-bromo-2-fluorophenyl)ethanone (1.50 g, 6.91 mmol), potassium acetate (1.35 g, 13.82 mmol), bis(pinacolato)diboron (1.92 g, 7.60 mmol) dioxane (30 ml) and [1,1'-Bis(diphenylphosphino)ferrocene]dichloro palladium(II).$CH_2Cl_2$ (0.282 g, 0.345 mmol). $^1$H-NMR ($\delta$ ppm, $CDCl_3$, 400 MHz): 7.84 (t, J=7.5 Hz, 1H), 7.62 (dd, J=7.6, 0.6 Hz, 1H), 7.55 (d, J=11.0 Hz, 1H), 2.62 (d, J=4.8 Hz, 3H), 1.35 (s, 12H).

Intermediate 131

3-(3-chloro-4-morpholinophenyl)-1H-pyrazolo[3,4-d]pyrimidin-4-amine: The title compound was obtained as a pale brown solid (0.250 g, 20%) by using a procedure that is similar to the one described for intermediate 13 from intermediate 123 (1.87 g, 5.74 mmol), 3-iodo-1H-pyrazolo[3,4-d]pyrimidin-4-amine (1.00 g, 3.83 mmol), DMF (6.4 ml), ethanol (2.1 ml), water (1.4 ml), sodium carbonate (1.21 g, 11.49 mmol) and tetrakis(triphenylphosphine)palladium(0) (0.220 g, 0.190 mmol) in microwave oven (microwave power=100 W, temperature=100° C.) for 1 h. $^1$H-NMR ($\delta$ ppm, DMSO-D$_6$, 400 MHz): 13.57 (s, 1H), 8.20 (s, 1H), 7.66 (d, J=1.9 Hz, 1H), 7.59 (dd, J=8.2, 1.9 Hz, 1H), 7.30 (d, J=8.3 Hz, 1H), 6.79 (s, 2H), 3.77 (t, J=4.3 Hz, 4H), 3.05 (t, J=4.3 Hz, 4H).

Intermediate 132

(3-(4,4,5,5-tetramethyl-1,3,2-dioxaborolan-2-yl)phenyl) methanesulfonamide: The title compound was obtained as a off-white solid (1.00 g, 84%) by using a procedure that is similar to the one described for intermediate 12 from N-(3-bromophenyl)methanesulfonamide (1.00 g, 3.99 mmol), potassium acetate (0.78 g, 7.98 mmol), bis(pinacolato)diboron (1.11 g, 4.39 mmol) dioxane (10 ml) and [1,1'-Bis(diphenylphosphino)ferrocene]dichloro palladium(II).CH$_2$Cl$_2$ (0.162 g, 0.199 mmol). $^1$H-NMR ($\delta$ ppm, DMSO-D$_6$, 400 MHz): 9.66 (s, 1H), 7.51 (d, J=1.3 Hz, 1H), 7.41 (dd, J=5.2, 0.9 Hz, 1H), 7.35 (m, 2H), 2.94 (s, 3H), 1.28 (s, 12H).

Intermediate 133: 2-ethyl-5-fluoro-3-(2-fluorophenyl)-4H-chromen-4-one

The title compound was obtained as a brown solid (0.500 g, 47%) by using a procedure that is similar to the one described for intermediate 21 from intermediate 20 (1.00 g, 3.68 mmol), 2-fluorophenylboronic acid (0.820 g, 5.90 mmol), dioxan (6 ml), potassium carbonate (1.50 g, 11.04 mmol), water (1.0 ml) and tetrakis(triphenylphosphine)palladium(0) (0.255 g, 0.220 mmol). Mass: 287.3 (M$^+$+1).

Intermediate 134

2-(1-bromoethyl)-5-fluoro-3-(2-fluorophenyl)-4H-chromen-4-one: The title compound was obtained as a brown solid (0.510 g, 78%) by using a procedure that is similar to the one described for intermediate 22 from intermediate 133 (0.500 g, 1.74 mmol), carbon tetrachloride (13 ml) N-bromosuccinimide (0.309 g, 1.74 mmol) and azobisisobutyronitrile (30 mg) which was used as such for next step.

Intermediate 135

5-fluoro-3-(2-fluorophenyl)-2-(1-hydroxyethyl)-4H-chromen-4-one: The title compound was obtained as a pale brown solid (0.210 g, 50%) by using a procedure that is similar to the one described for intermediate 23 from intermediate 134 (0.500 g, 1.36 mmol), DMSO (5 ml) and n-butanol (1 ml). Mass: 302.8 (M$^+$).

Intermediate 136

5-fluoro-3-(3-fluorophenyl)-2-propyl-4H-chromen-4-one: The title compound was obtained as a pale yellow solid (2.60 g, 69%) by using a procedure that is similar to the one described for intermediate 21 from intermediate 89 (2.80 g, 9.89 mmol), 3-fluorophenylboronic acid (2.20 g, 15.82 mmol), dioxan (18 ml), potassium carbonate (4.10 g, 29.67 mmol), water (2.6 ml) and tetrakis(triphenylphosphine)palladium(0) (0.685 g, 0.593 mmol) which was used as such in next step.

Intermediate 137

2-(1-bromopropyl)-5-fluoro-3-(3-fluorophenyl)-4H-chromen-4-one: The title compound was obtained as a brown solid (2.95 g, 89%) by using a procedure that is similar to the one described for intermediate 22 from intermediate 136 (2.60 g, 9.21 mmol), carbon tetrachloride (25 ml) N-bromosuccinimide (1.64 g, 9.21 mmol) and azobisisobutyronitrile (0.247 g) which was used as such in next step.

Intermediate 138

2-fluoro-9-trityl-9H-purin-6-amine: To a solution of 2-fluoro-9H-purin-6-amine (0.50 g, 3.26 mmol) in DMF (3 ml), pyridine (0.5 ml) followed bt trityl chloride (1.00 g, 3.91 mmol). After stirring at room temperature for 12, the reaction mass was quenched with water, the precipitate formed was filtered, washed with water and dried under vacuum to afford the title compound as off-white solid (1.20 g, 93%) which was used as such in next step.

Intermediate 139

N,N-Diboc-2-fluoro-9-trityl-9H-purin-6-amine: To a solution of intermediate 138 (1.10 g, 2.78 mmol) in THF (11 ml) cooled to 0° C., boc-anhydride (1.40 ml, 6.12 mmol) and 4-dimethylaminopyridine (0.034 g, 0.278 mmol0 were added and stirred at room temperature for 15 h. The reaction mass was quenched with water, extracted with ethyl acetate, dried over sodium sulphate and concentrated under vacuum to afford the title compound as off-white solid (1.60 g, 97%) which was used as such in next step.

Intermediate 140 tert-butyl 2-methoxy-9-trityl-9H-purin-6-ylcarbamate: To a solution of intermediate 139 (1.50 g, 2.51 mmol) in methanol (6 ml), potassium carbonate (0.34 g, 2.51 mmol) was added and heated to 90° C. for 2 h. The reaction mass was concentrated quenched with water, extracted with ethyl acetate, dried over sodium sulphate and concentrated under vacuum. The crude product was column chromatographed with ethyl acetate:petroleum ether to afford the title compound as off-white solid (0.255 g g, 20%). $^1$H-NMR ($\delta$ ppm, DMSO-D$_6$, 400 MHz): 10.00 (s, 1H), 7.89 (s, 1H), 7.89 (m, 9H), 7.19 (m, 6H), 3.33 (s, 3H), 1.44 (s, 9H).

Intermediate 141

(S)/(R)-1-(5-fluoro-3-(3-fluorophenyl)-4-oxo-4H-chromen-2-yl)ethyl methanesulfonate: To a cooled solution of intermediate 23a (0.800 g, 2.63 mmol) in dichloromethane (16 ml) and triethylamine (1.10 ml, 7.91 mmol), methanesulphonyl chloride (0.400 ml, 5.27 mmol) was added stirred at room temperature for 2 h. The reaction mass was quenched with water, extracted with dichloromethane, dried over sodium sulphate and concentrated to afford the title compound as brown solid (1.00 g, 100%) which was used as such in next step

Intermediate 142

(S)/(R)-2-(1-azidoethyl)-5-fluoro-3-(3-fluorophenyl)-4H-chromen-4-one: To a solution of intermediate 141 (0.900 g, 2.36 mmol) in DMF (18 ml), sodium azide (0.306 g, 4.72 mmol) was added heated to 60° C. After 2 h, reaction mass was quenched with water, extracted with dichloromethane, dried over sodium sulphate and concentrated. The crude product was column chromatographed with ethyl acetate:petroleum ether to afford the title compound as brown liquid (0.650 g, 84%) which was used as such in next step.

Intermediate 143

(S)/(R)-2 2-(1-aminoethyl)-5-fluoro-3-(3-fluorophenyl)-4H-chromen-4-one: To a solution of intermediate 142 (0.600 g, 1.82 mmol) in THF (2.4 ml) and water (1.2 ml), triphenylphosphine (0.455 g, 1.73 mmol) was added stirred at room temperature for 14 h. The reaction mass was quenched with water, extracted with ethyl acetate, dried over sodium sulphate and concentrated. The crude product was column chromatographed with methanol:dichloromethane to afford the title compound as brown liquid (0.300 g, 55%) which was used as such in next step.

Intermediate 144

2-methoxy-6-methylbenzaldehyde oxime: To 2-methoxy-6-methylbenzaldehyde (11.0 g, 73.25 mmol) in triethylamine (132 ml), hydroxylamine hydrochloride (6.10 g, 69.49 mmol) was added and heated to 80° C. After 3 h, the reaction mass was concentrated, quenched with water, extracted with ethyl acetate, dried over sodium sulphate and concentrated to afford the title compound as off-white solid (7.50 g, 62%). $^1$H-NMR (δ ppm, CDCl$_3$, 400 MHz): 8.54 (s, 1H), 8.31 (s, 1H), 7.24 (t, J=7.9 Hz, 1H), 6.84 (d, J=7.5 Hz, 1H), 6.78 (d, J=8.2 Hz, 1H), 3.85 (s, 3H), 2.46 (s, 3H).

Intermediate 145

2-methoxy-6-methylbenzonitrile: To intermediate 144 (7.50 g, 45.41 mmol) in dichloromethane (55 ml), N,N'-dicarbonyl diimidazole (8.09 g, 49.95 mmol) was added and stirred at room temperature for 15 h. The reaction mass was quenched with water, extracted with dichloromethane, dried over sodium sulphate and concentrated to afford the title compound as brown solid (5.0 g, 75%). $^1$H-NMR (δ ppm, CDCl$_3$, 400 MHz): 7.41 (t, J=8.1 Hz, 1H), 6.87 (d, J=7.7 Hz, 1H), 6.78 (d, J=8.5 Hz, 1H), 3.91 (s, 3H), 2.50 (s, 3H).

Intermediate 146

1-(2-methoxy-6-methylphenyl)-2-phenylethanone: To intermediate 145 (5.0 g, 34.03 mmol) in THF (50 ml), benzylmagnesium chloride (34 ml, 2M in THF, 68.02 mmol) was added at 0° C. over 30 min. and heated to reflux for 15 h. The reaction mixture was cooled to room temperature, 2N HCl (200 ml) was added and again refluxed for 4 h. The reaction mixture was cooled and extracted with ethyl acetate, dried over sodium sulphate and concentrated. The crude product was column chromatographed with ethyl acetate:petroleum ether to afford to afford the title compound as brown liquid (3.7 g, 45%). $^1$H-NMR (δ ppm, CDCl$_3$, 400 MHz): 7.30-7.18 (m, 6H), 6.76 (m, 2H), 4.07 (s, 2H), 3.83 (s, 3H), 2.02 (s, 3H).

Intermediate 147

1-(2-hydroxy-6-methylphenyl)-2-phenylethanone: To intermediate 146 (2.0 g, 8.31 mmol) in dichloromethane (20 ml) at −78° C., boron tribromide (2.84 ml, 1M in dichloromethane, 16.64 mmol) was added slowly and maintained for 4 h. The reaction mass was quenched at −78° C. using 2N HCl (50 ml), extracted with ethyl acetate, dried over sodium sulphate and concentrated. The crude product was column chromatographed with ethyl acetate:petroleum ether to afford to afford the title compound as off-white solid (1.20 g, 64%). $^1$H-NMR (δ ppm, CDCl$_3$, 400 MHz): 11.18 (s, 1H), 7.37-7.27 (m, 4H), 7.19 (m, 2H), 6.84 (d, J=8.3 Hz, 1H), 6.75 (d, J=7.5 Hz, 1H), 4.27 (s, 2H), 2.62 (s, 3H).

Intermediate 148

2-(1-(benzyloxy)ethyl)-5-methyl-3-phenyl-4H-chromen-4-one: To intermediate 147 (0.400 g, 1.76 mmol) in dichloromethane (4 ml), R(+)-benzyloxypropionic acid (0.382 g, 2.12 mmol) and HATU (2.01 g, 5.30 mmol) were added followed by triethylamine (2.6 ml, 19.08 mmol). After 20 h at room temperature, the reaction mixture was quenched with water, extracted with ethyl acetate, dried over sodium sulphate and concentrated. The crude product was column chromatographed with ethyl acetate:petroleum ether to afford to afford the title compound as off-white solid (0.080 g, 12%). $^1$H-NMR (δ ppm, CDCl$_3$, 400 MHz): 7.55 (t, J=8.1 Hz, 1H), 7.43-7.13 (m, 12H), 4.47 (m, 2H), 4.30 (d, J=11.8 Hz, 1H), 2.84 (s, 3H), 21.54 (d, J=6.5 Hz, 3H).

Intermediate 149

2-(1-hydroxyethyl)-5-methyl-3-phenyl-4H-chromen-4-one: To intermediate 148 (0.140 g, 0.377 mmol) in dichloromethane (2.0 ml) at −78° C., boron tribromide (0.12 ml, 1M in dichloromethane, 0.755 mmol) was added slowly and maintained for 4 h. The reaction mass was quenched at −78° C. using 2N HCl (50 ml), extracted with ethyl acetate, dried over sodium sulphate and concentrated. The crude product was column chromatographed with ethyl acetate:petroleum ether to afford to afford the title compound as pale-yellow liquid (0.100 g, 95%) which was used as such in next step.

Intermediate 150

3-bromo-5-fluoro-2-(1-hydroxyethyl)-4H-chromen-4-one: The title compound was obtained as a pale brown solid (1.90 g, 61%) by using a procedure that is similar to the one described for intermediate 23 from intermediate 28 (3.90 g, 11.14 mmol), DMSO (40 ml) and n-butanol (3.0 ml) which was used as such in next step.

Intermediate 151

2-acetyl-3-bromo-5-fluoro-4H-chromen-4-one: The title compound was obtained as a pale yellow solid (0.80 g, 80%) by using a procedure that is similar to the one described for intermediate 24 from intermediate 150 (1.00 g, 3.48 mmol), DMSO (0.98 ml, 13.92 mmol), dichloromethane (104 ml), oxalyl chloride (0.59 ml, 6.96 mmol) and triethylamine (2 ml). $^1$H-NMR (δ ppm, CDCl$_3$, 400 MHz): 7.73 (dt, J=8.4, 5.4 Hz, 1H), 7.36 (td, J=8.6, 0.9 Hz, 1H), 7.18 (m, 1H), 2.70 (s, 3H).

Intermediate 152

2-acetyl-5-fluoro-3-o-tolyl-4H-chromen-4-one: The title compound was obtained as a pale brown solid (0.165 g, 32%) by using a procedure that is similar to the one described for intermediate 21 from intermediate 151 (0.500 g, 1.75 mmol), 2-methylphenylboronic acid (0.382 g, 2.80 mmol), dioxane (11 ml), potassium acetate (0.573 g, 3.33 mmol) and tetrakis(triphenylphosphine)palladium(0) (0.162 g, 0.140 mmol) which was used as such in next step.

Intermediate 153

(R)/(S)-5-fluoro-2-(1-hydroxyethyl)-3-o-tolyl-4H-chromen-4-one: To a solution of intermediate 152 (0.155 g, 0.523 mmol) in DMF (2 ml) under nitrogen purging, formic acid:trietylamine 5:2 azeotrope (0.5 ml) was added followed by [(S,S)tethTsDpenRuCl] (1 mg). The reaction mixture was heated at 80° C. for 1.5 h under continuous nitrogen purging. The reaction mixture was quenched with water, extracted with ethyl acetate, dried over sodium sulphate and concentrated. The crude product was purified by column chromatography with ethyl acetate:petroleum ether to afford the title compound as a off-white solid (0.090 g, 66%) which was used as such in next step.

EXAMPLES

Example 1

2-(6-Amino-9H-purin-9-yl)methyl)-3-(3-fluorophenyl)-5-methoxy-4H-chromen-4-one 2-(6-Amino-9H-purin-9-yl)methyl)-3-(3-fluorophenyl)-5-methoxy-4H-chromen-4-one: To a solution of adenine (0.030 g, 0.222 mmol) in DMF (2 ml), potassium carbonate (0.061 g, 0.444 mmol) was added and stirred at RT for 10 min. To this mixture intermediate 10 (0.120 g, 0.333 mmol) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as an off-white solid (0.028 g, 30%). $^1$H-NMR ($\delta$ ppm, DMSO-Ds, 400 MHz): 8.09 (s, 1H), 8.07 (s, 1H), 7.64 (t, J=84 Hz, 1H), 7.46 (dd, J=15.0, 6.7 Hz, 1H), 7.22-7.20 (m, 5H), 6.98 (d, J=8.3 Hz, 1H), 6.91 (d, J=8.5 Hz, 1H), 5.26 (s, 2H), 3.81 (s, 3H).

Example 2

2-((4-Amino-3-(3-fluoro-4-isopropoxyphenyl)-1H-pyrazolo[3,4-d]pyrimidin-1-yl)methyl)-3-(3-fluorophenyl)-S-methoxy-4H-chromen-4-one 2-((4-Amino-3-(3-fluoro-4-isopropoxyphenyl)-1H-pyrazolo[3,4-d]pyrimidin-1-yl)methyl)-3-(3-fluorophenyl)-5-methoxy-4H-chromen-4-one: To a solution of Intermediate 13 (0.060 g, 0.220 mmol) in DMF (2 ml), potassium carbonate (0.060 g, 0.440 mmol) was added and stirred at RT for 10 min. To this mixture intermediate 9 (0.120 g, 0.330 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as a pale yellow solid (0.035 g, 28%). MP: 145-148° C. $^1$H-NMR ($\delta$ ppm, DMSO-D$_6$, 400 MHz): 8.37 (s, 1H), 7.51 (t, J=8.3 Hz, 1H), 7.42-7.29 (m, 3H), 7.18-7.09 (m, 3H), 7.00 (t, J=6.8 $^H$z, 1H), 6.84 (d, J=8.3 Hz, 1H), 6.78 (d, J=8.3 Hz, 1H), 5.53 (s, 2H), 5.47 (s, 2H), 4.66 (quintet, J=6.0 Hz, 1H), 3.98 (s, 3H), 1.41 (d, J=5.9 Hz, 6H).

Example 3

2-((4-amino-3-(3-fluoro-4-isopropoxyphenyl)-1H-pyrazolo[3,4-d]pyrimidin-1-yl)methyl)-5-fluoro-3-(3-fluorophenyl)-4H-chromen-4-one 2-((4-amino-3-(3-fluoro-4-isopropoxyphenyl)-1H-pyrazolo[3,4-d]pyrimidin-1-yl)methyl)-5-fluoro-3-(3-fluorophenyl)-4H-chromen-4-one: To a solution of Intermediate 13 (0.100 g, 0.367 mmol) in DMF (2 ml), potassium carbonate (0.101 g, 0.734 mmol) was added and stirred at RT for 10 min. To this mixture intermediate 17 (0.173 g, 0.550 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as a pale brown solid (0.011 g, 5%). MP: 156-159° C. $^1$H-NMR ($\delta$ ppm, DMSO-D$_6$, 400 MHz): 8.20 (s, 1H), 8.79 (dd, J=13.9, 8.2 Hz, 1H), 7.63-7.53 (m, 4H), 7.40-7.22 (m, 5H), 7.15 (m, 2H), 5.47 (s, 2H), 4.71 (quintet, J=5.9 Hz, 1H), 1.32 (d, J=5.9 Hz, 6H).

Example 4

2-((4-amino-3-(3-fluoro-5-methoxyphenyl)-1H-pyrazolo[3,4-d]pyrimidin-1-yl)methyl)-5-fluoro-3-(3-fluorophenyl)-4H-chromen-4-one 2-((4-amino-3-(3-fluoro-5-methoxyphenyl)-1H-pyrazolo[3,4-d]pyrimidin-1-yl)methyl)-5-fluoro-3-(3-fluorophenyl)-4H-chromen-4-one: To a solution of 3-(3-fluoro-5-methoxyphenyl)-1H-pyrazolo[3,4-d]pyrimidin-4-amine (0.150 g, 0.578 mmol) in DMF (2 ml), potassium carbonate (0.159 g, 1.15 mmol) was added and stirred at RT for 10 min. To this mixture intermediate 17 (0.564 g, 1.78 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as a pale brown solid (0.200 g, 65%) which is used as such for next step.

Example 5

2-((4-amino-3-(3-fluoro-5-hydroxyphenyl)-1H-pyrazolo[3,4-d]pyrimidin-1-yl)methyl)-5-fluoro-3-(3-fluorophenyl)-4H-chromen-4-one 2-((4-amino-3-(3-fluoro-5-hydroxyphenyl)-1H-pyrazolo[3,4-d]pyrimidin-1-yl)methyl)-5-fluoro-3-(3-fluorophenyl)-4H-chromen-4-one: To a solution example 4 (0.200 g, 0.377 mmol) in dichloromethane (2 ml) at 0° C., boron tribromide (1M in dichloromethane, 2 ml) was added and warmed to RT and stirred for 12 h. The reaction mixture was quenched by the addition of aq.HCl solution and extracted with ethyl acetate. The organic layer was dried over sodium sulphate and concentrated under reduced pressure to afford the title compound as a pale brown solid (0.030 g, 15%). MP: 136-138° C. $^1$H-NMR (δ ppm, DMSO-D$_6$, 400 MHz): 10.17 (s, 1H), 8.22 (s, 1H), 7.78 (dt, J=14.2, 8.3 Hz, 1H), 7.63 (dd, J=12.0, 7.3 Hz, 1H), 7.56 (m, 1H), 7.38-7.23 (m, 3H), 7.14-7.07 (m, 3H), 6.85 (s, 1H), 6.82 (d, J=9.0 Hz, 1H), 6.65 (d, J=10.8 Hz, 1H), 5.50 (s, 2H).

Example 6

2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one 2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one: To a solution of 13 (0.120 g, 0.440 mmol) in DMF (2 ml), potassium carbonate (0.121 g, 0.881 mmol) was added and stirred at RT for 10 min. To this mixture intermediate 22 (0.217 g, 0.661 mmoles) was added and stirred for 12 h. The reaction mixture was diluted with water and extracted with ethyl acetate. The organic layer was dried over sodium sulphate and concentrated under reduced pressure. The crude product was purified by column chromatography with methanol:dichloromethane to afford the title compound as a off-white solid (0.120 g, 48%). MP: 228-230° C. $^1$H-NMR (δ ppm, CDCl$_3$, 400 MHz): 8.23 (s, 1H), 7.62 (dt, J=8.4, 5.9 Hz, 1H), 7.44 (d, J=11.5, 1.8 Hz, 1H), 7.37 (d, J=8.4 Hz, 1H), 7.31 (m, 2H), 7.14 (t, J=8.4 Hz, 1H), 7.06 (m, 3H), 6.92 (d, J=9.5 Hz, 1H), 6.07 (q, J=7.1 Hz, 1H), 5.52 (s, 2H), 4.65 (quintet, J=6.1 Hz, 1H), 1.99 (d, J=7.1 Hz, 3H), 1.42 (d, J=6.1 Hz, 6H).

Example 7 and 8

(+)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one and (−)-2-(1-(4-amino-3-(3-fluoro-4-Isopropoxyphenyl)-1H-pyrazolo[3,4-d]pyrimidin-1-yl)ethyl)-5-fluoro-3-(3-fluorophenyl)-4H-chromen-4-one The two enantiomerically pure isomers were separated by preparative SFC conditions from example 6 (0.300 g) on a CHIRALPAK AS-H column (250×4.6 mm; 51 μm) using methanol: CO$_2$ (30:70) as the mobile phase at a flow rate of 3.0 ml/min.
Example 7: Off-white solid (0.145 g). e.e. 98.16%. Rt: 2.06 min. [α]$^{25}$$_D$ 177.47 (c=1, CHCl$_3$). MP: 217-220° C. Mass: 571.2 (M$^+$).
Example 8: Off-white solid (0.136 g). e.e. 100%. Rt: 2.73 min. [α]$^{25}$$_D$ −173.56 (c=1, CHCl$_3$). MP: 218-221° C. Mass: 571.8 (M$^+$).

Example 9

2-(1-(4-amino-3-(3-methyl-1H-indazol-6-yl)-1H-pyrazolo[3,4-d]pyrimidin-1-yl)ethyl)-5-fluoro-3-(3-fluorophenyl)-4H-chromen-4-one 2-(1-(4-amino-3-(3-methyl-1H-indazol-6-yl)-1H-pyrazolo[3,4-d]pyrimidin-1-yl)ethyl)-5-fluoro-3-(3-fluorophenyl)-4H-chromen-4-one: To a solution of intermediate 27 (0.100 g, 0.183 mmol) in 1,2-dimethoxyethane (2 ml), and water (1 ml), 3-methyl-6-(4,4,5,5-tetramethyl-1,3,2-dioxaborolan-2-yl)-1H-indazole (0.099 g, 0.275 mmol) and sodium carbonate (0.058 g, 0.549 mmol) were added and the system is degassed for 30 min. Bis(diphenylphosphino)ferrocene]dichloro palladium(II).CH$_2$Cl$_2$ (0.030 g, 0.036 mmol) was added under nitrogen atmosphere and degassed for 30 min and kept under microwave irradiation (microwave power=100 W, temperature=100° C.) for 1 h. The reaction mixture was filtered through celite, washed with ethyl acetate, dried over sodium sulphate and concentrated. The residue was dissolved in dichloromethane (2 ml) and trifluroacetic acid (2 ml) was added and stirred for 1 h. The reaction mixture neutralised with aq. sodium bicarbonate solution, extracted with ethyl acetate. The organic layer was dried over sodium sulphate and concentrated under reduced pressure. The crude product was purified by column chromatography with methanol:dichloromethane to afford the title compound as brown solid (0.033 g, 33% yield). MP: 156-159° C. $^1$H-NMR (δ ppm, CDCl$_3$, 400 MHz): 8.21 (s, 1H), 7.86 (d, J=8.2 Hz, 1H), 7.73 (s, 1H), 7.60 (dt, J=8.4, 5.5 Hz, 1H), 7.45 (dd, J=8.2, 1.1 Hz, 1H), 7.29 (m, 2H), 7.06-6.98 (m, 4H), 6.10 (q, J=7.2 Hz, 1H), 5.89 (m, 1H), 2.64 (s, 3H), 1.96 (d, J=7.2 Hz, 3H).

Example 9a and 9b (+)-2-(1-(4-amino-3-(3-methyl-H-indazol-6-yl)-1H-pyrazolo[3,4-d]pyrimidin-1-yl)ethyl)-5-fluoro-3-(3-fluorophenyl)-4H-chromen-4-one and (−)-2-(1-(4-amino-3-(3-methyl-1H-indazol-6-yl)-1H-pyrazolo[3,4-d]pyrimidin-1-yl)ethyl)-5-fluoro-3-(3-fluorophenyl)-4H-chromen-4-one The two enantiomerically pure isomers were separated by preparative SFC conditions from example 9 (0.300 g) on a CHIRALPAK AD-H column (250×4.6 mm; 5 μm) using methanol: CO$_2$ (30:70) as the mobile phase at a flow rate of 3.0 ml/min.
Example 9a: Brown solid (0.097 g). e.e. 98.12%. Rt: 4.54 min. [α]$^{25}$$_D$ 161.30 (c=1, CHCl$_3$). MP: 190-192° C. Mass: 549.8 (M$^+$).
Example 9b: Brown solid (0.098 g). e.e. 96.1%. Rt: 5.92 min. [α]$^{25}$$_D$ −209.90 (c=1, CHCl$_3$). MP: 193-195° C. Mass: 549.2 (M$^+$).

Example 10

2-(1-(4-amino-3-(1H-pyrazol-4-yl)-1H-pyrazolo[3,4-d]pyrimidin-1-yl)ethyl)-5-fluoro-3-(3-fluorophenyl)-4H-chromen-4-one 2-(1-(4-amino-3-(1H-pyrazol-4-yl)-1H-pyrazolo[3,4-d]pyrimidin-1-yl)ethyl)-5-fluoro-3-(3-fluorophenyl)-4H-chromen-4-one: The title compound was obtained as off-white solid (0.016 g, 18%) by using a procedure that is similar to the one described for example 9 from intermediate 27 (0.100 g, 0.183 mmol), 1,2-dimethoxyethane (2 ml), water (1 ml), 1-Boc-pyrazole-4-boronic acid (0.058 g, 0.275 mmol), sodium carbonate (0.058 g, 0.549 mmol) and bis (diphenylphosphino)ferrocene]dichloro palladium(II).CH$_2$Cl$_2$ (0.030 g, 0.036 mmol) MP: 165-168° C. $^1$H-NMR (δ ppm, CDCl$_3$, 400 MHz): 8.24 (s, 1H), 7.94 (s, 2H), 7.59 (m, 1H), 7.28 (m, 2H), 7.04-6.87 (m, 4H), 6.04 (q, J=7.0 Hz, 1H), 5.49 (s, 2H), 1.99 (d, J=7.1 Hz, 3H).

Example 11

2-(1-(6-amino-9H-purin-9-yl)ethyl)-5-fluoro-3-(3-fluorophenyl)-4H-chromen-4-one 2-(1-(6-amino-9H-purin-9-yl)ethyl)-5-fluoro-3-(3-fluorophenyl)-4H-chromen-4-one: The title compound was obtained as pale green solid (0.047 g, 26%) by using a procedure that is similar to the one described for example 6 from adenine (0.116 g, 0.864 mmol), DMF (5 ml), potassium carbonate (0.140 g, 1.08 mmol) and intermediate 22 (0.150 g, 0.432 mmol) MP: 222-224° C. $^1$H-NMR (δ ppm, DMSO-d$_6$, 400 MHz): 8.44 (s, 1H), 8.03 (s, 1H), 7.82 (dt, J=8.4, 5.7 Hz, 1H), 7.51 (m, 2H), 7.27-7.16 (m, 6H), 5.64 (q, J=7.0 Hz, 1H), 1.88 (d, J=7.2 Hz, 3H).

Example 12

2-(1-(4-amino-3-(3-fluoro-4-isopropoxyphenyl)-1H-pyrazolo[3,4-d]pyrimidin-1-yl)ethyl)-5-fluoro-3-(4-fluorophenyl)-4H-chromen-4-one 22-(1-(4-amino-3-(3-fluoro-4-isopropoxyphenyl)-1H-pyrazolo[3,4-d]pyrimidin-1-yl)ethyl)-5-fluoro-3-(4-fluorophenyl)-4H-chromen-4-one: The title compound was obtained as pale brown solid (0.085 g, 38%) by using a procedure that is similar to the one described for example 6 from intermediate 13 (0.150 g, 0.522 mmol), DMF (2 ml), potassium carbonate (0.152 g, 1.10 mmol) and intermediate 31 (0.272 g, 0.0.744 mmol) MP: 218-221° C. $^1$H-NMR (δ ppm, CDCl$_3$, 400 MHz): 8.24 (s, 1H), 7.61 (dt, J=8.5, 5.5 Hz, 1H), 7.44 (dd, J=11.5, 2.0 Hz, 1H), 7.35 (d, J=9.0 Hz, 1H), 7.23 (m, 3H), 7.15 (t, J=8.4 Hz, 1H), 7.08 (m, 3H), 6.06 (q, J=7.1 Hz, 1H), 5.79 (s, 2H), 4.67 (quintet, J=6.1 Hz, 1H), 1.99 (d, J=7.1 Hz, 3H), 1.42 (d, J=7.1 Hz, 6H).

Example 13

2-(1-(4-amino-3-(3-fluoro-4-Isopropoxyphenyl)-1H-pyrazolo[3,4-d]pyrimidin-1-yl)ethyl)-5-fluoro-3-phenyl-4H-chromen-4-one 2-(1-(4-amino-3-(3-fluoro-4-isopropoxyphenyl)-1H-pyrazolo[3,4-d]pyrimidin-1-yl)ethyl)-5-fluoro-3-phenyl-4H-chromen-4-one: The title compound was obtained as off-white solid (0.060 g, 25%) by using a procedure that is similar to the one described for example 6 from intermediate 13 (0.150 g, 0.522 mmol), DMF (2 ml), potassium carbonate (0.152 g, 1.10 mmol) and intermediate 33 (0.291 g, 0.838 mmol) MP: 226-229° C. $^1$H-NMR (δ ppm, CDCl$_3$, 400 MHz): 8.22 (s, 1H), 7.60 (dt, J=8.5, 5.5 Hz, 1H), 7.44 (dd, J=11.5, 2.0 Hz, 1H), 7.36 (m, 4H), 7.23 (m, 3H), 7.14 (t, J=8.4 Hz, 1H), 7.04 (t, J=9.7 Hz, 1H), 6.06 (q, J=7.2 Hz, 1H), 5.52 (s, 2H), 4.64 (quintet, J=6.1 Hz, H), 1.98 (d, J=7.1 Hz, 3H), 1.42 (d, J=6.0 Hz, 6H).

Example 14

2-(1-(4-amino-3-(benzofuran-2-yl)-1H-pyrazolo[3,4-d]pyrimidin-1-yl)ethyl)-5-fluoro-3-(3-fluorophenyl)-4H-chromen-4-one 2-(1-(4-amino-3-(benzofuran-2-yl)-1H-pyrazolo[3,4-d]pyrimidin-1-yl)ethyl)-5-fluoro-3-(3-fluorophenyl)-4H-chromen-4-one: The title compound was obtained as off-white solid (0.026 g, 26%) by using a procedure that is similar to the one described for example 9 from intermediate 27 (0.100 g, 0.183 mmol), 1,2-dimethoxyethane (2 ml), water (1 ml), benzofuran-2-boronic acid (0.045 g, 0.275 mmol), sodium carbonate (0.058 g, 0.549 mmol) and bis (diphenylphosphino)ferrocene]dichloro palladium(II).CH$_2$Cl$_2$ (0.062 g, 0.073 mmol) MP: 238-241° C. $^1$H-NMR (δ ppm, CDCl$_3$, 400 MHz): 8.27 (s, 1H), 7.70 (d, J=8.4 Hz, 1H), 7.62-7.57 (m, 2H), 7.41 (s, 1H), 7.39 (m, 3H), 7.28 (m, 1H), 7.07-6.99 (m, 4H), 6.07 (q, J=8.1 Hz, 1H), 2.05 (d, J=8.3 Hz, 3H).

Example 15

2-(1-(9H-purin-6-ylamino)ethyl)-5-fluoro-3-(3-fluorophenyl)-4H-chromen-4-one 2-(1-(9H-purin-6-ylamino)ethyl)-5-fluoro-3-(3-fluorophenyl)-4H-chromen-one: To a solution of intermediate 36 (0.20 g, 0.663 mmol), tert-butanol (1.5 ml) N,N-diisopropylethylamine (0.23 ml, 1.32 mmol) and 6-chloropurine (0.102 g, 0.663 mmol) were added and heated to reflux for 48 h. The reaction mixture was concentrated, quenched with water, extracted with ethyl acetate, dried with sodium sulphate and concentrated. The crude product was purified by column chromatography with methanol:ethyl acetate to afford the title compound as brown solid (0.080 g, 30% yield). MP: 195-198° C. $^1$H-NMR (δ ppm, DMSO-d$_6$, 400 MHz): 12.96 (s, 1H), 8.17 (s, 1H), 8.09 (s, 1H), 7.21-6.94 (m, 51H), 6.71 (m, 2H), 5.64 (m, 1H), 1.52 (br s, 3H).

Example 16

2-(1-(4-amino-1H-pyrazolo[3,4-d]pyrimidin-1-yl)ethyl)-5-fluoro-3-(3-fluorophenyl)-4H-chromen-4-one 22-(1-(4-amino-1H-pyrazolo[3,4-d]pyrimidin-1-yl)ethyl)-5-fluoro-3-(3-fluorophenyl)-4H-chromen-4-one: The title compound was obtained as brown solid (0.030 g, 25%) by using a procedure that is similar to the one described for example 6 from 1H-pyrazolo[3,4-d]pyrimidin-4-amine (0.077 g, 0.576 mmol), DMF (1 ml), potassium carbonate (0.099 g, 0.720 mmol) and intermediate 22 (0.100 g, 0.288 mmol). MP: 267-269° C. $^1$H-NMR (δ ppm, CDCl$_3$, 400 MHz): 8.25 (s, 1H), 7.92 (s, 1H), 7.61 (dt, J=8.4, 5.4 Hz, 1H), 7.32 (m, 2H), 7.06 (m, 3H), 6.92 (d, J=9.7 Hz, 1H), 6.02 (q, J=7.1 Hz, 1H), 5.41 (s, 2H), 1.96 (d, J=7.1 Hz, 3H).

Example 16a and 16b (+)-22-(1-(4-amino-1H-pyrazolo[3,4-d]pyrimidin-1-yl)ethyl)-5-fluoro-3-(3-fluorophenyl)-4H-chromen-4-one and (−)-2-(1-(4-amino-1H-pyrazolo[3,4-d]pyrimidin-1-yl)ethyl)-5-fluoro-3-(3-fluorophenyl)-4H-chromen-4-one The two enantiomerically pure isomers were separated by preparative SFC conditions from example 16 (0.300 g) on a CHIRALPAK AD-H column (250×4.6 mm; 5 μm) using methanol: CO$_2$ (30:70) as the mobile phase at a flow rate of 3.0 ml/min.
Example 16a: Off-white solid (0.145 g). e.e. 98.07%. Rt: 2.49 min. $[\alpha]^{25}_D$ 90.52 (c=1, CHCl$_3$). MP: 197-200° C. Mass: 419.8 (M$^+$).
Example 16b: Off-white solid (0.150 g). e.e. 98.8%. Rt: 3.56 min. $[\alpha]^{25}_D$ −73.03 (c=1, CHCl$_3$). MP: 198-201° C. Mass: 419.8 (M+).

Example 17

2-(1-(4-amino-3-(4-(difluoromethoxy)-3-fluorophenyl)-1H-pyrazolo[3,4-d]pyrimidin-1-yl)ethyl)-5-fluoro-3-(3-fluorophenyl)-4H-chromen-4-one 2-(1-(4-amino-3-(4-(difluoromethoxy)-3-fluorophenyl)-1H-pyrazolo[3,4-d]pyrimidin-1-yl)ethyl)-5-fluoro-3-(3- fluorophenyl)-4H-chromen-4-one: The title compound was obtained as pale brown solid (0.042 g, 27%) by using a procedure that is similar to the one described for example 6 from intermediate 39 (0.081 g, 0.273 mmol), DMF (2 ml), potassium carbonate (0.075 g, 0.546 mmol) and intermediate 22 (0.100 g, 0.0.273 mmol) MP: 230-233° C. $^1$H-NMR (δ ppm, CDCl$_3$, 400 MHz): 8.26 (s, 1H), 7.62 (dt, J=8.4, 5.4 Hz, 1H), 7.56 (dd, J=10.3, 1.3 Hz, 1H), 7.47 (m, 2H), 7.32 (d, J=6.5 Hz, 1H), 7.27 (m, 1H), 7.06 (m, 3H), 6.91 (d, J=9.1 Hz, 1H), 6.81 (t, J=72.9 Hz, 1H), 6.63 (s, 2H), 6.07 (q, J=7.2 Hz, 1H), 1.99 (d, J=7.1 Hz, 3H).

Example 18

2-(1-(4-amino-3-(3-fluoro-4-isopropoxyphenyl)-1H-pyrazolo[3,4-d]pyrimidin-1-yl)ethyl)-5-fluoro-3-(1H-pyrazol-4-yl)-4H-chromen-4-one 2-(1-(4-amino-3-(3-fluoro-4-isopropoxyphenyl)-1H-pyrazolo[3,4-d]pyrimidin-1-yl)ethyl)-5-fluoro-3-(1H-pyrazol-4-yl)-4H-chromen-4-one: The title compound was obtained as brown solid (0.020 g, 20%) by using a procedure that is similar to the one described for example 9 from intermediate 29 (0.100 g, 0.188 mmol), 1,2-dimethoxyethane (2 ml), water (1 ml), 1-Boc-pyrazole-4-boronic acid (0.098 g, 0.282 mmol), sodium carbonate (0.059 g, 0.565 mmol) and bis(diphenylphosphino)ferrocene]dichloro palladium(II).CH$_2$Cl$_2$ (0.030 g, 0.037 mmol). MP: 181-184° C. $^1$H-NMR (δ ppm, CDCl$_3$, 400 MHz): 8.34 (s, 1H), 7.93 (s, 2H), 7.57 (dt, J=8.4, 5.5 Hz, 1H), 7.47 (dd, J=11.5, 2.0 Hz, 1H), 7.40 (d, J=8.4 Hz, 1H), 7.24 (m, 1H), 7.15 (t, J=8.4 Hz, 1H), 7.04 (dd, J=10.2, 8.9 Hz, 1H), 6.36 (q, J=7.1 Hz, 1H), 5.51 (s, 2H), 4.65 (q, J=6.0 Hz, 1H), 2.03 (d, J=7.1 Hz, 3H), 1.42 (d, J=6.0 Hz, 6H).

Example 19

2-(1-(4-amino-3-(3-fluoro-4-(tetrahydro-2H-pyran-4-yloxy)phenyl)-1H-pyrazolo[3,4-d]pyrimidin-1-yl)ethyl)-1-fluoro-3-(3-fluorophenyl)-4H-chromen-4-one 2-(1-(4-amino-3-(3-fluoro-4-(tetrahydro-2H-pyran-4-yloxy)phenyl)-1H-pyrazolo[3,4-d]pyrimidin-1-yl)ethyl)-5-fluoro-3-(3-fluorophenyl)-4H-chromen-4-one: The title compound was obtained as brown solid (0.022 g, 22%) by using a procedure that is similar to the one described for example 9 from intermediate 27 (0.100 g, 0.183 mmol), 1,2-dimethoxyethane (2 ml), water (1 ml), intermediate 41 (0.070 g, 0.276 mmol), sodium carbonate (0.038 g, 0.366 mmol) and bis(diphenylphosphino)ferrocene]dichloro palladium(II).CH$_2$Cl$_2$ (0.030 g, 0.036 mmol). MP: 234-237° C. $^1$H-NMR (δ ppm, CDCl$_3$, 400 MHz): 8.24 (s, 1H), 7.62 (dt, J=8.4, 5.5 Hz, 1H), 7.46 (dd, J=11.4, 1.9 Hz, 1H), 7.37 (d, J=8.3 Hz, 1H), 7.32 (m, 2H), 7.17 (t, J=8.3 Hz, 1H), 7.06-6.96 (m, 3H), 6.90 (d, J=8.8 Hz, 1H), 6.08 (q, J=7.0 Hz, 1H), 5.44 (s, 2H), 4.58 (quintet, J=3.9 Hz, 1H), 4.05 (m, 2H), 3.62 (m, 2H), 2.09 (m, 2H), 1.99 (d, J=7.1 Hz, 3H), 1.91 (m, 2H).

Example 20

2-(1-(4-amino-3-(3-Isopropyl-1H-indazol-6-yl)-1H-pyrazolo[3,4-d]pyrimidin-1-yl)ethyl)-5-fluoro-3-(3-fluorophenyl)-4H-chromen-4-one 2-(1-(4-amino-3-(3-isopropyl-1H-indazol-6-yl)-1H-pyrazolo[3,4-d]pyrimidin-1-yl)ethyl)-5-fluoro-3-(3-fluorophenyl)-4H-chromen-4-one: The title compound was obtained as brown solid (0.026 g, 13%) by using a procedure that is similar to the one described for example 9 from intermediate 27 (0.100 g, 0.183 mmol), 1,2-dimethoxyethane (2 ml), water (1 ml), intermediate 46 (0.140 g, 0.276 mmol), sodium carbonate (0.038 g, 0.366 mmol) and bis(diphenylphosphino)ferrocene]dichloro palladium(II).CH$_2$Cl$_2$ (0.030 g, 0.036 mmol). MP: 249-252° C. $^1$H-NMR (δ ppm, CDCl$_3$, 400 MHz): 8.25 (s, 1H), 7.94 (d, J=8.3 Hz, 1H), 7.74 (s, 1H), 7.61 (dt, J=8.4, 5.4 Hz, 1H), 7.44 (dd, J=8.2, 1.2 Hz, 1H), 7.30 (m, 2H), 7.06-6.95 (m, 3H), 6.92 (d, J=8.0 Hz, 1H), 6.10 (q, J=7.1 Hz, 1H), 5.47 (s, 2H), 3.48 (q, J=7.1 Hz, 1H), 2.02 (d, J=7.1 Hz, 3H), 1.50 (d, J=7.1 Hz, 6H).

Example 21

2-(1-(4-amino-3-(3-fluoro-4-(piperidin-4-yloxy)phenyl)-1H-pyrazolo[3,4-d]pyrimidin-1-yl)ethyl)-5-fluoro-3-(3-fluorophenyl)-4H-chromen-4-one 2-(1-(4-amino-3-(3-fluoro-4-(piperidin-4-yloxy)phenyl)-1H-pyrazolo[3,4-d]pyrimidin-1-yl)ethyl)-5-fluoro-3-(3-fluorophenyl)-4H-chromen-4-one: The title compound was obtained as brown solid (0.030 g, 13%) by using a procedure that is similar to the one described for example 9 from intermediate 27 (0.100 g, 0.183 mmol), 1,2-dimethoxyethane (2 ml), water (1 ml), intermediate 48 (0.150 g, 0.276 mmol), sodium carbonate (0.038 g, 0.366 mmol) and bis(diphenylphosphino)ferrocene]dichloro palladium(II).CH$_2$Cl$_2$ (0.030 g, 0.036 mmol). MP: 280-283° C. $^1$H-NMR (δ ppm, DMSO-d$_6$, 400 MHz): 8.06 (s, 1H), 7.83 (dt, J=8.4, 5.7 Hz, 1H), 7.49 (d, J=8.5 Hz, 1H), 7.41 (dd, J=12.6, 1.5 Hz, 1H), 7.34 (m, 4H), 7.07 (dt, J=8.9, 2.6 Hz, 1H), 6.92 (m, 2H), 5.96 (q, J=7.0 Hz, 1H), 4.50 (m, 1H), 3.40 (m, 1H), 2.99 (m, 2H), 2.62 (m, 2H), 1.97 (m, 2H), 1.87 (d, J=7.0 Hz, 3H), 1.54 (m, 2H).

Example 22

2-(1-(4-amino-3-(3-fluoro-4-(2-hydroxyethylamino)phenyl)-1H-pyrazolo[3,4-d]pyrimidin-1-yl)ethyl)-5-fluoro-3-(3-fluorophenyl)-4H-chromen-4-one 2-(1-(4-amino-3-(3-fluoro-4-(2-hydroxyethylamino)phenyl)-1H-pyrazolo[3,4-d]pyrimidin-1-yl)ethyl)-5-fluoro-3-(3-fluorophenyl)-4H-chromen-4-one: The title compound was obtained as brown solid (0.018 g, 9%) by using a procedure that is similar to the one described for example 9 from intermediate 27 (0.150 g, 0.274 mmol), 1,2-dimethoxyethane (3 ml), water (1.5 ml), intermediate 52 (0.167 g, 0.411 mmol), sodium carbonate (0.058 g, 0.549 mmol) and bis(diphenylphosphino)ferrocene]dichloro palladium (II).CH$_2$Cl$_2$ (0.045 g, 0.054 mmol). MP: 154-157° C. $^1$H-NMR (δ ppm, CDCl$_3$, 400 MHz): 8.20 (s, 1H), 7.61 (dt, J=8.4, 5.4 Hz, 1H), 7.34-7.28 (m, 4H), 7.06-6.96 (m, 3H), 6.91 (d, J=9.0 Hz, 1H), 6.87 (t, J=8.3 Hz, 1H), 6.06 (q, J=7.1 Hz, 1H), 5.62 (s, 2H), 4.51 (s, 1H), 3.92 (t, J=5.1 Hz, 2H), 3.42 (t, J=5.2 Hz, 2H), 2.09 (s, 1H), 1.98 (d, J=7.1 Hz, 3H).

Example 23

2-(1-(4-amino-3-(3-fluoro-4-(isopropylamino)phenyl)-1H-pyrazolo[3,4-d]pyrimidin-1-yl)ethyl)-5-fluoro-3-(3-fluorophenyl)-4H-chromen-4-one 2-(1-(4-amino-3-(3-fluoro-4-(isopropylamino)phenyl)-1H-pyrazolo[3,4-d]pyrimidin-1-yl)ethyl)-5-fluoro-3-(3- fluorophenyl)-4H-chromen-4-one: The title compound was obtained as brown solid (0.065 g, 25%) by using a procedure that is similar to the one described for example 9 from intermediate 27 (0.250 g, 0.457 mmol), 1,2-dimethoxyethane (4 ml), water (1 ml), intermediate 56 (0.192 g, 0.686 mmol), sodium carbonate (0.097 g, 0.915 mmol) and bis(diphenylphosphino)ferrocene]dichloro palladium(II).CH$_2$Cl$_2$ (0.074 g, 0.091 mmol). MP: 224-226° C. $^1$H-NMR (δ ppm, DMSO-d$_6$, 400 MHz): 8.04 (s, 1H), 7.83 (dt, J=8.4, 5.6 Hz, 1H), 7.49 (d, J=8.6 Hz, 1H), 7.28-7.21 (m, 4H), 7.06 (dt, J=8.4, 1.8 Hz, 1H), 6.91-6.82 (m, 3H), 5.95 (q, J=6.7 Hz, 1H), 5.37 (d, J=6.6 Hz, 1H), 3.72 (m, 1H), 1.86 (d, J=7.0 Hz, 3H), 1.19 (d, J=6.2 Hz, 6H).

Example 24

2-(1-(4-amino-3-(4-(dimethylamino)-3-fluorophenyl)-1H-pyrazolo[3,4-d]pyrimidin-1-yl)ethyl)-5-fluoro-3-(3-fluorophenyl)-4H-chromen-4-one 2-(1-(4-amino-3-(4-(dimethylamino)-3-fluorophenyl)-1H-pyrazolo[3,4-d]pyrimidin-1-yl)ethyl)-5-fluoro-3-(3-fluorophenyl)-4H-chromen-4-one: The title compound was obtained as off-white solid (0.070 g, 28%) by using a procedure that is similar to the one described for example 9 from intermediate 27 (0.250 g, 0.457 mmol), 1,2-dimethoxyethane (4 ml), water (1 ml), intermediate 60 (0.182 g, 0.686 mmol), sodium carbonate (0.097 g, 0.915 mmol) and bis(diphenylphosphino)ferrocene]dichloro palladium(II).CH$_2$Cl$_2$ (0.074 g, 0.091 mmol). MP: 252-254° C. $^1$H-NMR NMR (δ ppm, DMSO-d$_6$, 400 MHz): 8.06 (s, 1H), 7.83 (dt, J=8.5, 5.7 Hz, 1H), 7.49 (d, J=8.7 Hz, 1H), 7.32-7.24 (m, 4H), 7.09 (m, 2H), 6.88 (m, 2H), 5.95 (q, J=7.0 Hz, 1H), 2.85 (s, 6H), 1.87 (d, J=7.0 Hz, 3H).

Example 25

2-(1-(4-amino-3-(3-fluoro-4-morpholinophenyl)-1H-pyrazolo[3,4-d]pyrimidin-1-yl)ethyl)-5-fluoro-3-(3-fluorophenyl)-4H-chromen-4-one 2-(1-(4-amino-3-(3-fluoro-4-morpholinophenyl)-1H-pyrazolo[3,4-d]pyrimidin-1-yl)ethyl)-5-fluoro-3-(3-fluorophenyl)-4H-chromen-4-one: The title compound was obtained as pale brown solid (0.055 g, 33%) by using a procedure that is similar to the one described for example 9 from intermediate 27 (0.150 g, 0.274 mmol), 1,2-dimethoxyethane (3 ml), water (1.5 ml), intermediate 61 (0.127 g, 0.411 mmol), sodium carbonate (0.058 g, 0.549 mmol) and bis(diphenylphosphino)ferrocene]dichloro palladium(II).CH$_2$Cl$_2$ (0.045 g, 0.054 mmol). MP: 270-272° C. $^1$H-NMR NMR (δ ppm, CDCl$_3$, 400 MHz): 8.24 (s, 1H), 7.59 (dt, J=8.4, 5.4 Hz, 1H), 7.40 (m, 2H), 7.27 (m, 2H), 7.09-6.86 (m, 5H), 6.06 (q, J=7.1 Hz, 1H), 5.43 (s, 2H), 3.91 (t, J=4.6 Hz, 4H), 3.48 (t, J=4.7 Hz, 4H), 1.99 (d, J=7.1 Hz, 3H).

Example 26

2-(1-(4-amino-3-(2-methyl-1H-benzo[d]imidazol-5-yl)-1H-pyrazolo[3,4-d]pyrimidin-1-yl)ethyl)-5-fluoro-3-(3-fluorophenyl)-4H-chromen-4-one 2-(1-(4-amino-3-(2-methyl-1H-benzo[d]imidazol-5-yl)-1H-pyrazolo[3,4-d]pyrimidin-1-yl)ethyl)-5-fluoro-3-(3-fluorophenyl)-4H-chromen-4-one: The title compound was obtained as pale brown solid (0.032 g, 13%) by using a procedure that is similar to the one described for example 9 from intermediate 27 (0.250 g, 0.457 mmol), 1,2-dimethoxyethane (4 ml), water (1 ml), tert-butyl 2-methyl-6-(4,4,5,5-tetramethyl-1,3,2-dioxaborolan-2-yl)-1H-benzo[d]imidazole-1-carboxylate (0.246 g, 0.686 mmol), sodium carbonate (0.097 g, 0.915 mmol) and bis(diphenylphosphino)ferrocene]dichloro palladium(II).CH$_2$Cl$_2$ (0.074 g, 0.091 mmol). MP: 236-238° C. $^1$H-NMR NMR (δ ppm, CDCl$_3$, 400 MHz): 8.25 (s, 1H), 7.81 (br s, 1H), 7.66 (m, 1H), 7.62 (dt, J=8.4, 5.4 Hz, 1H), 7.52 (dd, J=8.2, 1.6 Hz, 1H), 7.30 (m, 2H), 7.06-6.95 (m, 3H), 6.92 (d, J=9.3 Hz, 1H), 6.10 (q, J=6.9 Hz, 1H), 5.71 (s, 2H), 2.67 (s, 3H), 2.01 (d, J=7.2 Hz, 3H).

Example 27

2-(1-(4-amino-3-(3-fluoro-4-(4-methylpiperazin-1-yl)phenyl)-1H-pyrazolo[3,4-d]pyrimidin-1-yl)ethyl)-5-fluoro-3-(3-fluorophenyl)-4H-chromen-4-one 2-(1-(4-amino-3-(3-fluoro-4-(4-methylpiperazin-1-yl)phenyl)-1H-pyrazolo[3,4-d]pyrimidin-1-yl)ethyl)-5-fluoro-3-(3-fluorophenyl)-4H-chromen-4-one: The title compound was obtained as pale brown solid (0.080 g, 20%) by using a procedure that is similar to the one described for example 9 from intermediate 27 (0.300 g, 0.549 mmol), 1,2-dimethoxyethane (5 ml), water (2.5 ml), intermediate 63 (0.260 g, 0.604 mmol), sodium carbonate (0.116 g, 1.09 mmol) and tetrakistriphenylphosphine palladium(0) (0.032 g, 0.027 mmol). MP: 246-249° C. $^1$H-NMR NMR (δ ppm, CDCl$_3$, 400 MHz): 8.23 (s, 1H), 7.61 (dt, J=8.4, 5.4 Hz, 1H), 7.38 (m, 2H), 7.29 (m, 2H), 7.08-6.96 (m, 4H), 6.91 (d, J=9.2 Hz, 1H), 6.07 (q, J=7.2 Hz, 1H), 5.51 (s, 2H), 3.22 (t, J=4.6 Hz, 4H), 2.67 (t, J=4.6 Hz, 4H), 2.37 (s, 3H), 1.98 (d, J=7.2 Hz, 3H).

Example 28

2-(1-(4-(dimethylamino)-1H-pyrazolo[3,4-d]pyrimidin-1-yl)ethyl)-5-fluoro-3-(3-fluorophenyl)-4H-chromen-4-one 2-(1-(4-(dimethylamino)-1H-pyrazolo[3,4-d]pyrimidin-1-yl)ethyl)-5-fluoro-3-(3-fluorophenyl)-4H-chromen-4-one: The title compound was obtained as pale brown solid (0.040 g, 18%) by using a procedure that is similar to the one described for example 6 from N,N-dimethyl-1H-pyrazolo[3,4-d]pyrimidin-4-amine (0.080 g, 0.49 mmol for preparation see J. Amer. Chem. Soc. 1956, 784-790), DMF (10 ml), cesium carbonate (0.319 g, 0.546 mmol) and intermediate 22 (0.179 g, 0.0.490 mmol) MP: 200-202° C. $^1$H-NMR NMR (δ ppm, CDCl$_3$, 400 MHz): 8.20 (s, 1H), 7.95 (s, 1H), 7.60 (dt, J=8.4, 5.5 Hz, 1H), 7.31 (m, 2H), 7.05 (m, 3H), 6.86 (d, J=9.2 Hz, 1H), 6.02 (q, J=7.1 Hz, 1H), 3.36 (s, 6H), 1.93 (d, J=7.1 Hz, 3H).

Example 29

2-(1-(4-amino-1H-pyrazolo[3,4-d]pyrimidin-1-yl)ethyl)-5-fluoro-3-phenyl-4H-chromen-4-one 2-(1-(4-amino-1H-pyrazolo[3,4-d]pyrimidin-1-yl)ethyl)-5-fluoro-3-phenyl-4H-chromen-4-one: The title compound was obtained as pale green solid (0.030 g, 25%) by using a procedure that is similar to the one described for example 6 from 1H-pyrazolo[3,4-d]pyrimidin-4-amine (0.061 g, 0.455 mmol), DMF (1 ml), cesium carbonate (0.148 g, 0.455 mmol) and intermediate 33 (0.100 g, 0.0.303 mmol). MP: 223-226° C. $^1$H-NMR NMR (δ ppm, CDCl$_3$, 400 MHz): 8.23 (s, 1H), 7.92 (s, 1H), 7.57 (dt, J=8.4, 5.4 Hz, 1H), 7.34 (m, 3H), 7.23 (s, 1H), 7.19 (m, 2H), 7.04 (dt, J=8.2, 0.9 Hz, 1H), 6.01 (q, J=7.1 Hz, 1H), 5.40 (s, 2H), 1.95 (d, J=7.1 Hz, 3H).

Example 30

2-(1-(4-amino-1H-pyrazolo[3,4-d]pyrimidin-1-yl) ethyl)-5-fluoro-3-(4-fluorophenyl)-4H-chromen-4-one 2-(1-(4-amino-1H-pyrazolo[3,4-d]pyrimidin-1-yl)ethyl)-5-fluoro-3-(4-fluorophenyl)-4H-chromen-4-one: The title compound was obtained as pale green solid (0.040 g, 34%) by using a procedure that is similar to the one described for example 6 from 1H-pyrazolo[3,4-d]pyrimidin-4-amino (0.058 g, 0.432 mmol), DMF (1 ml), cesium carbonate (0.140 g, 0.432 mmol) and intermediate 31 (0.100 g, 0.0.288 mmol). MP: 242-245° C. $^1$H-NMR (δ ppm, CDCl$_3$, 400 MHz): 8.26 (s, 1H), 7.92 (s, 1H), 7.60 (dt, J=8.4, 5.4 Hz, 1H), 7.25 (m, 3H), 7.07-7.00 (m, 3H), 6.01 (q, J=7.2 Hz, 1H), 5.45 (s, 2H), 1.96 (d, J=7.1 Hz, 3H).

Example 31

2-(1-(4-amino-3-(4-(difluoromethoxy)-3-fluorophenyl)-1H-pyrazolo[3,4-d]pyrimidin-1-yl)ethyl)-5-fluoro-3-(4-fluorophenyl)-4H-chromen-4-one 2-(1-(4-amino-3-(4-(difluoromethoxy)-3-fluorophenyl)-1H-pyrazolo[3,4-d]pyrimidin-1-yl)ethyl)-5-fluoro-3-(4-fluorophenyl)-4H-chromen-4-one: The title compound was obtained as off-white solid (0.053 g, 33%) by using a procedure that is similar to the one described for example 6 from intermediate 39 (0.081 g, 0.273 mmol), DMF (2 ml), potassium carbonate (0.075 g, 0.546 mmol) and intermediate 31 (0.100 g, 0.0.273 mmol) MP: 233-235° C. $^1$H-NMR (δ ppm, CDCl$_3$, 400 MHz): 8.28 (s, 1H), 7.61-7.55 (m, 2H), 7.47 (m, 2H), 7.25 (m, 3H), 7.08 (m, 3H), 6.82 (t, J=72.9 Hz, 1H), 6.01 (q, J=7.1 Hz, 1H), 5.42 (s, 2H), 1.99 (d, J=7.2 Hz, 3H).

Example 32

2-(1-(4-amino-3-(4-(difluoromethoxy)-3-fluorophenyl)-1H-pyrazolo[3,4-d]pyrimidin-1-yl)ethyl)-5-fluoro-3-phenyl-4H-chromen-4-one 2-(1-(4-amino-3-(4-(difluoromethoxy)-3-fluorophenyl)-1H-pyrazolo[3,4-d]pyrimidin-1-yl)ethyl)-5-fluoro-3-phenyl-4H-chromen-4-one: The title compound was obtained as off-white solid (0.021 g, 33%) by using a procedure that is similar to the one described for example 6 from intermediate 39 (0.090 g, 0.303 mmol), DMF (2 ml), potassium carbonate (0.084 g, 0.607 mmol) and intermediate 33 (0.100 g, 0.0.303 mmol) MP: 247-250° C. $^1$H-NMR (δ ppm, CDCl$_3$, 400 MHz): 8.22 (s, 1H), 7.69-7.20 (m, 10H), 7.05 (dd, J=9.5, 8.5 Hz, 1H), 6.81 (t, J=72.9 Hz, 1H), 6.08 (q, J=7.1 Hz, 1H), 5.43 (s, 2H), 1.99 (d, J=7.1 Hz, 3H).

Example 33

2-(1-(4-amino-3-methyl-1H-pyrazolo[3,4-d]pyrimidin-1-yl)ethyl)-5-fluoro-3-(3-fluorophenyl)-4H-chromen-4-one 2-(1-(4-amino-3-methyl-1H-pyrazolo[3,4-d]pyrimidin-1-yl)ethyl)-5-fluoro-3-(3-fluorophenyl)-4H-chromen-4-one: The title compound was obtained as off-white solid (0.025 g, 21%) by using a procedure that is similar to the one described for example 6 from 3-methyl-1H-pyrazolo[3,4-d]pyrimidin-4-amine (0.043 g, 0.288 mmol for preparation see J. Org. Chem. 1956, 21, 1240-1256), DMF (2 ml), potassium carbonate (0.079 g, 0.576 mmol) and intermediate 22 (0.100 g, 0.0.288 mmol). MP: 240-242° C. $^1$H-NMR (δ ppm, CDCl$_3$, 400 MHz): δ 8.16 (s, 1H), 7.59 (dt, J=8.4, 3.4 Hz, 1H), 7.29 (m, 2H), 7.06-6.84 (m, 4H), 5.94 (q, J=7.1 Hz, 1H), 5.42 (s, 2H), 2.59 (s, 3H), 1.92 (d, J=7.1 Hz, 3H).

Example 34

2-(1-(4-amino-3-ethyl-1H-pyrazolo[3,4-d]pyrimidin-1-yl)ethyl)-5-fluoro-3-(3-fluorophenyl)-4H-chromen-4-one 2-(1-(4-amino-3-ethyl-1H-pyrazolo[3,4-d]pyrimidin-1-yl)ethyl)-5-fluoro-3-(3-fluorophenyl)-4H-chromen-4-one: The title compound was obtained as off-white solid (0.038 g, 30%) by using a procedure that is similar to the one described for example 6 from intermediate 66 (0.048 g, 0.288 mmol), DMF (2 ml), potassium carbonate (0.079 g, 0.576 mmol) and intermediate 22 (0.100 g, 0.0.288 mmol) MP: 196-198° C. H-NMR (δ ppm, CDCl$_3$, 400 MHz): 8.18 (s, 1H), 7.60 (dt, J=8.4, 3.0 Hz, 1H), 7.29 (m, 2H), 7.05-6.78 (m, 4H), 5.94 (q, J=7.2 Hz, 1H), 5.31 (s, 2H), 2.95 (q, J=6.6 Hz, 2H), 1.93 (d, J=7.2 Hz, 3H), 1.40 (d, J=76 Hz, 3H).

Example 35

2-(1-(4-amino-3-isopropyl-1H-pyrazolo[3,4-d]pyrimidin-1-yl)ethyl)-5-fluoro-3-(3-fluorophenyl)-4H-chromen-4-one 2-(1-(4-amino-3-isopropyl-1H-pyrazolo[3,4-d]pyrimidin-1-yl)ethyl)-5-fluoro-3-(3-fluoro phenyl)-4H-chromen-4-one: The title compound was obtained as off-white solid (0.035 g, 18%) by using a procedure that is similar to the one described for example 6 from 3-isopropyl-1H-pyrazolo[3,4-d]pyrimidin-4-amine (0.079 g, 0.432 mmol for preparation see J. Amer. Chem. Soc. 2002,124, 12118), DMF (3 ml), potassium carbonate (0.119 g, 0.864 mmol) and intermediate 22 (0.150 g, 0.0.432 mmol) MP: 212-214° C. $^1$H-NMR (δ ppm, CDCl$_3$, 400 MHz): δ 8.19 (s, 1H), 7.59 (dt, J=8.5, 5.4 Hz, 1H), 7.32 (m, 2H), 7.03-6.92 (m, 4H), 5.93 (q, J=7.5 Hz, 1H), 5.34 (s, 2H), 3.20 (m, 1H), 1.93 (d, J=7.2 Hz, 3H), 1.43 (d, J=6.9 Hz, 3H), 1.42 (d, J=6.8 Hz, 3H).

Example 36

2-(1-(4-amino-3-(benzo[b]thiophen-2-yl)-1H-pyrazolo[3,4-d]pyrimidin-1-yl)ethyl)-5-fluoro-3-(3-fluorophenyl)-4H-chromen-4-one 2-(1-(4-amino-3-(benzo[b]thiophen-2-yl)-1H-pyrazolo[3,4-d]pyrimidin-1-yl)ethyl)-5-fluoro-3-(3-fluorophenyl)-4H-chromen-4-one: The title compound was obtained as brown solid (0.070 g, 15%) by using a procedure that is similar to the one described for example 6 from intermediate 67 (0.294 g, 1.10 mmol), DMF (3 ml), cesium carbonate (0.358 g, 1.10 mmol) and intermediate 22 (0.300 g, 0.0.864 mmol). MP: 248-250° C. $^1$H-NMR (δ ppm, CDCl$_3$, 400 MHz): 8.28 (s, 1H), 7.91 (m, 2H), 7.62 (s, 1H), 7.60 (dt, J=8.0, 3.0 Hz, 1H), 7.44 (m, 2H), 7.29 (m, 2H), 7.06 (m, 4H), 6.08 (q, J=7.1 Hz, 1H), 5.73 (s, 2H), 2.02 (d, J=7.1 Hz, 3H).

Example 37

2-(1-(4-amino-3-morpholino-1H-pyrazolo[3,4-d]pyrimidin-1-yl)ethyl)-5-fluoro-3-(3-fluorophenyl)-4H-chromen-4-one 2-(1-(4-amino-3-morpholino-1H-pyrazolo[3,4-d]pyrimidin-1-yl)ethyl)-5-fluoro-3-(3-fluorophenyl)-4H-chromen-4-one: The title compound was obtained as yellow solid (0.040 g, 18%) by using a procedure that is similar to the one described for example 6 from intermediate 70 (0.114 g, 0.518 mmol), DMF (2 ml), potassium carbonate (0.119 g, 0.864 mmol) and intermediate 22 (0.150 g, 0.0.432 mmol). MP: 171-173° C. $^1$H-NMR (δ ppm, CDCl$_3$, 400 MHz): 8.15 (s, 1H), 7.62 (dt, J=8.4, 5.6 Hz, 1H), 7.29-7.23 (m, 2H), 7.06-6.99 (m, 3H), 6.90 (d, J=9.4 Hz, 1H), 5.89 (d, J=7.2 Hz, 1H), 5.29 (s, 2H), 3.88 (t, J=4.6 Hz, 4H), 3.32 (t, J=4.6 Hz, 4H), 1.91 (d, J=7.2 Hz, 3H).

Example 38

2-(1-(4-amino-3-(dimethylamino)-1H-pyrazolo[3,4d]pyrimidin-1-yl)ethyl)-5-fluoro-3-(3-fluorophenyl)-4H-chromen-4-one 2-(1-(4-amino-3-(dimethylamino)-1H-pyrazolo[3,4-d]pyrimidin-1-yl)ethyl)-5-fluoro-3-(3-fluorophenyl)-4H-chromen-4-one: The title compound was obtained as brown solid (0.032 g, 14%) by using a procedure that is similar to the one described for example 6 from intermediate 73 (0.092 g, 0.518 mmol), DMF (2 ml), cesium carbonate (0.119 g, 0.432 mmol) and intermediate 22 (0.150 g, 0.0.432 mmol). MP: 169-171° C. $^1$H-NMR (δ ppm, CDCl$_3$, 400 MHz): 8.14 (s, 1H), 7.61 (dt, J=8.4, 5.4 Hz, 1H), 7.29 (m, 2H), 7.05 (m, 3H), 6.89 (d, J=8.9 Hz, 1H), 5.87 (q, J=7.0 Hz, 1H), 5.46 (s, 2H), 2.86 (s, 6H), 1.01 (d, J=7.1 Hz, 3H).

Example 39

2-(1-(4-amino-3-(piperidin-1-yl)-1H-pyrazolo[3,4-d]pyrimidin-1-yl)ethyl)-5-fluoro-3-(3-fluorophenyl)-4H-chromen-4-one 2-(1-(4-amino-3-(piperidin-1-yl)-1H-pyrazolo[3,4-d]pyrimidin-1-yl)ethyl)-5-fluoro-3-(3-fluorophenyl)-4H-chromen-4-one: The title compound was obtained as brown solid (0.014 g, 10%) by using a procedure that is similar to the one described for example 6 from intermediate 76 (0.063 g, 0.288 mmol), DMF (1 ml), cesium hydroxide (0.048 g, 0.288 mmol) and intermediate 22 (0.100 g, 0.0.288 mmol). MP: 160-162° C. $^1$H-NMR (δ ppm, CDCl$_3$, 400 MHz): 8.14 (s, 1H), 7.55 (dt, J=8.4, 5.5 Hz, 1H), 7.29 (m, 2H), 7.05 (m, 3H), 6.89 (d, J=8.9 Hz, 1H), 5.85 (q, J=7.1 Hz, 1H), 5.41 (s, 2H), 3.48 (t, J=7.1 Hz, 4H), 1.90 (d, J=7.1 Hz, 3H), 1.73-1.61 (m, 6H).

Example 40

2-(1-(4-amino-3-(6-isopropoxypyridin-3-yl)-1H-pyrazolo[3,4-d]pyrimidin-1-yl)ethyl)-5-fluoro-3-(3-fluorophenyl)-4H-chromen-4-one 2-(1-(4-amino-3-(6-isopropoxypyridin-3-yl)-1H-pyrazolo[3,4-d]pyrimidin-1-yl)ethyl)-5-fluoro-3-(3-fluorophenyl)-4H-chromen-4-one: The title compound was obtained as pale brown solid (0.028 g, 28%) by using a procedure that is similar to the one described for example 9 from intermediate 27 (0.100 g, 0.183 mmol), 1,2-dimethoxyethane (2 ml), water (1 ml), 2-isopropoxy-5-(4,4,5,5-tetramethyl-1,3,2-dioxaborolan-2-yl)pyridine (0.072 g, 0.274 mmol), sodium carbonate (0.038 g, 0.366 mmol) and (1,1'-Bis(diphenylphosphino)ferrocene]dichloro palladium(II).CH$_2$Cl$_2$ (0.029 g, 0.036 mmol). MP: 196-199° C. $^1$H-NMR NMR (δ ppm, CDCl$_3$, 400 MHz): 8.45 (d, J=2.3 Hz, 1H), 8.25 (s, 1H), 7.87 (dd, J=8.6, 2.5 Hz, 1H), 7.62 (dt, J=8.4, 5.5 Hz, 1H), 7.32 (m, 2H), 7.06 (m, 3H), 6.92 (d, J=9.2 Hz, 1H), 6.85 (d, J=8.6 Hz, 1H), 6.06 (q, J=7.1 Hz, 1H), 5.40 (quintet, J=6.3 Hz, 1H), 5.37 (s, 2H), 1.99 (d, J=7.1 Hz, 3H), 1.40 (d, J=6.2 Hz, 6H).

Example 41

2-(1-(4-amino-3-(methylthio)-1H-pyrazolo[3,4-d]pyrimidin-1-yl)ethyl)-5-fluoro-3-(3-fluorophenyl)-4H-chromen-4-one 2-(1-(4-amino-3-(methylthio)-1H-pyrazolo[3,4-d]pyrimidin-1-yl)ethyl)-5-fluoro-3-(3-fluorophenyl)-4H-chromen-4-one: The title compound was obtained as brown solid (0.030 g, 22%) by using a procedure that is similar to the one described for example 6 from 3-(methylthio)-1H-pyrazolo[3,4-d]pyrimidin-4-amine (0.078 g, 0.432 mmol for preparation see J. Het. Chem. 1990, 27, 775-783), DMF (2 ml), cesium carbonate (0.140 g, 0.432 mmol) and intermediate 22 (0.100 g, 0.228 mmol). MP: 102-105° C. $^1$H-NMR (δ ppm, CDCl$_3$, 400 MHz): 8.19 (s, 1H), 7.61 (dt, J=8.4, 5.4 Hz, 1H), 7.34 (m, 2H), 7.06 (m, 3H), 6.95 (d, J=9.5 Hz, 1H), 5.95 (q, J=7.1 Hz, 1H), 5.82 (s, 2H), 2.63 (s, 6H), 1.95 (d, J=7.1 Hz, 3H).

Example 42

2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one 4-methylbenzenesulfonate 2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one 4-methylbenzenesulfonate: To example 6 (0.100 g, 0.174 mmol) in isopropanol (4 ml), p-toluenesulphonic acid (0.037 g, 0.192 mmol) was added and refluxed for 1 h. The reaction mixture was concentrated, co-distilled with pet. ether and dried. To the residue water (3 ml) was added and stirred for 30 min. The solid was filtered, washed with pet. ether and dried under vacuum to afford the title compound as off-white solid (0.102 g, 78%). MP: 153-156° C. $^1$H-NMR (δ ppm, CDCl$_3$, 400 MHz): 8.15 (s, 1H), 7.80 (d, J=8.1 Hz, 2H), 7.64 (dt, J=8.4, 5.4 Hz, 1H), 7.42 (dd, J=11.2, 2.0 Hz, 1H), 7.34 (m, 3H), 7.22 (d, J=8.0 Hz, 2H), 7.15 (t, J=8.4 Hz, 1H), 7.08-6.99 (m, 3H), 6.87 (m, 1H), 6.07 (q, J=7.1 Hz, 1H), 4.67 (quintet, J=6.1 Hz, 1H), 2.37 (s, 3H), 2.01 (d, J=7.2 Hz, 3H), 1.43 (d, J=6.1 Hz, 6H).

Example 43

2-(1-(4-amino-3-(3-methyl-1H-indazol-6-yl)-1H-pyrazolo[3,4-d]pyrimidin-1-yl)ethyl)-5-fluoro-3-(3-fluorophenyl)-4H-chromen-4-one 4-methylbenzenesulfonate 2-(1-(4-amino-3-(3-methyl-1H-indazol-6-yl)-1H-pyrazolo[3,4-d]pyrimidin-1-yl)ethyl)-5-fluoro-3-(3-fluorophenyl)-4H-chromen-4-one 4-methylbenzenesulfonate: The title compound was obtained as off-white solid (0.120 g, 84%) by using a procedure that is similar to the one described for example 43 from example 9 (0.10 g, 0.200 mmol), isopropanol (4 ml) and p-toluenesulphonic acid (0.042 g, 0.220 mmol). MP: 172-175° C. 86H-NMR (δ ppm, CDCl$_3$, 400 MHz): 10.15 (s, 1H), 8.08 (s, 1H), 7.78 (d, J=7.7 Hz, 1H), 7.76 (s, 1H), 7.73 (d, J=8.1 Hz, 2H), 7.61 (dt, J=8.2, 3.0 Hz, 1H), 7.38 (m, 3H), 7.27 (m, 1H), 7.11-6.88 (m, 7H), 6.08 (q, J=6.9 Hz, 1H), 2.53 (s, 3H), 2.28 (s, 3H), 2.04 (d, J=7.2 Hz, 3H).

Example 44

2-(1-(4-amino-3-(4-(1-benzhydrylazetidin-3-yloxy)-3-fluorophenyl)-1H-pyrazolo[3,4-d]pyrimidin-1-yl)ethyl)-1-fluoro-3-(3-fluorophenyl)-4H-chromen-4-one 2-(1-(4-amino-3-(4-(I-benzhydrylazetidin-3-yloxy)-3-fluorophenyl)-1H-pyrazolo[3,4-d]pyrimidin-1-yl)ethyl)-5-fluoro-3-(3-fluorophenyl)-4H-chromen-4-one: The title compound was obtained as off-white solid (0.035 g, 13%) by using a procedure that is similar to the one described for example 9 from intermediate 27 (0.200 g, 0.366 mmol), 1,2-dimethoxyethane (3 ml), water (1.5 ml), intermediate 81 (0.252 g, 0.550 mmol), sodium carbonate (0.116 g, 1.10 mmol) and [1,1'-Bis(diphenylphosphino)ferrocene]dichloro palladium(II).CH$_2$Cl$_2$ (0.060 g, 0.073 mmol). MP: 211-214° C. 8 $^1$H-NMR (δ ppm, CDCl$_3$, 400 MHz): 8.23 (s, 1H), 7.59 (dt, J=8.4, 5.4 Hz, 1H), 7.44 (m, 5H), 7.29-7.18 (m, 9H), 7.05 (m, 3H), 6.90 (m, 1H), 6.86 (t, J=8.4 Hz, 1H), 6.04 (q, J=7.2 Hz, 1H), 5.35 (s, 2H), 4.91 (quintet, J=4.7 Hz, 1H), 4.47 (s, 1H), 3.78 (m, 2H), 3.23 (m, 2H), 1.97 (d, J=7.2 Hz, 3H).

Example 45

2-(1-(4-amino-3-(3-fluoro-4-(trifluoromethoxy)phenyl)-1H-pyrazolo[3,4-d]pyrimidin-1-yl)ethyl)-5-fluoro-3-(3-fluorophenyl)-4H-chromen-4-one 2-(1-(4-amino-3-(3-fluoro-4-(trifluoromethoxy)phenyl)-1H-pyrazolo[3,4-d]pyrimidin-1-yl)ethyl)-5-fluoro-3-(3-fluorophenyl)-4H-chromen-4-one: The title compound was obtained as off-white solid (0.043 g, 19%) by using a procedure that is similar to the one described for example 9 from intermediate 27 (0.200 g, 0.366 mmol), 1,2-dimethoxyethane (3 ml), water (1.5 ml), 3-fluoro-4-(trifluoromethoxy)phenylboronic acid (0.122 g, 0.550 mmol for preparation see J. Med. Chem. 2010, 53, 8421-8439), sodium carbonate (0.116 g, 1.10 mmol) and [1,1'-Bis(diphenylphosphino)ferrocene]dichloro palladium(II).CH$_2$Cl$_2$ (0.060 g, 0.073 mmol). MP: 247-249° C. Mass: 598.0 (M$^+$)

Example 46

2-(1-(4-amino-3-(3-fluoro-4-(oxetan-3-yloxy)phenyl)-1H-pyrazolo[3,4-d]pyrimidin-1-yl)ethyl)-5-fluoro-3-(3-fluorophenyl)-4H-chromen-4-one 2-(1-(4-amino-3-(3-fluoro-4-(oxetan-3-yloxy)phenyl)-1H-pyrazolo[3,4-d]pyrimidin-1-yl)ethyl)-5-fluoro-3-(3-fluorophenyl)-4H-chromen-4-one: The title compound was obtained as pale brown solid (0.040 g, 18%) by using a procedure that is similar to the one described for example 9 from intermediate 27 (0.200 g, 0.366 mmol), 1,2-dimethoxyethane (3 ml), water (1.5 ml), intermediate 83 (0.162 g, 0.550 mmol), sodium carbonate (0.116 g, 1.10 mmol) and [1,1'-Bis(diphenylphosphino)ferrocene]dichloro palladium(II).CH$_2$Cl$_2$ (0.060 g, 0.073 mmol). MP: 235-237° C. Mass: 586.2.0 (M$^+$+1).

Example 47

2-(1-(4-amino-3-(pyrrolidin-1-yl)-1H-pyrazolo[3,4-d]pyrimidin-1-yl)ethyl)-5-fluoro-3-(3-fluorophenyl)-4H-chromen-4-one 2-(1-(4-amino-3-(pyrrolidin-1-yl)-1H-pyrazolo[3,4-d]pyrimidin-1-yl)ethyl)-5-fluoro-3-(3-fluorophenyl)-4H-chromen-4-one: The title compound was obtained as yellow solid (0.040 g, 10%) by using a procedure that is similar to the one described for example 6 from intermediate 79 (0.211 g, 1.03 mmol), DMF (4 ml), cesium carbonate (0.281 g, 0.864 mmol) and intermediate 22 (0.300 g, 0.0.864 mmol). MP: 203-205° C. Mass: 489.1 (M$^+$+1).

Example 48

N-(4-(4-amino-1-(1-(5-fluoro-3-(3-fluorophenyl)-4-oxo-4H-chromen-2-yl)ethyl)-1H-pyrazolo[3,4-d]pyrimidin-3-yl)phenyl)isobutyramide N-(4-(4-amino-1-(1-(5-fluoro-3-(3-fluorophenyl)-4-oxo-4H-chromen-2-yl)ethyl)-1H-pyrazolo[3,4-d]pyrimidin-3-yl)phenyl)isobutyramide: The title compound was obtained as pale brown solid (0.047 g, 22%) by using a procedure that is similar to the one described for example 9 from intermediate 27 (0.200 g, 0.366 mmol), 1,2-dimethoxyethane (3 ml), water (1.0 ml), 4-isobutyramidophenylboronic acid (0.114 g, 0.550 mmol), sodium carbonate (0.116 g, 1.10 mmol) and [1,1'-Bis(diphenylphosphino)ferrocene]dichloro palladium(II).CH$_2$Cl$_2$ (0.060 g, 0.073 mmol). MP: 154-157° C. Mass: 581.1 (M$^+$+1).

Example 49

2-(1-(4-amino-3-(4-Isobutylphenyl)-1H-pyrazolo[3,4-d]pyrimidin-1-yl)ethyl)-5-fluoro-3-(3-fluorophenyl)-4H-chromen-4-one 2-(1-(4-amino-3-(4-isobutylphenyl)-1H-pyrazolo[3,4-d]pyrimidin-1-yl)ethyl)-5-fluoro-3-(3-fluorophenyl)-4H-chromen-4-one: The title compound was obtained as brown solid (0.061 g, 30%) by using a procedure that is similar to the one described for example 9 from intermediate 27 (0.200 g, 0.366 mmol), 1,2-dimethoxyethane (3 ml), water (1.0 ml), 4-isobutylphenylboronic acid (0.098 g, 0.550 mmol), sodium carbonate (0.116 g, 1.10 mmol) and [1,1'-Bis(diphenylphosphino)ferrocene]dichloro palladium(II).CH$_2$Cl$_2$ (0.060 g, 0.073 mmol). MP: 221-223° C. Mass: 552.3 (M$^+$+1).

Example 50

2-(1-(4-amino-3-(4-isopropoxy-3-methylphenyl)-1H-pyrazolo[3,4-d]pyrimidin-1-yl)ethyl)-5-fluoro-3-(3-fluorophenyl)-4H-chromen-4-one 2-(1-(4-amino-3-(4-isopropoxy-3-methylphenyl)-1H-pyrazolo[3,4-d]pyrimidin-1-yl)ethyl)-5-fluoro-3-(3-fluorophenyl)-4H-chromen-4-one: The title compound was obtained as pale brown solid (0.038 g, 31%) by using a procedure that is similar to the one described for example 6 from intermediate 84 (0.060 g, 0.211 mmol), DMF (2 ml), sodium carbonate (0.059 g, 0.423 mmol) and intermediate 22 (0.116 g, 0.317 mmol). MP: 185-188° C. Mass: 568.0 (M$^+$+1).

Example 51

2-(1-(4-amino-3-(4-(5,6-dihydro-4H-1,3-oxazin-2-yl)phenyl)-1H-pyrazolo[3,4-d]pyrimidin-1-yl)ethyl)-5-fluoro-3-(3-fluorophenyl)-4H-chromen-4-one 2-(1-(4-amino-3-(4-(5,6-dihydro-4H-1,3-oxazin-2-yl)phenyl)-1H-pyrazolo[3,4-d]pyrimidin-1-yl)ethyl)-5-fluoro-3-(3-fluorophenyl)-4H-chromen-4-one: The title compound was obtained as brown solid (0.035 g, 17%) by using a procedure that is similar to the one described for example 9 from intermediate 27 (0.200 g, 0.366 mmol), 1,2-dimethoxyethane (3 ml), water (1.0 ml), 4-(5,6-dihydro-4H-1,3-oxazin-2-yl)phenylboronic acid (0.113 g, 0.550 mmol), sodium carbonate (0.116 g, 1.10 mmol) and (1,1'-Bis(diphenylphosphino)ferrocene]dichloro palladium(II).CH$_2$Cl$_2$ (0.060 g, 0.073 mmol). MP: 228-230° C. Mass: 579.1 (M$^+$+1).

Example 52

4-(4-amino-1-(1-(5-fluoro-3-(3-fluorophenyl)-4-oxo-4H-chromen-2-yl)ethyl)-1H-pyrazolo[3,4-d]pyrimidin-3-yl)-N-methylbenzenesulfonamide 4-(4-amino-1-(1-(5-fluoro-3-(3-fluorophenyl)-4-oxo-4H-chromen-2-yl)ethyl)-1H-pyrazolo[3,4-d]pyrimidin-3-yl)-N-methylbenzenesulfonamide: The title compound was obtained as brown solid (0.060 g, 28%) by using a procedure that is similar to the one described for example 9 from intermediate 27 (0.200 g, 0.366 mmol), 1,2-dimethoxyethane (3.5 ml), water (1.5 ml), 4-(N-methylsulfamoyl)phenylboronic acid (0.118 g, 0.550 mmol), sodium carbonate (0.077 g, 0.732 mmol) and [1,1'-Bis(diphenylphosphino)ferrocene]dichloro palladium(II).CH$_2$Cl$_2$ (0.060 g, 0.073 mmol). MP: 175-178° C. Mass: 589.1 (M$^+$+1).

Example 53

4-(4-amino-1-(1-(5-fluoro-3-(3-fluorophenyl)-4-oxo-4H-chromen-2-yl)ethyl)-1H-pyrazolo[3,4-d]pyrimidin-3-yl)-2-fluoro-N-isopropylbenzamide 4-(4-amino-1-(1-(5-fluoro-3-(3-fluorophenyl)-4-oxo-4H-chromen-2-yl)ethyl)-1H-pyrazolo[3,4-d]pyrimidin-3-yl)-2-fluoro-N-isopropylbenzamide: The title compound was obtained as brown solid (0.063 g, 29%) by using a procedure that is similar to the one described for example 9 from intermediate 27 (0.200 g, 0.366 mmol), 1,2-dimethoxyethane (3.5 ml), water (1.5 ml), 3-fluoro-4-(isopropylcarbamoyl)phenylboronic acid (0.123 g, 0.550 mmol), sodium carbonate (0.077 g, 0.732 mmol) and [1,1'-Bis(diphenylphosphino)ferrocene]dichloro palladium(II).CH$_2$Cl$_2$ (0.060 g, 0.073 mmol). MP: 254-257° C. Mass: 599.1 (M$^+$+1).

Example 54

2-(1-(4-amino-3-(4-(5-(methylamino)-1,3,4-thiadiazol-2-yl)phenyl)-1H-pyrazolo[3,4-d]pyrimidin-1-yl)ethyl)-5-fluoro-3-(3-fluorophenyl)-4H-chromen-4-one 2-(1-(4-amino-3-(4-(5-(methylamino)-1,3,4-thiadiazol-2-yl)phenyl)-1H-pyrazolo[3,4-d]pyrimidin-1-yl)ethyl)-5-fluoro-3-(3-fluorophenyl)-4H-chromen-4-one: The title compound was obtained as off-white solid (0.068 g, 41%) by using a procedure that is similar to the one described for example 9 from intermediate 27 (0.150 g, 0.274 mmol), 1,2-dimethoxyethane (3.0 ml), water (1.5 ml), 4-(5-(methylamino)-1,3,4-thiadiazol-2-yl)phenylboronic acid (0.097 g, 0.411 mmol), sodium carbonate (0.058 g, 0.55 mmol) and [1,1'-Bis(diphenylphosphino)ferrocene]dichloro palladium(II).CH$_2$Cl$_2$ (0.045 g, 0.055 mmol). MP: 199-201° C. Mass: 609.0 (M$^+$).

Example 55S

N-(4-(4-amino-1-(1-(5-fluoro-3-(3-fluorophenyl)-4-oxo-4H-chromen-2-yl)ethyl)-1H-pyrazolo[3,4-d]pyrimidin-3-yl)benzyl)methanesulfonamide N-(4-(4-amino-1-(1-(5-fluoro-3-(3-fluorophenyl)-4-oxo-4H-chromen-2-yl)ethyl)-1H-pyrazolo[3,4-d]pyrimidin-3-yl)benzyl)methanesulfonamide: The title compound was obtained as brown solid (0.055 g, 33%) by using a procedure that is similar to the one described for example 9 from intermediate 27 (0.150 g, 0.274 mmol), 1,2-dimethoxyethane (3.0 ml), water (1.5 ml), 4-(methylsulfonamidomethyl)phenylboronic acid (0.094 g, 0.411 mmol), sodium carbonate (0.058 g, 0.55 mmol) and [1,1'-Bis(diphenylphosphino)ferrocene]dichloro palladium(II).CH$_2$Cl$_2$ (0.045 g, 0.055 mmol). MP: 252-255° C. Mass: 603.0 (M$^+$+1).

Example 56

4-(4-amino-1-(1-(5-fluoro-3-(3-fluorophenyl)-4-oxo-4H-chromen-2-yl)ethyl)-1H-pyrazolo[3,4-d]pyrimidin-3-yl)-N-isopropylbenzenesulfonamide 4-(4-amino-1-(1-(5-fluoro-3-(3-fluorophenyl)-4-oxo-4H-chromen-2-yl)ethyl)-1H-pyrazolo[3,4-d]pyrimidin-3-yl)-N-isopropylbenzenesulfonamide: The title compound was obtained as off-white solid (0.075 g, 44%) by using a procedure that is similar to the one described for example 9 from intermediate 27 (0.150 g, 0.274 mmol), 1,2-dimethoxyethane (3.0 ml), water (1.5 ml), 4-(N-isopropylsulfamoyl)phenylboronic acid (0.100 g, 0.411 mmol), sodium carbonate (0.058 g, 0.55 mmol) and [1,1'-Bis(diphenylphosphino)ferrocene]dichloro palladium(II).CH$_2$Cl$_2$ (0.045 g, 0.055 mmol). MP: 211-214° C. Mass: 616.9 (M$^+$).

Example 57

4-(4-amino-1-(1-(5-fluoro-3-(3-fluorophenyl)-4-oxo-4H-chromen-2-yl)ethyl)-1H-pyrazolo[3,4-d]pyrimidin-3-yl)-N-cyclopropylbenzenesulfonamide 4-(4-amino-1-(1-(5-fluoro-3-(3-fluorophenyl)-4-oxo-4H-chromen-2-yl)ethyl)-1H-pyrazolo[3,4-d]pyrimidin-3-yl)-N-cyclopropylbenzenesulfonamide: The title compound was obtained as brown solid (0.043 g, 26%) by using a procedure that is similar to the one described for example 9 from intermediate 27 (0.150 g, 0.274 mmol), 1,2-dimethoxyethane (3.0 ml), water (1.5 ml), 4-(N-cyclopropylsulfamoyl)phenylboronic acid (0.099 g, 0.411 mmol), sodium carbonate (0.058 g, 0.55 mmol) and [1,1'-Bis(diphenylphosphino)ferrocene]dichloro palladium(II).CH$_2$Cl$_2$ (0.045 g, 0.055 mmol). MP: 225-228° C. Mass: 614.8 (M$^+$).

Example 58

2-(1-(4-amino-3-(2-isopropoxypyrimidin-5-yl)-1H-pyrazolo[3,4-d]pyrimidin-1-yl)ethyl)-5-fluoro-3-(3-fluorophenyl)-4H-chromen-4-one 2-(1-(4-amino-3-(2-isopropoxypyrimidin-5-yl)-1H-pyrazolo[3,4-d]pyrimidin-1-yl)ethyl)-5-fluoro-3-(3-fluorophenyl)-4H-chromen-4-one: The title compound was obtained as off-white solid (0.025 g, 12%) by using a procedure that is similar to the one described for example 9 from intermediate 27 (0.200 g, 0.366 mmol), 1,2-dimethoxyethane (3.0 ml), water (1.5 ml), intermediate 85 (0.146 g, 0.550 mmol), sodium carbonate (0.116 g, 1.10 mmol) and [1,1'-Bis(diphenylphosphino)ferrocene]dichloro palladium(II).CH$_2$Cl$_2$ (0.060 g, 0.073 mmol). MP: 230-232° C. Mass: 556.0 (M$^+$+1).

Example 59

(R)/(S)-2-(1-(4-amino-3-(3-fluoro-4-morpholinophenyl)-1H-pyrazolo-3,4-d]pyrimidin-1-yl)ethyl)-5-fluoro-phenyl)-4H-chromen-4-one (R)/(S)-2-(1-(4-amino-3-(3-fluoro-4-morpholinophenyl)-1H-pyrazolo[3,4-d]pyrimidin-1-yl)ethyl)-5-fluoro-3-(3-fluorophenyl)-4H-chromen-4-one: The title compound was obtained as off-white solid (0.015 g, 10%) by using a procedure that is similar to the one described for example 7 from intermediate 86 (0.080 g, 0.254 mmol), intermediate 23b (0.077 g, 0.254 mmol), tris(4-methoxyphenyl)phosphine (0.134 g, 0.381 mmol), THF (2 ml) and diisopropylazodicarboxylate (0.07 ml, 0.381 mmol). MP: 242-245° C. Enantiomeric excess: 96.21%. Mass: 599.1 (M$^+$+1).

Example 60

4-(4-amino-1-(1-(5-fluoro-3-(3-fluorophenyl)-4-oxo-4H-chromen-2-yl)ethyl)-1H-pyrazolo[3,4-d]pyrimidin-3-yl)benzenesulfonamide 4-(4-amino-1-(1-(5-fluoro-3-(3-fluorophenyl)-4-oxo-4H-chromen-2-yl)ethyl)-1H-pyrazolo[3,4-d]pyrimidin-3-yl)benzenesulfonamide: The title compound was obtained as brown solid (0.060 g, 38%) by using a procedure that is similar to the one described for example 9 from intermediate 27 (0.150 g, 0.274 mmol), 1,2-dimethoxyethane (3.0 ml), water (1.5 ml), 4-sulfamoylphenylboronic acid (0.083 g, 0.411 mmol), sodium carbonate (0.058 g, 0.55 mmol) and [1,1'-Bis(diphenylphosphino)ferrocene]dichloro palladium(II).CH$_2$Cl$_2$ (0.045 g, 0.055 mmol). MP: 232-235° C. Mass: 575.3 (M$^+$+1).

Example 61 methyl 4-(4-amino-1-(1-(5-fluoro-3-(3-fluorophenyl)-4-oxo-4H-chromen-2-yl)ethyl)-1H-pyrazolo[3,4-d]pyrimidin-3-yl)thiophene-2-carboxylate methyl 4-(4-amino-1-(1-(5-fluoro-3-(3-fluorophenyl)-4-oxo-4H-chromen-2-yl)ethyl)-1H-pyrazolo[3,4-d]pyrimidin-3-yl)thiophene-2-carboxylate: The title compound was obtained as brown solid (0.070 g, 46%) by using a procedure that is similar to the one described for example 9 from intermediate 27 (0.150 g, 0.274 mmol), 1,2-dimethoxyethane (3.0 ml), water (1.5 ml), 5-(methoxycarbonyl)thiophen-3-ylboronic acid (0.076 g, 0.411 mmol), sodium carbonate (0.058 g, 0.55 mmol) and [1,1'-Bis(diphenylphosphino)ferrocene]dichloro palladium(II).CH$_2$Cl$_2$ (0.045 g, 0.055 mmol). MP: 227-230° C. Mass: 560.2 (M$^+$+1).

Example 62

2-(1-(4-amino-3-(5-methylthiophen-2-yl)-1H-pyrazolo[3,4-d]pyrimidin-1-yl)ethyl)-5-fluoro-3-(3-fluorophenyl)-4H-chromen-4-one 2-(1-(4-amino-3-(5-methylthiophen-2-yl)-1H-pyrazolo[3,4-d]pyrimidin-1-yl)ethyl)-5-fluoro-3-(3-fluorophenyl)-4H-chromen-4-one: The title compound was obtained as brown solid (0.045 g, 32%) by using a procedure that is similar to the one described for example 9 from intermediate 27 (0.150 g, 0.274 mmol), 1,2-dimethoxyethane (3.0 ml), water (1.5 ml), 5-methylthiophen-2-ylboronic acid (0.092 g, 0.411 mmol), sodium carbonate (0.058 g, 0.55 mmol) and [1,1'-Bis(diphenylphosphino)ferrocene]dichloro palladium(II).CH$_2$Cl$_2$ (0.045 g, 0.055 mmol). MP: 223-226° C. Mass: 516.1 (M$^+$+1).

Example 63

2-(1-(4-amino-3-(1H-pyrrolo[2,3-b]pyridin-5-yl)-1H-pyrazolo[3,4-d]pyrimidin-1-yl)ethyl)-5-fluoro-3-(3-fluorophenyl)-4H-chromen-4-one 2-(1-(4-amino-3-(1H-pyrrolo[2,3-b]pyridin-5-yl)-1H-pyrazolo[3,4-d]pyrimidin-1-yl)ethyl)-5-fluoro-3-(3-fluorophenyl)-4H-chromen-4-one: The title compound was obtained as brown solid (0.030 g, 20%) by using a procedure that is similar to the one described for example 9 from intermediate 27 (0.150 g, 0.274 mmol), 1,2-dimethoxyethane (3.0 ml), water (1.5 ml), 1H-pyrrolo[2,3-b]pyridin-5-ylboronic acid (0.100 g, 0.411 mmol), sodium carbonate (0.058 g, 0.55 mmol) and [1,1'-Bis(diphenylphosphino)ferrocene]dichloro palladium(II).CH$_2$Cl$_2$ (0.045 g, 0.055 mmol). MP: 303-306° C. Mass: 536.4 (M$^+$+1).

Example 64 methyl 4-(4-amino-1-(1-(5-fluoro-3-(3-fluorophenyl)-4-oxo-4H-chromen-2-yl)ethyl)-1H-pyrazolo[3,4-d]pyrimidin-3-yl)-3-fluorobenzoate methyl 4-(4-amino-1-(1-(5-fluoro-3-(3-fluorophenyl)-4-oxo-4H-chromen-2-yl)ethyl)-1H-pyrazolo[3,4-d]pyrimidin-3-yl)-3-fluorobenzoate: The title compound was obtained as brown solid (0.017 g, 8%) by using a procedure that is similar to the one described for example 9 from intermediate 27 (0.200 g, 0.366 mmol), 1,2-dimethoxyethane (3.0 ml), water (1.0 ml), 2-fluoro-4-(methoxycarbonyl)phenylboronic acid (0.109 g, 0.550 mmol), sodium carbonate (0.116 g, 1.10 mmol) and [1,1'-Bis(diphenylphosphino)ferrocene]dichloro palladium(II).CH$_2$Cl$_2$ (0.060 g, 0.073 mmol). MP: 258-260° C. Mass: 572.4 (M$^+$+1).

Example 65

2-(1-(9H-purin-6-ylamino)propyl)-5-fluoro-3-phenyl-4H-chromen-4-one 2-(1-(9H-purin-6-ylamino)propyl)-5-fluoro-3-phenyl-4H-chromen-4-one: To a solution of intermediate 93 (0.190 g, 0.639 mmol), tert-butanol (2 ml) N,N-diisopropylethylamine (0.23 ml, 1.32 mmol) and 6-chloropurine (0.079 g, 0.511 mmol) were added and heated to reflux for 48 h. The reaction mixture was concentrated, quenched with water, extracted with ethyl acetate, dried with sodium sulphate and concentrated. The crude product was purified by column chromatography with methanol:ethyl acetate to afford the title compound as brown solid (0.030 g, 140% yield). MP: 210-212° C. $^1$H-NMR (δ ppm, DMSO-$d_6$, 400 MHz): δ 12.83 (s, 1H), 8.19 (s, 1H), 8.12 (s, 1H), 7.20-7.14 (m, 6H), 6.69 (d, J=8.1 Hz, 1H), 6.59 (t, J=8.7 Hz, 1H), 5.57 (m, 1H), 2.98 (m, 1H), 1.89 (m, 2H), 0.78 (t, J=7.1 Hz, 3H).

Example 66

2-(1-(4-amino-3-(3-hydroxyprop-1-ynyl)-1H-pyrazolo[3,4-d]pyrimidin-1-yl)ethyl)-5-fluoro-3-(3-fluorophenyl)-4H-chromen-4-one 2-(1-(4-amino-3-(3-hydroxyprop-1-ynyl)-1H-pyrazolo[3,4-d]pyrimidin-1-yl)ethyl)-5-fluoro-3-(3-fluorophenyl)-4H-chromen-4-one: To a solution of intermediate 27 (0.200 g, 0.364 mmol) in THF (4 ml) propargyl alcohol (0.025 ml, 0.437 mmol) was added and degassed with nitrogen for 10 min. Copper (I) iodide (7 mg, 0.036 mmol), tetrakistriphenylphosphine palladium (0 (0.042 g, 0.036 mmol) and diisopropylamine (0.23 ml, 1.82 mmol) were added and again degassed for 10 min. and heated to reflux. After 4 h, the reaction mixture was filtered through celite, washed with ethyl acetate, dried over sodium sulphate and concentrated. The crude product was purified by column chromatography with ethyl acetate:pet. ether to afford the title compound as brown solid (0.050 g, 29% yield). MP: 220-222° C. Mass: 474.3 (M$^+$+1).

Example 67

(S)/(R)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one 4-methyl benzenesulfonate (S)/(R)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one 4-methylbenzenesulfonate: To example 7 (0.100 g, 0.174 mmol) in isopropanol (4 ml), p-toluenesulphonic acid (0.037 g, 0.192 mmol) was added and refluxed for 1 h. The reaction mixture was concentrated, co-distilled with pet. ether and dried. To the residue water (3 ml) was added and stirred for 30 min. The solid was filtered, washed with pet. ether and dried under vacuum to afford the title compound as off-white solid (0.110 g, 82%). MP: 152-155° C. $^1$H-NMR (δ ppm, CDCl$_3$, 400 MHz): 8.15 (s, 1H), 7.81 (d, J=8.1 Hz, 2H), 7.64 (dt, J=8.4, 5.4 Hz, 1H), 7.42 (dd, J=11.3, 2.0 Hz, 1H), 7.34 (m, 3H), 7.22 (d, J=8.0 Hz, 2H), 7.16 (t, J=8.6 Hz, 1H), 7.08-6.97 (m, 3H), 6.88 (m, 1H), 6.08 (q, J=7.1 Hz, 1H), 4.687 (quintet, J 6.0 Hz, 1H), 2.37 (s, 3H), 2.02 (m, J=7.2 Hz, 3H), 1.43 (d, J=6.1 Hz, 6H).

Example 68

(+)-2-(1-(9H-purin-6-ylamino)ethyl)-5-fluoro-3-(3-fluorophenyl)-4H-chromen-4-one (+)-2-(1-(9H-purin-6-ylamino)ethyl)-5-fluoro-3-(3-fluorophenyl)-4H-chromen-4-one: The title compound was obtained as off-white solid (0.090 g, 43%) by using a procedure that is similar to the one described for example 7 from tert-butyl 9-trityl-9H-purin-6-ylcarbamate (0.235 g, 0.494 mmol), intermediate 23b (0.150 g, 0.494 mmol), triphenylphosphine (0.194 g, 0.741 mmol), THF (8 ml) and diisopropylazodicarboxylate (0.15 ml, 0.749 mmol), followed by the cleavage of the intermediate with trifluoroacetic acid (1.8 ml) and dichloromethane (5 ml). MP: 194-197° C. Enantiomeric excess: 99.62%. $[\alpha]^{25}_D$ 142.00 (c=1, CHCl$_3$). Mass: 420.1 (M$^+$+1).

Example 69

2-(1-(9H-purin-6-ylamino)ethyl)-1-fluoro-3-(3-fluorophenyl)-4H-chromen-4-one 2-(1-(9H-purin-6-ylamino)ethyl)-5-fluoro-3-(3-fluorophenyl)-4H-chromen-4-one: The title compound was obtained as off-white solid (0.081 g, 39%) by using a procedure that is similar to the one described for example 7 from tert-butyl 9-trityl-9H-purin-6-ylcarbamate (0.235 g, 0.494 mmol), intermediate 23 (0.150 g, 0.494 mmol), triphenylphosphine (0.194 g, 0.741 mmol), THF (8 ml) and diisopropylazodicarboxylate (0.15 ml, 0.749 mmol), followed by the cleavage of the intermediate with trifluoroacetic acid (1.3 ml) and dichloromethane (8 ml). MP: 247-249° C. Mass: 420.1 (M$^+$+1).

Example 70

(R)/(S)-2-(1-(4-amino-3-(3-fluoro-4-morpholinophenyl)-1H-pyrazolo[3,4-d]pyrimidin-1-yl)ethyl)-5-fluoro-3-(3-fluorophenyl)-4H-chromen-4-one (R)/(S)-2-(1-(4-amino-3-(3-fluoro-4-morpholinophenyl)-1H-pyrazolo[3,4-d]pyrimidin-1-yl)ethyl)-5-fluoro-3-(3-fluorophenyl)-4H-chromen-4-one: The title compound was obtained as off-white solid (0.022 g, 11%) by using a procedure that is similar to the one described for example 7 from intermediate 86 (0.100 g, 0.329 mmol), intermediate 23a (0.100 g, 0.329 mmol), tris(4-methoxyphenyl)phosphine (0.174 g, 0.494 mmol), THF (2 ml) and diisopropylazodicarboxylate (0.1 ml, 0.494 mmol). MP: 243-246° C. Enantiomeric excess: 85.4%. Mass: 599.4 (M$^+$+1).

Example 71

2-(1-(4-amino-3-(4-methoxy-3,5-dimethylphenyl)-1H-pyrazolo[3,4-d]pyrimidin-1-yl)ethyl)-5-fluoro-3-(3-fluorophenyl)-4H-chromen-4-one 2-(1-(4-amino-3-(4-methoxy-3,5-dimethylphenyl)-1H-pyrazolo[3,4-d]pyrimidin-1-yl)ethyl)-5-fluoro-3-(3-fluorophenyl)-4H-chromen-4-one: The title compound was obtained as brown solid (0.070 g, 46%) by using a procedure that is similar to the one described for example 9 from intermediate 27 (0.150 g, 0.274 mmol), 1,2-dimethoxyethane (3.0 ml), water (1.5 ml), 4-methoxy-3,5-dimethylphenylboronic acid (0.074 g, 0.411 mmol), sodium carbonate (0.058 g, 0.55 mmol) and [1,1'-Bis(diphenylphosphino)ferrocene]dichloro palladium(II).CH$_2$Cl$_2$ (0.045 g, 0.055 mmol). MP: 232-235° C. Mass: 554.0 (M$^+$+1).

Example 72

2-(1-(4-amino-3-(4-(methoxymethyl)phenyl)-1H-pyrazolo[3,4-d]pyrimidin-1-yl)ethyl)-5-fluoro-3-(3-fluorophenyl)-4H-chromen-4-one 2-(1-(4-amino-3-(4-(methoxymethyl)phenyl)-1H-pyrazolo[3,4-d]pyrimidin-1-yl)ethyl)-5-fluoro-3-(3-fluorophenyl)-4H-chromen-4-one: The title compound was obtained as brown solid (0.062 g, 42%) by using a procedure that is similar to the one described for example 9 from intermediate 27 (0.150 g, 0.274 mmol), 1,2-dimethoxyethane (3.0 ml), water (1.5 ml), 4-(methoxymethyl)phenylboronic acid (0.068 g, 0.411 mmol), sodium carbonate (0.058 g, 0.55 mmol) and [1,1'-Bis(diphenylphosphino)ferrocene]dichloro palladium(II).CH$_2$Cl$_2$ (0.045 g, 0.055 mmol). MP: 204-207° C. Mass: 540.3 (M$^+$+1).

Example 73

2-(1-(4-amino-3-(imidazo[1,2-a]pyridin-6-yl)-1H-pyrazolo[3,4-d]pyrimidin-1-yl)ethyl)-5-fluoro-3-(3-fluorophenyl)-4H-chromen-4-one 2-(1-(4-amino-3-(imidazo[1,2-a]pyridin-6-yl)-1H-pyrazolo[3,4-d]pyrimidin-1-yl)ethyl)-5-fluoro-3-(3-fluorophenyl)-4H-chromen-4-one: The title compound was obtained as brown solid (0.052 g, 36%) by using a procedure that is similar to the one described for example 9 from intermediate 27 (0.150 g, 0.274 mmol), 1,2-dimethoxyethane (3.0 ml), water (1.5 ml), imidazo[1,2-a]pyridin-6-ylboronic acid (0.066 g, 0.411 mmol), sodium carbonate (0.058 g, 0.55 mmol) and [1,1'-Bis(diphenylphosphino)ferrocene]dichloro palladium(II).CH$_2$Cl$_2$ (0.045 g, 0.055 mmol). MP: 317-320° C. Mass: 536.3 (M$^+$+1).

Example 74 tert-butyl (5-(4-amino-1-(1-(5-fluoro-3-(3-fluorophenyl)-4-oxo-4H-chromen-2-yl)ethyl)-1H-pyrazolo[3,4-d]pyrimidin-3-yl)furan-2-yl)methylcarbamate tert-butyl (5-(4-amino-1-(1-(5-fluoro-3-(3-fluorophenyl)-4-oxo-4H-chromen-2-yl)ethyl)-1H-pyrazolo[3,4-d]pyrimidin-3-yl)furan-2-yl)methylcarbamate: The title compound was obtained as brown solid (0.100 g, 63%) by using a procedure that is similar to the one described for example 9 from intermediate 27 (0.150 g, 0.274 mmol), 1,2-dimethoxyethane (3.0 ml), water (1.5 ml), 5-((tert-butoxycarbonylamino)methyl)furan-2-ylboronic acid (0.099 g, 0.411 mmol), sodium carbonate (0.058 g, 0.55 mmol) and [1,1'-Bis(diphenylphosphino)ferrocene]dichloro palladium(II).CH$_2$Cl$_2$ (0.045 g, 0.055 mmol). MP: 163-166° C. Mass: 615.7 (M$^+$+1).

Example 75

2-(1-(4-amino-3-(2,4-dimethylthiazol-5-yl)-1H-pyrazolo[3,4-d]pyrimidin-5-yl)ethyl)-5-fluoro-3-(3-fluorophenyl)-4H-chromen-4-one 2-(1-(4-amino-3-(2,4-dimethylthiazol-5-yl)-1H-pyrazolo[3,4-d]pyrimidin-1-yl)ethyl)-5-fluoro-3-(3-fluorophenyl)-4H-chromen-4-one: The title compound was obtained as brown solid (0.050 g, 39%) by using a procedure that is similar to the one described for example 9 from intermediate 27 (0.150 g, 0.274 mmol), 1,2-dimethoxyethane (3.0 ml), water (1.5 ml), 2,4-dimethyl-5-(4,4,5,5-tetramethyl-1,3,2-dioxaborolan-2-yl)thiazole (0.098 g, 0.411 mmol), sodium carbonate (0.058 g, 0.55 mmol) and [1,1'-Bis(diphenylphosphino)ferrocene]dichloro palladium(II).CH$_2$Cl$_2$ (0.045 g, 0.055 mmol). MP: 252-255° C. Mass: 531.3 (M$^+$+1).

Example 76

2-(1-(4-amino-3-(5-(morpholinomethyl)thiophen-2-yl)-1H-pyrazolo[3,4-d]pyrimidin-1-yl)ethyl)-5-fluoro-3-(3-fluorophenyl)-4H-chromen-4-one 2-(1-(4-amino-3-(5-(morpholinomethyl)thiophen-2-yl)-1H-pyrazolo[3,4-d]pyrimidin-1-yl)ethyl)-5-fluoro-3-(3-fluorophenyl)-4H-chromen-4-one: The title compound was obtained as brown solid (0.047 g, 29%) by using a procedure that is similar to the one described for example 9 from intermediate 27 (0.150 g, 0.274 mmol), 1,2-dimethoxyethane (3.0 ml), water (1.5 ml), 4-((5-(4,4,5,5-tetramethyl-1,3,2-dioxaborolan-2-yl)thiophen-2-yl)methyl)morpholine (0.127 g, 0.411 mmol), sodium carbonate (0.058 g, 0.55 mmol) and [1,1'-Bis(diphenylphosphino)ferrocene]dichloro palladium(II).CH$_2$Cl$_2$ (0.045 g, 0.055 mmol). MP: 193-196° C. Mass: 601.6 (M$^+$+1).

Example 77

2-(1-(4-amino-3-(4-(5-amino-1,3,4-thiadiazol-2-yl)phenyl)-1H-pyrazolo[3,4-d]pyrimidin-1-yl)ethyl)-5-fluoro-3-(3-fluorophenyl)-4H-chromen-4-one 2-(1-(4-amino-3-(4-(5-amino-1,3,4-thiadiazol-2-yl)phenyl)-1H-pyrazolo[3,4-d]pyrimidin-1-yl)ethyl)-5-fluoro-3-(3-fluorophenyl)-4H-chromen-4-one: The title compound was obtained as brown solid (0.071 g, 44%) by using a procedure that is similar to the one described for example 9 from intermediate 27 (0.150 g, 0.274 mmol), 1,2-dimethoxyethane (3.0 ml), water (1.5 ml), 4-(5-amino-1,3,4-thiadiazol-2-yl)phenylboronic acid (0.091 g, 0.411 mmol), sodium carbonate (0.058 g, 0.55 mmol) and [1,1'-Bis(diphenylphosphino)ferrocene]dichloro palladium(II).CH$_2$Cl$_2$ (0.045 g, 0.055 mmol). MP: 202-205° C. Mass: 595.6 (M$^+$+1).

Example 78

(−)-2-(1-(9H-purin-6-ylamino)ethyl)-5-fluoro-3-(3-fluorophenyl)-4H-chromen-4-one (−)-2-(1-(9H-purin-6-ylamino)ethyl)-5-fluoro-3-(3-fluorophenyl)-4H-chromen-4-one: The title compound was obtained as off-white solid (0.075 g, 36%) by using a procedure that is similar to the one described for example 7 from tert-butyl 9-trityl-9H-purin-6-ylcarbamate (0.235 g, 0.494 mmol), intermediate 23a (0.150 g, 0.494 mmol), triphenylphosphine (0.194 g, 0.741 mmol), THF (8 ml) and diisopropylazodicarboxylate (0.15 ml, 0.749 mmol), followed by the cleavage of the intermediate with trifluoroacetic acid (0.50 ml) and dichloromethane (6 ml). MP: 205-208° C. Enantiomeric excess: 100%. $[\alpha]^{25}_D$ −180.47 (c=1, CHCl$_3$). Mass: 420.5 (M$^+$+1).

Example 79

2-(1-(4-amino-3-(1,3-dimethyl-1H-indazol-6-yl)-1H-pyrazolo[3,4-d]pyrimidin-1-yl)ethyl)-5-fluoro-3-(3-fluorophenyl)-4H-chromen-4-one 2-(1-(4-amino-3-(1,3-dimethyl-1H-indazol-6-yl)-1H-pyrazolo[3,4-d]pyrimidin-1-yl)ethyl)-5-fluoro-3-(3-fluorophenyl)-4H-chromen-4-one: The title compound was obtained as brown solid (0.039 g, 26%) by using a procedure that is similar to the one described for example 9 from intermediate 27 (0.150 g, 0.274 mmol), 1,2-dimethoxyethane (3.0 ml), water (1.5 ml), 1,3-dimethyl-6-(4,4,5,5-tetramethyl-1,3,2-dioxaborolan-2-yl)-1H-indazole (0.112 g, 0.411 mmol), sodium carbonate (0.058 g, 0.55 mmol) and [1,1'-Bis(diphenylphosphino)ferrocene]dichloro palladium (II).CH$_2$Cl$_2$ (0.045 g, 0.055 mmol). MP: 220-224° C. Mass: 564.0 (M$^+$+1).

Example 80

2-(1-(4-amino-3-(2,3-dimethyl-2H-indazol-6-yl)-1H-pyrazolo[3,4-d]pyrimidin-1-yl)ethyl)-5-fluoro-3-(3-fluorophenyl)-4H-chromen-4-one 2-(1-(4-amino-3-(2,3-dimethyl-2H-indazol-6-yl)-1H-pyrazolo[3,4-d]pyrimidin-1-yl)ethyl)-5-fluoro-3-(3-fluorophenyl)-4H-chromen-4-one: The title compound was obtained as brown solid (0.060 g, 40%) by using a procedure that is similar to the one described for example 9 from intermediate 27 (0.150 g, 0.274 mmol), 1,2-dimethoxyethane (3.0 ml), water (1.5 ml), 2,3-dimethyl-6-(4,4,5,5-tetramethyl-1,3,2-dioxaborolan-2-yl)-2H-indazole (0.112 g, 0.411 mmol), sodium carbonate (0.058 g, 0.55 mmol) and [1,1'-Bis(diphenylphosphino)ferrocene]dichloro palladium (II).CH$_2$Cl$_2$ (0.045 g, 0.055 mmol). MP: 232-235° C. Mass: 563.8 (M$^+$).

Example 81

N-(4-(4-amino-1-(1-(5-fluoro-3-(3-fluorophenyl)-4-oxo-4H-chromen-2-yl)ethyl)-1H-pyrazolo[3,4-d]pyrimidin-3-yl)-2-fluorophenyl)isobutyramide N-(4-(4-amino-1-(1-(5-fluoro-3-(3-fluorophenyl)-4-oxo-4H-chromen-2-yl)ethyl)-1H-pyrazolo[3,4-d]pyrimidin-3-yl)-2-fluorophenyl)isobutyramide: The title compound was obtained as brown solid (0.061 g, 37%) by using a procedure that is similar to the one described for example 9 from intermediate 27 (0.150 g, 0.274 mmol), 1,2-dimethoxyethane (3.0 ml), water (1.5 ml), intermediate 95 (0.125 g, 0.411 mmol), sodium carbonate (0.058 g, 0.55 mmol) and [1,1'-Bis(diphenylphosphino)ferrocene]dichloro palladium (II).CH$_2$Cl$_2$ (0.045 g, 0.055 mmol). MP: 249-252° C. Mass: 598.8 (M$^+$).

Example 82

N-(4-(4-amino-1-(1-(5-fluoro-3-(3-fluorophenyl)-4-oxo-4H-chromen-2-yl)ethyl)-1H-pyrazolo[3,4-d]pyrimidin-3-yl)-2-fluorophenyl)acetamide N-(4-(4-amino-1-(1-(5-fluoro-3-(3-fluorophenyl)-4-oxo-4H-chromen-2-yl)ethyl)-1H-pyrazolo[3,4-d]pyrimidin-3-yl)-2-fluorophenyl)acetamide: The title compound was obtained as brown solid (0.030 g, 19%) by using a procedure that is similar to the one described for example 9 from intermediate 27 (0.150 g, 0.274 mmol), 1,2-dimethoxyethane (3.0 ml), water (1.5 ml), intermediate 97 (0.114 g, 0.411 mmol), sodium carbonate (0.058 g, 0.55 mmol) and [1,1'-Bis(diphenylphosphino)ferrocene]dichloro palladium (II).CH$_2$Cl$_2$ (0.045 g, 0.055 mmol). MP: 220-223° C. Mass: 571.198.8 (M$^+$+1).

Example 83

2-(1-(4-(dimethylamino)-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one 2-(1-(4-(dimethylamino)-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one: The title compound was obtained as pale-yellow solid (0.050 g, 13%) by using a procedure that is similar to the one described for example 7 from intermediate 99 (0.200 g, 0.630 mmol), intermediate 23 (0.229 g, 0.756 mmol), tris-4-methoxytriphenylphosphine (0.288 g, 0.819 mmol), THF (3 ml) and diisopropylazodicarboxylate (0.18 ml, 0.945 mmol). MP: 122-124° C. Mass: 600.2 (M$^+$+1).

Example 84

5-fluoro-2-(1-(3-(3-fluoro-4-isopropoxyphenyl)-4-(methylamino)-1H-pyrazolo[3,4-d]pyrimidin-1-yl)ethyl)-3-(3-fluorophenyl)-4H-chromen-4-one 5-fluoro-2-(1-(3-(3-fluoro-4-isopropoxyphenyl)-4-(methylamino)-1H-pyrazolo[3,4-d]pyrimidin-1-yl)ethyl)-3-(3-fluorophenyl)-4H-chromen-4-one: The title compound was obtained as brown solid (0.038 g, 25%) by using a procedure that is similar to the one described for example 9 from intermediate 101 (0.150 g, 0.267 mmol), 1,2-dimethoxyethane (3.0 ml), water (1.5 ml), intermediate 12 (0.110 g, 0.401 mmol), sodium carbonate (0.057 g, 0.535 mmol) and [1,1'-Bis(diphenylphosphino)ferrocene]dichloro palladium (II).CH$_2$Cl$_2$ (0.044 g, 0.053 mmol). MP: 193-196° C. Mass: 586.3 (M$^+$+1).

Example 85

5-fluoro-2-(1-(3-(3-fluoro-4-isopropoxyphenyl)-4-morpholino-H-pyrazolo[3,4-d]pyrimidin-1l-yl)ethyl)-3-(3-fluorophenyl)-4H-chromen-4-one 5-fluoro-2-(1-(3-(3-fluoro-4-isopropoxyphenyl)-4-morpholino-1H-pyrazolo[3,4-d]pyrimidin-1-yl)ethyl)-3-(3-fluorophenyl)-4H-chromen-4-one: The title compound was obtained as off-white solid (0.120 g, 46%) by using a procedure that is similar to the one described for example 7 from intermediate 104 (0.150 g, 0.402 mmol), intermediate 23 (0.146 g, 0.483 mmol), tris-4-methoxytriphenylphosphine (0.184 g, 0.523 mmol), THF (3 ml) and diisopropylazodicarboxylate (0.12 ml, 0.604 mmol). MP: 116-119° C. Mass: 641.8 (M$^+$+1).

Example 86

N-(2-fluoro-4-(1-(1-(5-fluoro-3-(4-fluorophenyl)-4-oxo-4H-chromen-2-yl)ethyl)-4-morpholino-1H-pyrazolo[3,4-d]pyrimidin-3-yl)phenyl)isobutyramide N-(2-fluoro-4-(1-(1-(5-fluoro-3-(4-fluorophenyl)-4-oxo-4H-chromen-2-yl)ethyl)-4-morpholino-1H-pyrazolo[3,4-d]pyrimidin-3-yl)phenyl)isobutyramide: The title compound was obtained as brown solid (0.030 g, 18%) by using a procedure that is similar to the one described for example 9 from intermediate 105 (0.150 g, 0.243 mmol), 1,2-dimethoxyethane (3.0 ml), water (1.5 ml), intermediate 95 (0.111 g, 0.365 mmol), sodium carbonate (0.051 g, 0.487 mmol) and [1,1'-Bis(diphenylphosphino)ferrocene]dichloro palladium(II).CH$_2$Cl$_2$ (0.040 g, 0.048 mmol). MP: 165-167° C. Mass: 669.2 (M$^+$+1).

Example 87

N-(2-fluoro-4-(1-(1-(5-fluoro-3-(3-fluorophenyl)-4-oxo-4H-chromen-2-yl)ethyl)-4-morpholino-1H-pyrazolo[3,4-d]pyrimidin-3-yl)phenyl)isobutyramide N-(2-fluoro-4-(1-(1-(5-fluoro-3-(3-fluorophenyl)-4-oxo-4H-chromen-2-yl)ethyl)-4-morpholino-1H-pyrazolo[3,4-d]

pyrimidin-3-yl)phenyl)isobutyramide: The title compound was obtained as brown solid (0.050 g, 31%) by using a procedure that is similar to the one described for example 9 from intermediate 106 (0.150 g, 0.243 mmol), 1,2-dimethoxyethane (3.0 ml), water (1.5 ml), intermediate 95 (0.111 g, 0.365 mmol), sodium carbonate (0.051 g, 0.487 mmol) and [1,1'-Bis(diphenylphosphino)ferrocene]dichloro palladium(II).CH$_2$Cl$_2$ (0.040 g, 0.048 mmol). MP: 168-170° C. Mass: 669.2 (M$^+$+1).

Example 88

(S)/(R)-2-(1-(4-amino-3-(3-fluoro-4-Isopropoxyphenyl)-1H-pyrazolo[3,4-d]pyrimidin-1-yl)ethyl)-5-fluoro-3-(3-fluorophenyl)-4H-chromen-4-one sulphate (S)/(R)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one sulphate: The title compound was obtained as off-white solid (0.120 g, 68%) by using a procedure that is similar to the one described for example 67 from example 6a (0.150 g, 0.262 mmol), isopropanol (6 ml), sulphuric acid (0.028 g, 0.288 mmol). MP: 205-207° C. $^1$H-NMR (δ ppm, CDCl$_3$, 400 MHz): δ 8.12 (s, 1H), 7.64 (dt, J=8.4, 5.4 Hz, 1H), 7.41 (dd, J=11.2, 2.0 Hz, 1H), 7.29 (m, 3H), 7.15 (t, J=8.3 Hz, 1H), 7.08 (m, 2H), 6.97 (d, J=6.9 Hz, 1H), 6.89 (d, J=7.1 Hz, 1H), 6.07 (q, J=6.9 Hz, 1H), 4.68 (quintet, J=6.1 Hz, 1H), 2.01 (d, J=7.1 Hz, 3H), 1.42 (d, J=6.1 Hz, 6H).

Example 89

(S)/(R)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one benzenesulfonate (S)/(R)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one benzenesulfonate The title compound was obtained as off-white solid (0.120 g, 62%) by using a procedure that is similar to the one described for example 67 from example 6a (0.150 g, 0.262 mmol), isopropanol (6 ml), benzenesulphonic acid (0.045 g, 0.288 mmol). MP: 172-174° C. $^1$H-NMR (δ ppm, CDCl$_3$, 400 MHz): δ 8.14 (s, 1H), 7.92 (dd, J=6.8, 1.7 Hz, 2H), 7.64 (dt, J=8.4, 5.4 Hz, 1H), 7.42-7.28 (m, 7H), 7.16 (t, J=8.3 Hz, 1H), 7.11 (m, 3H), 6.87 (d, J=7.1 Hz, 1H), 6.08 (q, J=7.0 Hz, 1H), 4.68 (quintet, J=6.1 Hz, 1H), 2.02 (d, J=7.1 Hz, 3H), 1.43 (d, J=6.0 Hz, 6H).

Example 90

(S)/(R)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one camphorsulphonate (S)/(R)-2-(1-(4-amino-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one camphorsulphonate: The title compound was obtained as off-white solid (0.120 g, 57%) by using a procedure that is similar to the one described for example 67 from example 6a (0.150 g, 0.262 mmol), isopropanol (6 ml), camphorsulphonic acid (0.066 g, 0.288 mmol). MP: 190-193° C. $^1$H-NMR (δ ppm, CDCl$_3$, 400 MHz): δ 8.23 (s, 1H), 7.64 (dt, J=8.4, 5.4 Hz, 1H), 7.42 (dd, J=11.2, 2.1 Hz, 1H), 7.35 (m, 3H), 7.16 (t, J=8.4 Hz, 1H), 7.08 (m, 3H), 6.92 (d, J=8.3 Hz, 1H), 6.08 (q, J=7.1 Hz, 1H), 4.68 (quintet, J=6.1 Hz, 1H), 3.36 (d, J=4.4 Hz, 1H), 2.95 (d, J=4.6 Hz, 1H), 2.59 (m, 1H), 2.35 (m, 1H), 2.09 (m, 2H), 2.02 (d, J=7.2 Hz, 3H), 1.93-1.83 (m, 3H), 1.43 (d, J=6.1 Hz, 6H), 1.07 (s, 3H), 0.84 (s, 3H).

Example 91

2-(1-(4-amino-3-(4-(difluoromethoxy)-3-fluorophenyl)-1H-pyrazolo[3,4-d]pyrimidin-1-yl)ethyl)-5-fluoro-3-(1H-pyrazol-4-yl)-4H-chromen-4-one 2-(1-(4-amino-3-(4-(difluoromethoxy)-3-fluorophenyl)-1H-pyrazolo[3,4-d]pyrimidin-1-yl)ethyl)-5-fluoro-3-(1 H-pyrazol-4-yl)-4H-chromen-4-one: The title compound was obtained as brown solid (0.120 g, 30%) by using a procedure that is similar to the one described for example 9 from intermediate 107 (0.400 g, 0.708 mmol), 1,2-dimethoxyethane (3.0 ml), water (1.5 ml), 1-boc-pyrazole-4-boronic acid (0.220 g, 1.06 mmol), sodium carbonate (0.220 g, 2.12 mmol) and [1,1'-Bis(diphenylphosphino)ferrocene]dichloro palladium(II).CH$_2$Cl$_2$ (0.115 g, 0.141 mmol). MP: 135-138° C. Mass: 552.0 (M$^+$+1).

Example 92

2-(1-(4-amino-3-(3-fluoro-4-morpholinophenyl)-1H-pyrazolo[3,4-d]pyrimidin-1-yl)ethyl)-5-fluoro-3-phenyl-4H-chromen-4-one 2-(1-(4-amino-3-(3-fluoro-4-morpholinophenyl)-1H-pyrazolo[3,4-d]pyrimidin-1-yl)ethyl)-5-fluoro-3-phenyl-4H-chromen-4-one: The title compound was obtained as brown solid (0.045 g, 27%) by using a procedure that is similar to the one described for example 9 from intermediate 108 (0.150 g, 0.285 mmol), 1,2-dimethoxyethane (3.0 ml), water (1.5 ml), intermediate 61 (0.130 g, 0.427 mmol), sodium carbonate (0.060 g, 0.570 mmol) and [1,1'-Bis(diphenylphosphino)ferrocene]dichloro palladium(II).CH$_2$Cl$_2$ (0.046 g, 0.057 mmol). MP: 256-258° C. $^1$H-NMR (δ ppm, CDCl$_3$, 400 MHz): δ 8.23 (s, 1H), 7.60 (dt, J=8.4, 5.5 Hz, 1H), 7.40-7.32 (m, 2H), 7.23 (m, 6H), 7.09 (m, 2H), 6.09 (q, J=7.1 Hz, 1H), 5.38 (s, 2H), 3.91 (t, J=4.5 Hz, 4H), 3.18 (t, J=4.7 Hz, 4H), 1.98 (d, J=7.1 Hz, 3H).

Example 93

2-(1-(4-amino-3-(3-fluoro-4-morpholinophenyl)-1H-pyrazolo[3,4-d]pyrimidin-1-yl)ethyl)-5-fluoro-3-(4-fluorophenyl)-4H-chromen-4-one 2-(1-(4-amino-3-(3-fluoro-4-morpholinophenyl)-1H-pyrazolo[3,4-d]pyrimidin-1-yl)ethyl)-5-fluoro-3-(4-fluorophenyl)-4H-chromen-4-one: The title compound was obtained as brown solid (0.040 g, 24%) by using a procedure that is similar to the one described for example 9 from intermediate 34 (0.150 g, 0.275 mmol), 1,2-dimethoxyethane (3.0 ml), water (1.5 ml), intermediate 61 (0.127 g, 0.412 mmol), sodium carbonate (0.058 g, 0.550 mmol) and [1,1'-Bis(diphenylphosphino)ferrocene]dichloro palladium (II).CH$_2$Cl$_2$ (0.045 g, 0.055 mmol). MP: 240-242° C. $^1$H-NMR (δ ppm, CDCl$_3$, 400 MHz): δ 8.26 (s, 1H), 7.60 (dt, J=8.3, 5.5 Hz, 1H), 7.40 (m, 2H), 7.28 (m, 3H), 7.09-6.99 (m, 4H), 6.06 (q, J=7.2 Hz, 1H), 5.45 (s, 2H), 3.91 (t, J=4.5 Hz, 4H), 3.18 (t, J=4.6 Hz, 4H), 1.99 (d, J=7.1 Hz, 3H).

Example 94

(S)/(R)-2-(1-(4-amino-3-(3-fluoro-4-isopropoxyphenyl)-1H-pyrazolo[3,4-d]pyrimidin-1-yl)ethyl)-5-fluoro-3-(4-fluorophenyl)-4H-chromen-4-one (S)/(R)-2-(1-(4-amino-3-(3-fluoro-4-isopropoxyphenyl)-1H-pyrazolo[3,4-d]pyrimidin-1-yl)ethyl)-5-fluoro-3-(4-fluorophenyl)-4H-chromen-4-one: The title compound was obtained as off-white solid (0.033 g, 10%) by using a procedure that is similar to the one described for example 7 from intermediate 13 (0.199 g, 0.692 mmol), intermediate 113 (0.175 g, 0.577 mmol), tris-4-methoxytriphenylphosphine (0.305 g, 0.865 mmol), THF (3 ml) and diisopropylazodicarboxylate (0.17 ml, 0.865 mmol). MP: 192-194° C. $^1$H-NMR (δ ppm, CDCl$_3$, 400 MHz): δ 8.22 (s, 1H), 7.58 (dt, J=8.4, 5.4 Hz, 1H), 7.44 (dd, J=11.5, 2.0 Hz, 1H), 7.37 (d, J=8.4 Hz, 1H), 7.23 (m, 2H), 7.15 (t, J=8.3 Hz, 1H), 7.07 (m, 3H), 6.04 (q, J=7.1 Hz, 1H), 5.42 (s, 2H), 4.65 (quintet, J=6.2 Hz, 1H), 1.99 (d, J=7.1 Hz, 3H), 1.42 (d, J=6.1 Hz, 6H). Enantiomeric excess: 68.2% as determined by HPLC on a chiralpak AD-H column, enriched in the fast eluting isomer (retention time=10.43 min.).

Example 95

(S)/(R)-2-(1-(4-amino-3-(3-fluoro-4-isopropoxyphenyl)-1H-pyrazolo[3,4-d]pyrimidin-1-yl)ethyl)-5-fluoro-3-(4-fluorophenyl)-4H-chromen-4-one (S)/(R)-2-(1-(4-amino-3-(3-fluoro-4-isopropoxyphenyl)-1H-pyrazolo[3,4-d]pyrimidin-1-yl)ethyl)-5-fluoro-3-(4-fluorophenyl)-4H-chromen-4-one: The title compound was obtained as off-white solid (0.071 g, 18%) by using a procedure that is similar to the one described for example 7 from intermediate 13 (0.277 g, 0.791 mmol), intermediate 114 (0.200 g, 0.659 mmol), tris-4-methoxytriphenylphosphine (0.348 g, 0.989 mmol), THF (4 ml) and diisopropylazodicarboxylate (0.19 ml, 0.989 mmol). MP: 209-212° C. $^1$H-NMR (δ ppm, CDCl$_3$, 400 MHz): δ 8.26 (s, 1H), 7.61 (dt, J=8.4, 5.4 Hz, 1H), 7.44 (dd, J=11.4, 2.0 Hz, 1H), 7.37 (dd, J=8.3, 1.0 Hz, 1H), 7.23 (m, 2H), 7.15 (t, J=8.4 Hz, 1H), 7.07 (m, 3H), 6.06 (q, J=7.1 Hz, 1H), 5.42 (s, 2H), 4.66 (quintet, J=6.1 Hz, 1H), 1.99 (d, J=7.1 Hz, 3H), 1.42 (d, J=6.0 Hz, 6H). Enantiomeric excess: 66% as determined by HPLC on a chiralpak AD-H column, enriched in the late eluting isomer (retention time=15.96 min.).

Example 96

(S)/(R)-2-(1-(4-amino-3-(4-(difluoromethoxy)-3-fluorophenyl)-1H-pyrazolo[3,4-d]pyrimidin-1-yl)ethyl)-5-fluoro-3-(4-fluorophenyl)-4H-chromen-4-one (S)/(R)-2-(1-(4-amino-3-(4-(difluoromethoxy)-3-fluorophenyl)-1H-pyrazolo[3,4-d]pyrimidin-1-yl)ethyl)-5-fluoro-3-(4-fluorophenyl)-4H-chromen-4-one: The title compound was obtained as pale yellow (0.018 g, 5%) by using a procedure that is similar to the one described for example 7 from intermediate 39 (0.204 g, 0.692 mmol), intermediate 113 (0.175 g, 0.577 mmol), tris-4-methoxytriphenylphosphine (0.305 g, 0.865 mmol), THF (3 ml) and diisopropylazodicarboxylate (0.17 ml, 0.865 mmol). MP: 246-248° C. $^1$H-NMR (δ ppm, CDCl$_3$, 400 MHz): δ 8.28 (s, 1H), 7.61 (m, 2H), 7.47 (m, 2H), 7.22 (m, 3H), 7.08 (m, 3H), 6.82 (t, J=73 Hz, 1H), 6.08 (q, J=7.1 Hz, 1H), 5.43 (s, 2H), 1.99 (d, J=7.1 Hz, 3H). Enantiomeric excess: 38.4% as determined by HPLC on a chiralpak AD-H column, enriched in the fast eluting isomer (retention time=10.34 min.).

Example 97

(S)/(R)-2-(1-(4-amino-3-(4-(difluoromethoxy)-3-fluorophenyl)-1H-pyrazolo[3,4-d]pyrimidin-1-yl)ethyl)-5-fluoro-3-(4-fluorophenyl)-4H-chromen-4-one (S)/(R)-2-(1-(4-amino-3-(4-(difluoromethoxy)-3-fluorophenyl)-1H-pyrazolo[3,4-d]pyrimidin-1-yl)ethyl)-5-fluoro-3-(4-fluorophenyl)-4H-chromen-4-one: The title compound was obtained as pale yellow solid (0.045 g, 12%) by using a procedure that is similar to the one described for example 7 from intermediate 39 (0.233 g, 0.791 mmol), intermediate 114 (0.200 g, 0.659 mmol), tris-4-methoxytriphenylphosphine (0.348 g, 0.989 mmol), THF (4 ml) and diisopropylazodicarboxylate (0.19 ml, 0.989 mmol). MP: 242-244° C. $^1$H-NMR (δ ppm, CDCl$_3$, 400 MHz): δ 8.29 (s, 1H), 7.61 (m, 2H), 7.47 (m, 2H), 7.25 (m, 3H), 7.08 (m, 3H), 6.82 (t, J=73 Hz, 1H), 6.06 (q, J=7.1 Hz, 1H), 5.39 (s, 2H), 1.99 (d, J=7.1 Hz, 3H). Enantiomeric excess: 46.8% as determined by HPLC on a chiralpak AD-H column, enriched in the late eluting isomer (retention time=18.36 min.).

Example 98

2-(1-(4-(dimethylamino)-3-(3-fluoro-4-morpholinophenyl)-1H-pyrazolo[3,4-d]pyrimidin-1-yl)ethyl)-5-fluoro-3-(3-fluorophenyl)-4H-chromen-4-one 2-(1-(4-(dimethylamino)-3-(3-fluoro-4-morpholinophenyl)-1H-pyrazolo[3,4-d]pyrimidin-1-yl)ethyl)-5-fluoro-3-(3-fluorophenyl)-4H-chromen-4-one: The title compound was obtained as a off-white solid (0.085 g, 31%) by using a procedure that is similar to the one described for example 6 from intermediate 117 (0.150 g, 0.438 mmol), DMF (2 ml), potassium carbonate (0.073 g, 0.525 mmol) and intermediate 22 (0.224 g, 0.0.613 mmol). MP: 208-210° C. $^1$H-NMR (δ ppm, CDCl$_3$, 400 MHz): 8.23 (s, 1H), 7.62 (dt, J=8.4, 5.5 Hz, 1H), 7.34-7.28 (m, 4H), 7.06-6.92 (m, 4H), 6.83 (d, J=8.1 Hz, 1H), 6.10 (q, J=7.1 Hz, 1H), 3.91 (t, J=4.5 Hz, 4H), 3.16 (t, J=4.6 Hz, 4H), 2.92 (s, 6H), 1.96 (d, J=7.1 Hz, 3H).

Example 99

5-fluoro-2-(1-(3-(3-fluoro-4-morpholinophenyl)-4-(methylamino) 1H-pyrazolo[3,4-d]pyrimidin-1-yl)-yl)ethyl)-3-(3-fluorophenyl)-4H-chromen-4-one 5-fluoro-2-(1-(3-(3-fluoro-4-morpholinophenyl)-4-(methylamino)-1H-pyrazolo[3,4-d]pyrimidin-1-yl)ethyl)-3-(3-fluorophenyl)-4H-chromen-4-one: The title compound was obtained as a off-white solid (0.075 g, 27%) by using a procedure that is similar to the one described for example 6 from intermediate 118 (0.150 g, 0.456 mmol), DMF (2 ml), potassium carbonate (0.075 g, 0.540 mmol) and intermediate 22 (0.237 g, 0.0.630 mmol). MP: 238-240° C. $^1$H-NMR (δ ppm, CDCl$_3$, 400 MHz): 8.30 (s, 1H), 7.62 (dt, J=8.4, 5.5 Hz, 1H), 7.36-7.27 (m, 4H), 7.06-6.98 (m, 4H), 6.89 (d, J=10.6 Hz, 1H), 6.04 (q, J=7.2 Hz, 1H), 5.32 (q, J=4.8 Hz, 1H), 3.92 (t, J=4.5 Hz, 4H), 3.19 (t, J=4.6 Hz, 4H), 3.09 (d, J=4.9 Hz, 3H), 1.97 (d, J=7.2 Hz, 3H).

Example 100

(S)/(R)-2-(1-(4-amino-3-(3-fluoro-4-isopropoxyphenyl)-1H-pyrazolo[3,4-d]pyrimidin-1-yl)ethyl)-5-fluoro-3-phenyl-4H-chromen-4-one (S)/(R)-2-(1-(4-amino-3-(3-fluoro-4-isopropoxyphenyl)-1H-pyrazolo[3,4-d]pyrimidin-1-yl)ethyl)-5-fluoro-3-phenyl-4H-chromen-4-one: The title compound was obtained as off-white solid (0.050 g, 14%) by using a procedure that is similar to the one described for example 7 from intermediate 13 (0.212 g, 0.738 mmol), intermediate 115 (0.175 g, 0.615 mmol), tris-4-methoxytriphenylphosphine (0.325 g, 0.923 mmol), THF (3 ml) and diisopropylazodicarboxylate (0.18 ml, 0.923 mmol). MP: 205-208° C. $^1$H-NMR (δ ppm, CDCl$_3$, 400 MHz): δ 8.23 (s, 1H), 7.60 (dt, J=8.4, 5.4 Hz, 1H), 7.44 (dd, J=11.5, 2.0 Hz, 1H), 7.37-7.29 9m, 4H), 7.23 (m, 3H), 7.14 (t, J=8.4 Hz, 1H), 7.04 (t, J=10.1 Hz, 1H), 6.08 (q, J=7.1 Hz, 1H), 5.42 (s, 2H), 4.65 (quintet, J=6.1 Hz, 1H), 1.98 (d, J=7.2 Hz, 3H), 1.42 (d, J=6.1 Hz, 6H). Enantiomeric excess: 81% as determined by HPLC on a chiralpak AD-H column, enriched in the fast eluting isomer (retention time=10.12 min.).

Example 101

(S)/(R)-2-(1-(4-amino-3-(3-fluoro-4-isopropoxyphenyl)-1H-pyrazolo[3,4-d]pyrimidin-1-yl)ethyl)-5-fluoro-3-phenyl-4H-chromen-4-one (S)/(R)-22-(1-(4-amino-3-(3-fluoro-4-isopropoxyphenyl)-1H-pyrazolo[3,4-d]pyrimidin-1-yl)ethyl)-5-fluoro-3-phenyl-4H-chromen-4-one: The title compound was obtained as off-white solid (0.067 g, 19%) by using a procedure that is similar to the one described for example 7 from intermediate 13 (0.212 g, 0.738 mmol), intermediate 116 (0.175 g, 0.615 mmol), tris-4-methoxytriphenylphosphine (0.325 g, 0.923 mmol), THF (3 ml) and diisopropylazodicarboxylate (0.18 ml, 0.923 mmol). MP: 185-188° C. $^1$H-NMR (5 ppm, CDCl$_3$, 400 MHz): δ 8.23 (s, 1H), 7.60 (dt, J=8.4, 5.5 Hz, 1H), 7.44 (dd, I=11.5, 2.0 Hz, 1H), 7.37-7.29 (m, 4H), 7.23 (m, 3H), 7.14 (t, J=8.3 Hz, 1H), 7.04 (t, J=9.9 Hz, 1H), 6.08 (q, J=7.1 Hz, 1H), 5.43 (s, 2H), 4.64 (quintet, J=6.0 Hz, 1H), 1.98 (d, J=7.2 Hz, 3H), 1.42 (d, J=6.0 Hz, 6H). Enantiomeric excess: 73.5% as determined by HPLC on a chiralpak AD-H column, enriched in the late eluting isomer (retention time=13.20 min.).

Example 102

(S)/(R)-2-(1-(4-amino-3-(4-(difluoromethoxy)-3-fluorophenyl)-1H-pyrazolo[3,4-d]pyrimidin-1-yl)ethyl)-5-fluoro-3-phenyl-4H-chromen-4-one (S)/(R)-2-(1-(4-amino-3-(4-(difluoromethoxy)-3-fluorophenyl)-1H-pyrazolo[3,4-d]pyrimidin-1-yl)ethyl)-5-fluoro-3-phenyl-4H-chromen-4-one: The title compound was obtained as pale yellow solid (0.069 g, 20%) by using a procedure that is similar to the one described for example 7 from intermediate 39 (0.218 g, 0.738 mmol), intermediate 115 (0.175 g, 0.615 mmol), tris-4-methoxytriphenylphosphine (0.325 g, 0.923 mmol), THF (3 ml) and diisopropylazodicarboxylate (0.18 ml, 0.923 mmol). MP: 247-250° C. $^1$H-NMR (δ ppm, CDCl$_3$, 400 MHz): δ 8.26 (s, 1H), 7.60 (m, 2H), 7.47 (m, 2H), 7.35 (m, 3H), 7.24 (m, 3H), 7.05 (t, J=10.1 Hz, 1H), 6.81 (t, J=73 Hz, 1H), 6.10 (q, J=7.1 Hz, 1H), 5.39 (s, 2H), 1.99 (d, J=7.1 Hz, 3H). Enantiomeric excess: 64.7% as determined by HPLC on a chiralpak AD-H column, enriched in the fast eluting isomer (retention time=9.78 min.).

Example 103

(S)/(R)-2-(1-(4-amino-3-(4-(difluoromethoxy)-3-fluorophenyl)-1H-pyrazolo[3,4-d]pyrimidin-1-yl)ethyl)-5-fluoro-3-phenyl-4H-chromen-4-one (S)/(R)-2-(1-(4-amino-3-(4-(difluoromethoxy)-3-fluorophenyl)-1H-pyrazolo[3,4-d]pyrimidin-1-yl)ethyl)-5-fluoro-3-phenyl-4H-chromen-4-one: The title compound was obtained as pal yellow solid (0.033 g, 6%) by using a procedure that is similar to the one described for example 7 from intermediate 39 (0.218 g, 0.738 mmol), intermediate 116 (0.175 g, 0.615 mmol), tris-4-methoxytriphenylphosphine (0.325 g, 0.923 mmol), THF (3 ml) and diisopropylazodicarboxylate (0.18 ml, 0.923 mmol). MP: 217-220° C. $^1$H-NMR (δ ppm, CDCl$_3$, 400 MHz): δ 8.26 (s, 1H), 7.60 (m, 2H), 7.47 (m, 2H), 7.35 (m, 3H), 7.26 (m, 3H), 7.05 (t, J=9.7 Hz, 1H), 6.81 (t, J=73 Hz, 1H), 6.08 (q, J=7.2 Hz, 1H), 5.38 (s, 2H), 1.99 (d, J=7.2 Hz, 3H). Enantiomeric excess: 47.4% as determined by HPLC on a chiralpak AD-H column, enriched in the late eluting isomer (retention time=14.01 min.).

Example 104

(+)-5-fluoro-2-(1-(3-(3-fluoro-4-isopropoxyphenyl)-4-(methylamino)-1H-pyrazolo[3,4-d]pyrimidin-1-yl)ethyl)-3-(3-fluorophenyl)-4H-chromen-4-one (+)-5-fluoro-2-(1-(3-(3-fluoro-4-isopropoxyphenyl)-4-(methylamino)-1H-pyrazolo[3,4-d]pyrimidin-1-yl)ethyl)-3-(3-fluorophenyl)-4H-chromen-4-one: The title compound was obtained as off-white solid (0.212 g, 54%) by using a procedure that is similar to the one described for example 7 from intermediate 119 (0.218 g, 0.725 mmol), intermediate 23b (0.200 g, 0.659 mmol), tris-4-methoxytriphenylphosphine (0.348 g, 0.980 mmol), THF (4 ml) and diisopropylazodicarboxylate (0.19 ml, 0.989 mmol). MP: 199-202° C. $^1$H-NMR (δ ppm, CDCl$_3$, 400 MHz): δ 8.30 (s, 1H), 7.61 (dt, J=8.4, 5.4 Hz, 1H), 7.39 (dd, J=11.5, 2.1 Hz, 1H), 7.31 (m, 3H), 7.15 (t, J=8.4 Hz, 1H), 7.06 (m, 3H), 6.90 (t, J=9.9 Hz, 1H), 6.04 (q, J=7.1 Hz, 1H), 5.31 (q, J=4.9 Hz, 1H), 4.66 (quintet, J=6.1 Hz, 1H), 3.09 (d, J=4.9 Hz, 3H), 1.97 (d, J=7.1 Hz, 3H), 1.43 (d, J=6.1 Hz, 6H). Enantiomeric excess: 96.5% as determined by HPLC on a chiralpak AD-H column, enriched in the fast eluting isomer (retention time=8.91 min.), $[\alpha]^{25}_D$ 181.67 (C=1, CHCl$_3$).

Example 105

(−)-5-fluoro-2-(1-(3-(3-fluoro-4-isopropoxyphenyl)-4-(methylamino)-1H-pyrazolo[3,4-d]pyrimidin-1-yl)ethyl)-3-(3-fluorophenyl)-4H-chromen-4-one (−)-5-fluoro-2-(1-(3-(3-fluoro-4-isopropoxyphenyl)-4-(methylamino)-1H-pyrazolo[3,4-d]pyrimidin-1-yl)ethyl)-3-(3-fluorophenyl)-4H-chromen-4-one: The title compound was obtained as off-white solid (0.201 g, 52%) by using a procedure that is similar to the one described for example 7 from intermediate 119 (0.218 g, 0.725 mmol), intermediate 23a (0.200 g, 0.659 mmol), tris-4-methoxytriphenylphosphine (0.348 g, 0.980 mmol), THF (4 ml) and diisopropylazodicarboxylate (0.19 ml, 0.989 mmol). MP: 216-218° C. $^1$H-NMR (δ ppm, CDCl$_3$, 400 MHz): δ 8.30 (s, 1H), 7.61 (dt, J=8.4, 5.4 Hz, 1H), 7.39 (dd, J=11.5, 2.1 Hz, 1H), 7.31 (m, 2H), 7.27 (m, 1H), 7.15 (t, J=8.4 Hz, 1H), 7.05 (m, 3H), 6.90 (t, J=9.8 Hz, 1H), 6.06 (q, J=7.1 Hz, 1H), 5.30 (q, J=4.7 Hz, 1H), 4.99 (quintet, J=6.2 Hz, 1H), 3.09 (d, J=4.9 Hz, 3H), 1.97 (d, J=7.2 Hz, 3H), 1.43 (d, I=6.0 Hz, 6H). Enantiomeric excess: 88.4% as determined by HPLC on a chiralpak AD-H column, enriched in the late eluting isomer (retention time=1.22 min.) $[α]^{25}{}_D$ 172.64 (c=1, CHCl$_3$).

Example 106

2-(1-(6-amino-2-fluoro-9H-purin-9-yl)ethyl)-5-fluoro-3-(3-fluorophenyl)-4H-chromen-4-one 2-(1-(6-amino-2-fluoro-9H-purin-9-yl)ethyl)-5-fluoro-3-(3-fluorophenyl)-4H-chromen-4-one: The title compound was obtained as a off-white solid (0.180 g, 63%) by using a procedure that is similar to the one described for example 6 from 2-fluoro-9H-purin-6-amine (0.100 g, 0.653 mmol), DMF (2 ml), potassium carbonate (0.108 g, 0.783 mmol) and intermediate 22 (0.330 g, 0.0.914 mmol). MP: 255-258° C. $^1$H-NMR (δ ppm, CDCl$_3$, 400 MHz): 8.42 (s, 1H), 7.83 (m, 3H), 7.53 (d, J=8.6 Hz, 1H), 7.49 (m, 1H), 7.28-7.13 (m, 4H), 5.52 (q, J=7.1 Hz, 1H), 1.87 (d, J=7.2 Hz, 3H). Mass: 437.7 (M$^+$).

Example 107

2-(1-(6-amino-2-fluoro-9H-purin-9-yl)ethyl)-5-fluoro-3-(4-fluorophenyl)-4H-chromen-4-one 2-(1-(6-amino-2-fluoro-9H-purin-9-yl)ethyl)-5-fluoro-3-(4-fluorophenyl)-4H-chromen-4-one: The title compound was obtained as a off-white solid (0.120 g, 42%) by using a procedure that is similar to the one described for example 6 from 2-fluoro-9H-purin-6-amine (0.100 g, 0.653 mmol), DMF (2 ml), potassium carbonate (0.108 g, 0.783 mmol) and intermediate 31 (0.330 g, 0.0.914 mmol). MP: 272-275° C. $^1$H-NMR (δ ppm, CDCl$_3$, 400 MHz): 8.41 (s, 1H), 7.83 (m, 3H), 7.52 (d, J=8.6 Hz, 1H), 7.35-7.22 (m, 5H), 5.49 (q, J=7.2 Hz, 1H), 1.87 (d, J=7.2 Hz, 3H).

Example 108

5-fluoro-3-(4-fluorophenyl)-2-(1-(6-morpholino-9H-purin-9-yl)ethyl)-4H-chromen-4-one 5-fluoro-3-(4-fluorophenyl)-2-(1-(6-morpholino-9H-purin-9-yl)ethyl)-4H-chromen-4-one: The title compound was obtained as a off-white solid (0.090 g, 47%) by using a procedure that is similar to the one described for example 6 from 4-(9H-purin-6-yl)morpholine (0.080 g, 0.389 mmol for preparation see Tetrahedron, 2007, 63, 5323-5328), DMF (1.5 ml), potassium carbonate (0.064 g, 0.467 mmol) and intermediate 31 (0.185 g, 0.0.506 mmol). MP: 186-189° C. $^1$H-NMR (δ ppm, CDCl$_3$, 400 MHz): 8.26 (s, 1H), 8.04 (s, 1H), 7.60 (dt, J=8.4, 5.4 Hz, 1H), 7.37 (m, 2H), 7.26 (m, 3H), 7.04 (t, J=9.4 Hz, 1H), 5.89 (q, J=7.3 Hz, 1H), 4.29 br s, 4H), 3.84 (t, J=4.9 Hz, 4H), 1.90 (d, J=7.3 Hz, 3H).

Example 109

5-fluoro-3-(4-fluorophenyl)-2-(1-(6-(4-methylpiperazin-1-yl)-9H-purin-9-yl)ethyl)-4H-chromen-4-one 5-fluoro-3-(4-fluorophenyl)-2-(1-(6-(4-methylpiperazin-1-yl)-9H-purin-9-yl)ethyl)-4H-chromen-4-one: The title compound was obtained as a off-white solid (0.012 g, 8%) by using a procedure that is similar to the one described for example 6 from 6-(4-methylpiperazin-1-yl)-9H-purine (0.060 g, 0.274 mmol), DMF (1.5 ml), potassium carbonate (0.046 g, 0.329 mmol) and intermediate 31 (0.130 g, 0.0.357 mmol). MP: 157-160° C. $^1$H-NMR (δ ppm, CDCl$_3$, 400 MHz): 8.25 (s, 1H), 8.04 (s, 1H), 7.62 (dt, J=8.4, 5.4 Hz, 1H), 7.37 (m, 2H), 7.25 (m, 3H), 7.07 (dt, J=9, 0.7 Hz, 1H), 5.90 (q, J=7.2 Hz, 1H), 4.31 br s, 4H), 2.54 (br s, 4H), 2.34 (s, 3H), 1.89 (d, J=7.3 Hz, 3H).

Example 110

2-(1-(6-(dimethylamino)-9H-purin-9-yl)ethyl)-5-fluoro-3-(3-fluorophenyl)-4H-chromen-4-one 2-(1-(6-(dimethylamino)-9H-purin-9-yl)ethyl)-5-fluoro-3-(3-fluorophenyl)-4H-chromen-4-one: The title compound was obtained as a brown solid (0.045 g, 20%) by using a procedure that is similar to the one described for example 6 from N,N-dimethyl-9H-purin-6-amine (0.080 g, 0.490 mmol for preparation see J. Het. Chem. 1983, 20, 295-199), DMF (2 ml), potassium carbonate (0.081 g, 0.588 mmol) and intermediate 22 (0.250 g, 0.0.686 mmol). MP: 166-169° C. $^1$H-NMR (δ ppm, CDCl$_3$, 400 MHz): 8.26 (s, 1H), 8.00 (s, 1H), 7.61 (dt, J=8.5, 5.5 Hz, 1H), 7.48 (dd, J=7.9, 5.9 Hz, 1H), 7.22 (m, 4H), 7.07 (dt, J=8.3, 0.8 Hz, 1H), 5.87 (q, J=7.2 Hz, 1H), 3.52 (s, 6H), 1.90 (d, J=7.3 Hz, 3H).

Example 111

2-(1-(6-(dimethylamino)-9H-purin-9-yl)ethyl)-5-fluoro-3-(3-fluorophenyl)-4H-chromen-4-one 5-fluoro-3-(3-fluorophenyl)-2-(1-(6-(methylamino)-9H-purin-9-yl)ethyl)-4H-chromen-4-one: The title compound was obtained as a off-white solid (0.020 g, 9%) by using a procedure that is similar to the one described for example 6 from N-methyl-9H-purin-6-amine (0.080 g, 0.534 mmol for preparation see Bull. Soc. Jpn. 1986, 62, 3155-3160. DMF (2 ml), potassium carbonate (0.087 g, 0.641 mmol) and intermediate 22 (0.273 g, 0.0.748 mmol). MP: 207-209° C. Mass: 433.9 (M').

Example 112

5-fluoro-3-(3-fluorophenyl)-2-(1-(3-(3-methyl-1H-indazol-6-yl)-4-morpholino-1H-pyrazolo[3,4-d]pyrimidin-1-yl)ethyl)-4H-chromen-4-one 5-fluoro-3-(3-fluorophenyl)-2-(1-(3-(3-methyl-1H-indazol-6-yl)-4-morpholino-1H-pyrazolo[3,4-d]pyrimidin-1-yl)ethyl)-4H-chromen-4-one: The title compound was obtained as brown solid (0.050 g, 25%) by using a procedure that is similar to the one described for example 9 from intermediate 106 (0.200 g, 0.325 mmol), 1,2-dimethoxyethane (3 ml), water (1.5 ml), tert-butyl 3-methyl-6-(4,4,5,5-tetramethyl-1,3,2-dioxaborolan-2-yl)-1H-indazole-1-carboxylate (0.174 g, 0.487 mmol), sodium carbonate (0.103 g, 0.975 mmol) and bis(diphenylphosphino)ferrocene]dichloro palladium(II).CH$_2$Cl$_2$ (0.053 g, 0.065 mmol) MP: 183-186° C. Mass: 619.8 (M$^+$+1).

Example 113

2-(1-(4-amino-3-(3-chloro-4-morpholinophenyl)-1H-pyrazolo[3,4-d]pyrimidin-1-yl)ethyl)-5-fluoro-3-(3-fluorophenyl)-4H-chromen-4-one 2-(1-(4-amino-3-(3-chloro-4-morpholinophenyl)-1H-pyrazolo[3,4-d]pyrimidin-1-yl)ethyl)-5-fluoro-3-(3-fluorophenyl)-4H-chromen-4-one: The title compound was obtained as brown solid (0.018 g, 10%) by using a procedure that is similar to the one described for example 9 from intermediate 27 (0.150 g, 0.275 mmol), 1,2-dimethoxyethane (3 ml), water (1.5 ml), intermediate 123 (0.134 g, 0.412 mmol), sodium carbonate (0.058 g, 0.550 mmol) and bis(diphenylphosphino)ferrocene]dichloro palladium(II).CH$_2$Cl$_2$ (0.044 g, 0.055 mmol) MP: 250-253° C. $^1$H-NMR (δ ppm, CDCl$_3$, 400 MHz): 8.25 (s, 1H), 7.71 (d, J=2.0 Hz, 1H), 7.59 (m, 2H), 7.27 (m, 2H), 7.19 (d, J=8.3 Hz, 1H), 7.05-6.99 (m, 4H), 6.06 (q, J=7.1 Hz, 1H), 5.38 (s, 2H), 3.92 (t, J=4.5 Hz, 4H), 3.14 (t, J=4.6 Hz, 4H), 1.99 (d, J=7.2 Hz, 3H).

Example 114

(+) 2-(1-(4-amino-3-(4-isopropoxy-3-methylphenyl)-1H-pyrazolo[3,4-d]pyrimidin-1-yl)ethyl)-5-fluoro-3-(3-fluorophenyl)-4H-chromen-4-one (+)-2-(1-(4-amino-3-(4-isopropoxy-3-methylphenyl)-1H-pyrazolo[3,4-d]pyrimidin-1-yl)ethyl)-5-fluoro-3-(3-fluorophenyl)-4H-chromen-4-one: The title compound was obtained as off-white solid (0.083 g, 30%) by using a procedure that is similar to the one described for example 7 from intermediate 84 (0.150 g, 0.529 mmol), intermediate 23b (0.145 g, 0.481 mmol), tris-4-methoxytriphenylphosphine (0.254 g, 0.721 mmol), THF (3 ml) and diisopropylazodicarboxylate (0.14 ml, 0.721 mmol). MP: 217-220° C. $^1$H-NMR (δ ppm, CDCl$_3$, 400 MHz): δ 8.22 (s, 1H), 7.61 (dt, J=8.4, 5.4 Hz, 1H), 7.43 (m, 2H), 7.29 (m, 2H), 7.05-6.97 (m, 4H), 6.92 (d, J=9.4 Hz, 1H), 6.07 (q, J=7.1 Hz, 1H), 5.42 (s, 2H), 4.63 (quintet, J=6.0 Hz, 1H), 2.28 (s, 3H), 1.97 (d, J=7.1 Hz, 3H), 1.39 (d, J=6.0 Hz, 6H). Enantiomeric excess: 100% as determined by HPLC on a chiralpak AD-H column, enriched in the fast eluting isomer (retention time=9.36 min.) [α]D 176.04 (c=1, CHCl$_3$).

Example 115

(−) 2-(1-(4-amino-3-(4-isopropoxy-3-methylphenyl)-1H-pyrazolo[3,4-d]pyrimidin-1-yl)ethyl)-5-fluoro-3-(3-fluorophenyl)-4H-chromen-4-one (−)-2-(1-(4-amino-3-(4-isopropoxy-3-methylphenyl)-1H-pyrazolo[3,4-d]pyrimidin-1-yl)ethyl)-5-fluoro-3-(3-fluorophenyl)-4H-chromen-4-one: The title compound was obtained as off-white solid (0.066 g, 28%) by using a procedure that is similar to the one described for example 7 from intermediate 84 (0.128 g, 0.453 mmol), intermediate 23a (0.125 g, 0.412 mmol), tris-4-methoxytriphenylphosphine (0.217 g, 0.618 mmol), THF (3 ml) and diisopropylazodicarboxylate (0.12 ml, 0.618 mmol). MP: 221-224° C. $^1$H-NMR (δ ppm, CDCl$_3$, 400 MHz): δ 8.22 (s, 1H), 7.61 (dt, J=8.4, 5.5 Hz, 1H), 7.43 (m, 2H), 7.29 (m, 2H), 7.05-6.95 (m, 4H), 6.92 (d, J=9.5 Hz, 1H), 6.05 (q, J=7.1 Hz, 1H), 5.40 (s, 2H), 4.62 (quintet, J=6.0 Hz, 1H), 2.28 (s, 3H), 1.99 (d, J=7.2 Hz, 3H), 1.39 (d, J=6.0 Hz, 6H). Enantiomeric excess: 99.6% as determined by HPLC on a chiralpak AD-H column, enriched in the late eluting isomer (retention time=11.43 min.) [α]$^{25}$$_D$ −183.59 (c=1, CHCl$_3$).

Example 116

(S)/(R)-5-fluoro-2-(1-(3-(3-fluoro-4-isopropoxyphenyl)-4-morpholino-1H-pyrazolo[3,4-d]pyrimidin-1-yl)ethyl)-3-(3-fluorophenyl)-4H-chromen-4-one (S)/(R)-5-fluoro-2-(1-(3-(3-fluoro-4-isopropoxyphenyl)-4-morpholino-1H-pyrazolo[3,4-d]pyrimidin-1-yl)ethyl)-3-(3-fluorophenyl)-4H-chromen-4-one: The title compound was obtained as pale yellow solid (0.044 g, 12%) by using a procedure that is similar to the one described for example 7 from intermediate 104 (0.243 g, 0.652 mmol), intermediate 23a (0.180 g, 0.593 mmol), tris-4-methoxytriphenylphosphine (0.272 g, 0.771 mmol), THF (3 ml) and diisopropylazodicarboxylate (0.17 ml, 0.890 mmol). MP: 136-138° C. Mass: 642.0 (M$^+$). Enantiomeric excess: 91.6% as determined by HPLC on a chiralpak AD-H column, enriched in the fast eluting isomer (retention time=10.27 min.).

Example 117

2-(1-(4-amino-3-(3-chloro-4-isopropoxyphenyl)-1H-pyrazolo[3,4-d]pyrimidin-1-yl)ethyl)-5-fluoro-3-(3-fluorophenyl)-4H-chromen-4-one 2-(1-(4-amino-3-(3-chloro-4-isopropoxyphenyl)-1H-pyrazolo[3,4-d]pyrimidin-1-yl)ethyl)-5-fluoro-3-(3-fluorophenyl)-4H-chromen-4-one: The title compound was obtained as brown solid (0.039 g, 24%) by using a procedure that is similar to the one described for example 9 from intermediate 27 (0.150 g, 0.275 mmol), 1,2-dimethoxyethane (3 ml), water (1.5 ml), intermediate 125 (0.107 g, 0.412 mmol), sodium carbonate (0.088 g, 0.825 mmol) and bis(diphenylphosphino)ferrocene]dichloro palladium(II).CH$_2$Cl$_2$ (0.044 g, 0.055 mmol). MP: 207-210° C. $^1$H-NMR (δ ppm, CDCl$_3$, 400 MHz): 8.24 (s, 1H), 7.70 (d, J=2.2 Hz, 1H), 7.62 (dt, J=8.3, 5.3 Hz, 1H), 7.51 (dd, J=8.4, 2.2 Hz, 1H), 7.31 (m, 2H), 7.10 (d, J=8.6 Hz, 1H), 7.06 (m, 3H), 6.92 (d, J=9.6 Hz, 1H), 6.06 (q, J=7.2 Hz, 1H), 5.38 (s, 2H), 4.66 (quintet, J=6.1 Hz, 1H), 1.99 (d, J=7.2 Hz, 3H), 1.44 (d, J=6.0 Hz, 6H).

Example 118

2-(1-(4-amino-3-(2-methylbenzo[d]oxazol-6-yl)-1H-pyrazolo[3,4-d]pyrimidin-1-yl)ethyl)-5-fluoro-3-(3-fluorophenyl)-4H-chromen-4-one 2-(1-(4-amino-3-(2-methylbenzo[d]oxazol-6-yl)-1H-pyrazolo[3,4-d]pyrimidin-1-yl)ethyl)-5-fluoro-3-(3-fluorophenyl)-4H-chromen-4-one: The title compound was obtained as brown solid (0.017 g, 11%) by using a procedure that is similar to the one described for example 9 from intermediate 27 (0.150 g, 0.275 mmol), 1,2-dimethoxyethane (3 ml), water (1.5 ml), intermediate 127 (0.107 g, 0.412 mmol), sodium carbonate (0.088 g, 0.825 mmol) and bis(diphenylphosphino)ferrocene]dichloro palladium(II).CH$_2$Cl$_2$ (0.044 g, 0.055 mmol). MP: 215-217° C. $^1$H-NMR (δ ppm, CDCl$_3$, 400 MHz): 8.26 (s, 1H), 7.81 (m, 2H), 7.63

(m, 2H), 7.30 (m, 2H), 7.06 (m, 3H), 6.94 (d, J=9.3 Hz, 1H), 6.10 (q, J=7.1 Hz, 1H), 5.48 (s, 2H), 2.70 (s, 3H), 2.01 (d, J=7.1 Hz, 3H).

Example 119

5-fluoro-3-(3-fluorophenyl)-2-(1-(6-morpholino-9H-purin-9-yl)ethyl)-4H-chromen-4-one 5-fluoro-3-(3-fluorophenyl)-2-(1-(6-morpholino-9H-purin-9-yl)ethyl)-4H-chromen-4-one: The title compound was obtained as a yellow solid (0.060 g, 31%) by using a procedure that is similar to the one described for example 6 from 4-(9H-purin-6-yl)morpholine (0.080 g, 0.389 mmol for preparation see J. Med. Chem. 2010, 53, 8421-8439), DMF (1.5 ml), potassium carbonate (0.064 g, 0.467 mmol) and intermediate 22 (0.185 g, 0.0.506 mmol). MP: 239-241° C. Mass: 490.1 (M$^+$+1).

Example 120

2-(1-(4-amino-3-(3-fluoro-4-Isopropoxyphenyl)-1H-pyrazolo[3,4-d]pyrimidin-1-yl)ethyl)-3-(3-fluorophenyl)-5-morpholino-4H-chromen-4-one 2-(1-(4-amino-3-(3-fluoro-4-isopropoxyphenyl)-1H-pyrazolo[3,4-d]pyrimidin-1-yl)ethyl)-3-(3-fluorophenyl)-5-morpholino-4H-chromen-4-one: To a solution of example 6 (0.100 g, 0.174 mmol) in dioxan (1 ml), morpholine (0.015 g, 0.174 mmol) was added and refluxed for 3 h. The reaction mixture was quenched with water, the product precipitated was filtered, washed with water, petroleum ether and dried under vacuum to afford the title compound as a pale yellow solid (0.090 g, 80%). MP: 227-229° C. $^1$H-NMR (δ ppm, CDCl$_3$, 400 MHz): 8.23 (s, 1H), 7.54 (t, J=8.3 Hz, 1H), 7.44 (dd, J=11.5, 2.0 Hz, 1H), 7.37 (d, J=8.3 Hz, 1H), 7.29 (m, 1H), 7.14 (t, J=8.4 Hz, 1H), 7.05 (d, J=8.3 Hz, 1H), 6.98 (m, 2H), 6.85 (m, 2H), 5.98 (q, J=7.2 Hz, 1H), 5.38 (s, 2H), 4.64 (quintet, J=6.1 Hz, 1H), 3.90 (t, J=4.2 Hz, 4H), 3.07 (t, J=4.2 Hz, 4H), 1.96 (d, J=7.2 Hz, 3H), 1.42 (d, J=6.0 Hz, 6H). Mass: 638.8 (M$^+$).

Example 121

2-(1-(4-amino-3-(3-fluoro-4-isopropoxyphenyl)-1H-pyrazolo[3,4-d]pyrimidin-1-yl)ethyl)-5-morpholino-3-phenyl-4H-chromen-4-one 2-(1-(4-amino-3-(3-fluoro-4-isopropoxyphenyl)-1H-pyrazolo[3,4-d]pyrimidin-1-yl)ethyl)-5-morpholino-3-phenyl-4H-chromen-4-one: To a solution of example 13 (0.040 g, 0.072 mmol) in dioxan (1 ml), morpholine (0.007 g, 0.072 mmol) was added and refluxed for 3 h. The reaction mixture was quenched with water, the product precipitated was filtered, washed with water, petroleum ether and dried under vacuum to afford the title compound as a pale yellow solid (0.030 g, 67%). MP: 211-214° C. Mass: 621.2 (M$^+$+1).

Example 122

6-(4-amino-1-(1-(5-fluoro-3-(3-fluorophenyl)-4-oxo-4H-chromen-2-yl)ethyl)-1H-pyrazolo[3,4-d]pyrimidin-3-yl)isoindolin-1-one 6-(4-amino-1-(1-(5-fluoro-3-(3-fluorophenyl)-4-oxo-4H-chromen-2-yl)ethyl)-1H-pyrazolo[3,4-d]pyrimidin-3-yl)isoindolin-1-one: The title compound was obtained as brown solid (0.045 g, 30%) by using a procedure that is similar to the one described for example 9 from intermediate 27 (0.150 g, 0.275 mmol), 1,2-dimethoxyethane (3 ml), water (1.5 ml), intermediate 128 (0.106 g, 0.412 mmol), sodium carbonate (0.058 g, 0.550 mmol) and bis(diphenylphosphino)ferrocene]dichloro palladium(II).CH$_2$Cl$_2$ (0.044 g, 0.055 mmol). MP: 242-245° C. Mass: 551.0 (M$^+$+1).

Example 123

5-(4-amino-1-(1-(5-fluoro-3-(3-fluorophenyl)-4-oxo-4H-chromen-2-yl)ethyl)-1H-pyrazolo[3,4-d]pyrimidin-3-yl)isoindolin-1-one 5-(4-amino-1-(1-(5-fluoro-3-(3-fluorophenyl)-4-oxo-4H-chromen-2-yl)ethyl)-1H-pyrazolo[3,4-d]pyrimidin-3-yl)isoindolin-1-one: The title compound was obtained as brown solid (0.052 g, 35%) by using a procedure that is similar to the one described for example 9 from intermediate 27 (0.150 g, 0.275 mmol), 1,2-dimethoxyethane (3 ml), water (1.5 ml), intermediate 129 (0.106 g, 0.412 mmol), sodium carbonate (0.058 g, 0.550 mmol) and bis(diphenylphosphino)ferrocene]dichloro palladium(II).CH$_2$Cl$_2$ (0.044 g, 0.055 mmol). MP: 293-296° C. Mass: 550.7 (M$^+$).

Example 124

2-(1-(3-(4-acetyl-3-fluorophenyl)-4-amino-1H-pyrazolo[3,4-d]pyrimidin-1-yl)ethyl)-5-fluoro-3-(3-fluorophenyl)-4H-chromen-4-one 2-(1-(3-(4-acetyl-3-fluorophenyl)-4-amino-1H-pyrazolo[3,4-d]pyrimidin-1-yl)ethyl)-5-fluoro-3-(3-fluorophenyl)-4H-chromen-4-one: The title compound was obtained as brown solid (0.045 g, 29%) by using a procedure that is similar to the one described for example 9 from intermediate 27 (0.150 g, 0.275 mmol), 1,2-dimethoxyethane (3 ml), water (1.5 ml), intermediate 130 (0.106 g, 0.412 mmol), sodium carbonate (0.087 g, 0.825 mmol) and bis(diphenylphosphino)ferrocene]dichloro palladium(II).CH$_2$Cl$_2$ (0.044 g, 0.055 mmol). MP: 237-239° C. $^1$H-NMR (δ ppm, CDCl$_3$, 400 MHz): 8.29 (s, 1H), 8.08 (t, J=7.7 Hz, 1H), 7.62 (m, 3H), 7.32 (m, 2H), 7.07 (m, 3H), 6.92 (d, J=9.1 Hz, 1H), 6.09 (q, J=7.1 Hz, 1H), 5.39 (s, 2H), 2.71 (d, J=4.8 Hz, 3H), 2.01 (d, J=7.1 Hz, 3H).

Example 125

5-fluoro-3-(3-fluorophenyl)-2-(1-(6-(4-methylpiperazin-1-yl)-9H-purin-9-yl)ethyl)-4H-chromen-4-one 5-fluoro-3-(3-fluorophenyl)-2-(1-(6-(4-methylpiperazin-1-yl)-9H-purin-9-yl)ethyl)-4H-chromen-4-one: The title compound was obtained as a off-white solid (0.052 g, 9%) by using a procedure that is similar to the one described for example 6 from 6-(4-methylpiperazin-1-yl)-9H-purine (0.240 g, 1.09 mmol for preparation see Tetrahedron, 2007, 63, 5323-5328.), DMF (4.8 ml), potassium carbonate (0.182 g, 1.31 mmol) and intermediate 22 (0.522 g, 0.1.429 mmol). MP: 199-201° C. Mass: 502.8 (M$^+$).

Example 126

(S)/(R)-2-(1-(4-amino-3-(3-chloro-4-morpholinophenyl)-1H-pyrazolo[3,4-d]pyrimidin-1-yl)ethyl)-5-fluoro-3-(3-fluorophenyl)-4H-chromen-4-one (S)/(R)-2-(1-(4-amino-3-(3-chloro-4-morpholinophenyl)-1H-pyrazolo[3,4-d]pyrimidin-1-yl)ethyl)-5-fluoro-3-(3- fluorophenyl)-4H-chromen-4-one: The title compound was obtained as off-white solid (0.036 g, 12%) by using a procedure that is similar to the one described for example 7 from intermediate 131 (0.196 g, 0.592 mmol), intermediate 23b (0.150 g, 0.494 mmol), tris-4-methoxytriphenylphosphine (0.261 g, 0.741 mmol), THF (4 ml) and diisopropylazodicarboxylate (0.13 ml, 0.741 mmol). MP: 256-258° C. $^1$H-NMR (δ ppm, CDCl$_3$, 400 MHz): δ 8.24 (s, 1H), 7.71 (d, J=2.1 Hz, 1H), 7.62 (dt, J=8.4, 5.4 Hz, 1H), 7.55 (dd, J=8.2, 2.0 Hz, 1H), 7.31 (m, 2H), 7.19 (d, J=8.3 Hz, 1H), 7.06 (m, 3H), 6.91 (d, J=9.7 Hz, 1H), 6.08 (q, J=7.1 Hz, 1H), 5.43 (s, 2H), 3.92 (t, J=4.4 Hz, 4H), 3.14 (d, J=4.5 Hz, 4H), 1.99 (d, J=7.2 Hz, 3H). Enantiomeric excess: 98.8% as determined by HPLC on a chiralpak AD-H column, enriched in the fast eluting isomer (retention time=15.07 min.).

Example 127

(S)/(R)-2-(1-(4-amino-3-(3-chloro-4-morpholinophenyl)-1H-pyrazolo[3,4-d]pyrimidin-1-yl)ethyl)-fluoro-3-(3-fluorophenyl)-4H-chromen-4-one (S)/(R)-2-(1-(4-amino-3-(3-chloro-4-morpholinophenyl)-1H-pyrazolo[3,4-d]pyrimidin-1-yl)ethyl)-5-fluoro-3-(3-fluorophenyl)-4H-chromen-4-one: The title compound was obtained as off-white solid (0.085 g, 28%) by using a procedure that is similar to the one described for example 7 from intermediate 131 (0.196 g, 0.592 mmol), intermediate 23a (0.150 g, 0.494 mmol), tris-4-methoxytriphenylphosphine (0.261 g, 0.741 mmol), THF (4 ml) and diisopropylazodicarboxylate (0.13 ml, 0.741 mmol). MP: 260-262° C. Mass: 616.9 (M$^+$+1). Enantiomeric excess: 96% as determined by HPLC on a chiralpak AD-H column, enriched in the late eluting isomer (retention time=22.42 min.).

Example 128

N-(3-(4-amino-1-(1-(5-fluoro-3-(3-fluorophenyl)-4-oxo-4H-chromen-2-yl)ethyl)H-pyrazolo[3,4-d]pyrimidin-3-yl)phenyl)methanesulfonamide N-(3-(4-amino-1-(1-(5-fluoro-3-(3-fluorophenyl)-4-oxo-4H-chromen-2-yl)ethyl)-1H-pyrazolo[3,4-d]pyrimidin-3-yl)phenyl)methanesulfonamide: The title compound was obtained as brown solid (0.050 g, 23%) by using a procedure that is similar to the one described for example 9 from intermediate 27 (0.200 g, 0.366 mmol), 1,2-dimethoxyethane (3 ml), water (1.5 ml), intermediate 132 (0.163 g, 0.549 mmol), sodium carbonate (0.116 g, 1.10 mmol) and bis(diphenylphosphino)ferrocene]dichloro palladium(II).CH$_2$Cl$_2$ (0.059 g, 0.073 mmol). MP: 259-261° C. $^1$H-NMR (δ ppm, CDCl$_3$, 400 MHz): 9.90 (s, 1H), 8.09 (s, 1H), 7.83 (dt, J=6.6, 1.0 Hz, 1H), 7.51 (m, 3H), 7.36-7.24 (m, 4H), 7.07 (dt, J=8.5, 2.5 Hz, 1H), 6.93 (m, 2H), 5.99 (q, J=7.1 Hz, 1H), 3.04 (s, 3H), 1.88 (d, J=7.1 Hz, 3H).

Example 129

(S)/(R)-2-(1-(6-(dimethylamino)-9H-purin-9-yl)ethyl)-1-fluoro-3-(3-fluorophenyl)-4H-chromen-4-one (S)/(R)-2-(1-(6-(dimethylamino)-9H-purin-9-yl)ethyl)-5-fluoro-3-(3-fluorophenyl)-4H-chromen-4-one: The title compound was obtained as off-white solid (0.020 g, 9%) by using a procedure that is similar to the one described for example 7 from N,N-dimethyl-9H-purin-6-amine (0.088 g, 0.543 mmol), intermediate 23b (0.150 g, 0.494 mmol), tris-4-methoxytriphenylphosphine (0.261 g, 0.741 mmol), THF (4 ml) and diisopropylazodicarboxylate (0.14 ml, 0.741 mmol). MP: 187-189° C. Mass: 448.0 (M$^+$+1). Enantiomeric excess: 100% as determined by HPLC on a chiralpak AD-H column, enriched in the fast eluting isomer (retention time=11.76 min.).

Example 130

(S)/(R)-2-(1-(6-(dimethylamino)-9H-purin-9-yl)ethyl)-5-fluoro-3-(3-fluorophenyl)-4H-chromen-4-one (S)/(R)-2-(1-(6-(dimethylamino)-9H-purin-9-yl)ethyl)-5-fluoro-3-(3-fluorophenyl)-4H-chromen-4-one: The title compound was obtained as off-white solid (0.016 g, 7%) by using a procedure that is similar to the one described for example 7 from N,N-dimethyl-9H-purin-6-amine (0.088 g, 0.543 mmol), intermediate 23a (0.150 g, 0.494 mmol), tris-4-methoxytriphenylphosphine (0.261 g, 0.741 mmol), THF (4 ml) and diisopropylazodicarboxylate (0.14 ml, 0.741 mmol). MP: 198-200° C. Mass: 447.7 (M$^+$). Enantiomeric excess: 94.8% as determined by HPLC on a chiralpak AD-H column, enriched in the late eluting isomer (retention time=19.68 min.).

Example 131

2-(1-(9H-purin-6-ylamino)ethyl)-5-fluoro-3-(2-fluorophenyl)-4H-chromen-4-one 2-(1-(9H-purin-6-ylamino)ethyl)-5-fluoro-3-(2-fluorophenyl)-4H-chromen-4-one: The title compound was obtained as pale-yellow solid (0.095 g, 33%) by using a procedure that is similar to the one described for example 7 from tert-butyl 9-trityl-9H-purin-6-ylcarbamate (0.396 g, 0.831 mmol), intermediate 135 (0.210 g, 0.692 mmol), triphenylphosphine (0.272 g, 1.03 mmol), THF (6 ml) and diisopropylazodicarboxylate (0.20 ml, 1.038 mmol), followed by the cleavage of the intermediate with trifluoroacetic acid (0.6 ml) and dichloromethane (3 ml). MP: 203-205° C. Mass: 419.7 (M$^+$).

Example 132

2-(1-(4-amino-3-(4-ethoxy-3-(trifluoromethyl)phenyl)-1H-pyrazolo[3,4-d]pyrimidin-1-yl)ethyl)-5-fluoro-3-(3-fluorophenyl)-4H-chromen-4-one 2-(1-(4-amino-3-(4-ethoxy-3-(trifluoromethyl)phenyl)-1H-pyrazolo[3,4-d]pyrimidin-1-yl)ethyl)-5-fluoro-3-(3-fluorophenyl)-4H-chromen-4-one: The title compound was obtained as brown solid (0.026 g, 12%) by using a procedure that is similar to the one described for example 9 from intermediate 27 (0.200 g, 0.366 mmol), 1,2-dimethoxyethane (3 ml), water (1.5 ml), 4-ethoxy-3-(trifluoromethyl)phenylboronic acid (0.128 g, 0.550 mmol), sodium carbonate (0.116 g, 1.10 mmol) and bis(diphenylphosphino)ferrocene]dichloro palladium(II).CH$_2$Cl$_2$ (0.059 g, 0.073 mmol). MP: 225-227° C. Mass: 608.1 (M$^+$+1).

Example 133

2-(1-(4-amino-3-(3-fluoro-4-isopropoxyphenyl)-1H-pyrazolo[3,4-d]pyrimidin-1-yl)propyl)-5-fluoro-3-(3-fluorophenyl)-4H-chromen-4-one 2-(1-(4-amino-3-(3-fluoro-4-isopropoxyphenyl)-1H-pyrazolo[3,4-d]pyrimidin-1-yl)propyl)-5-fluoro-3-(3-fluorophenyl)-4H-chromen-4-one: The title compound was obtained as a off-white solid (0.062 g, 36%) by using a procedure that is similar to the one described for example 6 from intermediate 13 (0.080 g, 0.293 mmol), DMF (2 ml), potassium carbonate (0.081 g, 0.587 mmol) and intermediate 137 (0.130 g, 0.0.440 mmol). MP: 241-243° C. $^1$H-NMR (δ ppm, CDCl$_3$, 400 MHz): 8.25 (s, 1H), 7.63 (dt, J=8.4, 5.4 Hz, 1H), 7.44 (dd, J=11.5, 2.0 Hz, 1H), 7.35 (m, 3H), 7.14 (t, J=8.4 Hz, 1H), 7.06 (m, 3H), 6.92 (d, J=7.5 Hz, 1H), 5.85 (dd, J=9.0, 6.6 Hz, 1H), 5.44 (s, 2H), 4.66 (quintet, J=6.2 Hz, 1H), 2.64 (m, 1H), 2.46 (m, 1H), 1.42 (d, J=6.0 Hz, 6H), 0.91 (t, J=7.3 Hz, 3H).

Example 134

(S)/(R)-5-fluoro-3-(3-fluorophenyl)-2-(1-(2-methoxy-9H-purin-6-ylamino)ethyl)-4H-chromen-4-one (S)/(R)-5-fluoro-3-(3-fluorophenyl)-2-(1-(2-methoxy-9H-purin-6-ylamino) ethyl)-4H-chromen-4-one: The title compound was obtained as pale-brown solid (0.055 g, 25%) by using a procedure that is similar to the one described for example 7 from intermediate 140 (0.245 g, 0.494 mmol), intermediate 23b (0.150 g, 0.494 mmol), triphenylphosphine (0.194 g, 0.741 mmol), THF (7 ml) and diisopropylazodicarboxylate (0.16 ml, 0.741 mmol), followed by the cleavage of the intermediate with trifluoroacetic acid (0.6 mil) and dichloromethane (8 ml). MP: 186-189° C. Mass: 449.8 (M$^+$).

Example 135

(S)/(R)-5-fluoro-3-(3-fluorophenyl)-2-(1-(2-methoxy-9H-purin-6-ylamino)ethyl)-4H-chromen-4-one (S)/(R)-5-fluoro-3-(3-fluorophenyl)-2-(1-(2-methoxy-9H-purin-6-ylamino) ethyl)-4H-chromen-4-one: The title compound was obtained as pale-brown solid (0.056 g, 34%) by using a procedure that is similar to the one described for example 7 from intermediate 140 (0.179 g, 0.362 mmol), intermediate 23a (0.110 g, 0.494 mmol), triphenylphosphine (0.142 g, 0.544 mmol), THF (7 ml) and diisopropylazodicarboxylate (0.11 ml, 0.544 mmol), followed by the cleavage of the intermediate with trifluoroacetic acid (0.6 mil) and dichloromethane (7 ml). MP: 219-222° C. Mass: 449.8 (M$^+$).

Example 136

(S)/(R)-5-fluoro-2-(1-(2-fluoro-9H-purin-6-ylamino) ethyl)-3-(3-fluorophenyl)-4H-chromen-4-one (S)/(R)-5-fluoro-2-(1-(2-fluoro-9H-purin-6-ylamino) ethyl)-3-(3-fluorophenyl)-4H-chromen-4-one: To a solution of intermediate 143 (0.22 g, 0.730 mmol), tert-butanol (1.5 ml) N,N-diisopropylethylamine (0.25 ml, 1.46 mmol) and 6-chloro-2-fluoro-9H-purine (0.102 g, 0.663 mmol) were added and heated to reflux for 248 h. The reaction mixture was concentrated, quenched with water, extracted with ethyl acetate, dried with sodium sulphate and concentrated. The crude product was purified by column chromatography with methanol:ethyl acetate to afford the title compound as brown solid (0.042 g, 13% yield). MP: 183-186° C. Mass: 437.9 (M$^+$). Enantiomeric excess: 33% as determined by HPLC on a chiralpak AD-H column, enriched in the fast eluting isomer (retention time=7.21 min.).

Example 137

(S)/(R)-2-(1-(4-amino-3-(3-fluoro-4-isopropoxyphenyl)-1H-pyrazolo[3,4-d]pyrimidin-1-yl)ethyl)-5-methyl-3-phenyl-4H-chromen-4-one (S)/(R)-22-(1-(4-amino-3-(3-fluoro-4-isopropoxyphenyl)-1H-pyrazolo[3,4-d]pyrimidin-1-yl)ethyl)-5-methyl-3-phenyl-4H-chromen-4-one: The title compound was obtained as off-white solid (0.030 g, 15%) by using a procedure that is similar to the one described for example 7 from intermediate 13 (0.122 g, 0.425 mmol), intermediate 149 (0.100 g, 0.354 mmol), triphenylphosphine (0.140 g, 0.531 mmol), THF (1 ml) and diisopropylazodicarboxylate (0.10 ml, 0.531 mmol). MP: 208-210° C. Mass: 549.7 (M$^4$). $^1$H-NMR (δ ppm, CDCl$_3$, 400 MHz): 8.20 (s, 1H), 7.48 (t, J=7.6 Hz, 1H), 7.43 (dd, J=11.4, 2.0 Hz, 1H), 7.34 (m, 5H), 7.20-7.10 (m, 4H), 6.09 (q, J=7.1 Hz, 1H), 4.67 (quintet, J=6.1 Hz, 1H), 2.80 (s, 3H), 1.99 (d, J=7.1 Hz, 3H), 1.42 (d, J=6.0 Hz, 6H). Enantiomeric excess: 99.34% as determined by HPLC on a chiralpak AD-H column, enriched in the fast eluting isomer (retention time=8.77 min).

Example 138

2-(1-(9H-purin-6-ylamino)ethyl)-5-fluoro-3-o-tolyl-4H-chromen-4-one 2-(1-(9H-purin-6-ylamino)ethyl)-5-fluoro-3-o-tolyl-4H-chromen-4-one: The title compound was obtained as off-white solid (0.025 g, 20%) by using a procedure that is similar to the one described for example 7 from tert-butyl 9-trityl-9H-purin-6-ylcarbamate (0.173 g, 0.362 mmol), intermediate 153 (0.090 g, 0.301 mmol), triphenylphosphine (0.119 g, 0.451 mmol), THF (2.3 ml) and diisopropylazodicarboxylate (0.10 ml, 0.451 mmol), followed by the cleavage of the intermediate with trifluoroacetic acid (0.4 ml) and dichloromethane (2 ml). MP: 275-277° C. Mass: 416.0 (M$^+$).

Biological Assay

The pharmacological properties of the compounds of this invention may be confirmed by a number of pharmacological assays. The pharmacological assays which can be been carried out with the compounds according to the invention and/or their pharmaceutically acceptable salts is exemplified below.

Assay 1: Fluorescent Determination of PI3Kinase Kinase Enzyme Activity

Phosphoinositide 3 kinases (PI3K) belong to a class of lipid kinases that play a critical role in the regulation of several key cellular processes. The PI3K are capable of phosphorylating the 3-hydroxy position of phosphoinositols thereby generating second messengers involved in downstream signalling events. The homogenous time resolved fluorescence (HTRF) assay allows detection of 3,4,5-triphosphate (PIP3) formed as a result of phosphorylation of phosphotidylinositol 4,5-biphosphate (PIP2) by PI3K isoforms such as α, β, γ or δ. PI3K isoform activity for a, 0, y or 8 was determined using a PI3K human HTRF™ Assay Kit (Millipore, Billerica, Mass.) with modifications. All incubations were carried out at room temperature. Briefly, 0.5 µl of 40× inhibitor (in 100% DMSO) or 100% DMSO were added to each well of a 384-well black plate (Greiner Bio-One, Monroe, N.C.) containing 14.5 µl 1× reaction buffer/PIP2 (10 mM MgCl$_2$, 5 mM DTT, 1.38 pM PIP2) mix with or without enzyme and incubated for 10 min. After the initial incubation, 5 μl/well of 400 pM ATP was added and incubated for an additional 30 minutes. Reaction was terminated by adding 5 μl/well stop solution (Millipore, Billerica, Mass.). Five microliters of detection mix (Millipore, Billerica, Mass.) were then added to each well and was incubated for 6-18 h in the dark. HRTF ratio was measured on a microplate reader (BMG Labtech., Germany) at an excitation wavelength of 337 nm and emission wavelengths of 665 and 620 nm with an integration time of 400 μsec.

TABLE 2

| Example | % inhibition (PI3kα) 1 uM | IC50 (nM) | % inhibition (PI3kβ) 1 uM | IC50 (nM) | % inhibition (PI3kγ) 300 nM | IC50 (nM) | % inhibition (PI3kδ) 300 nM | IC50 (nM) |
|---|---|---|---|---|---|---|---|---|
| 1. | C | – | C | – | — | – | B | – |
| 2. | D | – | D | – | — | – | B | – |
| 3. | C | – | D | – | B | +++ | B | ++++ |
| 4. | — | – | — | – | — | – | — | – |
| 5. | C | >10000 | D | ++ | — | – | B | – |
| 6. | D | >10000 | C | – | A | ++++ | A | +++++ |
| 7. | C | – | B | – | — | +++++ | — | +++++ |
| 8. | D | – | B | ++ | — | +++++ | — | +++++ |
| 9. | C | – | C | – | A | ++++ | A | +++++ |
| 9a | D | – | C | – | — | +++++ | — | +++++ |
| 9b | D | – | C | – | — | ++ | — | ++ |
| 10. | C | – | D | – | A | +++ | C | – |
| 11. | B | – | B | – | C | – | B | – |
| 12. | D | – | C | – | A | +++ | C | – |
| 13. | D | – | D | – | B | – | A | +++++ |
| 14. | C | – | D | – | A | ++++ | A | ++++ |
| 15. | — | – | — | – | D | – | D | – |
| 16. | C | – | D | – | D | – | A | ++++ |
| 17. | D | – | C | – | C | – | A | – |
| 18. | D | – | D | – | B | – | A | ++++ |
| 19. | C | – | C | – | A | – | B | – |
| 20. | D | – | C | – | D | – | A | ++++ |
| 21. | — | – | — | – | D | – | C | – |
| 22. | C | – | D | – | C | – | A | – |
| 23. | D | – | C | – | A | +++++ | A | ++++ |
| 24. | D | – | B | – | C | – | — | – |
| 25. | D | – | C | – | A | +++++ | — | – |
| 26. | D | – | C | – | A | ++++ | — | – |
| 27. | D | – | C | – | B | – | C | – |
| 28. | D | – | C | – | B | – | B | – |
| 29. | D | – | C | – | B | – | C | – |
| 30. | C | – | D | – | D | – | C | – |
| 31. | C | – | C | – | B | – | B | – |
| 32. | D | – | B | – | B | – | D | – |
| 33. | D | – | C | – | B | – | B | – |
| 34. | D | – | C | – | B | – | B | – |
| 35. | — | – | — | – | C | – | D | – |
| 36. | D | – | B | – | A | – | C | – |
| 37. | D | – | C | – | B | – | D | – |
| 38. | C | – | C | – | D | – | B | – |
| 39. | C | – | B | – | D | – | C | -- |
| 40. | C | – | B | – | D | – | B | – |
| 41. | C | – | C | – | B | – | B | |
| 42. | — | – | — | – | — | – | — | – |
| 43. | — | – | — | – | — | – | — | -- |
| 44. | D | – | D | – | C | – | C | ---- |
| 45. | — | – | — | – | C | – | B | |
| 46. | D | – | B | – | B | – | C | – |
| 47. | — | – | — | – | D | – | D | – |
| 48. | — | – | C | – | A | +++++ | B | – |
| 49. | B | – | B | – | B | – | B | -- |
| 50. | D | – | C | – | B | – | A | |
| 51. | — | – | — | – | B | – | C | – |
| 52. | C | – | B | – | B | – | B | – |
| 53. | — | – | — | – | B | – | D | – |
| 54. | C | – | C | – | B | – | B | – |
| 55. | — | – | — | – | B | – | C | |
| 56. | D | – | B | – | B | – | D | – |
| 57. | — | – | — | – | B | – | D | – |
| 58. | D | – | B | – | C | – | B | – |
| 59. | — | >10000 | C | + | — | +++++ | — | +++ |
| 60. | D | – | C | – | C | – | C | – |
| 61. | C | – | C | – | B | – | C | – |
| 62. | D | -- | B | – | C | – | B | – |
| 63. | C | – | D | – | C | – | C | – |
| 64. | — | – | C | – | C | – | B | – |
| 65. | C | – | C | – | B | – | D | – |
| 66. | C | – | C | – | C | – | C | – |
| 67. | — | – | — | – | — | – | — | – |
| 68. | C | – | B | – | B | – | C | – |
| 69. | — | – | C | – | A | – | B | – |
| 70. | D | – | C | – | C | – | C | – |
| 71. | — | – | — | – | C | – | D | – |
| 72. | — | – | — | – | — | -- | C | -- |
| 73. | — | – | — | – | C | – | C | – |
| 74. | D | – | C | – | C | – | B | – |
| 75. | | | | | D | – | C | |
| 76. | D | – | C | – | C | – | C | |
| 77. | C | – | B | – | C | – | B | ++++ |
| 78. | D | – | C | – | — | – | B | ++++ |
| 79. | C | – | C | – | C | – | D | |
| 80. | B | – | C | – | C | – | B | |
| 81. | C | – | C | – | C | – | B | |
| 82. | C | – | C | – | C | – | C | |
| 83. | | | | | A | +++++ | A | +++++ |
| 84. | | | | | C | + | B | +++++ |
| 85. | D | – | C | – | C | – | C | |
| 86. | D | – | — | – | C | + | B | |
| 87. | C | – | B | – | D | – | B | +++ |
| 88. | | | | | | | | |
| 89. | | | | | | | | |
| 90. | | | | | | | | |
| 91. | | | | | C | – | C | |
| 92. | | | | | D | – | D | |
| 93. | | | | | D | – | C | |
| 94. | C | – | C | – | C | – | C | |
| 95. | | | | | D | – | C | |
| 96. | | | | | D | – | D | |
| 97. | C | – | C | – | C | – | C | |
| 98. | | | | | | | | |
| 99. | | | | | C | – | C | |
| 100. | B | – | B | – | B | ++++ | C | +++ |
| 101. | B | – | C | – | B | +++ | D | |
| 102. | C | – | B | – | C | – | D | |
| 103. | | | | | C | – | D | |
| 104. | | | | | C | – | D | |
| 105. | | | | | C | – | D | |
| 106. | | | | | C | – | D | |
| 107. | D | – | C | – | C | – | D | |
| 108. | C | – | D | – | C | – | C | |
| 109. | | | | | D | – | C | |
| 110. | D | – | C | – | B | ++++ | A | +++++ |
| 111. | — | – | D | – | C | – | C | |
| 112. | B | – | D | – | B | – | B | |
| 113. | C | – | D | – | B | ++++ | B | +++++ |
| 114. | D | – | — | – | B | – | B | |
| 115. | C | – | D | – | C | – | C | |
| 116. | | | | | D | – | D | |
| 117. | B | – | — | – | C | – | C | |
| 118. | C | – | D | – | C | – | C | |
| 119. | | | | | C | – | D | |
| 120. | | | | | D | – | D | |
| 121. | C | – | C | – | B | – | D | |
| 122. | | | | | D | – | C | |
| 123. | D | – | C | – | D | – | B | |
| 124. | C | – | D | – | D | – | C | |
| 125. | D | – | — | – | — | – | C | |
| 126. | C | – | D | – | D | – | B | |
| 127. | D | – | B | – | D | – | B | |
| 128. | C | – | B | – | C | ++++ | B | ++++ |
| 129. | D | – | C | – | C | – | D | |
| 130. | | | | | C | – | C | |

TABLE 2-continued

| | | | | |
|---|---|---|---|---|
| 131. | C | D | C | C |
| 132. | | | C | B |
| 133. | | B | B | C |
| 134. | | | D | C |
| 135. | | | C | C |
| 136. | | | C | C |
| 137. | D | B | D | C |

Data were analyzed using Graphpad Prism (Graphpad software; San Diego Calif.) for $IC_{50}$ determination. Examples 1-59 were tested at 1 uM for Pi3kα & Pi3k β and at 0.3 uM for γ and δ. Examples 60-137 were tested at 1 uM for Pi3kα & Pi3k β and at 0.1 uM for γ and δ. Percent inhibition was calculated based on the values for the blank and enzyme controls. The results are as provided in Table 2 (wherein D=0 to 25%; C=>25 to 50%; B=>50 to 75%; A=>75 to 100%; +++++=≤50 nM; ++++=>50 to ≤100 nM; +++=>100 to ≤300 nM; ++=>300 to ≤500 nM; +=>500 nM)

Assay 2: In Vitro Cell Proliferation Assay in Leukemic Cell Lines

Growth inhibition assays were carried out using 10% FBS supplemented media. Cells were seeded at a concentration of 5000-20,000 cells/well in a 96-well plate. Test compound at a concentration range from 0.01 to 10000 nM were added after 24 h. Growth was assessed using the 3-[4,5-dimethylthiazol-2-yl]-2,5-diphenyltetrazolium bromide (MTT) dye reduction test at 0 h (prior to the addition of the test compound) and 48 h after the addition of test compound. Absorbance was read on a Fluostar Optima (BMG Labtech, Germany) at a wave length of 450 nm. Data were analysed using GraphPad Prism and % inhibition due to the test compound compared to the control was calculated accordingly. Exemplary compounds of the present invention when tested @ 1 uM in THP-1; DLBCL; HL-60; MOLT-4, RPMI8226 and TOLEDO cell lines showed a 20 to 80% inhibition.

Assay 3: Inhibition of AKT Phosphorylation in Leukemic Cell Lines:

Inhibition of AKT phosphorylation in leukemic cell lines: THP-1, HL-60, MOLT-4, RPMI-8226, or DLBCL cells were incubated with desired concentrations of compound for 48 h. Cells were lysed and pAKT was determined by Western Blotting. Bands were quantified using ImageJ and normalized to actin. Exemplary compounds of the present invention when tested @ 1 uM in showed a 50 to 90% inhibition.

Assay 4: Inhibition of PI3Kδ Signalling in Basophils from Human Whole Blood

PI3Kδ signalling in basophils manifested by an alteration of anti-FcεR1 induced CD63 expression is a useful pharmacodynamic marker determined using the Flow2CAST® kit (Buhlmann Laboratories, Switzerland). Briefly, it involves the following steps:

Mix the anti-coagulated blood sample by inverting the venipuncture tube several times Prepare fresh and pyrogen-free 3.5 ml polypropylene or polystyrene tubes suitable for Flow Cytometry measurements Add 49 μl of patient's whole blood to each tube.

Add 1 μl of 10% DMSO (background) or compound (10% DMSO) to the assigned tubes and mix gently. Incubate at room temperature for 15 min Pipet 50 μl of the Stimulation buffer (background) or anti-FcεRI Ab to each tube Add 100 μl of Stimulation Buffer to each tube Mix gently. Add 20 μl Staining Reagent (1:1 mix of FITC-CD63 and PE-CCR3) to each tube Mix gently, cover the tubes and incubate for 15 minutes at 37° C. in a water bath. (using an incubator will take about 10 minutes longer incubation time due to less efficient heat transfer)

Add 2 ml pre-warmed (18-28° C.) Lysing Reagent to each tube, mix gently

Incubate for 5-10 minutes at 18-28° C.

Centrifuge the tubes for 5 minutes at 500×g

Decant the supernatant by using blotting paper

Resuspend the cell pellet with 300-800 μl of Wash Buffer

Vortex gently and acquire the data on the flow cytometer within the same day.

Percent CD63 positive cells within the gated basophil population are to be determined in different treatment groups and normalized to vehicle control.

Assay 5: Inhibition of Apoptosis in Leukemic Cell Lines

Apoptosis in Leukemic Cells was Determined Using an In-Situ Caspase 3 Kit (Millipore, US)

as outlined below:

Seed leukemic cells—at a density of $1 \times 10^6$ cells/well in a 6 well plate Add test compound/DMSO at desired concentrations Incubate the plate for 24 hrs at 37° C. in 5% $CO_2$ incubator Collect cells in a 2 ml centrifuge tube Add 1.6 μL of freshly prepared 5×FLICA reagent and mix cells by slightly flicking the tubes Incubate tubes for 1 hour at 37° C. under 5% $CO_2$ Add 2 ml of 1× wash buffer to each tube and mix Centrifuge cells at <400×g for 5 minutes at room temperature.

Carefully remove and discard supernatant, and gently vortex cell pellet to disrupt any cell-to-cell clumping.

Resuspend cell pellet in 300 ul of 1× wash buffer

Place 100 μL of each cell suspension into each of two wells of a black microtiter plate. Avoid creation of bubbles.

Read absorbance of each microwell using an excitation wavelength of 490 nm and an emission wavelength of 520 nm Percent increase in caspase-3 activity manifested by an increase in fluorescence compared to the control blank is to be calculated.

Assay 6: Lipopolysaccharide Induced Pulmonary Neutrophilia in Male Sprague-Dawley Rat Model:

An exaggerated recruitment and subsequent activation of neutrophil is likely to be important for the development and course of several inflammatory diseases in the airways and lungs, such as severe asthma, chronic obstructive pulmonary disease, cystic fibrosis, and acute respiratory distress syndrome. The mechanisms by which neutrophil contribute to these diseases may involve the release of proteolytic enzymes, such as neutrophil elastase, and free oxygen radicals. When released, these compounds can cause bronchoconstriction, bronchial hyperreactivity, hyper-secretion, epithelial damage, and tissue remodelling in the airways.

After the quarantine period, fasted animals are to be randomized and divided into various groups depending on their body weights. Test compound is to be prepared as a suspension in a vehicle consisting of 0.5% methylcellulose in which Tween 80 as a suspending agent. The compound or vehicle is to be administered by oral gavage in a volume of 10 mL/kg. Animals are to be anaesthetised with ketamine and LPS solution was administered intratracheally one hour after compound administration at a dose of 1 mg/kg. 6 h after LPS instillation, animals are to be exsanguinated under anaesthesia, and then trachea is to be cannulated and the lungs are to be lavaged with 5-ml aliquots of heparinised PBS (1 unit/ml) four times through tracheal cannula (total volume 20 ml). BAL fluid has to be stored at 2-8° C. until assayed for total cell and differential leukocyte count. Bronchioalveolar fluid is to be centrifuged (500×g for 10 min) and the resulting cell pellet is to be resuspended in 0.5 ml of heparinised saline. The total numbers of white blood cells are to be determined in BAL fluid or blood by using a blood cell counter and has to be adjusted to $1 \times 10^6$ cell/ml. Differential cell count has to be calculated manually. One hundred microliters of the cell suspension is to be centrifuged using cytospin 3 to prepare a cell smear. The cell smear has to be stained with a blood staining solution for differentiation and slides have to be microscopically observed to identify eosinophil according to their morphological characteristics. The number of each cell type among 300 white blood cells in the cell smear is to be determined and expressed as a percentage. The number of eosinophil in each BALf or blood is to be calculated.

Assay 7: Lipopolysaccharide-Mediated Rat Air Pouch Model of Inflammation:

Leukocyte recruitment and the formation of pro-inflammatory mediators, including different cytokines, are the hallmark of an inflammatory response. The air-pouch model was originally developed as a facsimile synovium for the study of inflammatory processes that occur in RA. The model allows the differential quantification of leukocyte species that accumulate in the air-pouch wall (tissue) as well as those that transmigrate into the air-pouch cavity (lavage), and it allows the characterization of the chemokines and adhesion molecules responsible for diapedesis induced by a variety of inflammatory stimuli.

Male Wistar rats (175-200 g) are to be acclimatized for seven days prior to the start of the experiment. Animals are then to be randomly distributed to various groups based on their body weights. Animals are to be anaesthetised with ether and subcutaneous air pouches are to be formed by injecting 20 ml of sterile air under the skin in the intrascapular area (day 0) and maintained with a second 10-ml injection of sterile-filtered air on day 4. On day 6, oral treatment is to be commenced 1 h prior to induction of inflammation by s.c. injection of LPS solution on day 6. A volume of 5-ml of LPS solution dissolved in sterile saline (100 µg/kg) is to be injected into each pouch. Samples of pouch fluid are to be taken at 6 h after administration of LPS by flushing the pouch with 5 ml of sterile saline and withdrawing 4 ml of fluid. The numbers of leukocytes present in pouch fluid has to be determined microscopically using a haemocytometer. Differential cell content has to be determined by microscopic examination of fluid smears stained with Diff-Quik.

Assay 8: Lipopolysaccharide Induced TNF-α Production:

Fasted female wistar rats are to be randomized in to different groups depending on their body weights. Test compound has to be prepared as a suspension in a vehicle consisting of 0.5% methylcellulose. The compound or vehicle is to be administered by oral gavage in a volume of 10 mL/kg. LPS solution is to be administered intraperitoneally one hour after compound administration at a dose of 0.3 mg/kg. Blood has to be collected in serum separator tubes via cardiac puncture ninety minutes after LPS injection. Serum has to be separated and stored at −20° C. and will be analysed for TNFα by ELISA.

Assay 9: Ovalbumin Induced Pulmonary Eosinophilia in Male Guinea Pigs:

Airway inflammation and hyper-responsiveness (AHR) are hallmarks and distinguishing features of bronchial asthma. Provocation of pre-sensitized mice with the same allergen induces airway inflammation with preferential eosinophilic infiltration and, as a consequence, AHR. Pulmonary eosinophilia and airway remodelling in conjunction with altered neural control of airway tone and airway epithelial desquamation may contribute to AHR in asthma. After the quarantine period, 0.3 mL of blood samples is to be collected from orbital vein by retro-orbital plexus method from each individual animal and analysed on a cell analyser (ADVIA 2120, Siemens). Based on their total cell count, guinea pigs are to be randomized and divided into various groups. Ear pinna is to be marked with an indelible marking pen for identification. On day 0, weights are to be recorded and animals are then to be sensitized with 50 µg of Ovalbumin and 10 mg of alum solution (1 mL) intraperitoneally. On day 7 and day 14, the above sensitization protocol has to be repeated. On day 18, animals are to be treated with test compound by oral/intranasal route. On day 19, & 20, animals are to be treated with test compound by oral/intranasal administration and exposed to 0.5% w/v Ovalbumin for 10 min using ultrasonic nebulizer with flow rate of 0.2 ml per min. On day 21, fasted animals are to be treated with test compound by oral/intranasal administration and 15 min after dosing, animals are to be nebulized with 1% w/v Ovalbumin solution for 10 min. Control group animals are to be treated with 0.5% w/v methyl cellulose (vehicle). Sham control groups are to be sensitized with 10 mg of alum on day 0, 7 & 14 and exposed to saline solution with the same nebulization rate on d19, d20 & d21. Twenty four hours after OVA challenge, blood samples and BAL fluid has to be collected. Samples are to be analysed for total cell count by using blood analyser (ADVIA 2120, Siemens) and differential leukocyte count is to be done manually.

Assay 10: Collagen Induced Arthritis in Wistar Rats:

Female wistar rats are to be acclimatized for seven days prior to the start of the experiment and are randomly distributed to various groups based on their body weights. On day 0, animals are to be treated by intradermal injection of 500 µg of bovine collagen type II emulsified with complete Freund's adjuvant (IFA) containing MTB (4 mg/mL) delivered at the base of the tail. On day 7 after primary immunization, animals are to be treated by booster injection of 300 µg CII in incomplete Freund's adjuvant by intradermal injection at the base of the tail. Onset of arthritis in ankle joints usually became visually apparent between days 12 and 14. Animals are to be treated with test compound or vehicle (orally administered) from the day after onset of arthritis until end of the experiment (day 28) as a therapeutic group. Arthritis Scores have to be taken by visually examination for signs of joint inflammation regularly throughout the study period. Body weights and paw volumes, paw thickness have to be taken on day 0, 3, 7, 10, 12, 14, 17 21, 24 and 28. On d28, at the end of the study, blood has to be withdrawn at necropsy and processed to serum or plasma and all joints are to be taken and both fore paw and hind paws are to be fixed in 10% formalin for histopathology analysis after taking the small piece of tissue from each joint and stored at −80° C. for cytokine analysis in tissue homogenate. Clinical Scoring Criteria for Fore and Hind Paws: 0=normal; 1=1 hind or fore paw joint affected or minimal diffuse erythema and swelling; 2=2 hind or fore paw joints affected or mild diffuse erythema and swelling; 3=3 hind or fore paw joints affected or moderate diffuse erythema and swelling; 4=Marked diffuse erythema and swelling, or =4 digit joints affected); 5=Severe diffuse erythema and severe swelling entire paw, unable to flex digits)

Assay 11: Acute CSE Induced Cell Infiltration in Male Balb/c Mice:

Animals are to be acclimatized for seven days prior to the start of the experiment. Animals are to be randomly distributed to various groups based on their body weights. On day 1, mice are to be administered by test compound or vehicle by oral/intranasal route and after 1 hr test compound administration animals are to be anaesthetised with ether and cigarette smoke extract is to be administered by intranasal route in volume of 50 µl/mouse and repeated the CSE exposure to animals daily after the test compound administration for four days (d1 to d4). On day 5, 24 hours after last CSE exposure animals are to be exsanguinated under anesthesia, and the trachea is to be cannulated and the lungs are lavaged with 0.5-ml aliquots of heparinised PBS (1 unit/ml) four times through tracheal cannula (total volume 2 ml). BAL stored at 2-8° C. until assayed for total cell and differential leukocyte count. Bronchioalveolar fluid is to be centrifuged (500×g for 10 min) and the resulting cell pellet has to be resuspended in 0.5 ml of heparinised saline. The total number of white blood cells is to be determined in BAL fluid and blood using a blood cell counter and adjusted to $1 \times 10^6$ cell/ml. Differential cell count is to be calculated manually. Forty microliters of the cell suspension is to be centrifuged using cytospin 3 to prepare a cell smear. The cell smear is to be stained with a blood staining solution for differentiation and microscopically has to be observed to identify eosinophil according to their morphological characteristics. The number of each cell type among 300 white blood cells in the cell smear are to be determined and has to be expressed as a percentage, and the number of neutrophils & macrophages in each BALf are to be calculated.

Assay 12: Sub-Chronic CSE Induced Cell Infiltration in Male Balb/c Mice:

Animals are to be acclimatized for seven days prior to the start of the experiment. Animals are to be randomly distributed to various groups based on their body weights. On day 1, animals are to be anaesthetised with ether and cigarette smoke extract is to be administered by intranasal route in volume of 50 µl/mouse and repeated the CSE exposure to animals daily for eight days (d1 to d8). On day 9, mice are to be administered by test compound or vehicle by oral/intranasal route and after 1 hr test compound administration animals are to be anaesthetised with ether and cigarette smoke extract is to be administered by intranasal route in volume of 50 µl/mouse and animals are to be exposed to CSE daily after the test compound administration for next three days (d9 to d11), on day 12, twenty four hours after last CSE exposure animals are to be exsanguinated under anesthesia, and the trachea is to be cannulated and the lungs are to be lavaged with 0.5-ml aliquots of heparinised PBS (1 unit/ml) four times through tracheal cannula (total volume 2 ml). BAL stored at 2-8° C. until assayed for total cell and differential leukocyte count. Bronchioalveolar fluid was centrifuged (500×g for 10 min) and the resulting cell pellet is to be resuspended in 0.5 ml of heparinised saline. The total numbers of white blood cells are to be determined in BAL fluid and blood using a blood cell counter and adjusted to $1 \times 10^6$ cell/ml. Differential cell count was calculated manually. Forty microliters of the cell suspension is to be centrifuged using cytospin 3 to prepare a cell smear. The cell smear is to be stained with a blood staining solution for differentiation and microscopically observed to identify eosinophil according to their morphological characteristics. The number of each cell type among 300 white blood cells in the cell smear has to be determined and expressed as a percentage, and the number of neutrophils & macrophages in each BALf are to be calculated.

Assay 13: Reversal of Corticosteroid Insensitivity in Cigarette Smoke Extract Induced Pulmonary Inflammation (COPD) Model:

Female Balb/c mice are to be acclimatized for seven days prior to the start of the experiment. Animals are then to be randomly distributed to various groups based on their body weights. On day 1, animals are to be anaesthetised with ether and cigarette smoke extract is to be administered by intranasal route in volume of 50d/mouse and animals are to be exposed to CSE daily for next five days (d1 to d6). On day 7, mice are to be administered by dexamethasone at 10 mg/kg by oral gavage and 60 mins later, mice are to be administered with CSE by intranasal route and it has to be repeated for next four days (d7 to d11). From day 9 to day 11, animals are to be administered by test compound or vehicle by oral/intranasal route and 30 mins after dexamethasone administration and 30 mins later animals are to be anaesthetised with ether and cigarette smoke extract is to be administered by intranasal route in volume of 50 µl/mouse and animals are to be exposed to CSE daily after the test compound administration for next two days (i.e. d9 to d11), on d12, twenty four hours after last CSE exposure animals are to be exsanguinated under anesthesia, and the trachea is to be cannulated and the lungs are to be lavaged with 0.5-ml aliquots of heparinised PBS (1 unit/ml) four times through tracheal cannula (total volume 2 ml). BAL has to be stored at 2-8° C. until assayed for total cell and differential leukocyte count. Bronchioalveolar fluid is to be centrifuged (500×g for 10 min) and the resulting cell pellet has to be resuspended in 0.5 ml of heparinised saline. The total number of white blood cells is to be determined in BAL fluid and blood using a blood cell counter and adjusted to $1 \times 10^6$ cell/ml. Differential cell count is to be calculated manually. Forty microliters of the cell suspension is to be centrifuged using cytospin 3 to prepare a cell smear. The cell smear is to be stained with a blood staining solution for differentiation and microscopically has to be observed to identify eosinophil according to their morphological characteristics. The number of each cell type among 300 white blood cells in the cell smear are to be determined and will be expressed as a percentage, and the number of neutrophils and macrophages in each BAL fluid are to be calculated.

Assay 14: Acute Cigarette Smoke Induced Cell Infiltration in Male Balb/c Mice:

Animals are to be acclimatized for seven days prior to the start of the experiment. Animals are then to be randomly distributed to various groups based on their body weights. On day 1, mice is to be administered test compound or vehicle by oral/intranasal route and after 1 hr test compound administration animals are to be placed in whole body exposure box. On day 1 and d2 mice are exposed to the mainstream smoke of 6 cigarettes and of 8 cigarettes on day 3, and of 10 cigarettes on day 4. Exposure to the smoke of each cigarette lasts for 10 min (cigarette are to be completely burned in the first two minutes and followed by an air flow with animal ventilator and next 20 min exposure with fresh room air. After every second cigarette an additional break of 20 min with exposure to fresh room air is to be conducted. Control animals are to be exposed to room air chamber. From day 1 to d4 animals are administered by test compound either oral or intranasal route. On day 5, 24 hours after last cigarette smoke (CS) exposure animals are exsanguinated under anesthesia, and the trachea is to be cannulated and the lungs are lavaged with 0.5-ml aliquots of heparinised PBS (1 unit/ml) four times through tracheal cannula (total volume 2 ml). Bronchioalveolar (BAL) collected is to be stored at 2-8° C. until assayed for total cell and differential leukocyte count. BAL fluid is to be centrifuged (500×g for 10 min) and the resulting cell pellet is resuspended in 0.5 ml of heparinised saline. The total number of white blood cells is to be determined in BAL fluid and blood using a blood cell counter and adjusted to 1×10⁶ cell/ml. Differential cell count is calculated manually. Forty microliters of the cell suspension is centrifuged using cytospin 3 to prepare a cell smear. The cell smear is stained with a blood staining solution for differentiation and microscopically observed to identify eosinophil according to their morphological characteristics. The number of each cell type among 300 white blood cells in the cell smear are to be determined and expressed as a percentage, and the number of neutrophils & macrophages in each BAL fluid are to be calculated.

Assay 15: Ovalbumin-Induced Nasal Eosinophil and Neutrophil Accumulation in Mice:

Animals are to be acclimatized for seven days prior to the start of the experiment. Animals are then to be randomly distributed to various groups based on their body weights. Animals are to be immunized with OVA (40 µg/kg i.p.) on day 1 and 5. In order to elicit local inflammatory responses in the nose, mice are to be repeatedly challenged intra-nasally (10 µL/per nostril) on days 12-19 with OVA (3% OVA in saline). On day 19 non-fasted mice are to be dosed intra-nasally (10 µL/nostril) with either vehicle or test compound 2 hours before to the start of the final OVA challenge. Two hrs later, each animal is to be received a final intranasal OVA (3%) challenge). After a further 8 hr, each animal is to be anaesthetised and nasal lavage is to be carried out by instilling 1 ml of PBS into the posterior nares via a rostrally implanted tracheal cannula extending to a position that is approximately 1 mm before the posterior nares. This procedure has to be repeated to give a yield of approximately 2 ml of lavage fluid. Total cell numbers in the nasal lavage fluid samples are to be measured using a haemocytometer. Cytospin smears of the nasal lavage fluid samples are to be prepared by centrifugation at 1200 rpm for 2 min at RT and stained using a Diff-Quik stain system (Dade Behring) for differential cell counts. Cells are to be counted using oil immersion microscopy.

Assay 16: Poly-1:C-Induced Cell Accumulation in Mice:
Specific pathogen-free A/J mice (males, 5 weeks old) are to be acclimatized for seven days prior to the start of the experiment. Animals are then to be randomly distributed to various groups based on their body weights. Animals are to be administered with poly (1:C)-LMW (poly-IC; 1 mg/mL, 40 µL) intranasally twice daily for 3 days under anaesthesia with 3% isoflurane. Animals are to be treated with test compound by intra-nasally (35 µL of solution in 50% DMSO/PBS) 2 hr before each poly-1:C treatment. Twenty four hr after the last poly-1:C challenge, animals are to be anesthetized, the trachea has to be cannulated and BALF is to be collected. The concentrations of alveolar macrophages and neutrophils in BALF are to be determined by using a blood cell counter and adjusted to 1×10⁶ cell/ml. Differential cell count is calculated manually. Forty microliters of the cell suspension is centrifuged using cytospin 3 to prepare a cell smear. The cell smear is stained with a blood staining solution for differentiation and microscopically observed to identify eosinophil according to their morphological characteristics. The number of each cell type among 300 white blood cells in the cell smear are to be determined and expressed as a percentage, and the number of neutrophils & macrophages in each BAL fluid are to be calculated.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as described above. It is intended that the appended claims define the scope of the invention and that methods and structures within the scope of these claims and their equivalents be covered thereby.

All publications and patent and/or patent applications cited in this application are herein incorporated by reference to the same extent as if each individual publication or patent application was specifically and individually indicated to be incorporated herein by reference.

We claim:
1. A compound of formula (I)

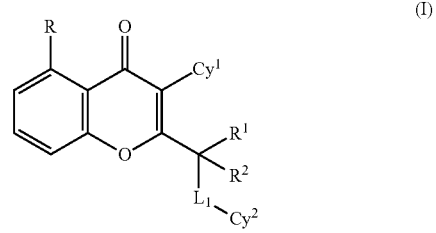

or a pharmaceutically acceptable salt, N-oxide or tautomer thereof,
wherein:
each occurrence of R is independently selected from hydroxy, halogen, carboxy, cyano, nitro, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, substituted or unsubstituted cycloalkenylalkyl, substituted or unsubstituted heterocyclyl, substituted or unsubstituted heterocyclylalkyl, substituted or unsubstituted aryl, substituted or unsubstituted arylalkyl, substituted or unsubstituted heteroaryl, substituted or unsubstituted heteroarylalkyl, —COOR$^x$, —C(O)R$^x$, —C(S)R$^x$, —C(O)NR$^x$R$^y$, —C(O)ONR$^x$R$^y$, —NR$^x$R$^y$, —NR$^x$CONR$^x$R$^y$, —N(R$^x$)SOR$^x$, —N(R$^x$)SO$_2$R$^y$, —(=N—N(R$^x$)R$^y$), —NR$^x$C(O)OR$^y$, —NR$^x$R$^y$, —NR$^x$C(O)R$^y$—, —NR$^x$C(S)R$^y$—NR$^x$C(S)NR$^x$R$^y$, —SONR$^x$R$^y$—, —SO$_2$NR$^x$R$^y$—, —OR$^x$, —OR$^x$C(O)NR$^x$R$^y$, —OR$^x$C(O)OR$^x$—, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^x$R$^y$, —R$^x$C(O)R$^y$, —R$^x$OC(O)R$^y$, —SR$^x$, —SOR$^x$, —SO$_2$R$^x$, or —ONO$_2$, wherein R$^x$, R$^y$ and R$^z$ in each of the above groups is hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted heteroaryl, substituted or unsubstituted heteroarylalkyl, substituted or unsubstituted cycloalkyl, substituted or unsubstituted cycloalkylalkyl, substituted or unsubstituted cycloalkenyl, substituted or unsubstituted heterocyclyl, substituted heterocyclylalkyl ring, or substituted or unsubstituted amino, or (i) any two of $R^x$ and $R^y$ may be joined to form a substituted or unsubstituted, saturated or unsaturated 3-14 membered ring, which may optionally include heteroatoms which may be the same or different and are selected from O, $NR^z$ or S, or (ii) any two of $R^x$ and $R^y$ join to form (=O), (—S) or (=$NR^f$) (wherein $R^f$ is hydrogen or substituted or unsubstituted alkyl);

$R^1$ and $R^2$ may be the same or different and are independently selected from hydrogen, halogen, and substituted or unsubstituted $C_{1-6}$ alkyl, substituted or unsubstituted alkenyl, substituted or unsubstituted alkynyl, substituted or unsubstituted cycloalkyl, substituted or unsubstituted cycloalkenyl, substituted or unsubstituted cycloalkylalkyl, and substituted or unsubstituted heterocyclyl, or both $R^1$ and $R^2$ directly bound to a common atom, may be joined to form (=O);

$Cy^1$ is selected from substituted or unsubstituted cycloalkyl, substituted or unsubstituted heterocyclyl, substituted or unsubstituted aryl and substituted or unsubstituted heteroaryl;

$Cy^2$ is selected from a substituted or unsubstituted heterocyclyl, substituted or unsubstituted aryl and substituted or unsubstituted heteroaryl;

$L_1$ is absent or selected from —$(CR^aR^b)_q$—, —O—, —S(=O)$_q$—, —$NR^a$— or —C(=Y)—;

each occurrence of $R^a$ and $R^b$ may be the same or different and are independently selected from hydrogen, halogen, hydroxy, cyano, substituted or unsubstituted ($C_{1-6}$)alkyl, —$NR^cR^d$ (wherein $R^c$ and $R^d$ are independently hydrogen, halogen, hydroxy, cyano, substituted or unsubstituted ($C_{1-6}$)alkyl, or ($C_{1-6}$)alkoxy) and —$OR^c$ (wherein $R^c$ is substituted or unsubstituted ($C_{1-6}$)alkyl) or when $R^a$ and $R^b$ are directly bound to a common atom, they may be joined to form (=O) or form a substituted or unsubstituted, saturated or unsaturated 3-10 member ring (including the common atom to which $R^a$ and $R^b$ are directly bound), which may optionally include one or more heteroatoms which may be the same or different and are selected from O, $NR^d$ (wherein $R^d$ is hydrogen or substituted or unsubstituted ($C_{1-6}$)alkyl) or S;

Y is selected from O, S, and $NR^a$; and q is 0, 1 or 2;

wherein the term "substituted" refers to substitution by any one or more of the following substituents, which may be the same or different, and are independently selected from hydroxy, halogen, cyano, A alkyl, alkoxy, fluorinated alkoxy, heteroaryl, heterocyclyl, alkylheterocyclyl, —$NH_2$, —NH(alkyl), N(alkyl)$_2$, —NHC(O)(alkyl), —S(alkyl), —$SO_2NH_2$, —$SO_2$NH(alkyl), —$SO_2$N(alkyl)$_2$, —$SO_2$NH(cycloalkyl), —$SO_2$N(cycloalkyl)$_2$, —C(O)$NH_2$, —C(O)NH(alkyl), —C(O)N(alkyl)$_2$, —O-heterocyclyl, —O-heterocyclyl-alkylaryl, —$SO_2$NH(cycloalkyl), and —$CO_2$(alkyl).

2. The compound of claim 1, wherein the compound has the formula (IA-1), formula (IA-II), formula (IA-III), formula (IA-IV), formula (IA-V), formula (IA-Ia), formula (IA-IIa), formula (IA-IIIa), formula (IA-Ib) or formula (IA-IIb):

-continued

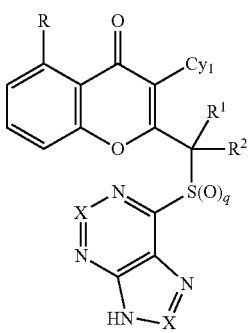
(IA-V)

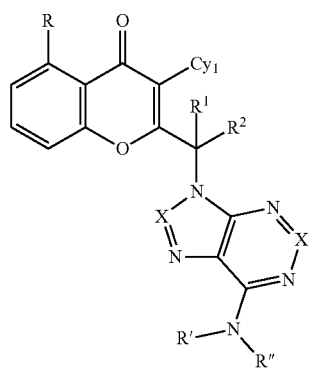
(IA-Ia)

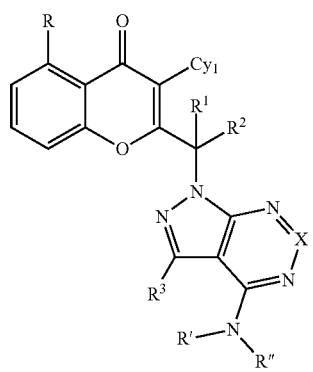
(IA-IIa)

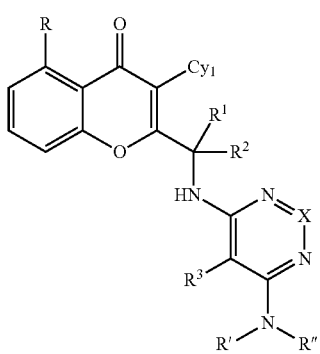
(IA-IIIa)

-continued

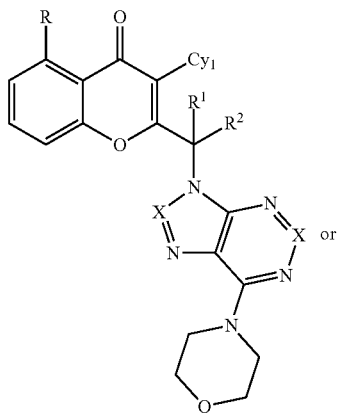
(IA-Ib)

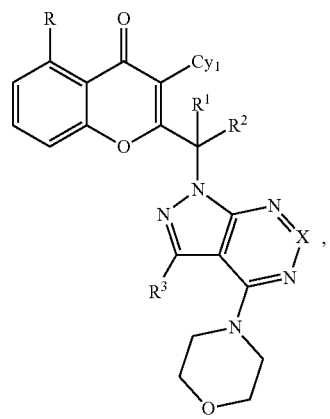
(IA-IIb)

or a pharmaceutically acceptable salt, N-oxide or tautomer thereof, wherein:

R is selected from halogen, hydroxy, substituted or unsubstituted alkoxy, cyano, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, and substituted or unsubstituted heterocyclyl;

$R^1$ and $R^2$ may be the same or different and are independently selected from hydrogen, halogen, and substituted or unsubstituted $C_{1-6}$ alkyl, or both $R^1$ and $R^2$ directly bound to a common atom, may be joined to form (=O);

$Cy^1$ is a monocyclic group selected from substituted or unsubstituted cycloalkyl, substituted or unsubstituted heterocyclyl, substituted or unsubstituted aryl and substituted or unsubstituted heteroaryl;

X is $CR^3$;

each occurrence of $R^3$ is independently selected from hydrogen, hydroxy, halogen, carboxy, cyano, nitro, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted heterocyclic ring, substituted or unsubstituted heterocyclylalkyl ring, substituted or unsubstituted aryl, substituted or unsubstituted arylalkyl, substituted or unsubstituted heteroaryl, substituted or unsubstituted heteroarylalkyl, substituted or unsubstituted guanidine, —COOR$^x$, C(O)R$^x$, —C(S)R$^x$, —C(O)NR$^x$R$^y$, —C(O)ONR$^x$R$^y$, —NR$^y$R$^z$, —NR$^x$CONR$^y$R$^z$, —N(R$^x$)SOR$^y$, —N(R$^x$)SO$_2$R$^y$, —(=N—N(R$^x$)R$^y$), —NR$^x$C(O)OR$^y$, —NR$^x$R$^y$, —NR$^x$C(O)R$^y$—, —NR$^x$C(S)R$^y$—NR$^x$C(S)NR$^y$R$^z$, —SONR$^x$R$^y$—, —SO$_2$NR$^x$R$^y$—, —OR$^x$, —OR$^x$C(O)NR$^y$R$^z$, —OR$^x$C(O)OR$^y$—, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, or —ONO$_2$;

each occurrence of R' and R" is independently selected from hydrogen, hydroxy, halogen, carboxy, cyano, nitro, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted heteroaryl, substituted or unsubstituted heteroarylalkyl, substituted or unsubstituted heterocyclyl, substituted or unsubstituted heterocyclylalkyl ring, substituted or unsubstituted guanidine, —COOR$^x$, —C(O)R$^x$, —C(S)R$^x$, —C(O)NR$^x$R$^y$, —C(O)ONR$^x$R$^y$, —NR$^y$R$^z$, —NR$^x$CONR$^y$R$^z$, —N(R$^x$)SOR$^y$, —N(R$^x$)SO$_2$R$^y$, —(=N—N(R$^x$)R$^y$), —NR$^x$C(O)OR$^y$, —NR$^x$R$^y$, —NR$^x$C(O)R$^y$—, —NR$^x$C(S)R$^y$—NR$^x$C(S)NR$^y$R$^z$, —SONR$^x$R$^y$—, —SO$_2$NR$^x$R$^y$—, —OR$^x$, —OR$^x$C(O)NR$^y$R$^z$, —OR$^x$C(O)OR$^y$—, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, or —ONO$_2$, or both the R' and R" together with the nitrogen atom may be joined to form a substituted or unsubstituted, saturated or unsaturated 3-10 membered ring, which may optionally include heteroatoms which may be the same or different and are selected from O, NR$^f$ (wherein R$^f$ is hydrogen or substituted or unsubstituted alkyl) or S;

each occurrence of R$^x$, R$^y$ and R$^z$ in each of the above groups are independently hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted heteroaryl, substituted or unsubstituted heteroarylalkyl, substituted or unsubstituted cycloalkyl, substituted or unsubstituted cycloalkylalkyl, substituted or unsubstituted cycloalkenyl, substituted or unsubstituted heterocyclyl, substituted heterocyclylalkyl ring, or substituted or unsubstituted amino, or any two of R$^x$, R$^y$ and R$^z$ may be joined to form a substituted or unsubstituted, saturated or unsaturated 3-10 membered ring, which may optionally include heteroatoms which may be the same or different and are selected from O, NR$^f$ or S (wherein R$^f$ is hydrogen or substituted or unsubstituted alkyl);

each occurrence of R$^a$ is independently selected from hydrogen, halogen, hydroxy, cyano, substituted or unsubstituted (C$_{1-6}$)alkyl, —NR$^c$R$^d$ (wherein R$^c$ and R$^d$ are independently hydrogen, halogen, hydroxy, cyano, substituted or unsubstituted (C$_{1-6}$)alkyl, or (C$_{1-6}$) alkoxy) and —OR$^c$ (wherein R$^c$ is substituted or unsubstituted (C$_{1-6}$)alkyl); and q is 0, 1 or 2.

3. The compound of claim 1, wherein each occurrence of R is independently selected from halogen, cyano, substituted or unsubstituted C$_{1-6}$ alkyl, substituted or unsubstituted alkoxy, substituted or unsubstituted C$_{2-6}$ alkenyl, substituted or unsubstituted C$_{2-6}$ alkynyl, substituted or unsubstituted C$_{3-8}$ cycloalkyl, and substituted or unsubstituted heterocyclyl.

4. The compound of claim 3, wherein each occurrence of R is independently selected from fluoro, methyl, methoxy and morpholinyl.

5. The compound of claim 1, wherein Cy$^1$ is selected from substituted or unsubstituted aryl and substituted or unsubstituted heteroaryl.

6. The compound of claim 1, wherein Cy$^1$ is selected from

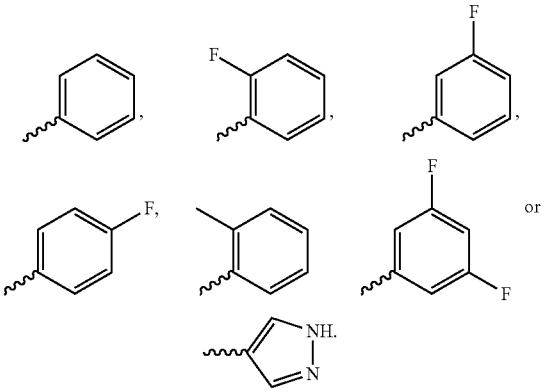

7. The compound of claim 1, wherein R$^1$ and R$^2$ are independently selected from hydrogen and substituted or unsubstituted C$_{1-6}$ alkyl.

8. The compound of claim 1, wherein L$_1$ is absent, or selected from S(=O)$_q$— or —NR$^a$—.

9. The compound of claim 8, wherein q is 0, L$_1$ is absent or L$_1$ is —NH—.

10. The compound of claim 1, wherein Cy$^2$ is selected from substituted or unsubstituted heterocyclyl and substituted or unsubstituted heteroaryl.

11. The compound of claim 1, in L$_1$-Cy$^2$ is selected from formula a, formula b, formula c, formula d, formula e, formula f, formula a$^1$, formula b$^1$, formula c$^1$, formula f$^1$, formula a$^2$, formula b$^2$, formula c$^2$ or formula f$^2$:

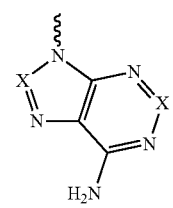

a

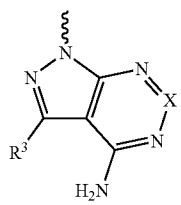

b c

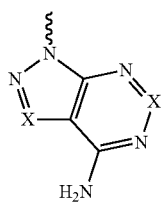

d

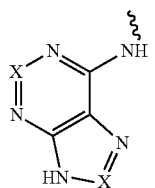

e

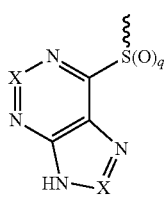

f

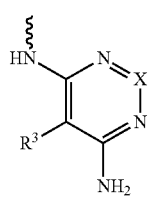

a¹

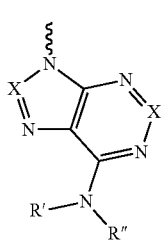

b¹

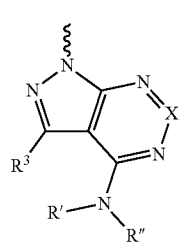

c¹

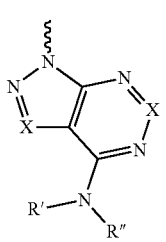

f¹

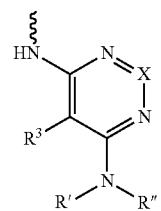

a²

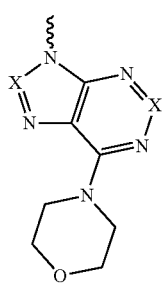

b²

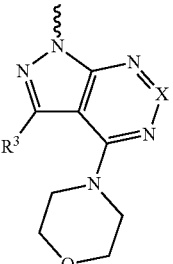

c² or

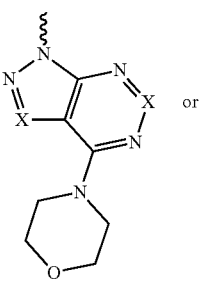

f²

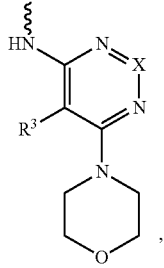

, wherein:
X is CR³; and
each occurrence of R³ is independently selected from hydrogen, hydroxy, halogen, carboxy, cyano, nitro, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted heterocyclyl, substituted or unsubstituted heterocyclylalkyl ring, substituted or unsubstituted aryl, substituted or unsubstituted arylalkyl, substituted or unsubstituted heteroaryl, substituted or unsubstituted heteroarylalkyl, substituted or unsubstituted guanidine, —COOR$^x$, C(O)R$^x$, —C(S) R$^x$, —C(O)NR$^x$R$^y$, —C(O)ONR$^x$R$^y$, —NR$^y$R$^z$, —NR$^x$-CONR$^y$R$^z$, —N(R$^x$)SOR$^y$, —N(R$^x$)SO$_2$R$^y$, —(=N—N(R$^x$)R$^y$), —NR$^x$C(O)OR$^y$, —NR$^x$R$^y$, —NR$^x$C(O)R$^y$—, —NR$^x$C(S)R$^y$—NR$^x$C(S)NR$^y$R$^z$, —SONR$^x$R$^y$—, —SO$_2$NR$^x$R$^y$—, —OR$^x$, —OR$^x$C(O)NR$^y$R$^z$, —OR$^x$C(O)OR$^y$—, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, or —ONO$_2$, wherein R$^x$, R$^y$ and R$^z$ in each of the above groups is hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted heteroaryl, substituted or unsubstituted heteroarylalkyl, substituted or unsubstituted cycloalkyl, substituted or unsubstituted cycloalkylalkyl, substituted or unsubstituted cycloalkenyl, substituted or unsubstituted heterocyclic ring, substituted heterocyclylalkyl ring, or substituted or unsubstituted amino, or any two of R$^x$, R$^y$ and R$^z$ may be joined to form a substituted or unsubstituted, saturated or unsaturated 3-10 membered ring, which may optionally include heteroatoms which may be the same or different and are selected from O, NR$^f$ or S (wherein R$^f$ is hydrogen or substituted or unsubstituted alkyl);

each occurrence of R' and R" is independently selected from hydrogen, hydroxy, halogen, carboxy, cyano, nitro, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted heteroaryl, substituted or unsubstituted heteroarylalkyl, substituted or unsubstituted heterocyclyl, substituted or unsubstituted heterocyclylalkyl ring, substituted or unsubstituted guanidine, —COOR$^x$, —C(O)R$^x$, —C(S) R$^x$, —C(O)NR$^x$R$^y$, —C(O)ONR$^x$R$^y$, —NR$^y$R$^z$, —NR$^x$-CONR$^y$R$^z$, —N(R$^x$)SOR$^y$, —N(R$^x$)SO$_2$R$^y$, —(=N—N(R$^x$)R$^y$), —NR$^x$C(O)OR$^y$, —NR$^x$R$^y$, —NR$^x$C(O)R$^y$—, —NR$^x$C(S)R$^y$—NR$^x$C(S)NR$^y$R$^z$, —SONR$^x$R$^y$—, —SO$_2$NR$^x$R$^y$—, —OR$^x$, —OR$^x$C(O)NR$^y$R$^z$, —OR$^x$C(O)OR$^y$—, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^x$, —ROC(O)R$^y$, —SR$^x$, —SOR$^x$, —SO$_2$R$^x$, or —ONO$_2$, or both the R' and R" together with the nitrogen atom may be joined to form a substituted or unsubstituted, saturated or unsaturated 3-10 membered ring, which may optionally include heteroatoms which may be the same or different and are selected from O, NR$^f$ (wherein R$^f$ is hydrogen or substituted or unsubstituted alkyl) or S;

wherein R$^x$, R$^y$ and R$^z$ in each of the above groups is hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted heteroaryl, substituted or unsubstituted heteroarylalkyl, substituted or unsubstituted cycloalkyl, substituted or unsubstituted cycloalkylalkyl, substituted or unsubstituted cycloalkenyl, substituted or unsubstituted heterocyclyl, substituted heterocyclylalkyl ring, or substituted or unsubstituted amino, or any two of R$^x$, R$^y$ and R$^z$ may be joined to form a substituted or unsubstituted, saturated or unsaturated 3-10 membered ring, which may optionally include heteroatoms which may be the same or different and are selected from O, NR$^f$ or S (wherein R$^f$ is hydrogen or substituted or unsubstituted alkyl); and q is 0, 1 or 2.

12. The compound of claim 11, wherein R$^3$ is independently selected from hydrogen, halogen, cyano, substituted or unsubstituted alkyl, substituted or unsubstituted alkynyl, substituted or unsubstituted heterocyclyl, substituted or unsubstituted aryl, or substituted or unsubstituted heteroaryl.

13. The compound of claim 12, wherein R$^3$ is independently selected from

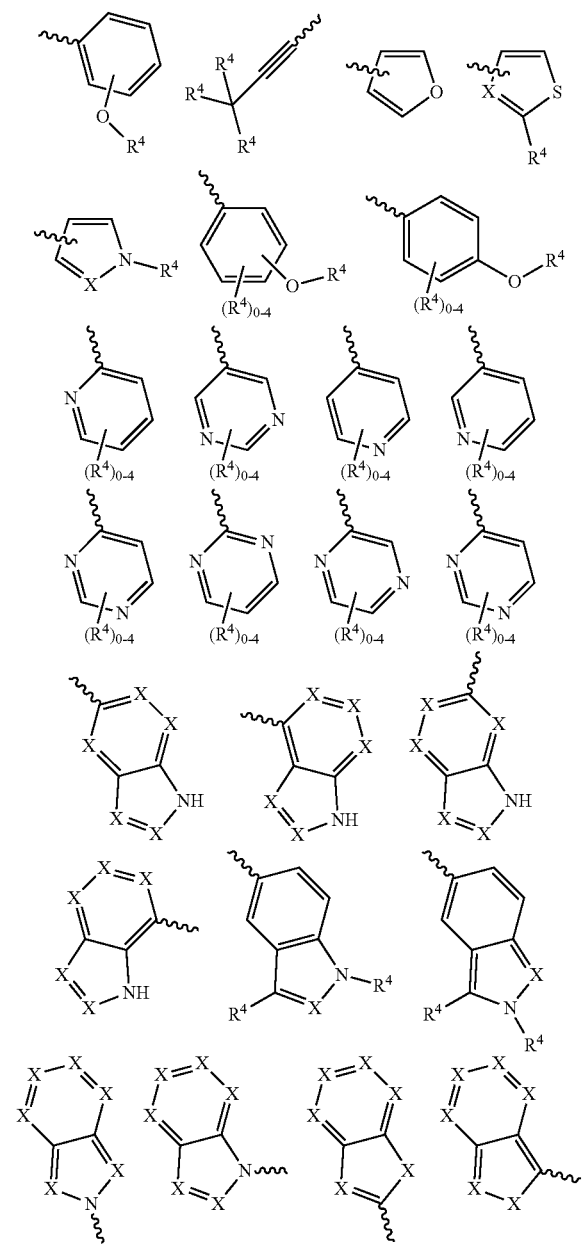

-continued

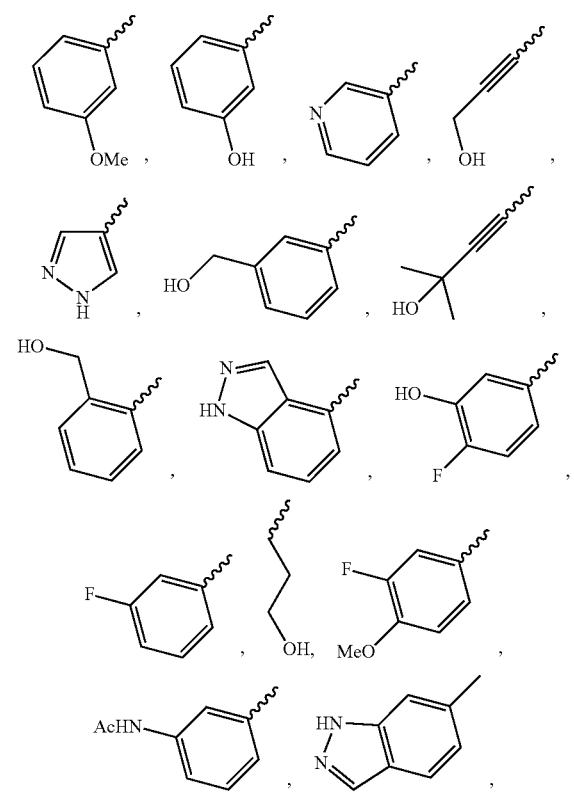

wherein:
each occurrence of X is independently $CR^4$ or N;
$X^1$ is O, S, or $NR^4$; and
each occurrence of $R^4$ is independently selected from hydrogen, hydroxy, halogen, carboxy, cyano, nitro, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted aryl, substituted or unsubstituted arylalkyl, substituted or unsubstituted heterocyclyl, substituted or unsubstituted heterocyclylalkyl ring, substituted or unsubstituted heteroaryl, substituted or unsubstituted heteroarylalkyl, substituted or unsubstituted guanidine, $-COOR^x$, $-C(O)R^x$, $-C(S)R^x$, $-C(O)NR^xR^y$, $-C(O)ONR^xR^y$, $-NR^yR^z$, $-NR^x-CONR^yR^z$, $-N(R^x)SOR^y$, $-N(R)SO_2R^y$, $-(=N-N(R^x)R^y)$, $-NR^xC(O)OR^y$, $-NR^xR^y$, $-NR^xC(O)R^y-$, $-NR^xC(S)R^y-NR^xC(S)NR^yR^z$, $-SONR^xR^y-$, $-SO_2NR^xR^y-$, $-OR^x$, $-OR^xC(O)NR^yR^z$, $-OR^xC(O)OR^y-$, $-OC(O)R^x$, $-OC(O)NR^xR^y$, $-R^xNR^yC(O)R^z$, $-R^xOR^y$, $-R^xC(O)OR^y$, $-R^xC(O)NR^yR^z$, $-R^xC(O)R^x$, $-R^xOC(O)R^y$, $-SR^x$, $-SOR^x$, $-SO_2R^x$, or $-ONO_2$, wherein $R^x$, $R^y$ and $R^z$ in each of the above groups can be hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted heteroaryl, substituted or unsubstituted heteroarylalkyl, substituted or unsubstituted cycloalkyl, substituted or unsubstituted cycloalkylalkyl, substituted or unsubstituted cycloalkenyl, substituted or unsubstituted heterocyclyl, substituted heterocyclylalkyl ring, or substituted or unsubstituted amino, or any two of $R^x$, $R^y$ and $R^z$ may be joined to form a substituted or unsubstituted, saturated or unsaturated 3-10 membered ring, which may optionally include heteroatoms which may be the same or different and are selected from O, $NR^f$ (wherein $R^f$ is hydrogen or substituted or unsubstituted alkyl) or S.

14. The compound of claim 12, wherein $R^3$ is independently selected from

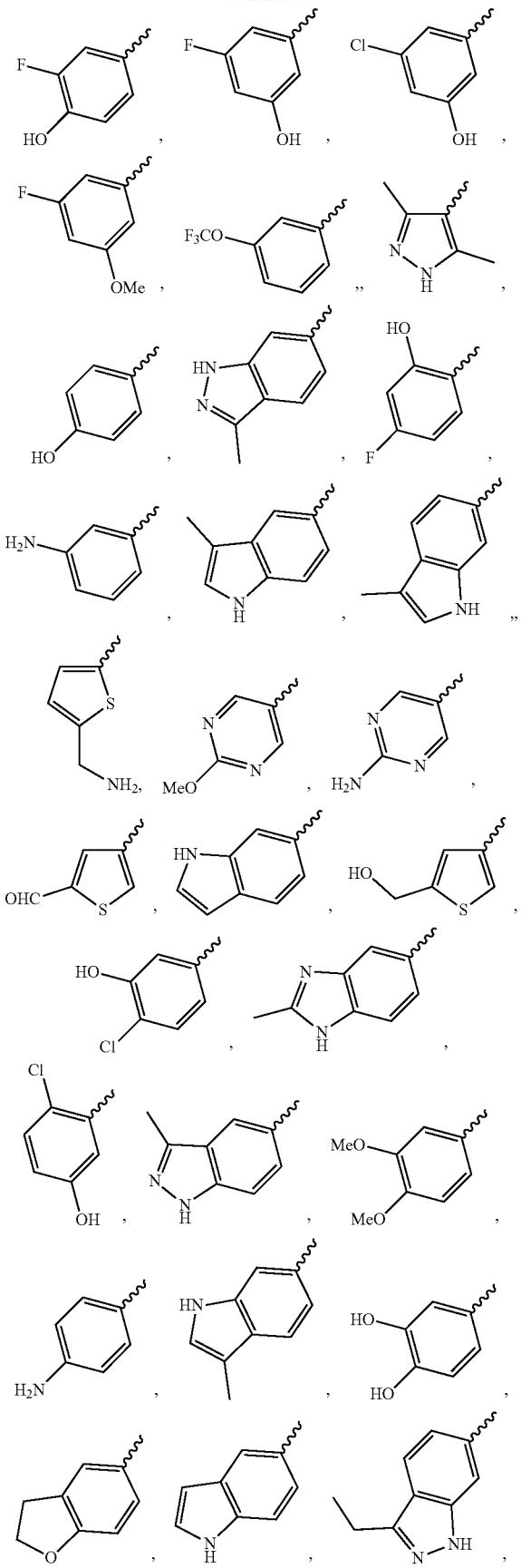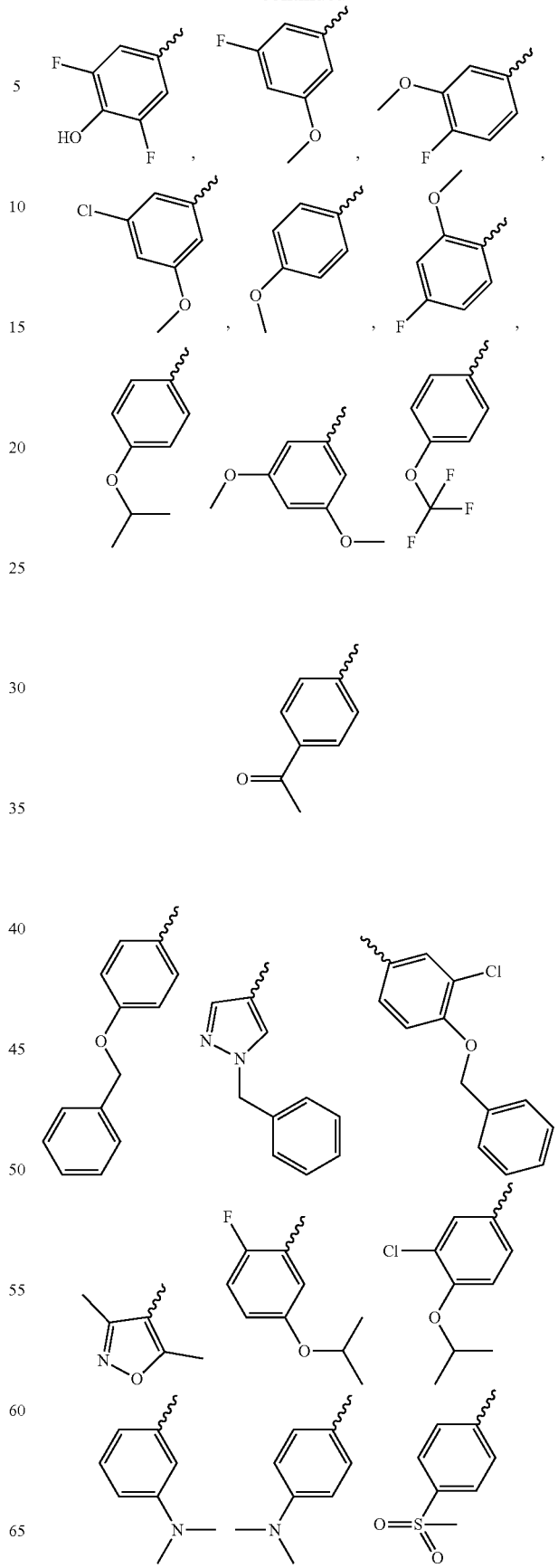

-continued
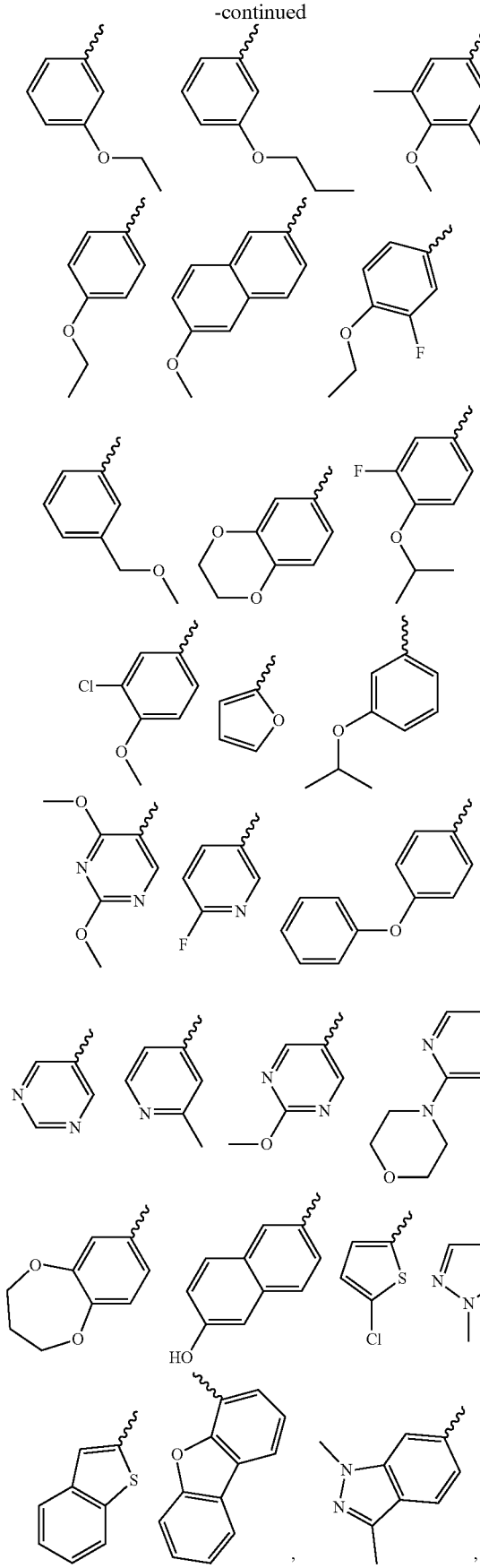
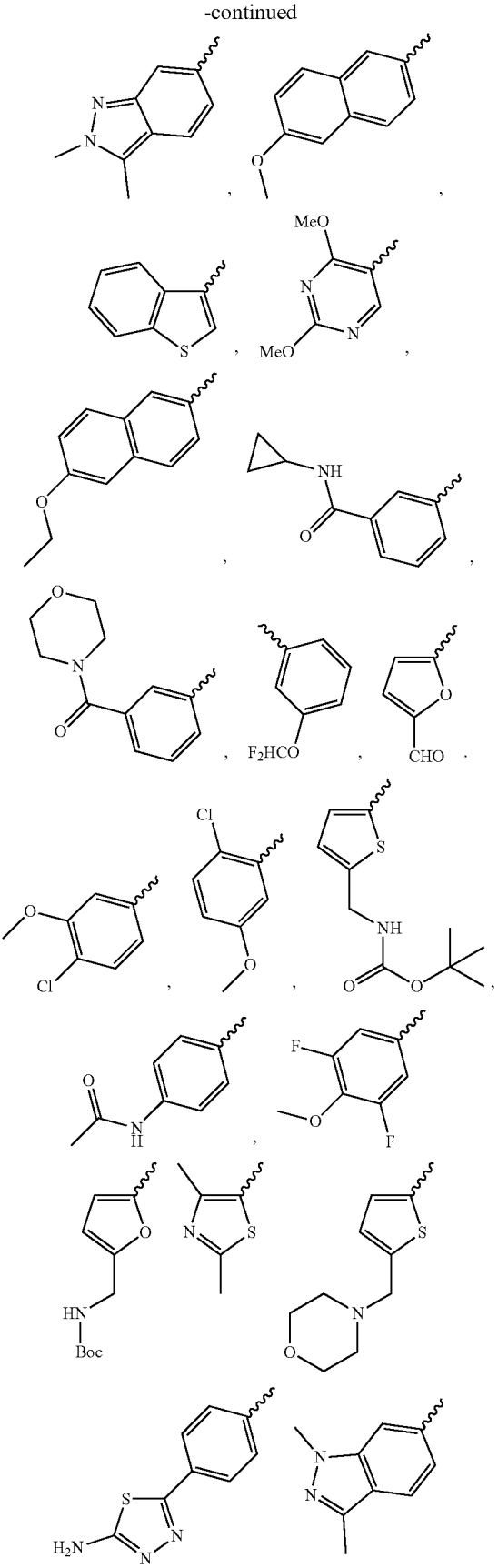

-continued
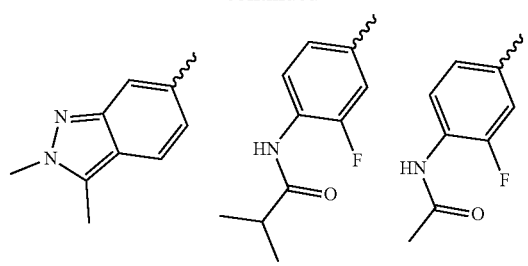
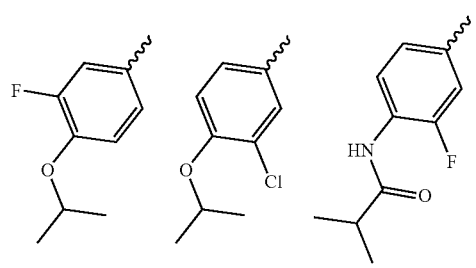
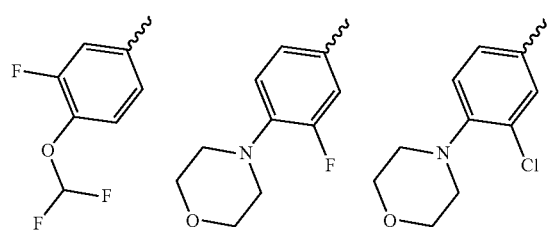
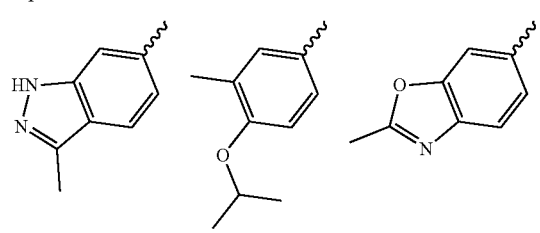
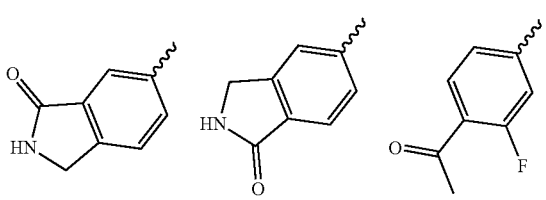
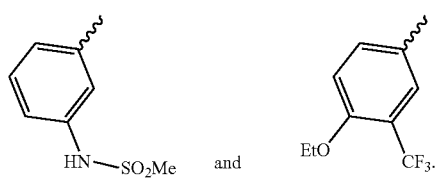
and
-continued
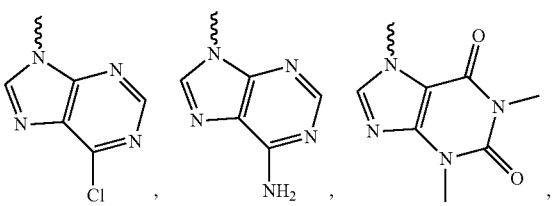
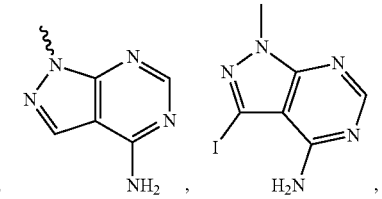
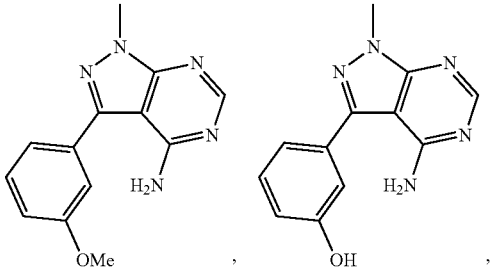
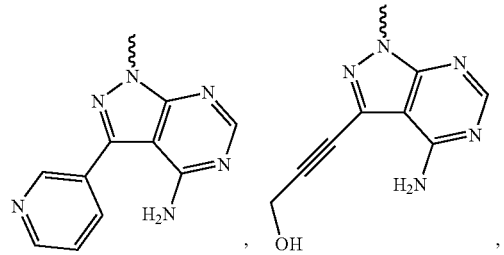
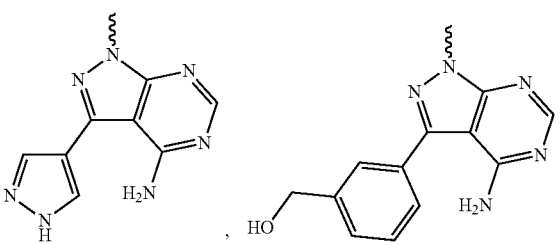
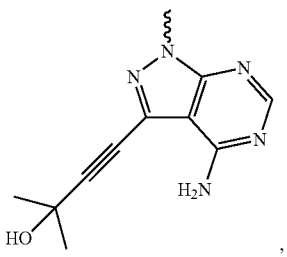
15. The compound of claim 1, wherein $L_1$-$Cy^2$ is selected from
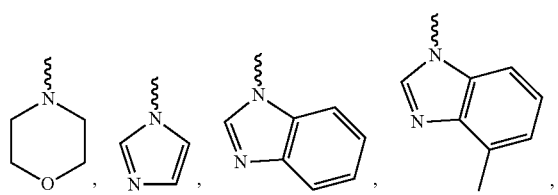

285
-continued
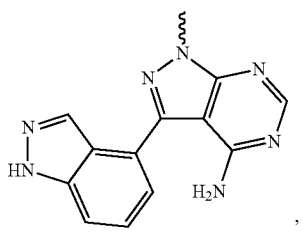,
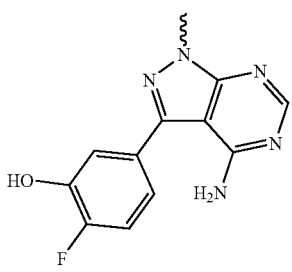,
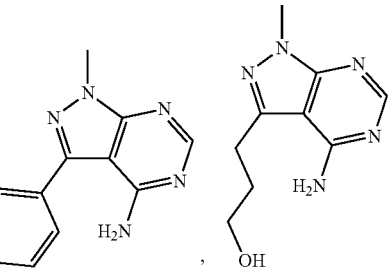,
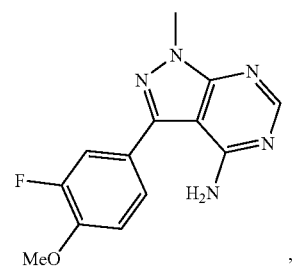,
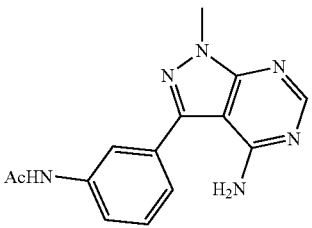,
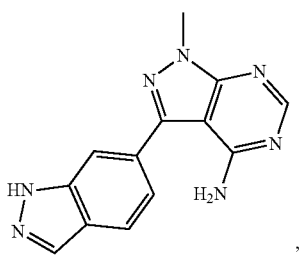,
286
-continued
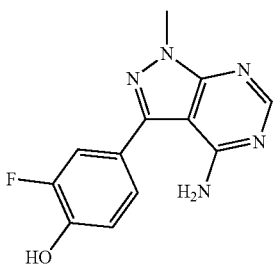,
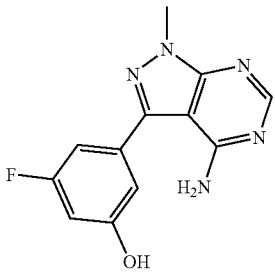,
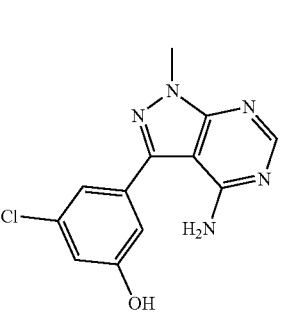,
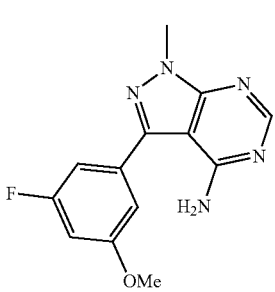,
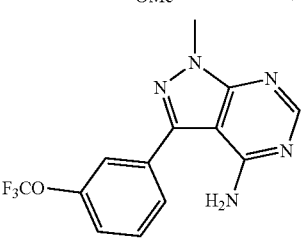,
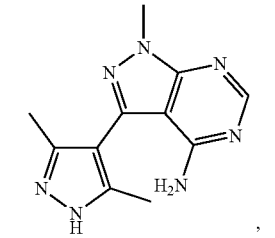, 287
-continued
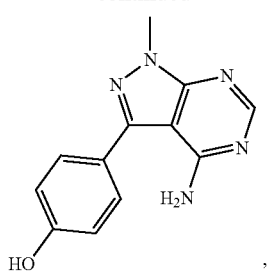
,
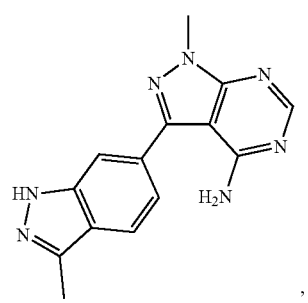
,
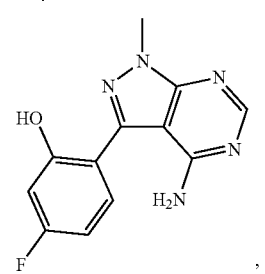
,
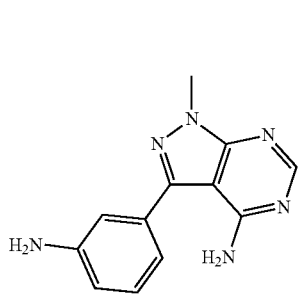
,
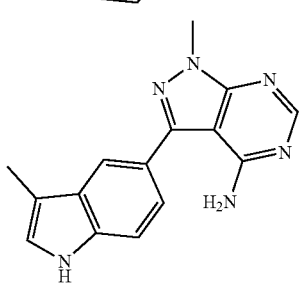
,
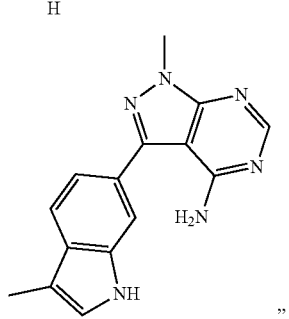
,
288
-continued
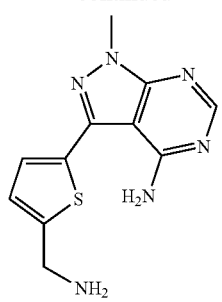
,
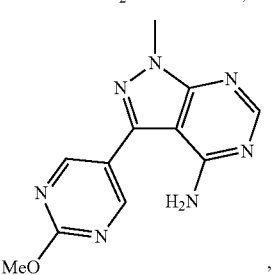
,
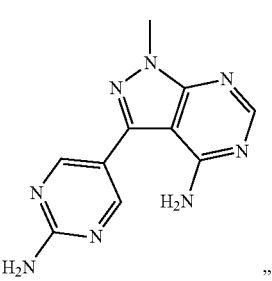
,
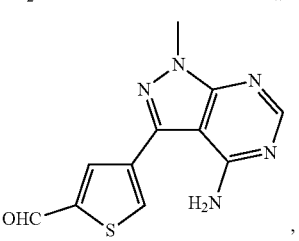
,
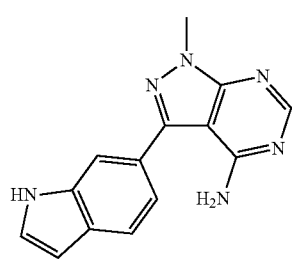
,
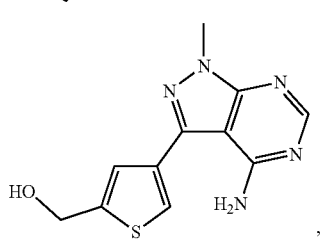
, 289
-continued
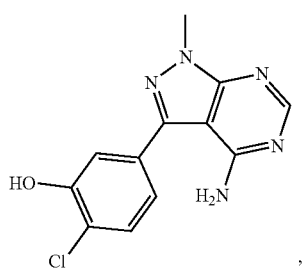
,
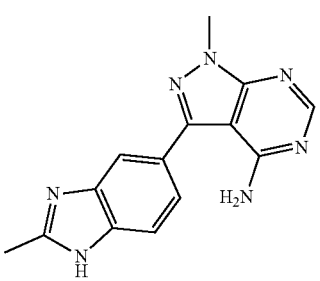
,
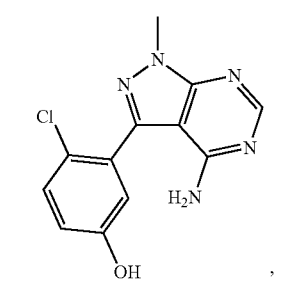
,
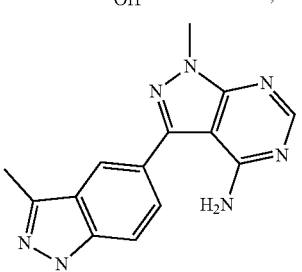
,
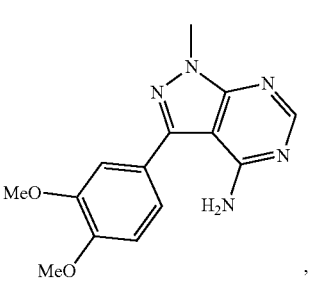
,
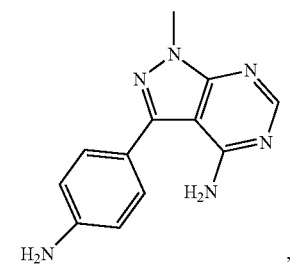
,
290
-continued
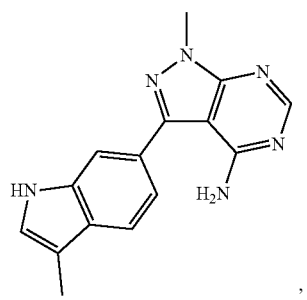
,
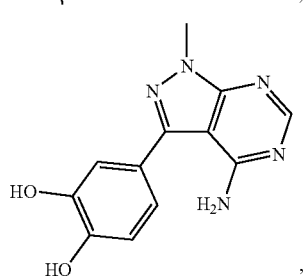
,
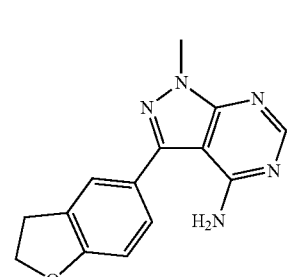
,
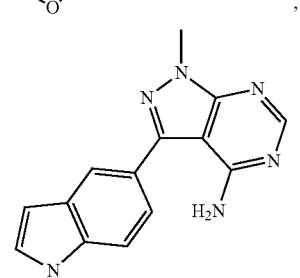
,
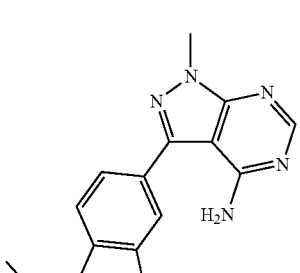
,
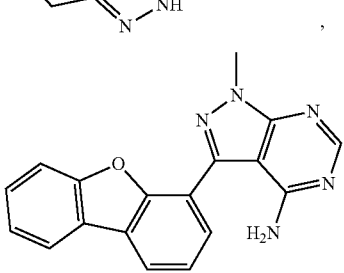

291
-continued
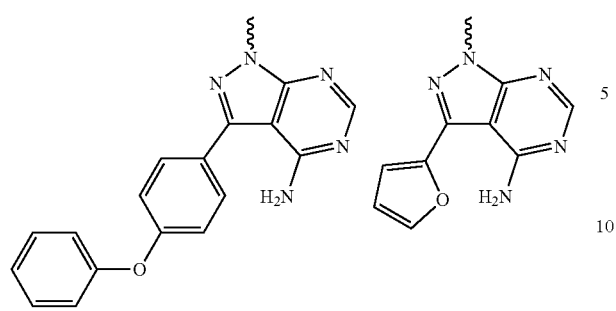
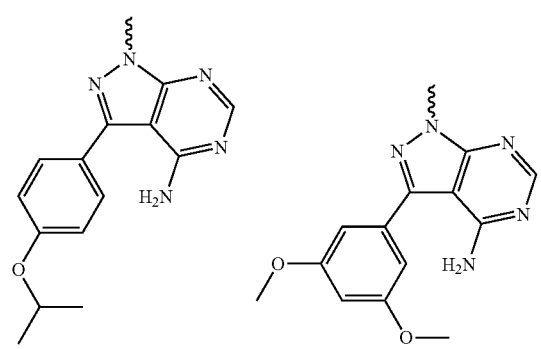
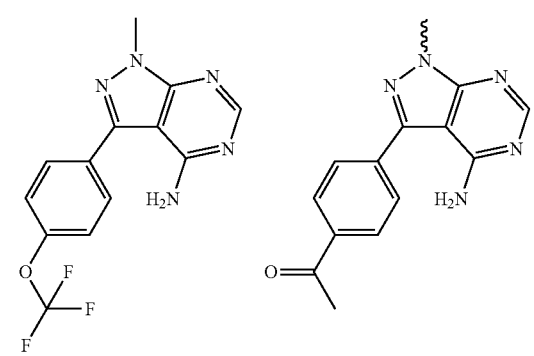
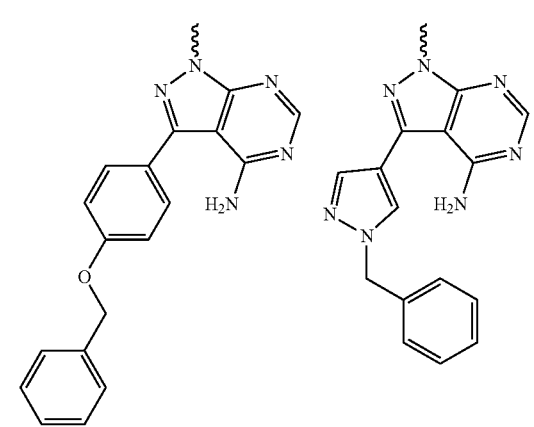
292
-continued
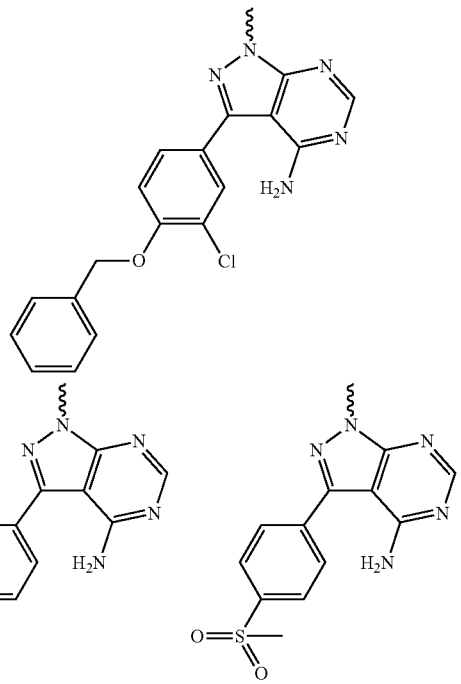
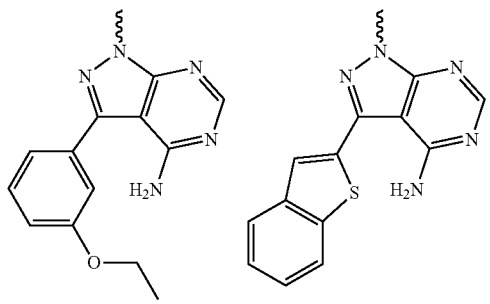
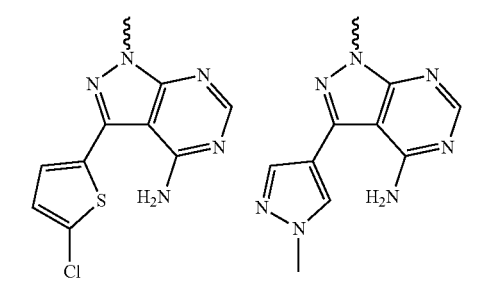
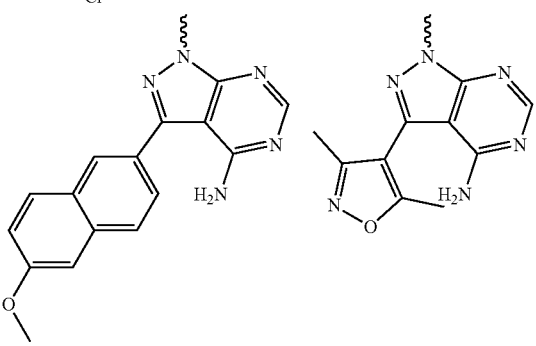

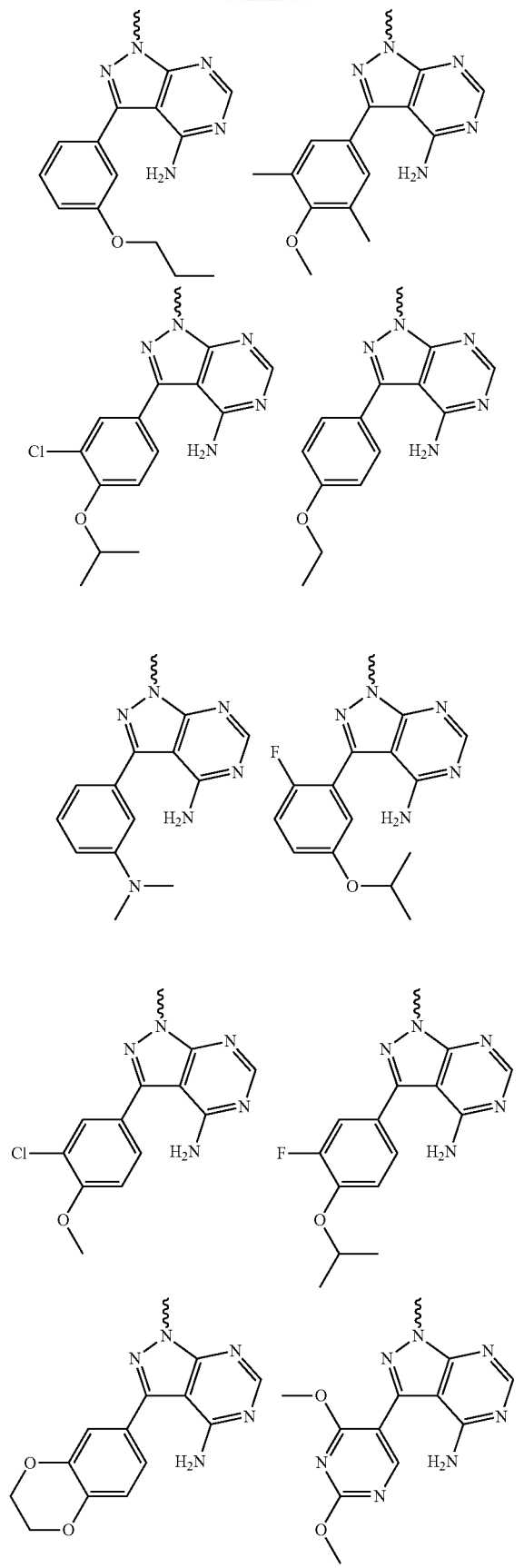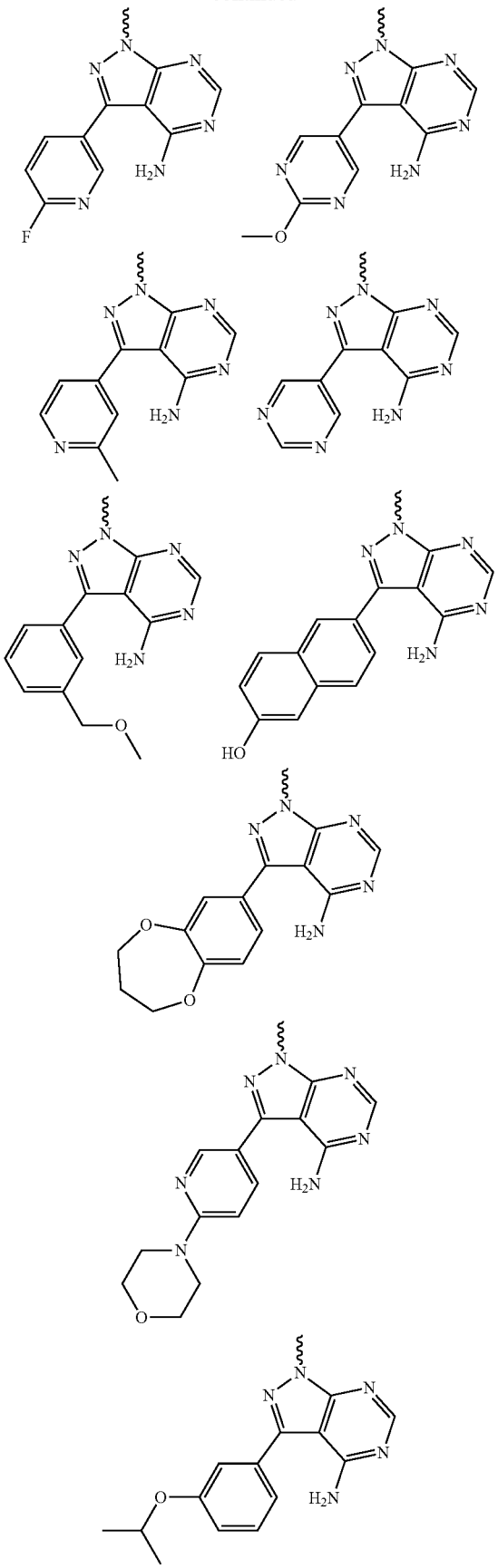

-continued
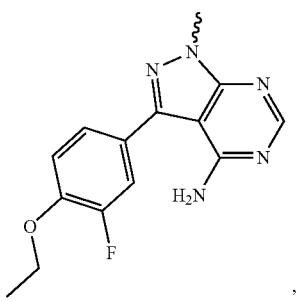
,
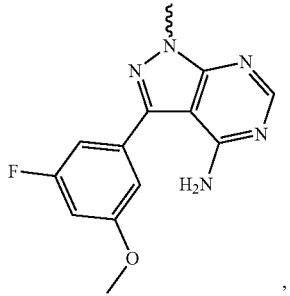
,
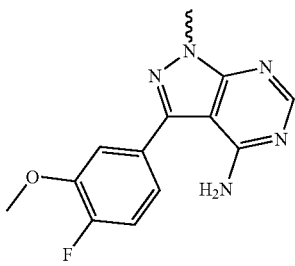
,
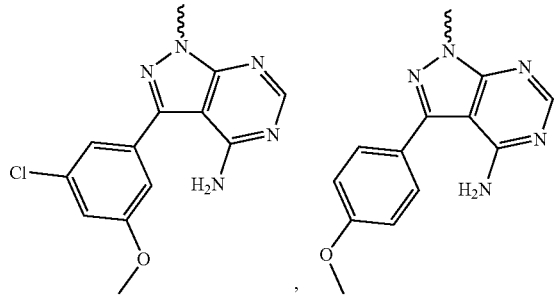
,
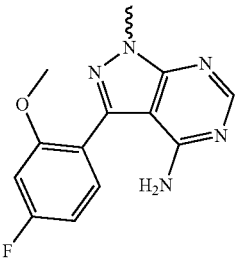
,
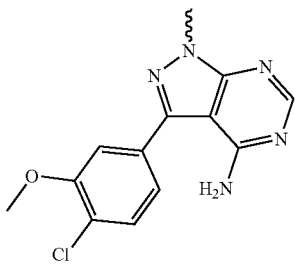
,
-continued
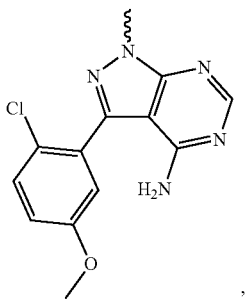
,
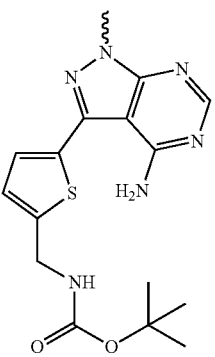
,
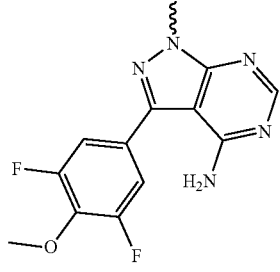
,
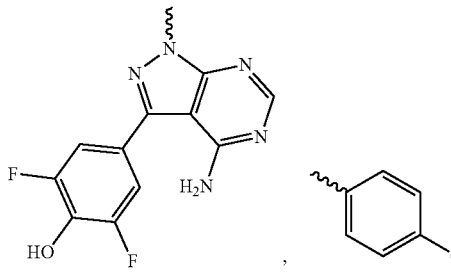
,
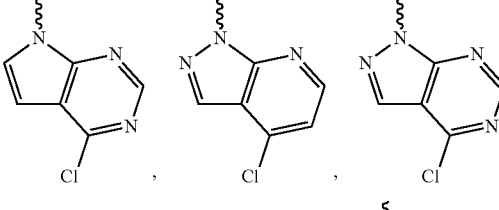
,
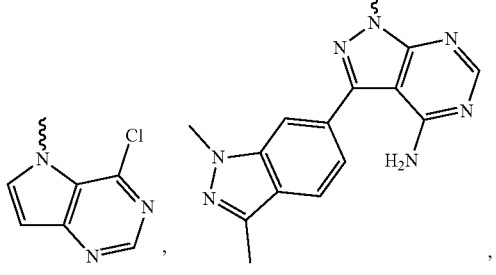
,

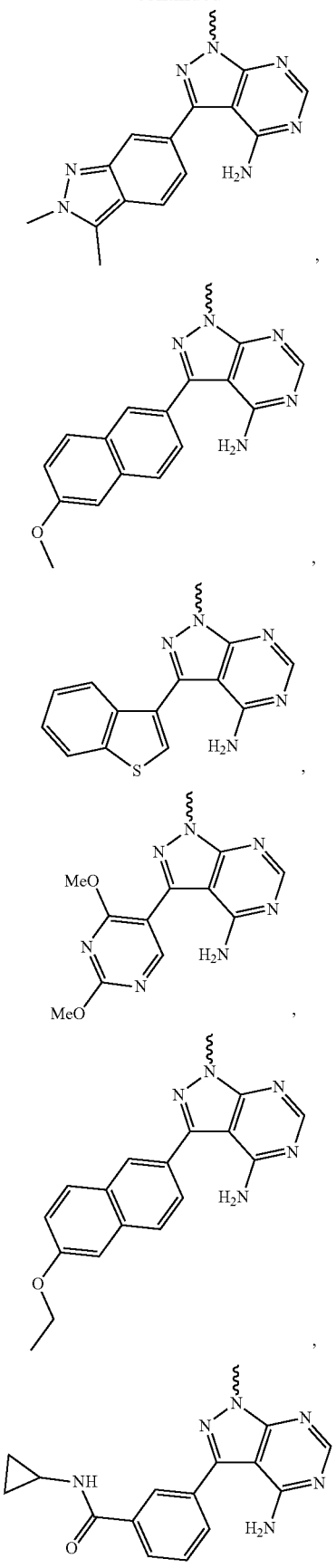
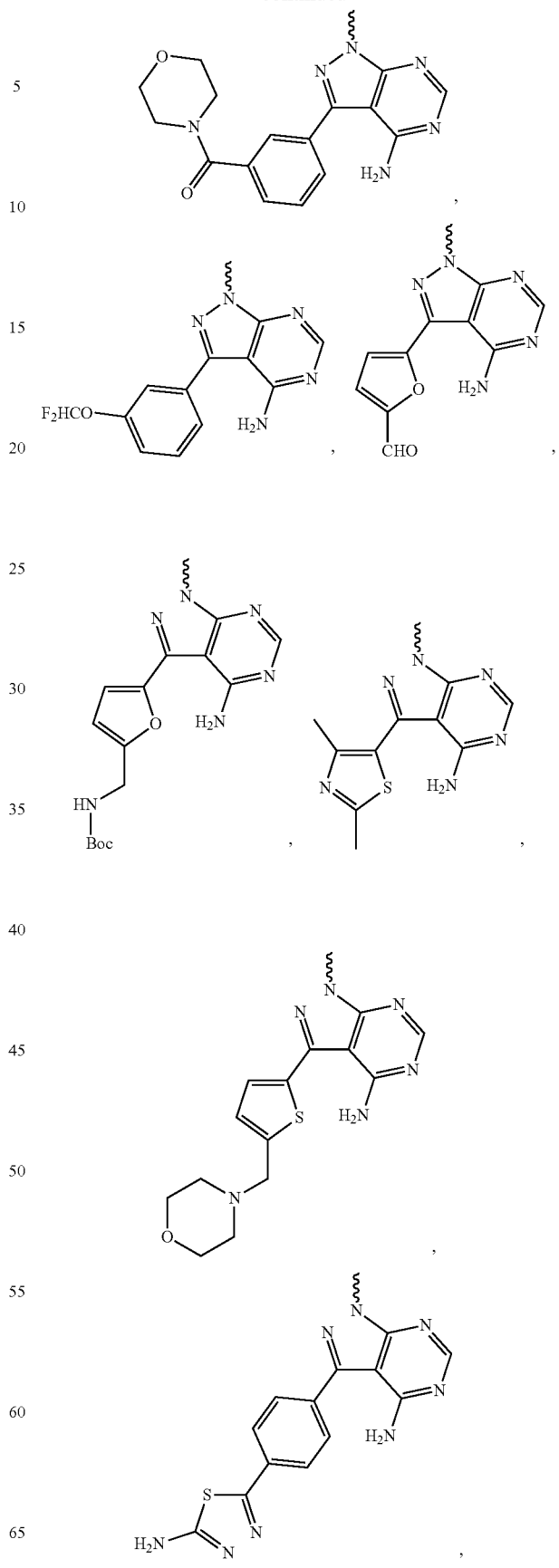

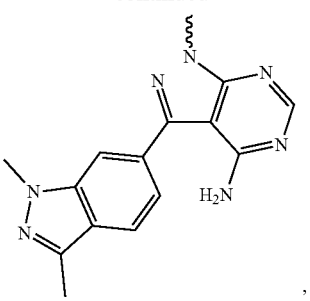
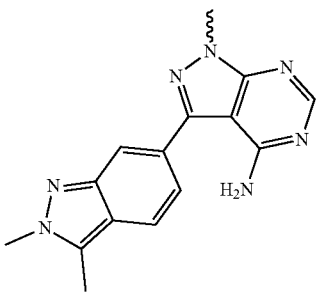
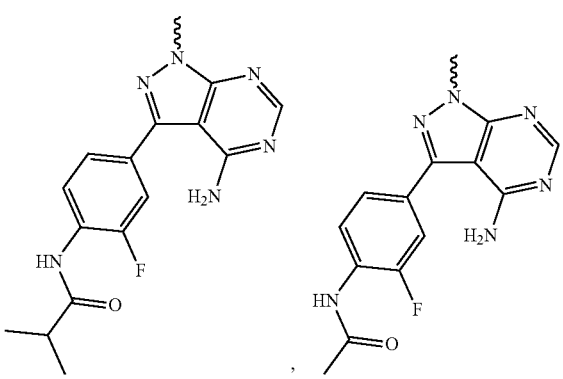
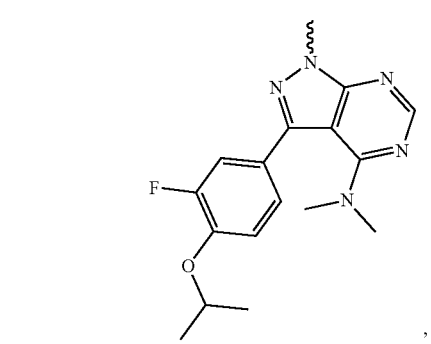
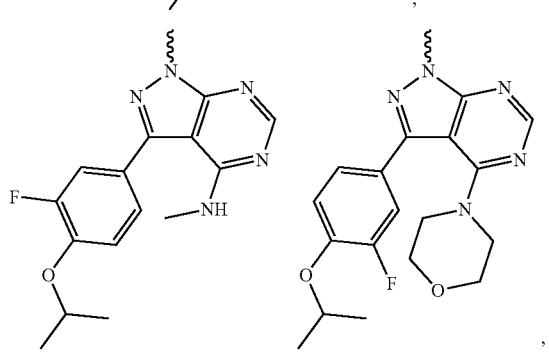
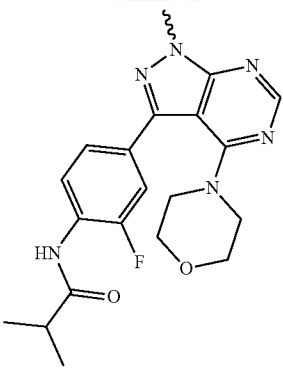
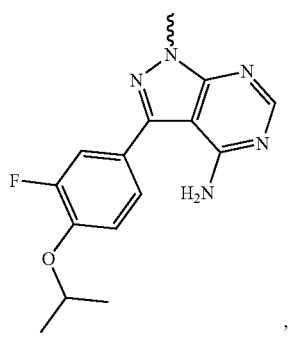
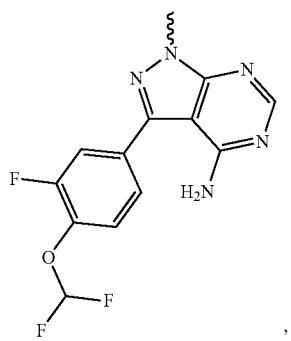
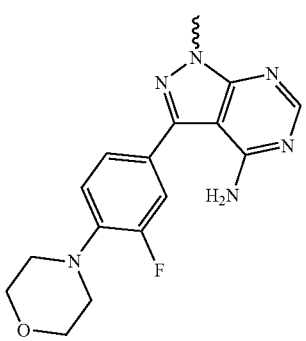
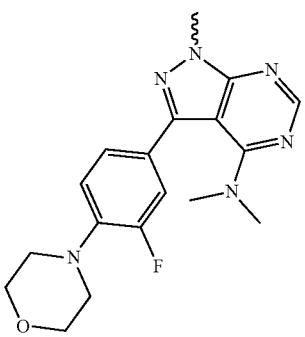

-continued
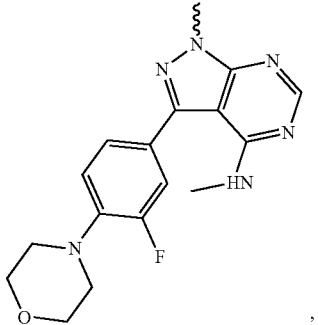
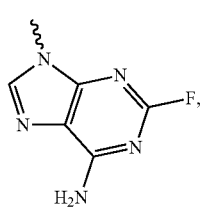
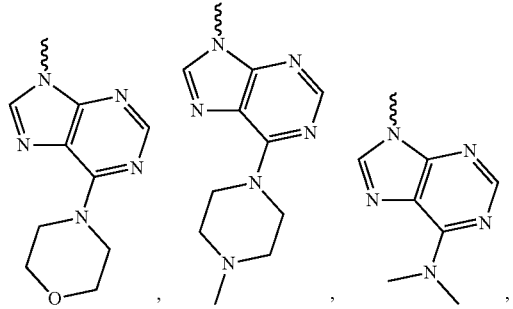
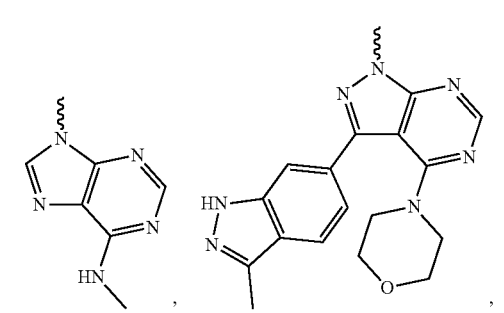
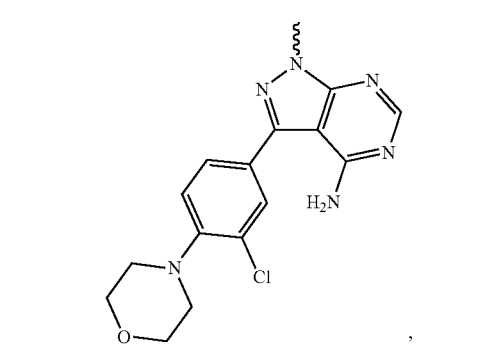
-continued
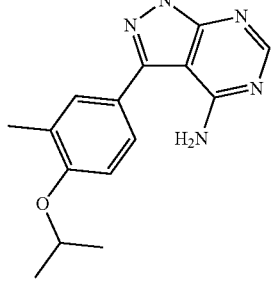
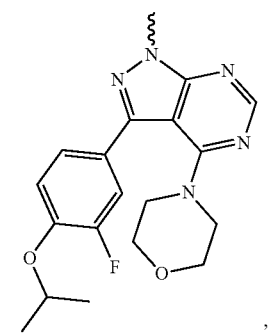
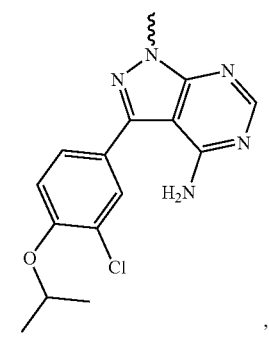
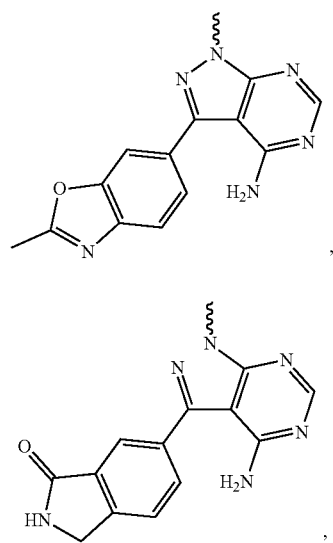

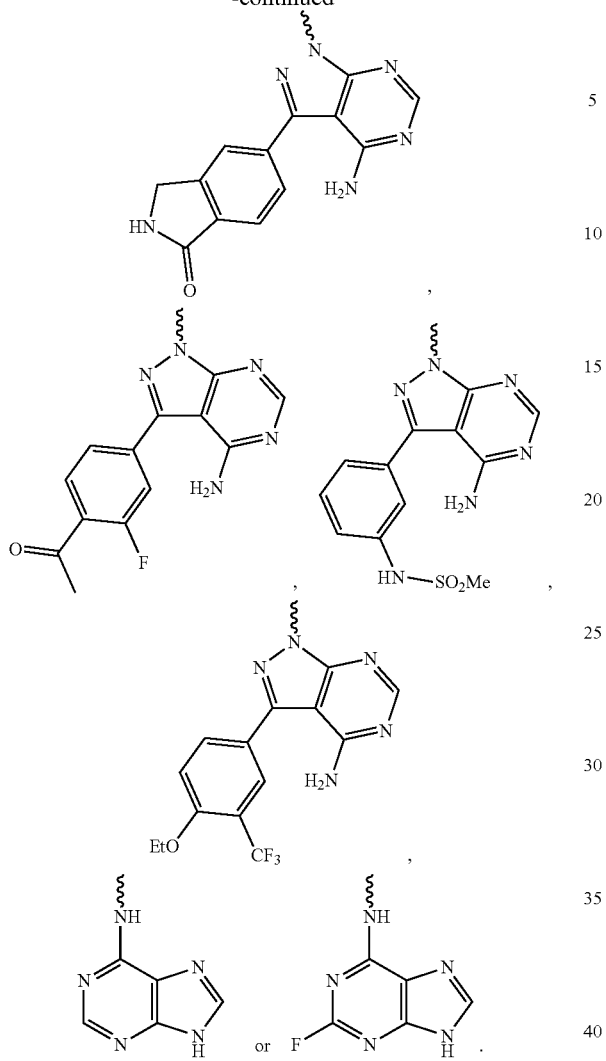

,

16. A pharmaceutical composition comprising a pharmaceutically acceptable carrier and a compound of claim 1, or a pharmaceutically acceptable salt, N-oxide or tautomer thereof.

17. The pharmaceutical composition of claim 16, wherein the composition further comprises one or more additional therapeutic agents selected from the group consisting of an anti-cancer agent, an anti-inflammatory agent, an immunosuppressive agent, a steroid, a non-steroidal anti-inflammatory agent, an antihistamine, an analgesic, or a mixture thereof.

18. A method of inhibiting a catalytic activity of a phophoinositol 3-kinase present in a cell, comprising contacting the cell with an effective amount of a compound of claim 1, or a pharmaceutically acceptable salt, N-oxide or tautomer thereof.

19. The method of claim 18, wherein the inhibition occurs in the cell of a subject suffering from a disease or disorder selected from the group consisting of cancer, a bone disorder, an inflammatory disease, an immune disease, a nervous system disease, a metabolic disease, a respiratory disease, thrombosis, and a cardiac disease.

20. A method of treating asthma in a subject, comprising administering to a subject in need thereof a therapeutically effective amount of a compound of claim 1, or a pharmaceutically acceptable salt, N-oxide or tautomer thereof.

21. A method of treating chronic obstructive pulmonary disease in a subject, comprising administering to a subject in need thereof a therapeutically effective amount of a compound of claim 1, or a pharmaceutically acceptable salt, N-oxide or tautomer thereof.

22. A compound of formula (IA-III), formula (IA-Ia), formula (IA-IIa), formula (IA-IIIa), formula (IA-Ib) or formula (IA-IIb):

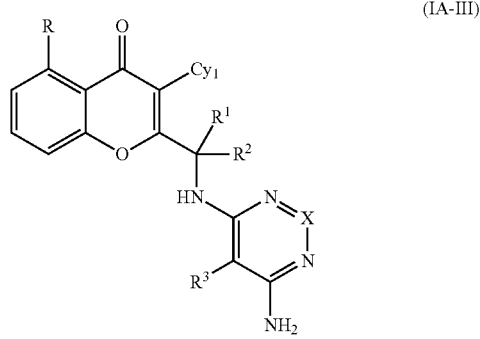

(IA-III)

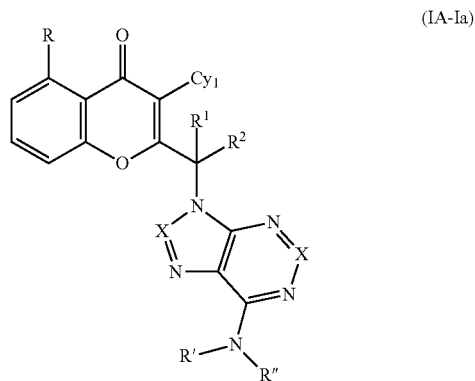

(IA-Ia)

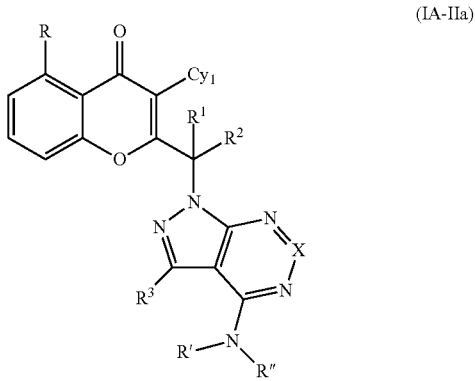

(IA-IIa)

-continued (IA-IIIa)

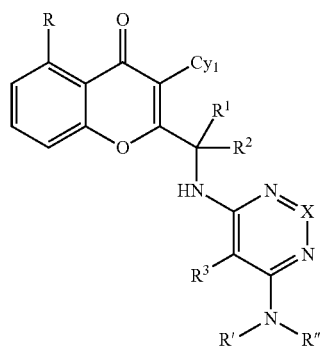

(IA-Ib)

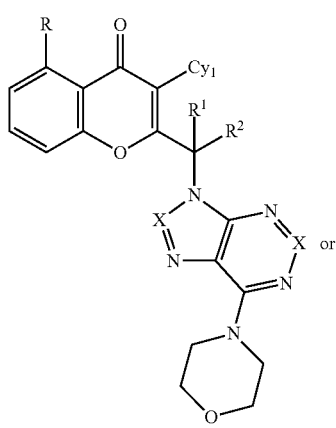

or (IA-IIb)

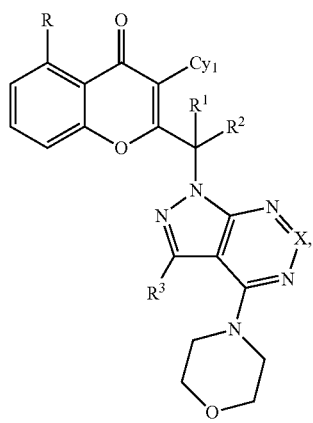

or a pharmaceutically acceptable salt, N-oxide or tautomer thereof;
wherein:
R is selected from hydrogen, halogen, hydroxy, substituted or unsubstituted alkoxy, cyano, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, and substituted or unsubstituted heterocyclyl;
$R^1$ and $R^2$ may be the same or different and are independently selected from hydrogen, halogen, and substituted or unsubstituted $C_{1-6}$ alkyl, or both $R^1$ and $R^2$ directly bound to a common atom, may be joined to form (=O);
$Cy^1$ is a monocyclic group selected from substituted or unsubstituted cycloalkyl, substituted or unsubstituted heterocyclyl, substituted or unsubstituted aryl and substituted or unsubstituted heteroaryl;

X is $CR^3$;
each occurrence of $R^3$ is independently selected from hydrogen, hydroxy, halogen, carboxy, cyano, nitro, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted heterocyclic ring, substituted or unsubstituted heterocyclylalkyl ring, substituted or unsubstituted aryl, substituted or unsubstituted arylalkyl, substituted or unsubstituted heteroaryl, substituted or unsubstituted heteroarylalkyl, substituted or unsubstituted guanidine, —$COOR^x$, —$C(O)R^x$, —$C(S)R^x$, —$C(O)NR^xR^y$, —$C(O)ONR^xR^y$, —$NR^yR^z$, —$NR^xCONR^yR^z$, —$N(R^x)SOR^y$, —$N(R^x)SO_2R^y$, —(=N—$N(R^x)R^y$), —$NR^xC(O)OR^y$, —$NR^xR^y$, —$NR^xC(O)R^y$—, —$NR^xC(S)R^y$—$NR^xC(S)NR^yR^z$, —$SONR^xR^y$—, —$SO_2NR^xR^y$—, —$OR^x$, —$OR^xC(O)NR^yR^z$, —$OR^xC(O)OR^y$—, —$OC(O)R^x$, —$OC(O)NR^xR^y$, —$R^xNR^yC(O)R^z$, —$R^xOR^y$, —$R^xC(O)OR^y$, —$R^xC(O)NR^yR^z$, —$R^xC(O)R^x$, —$ROC(O)R^y$, —$SR^x$, —$SOR^x$, —$SO_2R^x$, or —$ONO_2$;
R' and R" together with the nitrogen atom may be joined to form a substituted or unsubstituted, saturated or unsaturated 3-10 membered ring, which may optionally include heteroatoms which may be the same or different and are selected from O, $NR^f$ (wherein $R^f$ is hydrogen or substituted or unsubstituted alkyl) or S;
each occurrence of $R^x$, $R^y$ and $R^z$ in each of the above groups are independently hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted heteroaryl, substituted or unsubstituted heteroarylalkyl, substituted or unsubstituted cycloalkyl, substituted or unsubstituted cycloalkylalkyl, substituted or unsubstituted cycloalkenyl, substituted or unsubstituted heterocyclyl, substituted heterocyclylalkyl ring, or substituted or unsubstituted amino, or any two of $R^x$, $R^y$ and $R^z$ may be joined to form a substituted or unsubstituted, saturated or unsaturated 3-10 membered ring, which may optionally include heteroatoms which may be the same or different and are selected from O, $NR^f$ or S (wherein $R^f$ is hydrogen or substituted or unsubstituted alkyl);
each occurrence of $R^a$ is independently selected from hydrogen, halogen, hydroxy, cyano, substituted or unsubstituted ($C_{1-6}$)alkyl, —$NR^cR^d$ (wherein $R^c$ and $R^d$ are independently hydrogen, halogen, hydroxy, cyano, substituted or unsubstituted ($C_{1-6}$)alkyl, or ($C_{1-6}$) alkoxy) and —$OR^e$ (wherein $R^e$ is substituted or unsubstituted ($C_{1-6}$)alkyl; and
q is 0, 1 or 2,
wherein the term "substituted" refers to substitution by any one or more of the following substituents which may be the same or different, and are independently selected from hydroxy, halogen, cyano, alkyl, alkoxy, fluorinated alkoxy, heroroaryl, heterocyclyl, alkylheterocyclyl, —$NH_2$, —NH(alkyl), N(alkyl)$_2$, —NHC(O)(alkyl), —S(alkyl), —$SO_2NH_2$, —$SO_2NH$(alkyl), —$SO_2N$(alkyl)$_2$, —$SO_2NH$(cycloalkyl), —$SO_2N$(cycloalkyl)$_2$, —$C(O)NH_2$, —$C(O)NH$(alkyl), —$C(O)N$(alkyl)$_2$, —O-heterocyclyl, —O-heterocyclyl-alkylaryl, —$SO_2NH$(cycloalkyl), and —$CO_2$(alkyl).

23. A compound of formula (IA-VI):

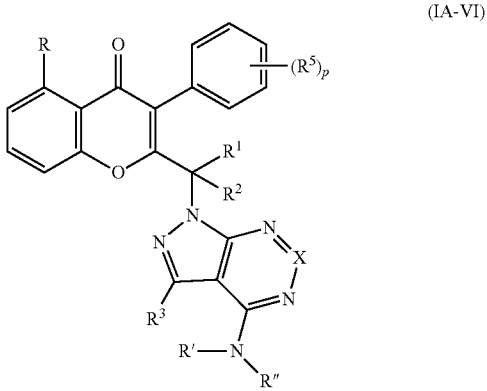

(IA-VI)

or a pharmaceutically acceptable salt thereof,
wherein:
each occurrence of R is independently selected from hydroxy, halogen, —OR$^a$, cyano, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, and substituted or unsubstituted heterocyclyl;

$R^1$ and $R^2$ may be the same or different and are independently selected from hydrogen, halogen, and substituted or unsubstituted $C_{1-6}$ alkyl, or both $R^1$ and $R^2$ directly bound to a common atom, may be joined to form (=O);

X is $CR^3$;

each occurrence of $R^3$ is independently selected from hydrogen, hydroxy, halogen, carboxy, cyano, nitro, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted heterocyclyl, substituted or unsubstituted heterocyclylalkyl ring, substituted or unsubstituted aryl, substituted or unsubstituted arylalkyl, substituted or unsubstituted heteroaryl, substituted or unsubstituted heteroarylalkyl, substituted or unsubstituted guanidine, —COOR$^x$, C(O)R$^x$, —C(S)R$^x$, —C(O)NR$^x$R$^y$, —C(O)ONR$^x$R$^y$, —NR$^y$R$^z$, —NR$^x$CONR$^y$R$^z$, —N(R$^x$)SOR$^y$, —N(R$^x$)SO$_2$R$^y$, —(=N—N(R$^x$)R$^y$), —NR$^x$C(O)OR$^y$, —NR$^x$R$^y$, —NR$^x$C(O)R$^y$—, —NR$^x$C(S)R$^y$—NR$^x$C(S)NR$^y$R$^z$, —SONR$^x$R$^y$—, —SO$_2$NR$^x$R$^y$—, —OR$^x$, —OR$^x$C(O)NR$^y$R$^z$, —OR$^x$C(O)OR$^y$—, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^x$, —R$^x$OC(O)R$^y$, —SR$^x$, —SOR$^x$, —SO$_2$R, or —ONO$_2$;

each occurrence of R' and R" is independently selected from hydrogen, hydroxy, halogen, carboxy, cyano, nitro, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted cycloalkyl, substituted or unsubstituted cycloalkylalkyl, substituted or unsubstituted cycloalkenyl, substituted or unsubstituted heteroaryl, substituted or unsubstituted heteroarylalkyl, substituted or unsubstituted heterocyclyl, substituted or unsubstituted heterocyclylalkyl ring, substituted or unsubstituted guanidine, —COOR$^x$, —C(O)R$^x$, —C(S)R$^x$, —C(O)NR$^x$R$^y$, —C(O)ONR$^x$R$^y$, —NR$^y$R$^z$, —NR$^x$CONR$^y$R$^z$, —N(R$^x$)SOR$^y$, —N(R$^x$)SO$_2$R$^y$, —(=N—N(R$^x$)R$^y$), —NR$^x$C(O)OR$^y$, —NR$^x$R$^y$, —NR$^x$C(O)R$^y$—, —NR$^x$C(S)R$^y$—NR$^x$C(S)NR$^y$R$^z$, —SONR$^x$R$^y$—, —SO$_2$NR$^x$R$^y$—, —OR$^x$, —OR$^x$C(O)NR$^y$R$^z$, —OR$^x$C(O)OR$^y$—, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^x$, —R$^x$OC(O)R$^y$, —SR$^x$, —SOR$^x$, —SO$_2$R$^x$, or —ONO$_2$, or both R' and R" together with the nitrogen atom may be joined to form a substituted or unsubstituted, saturated or unsaturated 3-10 membered ring, which may optionally include heteroatoms which may be the same or different and are selected from O, NR$^f$ (wherein R$^f$ is hydrogen or substituted or unsubstituted alkyl) or S;

each occurrence of R$^x$, R$^y$ and R$^z$ in each of the above groups are independently hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted heteroaryl, substituted or unsubstituted heteroarylalkyl, substituted or unsubstituted cycloalkyl, substituted or unsubstituted cycloalkylalkyl, substituted or unsubstituted cycloalkenyl, substituted or unsubstituted heterocyclyl, substituted heterocyclylalkyl ring, or substituted or unsubstituted amino, or any two of R$^x$, R$^y$ and R$^z$ may be joined to form a substituted or unsubstituted, saturated or unsaturated 3-10 membered ring, which may optionally include heteroatoms which may be the same or different and are selected from O, NR$^f$ or S (wherein R$^f$ is hydrogen or substituted or unsubstituted alkyl);

each occurrence of R$^a$ is independently selected from hydrogen, halogen, hydroxy, cyano, substituted or unsubstituted (C$_{1-6}$)alkyl, —NR$^c$R$^d$ (wherein R$^c$ and R$^d$ are independently hydrogen, halogen, hydroxy, cyano, substituted or unsubstituted (C$_{1-6}$)alkyl, or (C$_{1-6}$) alkoxy) and —OR$^e$ (wherein R$^e$ is substituted or unsubstituted (C$_{1-6}$)alkyl);

each occurrence of R$^5$ is hydrogen, C$_{1-6}$ alkyl or halogen; and p is 0, 1, 2, 3, 4 or 5, wherein the term "substituted" refers to substitution by any one or more of the following substituents which may be the same or different, and are independently selected from hydroxy, halogen, cyano, alkyl, alkoxy, fluorinated alkoxy, heroroaryl, heterocyclyl, alkylheterocyclyl, —NH$_2$, —NH(alkyl), N(alkyl)$_2$, —NHC(O)(alkyl), —S(alkyl), —SO$_2$NH$_2$, —SO$_2$NH(alkyl), —SO$_2$N(alkyl)$_2$, —SO$_2$NH(cycloalkyl), —SO$_2$N(cycloalkyl)$_2$, —C(O)NH$_2$, —C(O)NH(alkyl), —C(O)N(alkyl)$_2$, —O-heterocyclyl, —O-heterocyclyl-alkylaryl, —SO$_2$NH(cycloalkyl), and —CO$_2$(alkyl).

24. The compound of claim 23, wherein each of R' and R" is independently selected from hydrogen and C$_{1-6}$ alkyl, or both R' and R", together with the nitrogen atom to which they are attached, may be joined to form a substituted or unsubstituted, saturated or unsaturated 3-10 membered ring, which may optionally include heteroatoms which may be the same or different and are selected from O, NR$^f$ or S, wherein R$^f$ is hydrogen or substituted or unsubstituted alkyl.

25. The compound of claim 24, wherein each of R' and R" is independently selected from hydrogen and methyl, or both R' and R", together with the nitrogen atom to which they are attached, are joined to form a saturated 6-membered ring selected from morpholin-4-yl and 4-methylpiperidin-1-yl.

26. A method of treating asthma in a subject, comprising administering to a subject in need thereof a therapeutically effective amount of a compound of claim 23, or a pharmaceutically acceptable salt thereof.

27. A method of treating chronic obstructive pulmonary disease in a subject, comprising administering to a subject in need thereof a therapeutically effective amount of a compound of claim 23, or a pharmaceutically acceptable salt thereof.

28. A compound of formula (IA-VIII):

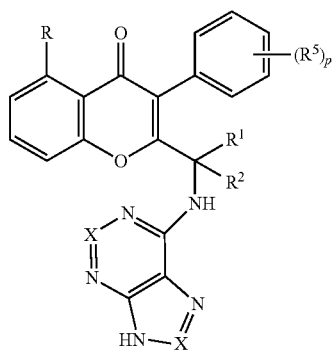

(IA-VIII)

or a pharmaceutically acceptable salt thereof, wherein:

each occurrence of R is independently selected from hydroxy, halogen, —OR$^a$, cyano, substituted or unsubstituted $C_{1-6}$ alkyl, substituted or unsubstituted $C_{2-6}$ alkenyl, substituted or unsubstituted $C_{2-6}$ alkynyl, substituted or unsubstituted $C_{3-8}$ cycloalkyl, and substituted or unsubstituted heterocyclyl;

$R^1$ and $R^2$ may be the same or different and are independently selected from hydrogen, halogen, and substituted or unsubstituted $C_{1-6}$ alkyl, or both $R^1$ and $R^2$ directly bound to a common atom, may be joined to form (=O);

X is $CR^3$;

each occurrence of $R^3$ is independently selected from hydrogen, hydroxy, halogen, carboxy, cyano, nitro, substituted or unsubstituted alkyl, substituted or unsubstituted alkoxy, substituted or unsubstituted alkenyl, substituted or unsubstituted alkynyl, substituted or unsubstituted cycloalkyl, substituted or unsubstituted cycloalkylalkyl, substituted or unsubstituted cycloalkenyl, substituted or unsubstituted heterocyclyl, substituted or unsubstituted heterocyclylalkyl ring, substituted or unsubstituted aryl, substituted or unsubstituted arylalkyl, substituted or unsubstituted heteroaryl, substituted or unsubstituted heteroarylalkyl, substituted or unsubstituted guanidine, —COOR$^x$, C(O)R$^x$, —C(S)R$^x$, —C(O)NR$^x$R$^y$, —C(O)ONR$^x$R$^y$, —NR$^y$R$^z$, —NR$^x$CONR$^y$R$^z$, —N(R$^x$)SOR$^y$, —N(R$^x$)SO$_2$R$^y$, —(=N—N(R$^x$)R$^y$), —NR$^x$C(O)OR$^y$, —NR$^x$R$^y$, —NR$^x$C(O)R$^y$—, —NR$^x$C(S)R$^y$—NR$^x$C(S)NR$^y$R$^z$, —SONR$^x$R$^y$—, —SO$_2$NR$^x$R$^y$—, —OR$^x$, —OR$^x$C(O)NR$^y$R$^z$, —OR$^x$C(O)OR$^y$—, —OC(O)R$^x$, —OC(O)NR$^x$R$^y$, —R$^x$NR$^y$C(O)R$^z$, —R$^x$OR$^y$, —R$^x$C(O)OR$^y$, —R$^x$C(O)NR$^y$R$^z$, —R$^x$C(O)R$^x$, —ROC(O)R$^y$, —SR$^x$, —SOR$^x$, —SO$_2$R$^x$, or —ONO$_2$;

each occurrence of R$^x$, R$^y$ and R$^z$ in each of the above groups are independently hydrogen, substituted or unsubstituted alkyl, substituted or unsubstituted alkoxy, substituted or unsubstituted alkenyl, substituted or unsubstituted alkynyl, substituted or unsubstituted aryl, substituted or unsubstituted arylalkyl, substituted or unsubstituted heteroaryl, substituted or unsubstituted heteroarylalkyl, substituted or unsubstituted cycloalkyl, substituted or unsubstituted cycloalkylalkyl, substituted or unsubstituted cycloalkenyl, substituted or unsubstituted heterocyclyl, substituted heterocyclylalkyl ring, or substituted or unsubstituted amino, or any two of R$^x$, R$^y$ and R$^z$ may be joined to form a substituted or unsubstituted, saturated or unsaturated 3-10 membered ring, which may optionally include heteroatoms which may be the same or different and are selected from O, NR$^f$ or S (wherein R$^f$ is hydrogen or substituted or unsubstituted alkyl);

each occurrence of R$^a$ is independently selected from hydrogen, halogen, hydroxy, cyano, substituted or unsubstituted ($C_{1-6}$)alkyl, —NR$^c$R$^d$ (wherein R$^c$ and R$^d$ are independently hydrogen, halogen, hydroxy, cyano, substituted or unsubstituted ($C_{1-6}$)alkyl, or ($C_{1-6}$) alkoxy) and —OR$^e$ (wherein R$^e$ is substituted or unsubstituted ($C_{1-6}$)alkyl);

each occurrence of R$^5$ is hydrogen, $C_{1-6}$ alkyl or halogen; and p is 0, 1, 2, 3, 4 or 5, wherein the term "substituted" refers to substitution by any one or more of the following substituents which may be the same or different, and are independently selected from hydroxy, halogen, cyano, alkyl, alkoxy, fluorinated alkoxy, heroroaryl, heterocyclyl, alkylheterocyclyl, —NH$_2$, —NH (alkyl), N(alkyl)$_2$, —NHC(O)(alkyl), —S(alkyl), —SO$_2$NH$_2$, —SO$_2$NH(alkyl), —SO$_2$N(alkyl)$_2$, —SO$_2$NH (cycloalkyl), —SO$_2$N(cycloalkyl)$_2$, —C(O)NH$_2$, —C(O) NH(alkyl), —C(O)N(alkyl)$_2$, —O-heterocyclyl, —O-heterocyclyl-alkylaryl, —SO$_2$NH(cycloalkyl), and —CO$_2$ (alkyl).

29. The compound of claim 28, wherein each occurrence of $R^3$ is independently selected from hydrogen, hydroxy, halogen and NH$_2$.

30. The compound of claim 29, wherein each occurrence of $R^3$ is independently selected from hydrogen and fluoro.

31. A method of treating asthma in a subject, comprising administering to a subject in need thereof a therapeutically effective amount of a compound of claim 28, or a pharmaceutically acceptable salt thereof.

32. A method of treating chronic obstructive pulmonary disease in a subject, comprising administering to a subject in need thereof a therapeutically effective amount of a compound of claim 28, or a pharmaceutically acceptable salt thereof.

33. A compound selected from the group consisting of:
2-(6-Amino-9H-purin-9-yl) methyl)-3-(3-fluorophenyl)-5-methoxy-4H-chromen-4-one;
2-((4-Amino-3-(3-fluoro-4-isopropoxyphenyl)-1H-pyrazolo[3,4-d]pyrimidin-1-yl) methyl)-3-(3-fluorophenyl)-5-methoxy-4H-chromen-4-one;
2-((4-amino-3-(3-fluoro-4-isopropoxyphenyl)-1H-pyrazolo[3,4-d]pyrimidin-1-yl) methyl)-5-fluoro-3-(3-fluorophenyl)-4H-chromen-4-one;
2-((4-amino-3-(3-fluoro-5-methoxyphenyl)-1H-pyrazolo[3,4-d]pyrimidin-1-yl)methyl)-5-fluoro-3-(3-fluorophenyl)-4H-chromen-4-one;

2-((4-amino-3-(3-fluoro-5-hydroxyphenyl)-1H-pyrazolo[3,4-d]pyrimidin-1-yl)methyl)-5-fluoro-3-(3-fluorophenyl)-4H-chromen-4-one;

2-(1-(4-amino-3-(3-methyl-1H-indazol-6-yl)-1H-pyrazolo[3,4-d]pyrimidin-1-yl)ethyl)-5-fluoro-3-(3-fluorophenyl)-4H-chromen-4-one;

(+)-2-(1-(4-amino-3-(3-methyl-1H-indazol-6-yl)-1H-pyrazolo[3,4-d]pyrimidin-1-yl) ethyl)-5-fluoro-3-(3-fluorophenyl)-4H-chromen-4-one;

(−)-2-(1-(4-amino-3-(3-methyl-1H-indazol-6-yl)-1H-pyrazolo[3,4-d]pyrimidin-1-yl) ethyl)-5-fluoro-3-(3-fluorophenyl)-4H-chromen-4-one;

2-(1-(4-amino-3-(1H-pyrazol-4-yl)-1H-pyrazolo[3,4-d]pyrimidin-1-yl)ethyl)-5-fluoro-3-(3-fluorophenyl)-4H-chromen-4-one;

2-(1-(6-amino-9H-purin-9-yl)ethyl)-5-fluoro-3-(3-fluorophenyl)-4H-chromen-4-one;

2-(1-(4-amino-3-(3-fluoro-4-isopropoxyphenyl)-1H-pyrazolo[3,4-d]pyrimidin-1-yl) ethyl)-5-fluoro-3-(4-fluorophenyl)-4H-chromen-4-one;

2-(1-(4-amino-3-(3-fluoro-4-isopropoxyphenyl)-1H-pyrazolo[3,4-d]pyrimidin-1-yl) ethyl)-5-fluoro-3-phenyl-4H-chromen-4-one;

2-(1-(4-amino-3-(benzofuran-2-yl)-1H-pyrazolo[3,4-d]pyrimidin-1-yl)ethyl)-5-fluoro-3-(3-fluorophenyl)-4H-chromen-4-one;

2-(1-(9H-purin-6-ylamino)ethyl)-5-fluoro-3-(3-fluorophenyl)-4H-chromen-4-one;

2-(1-(4-amino-1H-pyrazolo[3,4-d]pyrimidin-1-yl)ethyl)-5-fluoro-3-(3-fluorophenyl)-4H-chromen-4-one;

(+)-2-(1-(4-amino-1H-pyrazolo[3,4-d]pyrimidin-1-yl) ethyl)-5-fluoro-3-(3-fluorophenyl)-4H-chromen-4-one;

(−)-2-(1-(4-amino-1H-pyrazolo[3,4-d]pyrimidin-1-yl) ethyl)-5-fluoro-3-(3-fluorophenyl)-4H-chromen-4-one;

2-(1-(4-amino-3-(4-(difluoromethoxy)-3-fluorophenyl)-1H-pyrazolo[3,4-d]pyrimidin-1-yl)ethyl)-5-fluoro-3-(3-fluorophenyl)-4H-chromen-4-one;

2-(1-(4-amino-3-(3-fluoro-4-isopropoxyphenyl)-1H-pyrazolo[3,4-d]pyrimidin-1-yl) ethyl)-5-fluoro-3-(1H-pyrazol-4-yl)-4H-chromen-4-one;

2-(1-(4-amino-3-(3-fluoro-4-(tetrahydro-2H-pyran-4-yloxy)phenyl)-1H-pyrazolo[3,4-d]pyrimidin-1-yl) ethyl)-5-fluoro-3-(3-fluorophenyl)-4H-chromen-4-one;

2-(1-(4-amino-3-(3-isopropyl-1H-indazol-6-yl)-1H-pyrazolo[3,4-d]pyrimidin-1-yl)ethyl)-5-fluoro-3-(3-fluorophenyl)-4H-chromen-4-one;

2-(1-(4-amino-3-(3-fluoro-4-(piperidin-4-yloxy)phenyl)-1H-pyrazolo[3,4-d]pyrimidin-1-yl)ethyl)-5-fluoro-3-(3-fluorophenyl)-4H-chromen-4-one;

2-(1-(4-amino-3-(3-fluoro-4-(2-hydroxyethylamino)phenyl)-1H-pyrazolo[3,4-d]pyrimidin-1-yl)ethyl)-5-fluoro-3-(3-fluorophenyl)-4H-chromen-4-one;

2-(1-(4-amino-3-(3-fluoro-4-(isopropylamino)phenyl)-1H-pyrazolo[3,4-d]pyrimidin-1-yl)ethyl)-5-fluoro-3-(3-fluorophenyl)-4H-chromen-4-one;

2-(1-(4-amino-3-(4-(dimethylamino)-3-fluorophenyl)-1H-pyrazolo[3,4-d]pyrimidin-1-yl)ethyl)-5-fluoro-3-(3-fluorophenyl)-4H-chromen-4-one;

2-(1-(4-amino-3-(3-fluoro-4-morpholinophenyl)-1H-pyrazolo[3,4-d]pyrimidin-1-yl)ethyl)-5-fluoro-3-(3-fluorophenyl)-4H-chromen-4-one;

2-(1-(4-amino-3-(2-methyl-1H-benzo[d]imidazol-5-yl)-1H-pyrazolo[3,4-d]pyrimidin-1-yl)ethyl)-5-fluoro-3-(3-fluorophenyl)-4H-chromen-4-one;

2-(1-(4-amino-3-(3-fluoro-4-(4-methylpiperazin-1-yl)phenyl)-1H-pyrazolo[3,4-d]pyrimidin-1-yl)ethyl)-5-fluoro-3-(3-fluorophenyl)-4H-chromen-4-one;

2-(1-(4-(dimethylamino)-1H-pyrazolo[3,4-d]pyrimidin-1-yl)ethyl)-5-fluoro-3-(3-fluorophenyl)-4H-chromen-4-one;

2-(1-(4-amino-1H-pyrazolo[3,4-d]pyrimidin-1-yl)ethyl)-5-fluoro-3-phenyl-4H-chromen-4-one;

2-(1-(4-amino-1H-pyrazolo[3,4-d]pyrimidin-1-yl)ethyl)-5-fluoro-3-(4-fluorophenyl)-4H-chromen-4-one;

2-(1-(4-amino-3-(4-(difluoromethoxy)-3-fluorophenyl)-1H-pyrazolo[3,4-d]pyrimidin-1-yl)ethyl)-5-fluoro-3-(4-fluorophenyl)-4H-chromen-4-one;

2-(1-(4-amino-3-(4-(difluoromethoxy)-3-fluorophenyl)-1H-pyrazolo[3,4-d]pyrimidin-1-yl)ethyl)-5-fluoro-3-phenyl-4H-chromen-4-one;

2-(1-(4-amino-3-methyl-1H-pyrazolo[3,4-d]pyrimidin-1-yl)ethyl)-5-fluoro-3-(3-fluorophenyl)-4H-chromen-4-one;

2-(1-(4-amino-3-ethyl-1H-pyrazolo[3,4-d]pyrimidin-1-yl)ethyl)-5-fluoro-3-(3-fluorophenyl)-4H-chromen-4-one;

2-(1-(4-amino-3-isopropyl-1H-pyrazolo[3,4-d]pyrimidin-1-yl)ethyl)-5-fluoro-3-(3-fluorophenyl)-4H-chromen-4-one;

2-(1-(4-amino-3-(benzo[b]thiophen-2-yl)-1H-pyrazolo[3,4-d]pyrimidin-1-yl)ethyl)-5-fluoro-3-(3-fluorophenyl)-4H-chromen-4-one;

2-(1-(4-amino-3-morpholino-1H-pyrazolo[3,4-d]pyrimidin-1-yl)ethyl)-5-fluoro-3-(3-fluorophenyl)-4H-chromen-4-one;

2-(1-(4-amino-3-(dimethylamino)-1H-pyrazolo[3,4-d]pyrimidin-1-yl)ethyl)-5-fluoro-3-(3-fluorophenyl)-4H-chromen-4-one;

2-(1-(4-amino-3-(piperidin-1-yl)-1H-pyrazolo[3,4-d]pyrimidin-1-yl)ethyl)-5-fluoro-3-(3-fluorophenyl)-4H-chromen-4-one;

2-(1-(4-amino-3-(6-isopropoxypyridin-3-yl)-1H-pyrazolo[3,4-d]pyrimidin-1-yl)ethyl)-5-fluoro-3-(3-fluorophenyl)-4H-chromen-4-one;

2-(1-(4-amino-3-(methylthio)-1H-pyrazolo[3,4-d]pyrimidin-1-yl)ethyl)-5-fluoro-3-(3-fluorophenyl)-4H-chromen-4-one;

2-(1-(4-amino-3-(3-methyl-1H-indazol-6-yl)-1H-pyrazolo[3,4-d]pyrimidin-1-yl)ethyl)-5-fluoro-3-(3-fluorophenyl)-4H-chromen-4-one 4-methylbenzenesulfonate;

2-(1-(4-amino-3-(4-(1-benzhydrylazetidin-3-yloxy)-3-fluorophenyl)-1H-pyrazolo[3,4-d]pyrimidin-1-yl) ethyl)-5-fluoro-3-(3-fluorophenyl)-4H-chromen-4-one;

2-(1-(4-amino-3-(3-fluoro-4-(trifluoromethoxy)phenyl)-1H-pyrazolo[3,4-d]pyrimidin-1-yl)ethyl)-5-fluoro-3-(3-fluorophenyl)-4H-chromen-4-one;

2-(1-(4-amino-3-(3-fluoro-4-(oxetan-3-yloxy)phenyl)-1H-pyrazolo[3,4-d]pyrimidin-1-yl)ethyl)-5-fluoro-3-(3-fluorophenyl)-4H-chromen-4-one;

2-(1-(4-amino-3-(pyrrolidin-1-yl)-1H-pyrazolo[3,4-d]pyrimidin-1-yl)ethyl)-5-fluoro-3-(3-fluorophenyl)-4H-chromen-4-one;

N-(4-(4-amino-1-(1-(5-fluoro-3-(3-fluorophenyl)-4-oxo-4H-chromen-2-yl)ethyl)-1H-pyrazolo[3,4-d]pyrimidin-3-yl)phenyl)isobutyramide;

2-(1-(4-amino-3-(4-isobutylphenyl)-1H-pyrazolo[3,4-d]pyrimidin-1-yl)ethyl)-5-fluoro-3-(3-fluorophenyl)-4H-chromen-4-one;

2-(1-(4-amino-3-(4-isopropoxy-3-methylphenyl)-1H-pyrazolo[3,4-d]pyrimidin-1-yl)ethyl)-5-fluoro-3-(3-fluorophenyl)-4H-chromen-4-one;

2-(1-(4-amino-3-(4-(5,6-dihydro-4H-1,3-oxazin-2-yl)phenyl)-1H-pyrazolo[3,4-d]pyrimidin-1-yl)ethyl)-5-fluoro-3-(3-fluorophenyl)-4H-chromen-4-one;

4-(4-amino-1-(1-(5-fluoro-3-(3-fluorophenyl)-4-oxo-4H-chromen-2-yl)ethyl)-1H-pyrazolo[3,4-d]pyrimidin-3-yl)-N-methylbenzenesulfonamide;

4-(4-amino-1-(1-(5-fluoro-3-(3-fluorophenyl)-4-oxo-4H-chromen-2-yl)ethyl)-1H-pyrazolo[3,4-d]pyrimidin-3-yl)-2-fluoro-N-isopropylbenzamide;

2-(1-(4-amino-3-(4-(5-(methylamino)-1,3,4-thiadiazol-2-yl)phenyl)-1H-pyrazolo[3,4-d]pyrimidin-1-yl)ethyl)-5-fluoro-3-(3-fluorophenyl)-4H-chromen-4-one;

N-(4-(4-amino-1-(1-(5-fluoro-3-(3-fluorophenyl)-4-oxo-4H-chromen-2-yl)ethyl)-1H-pyrazolo[3,4-d]pyrimidin-3-yl)benzyl)methanesulfonamide;

4-(4-amino-1-(1-(5-fluoro-3-(3-fluorophenyl)-4-oxo-4H-chromen-2-yl)ethyl)-1H-pyrazolo[3,4-d]pyrimidin-3-yl)-N-isopropylbenzenesulfonamide;

4-(4-amino-1-(1-(5-fluoro-3-(3-fluorophenyl)-4-oxo-4H-chromen-2-yl)ethyl)-1H-pyrazolo[3,4-d]pyrimidin-3-yl)-N-cyclopropylbenzenesulfonamide;

2-(1-(4-amino-3-(2-isopropoxypyrimidin-5-yl)-1H-pyrazolo[3,4-d]pyrimidin-1-yl)ethyl)-5-fluoro-3-(3-fluorophenyl)-4H-chromen-4-one;

(R)/(S)-2-(1-(4-amino-3-(3-fluoro-4-morpholinophenyl)-1H-pyrazolo[3,4-d]pyrimidin-1-yl)ethyl)-5-fluoro-3-(3-fluorophenyl)-4H-chromen-4-one;

4-(4-amino-1-(1-(5-fluoro-3-(3-fluorophenyl)-4-oxo-4H-chromen-2-yl)ethyl)-1H-pyrazolo[3,4-d]pyrimidin-3-yl)benzenesulfonamide;

methyl 4-(4-amino-1-(1-(5-fluoro-3-(3-fluorophenyl)-4-oxo-4H-chromen-2-yl)ethyl)-1H-pyrazolo[3,4-d]pyrimidin-3-yl)thiophene-2-carboxylate;

2-(1-(4-amino-3-(5-methylthiophen-2-yl)-1H-pyrazolo[3,4-d]pyrimidin-1-yl)ethyl)-5-fluoro-3-(3-fluorophenyl)-4H-chromen-4-one;

2-(1-(4-amino-3-(1H-pyrrolo[2,3-b]pyridin-5-yl)-1H-pyrazolo[3,4-d]pyrimidin-1-yl)ethyl)-5-fluoro-3-(3-fluorophenyl)-4H-chromen-4-one;

methyl 4-(4-amino-1-(1-(5-fluoro-3-(3-fluorophenyl)-4-oxo-4H-chromen-2-yl)ethyl)-1H-pyrazolo[3,4-d]pyrimidin-3-yl)-3-fluorobenzoate;

2-(1-(9H-purin-6-ylamino)propyl)-5-fluoro-3-phenyl-4H-chromen-4-one;

2-(1-(4-amino-3-(3-hydroxyprop-1-ynyl)-1H-pyrazolo[3,4-d]pyrimidin-1-yl)ethyl)-5-fluoro-3-(3-fluorophenyl)-4H-chromen-4-one;

(+)-2-(1-(9H-purin-6-ylamino)ethyl)-5-fluoro-3-(3-fluorophenyl)-4H-chromen-4-one 2-(1-(9H-purin-6-ylamino)ethyl)-5-fluoro-3-(3-fluorophenyl)-4H-chromen-4-one;

(R)/(S)-2-(1-(4-amino-3-(3-fluoro-4-morpholinophenyl)-1H-pyrazolo[3,4-d]pyrimidin-1-yl)ethyl)-5-fluoro-3-(3-fluorophenyl)-4H-chromen-4-one;

2-(1-(4-amino-3-(4-methoxy-3,5-dimethylphenyl)-1H-pyrazolo[3,4-d]pyrimidin-1-yl)ethyl)-5-fluoro-3-(3-fluorophenyl)-4H-chromen-4-one;

2-(1-(4-amino-3-(4-(methoxymethyl)phenyl)-1H-pyrazolo[3,4-d]pyrimidin-1-yl)ethyl)-5-fluoro-3-(3-fluorophenyl)-4H-chromen-4-one;

2-(1-(4-amino-3-(imidazo[1,2-a]pyridin-6-yl)-1H-pyrazolo[3,4-d]pyrimidin-1-yl)ethyl)-5-fluoro-3-(3-fluorophenyl)-4H-chromen-4-one;

tert-butyl (5-(4-amino-1-(1-(5-fluoro-3-(3-fluorophenyl)-4-oxo-4H-chromen-2-yl)ethyl)-1H-pyrazolo[3,4-d]pyrimidin-3-yl)furan-2-yl)methylcarbamate;

2-(1-(4-amino-3-(2,4-dimethylthiazol-5-yl)-1H-pyrazolo[3,4-d]pyrimidin-1-yl)ethyl)-5-fluoro-3-(3-fluorophenyl)-4H-chromen-4-one;

2-(1-(4-amino-3-(5-(morpholinomethyl)thiophen-2-yl)-1H-pyrazolo[3,4-d]pyrimidin-1-yl)ethyl)-5-fluoro-3-(3-fluorophenyl)-4H-chromen-4-one;

2-(1-(4-amino-3-(4-(5-amino-1,3,4-thiadiazol-2-yl)phenyl)-1H-pyrazolo[3,4-d]pyrimidin-1-yl)ethyl)-5-fluoro-3-(3-fluorophenyl)-4H-chromen-4-one;

(−)-2-(1-(9H-purin-6-ylamino)ethyl)-5-fluoro-3-(3-fluorophenyl)-4H-chromen-4-one;

2-(1-(4-amino-3-(1,3-dimethyl-1H-indazol-6-yl)-1H-pyrazolo[3,4-d]pyrimidin-1-yl)ethyl)-5-fluoro-3-(3-fluorophenyl)-4H-chromen-4-one;

2-(1-(4-amino-3-(2,3-dimethyl-2H-indazol-6-yl)-1H-pyrazolo[3,4-d]pyrimidin-1-yl)ethyl)-5-fluoro-3-(3-fluorophenyl)-4H-chromen-4-one;

N-(4-(4-amino-1-(1-(5-fluoro-3-(3-fluorophenyl)-4-oxo-4H-chromen-2-yl)ethyl)-1H-pyrazolo[3,4-d]pyrimidin-3-yl)-2-fluorophenyl)isobutyramide;

N-(4-(4-amino-1-(1-(5-fluoro-3-(3-fluorophenyl)-4-oxo-4H-chromen-2-yl)ethyl)-1H-pyrazolo[3,4-d]pyrimidin-3-yl)-2-fluorophenyl)acetamide;

2-(1-(4-(dimethylamino)-3-(3-fluoro-4-isopropoxyphenyl)-1H-pyrazolo[3,4-d]pyrimidin-1-yl)ethyl)-5-fluoro-3-(3-fluorophenyl)-4H-chromen-4-one;

5-fluoro-2-(1-(3-(3-fluoro-4-isopropoxyphenyl)-4-(methylamino)-1H-pyrazolo[3,4-d]pyrimidin-1-yl)ethyl)-3-(3-fluorophenyl)-4H-chromen-4-one;

5-fluoro-2-(1-(3-(3-fluoro-4-isopropoxyphenyl)-4-morpholino-1H-pyrazolo[3,4-d]pyrimidin-1-yl)ethyl)-3-(3-fluorophenyl)-4H-chromen-4-one;

N-(2-fluoro-4-(1-(1-(5-fluoro-3-(4-fluorophenyl)-4-oxo-4H-chromen-2-yl)ethyl)-4-morpholino-1H-pyrazolo[3,4-d]pyrimidin-3-yl)phenyl)isobutyramide;

N-(2-fluoro-4-(1-(1-(5-fluoro-3-(3-fluorophenyl)-4-oxo-4H-chromen-2-yl)ethyl)-4-morpholino-1H-pyrazolo[3,4-d]pyrimidin-3-yl)phenyl)isobutyramide;

2-(1-(4-amino-3-(4-(difluoromethoxy)-3-fluorophenyl)-1H-pyrazolo[3,4-d]pyrimidin-1-yl)ethyl)-5-fluoro-3-(1H-pyrazol-4-yl)-4H-chromen-4-one;

2-(1-(4-amino-3-(3-fluoro-4-morpholinophenyl)-1H-pyrazolo[3,4-d]pyrimidin-1-yl)ethyl)-5-fluoro-3-phenyl-4H-chromen-4-one;

2-(1-(4-amino-3-(3-fluoro-4-morpholinophenyl)-1H-pyrazolo[3,4-d]pyrimidin-1-yl)ethyl)-5-fluoro-3-(4-fluorophenyl)-4H-chromen-4-one;

(S)-2-(1-(4-amino-3-(3-fluoro-4-isopropoxyphenyl)-1H-pyrazolo[3,4-d]pyrimidin-1-yl)ethyl)-5-fluoro-3-(4-fluorophenyl)-4H-chromen-4-one;

(R)-2-(1-(4-amino-3-(3-fluoro-4-isopropoxyphenyl)-1H-pyrazolo[3,4-d]pyrimidin-1-yl)ethyl)-5-fluoro-3-(4-fluorophenyl)-4H-chromen-4-one;

(S)-2-(1-(4-amino-3-(4-(difluoromethoxy)-3-fluorophenyl)-1H-pyrazolo[3,4-d]pyrimidin-1-yl)ethyl)-5-fluoro-3-(4-fluorophenyl)-4H-chromen-4-one;

(R)-2-(1-(4-amino-3-(4-(difluoromethoxy)-3-fluorophenyl)-1H-pyrazolo[3,4-d]pyrimidin-1-yl)ethyl)-5-fluoro-3-(4-fluorophenyl)-4H-chromen-4-one;

2-(1-(4-(dimethylamino)-3-(3-fluoro-4-morpholinophenyl)-1H-pyrazolo[3,4-d]pyrimidin-1-yl)ethyl)-5-fluoro-3-(3-fluorophenyl)-4H-chromen-4-one;

5-fluoro-2-(1-(3-(3-fluoro-4-morpholinophenyl)-4-(methylamino)-1H-pyrazolo[3,4-d]pyrimidin-1-yl)ethyl)-3-(3-fluorophenyl)-4H-chromen-4-one;

(S)-2-(1-(4-amino-3-(3-fluoro-4-isopropoxyphenyl)-1H-pyrazolo[3,4-d]pyrimidin-1-yl)ethyl)-5-fluoro-3-phenyl-4H-chromen-4-one;

(R)-2-(1-(4-amino-3-(3-fluoro-4-isopropoxyphenyl)-1H-pyrazolo[3,4-d]pyrimidin-1-yl)ethyl)-5-fluoro-3-phenyl-4H-chromen-4-one;

(S)-2-(1-(4-amino-3-(4-(difluoromethoxy)-3-fluorophenyl)-1H-pyrazolo[3,4-d]pyrimidin-1-yl)ethyl)-5-fluoro-3-phenyl-4H-chromen-4-one;

(R)-2-(1-(4-amino-3-(4-(difluoromethoxy)-3-fluorophenyl)-1H-pyrazolo[3,4-d]pyrimidin-1-yl)ethyl)-5-fluoro-3-phenyl-4H-chromen-4-one;

(+)-5-fluoro-2-(1-(3-(3-fluoro-4-isopropoxyphenyl)-4-(methylamino)-1H-pyrazolo[3,4-d]pyrimidin-1-yl)ethyl)-3-(3-fluorophenyl)-4H-chromen-4-one;

(−)-5-fluoro-2-(1-(3-(3-fluoro-4-isopropoxyphenyl)-4-(methylamino)-1H-pyrazolo[3,4-d]pyrimidin-1-yl)ethyl)-3-(3-fluorophenyl)-4H-chromen-4-one;

2-(1-(6-amino-2-fluoro-9H-purin-9-yl)ethyl)-5-fluoro-3-(3-fluorophenyl)-4H-chromen-4-one;

2-(1-(6-amino-2-fluoro-9H-purin-9-yl)ethyl)-5-fluoro-3-(4-fluorophenyl)-4H-chromen-4-one;

5-fluoro-3-(4-fluorophenyl)-2-(1-(6-morpholino-9H-purin-9-yl)ethyl)-4H-chromen-4-one;

5-fluoro-3-(4-fluorophenyl)-2-(1-(6-(4-methylpiperazin-1-yl)-9H-purin-9-yl)ethyl)-4H-chromen-4-one;

2-(1-(6-(dimethylamino)-9H-purin-9-yl)ethyl)-5-fluoro-3-(3-fluorophenyl)-4H-chromen-4-one;

2-(1-(6-(dimethylamino)-9H-purin-9-yl)ethyl)-5-fluoro-3-(3-fluorophenyl)-4H-chromen-4-one;

5-fluoro-3-(3-fluorophenyl)-2-(1-(3-(3-methyl-1H-indazol-6-yl)-4-morpholino-1H-pyrazolo[3,4-d]pyrimidin-1-yl)ethyl)-4H-chromen-4-one;

2-(1-(4-amino-3-(3-chloro-4-morpholinophenyl)-1H-pyrazolo[3,4-d]pyrimidin-1-yl)ethyl)-5-fluoro-3-(3-fluorophenyl)-4H-chromen-4-one;

(+)-2-(1-(4-amino-3-(4-isopropoxy-3-methylphenyl)-1H-pyrazolo[3,4-d]pyrimidin-1-yl)ethyl)-5-fluoro-3-(3-fluorophenyl)-4H-chromen-4-one;

(−)-2-(1-(4-amino-3-(4-isopropoxy-3-methylphenyl)-1H-pyrazolo[3,4-d]pyrimidin-1-yl)ethyl)-5-fluoro-3-(3-fluorophenyl)-4H-chromen-4-one;

(S)/(R)-5-fluoro-2-(1-(3-(3-fluoro-4-isopropoxyphenyl)-4-morpholino-1H-pyrazolo[3,4-d]pyrimidin-1-yl)ethyl)-3-(3-fluorophenyl)-4H-chromen-4-one;

2-(1-(4-amino-3-(3-chloro-4-isopropoxyphenyl)-1H-pyrazolo[3,4-d]pyrimidin-1-yl)ethyl)-5-fluoro-3-(3-fluorophenyl)-4H-chromen-4-one;

2-(1-(4-amino-3-(2-methylbenzo[d]oxazol-6-yl)-1H-pyrazolo[3,4-d]pyrimidin-1-yl)ethyl)-5-fluoro-3-(3-fluorophenyl)-4H-chromen-4-one;

5-fluoro-3-(3-fluorophenyl)-2-(1-(6-morpholino-9H-purin-9-yl)ethyl)-4H-chromen-4-one;

2-(1-(4-amino-3-(3-fluoro-4-isopropoxyphenyl)-1H-pyrazolo[3,4-d]pyrimidin-1-yl)ethyl)-3-(3-fluorophenyl)-5-morpholino-4H-chromen-4-one;

2-(1-(4-amino-3-(3-fluoro-4-isopropoxyphenyl)-1H-pyrazolo[3,4-d]pyrimidin-1-yl)ethyl)-5-morpholino-3-phenyl-4H-chromen-4-one;

6-(4-amino-1-(1-(5-fluoro-3-(3-fluorophenyl)-4-oxo-4H-chromen-2-yl)ethyl)-1H-pyrazolo[3,4-d]pyrimidin-3-yl)isoindolin-1-one;

5-(4-amino-1-(1-(5-fluoro-3-(3-fluorophenyl)-4-oxo-4H-chromen-2-yl)ethyl)-1H-pyrazolo[3,4-d]pyrimidin-3-yl)isoindolin-1-one;

2-(1-(3-(4-acetyl-3-fluorophenyl)-4-amino-1H-pyrazolo[3,4-d]pyrimidin-1-yl)ethyl)-5-fluoro-3-(3-fluorophenyl)-4H-chromen-4-one;

5-fluoro-3-(3-fluorophenyl)-2-(1-(6-(4-methylpiperazin-1-yl)-9H-purin-9-yl)ethyl)-4H-chromen-4-one;

(S)-2-(1-(4-amino-3-(3-chloro-4-morpholinophenyl)-1H-pyrazolo[3,4-d]pyrimidin-1-yl)ethyl)-5-fluoro-3-(3-fluorophenyl)-4H-chromen-4-one;

(R)-2-(1-(4-amino-3-(3-chloro-4-morpholinophenyl)-1H-pyrazolo[3,4-d]pyrimidin-1-yl)ethyl)-5-fluoro-3-(3-fluorophenyl)-4H-chromen-4-one;

N-(3-(4-amino-1-(1-(5-fluoro-3-(3-fluorophenyl)-4-oxo-4H-chromen-2-yl)ethyl)-1H-pyrazolo[3,4-d]pyrimidin-3-yl)phenyl)methanesulfonamide;

(S)-2-(1-(6-(dimethylamino)-9H-purin-9-yl)ethyl)-5-fluoro-3-(3-fluorophenyl)-4H-chromen-4-one;

(R)-2-(1-(6-(dimethylamino)-9H-purin-9-yl)ethyl)-5-fluoro-3-(3-fluorophenyl)-4H-chromen-4-one;

2-(1-(9H-purin-6-ylamino)ethyl)-5-fluoro-3-(2-fluorophenyl)-4H-chromen-4-one;

2-(1-(4-amino-3-(4-ethoxy-3-(trifluoromethyl)phenyl)-1H-pyrazolo[3,4-d]pyrimidin-1-yl)ethyl)-5-fluoro-3-(3-fluorophenyl)-4H-chromen-4-one;

2-(1-(4-amino-3-(3-fluoro-4-isopropoxyphenyl)-1H-pyrazolo[3,4-d]pyrimidin-1-yl)propyl)-5-fluoro-3-(3-fluorophenyl)-4H-chromen-4-one;

(S)-5-fluoro-3-(3-fluorophenyl)-2-(1-(2-methoxy-9H-purin-6-ylamino)ethyl)-4H-chromen-4-one;

(R)-5-fluoro-3-(3-fluorophenyl)-2-(1-(2-methoxy-9H-purin-6-ylamino)ethyl)-4H-chromen-4-one;

(S)/(R)-5-fluoro-2-(1-(2-fluoro-9H-purin-6-ylamino)ethyl)-3-(3-fluoro phenyl)-4H-chromen-4-one;

(S)/(R)-2-(1-(4-amino-3-(3-fluoro-4-isopropoxyphenyl)-1H-pyrazolo[3,4-d]pyrimidin-1-yl)ethyl)-5-methyl-3-phenyl-4H-chromen-4-one; and 2-(1-(9H-purin-6-ylamino)ethyl)-5-fluoro-3-o-tolyl-4H-chromen-4-one;

and pharmaceutically acceptable salts thereof.

34. A method of treating asthma in a subject, comprising administering to a subject in need thereof a therapeutically effective amount of a compound of claim 33, and pharmaceutically acceptable salts thereof.

35. A method of treating chronic obstructive pulmonary disease in a subject, comprising administering to a subject in need thereof a therapeutically effective amount of a compound of claim 33, and pharmaceutically acceptable salts thereof.

* * * * *